United States Patent
Umetani et al.

(10) Patent No.: US 11,234,970 B2
(45) Date of Patent: Feb. 1, 2022

(54) PARASITIC PEST CONTROL AGENTS COMPRISING PYRIDONE COMPOUNDS AS ACTIVE INGREDIENTS AND METHODS FOR USING THE SAME

(71) Applicant: MITSUI CHEMICALS AGRO, INC., Tokyo (JP)

(72) Inventors: Hideki Umetani, Ritto (JP); Ryohei Naito, Kusatsu (JP); Hideaki Ikishima, Chiba (JP); Mai Hirose, Chiba (JP)

(73) Assignee: MITSUI CHEMICALS AGRO, INC., Tokyo (JP)

( * ) Notice: Subject to any disclaimer, the term of this patent is extended or adjusted under 35 U.S.C. 154(b) by 99 days.

(21) Appl. No.: 16/497,575

(22) PCT Filed: Apr. 10, 2018

(86) PCT No.: PCT/JP2018/015003
§ 371 (c)(1),
(2) Date: Sep. 25, 2019

(87) PCT Pub. No.: WO2018/190321
PCT Pub. Date: Oct. 18, 2018

(65) Prior Publication Data
US 2021/0100782 A1    Apr. 8, 2021

(30) Foreign Application Priority Data
Apr. 10, 2017 (JP) .............................. JP2017-077473

(51) Int. Cl.
A61K 31/4412 (2006.01)
A61K 31/444 (2006.01)
A01N 43/40 (2006.01)

(52) U.S. Cl.
CPC .......... *A61K 31/4412* (2013.01); *A01N 43/40* (2013.01); *A61K 31/444* (2013.01)

(58) Field of Classification Search
None
See application file for complete search history.

(56) References Cited

U.S. PATENT DOCUMENTS

| 6,200,982 | B1 | 3/2001 | Collins et al. |
| 2001/0018438 | A1 | 8/2001 | Collins et al. |
| 2005/0182103 | A1 | 8/2005 | Finke et al. |
| 2010/0160385 | A1 | 6/2010 | Finkelstein |
| 2015/0080362 | A1 | 3/2015 | Branstrom et al. |
| 2018/0279614 | A1 | 10/2018 | Umetani et al. |

FOREIGN PATENT DOCUMENTS

| EP | 0308020 | A2 | 3/1989 |
| JP | H01128969 | A | 5/1989 |
| JP | H03-178964 | A | 8/1991 |
| JP | 2005531520 | A | 10/2005 |
| JP | 2014525452 | A | 9/2014 |
| WO | 9855480 | A1 | 12/1998 |
| WO | 2010/093595 | A1 | 8/2010 |
| WO | 2017061525 | A1 | 4/2017 |

OTHER PUBLICATIONS

First Examination Report dated Mar. 30, 2021, by the Intellectual Property India in corresponding India Patent Application No. 201917041738 with an English translation of the Report. (5 pages).
International Search Report (PCT/ISA/210) and translation and Written Opinion (PCT/ISA/237) dated Jun. 12, 2018, by the Japanese Patent Office as the International Searching Authority for International Application No. PCT/JP2018/015003.
Extended European Search Report dated Dec. 11, 2020, issued by the European Patent Office in corresponding European Application No. 18784834.6-1110, (6 pages).

*Primary Examiner* — Samantha L Shterengarts
(74) *Attorney, Agent, or Firm* — Buchanan, Ingersoll & Rooney PC

(57) ABSTRACT

A compound of formula (1) or a salt thereof, which is effective as a parasitic pest control agent, is provided. In the formula, R1 represents, for example an optionally substituted C1-C6 alkyl group, a C1-C6 haloalkyl group, R2 represents, for example a halogen atom, an optionally substituted C1-C6 alkyl group, an optionally substituted C1-C6 alkoxy group, R3 represents, for example a hydrogen atom, a halogen atom, an optionally substituted C1-C6 alkyl group, n represents an integer of 0 to 5, X represents an oxygen atom or sulfur atom, Y represents, for example phenyl substituted at an ortho position, pyridyl, and the bond with a broken line represents a double bond or a single bond.

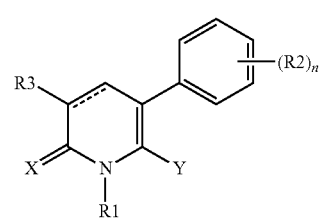

(1)

7 Claims, No Drawings

PARASITIC PEST CONTROL AGENTS COMPRISING PYRIDONE COMPOUNDS AS ACTIVE INGREDIENTS AND METHODS FOR USING THE SAME

TECHNICAL FIELD

The present invention relates to a parasitic pest control agent comprising a pyridone compound as an active ingredient.

BACKGROUND ART

Parasitic pests generally cause various serious problems by parasitically infesting animals and plants.

Parasitic diseases, due to animal parasitic pests, are caused by the parasitic infestation of parasites (i.e. for example, a single-cell protozoan (protozoa), multicellular helminths, arthropods) to an animal host, and their infection can be a serious problem in domestic animals (such as pigs, horses, cows, sheep, dogs, cats and poultry). Namely, animals infected by parasites undergo anemia, malnutrition, debilitation, weight loss and serious damage to the intestinal wall, tissue and organs which cause decreased feed efficiency and decreased productivity, thereby leading to serious economic loss.

Problems attributable to plant parasitic pests include prominent economic losses in the fields of agriculture and forestry, such as significant inhibition of the growth of crops that have infected by these pests.

Many parasitic pest control agents are conventionally used against these parasitic pests. Although some conventional parasitic pest control agents have good properties such as fast-acting, penetration transferability and gasification, they do not completely satisfy users in terms of, for example anti-parasitic pest spectrum, residual efficacy, toxicity to humans, livestock and fish, and reduction of environmental pollution. Moreover, the appearance of parasitic pests exhibiting strong resistance to known parasitic pest control agents is recently a problem. With this in mind, the development of novel parasitic pest control agents that are safer and have good parasitic pest control activity at low doses are continuously desired.

Regarding 1,3,5,6-substituted-2-pyridone compounds, for example 1,3,5,6-substituted-2-pyridone compounds having an aryl or a heteroaryl at the 3-position are disclosed as GABA alpha 2/3 ligands (see, for example WO 98/55480). Further, 1,3,5,6-substituted-2-pyridone compounds having a carboxyl at the 3-position are disclosed as the therapeutic drugs for bacterial infections (see, for example EP Patent No. 0308020).

CITATION LIST

Patent Literature

Patent Literature 1: WO 98/55480
Patent Literature 2: EP Patent No. 0308020

SUMMARY OF INVENTION

Technical Problem

However, WO 98/5548 and EP Patent No. 0308020 both discloses the compounds for use as a pharmaceutical, which is a different technical field of the parasitic pest control agents according to the present invention.

An object of the present invention is to provide novel parasitic pest control agents that have good parasitic pest control activity.

Solution to Problem

As a result of conducting extensive studies on 1,3,5,6-substituted-2-pyridone compounds and 1,5,6-substituted-2-pyridone compounds to achieve the aforementioned object, the inventors of the present invention have found that the compounds that have an ortho-substituted aryl or heteroaryl introduced at the 6-position in the 2-pyridone skeleton demonstrate good parasitic pest control activity against parasitic pests; thereby completed the present invention.

Namely, the present invention is as described below.

[1] A parasitic pest control agent comprising a compound of Formula (1) or a salt thereof as an active ingredient:

[Chem. 1]

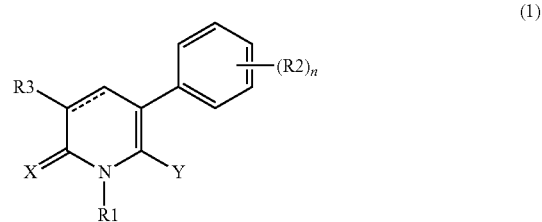

(1)

[wherein
R1 represents a hydroxyl group,
a cyano group,
a C1-C6 alkyl group optionally substituted with substituent A,
a C1-C6 haloalkyl group,
a C3-C8 cycloalkyl group optionally substituted with substituent A,
a C2-C6 alkenyl group optionally substituted with substituent A,
a C2-C6 haloalkenyl group,
a C2-C6 alkynyl group optionally substituted with substituent A,
a C2-C6 haloalkynyl group,
a C1-C6 alkoxy group optionally substituted with substituent A,
a C1-C6 haloalkoxy group,
a C3-C8 cycloalkoxy group optionally substituted with substituent A,
a C2-C6 alkenyloxy group optionally substituted with substituent A,
a C2-C6 haloalkenyloxy group,
a C3-C6 alkynyloxy group optionally substituted with substituent A,
a C3-C6 haloalkynyloxy group, or
a R10R11N— group (wherein R10 and R11 each independently represents a hydrogen atom or a C1-C6 alkyl group);
R2 represents a halogen atom,
a hydroxyl group,
a cyano group,
a nitro group,
a C1-C6 alkyl group optionally substituted with substituent B,
a C1-C6 haloalkyl group, a C3-C8 cycloalkyl group optionally substituted with substituent B,
a C2-C6 alkenyl group optionally substituted with substituent B,
a C2-C6 haloalkenyl group,
a C2-C6 alkynyl group optionally substituted with substituent B,
a C2-C6 haloalkynyl group,
a C1-C6 alkoxy group optionally substituted with substituent B,
a C1-C6 haloalkoxy group,
a C3-C8 cycloalkoxy group optionally substituted with substituent B,
a C2-C6 alkenyloxy group optionally substituted with substituent B,
a C2-C6 haloalkenyloxy group,
a C3-C6 alkynyloxy group optionally substituted with substituent B,
a C3-C6 haloalkynyloxy group,
a R20C(=O)— group (wherein R20 represents a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or a R21R22N— group (wherein R21 and R22 each independently represents a hydrogen atom, a C1-C6 alkyl group optionally substituted with substituent B1, a C1-C6 haloalkyl group or a C3-C8 cycloalkyl group, or R21 and R22 together with the nitrogen atom to which they are bonded form aziridinyl, azetidinyl, pyrrolidinyl, piperidinyl, homopiperidinyl or azocanyl)),
a R20C(=O)O— group (wherein R20 is the same as defined hereinabove),
a 3 to 6-membered ring group containing 1 to 2 oxygen atoms,
a R23-L2- group (wherein R23 represents a C1-C6 alkyl group or a C1-C6 haloalkyl group, and L2 represents S, SO or SO$_2$),
a R21R22N— group (wherein R21 and R22 are the same as defined hereinabove), or
a R24C(=O)N(R25)— group (wherein R24 represents a hydrogen atom, a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or a R21R22N— group (wherein R21 and R22 are the same as defined hereinabove), and R25 represents a hydrogen atom, a C1-C6 alkyl group optionally substituted with substituent B1, a C1-C6 haloalkyl group or a C3-C8 cycloalkyl group);
R3 represents a hydrogen atom,
a halogen atom,
a nitro group,
a C1-C6 alkyl group optionally substituted with substituent C,
a C1-C6 haloalkyl group,
a C3-C8 cycloalkyl group optionally substituted with substituent C,
a C1-C6 alkoxy group optionally substituted with substituent C,
a C1-C6 haloalkoxy group,
a C2-C6 alkenyl group optionally substituted with substituent C,
a C2-C6 haloalkenyl group,
a C2-C6 alkynyl group optionally substituted with substituent C,
a C2-C6 haloalkynyl group,
a R30-L3- group (wherein R30 has the same definition as R23, and L3 has the same definition as L2),
a R31R32N— group (wherein R31 and R32 have the same definition as R21 and R22), or
a R33C(=O)— group (wherein R33 represents a C1-C6 alkyl group, a C1-C6 haloalkyl group or a C3-C8 cycloalkyl group);
n represents an integer of 0 to 5 (with the proviso that when n is 2 or greater, the two or more R2 represent independent substituents);
X represents an oxygen atom or a sulfur atom;
Y represents phenyl, pyridyl, pyridazinyl, pyrimidinyl, pyrazinyl, triazinyl, tetrazinyl, thienyl, thiazolyl, isothiazolyl or thiadiazolyl,
the phenyl is substituted with substituent D at an ortho position and is optionally further substituted with 0 to 4 independent substituents D1,
the pyridyl, the pyrazinyl, the pyrimidinyl, the pyridazinyl, the triazinyl or the tetrazinyl is substituted with substituent D at an ortho position and is optionally further substituted with 0 to 3 independent substituents D1,
the thienyl, the thiazolyl, the isothiazolyl or the thiadiazolyl is substituted with substituent D at an ortho position and is optionally further substituted with 0 to 2 independent substituents D1;
the bond with a broken line represents a double bond or a single bond,
the substituent A is at least one selected from the group consisting of:
a hydroxyl group, a cyano group, a C3-C8 cycloalkyl group, a C1-C6 alkoxy group, a C1-C6 haloalkoxy group, a C3-C8 cycloalkoxy group, a R12R13N— group (wherein R12 and R13 each independently represents a hydrogen atom, a C1-C6 alkyl group, a C1-C6 haloalkyl group or a C3-C8 cycloalkyl group, or R12 and R13 together with the nitrogen atom to which they are bonded form aziridinyl, azetidinyl, pyrrolidinyl, piperidinyl, homopiperidinyl or azocanyl), and a R14-L1- group (wherein R14 represents a C1-C6 alkyl group or a C1-C6 haloalkyl group, and L1 represents S, SO or SO$_2$);
the substituent B is at least one selected from the group consisting of:
a hydroxyl group, a cyano group, a C3-C8 cycloalkyl group, a C1-C6 alkoxy group, a C1-C6 haloalkoxy group, a C3-C8 cycloalkoxy group, a C2-C6 alkoxyalkoxy group, a R21R22N— group (wherein R21 and R22 are the same as defined hereinabove), a R23-L2- group (wherein R23 and L2 are the same as defined hereinabove), a R26R27R28Si— group (wherein R26, R27 and R28 each independently represents a C1-C6 alkyl group), a R26R27R28Si—(CH$_2$)s-O— group (wherein s represents an integer of 1 to 3, and R26, R27 and R28 are the same as defined hereinabove), a R20C(=O)— group (wherein R20 is the same as defined hereinabove) and a 3 to 6-membered ring group containing 1 to 2 oxygen atoms;
the substituent B1 is at least one selected from the group consisting of:
a cyano group, a C1-C6 alkoxy group, a C1-C6 haloalkoxy group and a C3-C8 cycloalkoxy group;
the substituent C is at least one selected from the group consisting of:
a hydroxyl group, a cyano group, a C3-C8 cycloalkyl group, a C1-C6 alkoxy group, a C1-C6 haloalkoxy group, a C3-C8 cycloalkoxy group, a R31R32N— group (wherein R31 and R32 have the same definition as R21 and R22) and a R30-L3- group (wherein R30 has the same definition as R14, and L3 has the same definition as L1);

the substituent D is at least one selected from the group consisting of:

a halogen atom, a C1-C6 alkyl group, a C1-C6 haloalkyl group, a C1-C6 alkoxy group and a C1-C6 haloalkoxy group; and the substituent D1 is at least one selected from the group consisting of:

a hydroxyl group, a halogen atom, a C1-C6 alkyl group, a C1-C6 haloalkyl group, a C3-C8 cycloalkyl group, a C1-C6 alkoxy group, a C1-C6 haloalkoxy group and a C3-C8 cycloalkoxy group].

[2] The parasitic pest control agent comprising the compound defined in [1] or a salt thereof as an active ingredient, wherein R1 represents a cyano group, a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, or a R10R11N— group (wherein R10 and R11 each independently represents a hydrogen atom or a C1-C6 alkyl group);

R2 represents a halogen atom, a hydroxyl group, a cyano group, a C1-C6 alkyl group optionally substituted with substituent B, a C1-C6 haloalkyl group, a C1-C6 alkoxy group optionally substituted with substituent B, a C1-C6 haloalkoxy group, a C3-C8 cycloalkoxy group optionally substituted with substituent B, a C2-C6 alkenyloxy group optionally substituted with substituent B, a C3-C6 alkynyloxy group optionally substituted with substituent B, a R20C(=O)O— group (wherein R20 represents a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or a R21R22N— group (wherein R21 and R22 each independently represents a hydrogen atom, a C1-C6 alkyl group optionally substituted with substituent B1, a C1-C6 haloalkyl group or a C3-C8 cycloalkyl group, or R21 and R22 together with the nitrogen atom to which they are bonded form aziridinyl, azetidinyl, pyrrolidinyl, piperidinyl, homopiperidinyl or azocanyl), or a R23-L2- group (wherein R23 represents a C1-C6 alkyl group or a C1-C6 haloalkyl group, and L2 represents S, SO or SO₂);

R3 represents a hydrogen atom, a halogen atom, a C1-C6 alkyl group optionally substituted with substituent C, a C3-C8 cycloalkyl group optionally substituted with substituent C, a C1-C6 alkoxy group optionally substituted with substituent C, a C2-C6 alkynyl group optionally substituted with substituent C, or a R30-L3- group (wherein R30 has the same definition as R23, and L3 has the same definition as L2);

Y represents phenyl or pyridyl, the phenyl is substituted with substituent D at an ortho position and is optionally further substituted with 0 to 4 independent substituents D1, and the pyridyl is substituted with substituent D at an ortho position and is optionally further substituted with 0 to 3 independent substituents D1.

[3] The parasitic pest control agent comprising the compound defined in [2] or a salt thereof as an active ingredient, wherein R1 represents a C1-C6 alkyl group optionally substituted with substituent A, or a C1-C6 haloalkyl group;

R2 represents a halogen atom, a C1-C6 alkyl group optionally substituted with substituent B, or a C1-C6 alkoxy group optionally substituted with substituent B; and R3 represents a hydrogen atom, a halogen atom, or a C1-C6 alkyl group optionally substituted with substituent C.

[4] The parasitic pest control agent described in [1], wherein the parasitic pest is an insect pest of the order Acarina or nematodes.

[5] The parasitic pest control agent described in [1], wherein the parasitic pest is a plant parasitic insect pest of the order Acarina, animal parasitic nematodes or plant parasitic nematodes.

[6] The parasitic pest control agent described in [1], wherein the parasitic pest is spider mites, nematodes of the order Spirurida or root-knot nematodes.

[7] The parasitic pest control agent described in [1], wherein the parasitic pest is a two-spotted spider mite, a heartworm or a southern root-knot nematode.

[8] A method for controlling parasitic pests using the parasitic pest control agent described in [1].

[9] A method for controlling parasitic pests, wherein the method comprises the application of an effective amount of the compound defined in [1] or a salt thereof to a subject in need thereof.

[10] A use of the compound defined in [1] or a salt thereof, as a parasitic pest control agent in a plant.

[11] The compound defined in [1] or a salt thereof, for use as a parasitic pest control agent in an animal.

Advantageous Effects of Invention

The novel pyridone compounds according to the present invention can efficiently control parasitic pests.

DESCRIPTION OF EMBODIMENTS

Embodiments for carrying out the present invention are hereinbelow described in detail.

Each term used in the claims and the specification is in accordance with the definitions that are generally used in the art, unless otherwise specified.

The symbols used in the specification indicate the following:

DMF: N,N-dimethylformamide, THF: tetrahydrofuran, Me: methyl, Et: ethyl, Pr: propyl, Bu: butyl, Pentyl: pentyl, Hexyl: hexyl, Ac: acetyl, Ph: phenyl, Py: pyridyl, i: iso, sec: secondary, t: tertiary, c: cyclo, =: double bond, and ≡: triple bond. In the columns in the tables, a simple hyphen "-"

indicates no substituents, and Pr, Bu, Pentyl and Hexyl used without any prefix indicate that the respective groups have a normal form.

The definitions of the terms used in the specification are illustrated below.

The term Cx-Cy indicates that the group or compound has as many carbon atoms as indicated by a number between x and y inclusive.

The phrase "optionally substituted" means that the group or compound may be substituted or unsubstituted. When this phrase is used, the absence of indication of the number of substituents means that there is only one substituent.

The term C1-C6 alkyl group may be a linear or branched, and is, for example methyl, ethyl, propyl, isopropyl, butyl, isobutyl, sec-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl.

The halogen atom is, for example fluorine atom, chlorine atom, bromine atom or iodine atom.

The term C1-C6 haloalkyl group indicates a group wherein any hydrogen atom of the aforementioned C1-C6 alkyl group are substituted with one or two or more halogen atoms. When the group is substituted with two or more halogen atoms, these halogen atoms may be the same or different, and the number of such substitutions is not particularly limited as long as the group can exist as a substituent. Specific examples of the C1-C6 haloalkyl group include monofluoromethyl, difluoromethyl, trifluoromethyl, monochloromethyl, monobromomethyl, monoiodomethyl, chlorodifluoromethyl, bromodifluoromethyl, 1-fluoroethyl, 2-fluoroethyl, 1,1-difluoroethyl, 2,2-difluoroethyl, 2,2,2-trifluoroethyl, 1,1,2,2-tetrafluoroethyl, pentafluoroethyl, 2,2,2-trichloroethyl, 3,3-difluoropropyl, 3,3,3-trifluoropropyl, heptafluoropropyl, heptafluoroisopropyl, 2,2,2-trifluoro-1-(trifluoromethyl)ethyl, nonafluorobutyl, nonafluoro-sec-butyl, 3,3,4,4,5,5,5-heptafluoropentyl, undecafluoropentyl, tridecafluorohexyl.

The term C3-C8 cycloalkyl group includes cyclopropyl, cyclobutyl, cyclopentyl, cyclohexyl, cycloheptyl or cyclooctyl.

The term C2-C6 alkenyl group indicates a linear or branched, unsaturated hydrocarbon group having one or two or more double bonds. When the group has geometric isomeric forms, the group may be either the E-isomer or the Z-isomer, or may be a mixture of the E-isomer and the Z-isomer in an appropriate ratio, without limitation as long as the number of carbon atoms falls within the range indicated. Specific examples of the C2-C6 alkenyl group include vinyl, 1-propenyl, allyl, 1-butenyl, 2-butenyl, 3-butenyl, 1-pentenyl, 2-pentenyl, 3-pentenyl, 4-pentenyl, 3-methyl-2-butenyl, 1-hexenyl, 2-hexenyl, 3-hexenyl, 4-hexenyl, 5-hexenyl, 4-methyl-3-pentenyl, 3-methyl-2-pentenyl.

The term C2-C6 haloalkenyl group indicates a group wherein any hydrogen atom of the aforementioned C2-C6 alkenyl group is substituted with one or two or more halogen atoms. When the group is substituted with two or more halogen atoms, these halogen atoms may be the same or different, and the number of such substitutions is not particularly limited as long as the group can exist as a substituent. Specific examples of the C2-C6 haloalkenyl group include 2-fluorovinyl, 2,2-difluorovinyl, 2,2-dichlorovinyl, 3-fluoroallyl, 3,3-difluoroallyl, 3,3-dichloroallyl, 4,4-difluoro-3-butenyl, 5,5-difluoro-4-pentenyl, 6,6-difluoro-5-hexenyl.

The term C2-C6 alkynyl group indicates a linear or branched, unsaturated hydrocarbon group having one or two or more triple bonds. Specific examples of the C2-C6 alkynyl group include ethynyl, 1-propynyl, propargyl, 1-butynyl, 2-butynyl, 3-butynyl, 1-pentynyl, 2-pentynyl, 3-pentynyl, 4-pentynyl, 1,1-dimethyl-2-propynyl, 1-hexynyl, 2-hexynyl, 3-hexynyl, 4-hexynyl, 5-hexynyl.

The term C2-C6 haloalkynyl group indicates a group wherein any hydrogen atom of the aforementioned C2-C6 alkynyl group is substituted with one or two or more halogen atoms. When the group is substituted with two or more halogen atoms, these halogen atoms may be the same or different, and the number of such substitutions is not particularly limited as long as the group can exist as a substituent. Specific examples of the C2-C6 haloalkynyl group include 2-fluoroethynyl, 2-chloroethynyl, 2-bromoethynyl, 2-iodoethynyl, 3,3-difluoro-1-propynyl, 3-chloro-3,3-difluoro-1-propynyl, 3-bromo-3,3-difluoro-1-propynyl, 3,3,3-trifluoro-1-propynyl, 4,4-difluoro-1-butynyl, 4,4-difluoro-2-butynyl, 4-chloro-4,4-difluoro-1-butynyl, 4-chloro-4,4-difluoro-2-butynyl, 4-bromo-4,4-difluoro-1-butynyl, 4-bromo-4,4-difluoro-2-butynyl, 4,4,4-trifluoro-1-butynyl, 4,4,4-trifluoro-2-butynyl, 5,5-difluoro-3-pentynyl, 5-chloro-5,5-difluoro-3-pentynyl, 5-bromo-5,5-difluoro-3-pentynyl, 5,5,5-trifluoro-3-pentynyl, 6,6-difluoro-4-hexynyl, 6-chloro-6,6-difluoro-4-hexynyl, 6-bromo-6,6-difluoro-4-hexynyl, 6,6,6-trifluoro-4-hexynyl.

The term C1-C6 alkoxy group indicates a group resulting from the bonding of an oxygen atom to the aforementioned C1-C6 alkyl group. Specific examples of the C1-C6 alkoxy group include methoxy, ethoxy, propyloxy, isopropyloxy, butoxy, isobutoxy, sec-butoxy, t-butoxy, pentyloxy, isopentyloxy, 2-methylbutoxy, neopentyloxy, 1-ethylpropyloxy, hexyloxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy and 2-ethylbutoxy.

The term C1-C6 haloalkoxy group indicates a group wherein any hydrogen atom of the aforementioned C1-C6 alkoxy group is substituted with one or two or more halogen atoms. When the group is substituted with two or more halogen atoms, these halogen atoms may be the same or different, and the number of such substitutions is not particularly limited as long as the group can exist as a substituent. Specific examples of the C1-C6 alkoxy group include difluoromethoxy, trifluoromethoxy, chlorodifluoromethoxy, bromodifluoromethoxy, 2-fluoroethoxy, 2,2-difluoroethoxy, 2,2,2-trifluoroethoxy, 1,1,2,2-tetrafluoroethoxy, pentafluoroethoxy, 2,2,2-trichloroethoxy, 3,3-difluoropropyloxy, 3,3,3-trifluoropropyloxy, heptafluoropropyloxy, heptafluoroisopropyloxy, 2,2,2-trifluoro-1-(trifluoromethyl)-ethoxy, nonafluorobutoxy, nonafluoro-sec-butoxy, 3,3,4,4,5,5,5-heptafluoropentyloxy, undecafluoropentyloxy and tridecafluorohexyloxy.

The term C3-C8 cycloalkoxy group indicates a group resulting from the bonding of an oxygen atom to the aforementioned C3-C8 cycloalkyl group. Specific examples of the C3-C8 cycloalkoxy group include cyclopropyloxy, cyclobutoxy, cyclopentyloxy, cyclohexyloxy, cycloheptyloxy and cyclooctyloxy.

The term C2-C6 alkenyloxy group indicates a group resulting from the bonding of an oxygen atom to the aforementioned C2-C6 alkenyl group. When the group has geometric isomers, the group may be either the E form or the Z form, or may be a mixture of the E form and the Z form in an appropriate ratio, without limitation as long as the number of carbon atoms fall within the range indicated.

Specific examples of the C2-C6 alkenyloxy group include vinyloxy, 1-propenyloxy, allyloxy, 1-butenyloxy, 2-butenyloxy, 3-butenyloxy, 1-pentenyloxy, 2-pentenyloxy, 3-pentenyloxy, 4-pentenyloxy, 3-methyl-2-butenyloxy, 1-hexenyloxy, 2-hexenyloxy, 3-hexenyloxy, 4-hexenyloxy, 5-hexenyloxy, 4-methyl-3-pentenyloxy and 3-methyl-2-pentenyloxy.

The term C2-C6 haloalkenyloxy group indicates a group wherein any hydrogen atom of the aforementioned C2-C6 alkenyloxy group is substituted with one or two or more halogen atoms. When the group is substituted with two or more halogen atoms, these halogen atoms may be the same or different, and the number of such substitutions is not particularly limited as long as the group can exist as a substituent. Specific examples of the C2-C6 haloalkenyloxy group include 2-fluorovinyloxy, 2,2-difluorovinyloxy, 2,2-dichlorovinyloxy, 3-fluoroallyloxy, 3,3-difluoroallyloxy, 3,3-dichloroallyloxy, 4,4-difluoro-3-butenyloxy, 5,5-difluoro-4-pentenyloxy and 6,6-difluoro-5-hexenyloxy.

The term C3-C6 alkynyloxy group indicates a group resulting from the bonding of an oxygen atom to the C3-C6 alkynyl group among the aforementioned C2-C6 alkynyl groups. Specific examples of the C3-C6 alkynyloxy group include propargyloxy, 2-butynyloxy, 3-butynyloxy, 2-pentynyloxy, 3-pentynyloxy, 4-pentynyloxy, 1,1-dimethyl-2-propynyloxy, 2-hexynyloxy, 3-hexynyloxy, 4-hexynyloxy and 5-hexynyloxy.

The term C3-C6 haloalkynyloxy group indicates a group wherein any hydrogen atom of the aforementioned C3-C6 alkynyloxy group is substituted with one or two or more halogen atoms. When the group is substituted with two or more halogen atoms, these halogen atoms may be the same or different, and the number of such substitutions is not particularly limited as long as the group can exist as a substituent. Specific examples of the C3-C6 haloalkynyloxy group include 1,1-difluoro-2-propynyloxy, 4,4-difluoro-2-butynyloxy, 4-chloro-4,4-difluoro-2-butynyloxy, 4-bromo-4,4-difluoro-2-butynyloxy, 4,4,4-trifluoro-2-butynyloxy, 5,5-difluoro-3-pentynyloxy, 5-chloro-5,5-difluoro-3-pentynyloxy, 5-bromo-5,5-difluoro-3-pentynyloxy, 5,5,5-trifluoro-3-pentynyloxy, 6,6-difluoro-4-hexynyloxy, 6-chloro-6,6-difluoro-4-hexynyloxy, 6-bromo-6,6-difluoro-4-hexynyloxy and 6,6,6-trifluoro-4-hexynyloxy.

The term C2-C6 alkoxyalkoxy group indicates a group wherein any hydrogen atom of a C1-05 alkoxy group, among the aforementioned C1-C6 alkoxy groups, is substituted with one or two or more C1-C5 alkoxy groups. The substitution is not particularly limited as long as the total number of carbon atoms fall within the range indicated. Specific examples of the C2-C6 alkoxyalkoxy group include methoxymethoxy, ethoxymethoxy, propyloxymethoxy, isopropyloxymethoxy, methoxyethoxy, ethoxyethoxy, propyloxyethoxy, isopropyloxyethoxy, methoxypropyloxy, ethoxypropyloxy, propyloxypropyloxy and isopropyloxypropyloxy.

Specific examples of 3 to 6-membered ring group containing 1 to 2 oxygen atoms include 1,2-epoxyethanyl, oxetanyl, oxoranyl, oxanyl, 1,3-dioxoranyl, 1,3-dioxanyl and 1,4-dioxanyl.

The parasitic pest control agents of the present invention include the pyridone compounds of Formula (1) or salts thereof (which may simply be referred to as compounds of Formula (1) or compounds of the present invention).

[Chem. 2]

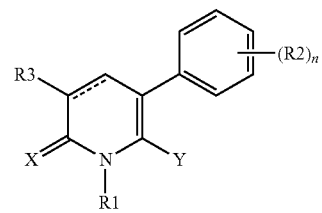

(1)

Formula (1) is hereinbelow described.

R1 in Formula (1) is a hydroxy group, a cyano group, a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, a C2-C6 haloalkynyl group, a C1-C6 alkoxy group optionally substituted with substituent A, a C1-C6 haloalkoxy group, a C3-C8 cycloalkoxy group optionally substituted with substituent A, a C2-C6 alkenyloxy group optionally substituted with substituent A, a C2-C6 haloalkenyloxy group, a C3-C6 alkynyloxy group optionally substituted with substituent A, a C3-C6 haloalkynyloxy group, or an R10R11N— (wherein R10 and R11 each independently represents a hydrogen atom or a C1-C6 alkyl group).

In particular, R1 is preferably a cyano group, a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, or an R10R11N— (wherein R10 and R11 are the same as defined hereinabove).

More particularly, R1 is preferably a C1-C6 alkyl group optionally substituted with substituent A, or a C1-C6 haloalkyl group.

The term "substituent A" in Formula (1) represents at least one selected from the group consisting of: a hydroxy group, a cyano group, a C3-C8 cycloalkyl group, a C1-C6 alkoxy group, a C1-C6 haloalkoxy group, a C3-C8 cycloalkoxy group, an R12R13N— (wherein R12 and R13 each independently represents a hydrogen atom, a C1-C6 alkyl group, a C1-C6 haloalkyl group or a C3-C8 cycloalkyl group, or R12 and R13 together with the nitrogen atom to which they are bonded form aziridinyl, azetidinyl, pyrrolidinyl, piperidinyl, homopiperidinyl or azocanyl), and an R14-L1- (wherein R14 represents a C1-C6 alkyl group or a C1-C6 haloalkyl group, and L1 represents S, SO or SO$_2$).

In particular, the substituent A is preferably a cyano group, a C1-C6 alkoxy group or an R14-L1- (wherein R14 and L1 are the same as defined hereinabove).

More particularly, substituent A is preferably a cyano group or a C1-C6 alkoxy group.

Preferred specific examples of the substituents A include a hydroxy group; a cyano group;

a C3-C8 cycloalkyl group such as cyclopropyl, cyclobutyl, cyclopentyl and cyclohexyl;

a C1-C6 alkoxy group such as methoxy, ethoxy, propyloxy and isopropyloxy;

a C1-C6 haloalkoxy group such as difluoromethoxy, trifluoromethoxy, 2,2-difluoroethoxy, 2,2,2-trifluoroethoxy, 3,3-difluoropropyloxy and 3,3,3-trifluoropropyloxy;

a C3-C8 cycloalkoxy group such as cyclopropyloxy, cyclobutoxy, cyclopentyloxy and cyclohexyloxy;

an R12R13N— (wherein R12 and R13 are the same as defined hereinabove) such as amino, dimethylamino, ethylmethylamino and diethylamino; and an R14-L1- (wherein R14 and L1 are the same as defined hereinabove) such as methylthio, methanesulfinyl, methanesulfonyl, trifluoromethylthio, trifluoromethanesulfinyl and trifluoromethanesulfonyl.

More preferred specific examples of the substituents A include a hydroxy group; a cyano group;

a C3-C8 cycloalkyl group such as cyclopropyl and cyclobutyl;

a C1-C6 alkoxy group such as methoxy and ethoxy;

a C1-C6 haloalkoxy group such as difluoromethoxy, trifluoromethoxy, 2,2-difluoroethoxy and 2,2,2-trifluoroethoxy;

a C3-C8 cycloalkoxy group such as cyclopropyloxy and cyclobutoxy;

an R12R13N— (wherein R12 and R13 are the same as defined hereinabove) such as dimethylamino, ethylmethylamino and diethylamino; and an R14-L1- (wherein R14 and L1 are the same as defined hereinabove) such as methylthio, methanesulfinyl and methanesulfonyl.

R1 in Formula (1) may represent a hydroxy group or a cyano group.

The C1-C6 alkyl group in the "C1-C6 alkyl group optionally substituted with substituent A" represented by R1 in Formula (1) is the same as defined hereinabove, and is preferably methyl, ethyl, propyl, isopropyl, butyl or isobutyl, and more preferably methyl or ethyl. When the group is substituted with substituent A, any hydrogen atom in the C1-C6 alkyl group is substituted with the substituent A.

The "C1-C6 haloalkyl group" represented by R1 in Formula (1) is the same as defined hereinabove, and is preferably 2-fluoroethyl, 2,2-difluoroethyl, 2,2,2-trifluoroethyl, 3,3-difluoropropyl or 3,3,3-trifluoropropyl, and more preferably 2-fluoroethyl, 2,2-difluoroethyl or 2,2,2-trifluoroethyl.

The C3-C8 cycloalkyl group in the "C3-C8 cycloalkyl group optionally substituted with substituent A" represented by R1 in Formula (1) is the same as defined hereinabove, and is preferably cyclopropyl, cyclobutyl, cyclopentyl or cyclohexyl, and more preferably cyclopropyl or cyclobutyl. When the group is substituted with substituent A, any hydrogen atom in the C3-C8 cycloalkyl group is substituted with the substituent A.

The C2-C6 alkenyl group in the "C2-C6 alkenyl group optionally substituted with substituent A" represented by R1 in Formula (1) is the same as defined hereinabove, and is preferably vinyl, 1-propenyl or allyl, and more preferably vinyl or allyl. When the group is substituted with substituent A, any hydrogen atom in the C2-C6 alkenyl group is substituted with the substituent A.

The "C2-C6 haloalkenyl group" represented by R1 in Formula (1) is the same as defined hereinabove, and is preferably 2-fluorovinyl, 2,2-difluorovinyl, 3-fluoroallyl or 3,3-difluoroallyl, and more preferably 2-fluorovinyl or 2,2-difluorovinyl.

The C2-C6 alkynyl group in the "C2-C6 alkynyl group optionally substituted with substituent A" represented by R1 in Formula (1) is the same as defined hereinabove, and is preferably propargyl, 2-butynyl or 3-butynyl, and more preferably propargyl. When the group is substituted with substituent A, any hydrogen atom in the C2-C6 alkynyl group is substituted with the substituent A.

The "C2-C6 haloalkynyl group" represented by R1 in Formula (1) is the same as defined hereinabove, and is preferably 4,4-difluoro-2-butynyl, 4-chloro-4,4-difluoro-2-butynyl, 4-bromo-4,4-difluoro-2-butynyl or 4,4,4-trifluoro-2-butynyl, and more preferably 4,4-difluoro-2-butynyl or 4,4,4-trifluoro-2-butynyl.

The C1-C6 alkoxy group in the "C1-C6 alkoxy group optionally substituted with substituent A" represented by R1 in Formula (1) is the same as defined hereinabove, and is preferably methoxy, ethoxy, propyloxy, isopropyloxy, butoxy or isobutoxy, and more preferably methoxy or ethoxy. When the group is substituted with substituent A, any hydrogen atom in the C1-C6 alkoxy group is substituted with the substituent A.

The "C1-C6 haloalkoxy group" represented by R1 in Formula (1) is the same as defined hereinabove, and is preferably difluoromethoxy, trifluoromethoxy, 2,2-difluoroethoxy, 2,2,2-trifluoroethoxy, 3,3-difluoropropyloxy or 3,3,3-trifluoropropyloxy, and more preferably difluoromethoxy, trifluoromethoxy, 2,2-difluoroethoxy or 2,2,2-trifluoroethoxy.

The C3-C8 cycloalkoxy group in the "C3-C8 cycloalkoxy group optionally substituted with substituent A" represented by R1 in Formula (1) is the same as defined hereinabove, and is preferably cyclopropyloxy, cyclobutoxy, cyclopentyloxy or cyclohexyloxy, and more preferably cyclopropyloxy or cyclobutoxy. When the group is substituted with substituent A, any hydrogen atom in the C3-C8 cycloalkoxy group is substituted with the substituent A.

The C2-C6 alkenyloxy group in the "C2-C6 alkenyloxy group optionally substituted with substituent A" represented by R1 in Formula (1) is the same as defined hereinabove, and is preferably vinyloxy, 1-propenyloxy or allyloxy, and more preferably vinyloxy. When the group is substituted with substituent A, any hydrogen atom in the C2-C6 alkenyloxy group is substituted with the substituent A.

The "C2-C6 haloalkenyloxy group" represented by R1 in Formula (1) is the same as defined hereinabove, and is preferably 2-fluorovinyloxy, 2,2-difluorovinyloxy, 3-fluoroallyloxy or 3,3-difluoroallyloxy, and more preferably 2-fluorovinyloxy or 2,2-difluorovinyloxy.

The C3-C6 alkynyloxy group in the "C3-C6 alkynyloxy group optionally substituted with substituent A" represented by R1 in Formula (1) is the same as defined hereinabove, and is preferably propargyloxy, 2-butynyloxy or 3-butynyloxy, and more preferably propargyloxy. When the group is substituted with substituent A, for any hydrogen atom in the C3-C6 alkynyloxy group is substituted with the substituent A.

The "C3-C6 haloalkynyloxy group" represented by R1 in Formula (1) is the same as defined hereinabove, and is preferably 4,4-difluoro-2-butynyloxy, 4-chloro-4,4-difluoro-2-butynyloxy, 4-bromo-4,4-difluoro-2-butynyloxy or 4,4,4-trifluoro-2-butynyloxy, and more preferably 4,4-difluoro-2-butynyloxy or 4,4,4-trifluoro-2-butynyloxy.

The C1-C6 alkyl group in the "R10R11N—" (wherein R10 and R11 each independently represents a hydrogen atom or a C1-C6 alkyl group) represented by R1 in Formula (1) is the same as defined hereinabove. The "R10R11N—" may be preferably amino, dimethylamino, ethylmethylamino or diethylamino, and more preferably amino or dimethylamino.

R2 represents a halogen atom, a hydroxy group, a cyano group, a nitro group, a C1-C6 alkyl group optionally substituted with substituent B, a C1-C6 haloalkyl group, a C3-C8 cycloalkyl group optionally substituted with substituent B, a C2-C6 alkenyl group optionally substituted with substituent B, a C2-C6 haloalkenyl group, a C2-C6 alkynyl group optionally substituted with substituent B, a C2-C6 haloalkynyl group, a C1-C6 alkoxy group optionally substituted with substituent B, a C1-C6 haloalkoxy group, a C3-C8 cycloalkoxy group optionally substituted with substituent B, a C2-C6 alkenyloxy group optionally substituted with substituent B, a C2-C6 haloalkenyloxy group, a C3-C6 alkynyloxy group optionally substituted with substituent B, a C3-C6 haloalkynyloxy group, an R20C(=O)— group (wherein R20 is a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or an R21R22N— group (wherein R21 and R22 each independently represents a hydrogen atom, a C1-C6 alkyl group optionally substituted with substituent B1, a C1-C6 haloalkyl group or a C3-C8 cycloalkyl group, or R21 and R22 together with the nitrogen atom to which they are bonded form aziridinyl, azetidinyl, pyrrolidinyl, piperidinyl, homopiperidinyl or azocanyl)), an R20C(=O)O— group (wherein R20 is the same as defined hereinabove), a 3 to 6-membered ring group containing 1 to 2 oxygen atoms, an R23-L2- group (wherein R23 is a C1-C6 alkyl group or a C1-C6 haloalkyl group, and L2 is S, SO or SO$_2$), an R21R22N— group (wherein R21 and R22 are the same as defined hereinabove), or an R24C(=O)N(R25)— group (wherein R24 is a hydrogen atom, a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or an R21R22N— group (wherein R21 and R22 are the same as defined hereinabove), and R25 is a hydrogen atom, a C1-C6 alkyl group optionally substituted with substituent B1, a C1-C6 haloalkyl group or a C3-C8 cycloalkyl group).

In particular, R2 is preferably a halogen atom, a hydroxy group, a cyano group, a C1-C6 alkyl group optionally substituted with substituent B, a C1-C6 haloalkyl group, a C1-C6 alkoxy group optionally substituted with substituent B, a C1-C6 haloalkoxy group, a C3-C8 cycloalkoxy group optionally substituted with substituent B, a C2-C6 alkenyloxy group optionally substituted with substituent B, a C3-C6 alkynyloxy group optionally substituted with substituent B, an R20C(=O)O— group (wherein R20 is the same as defined hereinabove), or an R23-L2- (wherein R23 and L2 are the same as defined hereinabove).

More particularly, R2 is preferably a halogen atom, a C1-C6 alkyl group optionally substituted with substituent B, or a C1-C6 alkoxy group optionally substituted with substituent B.

The "substituent B" in Formula (1) represents at least one selected from the group consisting of: a hydroxy group, a cyano group, a C3-C8 cycloalkyl group, a C1-C6 alkoxy group, a C1-C6 haloalkoxy group, a C3-C8 cycloalkoxy group, a C2-C6 alkoxyalkoxy group, an R21R22N— group (wherein R21 and R22 are the same as defined hereinabove), an R23-L2- group (wherein R23 and L2 are the same as defined hereinabove), an R26R27R28Si— group (wherein R26, R27 and R28 each independently represents a C1-C6 alkyl group), an R26R27R28Si—(CH$_2$)s-O— group (wherein s represents an integer of 1 to 3, and R26, R27 and R28 are the same as defined hereinabove), an R20C(=O)— group (wherein R20 has the same definition as R20 described hereinabove), and a 3 to 6-membered ring group containing 1 to 2 oxygen atoms.

In particular, the substituent B is preferably a cyano group, a C3-C8 cycloalkyl group, a C1-C6 alkoxy group, a C2-C6 alkoxyalkoxy group, an R23-L2- group (wherein R23 and L2 are the same as defined hereinabove), R26R27R28Si— group (wherein R26, R27 and R28 are the same as defined hereinabove), R26R27R28Si—(CH$_2$)s-O— group (wherein s, R26, R27 and R28 are the same as defined hereinabove), R20C(=O)— group (wherein R20 is the same as defined hereinabove), or a 3 to 6-membered ring group containing 1 to 2 oxygen atoms.

More particularly, the substituent B is preferably a cyano group or a C1-C6 alkoxy group.

Preferred specific examples of the substituents B include a hydroxy group; a cyano group;
a C3-C8 cycloalkyl group such as cyclopropyl, cyclobutyl, cyclopentyl and cyclohexyl;
a C1-C6 alkoxy group such as methoxy, ethoxy, propyloxy, isopropyloxy, butoxy and isobutoxy;
a C1-C6 haloalkoxy group such as difluoromethoxy, trifluoromethoxy, 2,2-difluoroethoxy, 2,2,2-trifluoroethoxy, 3,3-difluoropropyloxy and 3,3,3-trifluoropropyloxy;
a C3-C8 cycloalkoxy group such as cyclopropyloxy, cyclobutoxy, cyclopentyloxy and cyclohexyloxy;
a C2-C6 alkoxyalkoxy group such as methoxymethoxy, ethoxymethoxy, methoxyethoxy, ethoxyethoxy and methoxypropyloxy;
an R21R22N— group (wherein R21 and R22 are the same as defined hereinabove) such as amino, dimethylamino, ethylmethylamino, diethylamino, pyrrolidinyl and piperidinyl;
an R23-L2- group (wherein R23 and L2 are the same as defined hereinabove) such as methylthio, methanesulfinyl, methanesulfonyl, trifluoromethylthio, trifluoromethanesulfinyl and trifluoromethanesulfonyl;
an R26R27R28Si— group (wherein R26, R27 and R28 are the same as defined hereinabove) such as trimethylsilyl and triethylsilyl;
an R26R27R28Si—(CH$_2$)s-O— group (wherein s, R26, R27 and R28 are the same as defined hereinabove) such as 2-(trimethylsilyl)ethoxy and 2-(triethylsilyl)ethoxy;
an R20C(=O)— group (wherein R20 is the same as defined hereinabove) such as acetyl, propionyl, difluoroacetyl, trifluoroacetyl, cyclopropanecarbonyl, methoxycarbonyl, ethoxycarbonyl, 2,2-difluoroethoxycarbonyl, 3,3,3-trifluoropropyloxycarbonyl, cyclopropyloxycarbonyl, aminocarbonyl, dimethylaminocarbonyl, ethylmethylaminocarbonyl, diethylaminocarbonyl, pyrrolidinylcarbonyl and piperidinylcarbonyl; and
a 3 to 6-membered ring group containing 1 to 2 oxygen atoms such as oxoranyl, oxanyl, 1,3-dioxoranyl and 1,3-dioxanyl.

More preferred specific examples of the substituents B include a hydroxy group; a cyano group;
a C3-C8 cycloalkyl group such as cyclopropyl and cyclobutyl;
a C1-C6 alkoxy group such as methoxy and ethoxy;
a C1-C6 haloalkoxy group such as difluoromethoxy, trifluoromethoxy, 2,2-difluoroethoxy and 2,2,2-trifluoroethoxy;
a C3-C8 cycloalkoxy group such as cyclopropyloxy and cyclobutoxy;
a C2-C6 alkoxyalkoxy group such as methoxymethoxy, ethoxymethoxy, methoxyethoxy and ethoxyethoxy;
an R21R22N— group (wherein R21 and R22 are the same as defined hereinabove) such as dimethylamino, ethylmethylamino and diethylamino;
an R23-L2- group (wherein R23 and L2 are the same as defined hereinabove) such as methylthio, methanesulfinyl and methanesulfonyl;

an R26R27R28Si— group (wherein R26, R27 and R28 are the same as defined hereinabove) such as trimethylsilyl;

an R26R27R28Si—(CH$_2$)s-O— group (wherein s, R26, R27 and R28 are the same as defined hereinabove) such as 2-(trimethylsilyl)ethoxy;

an R20C(=O)— group (wherein R20 is the same as defined hereinabove) such as acetyl, difluoroacetyl, trifluoroacetyl, methoxycarbonyl, ethoxycarbonyl, aminocarbonyl, dimethylaminocarbonyl, ethylmethylaminocarbonyl and diethylaminocarbonyl; and a 3 to 6-membered ring group containing 1 to 2 oxygen atoms such as 1,3-dioxoranyl and 1,3-dioxanyl.

The "substituent B1" in Formula (1) represents at least one selected from the group consisting of: a cyano group, a C1-C6 alkoxy group, a C1-C6 haloalkoxy group and a C3-C8 cycloalkoxy group. In particular, the substituent B1 is preferably a cyano group or a C1-C6 alkoxy group.

Preferred specific examples of the substituents B1 include a cyano group;

a C1-C6 alkoxy group such as methoxy, ethoxy, propyloxy, isopropyloxy, butoxy and isobutoxy;

a C1-C6 haloalkoxy group such as difluoromethoxy, trifluoromethoxy, 2,2-difluoroethoxy, 2,2,2-trifluoroethoxy, 3,3-difluoropropyloxy and 3,3,3-trifluoropropyloxy; and a C3-C8 cycloalkoxy group such as cyclopropyloxy, cyclobutoxy, cyclopentyloxy and cyclohexyloxy.

More preferred specific examples of the substituents B1 include a cyano group;

a C1-C6 alkoxy group such as methoxy and ethoxy;

a C1-C6 haloalkoxy group such as difluoromethoxy, trifluoromethoxy, 2,2-difluoroethoxy and 2,2,2-trifluoroethoxy; and a C3-C8 cycloalkoxy group such as cyclopropyloxy and cyclobutoxy.

The halogen atom in R2 in Formula (1) is the same as defined hereinabove and is preferably fluorine atom, chlorine atom, bromine atom or iodine atom.

R2 in Formula (1) includes a hydroxyl group, a cyano group and a nitro group.

The C1-C6 alkyl group in the "C1-C6 alkyl group optionally substituted with substituent B" represented by R2 in Formula (1) is the same as defined hereinabove, and is preferably methyl, ethyl, propyl, isopropyl, butyl or isobutyl, and more preferably methyl, ethyl, propyl or isopropyl. When the group is substituted with substituent B, any hydrogen atom in the C1-C6 alkyl group is substituted with the substituent B.

The "C1-C6 haloalkyl group" represented by R2 in Formula (1) is the same as defined hereinabove, and is preferably difluoromethyl, trifluoromethyl, 2,2-difluoroethyl, 2,2,2-trifluoroethyl, 3,3-difluoropropyl or 3,3,3-trifluoropropyl, and more preferably difluoromethyl, trifluoromethyl, 2,2-difluoroethyl or 2,2,2-trifluoroethyl.

The C3-C8 cycloalkyl group in the "C3-C8 cycloalkyl group optionally substituted with substituent B" represented by R2 in Formula (1) is the same as defined hereinabove, and is preferably cyclopropyl, cyclobutyl, cyclopentyl or cyclohexyl, and more preferably cyclopropyl or cyclobutyl. When the group is substituted with substituent B, any hydrogen atom in the C3-C8 cycloalkyl group is substituted with the substituent B.

The C2-C6 alkenyl group in the "C2-C6 alkenyl group optionally substituted with substituent B" represented by R2 in Formula (1) is the same as defined hereinabove, and is preferably vinyl, 1-propenyl, allyl, 1-butenyl, 2-butenyl or 3-butenyl, and more preferably vinyl, 1-propenyl or allyl. When the group is substituted with substituent B, any hydrogen atom in the C2-C6 alkenyl group is substituted with the substituent B.

The "C2-C6 haloalkenyl group" represented by R2 in Formula (1) is the same as defined hereinabove, and is preferably 2-fluorovinyl, 2,2-difluorovinyl, 2,2-dichlorovinyl, 3-fluoroallyl, 3,3-difluoroallyl or 3,3-dichloroallyl, and more preferably 2-fluorovinyl or 2,2-difluorovinyl.

The C2-C6 alkynyl group in the "C2-C6 alkynyl group optionally substituted with substituent B" represented by R2 in Formula (1) is the same as defined hereinabove, and is preferably ethynyl, 1-propynyl, propargyl, 1-butynyl, 2-butynyl or 3-butynyl, and more preferably ethynyl, 1-propynyl or propargyl. When the group is substituted with substituent B, any hydrogen atom in the C2-C6 alkynyl group is substituted with the substituent B.

The "C2-C6 haloalkynyl group" represented by R2 in Formula (1) is the same as defined hereinabove, and is preferably 3,3-difluoro-1-propynyl, 3,3,3-trifluoro-1-propynyl, 4,4-difluoro-1-butynyl, 4,4-difluoro-2-butynyl, 4,4,4-trifluoro-1-butynyl or 4,4,4-trifluoro-2-butynyl, and more preferably 3,3-difluoro-1-propynyl or 3,3,3-trifluoro-1-propynyl.

The C1-C6 alkoxy group in the "C1-C6 alkoxy group optionally substituted with substituent B" represented by R2 in Formula (1) is the same as defined hereinabove, and is preferably methoxy, ethoxy, propyloxy, isopropyloxy, butoxy, isobutoxy or pentyloxy, and more preferably methoxy, ethoxy, propyloxy, isopropyloxy, butoxy or pentyloxy. When the group is substituted with substituent B, any hydrogen atom in the C1-C6 alkoxy group is substituted with the substituent B.

The "C1-C6 haloalkoxy group" represented by R2 in Formula (1) is the same as defined hereinabove, and is preferably difluoromethoxy, trifluoromethoxy, 2,2-difluoroethoxy, 2,2,2-trifluoroethoxy, 3,3-difluoropropyloxy or 3,3,3-trifluoropropyloxy, and more preferably difluoromethoxy, trifluoromethoxy, 2,2-difluoroethoxy or 2,2,2-trifluoroethoxy.

The C3-C8 cycloalkoxy group in the "C3-C8 cycloalkoxy group optionally substituted with substituent B" represented by R2 in Formula (1) is the same as defined hereinabove, and is preferably cyclopropyloxy, cyclobutoxy, cyclopentyloxy or cyclohexyloxy, and more preferably cyclopropyloxy or cyclobutoxy. When the group is substituted with substituent B, any hydrogen atom in the C3-C8 cycloalkoxy group is substituted with the substituent B.

The C2-C6 alkenyloxy group in the "C2-C6 alkenyloxy group optionally substituted with substituent B" represented by R2 in Formula (1) is the same as defined hereinabove, and is preferably vinyloxy, 1-propenyloxy, allyloxy, 1-butenyloxy, 2-butenyloxy or 3-butenyloxy, and more preferably vinyloxy, 1-propenyloxy or allyloxy. When the group is substituted with substituent B, any hydrogen atom in the C2-C6 alkenyloxy group is substituted with the substituent B.

The "C2-C6 haloalkenyloxy group" represented by R2 in Formula (1) is the same as defined hereinabove, and is preferably 2-fluorovinyloxy, 2,2-difluorovinyloxy, 2,2-dichlorovinyloxy, 3-fluoroallyloxy, 3,3-difluoroallyloxy or 3,3-dichloroallyloxy, and more preferably 2-fluorovinyloxy or 2,2-difluorovinyloxy.

The C3-C6 alkynyloxy group in the "C3-C6 alkynyloxy group optionally substituted with substituent B" represented by R2 in Formula (1) is the same as defined hereinabove, and is preferably propargyloxy, 2-butynyloxy or 3-butynyloxy, and more preferably propargyloxy. When the group is substituted with substituent B, any hydrogen atom in the C3-C6 alkynyloxy group is substituted with the substituent B.

The "C3-C6 haloalkynyloxy group" represented by R2 in Formula (1) is the same as defined hereinabove, and is preferably 4,4-difluoro-2-butynyloxy, 4-chloro-4,4-difluoro-2-butynyloxy, 4-bromo-4,4-difluoro-2-butynyloxy or 4,4,4-trifluoro-2-butynyloxy, and more preferably 4,4-difluoro-2-butynyloxy or 4,4,4-trifluoro-2-butynyloxy.

The definitions for "R20C(=O)—" group (wherein R20 represents a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or an R21R22N— group (wherein R21 and R22 each independently represents a hydrogen atom, a C1-C6 alkyl group optionally substituted with substituent B1, a C1-C6 haloalkyl group or a C3-C8 cycloalkyl group, or R21 and R22 together with the nitrogen atom to which they are bonded form aziridinyl, azetidinyl, pyrrolidinyl, piperidinyl, homopiperidinyl or azocanyl)) represented by R2 in Formula (1) are the same as described hereinabove. Examples of the "R20C(=O)— group" preferably include acetyl, propionyl, difluoroacetyl, trifluoroacetyl, cyclopropanecarbonyl, methoxycarbonyl, ethoxycarbonyl, 2,2-difluoroethoxycarbonyl, 2,2,2-trifluoroethoxycarbonyl, cyclopropyloxycarbonyl, aminocarbonyl, dimethylaminocarbonyl, ethylmethylaminocarbonyl, diethylaminocarbonyl, pyrrolidinylcarbonyl and piperidinylcarbonyl, and more preferably include acetyl, difluoroacetyl, trifluoroacetyl, methoxycarbonyl, ethoxycarbonyl, aminocarbonyl, dimethylaminocarbonyl, ethylmethylaminocarbonyl and diethylaminocarbonyl.

R20 in "R20C(=O)O— group" represented by R2 in Formula (1) is the same as defined hereinabove. Examples of the "R20C(=O)O— group" preferably include acetyloxy, propionyloxy, difluoroacetyloxy, trifluoroacetyloxy, cyclopropanecarbonyloxy, methoxycarbonyloxy, ethoxycarbonyloxy, 2,2-difluoroethoxycarbonyloxy, 2,2,2-trifluoroethoxycarbonyloxy, cyclopropyloxycarbonyloxy, aminocarbonyloxy, dimethylaminocarbonyloxy, ethylmethylaminocarbonyloxy, diethylaminocarbonyloxy, pyrrolidinylcarbonyloxy and piperidinylcarbonyloxy, and more preferably include acetyloxy, difluoroacetyloxy, trifluoroacetyloxy, methoxycarbonyloxy, ethoxycarbonyloxy, aminocarbonyloxy, dimethylaminocarbonyloxy, ethylmethylaminocarbonyloxy and diethylaminocarbonyloxy.

The "3 to 6-membered ring group containing 1 to 2 oxygen atoms" represented by R2 in Formula (1) is the same as defined hereinabove, and is preferably oxoranyl, oxanyl, 1,3-dioxoranyl or 1,3-dioxanyl, and more preferably 1,3-dioxoranyl or 1,3-dioxanyl.

The definitions for "R23-L2- group" (wherein R23 represents a C1-C6 alkyl group or a C1-C6 haloalkyl group, and L2 represents S, SO or SO$_2$) represented by R2 in Formula (1) are the same as described hereinabove. Examples of the "R23-L2- group" preferably include methylthio, methanesulfinyl, methanesulfonyl, trifluoromethylthio, trifluoromethanesulfinyl, trifluoromethanesulfonyl, (chloromethyl)thio, (chloromethane)sulfinyl or (chloromethane)sulfonyl, and more preferably include methylthio, methanesulfinyl, methanesulfonyl, (chloromethyl)thio, (chloromethane)sulfinyl and (chloromethane)sulfonyl.

R21 and R22 in the "R21R22N— group" represented by R2 in Formula (1) are the same as defined hereinabove. Examples of the "R21R22N— group" preferably include amino, dimethylamino, ethylmethylamino, diethylamino, pyrrolidinyl and piperidinyl, and more preferably include dimethylamino, ethylmethylamino and diethylamino.

The definitions for "R24C(=O)N(R25)— group" (wherein R24 represents a hydrogen atom, a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or an R21R22N— group (wherein R21 and R22 are the same as defined hereinabove), and R25 represents a hydrogen atom, a C1-C6 alkyl group optionally substituted with substituent B1, a C1-C6 haloalkyl group or a C3-C8 cycloalkyl group) represented by R2 in Formula (1) are the same as described hereinabove. Examples of R24 preferably include a hydrogen atom, methyl, ethyl, difluoromethyl, trifluoromethyl, cyclopropyl, methoxy, ethoxy, 2,2-difluoroethoxy, 2,2,2-trifluoroethoxy, cyclopropyloxy, amino, dimethylamino, ethylmethylamino, diethylamino, pyrrolidinyl and piperidinyl, and more preferably include a hydrogen atom, methyl, difluoromethyl, trifluoromethyl, methoxy, ethoxy, amino, dimethylamino, ethylmethylamino and diethylamino. Examples of R25 include preferably a hydrogen atom, methyl, ethyl, propyl, methoxymethyl, ethoxymethyl, methoxyethyl, ethoxyethyl, cyanomethyl, 2-cyanoethyl, 2,2-difluoroethyl, 2,2,2-trifluoroethyl and cyclopropyl, and more preferably a hydrogen atom, methyl, ethyl, methoxymethyl, ethoxymethyl, methoxyethyl, ethoxyethyl, cyanomethyl, 2,2-difluoroethyl and 2,2,2-trifluoroethyl.

The letter n in Formula (1) is an integer of 0 to 5. When n is 2 or greater, the two or more R2 represent independent substituents which may be the same or different from one another and are selected appropriately.

R3 in Formula (1) represents a hydrogen atom, a halogen atom, a nitro group, a C1-C6 alkyl group optionally substituted with substituent C, a C1-C6 haloalkyl group, a C3-C8 cycloalkyl group optionally substituted with substituent C, a C1-C6 alkoxy group optionally substituted with substituent C, a C1-C6 haloalkoxy group, a C2-C6 alkenyl group optionally substituted with substituent C, a C2-C6 haloalkenyl group, a C2-C6 alkynyl group optionally substituted with substituent C, a C2-C6 haloalkynyl group, an R30-L3- group (wherein R30 has the same definition as R23, and L3 has the same definition as L2), an R31R32N— group (wherein R31 and R32 have the same definition as R21 and R22), or an R33C(=O)— group (wherein R33 represents a C1-C6 alkyl group, a C1-C6 haloalkyl group or a C3-C8 cycloalkyl group).

In particular, R3 is preferably a hydrogen atom, a halogen atom, a C1-C6 alkyl group optionally substituted with substituent C, a C3-C8 cycloalkyl group optionally substituted with substituent C, a C1-C6 alkoxy group optionally substituted with substituent C, a C2-C6 alkynyl group optionally substituted with substituent C, or an R30-L3- group (wherein R30 and L3 are the same as defined hereinabove).

More particularly, R3 is preferably a hydrogen atom, a halogen atom or a C1-C6 alkyl group optionally substituted with substituent C.

The "substituent C" in Formula (1) represents at least one selected from the group consisting of: a hydroxy group, a cyano group, a C3-C8 cycloalkyl group, a C1-C6 alkoxy group, a C1-C6 haloalkoxy group, a C3-C8 cycloalkoxy group, an R31R32N— group (wherein R31 and R32 have the same definition as R21 and R22), and an R30-L3- group (wherein R30 has the same definition as R14, and L3 has the same definition as L1). In particular, the substituent C is preferably a cyano group, a C1-C6 alkoxy group or an R30-L3- group (wherein R30 and L3 are the same as defined hereinabove).

More particularly, the substituent C is preferably a cyano group or a C1-C6 alkoxy group.

Preferred specific examples of the substituents C include a hydroxy group; a cyano group;

a C3-C8 cycloalkyl group such as cyclopropyl, cyclobutyl, cyclopentyl and cyclohexyl;

a C1-C6 alkoxy group such as methoxy, ethoxy, propyloxy, isopropyloxy, butoxy and isobutoxy;

a C1-C6 haloalkoxy group such as difluoromethoxy, trifluoromethoxy, 2,2-difluoroethoxy, 2,2,2-trifluoroethoxy, 3,3-difluoropropyloxy and 3,3,3-trifluoropropyloxy;

a C3-C8 cycloalkoxy group such as cyclopropyloxy, cyclobutoxy, cyclopentyloxy and cyclohexyloxy;

an R31R32N— group (wherein R31 and R32 have the same definition as R21 and R22) such as amino, dimethylamino, ethylmethylamino, diethylamino, pyrrolidinyl and piperidinyl; and an R30-L3- group (wherein R30 has the same definition as R14, and L3 has the same definition as L1) such as methylthio, methanesulfinyl, methanesulfonyl, trifluoromethylthio, trifluoromethanesulfinyl and trifluoromethanesulfonyl.

More preferred specific examples of the substituents C include a hydroxy group; a cyano group;

a C3-C8 cycloalkyl group such as cyclopropyl and cyclobutyl;

a C1-C6 alkoxy group such as methoxy and ethoxy;

a C1-C6 haloalkoxy group such as difluoromethoxy, trifluoromethoxy, 2,2-difluoroethoxy and 2,2,2-trifluoroethoxy;

a C3-C8 cycloalkoxy group such as cyclopropyloxy and cyclobutoxy;

an R31R32N— group (wherein R31 and R32 are the same as defined hereinabove) such as dimethylamino, ethylmethylamino and diethylamino; and an R30-L3- group (wherein R30 and L3 are the same as defined hereinabove) such as methylthio, methanesulfinyl and methanesulfonyl.

The R3 in Formula (1) includes a hydrogen atom and nitro group.

The "halogen atom" in R3 in Formula (1) is the same as defined hereinabove and is preferably fluorine atom, chlorine atom, bromine atom or iodine atom.

The C1-C6 alkyl group in the "C1-C6 alkyl group optionally substituted with substituent C" represented by R3 in Formula (1) is the same as defined hereinabove, and is preferably methyl, ethyl, propyl, isopropyl, butyl or isobutyl, and more preferably methyl, ethyl or propyl. When the group is substituted with substituent C, any hydrogen atom in the C1-C6 alkyl group is substituted with the substituent C.

The "C1-C6 haloalkyl group" represented by R3 in Formula (1) is the same as defined hereinabove, and is preferably difluoromethyl, trifluoromethyl, 2,2-difluoroethyl, 2,2,2-trifluoroethyl, 3,3-difluoropropyl or 3,3,3-trifluoropropyl, and more preferably difluoromethyl, trifluoromethyl, 2,2-difluoroethyl or 2,2,2-trifluoroethyl.

The C3-C8 cycloalkyl group in the "C3-C8 cycloalkyl group optionally substituted with substituent C" represented by R3 in Formula (1) is the same as defined hereinabove, and is preferably cyclopropyl, cyclobutyl, cyclopentyl or cyclohexyl, and more preferably cyclopropyl or cyclobutyl. When the group is substituted with substituent C, any hydrogen atom in the C3-C8 cycloalkyl group is substituted with the substituent C.

The C1-C6 alkoxy group in the "C1-C6 alkoxy group optionally substituted with substituent C" represented by R3 in Formula (1) is the same as defined hereinabove, and is preferably methoxy, ethoxy, propyloxy, isopropyloxy, butoxy or isobutoxy, and more preferably methoxy, ethoxy, propyloxy or isopropyloxy. When the group is substituted with substituent C, any hydrogen atom in the C1-C6 alkoxy group is substituted with the substituent C.

The "C1-C6 haloalkoxy group" represented by R3 in Formula (1) is the same as defined hereinabove, and is preferably difluoromethoxy, trifluoromethoxy, 2,2-difluoroethoxy, 2,2,2-trifluoroethoxy, 3,3-difluoropropyloxy or 3,3,3-trifluoropropyloxy, and more preferably difluoromethoxy, trifluoromethoxy, 2,2-difluoroethoxy or 2,2,2-trifluoroethoxy.

The C2-C6 alkenyl group in the "C2-C6 alkenyl group optionally substituted with substituent C" represented by R3 in Formula (1) is the same as defined hereinabove, and is preferably vinyl, 1-propenyl, allyl, 1-butenyl, 2-butenyl or 3-butenyl, and more preferably vinyl, 1-propenyl or allyl. When the group is substituted with substituent C, any hydrogen atom in the C2-C6 alkenyl group is substituted with the substituent C.

The "C2-C6 haloalkenyl group" represented by R3 in Formula (1) is the same as defined hereinabove, and is preferably 2-fluorovinyl, 2,2-difluorovinyl, 2,2-dichlorovinyl, 3-fluoroallyl, 3,3-difluoroallyl or 3,3-dichloroallyl, and more preferably 2-fluorovinyl or 2,2-difluorovinyl.

The C2-C6 alkynyl group in the "C2-C6 alkynyl group optionally substituted with substituent C" represented by R3 in Formula (1) is the same as defined hereinabove, and is preferably ethynyl, 1-propynyl, propargyl, 1-butynyl, 2-butynyl or 3-butynyl, and more preferably ethynyl, 1-propynyl or propargyl. When the group is substituted with substituent C, any hydrogen atom in the C2-C6 alkynyl group is substituted with the substituent C.

The "C2-C6 haloalkynyl group" represented by R3 in Formula (1) is the same as defined hereinabove, and is preferably 3,3-difluoro-1-propynyl, 3,3,3-trifluoro-1-propynyl, 4,4-difluoro-1-butynyl, 4,4-difluoro-2-butynyl, 4,4,4-trifluoro-1-butynyl or 4,4,4-trifluoro-2-butynyl, and more preferably 3,3-difluoro-1-propynyl or 3,3,3-trifluoro-1-propynyl.

As for "R30-L3-" represented by R3 in Formula (1), R30 has the same definition as R23, and L3 has the same definition as L2. Examples of the "R30-L3-" is preferably methylthio, methanesulfinyl, methanesulfonyl, trifluoromethylthio, trifluoromethanesulfinyl and trifluoromethanesulfonyl, and more preferably methylthio, methanesulfinyl and methanesulfonyl.

R31 and R32 in the "R31R32N—" represented by R3 in Formula (1) have the same definition as R21 and R22, and is preferably an amino, dimethylamino, ethylmethylamino, diethylamino, pyrrolidinyl or piperidinyl, and more preferably dimethylamino, ethylmethylamino or diethylamino.

The definitions for "R33C(=O)— group" (wherein R33 represents a C1-C6 alkyl group, a C1-C6 haloalkyl group or a C3-C8 cycloalkyl group) represented by R3 in Formula (1) are the same as described hereinabove. The "R33C(=O)— group" is preferably acetyl, propionyl, difluoroacetyl, trifluoroacetyl and cyclopropanecarbonyl, and more preferably acetyl, difluoroacetyl and trifluoroacetyl.

X in Formula (1) represents an oxygen atom or a sulfur atom. Preferably, X is an oxygen atom.

Y in Formula (1) represents phenyl, pyridyl, pyridazinyl, pyrimidinyl, pyrazinyl, triazinyl, tetrazinyl, thienyl, thiazolyl, isothiazolyl or thiadiazolyl.

The phenyl is substituted with substituent D at an ortho position and is optionally further substituted with 0 to 4 independent substituents D1.

The pyridyl, the pyridazinyl, the pyrimidinyl, the pyrazinyl, the triazinyl or the tetrazinyl is substituted with substituent D at an ortho position and is optionally further substituted with 0 to 3 independent substituents D1.

The thienyl, the thiazolyl, the isothiazolyl or the thiadiazolyl is substituted with substituent D at an ortho position and is optionally further substituted with 0 to 2 independent substituents D1.

The "substituent D" in Formula (1) represents at least one selected from the group consisting of: a halogen atom, a C1-C6 alkyl group, a C1-C6 haloalkyl group, a C1-C6 alkoxy group and a C1-C6 haloalkoxy group.

In particular, the substituent D is preferably a halogen atom or a C1-C6 alkyl group More particularly, the substituent D is preferably a halogen atom.

Preferred specific examples of the substituents D include:

a halogen atom such as fluorine atom, chlorine atom, bromine atom and iodine atom;

a C1-C6 alkyl group such as methyl, ethyl and propyl;

a C1-C6 haloalkyl group such as difluoromethyl, trifluoromethyl, 2,2-difluoroethyl and 2,2,2-trifluoroethyl;

a C1-C6 alkoxy group such as methoxy, ethoxy, propyloxy, isopropyloxy, butoxy, isobutoxy and t-butoxy; and a C1-C6 haloalkoxy group such as difluoromethoxy, trifluoromethoxy, 2,2-difluoroethoxy, 2,2,2-trifluoroethoxy, 3,3-difluoropropyloxy and 3,3,3-trifluoropropyloxy.

More preferred specific examples of the substituents D include:

a halogen atom such as fluorine atom, chlorine atom and bromine atom;

a C1-C6 alkyl group such as methyl and ethyl;

a C1-C6 alkoxy group such as methoxy, ethoxy, propyloxy and isopropyloxy; and a C1-C6 haloalkoxy group such as difluoromethoxy, trifluoromethoxy, 2,2-difluoroethoxy and 2,2,2-trifluoroethoxy.

The "substituent D1" in Formula (1) represents at least one selected from the group consisting of: a hydroxy group, a halogen atom, a C1-C6 alkyl group, a C1-C6 haloalkyl group, a C3-C8 cycloalkyl group, a C1-C6 alkoxy group, a C1-C6 haloalkoxy group and a C3-C8 cycloalkoxy group.

In particular, the substituent D1 is preferably a hydroxy group, a halogen atom, a C1-C6 alkyl group, a C1-C6 alkoxy group or a C1-C6 haloalkyl group, and more preferably a halogen atom, a C1-C6 alkyl group, a C1-C6 alkoxy group or a C1-C6 haloalkoxy group.

Preferred specific examples of the substituents D1 include a hydroxy group;

a halogen atom such as fluorine atom, chlorine atom, bromine atom and iodine atom;

a C1-C6 alkyl group such as methyl, ethyl and propyl;

a C1-C6 haloalkyl group such as difluoromethyl, trifluoromethyl, 2,2-difluoroethyl and 2,2,2-trifluoroethyl;

a C3-C8 cycloalkyl group such as cyclopropyl, cyclobutyl, cyclopentyl and cyclohexyl;

a C1-C6 alkoxy group such as methoxy, ethoxy, propyloxy, isopropyloxy, butoxy, isobutoxy and t-butoxy;

a C1-C6 haloalkoxy group such as difluoromethoxy, trifluoromethoxy, 2,2-difluoroethoxy, 2,2,2-trifluoroethoxy, 3,3-difluoropropyloxy and 3,3,3-trifluoropropyloxy; and a C3-C8 cycloalkoxy group such as cyclopropyloxy, cyclobutoxy, cyclopentyloxy and cyclohexyloxy.

More preferred specific examples of the substituents D1 include a hydroxy group;

a halogen atom such as fluorine atom, chlorine atom and bromine atom;

a C1-C6 alkyl group such as methyl and ethyl;

a C1-C6 haloalkyl group such as difluoromethyl and trifluoromethyl;

a C3-C8 cycloalkyl group such as cyclopropyl and cyclobutyl;

a C1-C6 alkoxy group such as methoxy, ethoxy, propyloxy and isopropyloxy;

a C1-C6 haloalkoxy group such as difluoromethoxy, trifluoromethoxy, 2,2-difluoroethoxy and 2,2,2-trifluoroethoxy; and a C3-C8 cycloalkoxy group such as cyclopropyloxy and cyclobutoxy.

The specific examples of Y in Formula (1) is hereinbelow described in detail.

A) When Y is phenyl, Y indicates a partial structure represented by Formula (a):

[Chem.3]

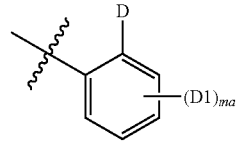

(a)

wherein D and D1 are the same as defined hereinabove, and ma represents an integer of 0 to 4.

The letter ma in Formula (a) represents an integer of 0 to 4.

When ma in Formula (a) is 2 or greater, the two or more D1 represent independent substituents which may be the same or different from one another and may be selected appropriately.

In the specification, when Y is phenyl, the ortho position indicates the position in the phenyl at which the substituent D substitutes as illustrated in Formula (a).

The phenyl having the substituent D at the ortho position satisfies the characteristics of the invention.

Some preferred combinations represented by Formula (a) are 2-D-6-D1-phenyl, 2-D-4-D1-phenyl and 2-D-4-D1-6-D1-phenyl. For example, "2-D-6-D1-phenyl" indicates a disubstituted phenyl having substituent D at the 2-position and substituent D1 at the 6-position. The same applies hereinafter.

B) When Y is pyridyl, pyridazinyl, pyrimidinyl, pyrazinyl, triazinyl or tetrazinyl, Y indicates a partial structure represented by Formula (b):

[Chem. 4]

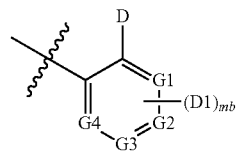

(b)

wherein D and D1 are the same as defined hereinabove, and mb is an integer of 0 to 3.

G1, G2, G3 and G4 in Formula (b) each independently represents a carbon atom or a nitrogen atom. At least one of G1, G2, G3 and G4 is a nitrogen atom. Preferably, any one of G1, G2, G3 and G4 is a nitrogen atom, i.e. the structure is pyridyl.

The letter mb in Formula (b) represents an integer of 0 to 3.

When mb in Formula (b) is 2 or greater, the two or more D1 represent independent substituents which may be the same or different from one another and may be selected appropriately.

In the specification, when Y is pyridyl, pyridazinyl, pyrimidinyl, pyrazinyl, triazinyl or tetrazinyl, the ortho position indicates the position in the 6-membered ring at which the substituent D substitutes as illustrated in Formula (b).

Specific examples of the partial structures of Formula (b) are illustrated below.

[Chem. 5]

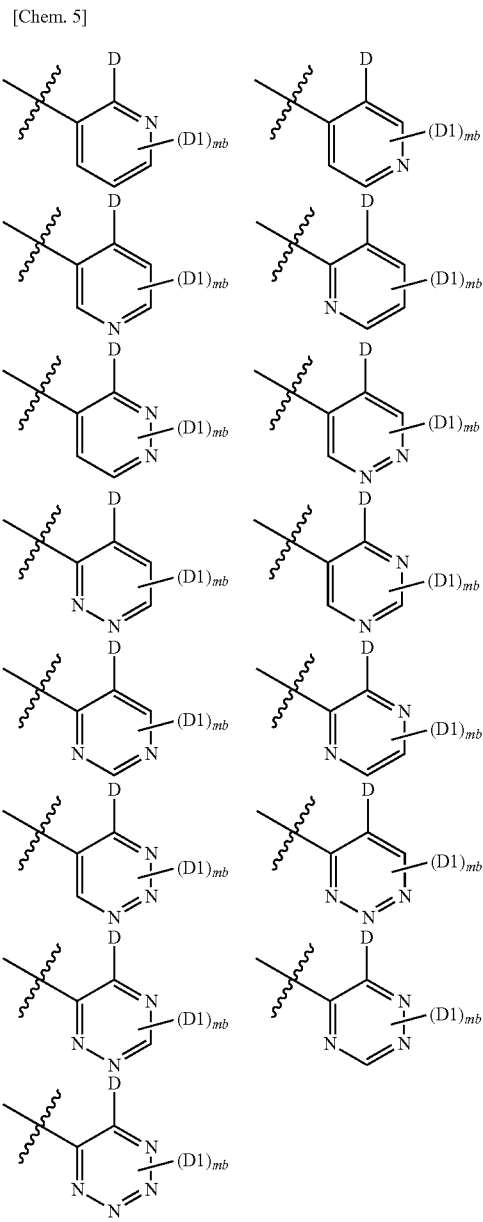

The pyridyl, the pyridazinyl, the pyrimidinyl, the pyrazinyl, the triazinyl or the tetrazinyl having the substituent D at the ortho position satisfies the characteristics of the invention.

Some preferred combinations represented by Formula (b) are 3-D-2-pyridyl, 3-D-5-D1-2-pyridyl, 2-D-3-pyridyl, 2-D-4-D1-3-pyridyl, 2-D-6-D1-3-pyridyl, 2-D-4-D1-6-D1-3-pyridyl, 4-D-3-pyridyl, 4-D-2-D1-3-pyridyl, 4-D-6-D1-3-pyridyl, 4-D-2-D1-6-D1-3-pyridyl, 3-D-4-pyridyl and 3-D-5-D1-4-pyridyl.

C) When Y is thienyl, thiazolyl, isothiazolyl or thiadiazolyl, Y indicates a partial structure represented by Formula (c-1):

[Chem. 6]

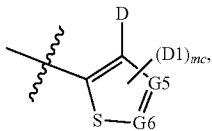

(c-1)

Formula (c-2):

[Chem. 7]

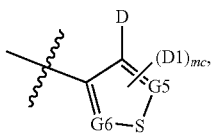

(c-2)

or
Formula (c-3):

[Chem. 8]

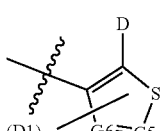

(c-3)

wherein D and D1 are the same as defined hereinabove, and mc is an integer of 0 to 2.

G5 and G6 in Formula (c-1), Formula (c-2) and Formula (c-3) each independently represents a carbon atom or a nitrogen atom.

The letter mc in Formula (c-1), Formula (c-2) and Formula (c-3) represents an integer of 0 to 2.

When mc in Formula (c-1), Formula (c-2) and Formula (c-3) is 2, the two D1 represent independent substituents which may be the same or different from each other and may be selected appropriately.

In the specification, when Y is thienyl, thiazolyl, isothiazolyl or thiadiazolyl, the ortho position indicates the position in the 5-membered ring at which the substituent D substitutes as illustrated in Formula (c-1), Formula (c-2) and Formula (c-3).

Specific examples of the partial structures of Formula (c-1) are illustrated below.

[Chem. 9]

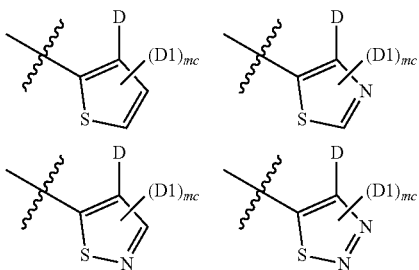

Specific examples of the partial structures of Formula (c-2) are illustrated below.

[Chem. 10]

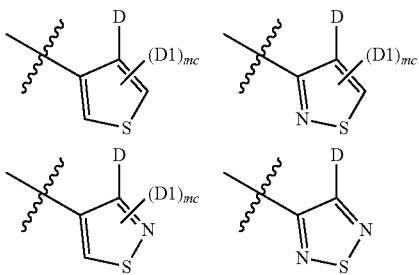

Specific examples of the substituents forming the partial structures of Formula (c-3) are illustrated below.

[Chem. 11]

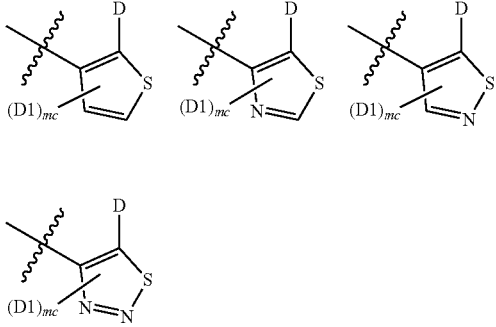

The thienyl, the thiazolyl, the isothiazolyl or the thiadiazolyl having the substituent D at the ortho position satisfies the characteristics of the invention.

Formula (1) includes a bond indicated with a broken line, as represented by:

[Chem. 12]

=
----

The bond indicated with a broken line in Formula (1) represents a double bond or a single bond.

When the bond indicated with a broken line in Formula (1) is a double bond, the compound or a salt thereof is represented by Formula (1a):

[Chem. 13]

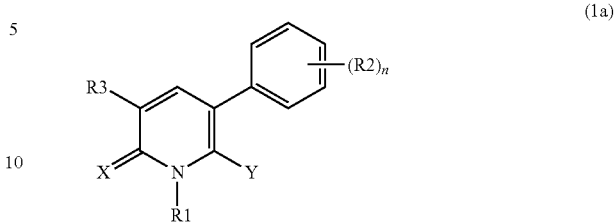

(1a)

In the formula, R1, R2, R3, X, Y and n are the same as defined in Formula (1).

When the bond indicated with a broken line in Formula (1) is a single bond, the compound or a salt thereof is represented by Formula (1b):

[Chem. 14]

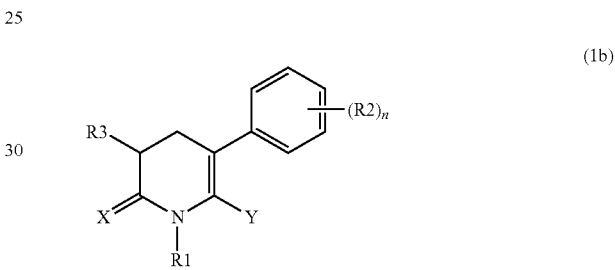

(1b)

In the formula, R1, R2, R3, X, Y and n are the same as defined in Formula (1).

When R3 in Formula (1b) is a substituent other than hydrogen, the compound is either the R-isomer or the S-isomer, or a mixture of the R-isomer and the S-isomer in an appropriate ratio.

The compound of Formula (1) may have one or two chiral axes. In this case, the compound is a single isomer or a mixture of isomers in an appropriate ratio without limitation.

The compound of Formula (1) may have a chiral atom. In this case, the compound is a single isomer or a mixture of isomers in an appropriate ratio without limitation.

The compound of Formula (1) may have geometric isomeric forms. In this case, the compound is a single isomer or a mixture of isomers in an appropriate ratio without limitation.

The compounds of Formula (1) can form salts. Although examples for such salts include acid salts such as those of hydrochloric acid, sulfuric acid, acetic acid, fumaric acid or maleic acid, and metal salts such as those of sodium, potassium or calcium, the salts are not particularly limited as long as they can be used as parasitic pest control agents.

The specific compounds of the present invention are shown by combinations of the structural formulae depicted in Table 1, (R2)n described in Table 2 and an oxygen atom or sulfur atom represented by X. The compounds are only illustrative and the scope of the invention is not limited to such compounds.

TABLE 1
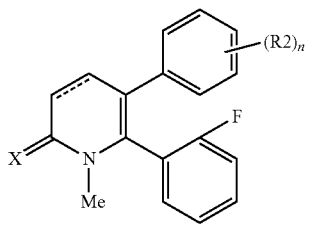 P-1
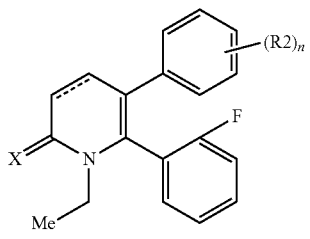 P-2
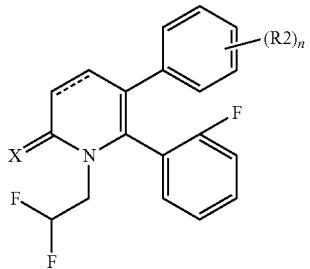 P-3
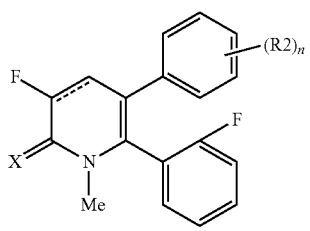 P-4
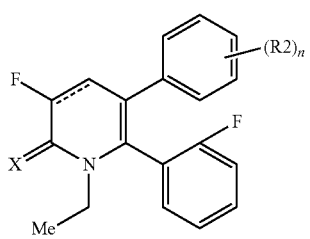 P-5
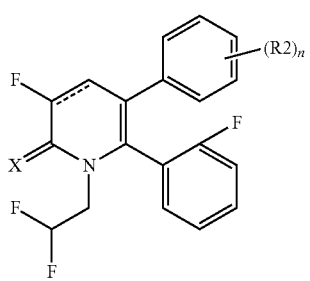 P-6
TABLE 1-continued
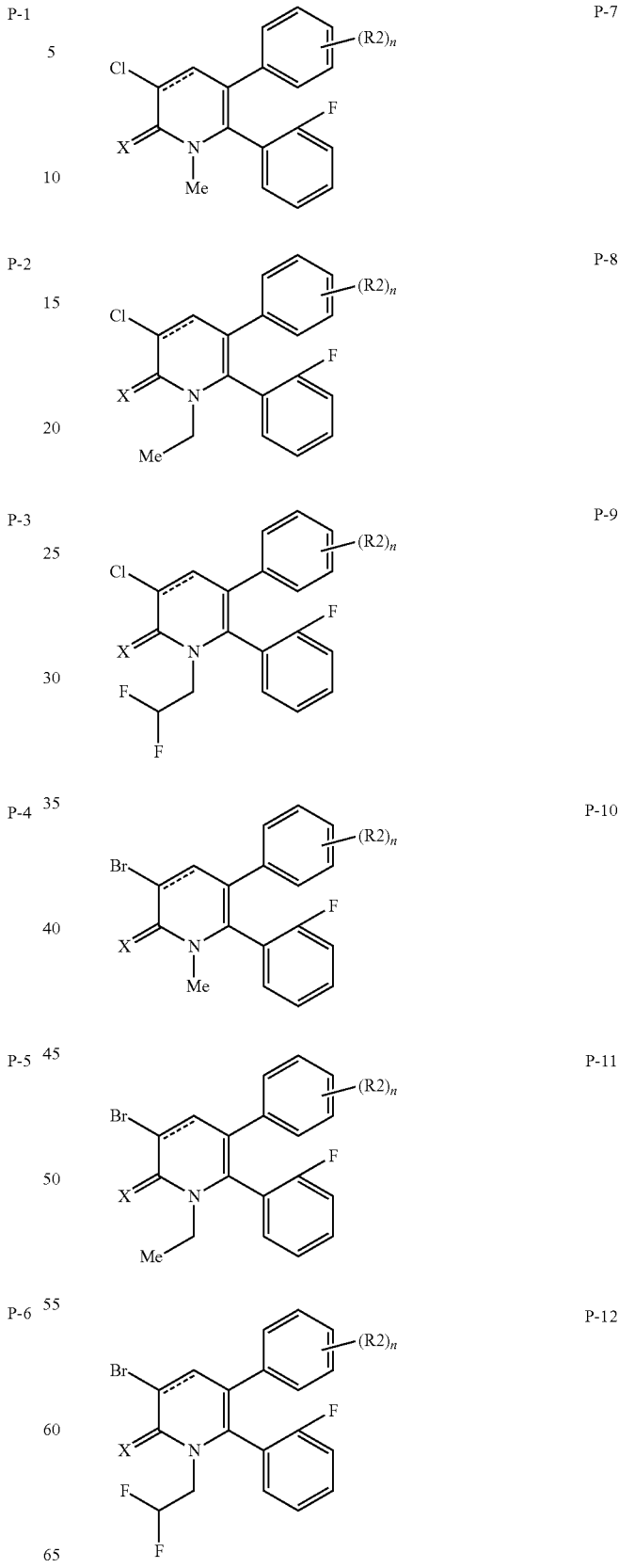

TABLE 1-continued
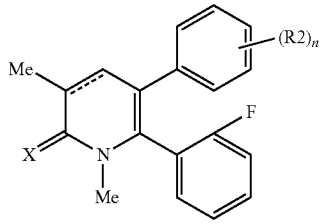 P-13
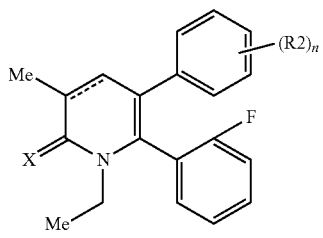 P-14
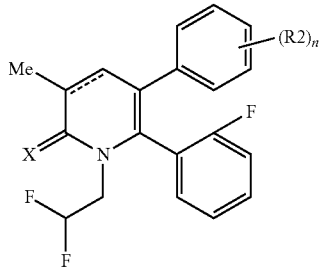 P-15
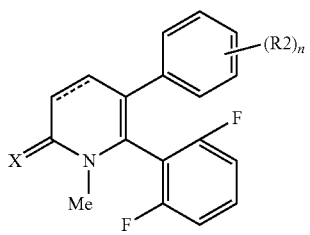 P-16
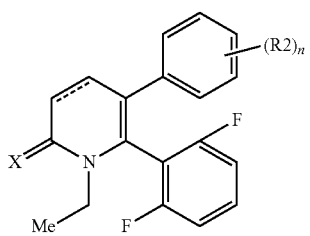 P-17
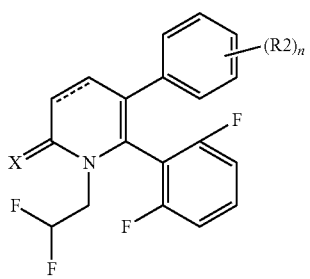 P-18
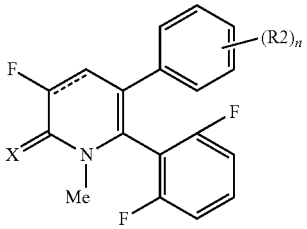 P-19
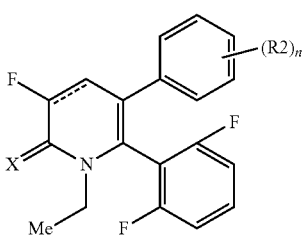 P-20
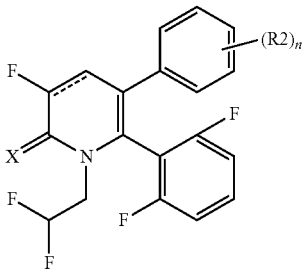 P-21
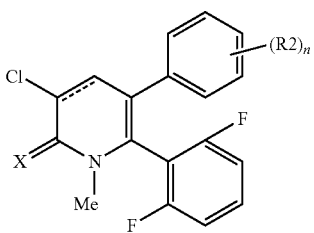 P-22
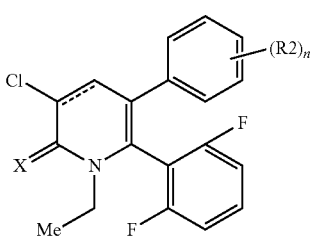 P-23
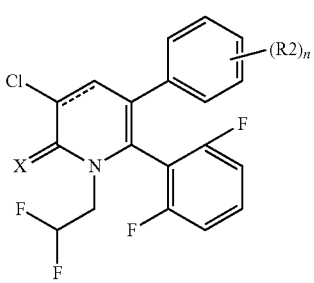 P-24

TABLE 1-continued
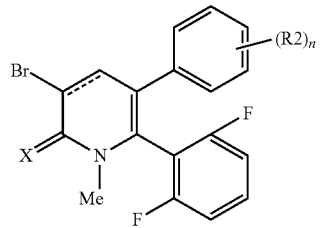 P-25
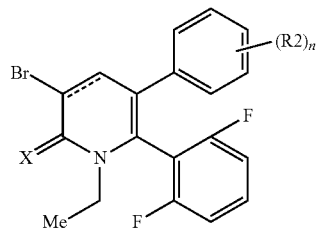 P-26
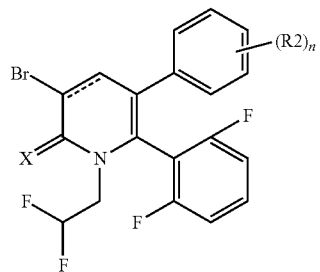 P-27
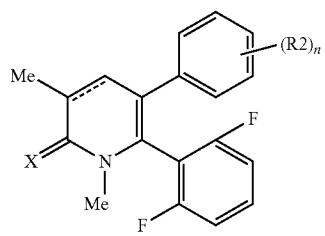 P-28
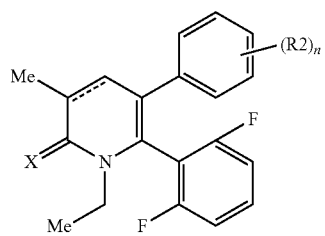 P-29
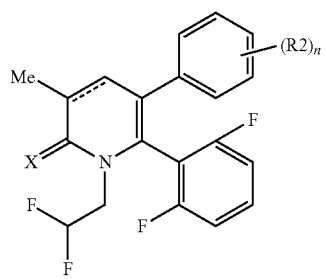 P-30
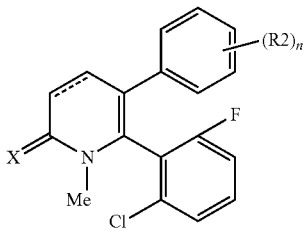 P-31
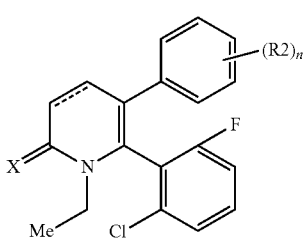 P-32
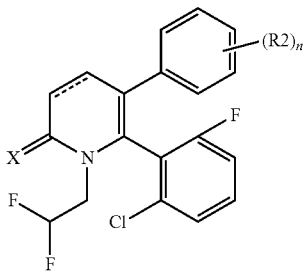 P-33
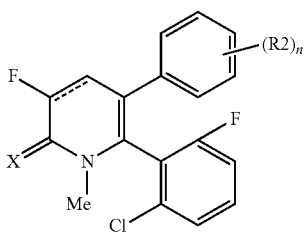 P-34
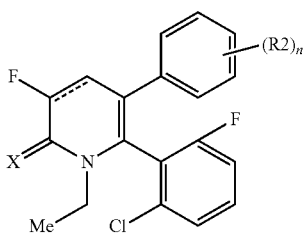 P-35
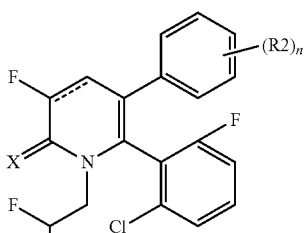 P-36

TABLE 1-continued
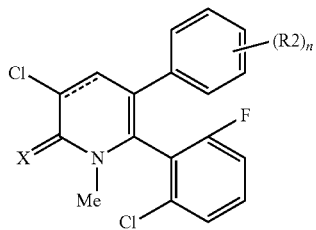 P-37
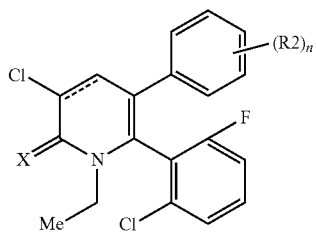 P-38
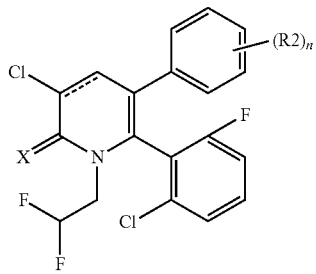 P-39
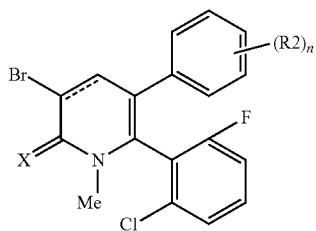 P-40
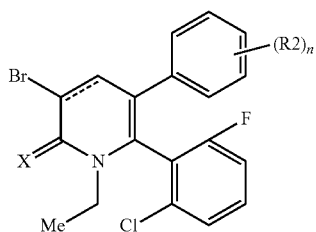 P-41
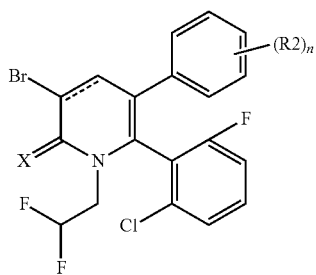 P-42
TABLE 1-continued
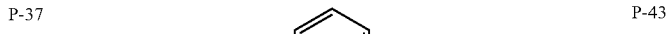 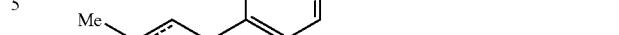 P-43
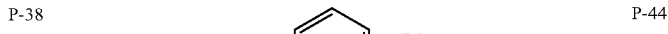 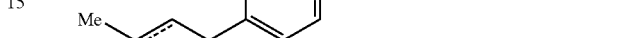 P-44
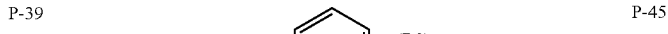 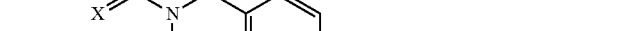 P-45
 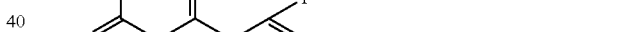 P-46
 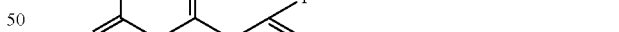 P-47
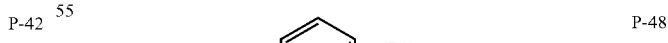  P-48
 

TABLE 1-continued
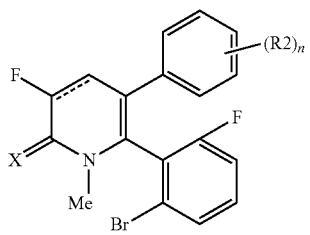 P-49
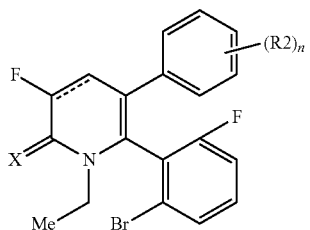 P-50
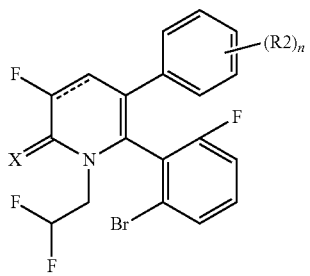 P-51
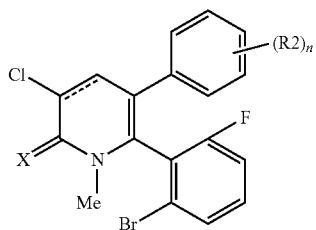 P-52
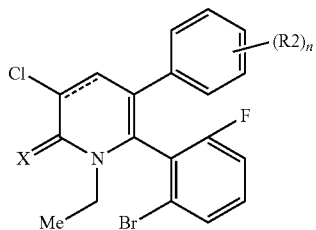 P-53
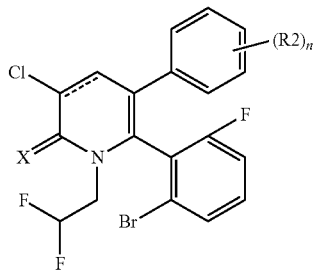 P-54
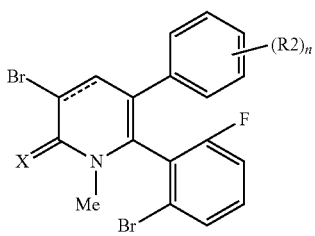 P-55
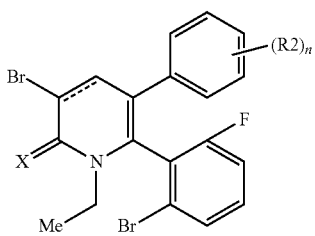 P-56
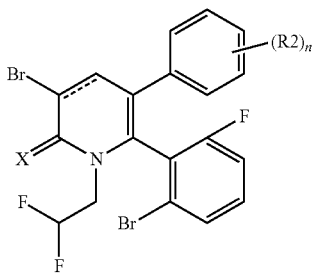 P-57
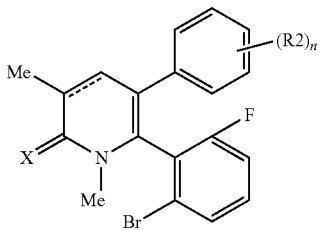 P-58
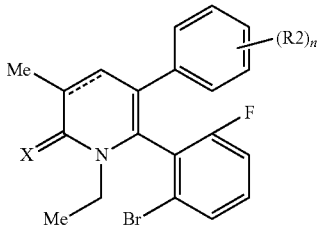 P-59
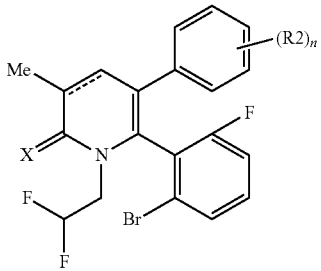 P-60

TABLE 1-continued
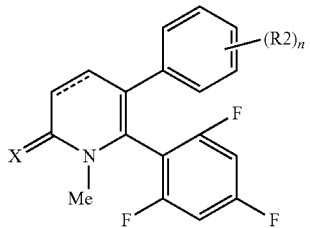 P-61
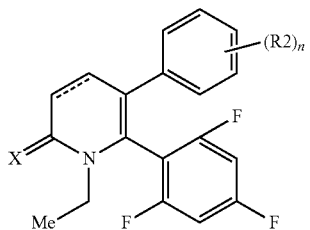 P-62
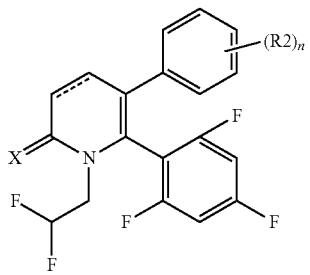 P-63
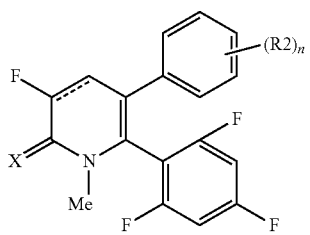 P-64
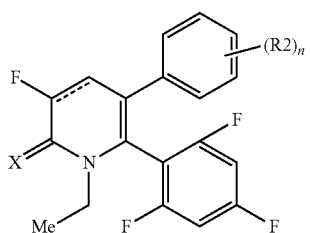 P-65
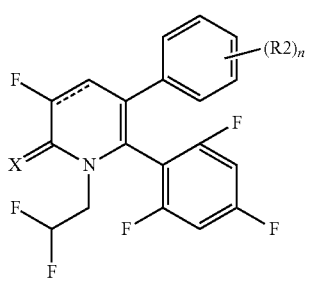 P-66
TABLE 1-continued
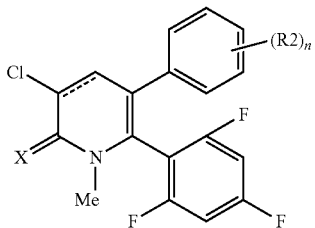 P-67
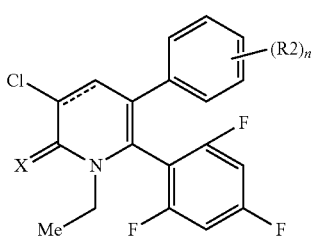 P-68
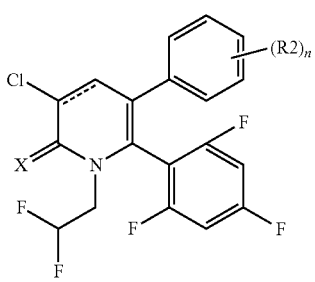 P-69
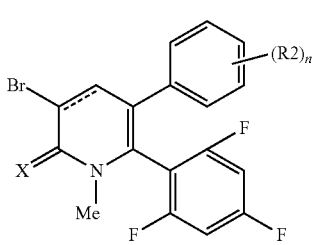 P-70
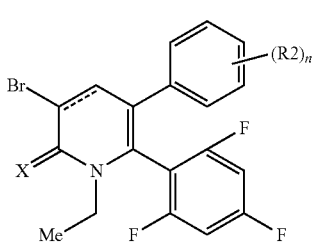 P-71
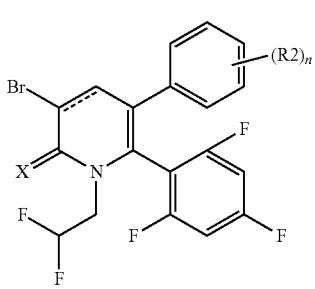 P-72

TABLE 1-continued

| Structure | ID |
|---|---|
| (structure) | P-73 |
| (structure) | P-74 |
| (structure) | P-75 |
| (structure) | P-76 |
| (structure) | P-77 |
| (structure) | P-78 |
| (structure) | P-79 |
| (structure) | P-80 |
| (structure) | P-81 |
| (structure) | P-82 |
| (structure) | P-83 |
| (structure) | P-84 |

TABLE 1-continued
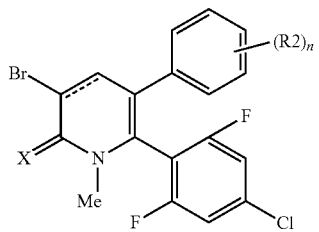
P-85
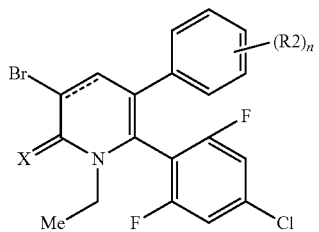
P-86
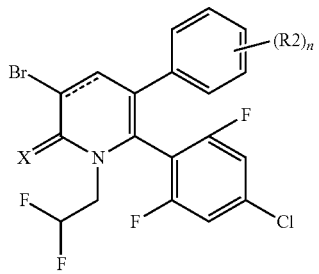
P-87
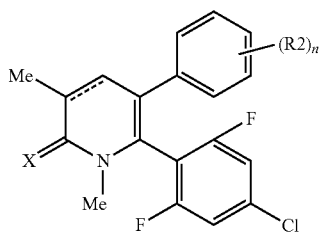
P-88
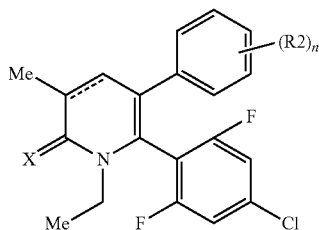
P-89
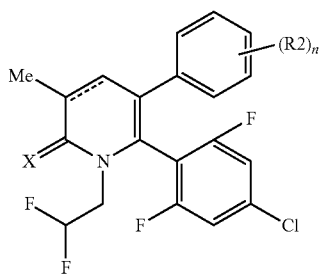
P-90
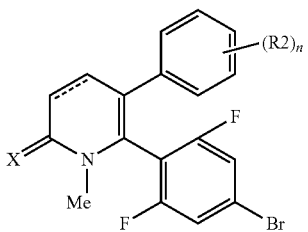
P-91
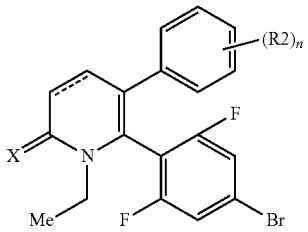
P-92
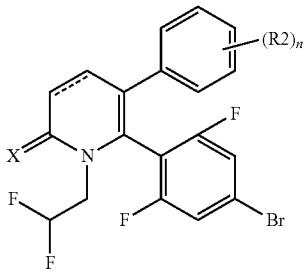
P-93
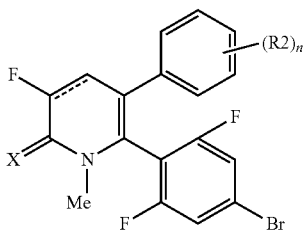
P-94
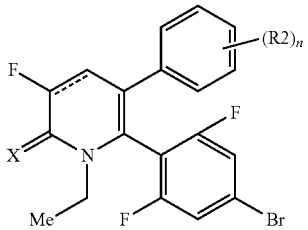
P-95
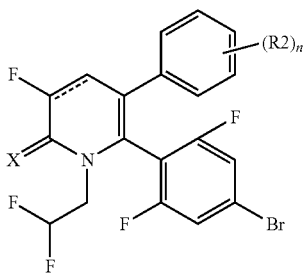
P-96

TABLE 1-continued
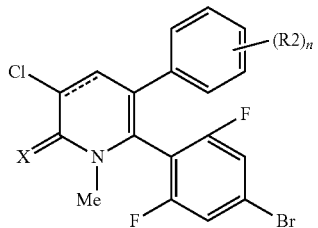 P-97
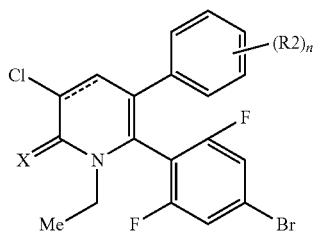 P-98
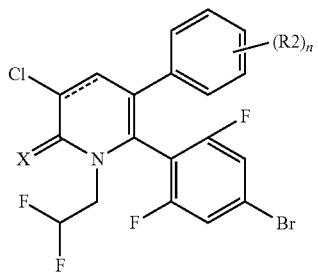 P-99
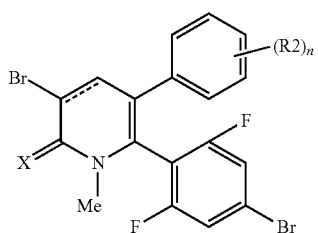 P-100
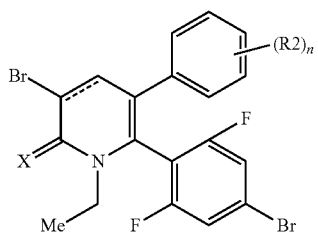 P-101
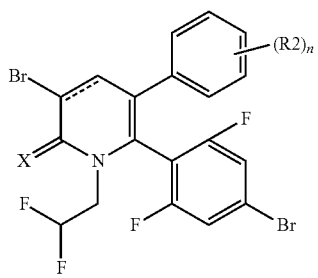 P-102
TABLE 1-continued
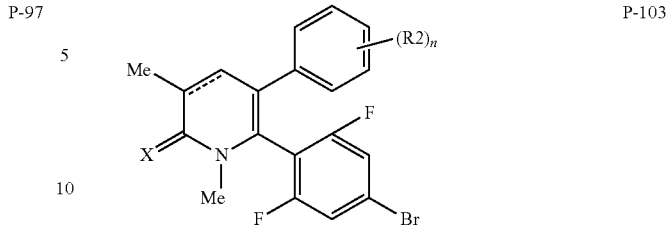 P-103
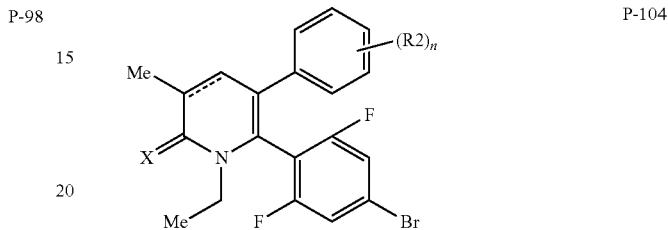 P-104
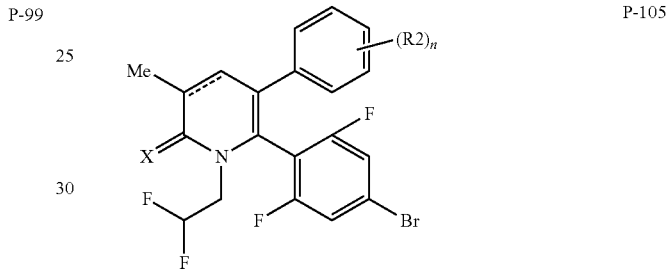 P-105
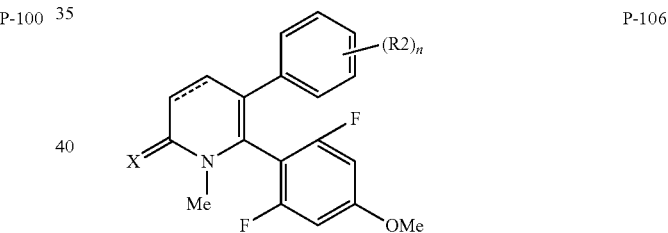 P-106
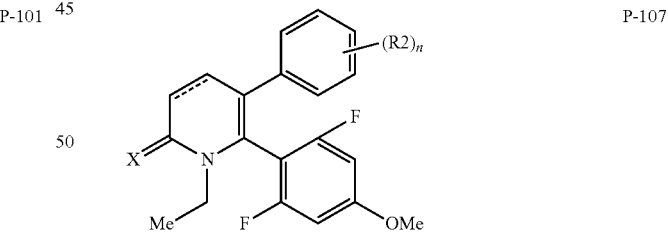 P-107
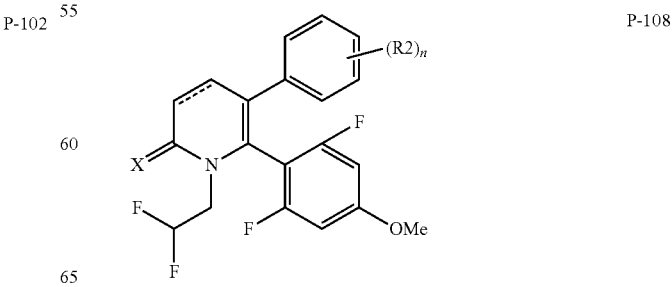 P-108

TABLE 1-continued
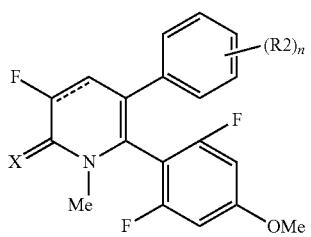 P-109
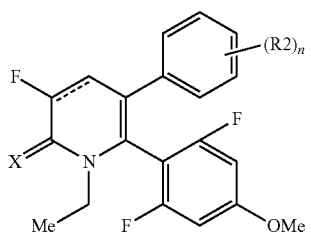 P-110
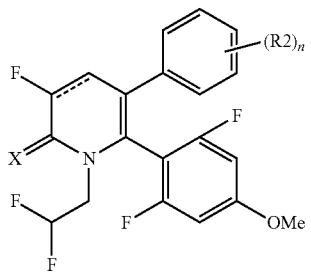 P-111
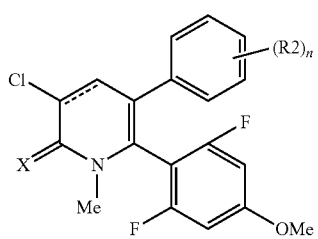 P-112
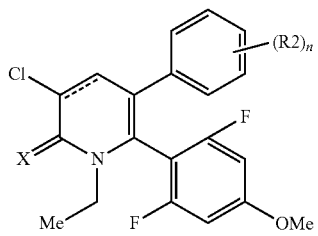 P-113
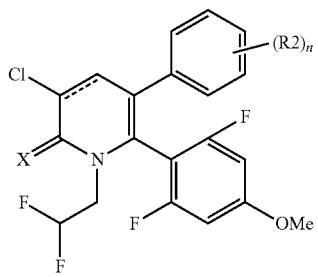 P-114
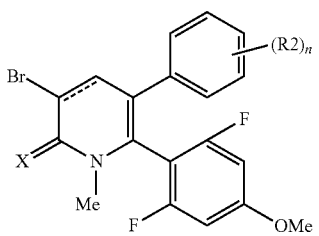 P-115
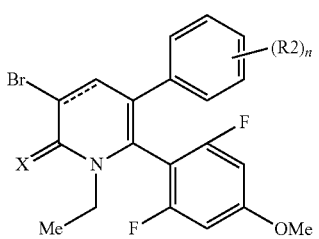 P-116
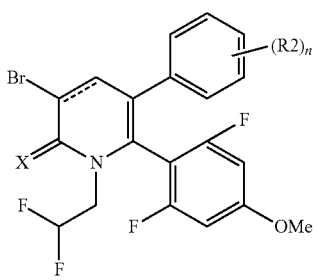 P-117
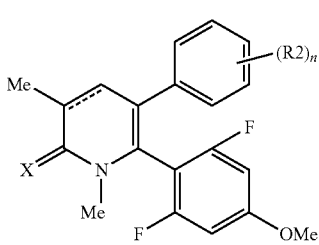 P-118
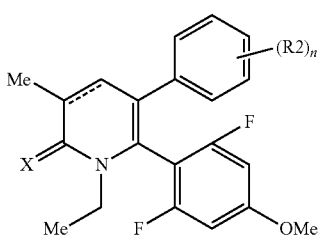 P-119
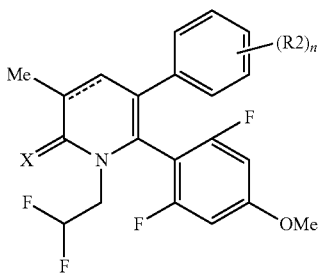 P-120

TABLE 1-continued
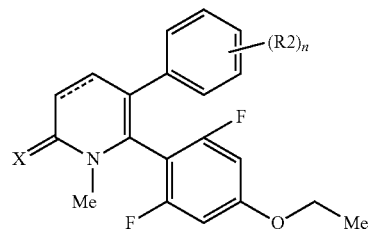 P-121
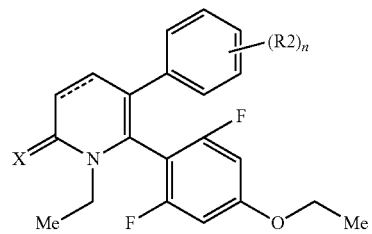 P-122
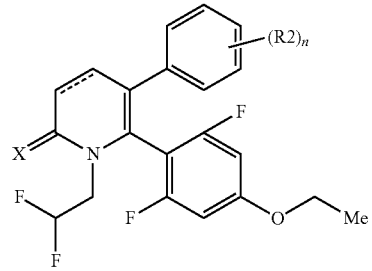 P-123
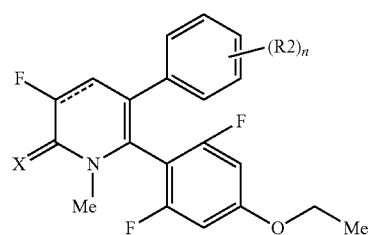 P-124
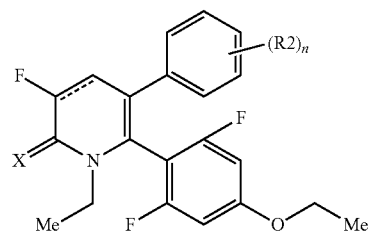 P-125
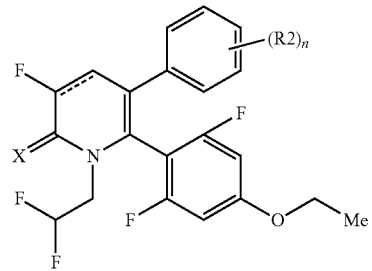 P-126
TABLE 1-continued
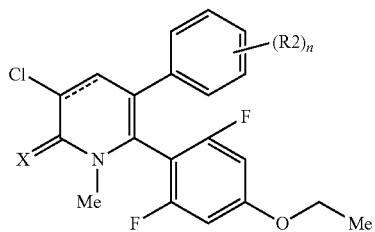 P-127
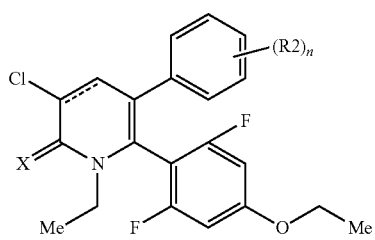 P-128
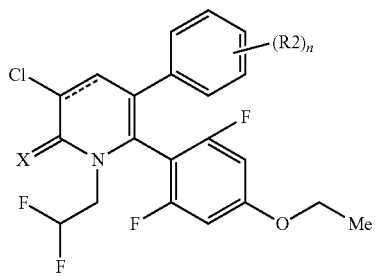 P-129
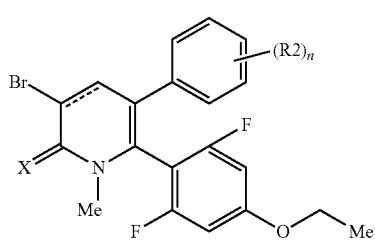 P-130
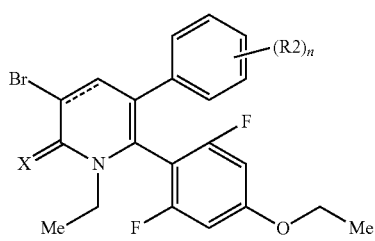 P-131
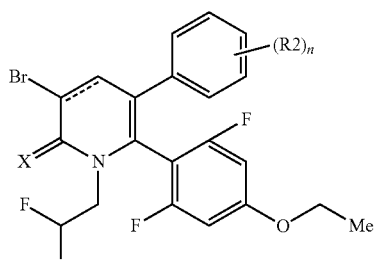 P-132

TABLE 1-continued
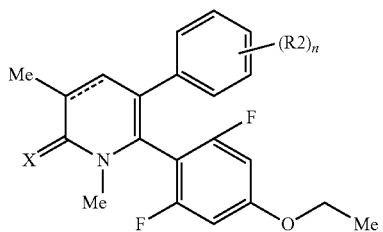 P-133
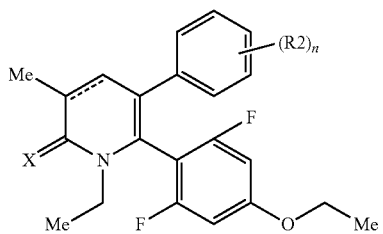 P-134
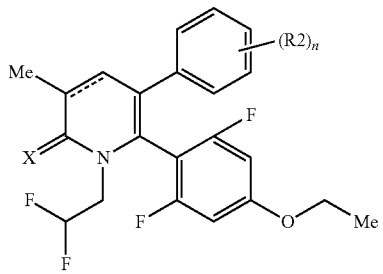 P-135
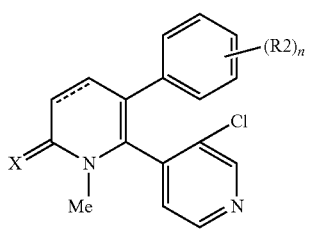 P-136
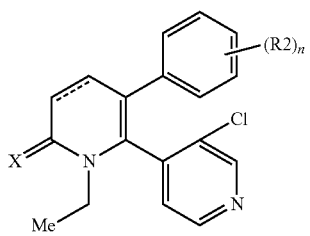 P-137
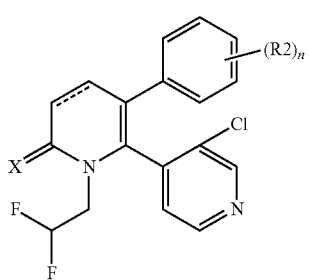 P-138
TABLE 1-continued
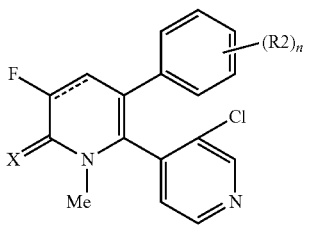 P-139
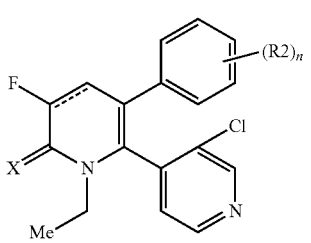 P-140
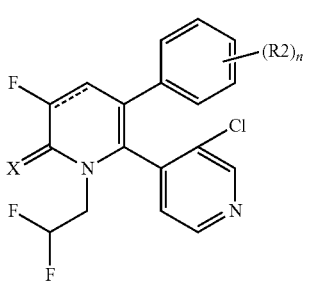 P-141
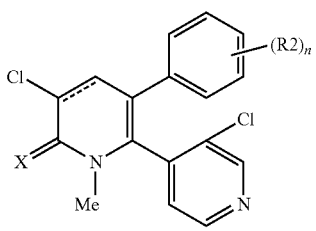 P-142
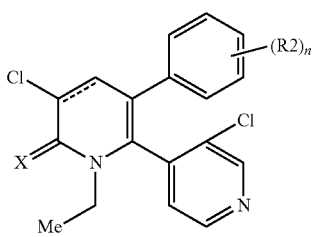 P-143
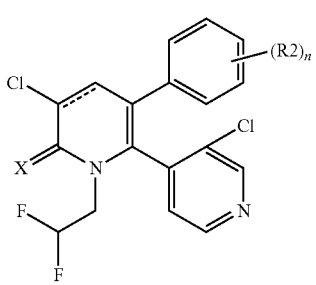 P-144

TABLE 1-continued
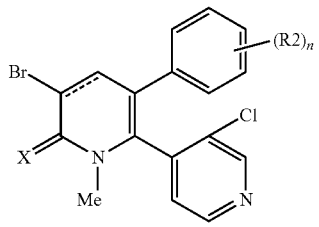 P-145
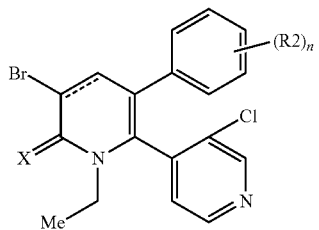 P-146
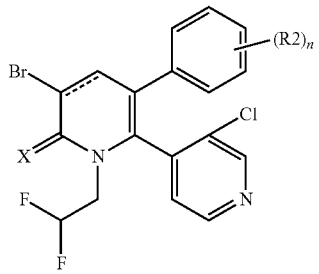 P-147
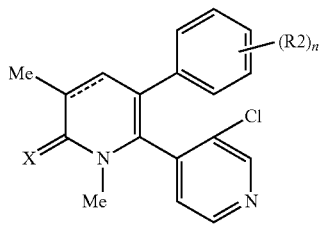 P-148
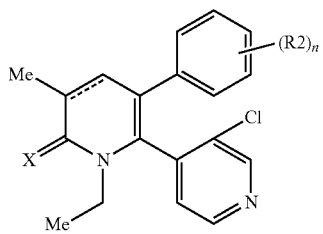 P-149
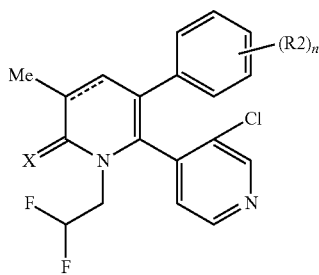 P-150
TABLE 1-continued
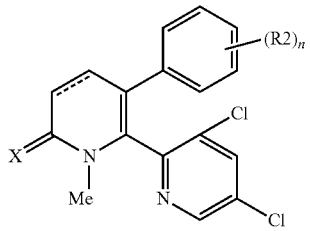 P-151
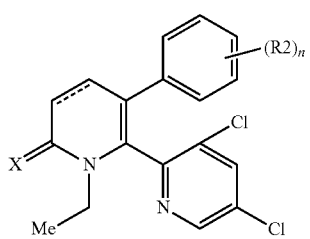 P-152
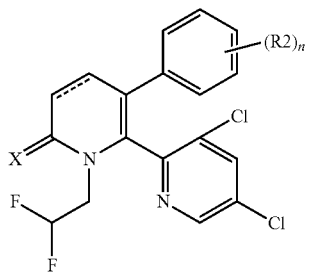 P-153
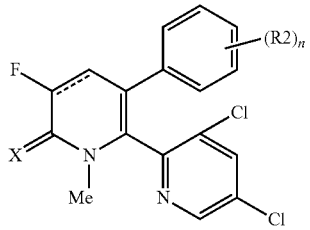 P-154
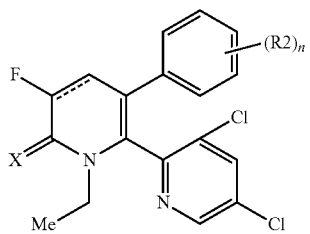 P-155
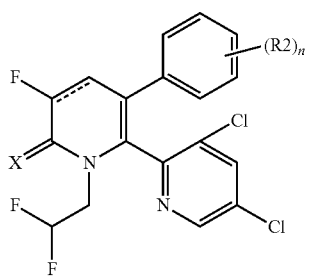 P-156

TABLE 1-continued
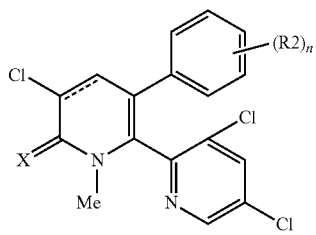 P-157
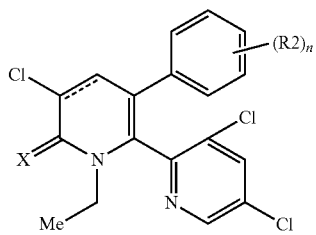 P-158
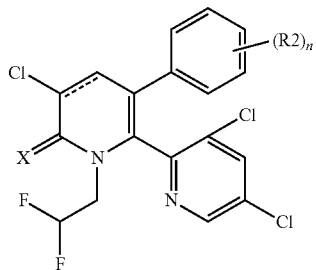 P-159
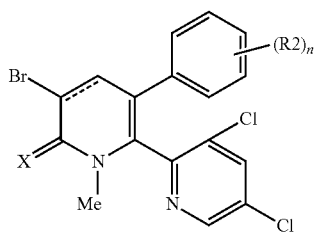 P-160
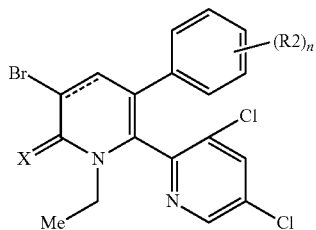 P-161
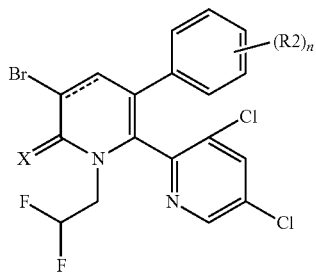 P-162
TABLE 1-continued
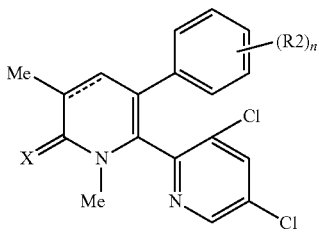 P-163
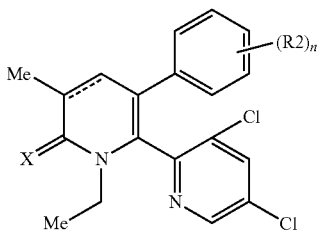 P-164
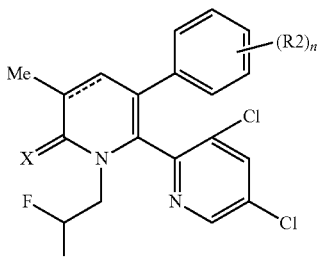 P-165
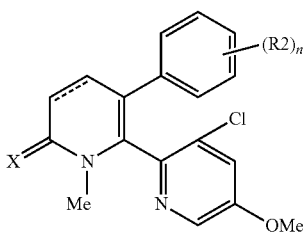 P-166
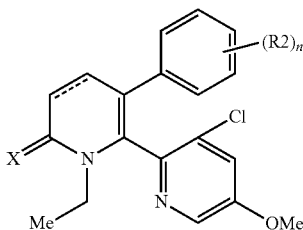 P-167
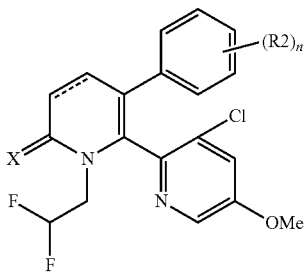 P-168

TABLE 1-continued
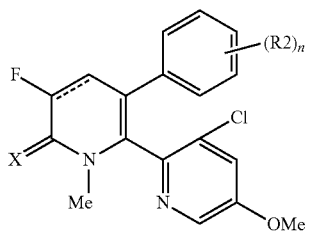 P-169
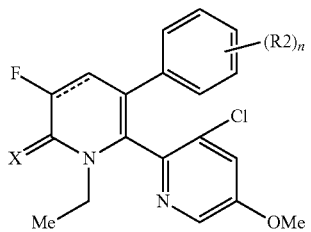 P-170
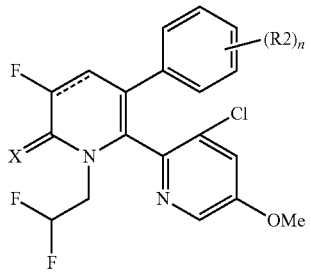 P-171
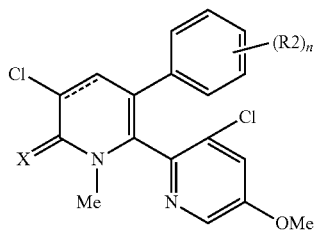 P-172
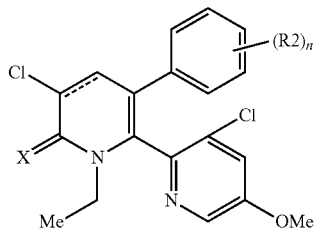 P-173
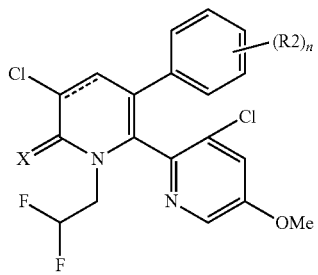 P-174
TABLE 1-continued
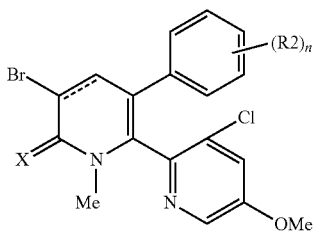 P-175
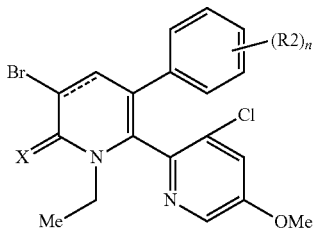 P-176
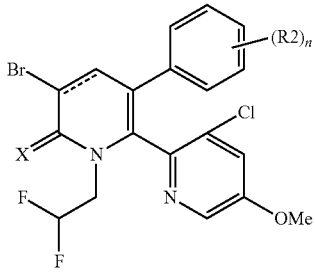 P-177
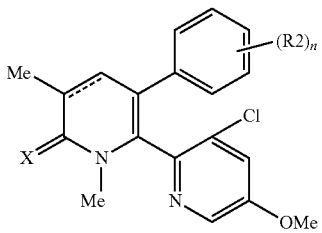 P-178
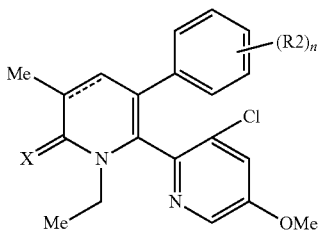 P-179
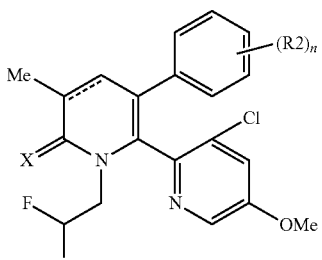 P-180

TABLE 1-continued
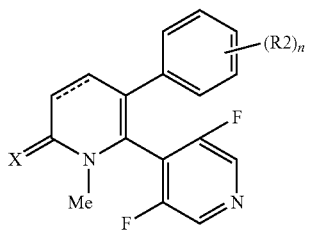 P-181
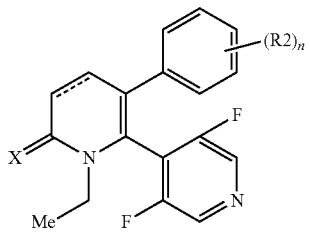 P-182
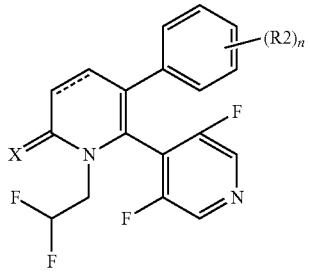 P-183
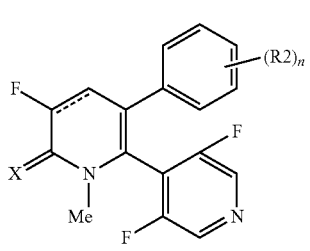 P-184
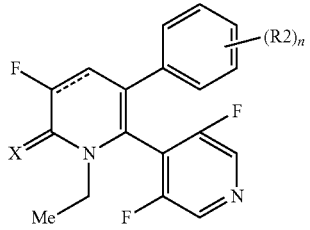 P-185
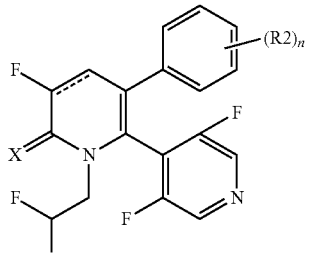 P-186
TABLE 1-continued
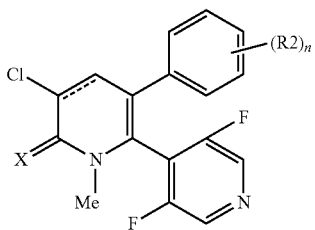 P-187
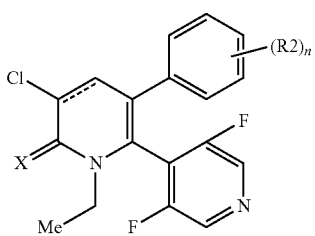 P-188
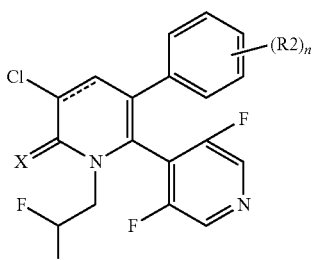 P-189
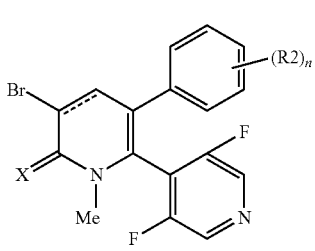 P-190
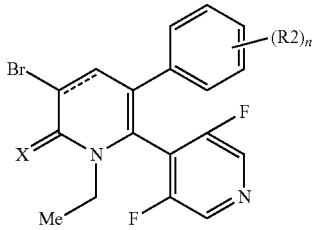 P-191
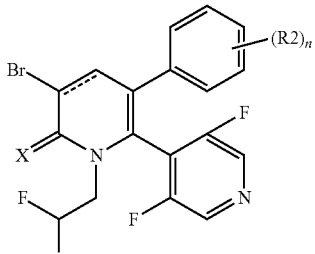 P-192

TABLE 1-continued
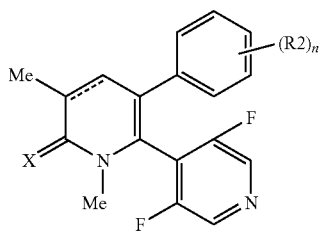 P-193
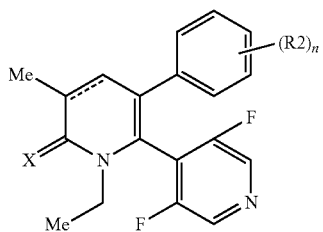 P-194
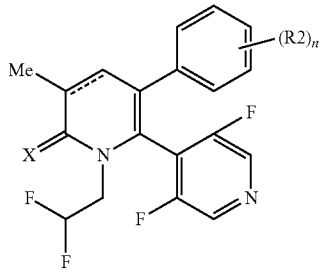 P-195
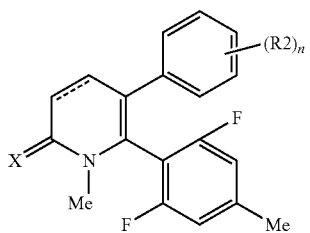 P-196
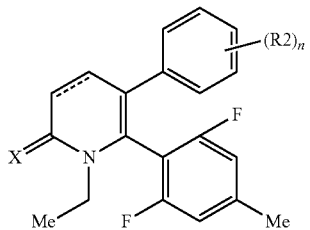 P-197
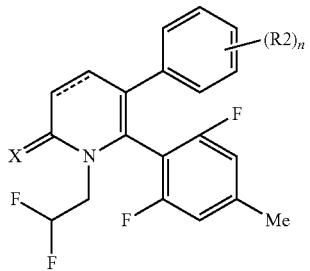 P-198
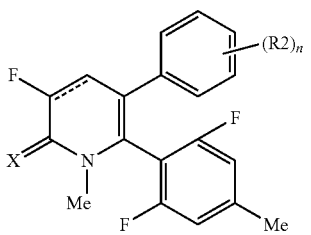 P-199
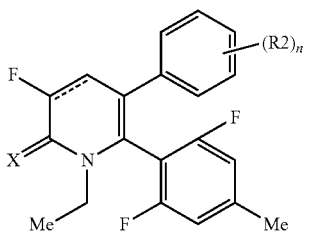 P-200
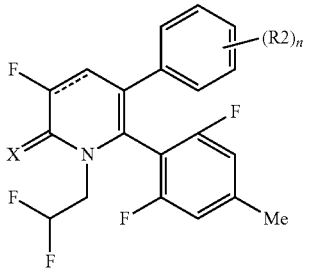 P-201
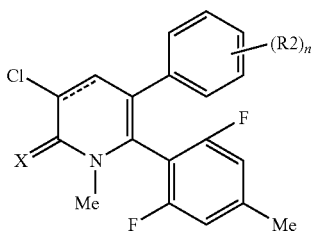 P-202
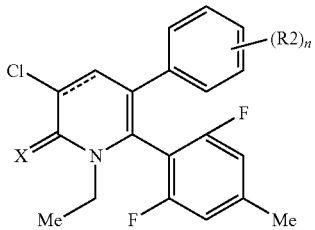 P-203
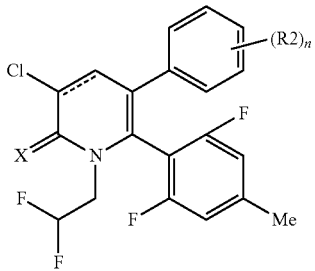 P-204

TABLE 1-continued
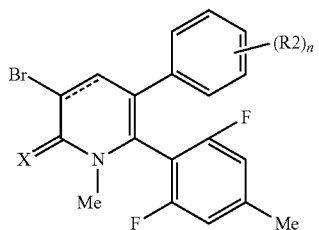 P-205
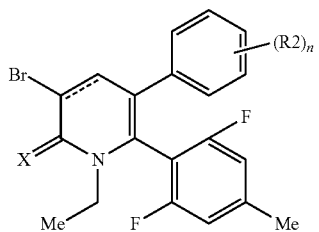 P-206
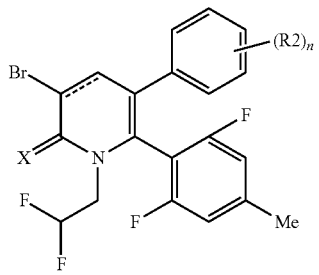 P-207
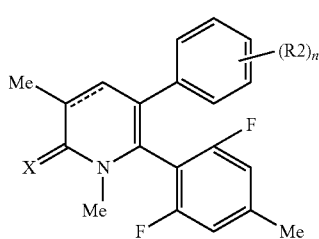 P-208
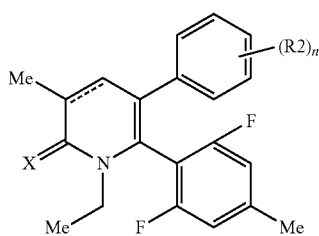 P-209
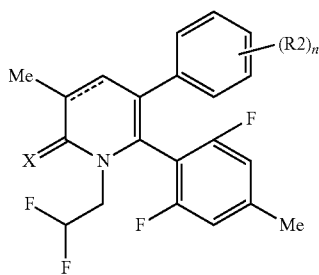 P-210
TABLE 1-continued
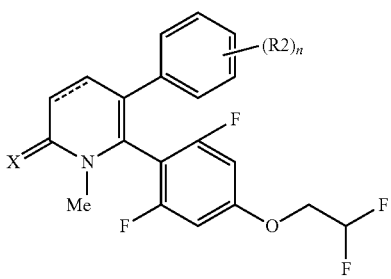 P-211
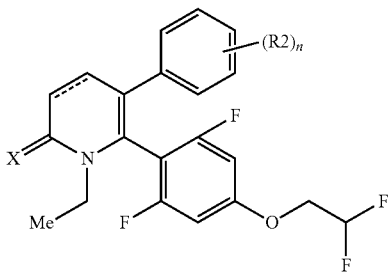 P-212
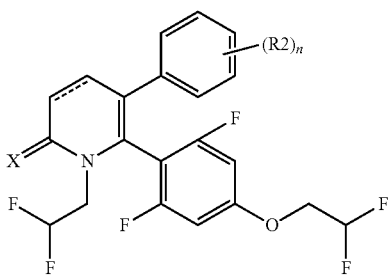 P-213
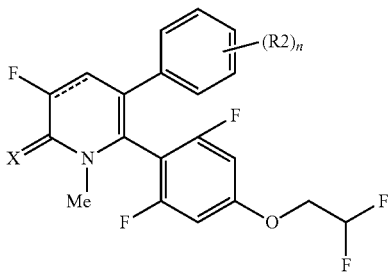 P-214
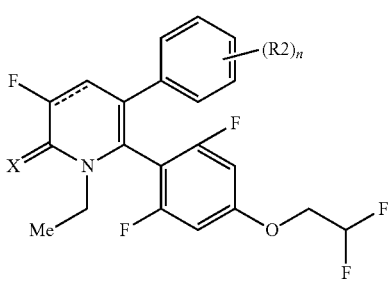 P-215

TABLE 1-continued
P-216
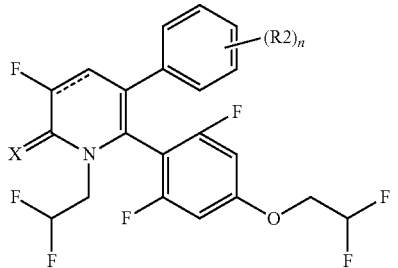
P-217
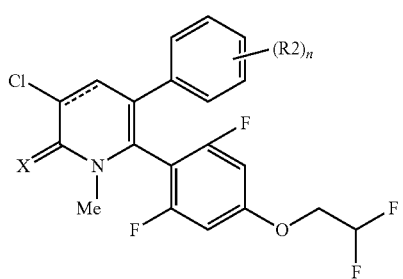
P-218

P-219
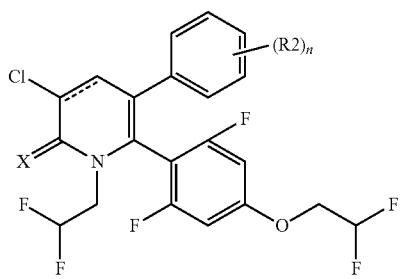
P-220
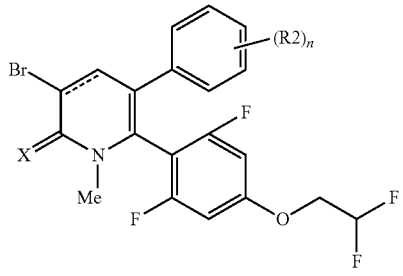
TABLE 1-continued
P-221
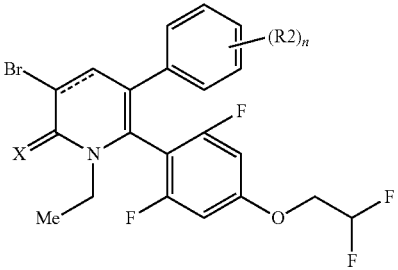
P-222
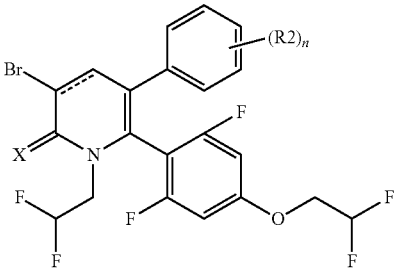
P-223
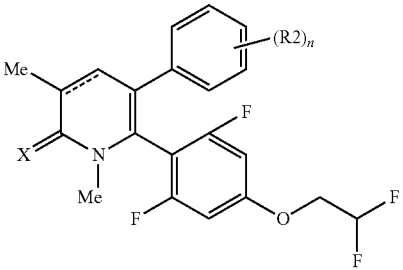
P-224
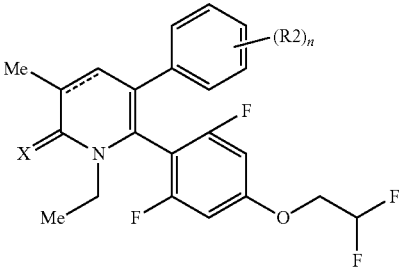
P-225
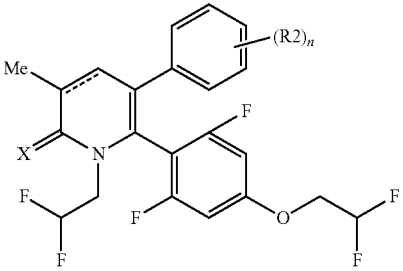
P-226
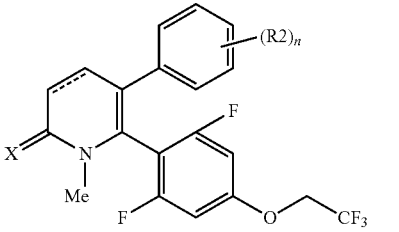

TABLE 1-continued
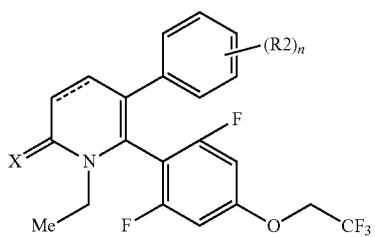 P-227
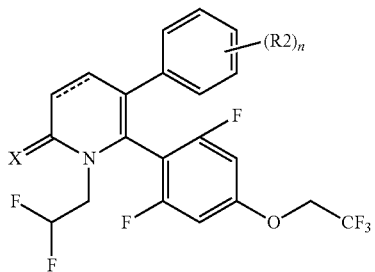 P-228
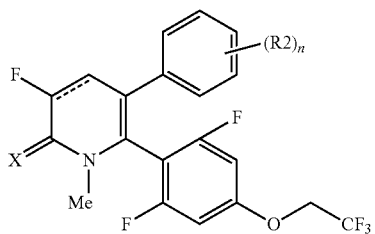 P-229
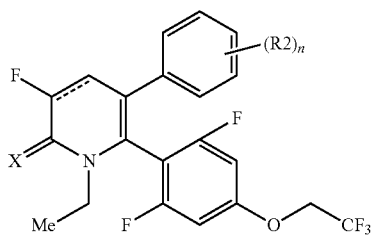 P-230
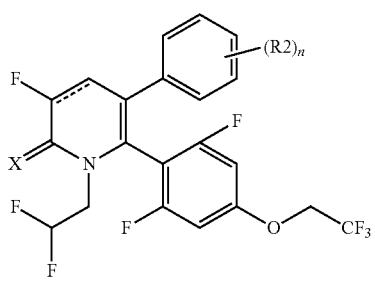 P-231
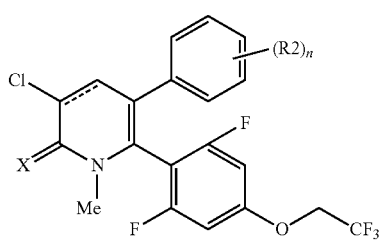 P-232
TABLE 1-continued
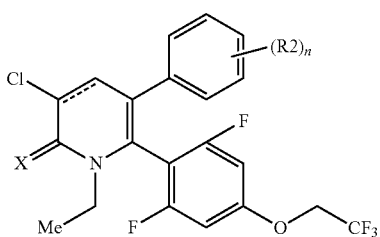 P-233
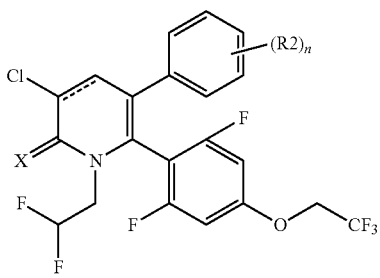 P-234
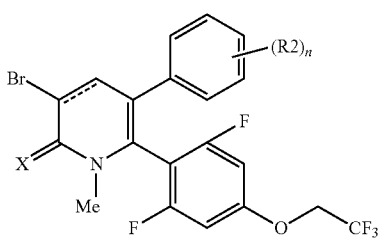 P-235
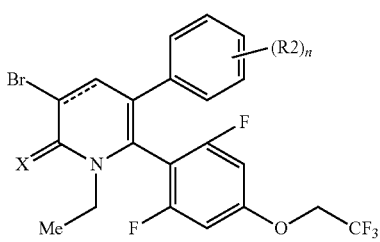 P-236
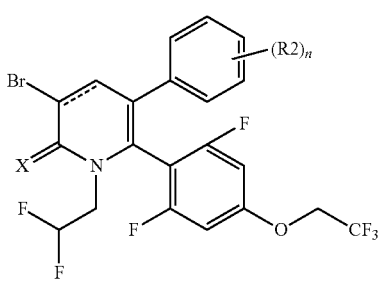 P-237
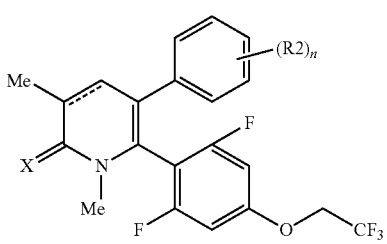 P-238

| | |
|---|---|
| 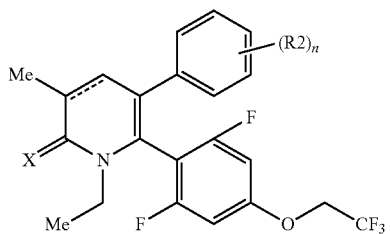 P-239 | 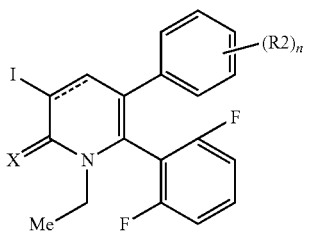 P-245 |
| 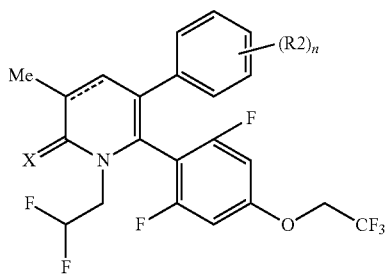 P-240 | 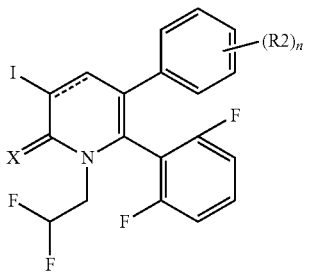 P-246 |
| 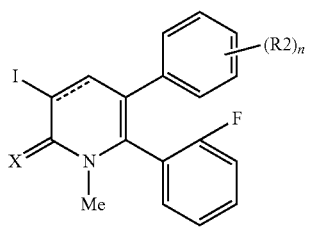 P-241 | 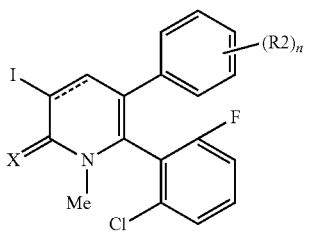 P-247 |
| 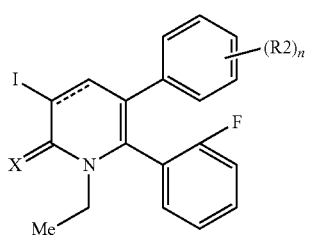 P-242 | 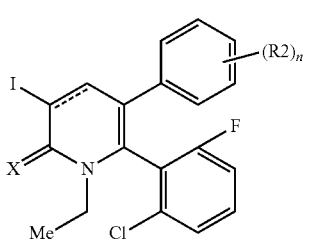 P-248 |
| 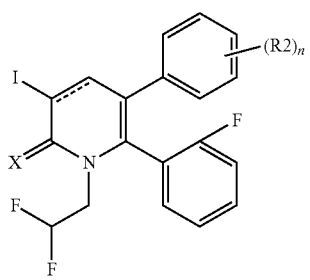 P-243 | 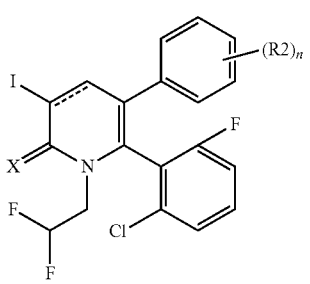 P-249 |
| 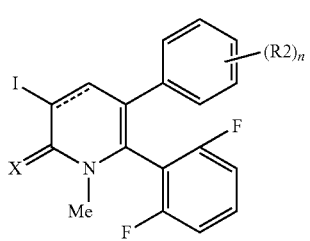 P-244 | 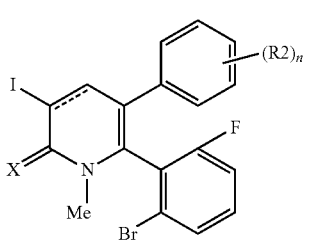 P-250 |

TABLE 1-continued
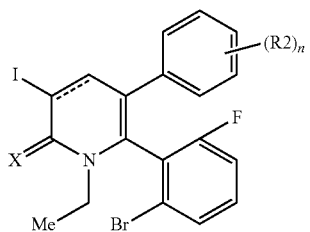 P-251
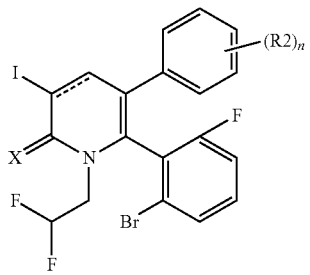 P-252
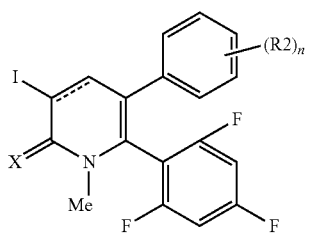 P-253
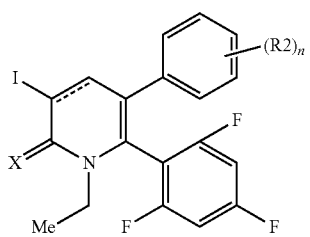 P-254
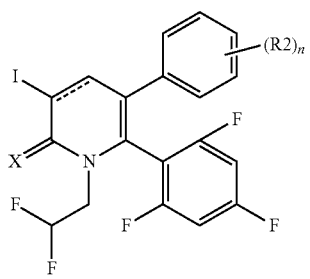 P-255
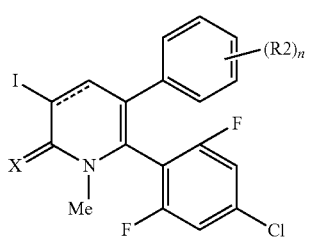 P-256
TABLE 1-continued
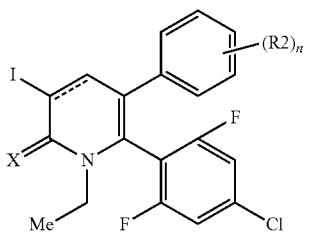 P-257
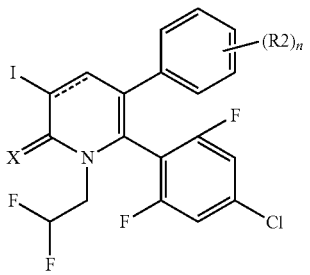 P-258
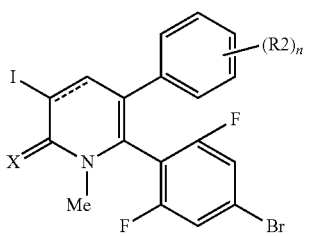 P-259
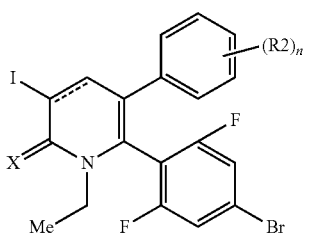 P-260
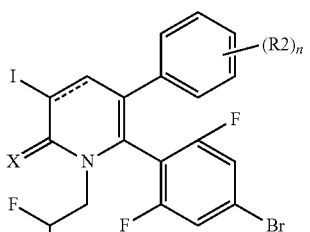 P-261
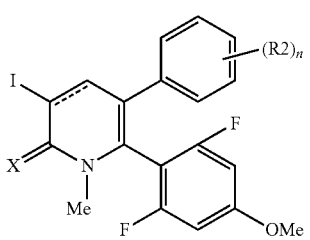 P-262

TABLE 1-continued
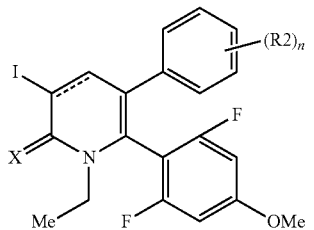 P-263
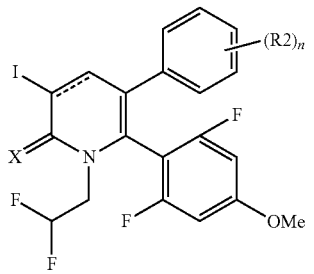 P-264
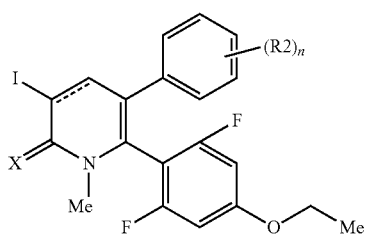 P-265
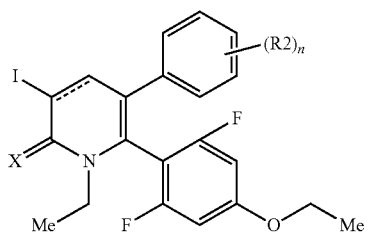 P-266
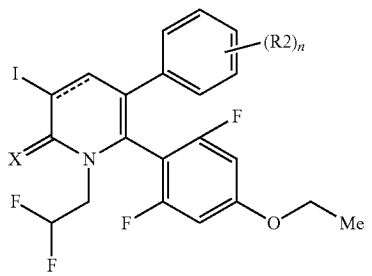 P-267
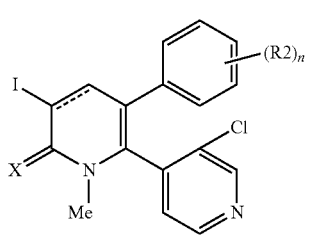 P-268
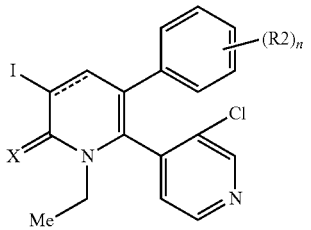 P-269
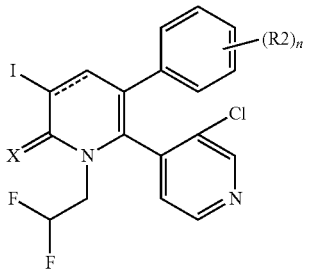 P-270
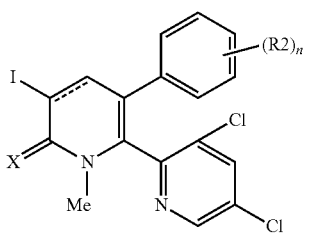 P-271
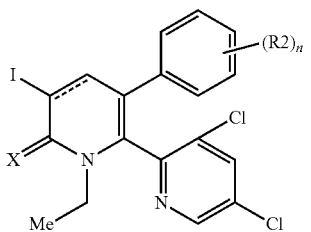 P-272
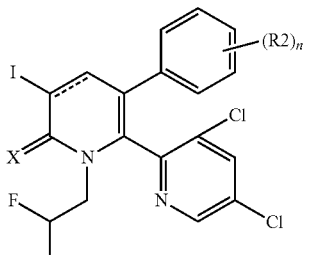 P-273
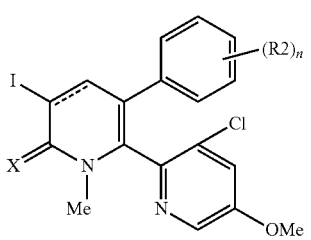 P-274

TABLE 1-continued
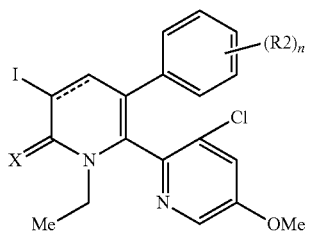 P-275
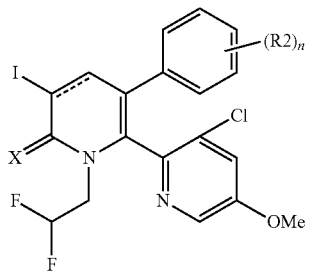 P-276
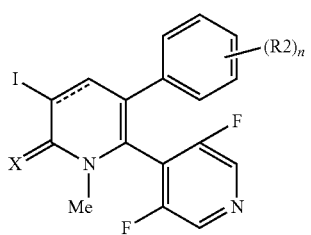 P-277
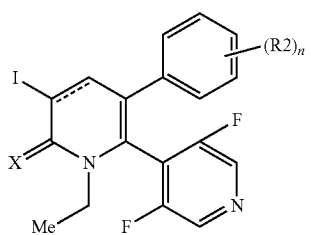 P-278
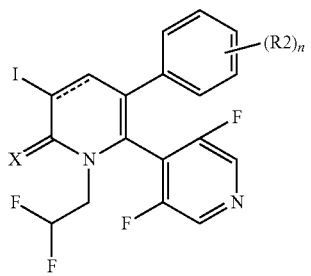 P-279
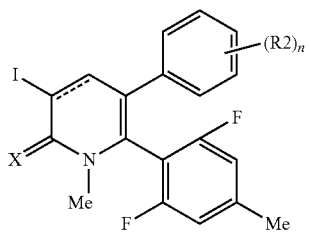 P-280
TABLE 1-continued
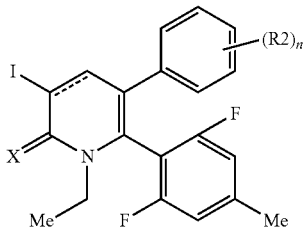 P-281
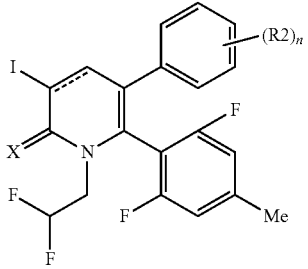 P-282
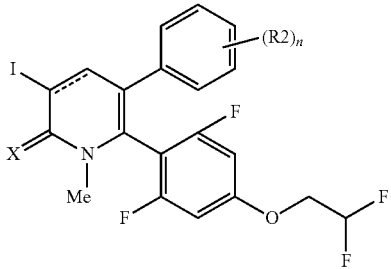 P-283
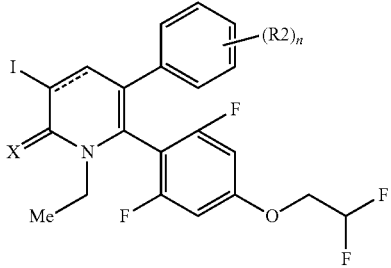 P-284
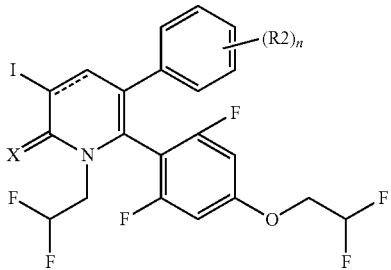 P-285
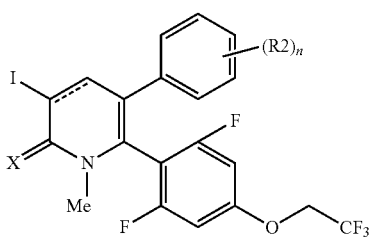 P-286

TABLE 1-continued

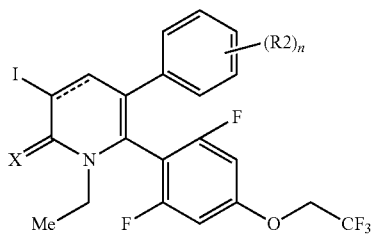

P-287

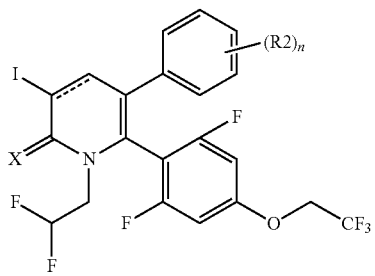

P-288

For example, the term "2-F—" in Table 2 indicates that fluorine atom is bonded to the 2-position of the phenyl to which (R2)n is bonded, the term "2-F-3-HO—" indicates that fluorine atom is bonded to the 2-position and a hydroxy group at the 3-position, and the term "2,3-di-F" indicates that fluorine atoms are bonded to the 2- and 3-positions. This also applies to other similar expressions.

TABLE 2

| No. | (R2)n | No. | (R2)n | No. | (R2)n |
| --- | --- | --- | --- | --- | --- |
| 1 | — (Unsubstituted) | 2 | 2-F— | 3 | 3-F— |
| 4 | 4-F— | 5 | 2-Cl— | 6 | 3-Cl— |
| 7 | 4-Cl— | 8 | 2-Br— | 9 | 3-Br— |
| 10 | 4-Br— | 11 | 2-I— | 12 | 3-I— |
| 13 | 4-I— | 14 | 2-HO— | 15 | 3-HO— |
| 16 | 4-HO— | 17 | 2-N≡C— | 18 | 3-N≡C— |
| 19 | 4-N≡C— | 20 | $2-O_2N-$ | 21 | $3-O_2N-$ |
| 22 | $4-O_2N-$ | 23 | 2-Me— | 24 | 3-Me— |
| 25 | 4-Me— | 26 | 2-Et— | 27 | 3-Et— |
| 28 | 4-Et— | 29 | 2-Pr— | 30 | 3-Pr— |
| 31 | 4-Pr— | 32 | 2-iPr— | 33 | 3-iPr— |
| 34 | 4-iPr— | 35 | $2-N=CCH_2-$ | 36 | $3-N=CCH_2-$ |
| 37 | $4-N=CCH_2-$ | 38 | $2-N=CCH_2CH_2-$ | 39 | $3-N=CCH_2CH_2-$ |
| 40 | $4-N=CCH_2CH_2-$ | 41 | $2-cPrCH_2-$ | 42 | $3-cPrCH_2-$ |
| 43 | $4-cPrCH_2-$ | 44 | $2-cBuCH_2-$ | 45 | $3-cBuCH_2-$ |
| 46 | $4-cBuCH_2-$ | 47 | $2-MeOCH_2-$ | 48 | $3-MeOCH_2-$ |
| 49 | $4-MeOCH_2-$ | 50 | $2-MeOCH_2CH_2-$ | 51 | $3-MeOCH_2CH_2-$ |
| 52 | $4-MeOCH_2CH_2-$ | 53 | $2-MeOCH_2CH_2CH_2-$ | 54 | $3-MeOCH_2CH_2CH_2-$ |
| 55 | $4-MeOCH_2CH_2CH_2-$ | 56 | $2-EtOCH_2-$ | 57 | $3-EtOCH_2-$ |
| 58 | $4-EtOCH_2-$ | 59 | $2-EtOCH_2CH_2-$ | 60 | $3-EtOCH_2CH_2-$ |
| 61 | $4-EtOCH_2CH_2-$ | 62 | $2-cPrOCH_2-$ | 63 | $3-cPrOCH_2-$ |
| 64 | $4-cPrOCH_2-$ | 65 | $2-F_3COCH_2-$ | 66 | $3-F_3COCH_2-$ |
| 67 | $4-F_3COCH_2-$ | 68 | $2-F_2CHOCH_2-$ | 69 | $3-F_2CHOCH_2-$ |
| 70 | $4-F_2CHOCH_2-$ | 71 | $2-MeOCH_2CH_2OCH_2-$ | 72 | $3-MeOCH_2CH_2OCH_2-$ |
| 73 | $4-MeOCH_2CH_2OCH_2-$ | 74 | $2-Me_2NCH_2-$ | 75 | $3-Me_2NCH_2-$ |
| 76 | $4-Me_2NCH_2-$ | 77 | $2-MeSCH_2-$ | 78 | $3-MeSCH_2-$ |
| 79 | $4-MeSCH_2-$ | 80 | $2-MeS(O)CH_2-$ | 81 | $3-MeS(O)CH_2-$ |
| 82 | $4-MeS(O)CH_2-$ | 83 | $2-MeSO_2CH_2-$ | 84 | $3-MeSO_2CH_2-$ |
| 85 | $4-MeSO_2CH_2-$ | 86 | 2-cPr— | 87 | 3-cPr— |
| 88 | 4-cPr— | 89 | 2-cBu— | 90 | 3-cBu— |
| 91 | 4-cBu— | 92 | $2-F_3C-$ | 93 | $3-F_3C-$ |
| 94 | $4-F_3C-$ | 95 | $2-F_2CH-$ | 96 | $3-F_2CH-$ |
| 97 | $4-F_2CH-$ | 98 | $2-H_2C=CH-$ | 99 | $3-H_2C=CH-$ |
| 100 | $4-H_2C=CH-$ | 101 | $2-H_2C=CHCH_2-$ | 102 | $3-H_2C=CHCH_2-$ |
| 103 | $4-H_2C=CHCH_2-$ | 104 | $2-F_2C=CH-$ | 105 | $3-F_2C=CH-$ |
| 106 | $4-F_2C=CH-$ | 107 | $2-F_2C=CHCH_2-$ | 108 | $3-F_2C=CHCH_2-$ |
| 109 | $4-F_2C=CHCH_2-$ | 110 | 2-HC≡C— | 111 | 3-HC≡C— |
| 112 | 4-HC≡C— | 113 | $2-HC≡CCH_2-$ | 114 | $3-HC≡CCH_2-$ |
| 115 | $4-HC≡CCH_2-$ | 116 | $2-F_3CC≡C-$ | 117 | $3-F_3CC≡C-$ |
| 118 | $4-F_3CC≡C-$ | 119 | $2-F_3CC≡CCH_2-$ | 120 | $3-F_3CC≡CCH_2-$ |

TABLE 2-continued

| No. | (R2)n | No. | (R2)n | No. | (R2)n |
|---|---|---|---|---|---|
| 121 | 4-F₃CC≡CCH₂— | 122 | 2-MeO— | 123 | 3-MeO— |
| 124 | 4-MeO— | 125 | 2-EtO— | 126 | 3-EtO— |
| 127 | 4-EtO— | 128 | 2-PrO— | 129 | 3-PrO— |
| 130 | 4-PrO— | 131 | 2-iPrO— | 132 | 3-iPrO— |
| 133 | 4-iPrO— | 134 | 2-BuO— | 135 | 3-BuO— |
| 136 | 4-BuO— | 137 | 2-iBuO— | 138 | 3-iBuO— |
| 139 | 4-iBuO— | 140 | 2-PentylO— | 141 | 3-PentylO— |
| 142 | 4-PentylO— | 143 | 2-N≡CCH₂O— | 144 | 3-N≡CCH₂O— |
| 145 | 4-N≡CCH₂O— | 146 | 2-N≡CCH₂CH₂O— | 147 | 3-N≡CCH₂CH₂O— |
| 148 | 4-N≡CCH₂CH₂O— | 149 | 2-cPrCH₂O— | 150 | 3-cPrCH₂O— |
| 151 | 4-cPrCH₂O— | 152 | 2-cBuCH₂O— | 153 | 3-cBuCH₂O— |
| 154 | 4-cBuCH₂O— | 155 | 2-cPentylCH₂O— | 156 | 3-cPentylCH₂O— |
| 157 | 4-cPentylCH₂O— | 158 | 2-cHexylCH₂O— | 159 | 3-cHexylCH₂O— |
| 160 | 4-cHexylCH₂O— | 161 | 2-MeOCH₂O— | 162 | 3-MeOCH₂O— |
| 163 | 4-MeOCH₂O— | 164 | 2-EtOCH₂O— | 165 | 3-EtOCH₂O— |
| 166 | 4-EtOCH₂O— | 167 | 2-MeOCH₂CH₂O— | 168 | 3-MeOCH₂CH₂O— |
| 169 | 4-MeOCH₂CH₂O— | 170 | 2-MeOCH₂CH₂CH₂O— | 171 | 3-MeOCH₂CH₂CH₂O— |
| 172 | 4-MeOCH₂CH₂CH₂O— | 173 | 2-MeOCH₂CH₂OCH₂O— | 174 | 3-MeOCH₂CH₂OCH₂O— |
| 175 | 4-MeOCH₂CH₂OCH₂O— | 176 | 2-MeSCH₂O— | 177 | 3-MeSCH₂O— |
| 178 | 4-MeSCH₂O— | 179 | 2-MeS(O)CH₂O— | 180 | 3-MeS(O)CH₂O— |
| 181 | 4-MeS(O)CH₂O— | 182 | 2-MeSO₂CH₂O— | 183 | 3-MeSO₂CH₂O— |
| 184 | 4-MeSO₂CH₂O— | 185 | 2-Me₃SiCH₂O— | 186 | 3-Me₃SiCH₂O— |
| 187 | 4-Me₃SiCH₂O— | 188 | 2-Me₃SiCH₂CH₂O— | 189 | 3-Me₃SiCH₂CH₂O— |
| 190 | 4-Me₃SiCH₂CH₂O— | 191 | 2-Me₃SiCH₂CH₂CH₂O— | 192 | 3-Me₃SiCH₂CH₂CH₂O— |
| 193 | 4-Me₃SiCH₂CH₂CH₂O— | 194 | 2-AcCH₂O— | 195 | 3-AcCH₂O— |
| 196 | 4-AcCH₂O— | 197 | 2-MeOC(=O)CH₂O— | 198 | 3-MeOC(=O)CH₂O— |
| 199 | 4-MeOC(=O)CH₂O— | 200 | 2-EtOC(=O)CH₂O— | 201 | 3-EtOC(=O)CH₂O— |
| 202 | 4-EtOC(=O)CH₂O— | 203 | 2-(1,3-dioxolan-2-yl)CH₂O— | 204 | 3-(1,3-dioxolan-2-yl)CH₂O— |
| 205 | 4-(1,3-dioxolan-2-yl)CH₂O— | 206 | 2-(1,3-dioxolan-2-yl)CH₂CH₂O— | 207 | 3-(1,3-dioxolan-2-yl)CH₂CH₂O— |
| 208 | 4-(1,3-dioxolan-2-yl)CH₂CH₂O— | 209 | 2-(1,3-dioxan-2-yl)CH₂O— | 210 | 3-(1,3-dioxan-2-yl)CH₂O— |
| 211 | 4-(1,3-dioxan-2-yl)CH₂O— | 212 | 2-(1,3-dioxan-2-yl)CH₂CH₂O— | 213 | 3-(1,3-dioxan-2-yl)CH₂CH₂O— |
| 214 | 4-(1,3-dioxan-2-yl)CH₂CH₂O— | 215 | 2-cPrO— | 216 | 3-cPrO— |
| 217 | 4-cPrO— | 218 | 2-cBuO— | 219 | 3-cBuO— |
| 220 | 4-cBuO— | 221 | 2-cPentylO— | 222 | 3-cPentylO— |
| 223 | 4-cPentylO— | 224 | 2-cHexylO— | 225 | 3-cHexylO— |
| 226 | 4-cHexylO— | 227 | 2-F₃CO— | 228 | 3-F₃CO— |
| 229 | 4-F₃CO— | 230 | 2-F₂CHO— | 231 | 3-F₂CHO— |
| 232 | 4-F₂CHO— | 233 | 2-F₃CCH₂O— | 234 | 3-F₃CCH₂O— |
| 235 | 4-F₃CCH₂O— | 236 | 2-F₂CHCH₂O— | 237 | 3-F₂CHCH₂O— |
| 238 | 4-F₂CHCH₂O— | 239 | 2-H₂C=CHCH₂O— | 240 | 3-H₂C=CHCH₂O— |
| 241 | 4-H₂C=CHCH₂O— | 242 | 2-HC≡CCH₂O— | 243 | 3-HC≡CCH₂O— |
| 244 | 4-HC≡CCH₂O— | 245 | 2-Ac | 246 | 3-Ac |
| 247 | 4-Ac | 248 | 2-MeOC(=O)— | 249 | 3-MeOC(=O)— |
| 250 | 4-MeOC(=O)— | 251 | 2-EtOC(=O)— | 252 | 3-EtOC(=O)— |
| 253 | 4-EtOC(=O)— | 254 | 2-AcO— | 255 | 3-AcO— |
| 256 | 4-AcO— | 257 | 2-MeOC(=O)O— | 258 | 3-MeOC(=O)O— |
| 259 | 4-MeOC(=O)O— | 260 | 2-EtOC(=O)O— | 261 | 3-EtOC(=O)O— |
| 262 | 4-EtOC(=O)O— | 263 | 2-(1,3-dioxolan-2-yl)- | 264 | 3-(1,3-dioxolan-2-yl)- |
| 265 | 4-(1,3-dioxolan-2-yl)- | 266 | 2-(1,3-dioxan-2-yl)- | 267 | 3-(1,3-dioxan-2-yl)- |
| 268 | 4-(1,3-dioxan-2-yl)- | 269 | 2-MeS— | 270 | 3-MeS— |
| 271 | 4-MeS— | 272 | 2-MeS(O)— | 273 | 3-MeS(O)— |
| 274 | 4-MeS(O)— | 275 | 2-MeSO₂— | 276 | 3-MeSO₂— |
| 277 | 4-MeSO₂— | 278 | 2-ClCH₂S— | 279 | 3-ClCH₂S— |
| 280 | 4-ClCH₂S— | 281 | 2-ClCH₂S(O)— | 282 | 3-ClCH₂S(O)— |
| 283 | 4-ClCH₂S(O)— | 284 | 2-ClCH₂SO₂— | 285 | 3-ClCH₂SO₂— |
| 286 | 4-ClCH₂SO₂— | 287 | 2-F-3-HO— | 288 | 2-F-4-HO— |
| 289 | 2-F-5-HO— | 290 | 2-F-6-HO— | 291 | 2-Cl-3-HO— |
| 292 | 2-Cl-4-HO— | 293 | 2-Cl-5-HO— | 294 | 2-Cl-6-HO— |
| 295 | 2-Br-3-HO— | 296 | 2-Br-4-HO— | 297 | 2-Br-5-HO— |
| 298 | 2-Br-6-HO— | 299 | 2-I-3-HO— | 300 | 2-I-4-HO— |
| 301 | 2-I-5-HO— | 302 | 2-I-6-HO— | 303 | 2-Me-3-HO— |
| 304 | 2-Me-4-HO— | 305 | 2-Me-5-HO— | 306 | 2-Me-6-HO— |
| 307 | 2,3-di-F— | 308 | 2,4-di-F— | 309 | 2,5-di-F— |
| 310 | 2,6-di-F— | 311 | 2-Cl-3-F— | 312 | 2-Cl-4-F— |
| 313 | 2-Cl-5-F— | 314 | 2-Cl-6-F— | 315 | 2-Br-3-F— |
| 316 | 2-Br-4-F— | 317 | 2-Br-5-F— | 318 | 2-Br-6-F— |
| 319 | 3-F-2-I— | 320 | 4-F-2-I— | 321 | 5-F-2-I— |
| 322 | 6-F-2-I— | 323 | 3-F-2-Me— | 324 | 4-F-2-Me— |
| 325 | 5-F-2-Me— | 326 | 6-F-2-Me— | 327 | 3-Cl-2-F— |
| 328 | 4-Cl-2-F— | 329 | 5-Cl-2-F— | 330 | 6-Cl-2-F— |
| 331 | 2,3-di-Cl— | 332 | 2,4-di-Cl— | 333 | 2,5-di-Cl— |
| 334 | 2,6-di-Cl— | 335 | 2-Br-3-Cl— | 336 | 2-Br-4-Cl— |
| 337 | 2-Br-5-Cl— | 338 | 2-Br-6-Cl— | 339 | 3-Cl-2-I— |

TABLE 2-continued

| No. | (R2)n | No. | (R2)n | No. | (R2)n |
|---|---|---|---|---|---|
| 340 | 4-Cl-2-I— | 341 | 5-Cl-2-I— | 342 | 6-Cl-2-I— |
| 343 | 3-Cl-2-Me— | 344 | 4-Cl-2-Me— | 345 | 5-Cl-2-Me— |
| 346 | 6-Cl-2-Me— | 347 | 3-Br-2-F— | 348 | 4-Br-2-F— |
| 349 | 5-Br-2-F— | 350 | 6-Br-2-F— | 351 | 3-Br-2-Cl— |
| 352 | 4-Br-2-Cl— | 353 | 5-Br-2-Cl— | 354 | 6-Br-2-Cl— |
| 355 | 2,3-di-Br— | 356 | 2,4-di-Br— | 357 | 2,5-di-Br— |
| 358 | 2,6-di-Br— | 359 | 3-Br-2-I— | 360 | 4-Br-2-I— |
| 361 | 5-Br-2-I— | 362 | 6-Br-2-I— | 363 | 3-Br-2-Me— |
| 364 | 4-Br-2-Me— | 365 | 5-Br-2-Me— | 366 | 6-Br-2-Me— |
| 367 | 2-F-3-I— | 368 | 2-F-4-I— | 369 | 2-F-5-I— |
| 370 | 2-F-6-I— | 371 | 2-Cl-3-I— | 372 | 2-Cl-4-I— |
| 373 | 2-Cl-5-I— | 374 | 2-Cl-6-I— | 375 | 2-Br-3-I— |
| 376 | 2-Br-4-I— | 377 | 2-Br-5-I— | 378 | 2-Br-6-I— |
| 379 | 2,3-di-I— | 380 | 2,4-di-I— | 381 | 2,5-di-I— |
| 382 | 2,6-di-I— | 383 | 2-Me-3-I— | 384 | 2-Me-4-I— |
| 385 | 2-Me-5-I— | 386 | 2-Me-6-I— | 387 | 2-F-3-N≡C— |
| 388 | 2-F-4-N≡C— | 389 | 2-F-5-N≡C— | 390 | 2-F-6-N≡C— |
| 391 | 2-Cl-3-N≡C— | 392 | 2-Cl-4-N≡C— | 393 | 2-Cl-5-N≡C— |
| 394 | 2-Cl-6-N≡C— | 395 | 2-Br-3-N≡O | 396 | 2-Br-4-N≡C— |
| 397 | 2-Br-5-N≡C— | 398 | 2-Br-6-N≡O | 399 | 2-I-3-N≡O |
| 400 | 2-I-4-N≡O— | 401 | 2-I-5-N≡C— | 402 | 2-I-6-N≡C— |
| 403 | 2-Me-3-N≡C— | 404 | 2-Me-4-N≡C— | 405 | 2-Me-5-N≡C— |
| 406 | 2-Me-6-N≡C— | 407 | 2-F-3-O$_2$N— | 408 | 2-F-4-O$_2$N— |
| 409 | 2-F-5-O$_2$N— | 410 | 2-F-6-O$_2$N— | 411 | 2-Cl-3-O$_2$N— |
| 412 | 2-Cl-4-O$_2$N— | 413 | 2-Cl-5-O$_2$N— | 414 | 2-Cl-6-O$_2$N— |
| 415 | 2-Br-3-O$_2$N— | 416 | 2-Br-4-O$_2$N— | 417 | 2-Br-5-O$_2$N— |
| 418 | 2-Br-6-O$_2$N— | 419 | 2-I-3-O$_2$N— | 420 | 2-I-4-O$_2$N— |
| 421 | 2-I-5-O$_2$N— | 422 | 2-I-6-O$_2$N— | 423 | 2-Me-3-O$_2$N— |
| 424 | 2-Me-4-O$_2$N— | 425 | 2-Me-5-O$_2$N— | 426 | 2-Me-6-O$_2$N— |
| 427 | 2-F-3-Me— | 428 | 2-F-4-Me— | 429 | 2-F-5-Me— |
| 430 | 2-F-6-Me— | 431 | 2-Cl-3-Me— | 432 | 2-Cl-4-Me— |
| 433 | 2-Cl-5-Me— | 434 | 2-Cl-6-Me— | 435 | 2-Br-3-Me— |
| 436 | 2-Br-4-Me— | 437 | 2-Br-5-Me— | 438 | 2-Br-6-Me— |
| 439 | 2-I-3-Me— | 440 | 2-I-4-Me— | 441 | 2-I-5-Me— |
| 442 | 2-I-6-Me— | 443 | 2,3-di-Me— | 444 | 2,4-di-Me— |
| 445 | 2,5-di-Me— | 446 | 2,6-di-Me— | 447 | 2-F-3-Et— |
| 448 | 2-F-4-Et— | 449 | 2-F-5-Et— | 450 | 2-F-6-Et— |
| 451 | 2-Cl-3-Et— | 452 | 2-Cl-4-Et— | 453 | 2-Cl-5-Et— |
| 454 | 2-Cl-6-Et— | 455 | 2-Br-3-Et— | 456 | 2-Br-4-Et— |
| 457 | 2-Br-5-Et— | 458 | 2-Br-6-Et— | 459 | 2-I-3-Et— |
| 460 | 2-I-4-Et— | 461 | 2-I-5-Et— | 462 | 2-I-6-Et— |
| 463 | 2-Me-3-Et— | 464 | 2-Me-4-Et— | 465 | 2-Me-5-Et— |
| 466 | 2-Me-6-Et— | 467 | 2-F-3-Pr— | 468 | 2-F-4-Pr— |
| 469 | 2-F-5-Pr— | 470 | 2-F-6-Pr— | 471 | 2-Cl-3-Pr— |
| 472 | 2-Cl-4-Pr— | 473 | 2-Cl-5-Pr— | 474 | 2-Cl-6-Pr— |
| 475 | 2-Br-3-Pr— | 476 | 2-Br-4-Pr— | 477 | 2-Br-5-Pr— |
| 478 | 2-Br-6-Pr— | 479 | 2-I-3-Pr— | 480 | 2-I-4-Pr— |
| 481 | 2-I-5-Pr— | 482 | 2-I-6-Pr— | 483 | 2-Me-3-Pr— |
| 484 | 2-Me-4-Pr— | 485 | 2-Me-5-Pr— | 486 | 2-Me-6-Pr— |
| 487 | 2-F-3-iPr— | 488 | 2-F-4-iPr— | 489 | 2-F-5-iPr— |
| 490 | 2-F-6-iPr— | 491 | 2-Cl-3-iPr— | 492 | 2-Cl-4-iPr— |
| 493 | 2-Cl-5-iPr— | 494 | 2-Cl-6-iPr— | 495 | 2-Br-3-iPr— |
| 496 | 2-Br-4-iPr— | 497 | 2-Br-5-iPr— | 498 | 2-Br-6-iPr— |
| 499 | 2-I-3-iPr— | 500 | 2-I-4-iPr— | 501 | 2-I-5-iPr— |
| 502 | 2-I-6-iPr— | 503 | 2-Me-3-iPr— | 504 | 2-Me-4-iPr— |
| 505 | 2-Me-5-iPr— | 506 | 2-Me-6-iPr— | 507 | 2-F-3-N≡CCH$_2$— |
| 508 | 2-F-4-N≡CCH$_2$— | 509 | 2-F-5-N≡CCH$_2$— | 510 | 2-F-6-N≡CCH$_2$— |
| 511 | 2-Cl-3-N≡CCH$_2$— | 512 | 2-Cl-4-N≡CCH$_2$— | 513 | 2-Cl-5-N≡CCH$_2$— |
| 514 | 2-Cl-6-N≡CCH$_2$— | 515 | 2-Br-3-N≡CCH$_2$— | 516 | 2-Br-4-N≡CCH$_2$— |
| 517 | 2-Br-5-N≡CCH$_2$— | 518 | 2-Br-6-N≡CCH$_2$— | 519 | 2-I-3-N≡CCH$_2$— |
| 520 | 2-I-4-N≡CCH$_2$— | 521 | 2-I-5-N≡CCH$_2$— | 522 | 2-I-6-N≡CCH$_2$— |
| 523 | 2-Me-3-N≡CCH$_2$— | 524 | 2-Me-4-N≡CCH$_2$— | 525 | 2-Me-5-N≡CCH$_2$— |
| 526 | 2-Me-6-N≡CCH$_2$— | 527 | 2-F-3-N≡CCH$_2$CH$_2$— | 528 | 2-F-4-N≡CCH$_2$CH$_2$— |
| 529 | 2-F-5-N≡CCH$_2$CH$_2$— | 530 | 2-F-6-N≡CCH$_2$CH$_2$— | 531 | 2-Cl-3-N≡CCH$_2$CH$_2$— |
| 532 | 2-Cl-4-N≡CCH$_2$CH$_2$— | 533 | 2-Cl-5-N≡CCH$_2$CH$_2$— | 534 | 2-Cl-6-N≡CCH$_2$CH$_2$— |
| 535 | 2-Br-3-N≡CCH$_2$CH$_2$— | 536 | 2-Br-4-N≡CCH$_2$CH$_2$— | 537 | 2-Br-5-N≡CCH$_2$CH$_2$— |
| 538 | 2-Br-6-N≡CCH$_2$CH$_2$— | 539 | 2-I-3-N≡CCH$_2$CH$_2$— | 540 | 2-I-4-N≡CCH$_2$CH$_2$— |
| 541 | 2-I-5-N≡CCH$_2$CH$_2$— | 542 | 2-I-6-N≡CCH$_2$CH$_2$— | 543 | 2-Me-3-N≡CCH$_2$CH$_2$— |
| 544 | 2-Me-4-N≡CCH$_2$CH$_2$— | 545 | 2-Me-5-N≡CCH$_2$CH$_2$— | 546 | 2-Me-6-N≡CCH$_2$CH$_2$— |
| 547 | 2-F-3-cPrCH$_2$— | 548 | 2-F-4-cPrCH$_2$— | 549 | 2-F-5-cPrCH$_2$— |
| 550 | 2-F-6-cPrCH$_2$— | 551 | 2-Cl-3-cPrCH$_2$— | 552 | 2-Cl-4-cPrCH$_2$— |
| 553 | 2-Cl-5-cPrCH$_2$— | 554 | 2-Cl-6-cPrCH$_2$— | 555 | 2-Br-3-cPrCH$_2$— |
| 556 | 2-Br-4-cPrCH$_2$— | 557 | 2-Br-5-cPrCH$_2$— | 558 | 2-Br-6-cPrCH$_2$— |
| 559 | 2-I-3-cPrCH$_2$— | 560 | 2-I-4-cPrCH$_2$— | 561 | 2-I-5-cPrCH$_2$— |
| 562 | 2-I-6-cPrCH$_2$— | 563 | 2-Me-3-cPrCH$_2$— | 564 | 2-Me-4-cPrCH$_2$— |
| 565 | 2-Me-5-cPrCH$_2$— | 566 | 2-Me-6-cPrCH$_2$— | 567 | 2-F-3-cBuCH$_2$— |
| 568 | 2-F-4-cBuCH$_2$— | 569 | 2-F-5-cBuCH$_2$— | 570 | 2-F-6-cBuCH$_2$— |
| 571 | 2-Cl-3-cBuCH$_2$— | 572 | 2-Cl-4-cBuCH$_2$— | 573 | 2-Cl-5-cBuCH$_2$— |

TABLE 2-continued

| No. | (R2)n | No. | (R2)n | No. | (R2)n |
|---|---|---|---|---|---|
| 574 | 2-Cl-6-cBuCH$_2$— | 575 | 2-Br-3-cBuCH$_2$— | 576 | 2-Br-4-cBuCH$_2$— |
| 577 | 2-Br-5-cBuCH$_2$— | 578 | 2-Br-6-cBuCH$_2$— | 579 | 2-I-3-cBuCH$_2$— |
| 580 | 2-I-4-cBuCH$_2$— | 581 | 2-I-5-cBuCH$_2$— | 582 | 2-I-6-cBuCH$_2$— |
| 583 | 2-Me-3-cBuCH$_2$— | 584 | 2-Me-4-cBuCH$_2$— | 585 | 2-Me-5-cBuCH$_2$— |
| 586 | 2-Me-6-cBuCH$_2$— | 587 | 2-F-3-MeOCH$_2$— | 588 | 2-F-4-MeOCH$_2$— |
| 589 | 2-F-5-MeOCH$_2$— | 590 | 2-F-6-MeOCH$_2$— | 591 | 2-Cl-3-MeOCH$_2$— |
| 592 | 2-Cl-4-MeOCH$_2$- | 593 | 2-Cl-5-MeOCH$_2$— | 594 | 2-Cl-6-MeOCH$_2$— |
| 595 | 2-Br-3-MeOCH$_2$— | 596 | 2-Br-4-MeOCH$_2$— | 597 | 2-Br-5-MeOCH$_2$— |
| 598 | 2-Br-6-MeOCH$_2$— | 599 | 2-I-3-MeOCH$_2$— | 600 | 2-I-4-MeOCH$_2$— |
| 601 | 2-I-5-MeOCH$_2$— | 602 | 2-I-6-MeOCH$_2$— | 603 | 2-Me-3-MeOCH$_2$— |
| 604 | 2-Me-4-MeOCH$_2$— | 605 | 2-Me-5-MeOCH$_2$— | 606 | 2-Me-6-MeOCH$_2$— |
| 607 | 2-F-3-MeOCH$_2$CH$_2$— | 608 | 2-F-4-MeOCH$_2$CH$_2$— | 609 | 2-F-5-MeOCH$_2$CH$_2$— |
| 610 | 2-F-6-MeOCH$_2$CH$_2$— | 611 | 2-Cl-3-MeOCH$_2$CH$_2$— | 612 | 2-Cl-4-MeOCH$_2$CH$_2$— |
| 613 | 2-Cl-5-MeOCH$_2$CH$_2$— | 614 | 2-Cl-6-MeOCH$_2$CH$_2$— | 615 | 2-Br-3-MeOCH$_2$CH$_2$— |
| 616 | 2-Br-4-MeOCH$_2$CH$_2$— | 617 | 2-Br-5-MeOCH$_2$CH$_2$— | 618 | 2-Br-6-MeOCH$_2$CH$_2$— |
| 619 | 2-I-3-MeOCH$_2$CH$_2$— | 620 | 2-I-4-MeOCH$_2$CH$_2$— | 621 | 2-I-5-MeOCH$_2$CH$_2$— |
| 622 | 2-I-6-MeOCH$_2$CH$_2$— | 623 | 2-Me-3-MeOCH$_2$CH$_2$— | 624 | 2-Me-4-MeOCH$_2$CH$_2$— |
| 625 | 2-Me-5-MeOCH$_2$CH$_2$— | 626 | 2-Me-6-MeOCH$_2$CH$_2$— | 627 | 2-F-3-MeOCH$_2$CH$_2$CH$_2$— |
| 628 | 2-F-4-MeOCH$_2$CH$_2$CH$_2$— | 629 | 2-F-5-MeOCH$_2$CH$_2$CH$_2$— | 630 | 2-F-6-MeOCH$_2$CH$_2$CH$_2$— |
| 631 | 2-Cl-3-MeOCH$_2$CH$_2$CH$_2$— | 632 | 2-Cl-4-MeOCH$_2$CH$_2$CH$_2$— | 633 | 2-Cl-5-MeOCH$_2$CH$_2$CH$_2$— |
| 634 | 2-Cl-6-MeOCH$_2$CH$_2$CH$_2$— | 635 | 2-Br-3-MeOCH$_2$CH$_2$CH$_2$— | 636 | 2-Br-4-MeOCH$_2$CH$_2$CH$_2$— |
| 637 | 2-Br-5-MeOCH$_2$CH$_2$CH$_2$— | 638 | 2-Br-6-MeOCH$_2$CH$_2$CH$_2$— | 639 | 2-I-3-MeOCH$_2$CH$_2$CH$_2$— |
| 640 | 2-I-4-MeOCH$_2$CH$_2$CH$_2$— | 641 | 2-I-5-MeOCH$_2$CH$_2$CH$_2$— | 642 | 2-I-6-MeOCH$_2$CH$_2$CH$_2$— |
| 643 | 2-Me-3-MeOCH$_2$CH$_2$CH$_2$— | 644 | 2-Me-4-MeOCH$_2$CH$_2$CH$_2$— | 645 | 2-Me-5-MeOCH$_2$CH$_2$CH$_2$— |
| 646 | 2-Me-6-MeOCH$_2$CH$_2$CH$_2$— | 647 | 2-F-3-EtOCH$_2$— | 648 | 2-F-4-EtOCH$_2$— |
| 649 | 2-F-5-EtOCH$_2$— | 650 | 2-F-6-EtOCH$_2$— | 651 | 2-Cl-3-EtOCH$_2$— |
| 652 | 2-Cl-4-EtOCH$_2$— | 653 | 2-Cl-5-EtOCH$_2$— | 654 | 2-Cl-6-EtOCH$_2$— |
| 655 | 2-Br-3-EtOCH$_2$— | 656 | 2-Br-4-EtOCH$_2$— | 657 | 2-Br-5-EtOCH$_2$— |
| 658 | 2-Br-6-EtOCH$_2$— | 659 | 2-I-3-EtOCH$_2$— | 660 | 2-I-4-EtOCH$_2$— |
| 661 | 2-I-5-EtOCH$_2$— | 662 | 2-I-6-EtOCH$_2$— | 663 | 2-Me-3-EtOCH$_2$— |
| 664 | 2-Me-4-EtOCH$_2$— | 665 | 2-Me-5-EtOCH$_2$— | 666 | 2-Me-6-EtOCH$_2$— |
| 667 | 2-F-3-EtOCH$_2$CH$_2$— | 668 | 2-F-4-EtOCH$_2$CH$_2$— | 669 | 2-F-5-EtOCH$_2$CH$_2$— |
| 670 | 2-F-6-EtOCH$_2$CH$_2$— | 671 | 2-Cl-3-EtOCH$_2$CH$_2$— | 672 | 2-Cl-4-EtOCH$_2$CH$_2$— |
| 673 | 2-Cl-5-EtOCH$_2$CH$_2$— | 674 | 2-Cl-6-EtOCH$_2$CH$_2$— | 675 | 2-Br-3-EtOCH$_2$CH$_2$— |
| 676 | 2-Br-4-EtOCH$_2$CH$_2$— | 677 | 2-Br-5-EtOCH$_2$CH$_2$— | 678 | 2-Br-6-EtOCH$_2$CH$_2$— |
| 679 | 2-I-3-EtOCH$_2$CH$_2$— | 680 | 2-I-4-EtOCH$_2$CH$_2$— | 681 | 2-I-5-EtOCH$_2$CH$_2$— |
| 682 | 2-I-6-EtOCH$_2$CH$_2$— | 683 | 2-Me-3-EtOCH$_2$CH$_2$- | 684 | 2-Me-4-EtOCH$_2$CH$_2$— |
| 685 | 2-Me-5-EtOCH$_2$CH$_2$— | 686 | 2-Me-6-EtOCH$_2$CH$_2$— | 687 | 2-F-3-cPrOCH$_2$— |
| 688 | 2-F-4-cPrOCH$_2$— | 689 | 2-F-5-cPrOCH$_2$— | 690 | 2-F-6-cPrOCH$_2$— |
| 691 | 2-Cl-3-cPrOCH$_2$— | 692 | 2-Cl-4-cPrOCH$_2$— | 693 | 2-Cl-5-cPrOCH$_2$— |
| 694 | 2-Cl-6-cPrOCH$_2$— | 695 | 2-Br-3-cPrOCH$_2$— | 696 | 2-Br-4-cPrOCH$_2$— |
| 697 | 2-Br-5-cPrOCH$_2$— | 698 | 2-Br-6-cPrOCH$_2$— | 699 | 2-I-3-cPrOCH$_2$— |
| 700 | 2-I-4-cPrOCH$_2$— | 701 | 2-I-5-cPrOCH$_2$— | 702 | 2-I-6-cPrOCH$_2$— |
| 703 | 2-Me-3-cPrOCH$_2$— | 704 | 2-Me-4-cPrOCH$_2$— | 705 | 2-Me-5-cPrOCH$_2$— |
| 706 | 2-Me-6-cPrOCH$_2$— | 707 | 2-F-3-F$_3$COCH$_2$— | 708 | 2-F-4-F$_3$COCH$_2$— |
| 709 | 2-F-5-F$_3$COCH$_2$— | 710 | 2-F-6-F$_3$COCH$_2$— | 711 | 2-Cl-3-F$_3$COCH$_2$— |
| 712 | 2-Cl-4-F$_3$COCH$_2$— | 713 | 2-Cl-5-F$_3$COCH$_2$— | 714 | 2-Cl-6-F$_3$COCH$_2$— |
| 715 | 2-Br-3-F$_3$COCH$_2$— | 716 | 2-Br-4-F$_3$COCH$_2$— | 717 | 2-Br-5-F$_3$COCH$_2$— |
| 718 | 2-Br-6-F$_3$COCH$_2$— | 719 | 2-I-3-F$_3$COCH$_2$— | 720 | 2-I-4-F$_3$COCH$_2$— |
| 721 | 2-I-5-F$_3$COCH$_2$— | 722 | 2-I-6-F$_3$COCH$_2$— | 723 | 2-Me-3-F$_3$COCH$_2$— |
| 724 | 2-Me-4-F$_3$COCH$_2$— | 725 | 2-Me-5-F$_3$COCH$_2$— | 726 | 2-Me-6-F$_3$COCH$_2$— |
| 727 | 2-F-3-F$_2$CHOCH$_2$— | 728 | 2-F-4-F$_2$CHOCH$_2$— | 729 | 2-F-5-F$_2$CHOCH$_2$— |
| 730 | 2-F-6-F$_2$CHOCH$_2$— | 731 | 2-Cl-3-F$_2$CHOCH$_2$— | 732 | 2-Cl-4-F$_2$CHOCH$_2$— |
| 733 | 2-Cl-5-F$_2$CHOCH$_2$— | 734 | 2-Cl-6-F$_2$CHOCH$_2$— | 735 | 2-Br-3-F$_2$CHOCH$_2$— |
| 736 | 2-Br-4-F$_2$CHOCH$_2$— | 737 | 2-Br-5-F$_2$CHOCH$_2$— | 738 | 2-Br-6-F$_2$CHOCH$_2$— |
| 739 | 2-I-3-F$_2$CHOCH$_2$— | 740 | 2-I-4-F$_2$CHOCH$_2$— | 741 | 2-I-5-F$_2$CHOCH$_2$— |
| 742 | 2-I-6-F$_2$CHOCH$_2$— | 743 | 2-Me-3-F$_2$CHOCH$_2$— | 744 | 2-Me-4-F$_2$CHOCH$_2$— |
| 745 | 2-Me-5-F$_2$CHOCH$_2$— | 746 | 2-Me-6-F$_2$CHOCH$_2$— | 747 | 2-F-3-MeOCH$_2$CH$_2$OCH$_2$— |
| 748 | 2-F-4-MeOCH$_2$CH$_2$OCH$_2$— | 749 | 2-F-5-MeOCH$_2$CH$_2$OCH$_2$— | 750 | 2-F-6-MeOCH$_2$CH$_2$OCH$_2$— |
| 751 | 2-Cl-3-MeOCH$_2$CH$_2$OCH$_2$— | 752 | 2-Cl-4-MeOCH$_2$CH$_2$OCH$_2$— | 753 | 2-Cl-5-MeOCH$_2$CH$_2$OCH$_2$— |
| 754 | 2-Cl-6-MeOCH$_2$CH$_2$OCH$_2$— | 755 | 2-Br-3-MeOCH$_2$CH$_2$OCH$_2$— | 756 | 2-Br-4-MeOCH$_2$CH$_2$OCH$_2$— |
| 757 | 2-Br-5-MeOCH$_2$CH$_2$OCH$_2$— | 758 | 2-Br-6-MeOCH$_2$CH$_2$OCH$_2$— | 759 | 2-I-3-MeOCH$_2$CH$_2$OCH$_2$— |
| 760 | 2-I-4-MeOCH$_2$CH$_2$OCH$_2$— | 761 | 2-I-5-MeOCH$_2$CH$_2$OCH$_2$— | 762 | 2-I-6-MeOCH$_2$CH$_2$OCH$_2$— |
| 763 | 2-Me-3-MeOCH$_2$CH$_2$OCH$_2$— | 764 | 2-Me-4-MeOCH$_2$CH$_2$OCH$_2$— | 765 | 2-Me-5-MeOCH$_2$CH$_2$OCH$_2$— |

TABLE 2-continued

| No. | (R2)n | No. | (R2)n | No. | (R2)n |
|---|---|---|---|---|---|
| 766 | 2-Me-6-MeOCH$_2$CH$_2$OCH$_2$— | 767 | 2-F-3-Me$_2$NCH$_2$— | 768 | 2-F-4-Me$_2$NCH$_2$— |
| 769 | 2-F-5-Me$_2$NCH$_2$— | 770 | 2-F-6-Me$_2$NCH$_2$— | 771 | 2-Cl-3-Me$_2$NCH$_2$— |
| 772 | 2-Cl-4-Me$_2$NCH$_2$— | 773 | 2-Cl-5-Me$_2$NCH$_2$— | 774 | 2-Cl-6-Me$_2$NCH$_2$— |
| 775 | 2-Br-3-Me$_2$NCH$_2$— | 776 | 2-Br-4-Me$_2$NCH$_2$— | 777 | 2-Br-5-Me$_2$NCH$_2$— |
| 778 | 2-Br-6-Me$_2$NCH$_2$— | 779 | 2-I-3-Me$_2$NCH$_2$— | 780 | 2-I-4-Me$_2$NCH$_2$— |
| 781 | 2-I-5-Me$_2$NCH$_2$— | 782 | 2-I-6-Me$_2$NCH$_2$— | 783 | 2-Me-3-Me$_2$NCH$_2$— |
| 784 | 2-Me-4-Me$_2$NCH$_2$— | 785 | 2-Me-5-Me$_2$NCH$_2$— | 786 | 2-Me-6-Me$_2$NCH$_2$— |
| 787 | 2-F-3-MeSCH$_2$— | 788 | 2-F-4-MeSCH$_2$— | 789 | 2-F-5-MeSCH$_2$— |
| 790 | 2-F-6-MeSCH$_2$— | 791 | 2-Cl-3-MeSCH$_2$— | 792 | 2-Cl-4-MeSCH$_2$— |
| 793 | 2-Cl-5-MeSCH$_2$— | 794 | 2-Cl-6-MeSCH$_2$— | 795 | 2-Br-3-MeSCH$_2$— |
| 796 | 2-Br-4-MeSCH$_2$— | 797 | 2-Br-5-MeSCH$_2$— | 798 | 2-Br-6-MeSCH$_2$— |
| 799 | 2-I-3-MeSCH$_2$— | 800 | 2-I-4-MeSCH$_2$— | 801 | 2-I-5-MeSCH$_2$— |
| 802 | 2-I-6-MeSCH$_2$— | 803 | 2-Me-3-MeSCH$_2$— | 804 | 2-Me-4-MeSCH$_2$— |
| 805 | 2-Me-5-MeSCH$_2$— | 806 | 2-Me-6-MeSCH$_2$— | 807 | 2-F-3-MeS(O)CH$_2$— |
| 808 | 2-F-4-MeS(O)CH$_2$— | 809 | 2-F-5-MeS(O)CH$_2$— | 810 | 2-F-6-MeS(O)CH$_2$— |
| 811 | 2-Cl-3-MeS(O)CH$_2$— | 812 | 2-Cl-4-MeS(O)CH$_2$— | 813 | 2-Cl-5-MeS(O)CH$_2$— |
| 814 | 2-Cl-6-MeS(O)CH$_2$— | 815 | 2-Br-3-MeS(O)CH$_2$— | 816 | 2-Br-4-MeS(O)CH$_2$— |
| 817 | 2-Br-5-MeS(O)CH$_2$— | 818 | 2-Br-6-MeS(O)CH$_2$— | 819 | 2-I-3-MeS(O)CH$_2$— |
| 820 | 2-I-4-MeS(O)CH$_2$— | 821 | 2-I-5-MeS(O)CH$_2$— | 822 | 2-I-6-MeS(O)CH$_2$— |
| 823 | 2-Me-3-MeS(O)CH$_2$— | 824 | 2-Me-4-MeS(O)CH$_2$— | 825 | 2-Me-5-MeS(O)CH$_2$— |
| 826 | 2-Me-6-MeS(O)CH$_2$— | 827 | 2-F-3-MeSO$_2$CH$_2$— | 828 | 2-F-4-MeSO$_2$CH$_2$— |
| 829 | 2-F-5-MeSO$_2$CH$_2$— | 830 | 2-F-6-MeSO$_2$CH$_2$— | 831 | 2-Cl-3-MeSO$_2$CH$_2$— |
| 832 | 2-Cl-4-MeSO$_2$CH$_2$— | 833 | 2-Cl-5-MeSO$_2$CH$_2$— | 834 | 2-Cl-6-MeSO$_2$CH$_2$— |
| 835 | 2-Br-3-MeSO$_2$CH$_2$— | 836 | 2-Br-4-MeSO$_2$CH$_2$— | 837 | 2-Br-5-MeSO$_2$CH$_2$— |
| 838 | 2-Br-6-MeSO$_2$CH$_2$— | 839 | 2-I-3-MeSO$_2$CH$_2$— | 840 | 2-I-4-MeSO$_2$CH$_2$— |
| 841 | 2-I-5-MeSO$_2$CH$_2$— | 842 | 2-I-6-MeSO$_2$CH$_2$— | 843 | 2-Me-3-MeSO$_2$CH$_2$— |
| 844 | 2-Me-4-MeSO$_2$CH$_2$— | 845 | 2-Me-5-MeSO$_2$CH$_2$— | 846 | 2-Me-6-MeSO$_2$CH$_2$— |
| 847 | 2-F-3-cPr— | 848 | 2-F-4-cPr— | 849 | 2-F-5-cPr— |
| 850 | 2-F-6-cPr— | 851 | 2-Cl-3-cPr— | 852 | 2-Cl-4-cPr— |
| 853 | 2-Cl-5-cPr— | 854 | 2-Cl-6-cPr— | 855 | 2-Br-3-cPr— |
| 856 | 2-Br-4-cPr— | 857 | 2-Br-5-cPr— | 858 | 2-Br-6-cPr— |
| 859 | 2-I-3-cPr— | 860 | 2-I-4-cPr— | 861 | 2-I-5-cPr— |
| 862 | 2-I-6-cPr— | 863 | 2-Me-3-cPr— | 864 | 2-Me-4-cPr— |
| 865 | 2-Me-5-cPr— | 866 | 2-Me-6-cPr— | 867 | 2-F-3-cBu— |
| 868 | 2-F-4-cBu— | 869 | 2-F-5-cBu— | 870 | 2-F-6-cBu— |
| 871 | 2-Cl-3-cBu— | 872 | 2-Cl-4-cBu— | 873 | 2-Cl-5-cBu— |
| 874 | 2-Cl-6-cBu— | 875 | 2-Br-3-cBu— | 876 | 2-Br-4-cBu— |
| 877 | 2-Br-5-cBu— | 878 | 2-Br-6-cBu— | 879 | 2-I-3-cBu— |
| 880 | 2-I-4-cBu— | 881 | 2-I-5-cBu— | 882 | 2-I-6-cBu— |
| 883 | 2-Me-3-cBu— | 884 | 2-Me-4-cBu— | 885 | 2-Me-5-cBu— |
| 886 | 2-Me-6-cBu— | 887 | 2-F-3-F$_3$C— | 888 | 2-F-4-F$_3$C— |
| 889 | 2-F-5-F$_3$C— | 890 | 2-F-6-F$_3$C— | 891 | 2-Cl-3-F$_3$C— |
| 892 | 2-Cl-4-F$_3$C— | 893 | 2-Cl-5-F$_3$C— | 894 | 2-Cl-6-F$_3$C— |
| 895 | 2-Br-3-F$_3$C— | 896 | 2-Br-4-F$_3$C— | 897 | 2-Br-5-F$_3$C— |
| 898 | 2-Br-6-F$_3$C— | 899 | 2-I-3-F$_3$C— | 900 | 2-I-4-F$_3$C— |
| 901 | 2-I-5-F$_3$C— | 902 | 2-I-6-F$_3$C— | 903 | 2-Me-3-F$_3$C— |
| 904 | 2-Me-4-F$_3$C— | 905 | 2-Me-5-F$_3$C— | 906 | 2-Me-6-F$_3$C— |
| 907 | 2-F-3-F$_2$CH— | 908 | 2-F-4-F$_2$CH— | 909 | 2-F-5-F$_2$CH— |
| 910 | 2-F-6-F$_2$CH— | 911 | 2-Cl-3-F$_2$CH— | 912 | 2-Cl-4-F$_2$CH— |
| 913 | 2-Cl-5-F$_2$CH— | 914 | 2-Cl-6-F$_2$CH— | 915 | 2-Br-3-F$_2$CH— |
| 916 | 2-Br-4-F$_2$CH— | 917 | 2-Br-5-F$_2$CH— | 918 | 2-Br-6-F$_2$CH— |
| 919 | 2-I-3-F$_2$CH— | 920 | 2-I-4-F$_2$CH— | 921 | 2-I-5-F$_2$CH— |
| 922 | 2-I-6-F$_2$CH— | 923 | 2-Me-3-F$_2$CH— | 924 | 2-Me-4-F$_2$CH— |
| 925 | 2-Me-5-F$_2$CH— | 926 | 2-Me-6-F$_2$CH— | 927 | 2-F-3-H$_2$C=CH— |
| 928 | 2-F-4-H$_2$C=CH— | 929 | 2-F-5-H$_2$C=CH— | 930 | 2-F-6-H$_2$C=CH— |
| 931 | 2-Cl-3-H$_2$C=CH— | 932 | 2-Cl-4-H$_2$C=CH— | 933 | 2-Cl-5-H$_2$C=CH— |
| 934 | 2-Cl-6-H$_2$C=CH— | 935 | 2-Br-3-H$_2$C=CH— | 936 | 2-Br-4-H$_2$C=CH— |
| 937 | 2-Br-5-H$_2$C=CH— | 938 | 2-Br-6-H$_2$C=CH— | 939 | 2-I-3-H$_2$C=CH— |
| 940 | 2-I-4-H$_2$C=CH— | 941 | 2-I-5-H$_2$C=CH— | 942 | 2-I-6-H$_2$C=CH— |
| 943 | 2-Me-3-H$_2$C=CH— | 944 | 2-Me-4-H$_2$C=CH— | 945 | 2-Me-5-H$_2$C=CH— |
| 946 | 2-Me-6-H$_2$C=CH— | 947 | 2-F-3-H$_2$C=CHCH$_2$— | 948 | 2-F-4-H$_2$C=CHCH$_2$— |
| 949 | 2-F-5-H$_2$C=CHCH$_2$— | 950 | 2-F-6-H$_2$C=CHCH$_2$— | 951 | 2-Cl-3-H$_2$C=CHCH$_2$— |
| 952 | 2-Cl-4-H$_2$C=CHCH$_2$— | 953 | 2-Cl-5-H$_2$C=CHCH$_2$— | 954 | 2-Cl-6-H$_2$C=CHCH$_2$— |
| 955 | 2-Br-3-H$_2$C=CHCH$_2$— | 956 | 2-Br-4-H$_2$C=CHCH$_2$— | 957 | 2-Br-5-H$_2$C=CHCH$_2$— |
| 958 | 2-Br-6-H$_2$C=CHCH$_2$— | 959 | 2-I-3-H$_2$C=CHCH$_2$— | 960 | 2-I-4-H$_2$C=CHCH$_2$— |
| 961 | 2-I-5-H$_2$C=CHCH$_2$— | 962 | 2-I-6-H$_2$C=CHCH$_2$— | 963 | 2-Me-3-H$_2$C=CHCH$_2$— |
| 964 | 2-Me-4-H$_2$C=CHCH$_2$— | 965 | 2-Me-5-H$_2$C=CHCH$_2$— | 966 | 2-Me-6-H$_2$C=CHCH$_2$— |
| 967 | 2-F-3-F$_2$C=CH— | 968 | 2-F-4-F$_2$C=CH— | 969 | 2-F-5-F$_2$C=CH— |
| 970 | 2-F-6-F$_2$C=CH— | 971 | 2-Cl-3-F$_2$C=CH— | 972 | 2-Cl-4-F$_2$C=CH— |
| 973 | 2-Cl-5-F$_2$C=CH— | 974 | 2-Cl-6-F$_2$C=CH— | 975 | 2-Br-3-F$_2$C=CH— |
| 976 | 2-Br-4-F$_2$C=CH— | 977 | 2-Br-5-F$_2$C=CH— | 978 | 2-Br-6-F$_2$C=CH— |
| 979 | 2-I-3-F$_2$C=CH— | 980 | 2-I-4-F$_2$C=CH— | 981 | 2-I-5-F$_2$C=CH— |
| 982 | 2-I-6-F$_2$C=CH— | 983 | 2-Me-3-F$_2$C=CH— | 984 | 2-Me-4-F$_2$C=CH— |
| 985 | 2-Me-5-F$_2$C=CH— | 986 | 2-Me-6-F$_2$C=CH— | 987 | 2-F-3-F$_2$C=CHCH$_2$— |
| 988 | 2-F-4-F$_2$C=CHCH$_2$— | 989 | 2-F-5-F$_2$C=CHCH$_2$— | 990 | 2-F-6-F$_2$C=CHCH$_2$— |
| 991 | 2-Cl-3-F$_2$C=CHCH$_2$— | 992 | 2-Cl-4-F$_2$C=CHCH$_2$— | 993 | 2-Cl-5-F$_2$C=CHCH$_2$— |
| 994 | 2-Cl-6-F$_2$C=CHCH$_2$— | 995 | 2-Br-3-F$_2$C=CHCH$_2$— | 996 | 2-Br-4-F$_2$C=CHCH$_2$— |

TABLE 2-continued

| No. | (R2)n | No. | (R2)n | No. | (R2)n |
|---|---|---|---|---|---|
| 997 | 2-Br-5-F$_2$C=CHCH$_2$— | 998 | 2-Br-6-F$_2$C=CHCH$_2$— | 999 | 2-I-3-F$_2$C=CHCH$_2$— |
| 1000 | 2-I-4-F$_2$C=CHCH$_2$— | 1001 | 2-I-5-F$_2$C=CHCH$_2$— | 1002 | 2-I-6-F$_2$C=CHCH$_2$— |
| 1003 | 2-Me-3-F$_2$C=CHCH$_2$— | 1004 | 2-Me-4-F$_2$C=CHCH$_2$— | 1005 | 2-Me-5-F$_2$C=CHCH$_2$— |
| 1006 | 2-Me-6-F$_2$C=CHCH$_2$— | 1007 | 2-F-3-HC≡C— | 1008 | 2-F-4-HC≡C— |
| 1009 | 2-F-5-HC≡C— | 1010 | 2-F-6-HC≡C— | 1011 | 2-Cl-3-HC≡C— |
| 1012 | 2-Cl-4-HC≡C— | 1013 | 2-Cl-5-HC≡C— | 1014 | 2-Cl-6-HC≡C— |
| 1015 | 2-Br-3-HC≡C— | 1016 | 2-Br-4-HC≡C— | 1017 | 2-Br-5-HC≡C— |
| 1018 | 2-Br-6-HC≡C— | 1019 | 2-I-3-HC≡C— | 1020 | 2-I-4-HC≡C— |
| 1021 | 2-I-5-HC≡C— | 1022 | 2-I-6-HC≡C— | 1023 | 2-Me-3-HC≡C— |
| 1024 | 2-Me-4-HC≡C— | 1025 | 2-Me-5-HC≡C— | 1026 | 2-Me-6-HC≡C— |
| 1027 | 2-F-3-HC≡CCH$_2$— | 1028 | 2-F-4-HC≡CCH$_2$— | 1029 | 2-F-5-HC≡CCH$_2$— |
| 1030 | 2-F-6-HC≡CCH$_2$— | 1031 | 2-Cl-3-HC≡CCH$_2$— | 1032 | 2-Cl-4-HC≡CCH$_2$— |
| 1033 | 2-Cl-5-HC≡CCH$_2$— | 1034 | 2-Cl-6-HC≡CCH$_2$— | 1035 | 2-Br-3-HC≡CCH$_2$— |
| 1036 | 2-Br-4-HC≡CCH$_2$— | 1037 | 2-Br-5-HC≡CCH$_2$— | 1038 | 2-Br-6-HC≡CCH$_2$— |
| 1039 | 2-I-3-HC≡CCH$_2$— | 1040 | 2-I-4-HC≡CCH$_2$— | 1041 | 2-I-5-HC≡CCH$_2$— |
| 1042 | 2-I-6-HC≡CCH$_2$— | 1043 | 2-Me-3-HC≡CCH$_2$— | 1044 | 2-Me-4-HC≡CCH$_2$— |
| 1045 | 2-Me-5-HC≡CCH$_2$— | 1046 | 2-Me-6-HC≡CCH$_2$— | 1047 | 2-F-3-F$_3$CC≡C— |
| 1048 | 2-F-4-F$_3$CC≡C— | 1049 | 2-F-5-F$_3$CC≡C— | 1050 | 2-F-6-F$_3$CC≡C— |
| 1051 | 2-Cl-3-F$_3$CC≡C— | 1052 | 2-Cl-4-F$_3$CC≡C— | 1053 | 2-Cl-5-F$_3$CC≡C— |
| 1054 | 2-Cl-6-F$_3$CC≡C— | 1055 | 2-Br-3-F$_3$CC≡C— | 1056 | 2-Br-4-F$_3$CC≡C— |
| 1057 | 2-Br-5-F$_3$CC≡C— | 1058 | 2-Br-6-F$_3$CC≡C— | 1059 | 2-I-3-F$_3$CC≡C— |
| 1060 | 2-I-4-F$_3$CC≡C— | 1061 | 2-I-5-F$_3$CC≡C— | 1062 | 2-I-6-F$_3$CC≡C— |
| 1063 | 2-Me-3-F$_3$CC≡C— | 1064 | 2-Me-4-F$_3$CC≡C— | 1065 | 2-Me-5-F$_3$CC≡C— |
| 1066 | 2-Me-6-F$_3$CC≡C— | 1067 | 2-F-3-F$_3$CC≡CCH$_2$— | 1068 | 2-F-4-F$_3$CC≡CCH$_2$— |
| 1069 | 2-F-5-F$_3$CC≡CCH$_2$— | 1070 | 2-F-6-F$_3$CC≡CCH$_2$— | 1071 | 2-Cl-3-F$_3$CC≡CCH$_2$— |
| 1072 | 2-Cl-4-F$_3$CC≡CCH$_2$— | 1073 | 2-Cl-5-F$_3$CC≡CCH$_2$— | 1074 | 2-Cl-6-F$_3$CC≡CCH$_2$— |
| 1075 | 2-Br-3-F$_3$CC≡CCH$_2$— | 1076 | 2-Br-4-F$_3$CC≡CCH$_2$— | 1077 | 2-Br-5-F$_3$CC≡CCH$_2$— |
| 1078 | 2-Br-6-F$_3$CC≡CCH$_2$— | 1079 | 2-I-3-F$_3$CC≡CCH$_2$— | 1080 | 2-I-4-F$_3$CC≡CCH$_2$— |
| 1081 | 2-I-5-F$_3$CC≡CCH$_2$— | 1082 | 2-I-6-F$_3$CC≡CCH$_2$— | 1083 | 2-Me-3-F$_3$CC≡CCH$_2$— |
| 1084 | 2-Me-4-F$_3$CC≡CCH$_2$— | 1085 | 2-Me-5-F$_3$CC≡CCH$_2$— | 1086 | 2-Me-6-F$_3$CC≡CCH$_2$— |
| 1087 | 2-F-3-MeO— | 1088 | 2-F-4-MeO— | 1089 | 2-F-5-MeO— |
| 1090 | 2-F-6-MeO— | 1091 | 2-Cl-3-MeO— | 1092 | 2-Cl-4-MeO— |
| 1093 | 2-Cl-5-MeO— | 1094 | 2-Cl-6-MeO— | 1095 | 2-Br-3-MeO— |
| 1096 | 2-Br-4-MeO— | 1097 | 2-Br-5-MeO— | 1098 | 2-Br-6-MeO— |
| 1099 | 2-I-3-MeO— | 1100 | 2-I-4-MeO— | 1101 | 2-I-5-MeO— |
| 1102 | 2-I-6-MeO— | 1103 | 2-Me-3-MeO— | 1104 | 2-Me-4-MeO— |
| 1105 | 2-Me-5-MeO— | 1106 | 2-Me-6-MeO— | 1107 | 2-F-3-EtO— |
| 1108 | 2-F-4-EtO— | 1109 | 2-F-5-EtO— | 1110 | 2-F-6-EtO— |
| 1111 | 2-Cl-3-EtO— | 1112 | 2-Cl-4-EtO— | 1113 | 2-Cl-5-EtO— |
| 1114 | 2-Cl-6-EtO— | 1115 | 2-Br-3-EtO— | 1116 | 2-Br-4-EtO— |
| 1117 | 2-Br-5-EtO— | 1118 | 2-Br-6-EtO— | 1119 | 2-I-3-EtO— |
| 1120 | 2-I-4-EtO— | 1121 | 2-I-5-EtO— | 1122 | 2-I-6-EtO— |
| 1123 | 2-Me-3-EtO— | 1124 | 2-Me-4-EtO— | 1125 | 2-Me-5-EtO— |
| 1126 | 2-Me-6-EtO— | 1127 | 2-F-3-PrO— | 1128 | 2-F-4-PrO— |
| 1129 | 2-F-5-PrO— | 1130 | 2-F-6-PrO— | 1131 | 2-Cl-3-PrO— |
| 1132 | 2-Cl-4-PrO— | 1133 | 2-Cl-5-PrO— | 1134 | 2-Cl-6-PrO— |
| 1135 | 2-Br-3-PrO— | 1136 | 2-Br-4-PrO— | 1137 | 2-Br-5-PrO— |
| 1138 | 2-Br-6-PrO— | 1139 | 2-I-3-PrO— | 1140 | 2-I-4-PrO— |
| 1141 | 2-I-5-PrO— | 1142 | 2-I-6-PrO— | 1143 | 2-Me-3-PrO— |
| 1144 | 2-Me-4-PrO— | 1145 | 2-Me-5-PrO— | 1146 | 2-Me-6-PrO— |
| 1147 | 2-F-3-iPrO— | 1148 | 2-F-4-iPrO— | 1149 | 2-F-5-iPrO— |
| 1150 | 2-F-6-iPrO— | 1151 | 2-Cl-3-iPrO— | 1152 | 2-Cl-4-iPrO— |
| 1153 | 2-Cl-5-iPrO— | 1154 | 2-Cl-6-iPrO— | 1155 | 2-Br-3-iPrO— |
| 1156 | 2-Br-4-iPrO— | 1157 | 2-Br-5-iPrO— | 1158 | 2-Br-6-iPrO— |
| 1159 | 2-I-3-iPrO— | 1160 | 2-I-4-iPrO— | 1161 | 2-I-5-iPrO— |
| 1162 | 2-I-6-iPrO— | 1163 | 2-Me-3-iPrO— | 1164 | 2-Me-4-iPrO— |
| 1165 | 2-Me-5-iPrO— | 1166 | 2-Me-6-iPrO— | 1167 | 2-F-3-BuO— |
| 1168 | 2-F-4-BuO— | 1169 | 2-F-5-BuO— | 1170 | 2-F-6-BuO— |
| 1171 | 2-Cl-3-BuO— | 1172 | 2-Cl-4-BuO— | 1173 | 2-Cl-5-BuO— |
| 1174 | 2-Cl-6-BuO— | 1175 | 2-Br-3-BuO— | 1176 | 2-Br-4-BuO— |
| 1177 | 2-Br-5-BuO— | 1178 | 2-Br-6-BuO— | 1179 | 2-I-3-BuO— |
| 1180 | 2-I-4-BuO— | 1181 | 2-I-5-BuO— | 1182 | 2-I-6-BuO— |
| 1183 | 2-Me-3-BuO— | 1184 | 2-Me-4-BuO— | 1185 | 2-Me-5-BuO— |
| 1186 | 2-Me-6-BuO— | 1187 | 2-F-3-iBuO— | 1188 | 2-F-4-iBuO— |
| 1189 | 2-F-5-iBuO— | 1190 | 2-F-6-iBuO— | 1191 | 2-Cl-3-iBuO— |
| 1192 | 2-Cl-4-iBuO— | 1193 | 2-Cl-5-iBuO— | 1194 | 2-Cl-6-iBuO— |
| 1195 | 2-Br-3-iBuO— | 1196 | 2-Br-4-iBuO— | 1197 | 2-Br-5-iBuO— |
| 1198 | 2-Br-6-iBuO— | 1199 | 2-I-3-iBuO— | 1200 | 2-I-4-iBuO— |
| 1201 | 2-I-5-iBuO— | 1202 | 2-I-6-iBuO— | 1203 | 2-Me-3-iBuO— |
| 1204 | 2-Me-4-iBuO— | 1205 | 2-Me-5-iBuO— | 1206 | 2-Me-6-iBuO— |
| 1207 | 2-F-3-PentylO— | 1208 | 2-F-4-PentylO— | 1209 | 2-F-5-PentylO— |
| 1210 | 2-F-6-PentylO— | 1211 | 2-Cl-3-PentylO— | 1212 | 2-Cl-4-PentylO— |
| 1213 | 2-Cl-5-PentylO— | 1214 | 2-Cl-6-PentylO— | 1215 | 2-Br-3-PentylO— |
| 1216 | 2-Br-4-PentylO— | 1217 | 2-Br-5-PentylO— | 1218 | 2-Br-6-PentylO— |
| 1219 | 2-I-3-PentylO— | 1220 | 2-I-4-PentylO— | 1221 | 2-I-5-PentylO— |
| 1222 | 2-I-6-PentylO— | 1223 | 2-Me-3-PentylO— | 1224 | 2-Me-4-PentylO— |
| 1225 | 2-Me-5-PentylO— | 1226 | 2-Me-6-PentylO— | 1227 | 2-F-3-N=CCH$_2$O— |
| 1228 | 2-F-4-N=CCH$_2$O— | 1229 | 2-F-5-N=CCH$_2$O— | 1230 | 2-F-6-N=CCH$_2$O— |

TABLE 2-continued

| No. | (R2)n | No. | (R2)n | No. | (R2)n |
|---|---|---|---|---|---|
| 1231 | 2-Cl-3-N=CCH$_2$O— | 1232 | 2-Cl-4-N=CCH$_2$O— | 1233 | 2-Cl-5-N=CCH2O— |
| 1234 | 2-Cl-6-N=CCH$_2$O— | 1235 | 2-Br-3-N=CCH$_2$O— | 1236 | 2-Br-4-N=CCH$_2$O— |
| 1237 | 2-Br-5-N=CCH$_2$O— | 1238 | 2-Br-6-N=CCH$_2$O— | 1239 | 2-I-3-N=CCH$_2$O— |
| 1240 | 2-I-4-N=CCH$_2$O— | 1241 | 2-I-5-N=CCH$_2$O— | 1242 | 2-I-6-N=CCH$_2$O— |
| 1243 | 2-Me-3-N=CCH$_2$O— | 1244 | 2-Me-4-N=CCH$_2$O | 1245 | 2-Me-5-N=CCH$_2$O |
| 1246 | 2-Me-6-N=CCH$_2$O— | 1247 | 2-F-3-N=CCH$_2$CH$_2$O— | 1248 | 2-F-4-N=CCH$_2$CH$_2$O— |
| 1249 | 2-F-5-N=CCH$_2$CH$_2$O— | 1250 | 2-F-6-N=CCH$_2$CH$_2$O— | 1251 | 2-Cl-3-N=CCH$_2$CH$_2$O— |
| 1252 | 2-Cl-4-N=CCH$_2$CH$_2$O— | 1253 | 2-Cl-5-N=CCH$_2$CH$_2$O— | 1254 | 2-Cl-6-N=CCH$_2$CH$_2$O— |
| 1255 | 2-Br-3-N=CCH$_2$CH$_2$O— | 1256 | 2-Br-4-N=CCH$_2$CH$_2$O— | 1257 | 2-Br-5-N=CCH$_2$CH$_2$O— |
| 1258 | 2-Br-6-N=CCH$_2$CH$_2$O— | 1259 | 2-I-3-N=CCH$_2$CH$_2$O— | 1260 | 2-I-4-N=CCH$_2$CH$_2$O— |
| 1261 | 2-I-5-N=CCH$_2$CH$_2$O— | 1262 | 2-I-6-N=CCH$_2$CH$_2$O— | 1263 | 2-Me-3-N=CCH$_2$CH$_2$O— |
| 1264 | 2-Me-4-N=CCH$_2$CH$_2$O— | 1265 | 2-Me-5-N=CCH$_2$CH$_2$O— | 1266 | 2-Me-6-N=CCH$_2$CH$_2$O— |
| 1267 | 2-F-3-cPrCH$_2$O— | 1268 | 2-F-4-cPrCH$_2$O— | 1269 | 2-F-5-cPrCH$_2$O— |
| 1270 | 2-F-6-cPrCH$_2$O— | 1271 | 2-Cl-3-cPrCH$_2$O— | 1272 | 2-Cl-4-cPrCH$_2$O— |
| 1273 | 2-Cl-5-cPrCH$_2$O— | 1274 | 2-Cl-6-cPrCH$_2$O— | 1275 | 2-Br-3-cPrCH$_2$O— |
| 1276 | 2-Br-4-cPrCH$_2$O— | 1277 | 2-Br-5-cPrCH$_2$O— | 1278 | 2-Br-6-cPrCH$_2$O— |
| 1279 | 2-I-3-cPrCH$_2$O— | 1280 | 2-I-4-cPrCH$_2$O— | 1281 | 2-I-5-cPrCH$_2$O— |
| 1282 | 2-I-6-cPrCH$_2$O— | 1283 | 2-Me-3-cPrCH$_2$O— | 1284 | 2-Me-4-cPrCH$_2$O— |
| 1285 | 2-Me-5-cPrCH$_2$O— | 1286 | 2-Me-6-cPrCH$_2$O— | 1287 | 2-F-3-cBuCH$_2$O— |
| 1288 | 2-F-4-cBuCH$_2$O— | 1289 | 2-F-5-cBuCH$_2$O— | 1290 | 2-F-6-cBuCH$_2$O— |
| 1291 | 2-Cl-3-cBuCH$_2$O— | 1292 | 2-Cl-4-cBuCH$_2$O— | 1293 | 2-Cl-5-cBuCH$_2$O— |
| 1294 | 2-Cl-6-cBuCH$_2$O— | 1295 | 2-Br-3-cBuCH$_2$O— | 1296 | 2-Br-4-cBuCH$_2$O— |
| 1297 | 2-Br-5-cBuCH$_2$O— | 1298 | 2-Br-6-cBuCH$_2$O— | 1299 | 2-I-3-cBuCH$_2$O— |
| 1300 | 2-I-4-cBuCH$_2$O— | 1301 | 2-I-5-cBuCH$_2$O— | 1302 | 2-I-6-cBuCH$_2$O— |
| 1303 | 2-Me-3-cBuCH$_2$O— | 1304 | 2-Me-4-cBuCH$_2$O— | 1305 | 2-Me-5-cBuCH$_2$O— |
| 1306 | 2-Me-6-cBuCH$_2$O— | 1307 | 2-F-3-cPentylCH$_2$O— | 1308 | 2-F-4-cPentylCH$_2$O— |
| 1309 | 2-F-5-cPentylCH$_2$O— | 1310 | 2-F-6-cPentylCH$_2$O— | 1311 | 2-Cl-3-cPentylCH$_2$O— |
| 1312 | 2-Cl-4-cPentylCH$_2$O— | 1313 | 2-Cl-5-cPentylCH$_2$O— | 1314 | 2-Cl-6-cPentylCH$_2$O— |
| 1315 | 2-Br-3-cPentylCH$_2$O— | 1316 | 2-Br-4-cPentylCH$_2$O— | 1317 | 2-Br-5-cPentylCH$_2$O— |
| 1318 | 2-Br-6-cPentylCH$_2$O— | 1319 | 2-I-3-cPentylCH$_2$O— | 1320 | 2-I-4-cPentylCH$_2$O— |
| 1321 | 2-I-5-cPentylCH$_2$O— | 1322 | 2-I-6-cPentylCH$_2$O— | 1323 | 2-Me-3-cPentylCH$_2$O— |
| 1324 | 2-Me-4-cPentylCH$_2$O— | 1325 | 2-Me-5-cPentylCH$_2$O— | 1326 | 2-Me-6-cPentylCH$_2$O— |
| 1327 | 2-F-3-cHexylCH$_2$O— | 1328 | 2-F-4-cHexylCH$_2$O— | 1329 | 2-F-5-cHexylCH$_2$O— |
| 1330 | 2-F-6-cHexylCH$_2$O— | 1331 | 2-Cl-3-cHexylCH$_2$O— | 1332 | 2-Cl-4-cHexylCH$_2$O— |
| 1333 | 2-Cl-5-cHexylCH$_2$O— | 1334 | 2-Cl-6-cHexylCH$_2$O— | 1335 | 2-Br-3-cHexylCH$_2$O— |
| 1336 | 2-Br-4-cHexylCH$_2$O— | 1337 | 2-Br-5-cHexylCH$_2$O— | 1338 | 2-Br-6-cHexylCH$_2$O— |
| 1339 | 2-I-3-cHexylCH$_2$O— | 1340 | 2-I-4-cHexylCH$_2$O— | 1341 | 2-I-5-cHexylCH$_2$O— |
| 1342 | 2-I-6-cHexylCH$_2$O— | 1343 | 2-Me-3-cHexylCH$_2$O— | 1344 | 2-Me-4-cHexylCH$_2$O— |
| 1345 | 2-Me-5-cHexylCH$_2$O— | 1346 | 2-Me-6-cHexylCH$_2$O— | 1347 | 2-F-3-MeOCH$_2$O— |
| 1348 | 2-F-4-MeOCH$_2$O— | 1349 | 2-F-5-MeOCH$_2$O— | 1350 | 2-F-6-MeOCH$_2$O— |
| 1351 | 2-Cl-3-MeOCH$_2$O— | 1352 | 2-Cl-4-MeOCH$_2$O— | 1353 | 2-Cl-5-MeOCH$_2$O— |
| 1354 | 2-Cl-6-MeOCH$_2$O— | 1355 | 2-Br-3-MeOCH$_2$O— | 1356 | 2-Br-4-MeOCH$_2$O— |
| 1357 | 2-Br-5-MeOCH$_2$O— | 1358 | 2-Br-6-MeOCH$_2$O— | 1359 | 2-I-3-MeOCH$_2$O— |
| 1360 | 2-I-4-MeOCH$_2$O— | 1361 | 2-I-5-MeOCH$_2$O— | 1362 | 2-I-6-MeOCH$_2$O— |
| 1363 | 2-Me-3-MeOCH$_2$O— | 1364 | 2-Me-4-MeOCH$_2$O— | 1365 | 2-Me-5-MeOCH$_2$O— |
| 1366 | 2-Me-6-MeOCH$_2$O— | 1367 | 2-F-3-EtOCH$_2$O— | 1368 | 2-F-4-EtOCH$_2$O— |
| 1369 | 2-F-5-EtOCH$_2$O— | 1370 | 2-F-6-EtOCH$_2$O— | 1371 | 2-Cl-3-EtOCH$_2$O— |
| 1372 | 2-Cl-4-EtOCH$_2$O— | 1373 | 2-Cl-5-EtOCH$_2$O— | 1374 | 2-Cl-6-EtOCH$_2$O— |
| 1375 | 2-Br-3-EtOCH$_2$O— | 1376 | 2-Br-4-EtOCH$_2$O— | 1377 | 2-Br-5-EtOCH$_2$O— |
| 1378 | 2-Br-6-EtOCH$_2$O— | 1379 | 2-I-3-EtOCH$_2$O— | 1380 | 2-I-4-EtOCH$_2$O— |
| 1381 | 2-I-5-EtOCH$_2$O— | 1382 | 2-I-6-EtOCH$_2$O— | 1383 | 2-Me-3-EtOCH$_2$O— |
| 1384 | 2-Me-4-EtOCH$_2$O— | 1385 | 2-Me-5-EtOCH$_2$O— | 1386 | 2-Me-6-EtOCH$_2$O— |
| 1387 | 2-F-3-MeOCH$_2$CH$_2$O— | 1388 | 2-F-4-MeOCH$_2$CH$_2$O— | 1389 | 2-F-5-MeOCH$_2$CH$_2$O— |
| 1390 | 2-F-6-MeOCH$_2$CH$_2$O— | 1391 | 2-Cl-3-MeOCH$_2$CH$_2$O— | 1392 | 2-Cl-4-MeOCH$_2$CH$_2$O— |
| 1393 | 2-Cl-5-MeOCH$_2$CH$_2$O— | 1394 | 2-Cl-6-MeOCH$_2$CH$_2$O— | 1395 | 2-Br-3-MeOCH$_2$CH$_2$O— |
| 1396 | 2-Br-4-MeOCH$_2$CH$_2$O— | 1397 | 2-Br-5-MeOCH$_2$CH$_2$O— | 1398 | 2-Br-6-MeOCH$_2$CH$_2$O— |
| 1399 | 2-I-3-MeOCH$_2$CH$_2$O— | 1400 | 2-I-4-MeOCH$_2$CH$_2$O— | 1401 | 2-I-5-MeOCH$_2$CH$_2$O— |
| 1402 | 2-I-6-MeOCH$_2$CH$_2$O— | 1403 | 2-Me-3-MeOCH$_2$CH$_2$O— | 1404 | 2-Me-4-MeOCH$_2$CH$_2$O— |
| 1405 | 2-Me-5-MeOCH$_2$CH$_2$O— | 1406 | 2-Me-6-MeOCH$_2$CH$_2$O— | 1407 | 2-F-3-MeOCH$_2$CH$_2$CH$_2$O— |
| 1408 | 2-F-4-MeOCH$_2$CH$_2$CH$_2$O— | 1409 | 2-F-5-MeOCH$_2$CH$_2$CH$_2$O— | 1410 | 2-F-6-MeOCH$_2$CH$_2$CH$_2$O— |
| 1411 | 2-Cl-3-MeOCH$_2$CH$_2$CH$_2$O— | 1412 | 2-Cl-4-MeOCH$_2$CH$_2$CH$_2$O— | 1413 | 2-Cl-5-MeOCH$_2$CH$_2$CH$_2$O— |
| 1414 | 2-Cl-6-MeOCH$_2$CH$_2$CH$_2$O— | 1415 | 2-Br-3-MeOCH$_2$CH$_2$CH$_2$O— | 1416 | 2-Br-4-MeOCH$_2$CH$_2$CH$_2$O— |
| 1417 | 2-Br-5-MeOCH$_2$CH$_2$CH$_2$O— | 1418 | 2-Br-6-MeOCH$_2$CH$_2$CH$_2$O— | 1419 | 2-I-3-MeOCH$_2$CH$_2$CH$_2$O— |
| 1420 | 2-I-4-MeOCH$_2$CH$_2$CH$_2$O— | 1421 | 2-I-5-MeOCH$_2$CH$_2$CH$_2$O— | 1422 | 2-I-6-MeOCH$_2$CH$_2$CH$_2$O— |
| 1423 | 2-Me-3-MeOCH$_2$CH$_2$CH$_2$O— | 1424 | 2-Me-4-MeOCH$_2$CH$_2$CH$_2$O— | 1425 | 2-Me-5-MeOCH$_2$CH$_2$CH$_2$O— |
| 1426 | 2-Me-6-MeOCH$_2$CH$_2$CH$_2$O— | 1427 | 2-F-3-MeOCH$_2$CH$_2$OCH$_2$O— | 1428 | 2-F-4-MeOCH$_2$CH$_2$OCH$_2$O— |
| 1429 | 2-F-5-MeOCH$_2$CH$_2$OCH$_2$O— | 1430 | 2-F-6-MeOCH$_2$CH$_2$OCH$_2$O— | 1431 | 2-Cl-3-MeOCH$_2$CH$_2$OCH$_2$O— |
| 1432 | 2-Cl-4-MeOCH$_2$CH$_2$OCH$_2$O— | 1433 | 2-Cl-5-MeOCH$_2$CH$_2$OCH$_2$O— | 1434 | 2-Cl-6-MeOCH$_2$CH$_2$OCH$_2$O— |

TABLE 2-continued

| No. | (R2)n | No. | (R2)n | No. | (R2)n |
|---|---|---|---|---|---|
| 1435 | 2-Br-3-MeOCH$_2$CH$_2$OCH$_2$O— | 1436 | 2-Br-4-MeOCH$_2$CH$_2$OCH$_2$O— | 1437 | 2-Br-5-MeOCH$_2$CH$_2$OCH$_2$O— |
| 1438 | 2-Br-6-MeOCH$_2$CH$_2$OCH$_2$O— | 1439 | 2-I-3-MeOCH$_2$CH$_2$OCH$_2$O— | 1440 | 2-I-4-MeOCH$_2$CH$_2$OCH$_2$O— |
| 1441 | 2-I-5-MeOCH$_2$CH$_2$OCH$_2$O— | 1442 | 2-I-6-MeOCH$_2$CH$_2$OCH$_2$O— | 1443 | 2-Me-3-MeOCH$_2$CH$_2$OCH$_2$O— |
| 1444 | 2-Me-4-MeOCH$_2$CH$_2$OCH$_2$O— | 1445 | 2-Me-5-MeOCH$_2$CH$_2$OCH$_2$O— | 1446 | 2-Me-6-MeOCH$_2$CH$_2$OCH$_2$O— |
| 1447 | 2-F-3-MeSCH$_2$O— | 1448 | 2-F-4-MeSCH$_2$O— | 1449 | 2-F-5-MeSCH$_2$O— |
| 1450 | 2-F-6-MeSCH$_2$O— | 1451 | 2-Cl-3-MeSCH$_2$O— | 1452 | 2-Cl-4-MeSCH$_2$O— |
| 1453 | 2-Cl-5-MeSCH$_2$O— | 1454 | 2-Cl-6-MeSCH$_2$O— | 1455 | 2-Br-3-MeSCH$_2$O— |
| 1456 | 2-Br-4-MeSCH$_2$O— | 1457 | 2-Br-5-MeSCH$_2$O— | 1458 | 2-Br-6-MeSCH$_2$O— |
| 1459 | 2-I-3-MeSCH$_2$O— | 1460 | 2-I-4-MeSCH$_2$O— | 1461 | 2-I-5-MeSCH$_2$O— |
| 1462 | 2-I-6-MeSCH$_2$O— | 1463 | 2-Me-3-MeSCH$_2$O— | 1464 | 2-Me-4-MeSCH$_2$O— |
| 1465 | 2-Me-5-MeSCH$_2$O— | 1466 | 2-Me-6-MeSCH$_2$O— | 1467 | 2-F-3-MeS(O)CH$_2$O— |
| 1468 | 2-F-4-MeS(O)CH$_2$O— | 1469 | 2-F-5-MeS(O)CH$_2$O— | 1470 | 2-F-6-MeS(O)CH$_2$O— |
| 1471 | 2-Cl-3-MeS(O)CH$_2$O— | 1472 | 2-Cl-4-MeS(O)CH$_2$O— | 1473 | 2-Cl-5-MeS(O)CH$_2$O— |
| 1474 | 2-Cl-6-MeS(O)CH$_2$O— | 1475 | 2-Br-3-MeS(O)CH$_2$O— | 1476 | 2-Br-4-MeS(O)CH$_2$O— |
| 1477 | 2-Br-5-MeS(O)CH$_2$O— | 1478 | 2-Br-6-MeS(O)CH$_2$O— | 1479 | 2-I-3-MeS(O)CH$_2$O— |
| 1480 | 2-I-4-MeS(O)CH$_2$O— | 1481 | 2-I-5-MeS(O)CH$_2$O— | 1482 | 2-I-6-MeS(O)CH$_2$O— |
| 1483 | 2-Me-3-MeS(O)CH$_2$O— | 1484 | 2-Me-4-MeS(O)CH$_2$O— | 1485 | 2-Me-5-MeS(O)CH$_2$O— |
| 1486 | 2-Me-6-MeS(O)CH$_2$O— | 1487 | 2-F-3-MeSO$_2$CH$_2$O— | 1488 | 2-F-4-MeSO$_2$CH$_2$O— |
| 1489 | 2-F-5-MeSO$_2$CH$_2$O— | 1490 | 2-F-6-MeSO$_2$CH$_2$O— | 1491 | 2-Cl-3-MeSO$_2$CH$_2$O— |
| 1492 | 2-Cl-4-MeSO$_2$CH$_2$O— | 1493 | 2-Cl-5-MeSO$_2$CH$_2$O— | 1494 | 2-Cl-6-MeSO$_2$CH$_2$O— |
| 1495 | 2-Br-3-MeSO$_2$CH$_2$O— | 1496 | 2-Br-4-MeSO$_2$CH$_2$O— | 1497 | 2-Br-5-MeSO$_2$CH$_2$O— |
| 1498 | 2-Br-6-MeSO$_2$CH$_2$O— | 1499 | 2-I-3-MeSO$_2$CH$_2$O— | 1500 | 2-I-4-MeSO$_2$CH$_2$O— |
| 1501 | 2-I-5-MeSO$_2$CH$_2$O— | 1502 | 2-I-6-MeSO$_2$CH$_2$O— | 1503 | 2-Me-3-MeSO$_2$CH$_2$O— |
| 1504 | 2-Me-4-MeSO$_2$CH$_2$O— | 1505 | 2-Me-5-MeSO$_2$CH$_2$O— | 1506 | 2-Me-6-MeSO$_2$CH$_2$O— |
| 1507 | 2-F-3-Me$_3$SiCH$_2$O— | 1508 | 2-F-4-Me$_3$SiCH$_2$O— | 1509 | 2-F-5-Me$_3$SiCH$_2$O— |
| 1510 | 2-F-6-Me$_3$SiCH$_2$O— | 1511 | 2-Cl-3-Me$_3$SiCH$_2$O— | 1512 | 2-Cl-4-Me$_3$SiCH$_2$O— |
| 1513 | 2-Cl-5-Me$_3$SiCH$_2$O— | 1514 | 2-Cl-6-Me$_3$SiCH$_2$O— | 1515 | 2-Br-3-Me$_3$SiCH$_2$O— |
| 1516 | 2-Br-4-Me$_3$SiCH$_2$O— | 1517 | 2-Br-5-Me$_3$SiCH$_2$O— | 1518 | 2-Br-6-Me$_3$SiCH$_2$O— |
| 1519 | 2-I-3-Me$_3$SiCH$_2$O— | 1520 | 2-I-4-Me$_3$SiCH$_2$O— | 1521 | 2-I-5-Me$_3$SiCH$_2$O— |
| 1522 | 2-I-6-Me$_3$SiCH$_2$O— | 1523 | 2-Me-3-Me$_3$SiCH$_2$O— | 1524 | 2-Me-4-Me$_3$SiCH$_2$O— |
| 1525 | 2-Me-5-Me$_3$SiCH$_2$O— | 1526 | 2-Me-6-Me$_3$SiCH$_2$O— | 1527 | 2-F-3-Me$_3$SiCH$_2$CH$_2$O— |
| 1528 | 2-F-4-Me$_3$SiCH$_2$CH$_2$O— | 1529 | 2-F-5-Me$_3$SiCH$_2$CH$_2$O— | 1530 | 2-F-6-Me$_3$SiCH$_2$CH$_2$O— |
| 1531 | 2-Cl-3-Me$_3$SiCH$_2$CH$_2$O— | 1532 | 2-Cl-4-Me$_3$SiCH$_2$CH$_2$O— | 1533 | 2-Cl-5-Me$_3$SiCH$_2$CH$_2$O— |
| 1534 | 2-Cl-6-Me$_3$SiCH$_2$CH$_2$O— | 1535 | 2-Br-3-Me$_3$SiCH$_2$CH$_2$O— | 1536 | 2-Br-4-Me$_3$SiCH$_2$CH$_2$O— |
| 1537 | 2-Br-5-Me$_3$SiCH$_2$CH$_2$O— | 1538 | 2-Br-6-Me$_3$SiCH$_2$CH$_2$O— | 1539 | 2-I-3-Me$_3$SiCH$_2$CH$_2$O— |
| 1540 | 2-I-4-Me$_3$SiCH$_2$CH$_2$O— | 1541 | 2-I-5-Me$_3$SiCH$_2$CH$_2$O- | 1542 | 2-I-6-Me$_3$SiCH$_2$CH$_2$O— |
| 1543 | 2-Me-3-Me$_3$SiCH$_2$CH$_2$O— | 1544 | 2-Me-4-Me$_3$SiCH$_2$CH$_2$O— | 1545 | 2-Me-5-Me$_3$SiCH$_2$CH$_2$O— |
| 1546 | 2-Me-6-Me$_3$SiCH$_2$CH$_2$O— | 1547 | 2-F-3-Me$_3$SiCH$_2$CH$_2$O— | 1548 | 2-F-4-Me$_3$SiCH$_2$CH$_2$O— |
| 1549 | 2-F-5-Me$_3$SiCH$_2$CH$_2$O— | 1550 | 2-F-6-Me$_3$SiCH$_2$CH$_2$O— | 1551 | 2-Cl-3-Me$_3$SiCH$_2$CH$_2$O— |
| 1552 | 2-Cl-4-Me$_3$SiCH$_2$CH$_2$O— | 1553 | 2-Cl-5-Me$_3$SiCH$_2$CH$_2$O— | 1554 | 2-Cl-6-Me$_3$SiCH$_2$CH$_2$O— |
| 1555 | 2-Br-3-Me$_3$SiCH$_2$CH$_2$O— | 1556 | 2-Br-4-Me$_3$SiCH$_2$CH$_2$O— | 1557 | 2-Br-5-Me$_3$SiCH$_2$CH$_2$O— |
| 1558 | 2-Br-6-Me$_3$SiCH$_2$CH$_2$O— | 1559 | 2-I-3-Me$_3$SiCH$_2$CH$_2$O— | 1560 | 2-I-4-Me$_3$SiCH$_2$CH$_2$O— |
| 1561 | 2-I-5-Me$_3$SiCH$_2$CH$_2$O— | 1562 | 2-I-6-Me$_3$SiCH$_2$CH$_2$O— | 1563 | 2-Me-3-Me$_3$SiCH$_2$CH$_2$O— |
| 1564 | 2-Me-4-Me$_3$SiCH$_2$CH$_2$O— | 1565 | 2-Me-5-Me$_3$SiCH$_2$CH$_2$O— | 1566 | 2-Me-6-Me$_3$SiCH$_2$CH$_2$O— |
| 1567 | 2-F-3-AcCH$_2$O— | 1568 | 2-F-4-AcCH$_2$O— | 1569 | 2-F-5-AcCH$_2$O— |
| 1570 | 2-F-6-AcCH$_2$O— | 1571 | 2-Cl-3-AcCH$_2$O— | 1572 | 2-Cl-4-AcCH$_2$O— |
| 1573 | 2-Cl-5-AcCH$_2$O— | 1574 | 2-Cl-6-AcCH$_2$O— | 1575 | 2-Br-3-AcCH$_2$O— |
| 1576 | 2-Br-4-AcCH$_2$O— | 1577 | 2-Br-5-AcCH$_2$O— | 1578 | 2-Br-6-AcCH$_2$O— |
| 1579 | 2-I-3-AcCH$_2$O— | 1580 | 2-I-4-AcCH$_2$O— | 1581 | 2-I-5-AcCH$_2$O— |
| 1582 | 2-I-6-AcCH$_2$O— | 1583 | 2-Me-3-AcCH$_2$O— | 1584 | 2-Me-4-AcCH$_2$O— |
| 1585 | 2-Me-5-AcCH$_2$O— | 1586 | 2-Me-6-AcCH$_2$O— | 1587 | 2-F-3-MeOC(=O)CH$_2$O— |
| 1588 | 2-F-4-MeOC(=O)CH$_2$O— | 1589 | 2-F-5-MeOC(=O)CH$_2$O— | 1590 | 2-F-6-MeOC(=O)CH$_2$O— |
| 1591 | 2-Cl-3-MeOC(=O)CH$_2$O— | 1592 | 2-Cl-4-MeOC(=O)CH$_2$O— | 1593 | 2-Cl-5-MeOC(=O)CH$_2$O— |
| 1594 | 2-Cl-6-MeOC(=O)CH$_2$O— | 1595 | 2-Br-3-MeOC(=O)CH$_2$O— | 1596 | 2-Br-4-MeOC(=O)CH$_2$O— |
| 1597 | 2-Br-5-MeOC(=O)CH$_2$O— | 1598 | 2-Br-6-MeOC(=O)CH$_2$O— | 1599 | 2-I-3-MeOC(=O)CH$_2$O— |
| 1600 | 2-I-4-MeOC(=O)CH$_2$O— | 1601 | 2-I-5-MeOC(=O)CH$_2$O— | 1602 | 2-I-6-MeOC(=O)CH$_2$O— |
| 1603 | 2-Me-3-MeOC(=O)CH$_2$O— | 1604 | 2-Me-4-MeOC(=O)CH$_2$O— | 1605 | 2-Me-5-MeOC(=O)CH$_2$O— |
| 1606 | 2-Me-6-MeOC(=O)CH$_2$O— | 1607 | 2-F-3-EtOC(=O)CH$_2$O— | 1608 | 2-F-4-EtOC(=O)CH$_2$O— |

TABLE 2-continued

| No. | (R2)n | No. | (R2)n | No. | (R2)n |
|---|---|---|---|---|---|
| 1609 | 2-F-5-EtOC(=O)CH₂O— | 1610 | 2-F-6-EtOC(=O)CH₂O— | 1611 | 2-Cl-3-EtOC(=O)CH₂O— |
| 1612 | 2-Cl-4-EtOC(=O)CH₂O— | 1613 | 2-Cl-5-EtOC(=O)CH₂O— | 1614 | 2-Cl-6-EtOC(=O)CH₂O— |
| 1615 | 2-Br-3-EtOC(=O)CH₂O— | 1616 | 2-Br-4-EtOC(=O)CH₂O— | 1617 | 2-Br-5-EtOC(=O)CH₂O— |
| 1618 | 2-Br-6-EtOC(=O)CH₂O— | 1619 | 2-I-3-EtOC(=O)CH₂O— | 1620 | 2-I-4-EtOC(=O)CH₂O— |
| 1621 | 2-I-5-EtOC(=O)CH₂O— | 1622 | 2-I-6-EtOC(=O)CH₂O— | 1623 | 2-Me-3-EtOC(=O)CH₂O— |
| 1624 | 2-Me-4-EtOC(=O)CH₂O— | 1625 | 2-Me-5-EtOC(=O)CH₂O— | 1626 | 2-Me-6-EtOC(=O)CH₂O— |
| 1627 | 2-F-3-(1,3-dioxolan-2-yl)CH₂O— | 1628 | 2-F-4-(1,3-dioxolan-2-yl)CH₂O— | 1629 | 2-F-5-(1,3-dioxolan-2-yl)CH₂O— |
| 1630 | 2-F-6-(1,3-dioxolan-2-yl)CH₂O— | 1631 | 2-Cl-3-(1,3-dioxolan-2-yl)CH₂O— | 1632 | 2-Cl-4-(1,3-dioxolan-2-yl)CH₂O— |
| 1633 | 2-Cl-5-(1,3-dioxolan-2-yl)CH₂O— | 1634 | 2-Cl-6-(1,3-dioxolan-2-yl)CH₂O— | 1635 | 2-Br-3-(1,3-dioxolan-2-yl)CH₂O— |
| 1636 | 2-Br-4-(1,3-dioxolan-2-yl)CH₂O— | 1637 | 2-Br-5-(1,3-dioxolan-2-yl)CH₂O— | 1638 | 2-Br-6-(1,3-dioxolan-2-yl)CH₂O— |
| 1639 | 2-I-3-(1,3-dioxolan-2-yl)CH₂O— | 1640 | 2-I-4-(1,3-dioxolan-2-yl)CH₂O— | 1641 | 2-I-5-(1,3-dioxolan-2-yl)CH₂O— |
| 1642 | 2-I-6-(1,3-dioxolan-2-yl)CH₂O— | 1643 | 2-Me-3-(1,3-dioxolan-2-yl)CH₂O— | 1644 | 2-Me-4-(1,3-dioxolan-2-yl)CH₂O— |
| 1645 | 2-Me-5-(1,3-dioxolan-2-yl)CH₂O— | 1646 | 2-Me-6-(1,3-dioxolan-2-yl)CH₂O— | 1647 | 2-F-3-(1,3-dioxolan-2-yl)CH₂CH₂O— |
| 1648 | 2-F-4-(1,3-dioxolan-2-yl)CH₂CH₂O— | 1649 | 2-F-5-(1,3-dioxolan-2-yl)CH₂CH₂O— | 1650 | 2-F-6-(1,3-dioxolan-2-yl)CH₂CH₂O— |
| 1651 | 2-Cl-3-(1,3-dioxolan-2-yl)CH₂CH₂O— | 1652 | 2-Cl-4-(1,3-dioxolan-2-yl)CH₂CH₂O— | 1653 | 2-Cl-5-(1,3-dioxolan-2-yl)CH₂CH₂O— |
| 1654 | 2-Cl-6-(1,3-dioxolan-2-yl)CH₂CH₂O— | 1655 | 2-Br-3-(1,3-dioxolan-2-yl)CH₂CH₂O— | 1656 | 2-Br-4-(1,3-dioxolan-2-yl)CH₂CH₂O— |
| 1657 | 2-Br-5-(1,3-dioxolan-2-yl)CH₂CH₂O— | 1658 | 2-Br-6-(1,3-dioxolan-2-yl)CH₂CH₂O— | 1659 | 2-I-3-(1,3-dioxolan-2-yl)CH₂CH₂O— |
| 1660 | 2-I-4-(1,3-dioxolan-2-yl)CH₂CH₂O— | 1661 | 2-I-5-(1,3-dioxolan-2-yl)CH₂CH₂O— | 1662 | 2-I-6-(1,3-dioxolan-2-yl)CH₂CH₂O— |
| 1663 | 2-Me-3-(1,3-dioxolan-2-yl)CH₂CH₂O— | 1664 | 2-Me-4-(1,3-dioxolan-2-yl)CH₂CH₂O— | 1665 | 2-Me-5-(1,3-dioxolan-2-yl)CH₂CH₂O— |
| 1666 | 2-Me-6-(1,3-dioxolan-2-yl)CH₂CH₂O— | 1667 | 2-F-3-(1,3-dioxan-2-yl)CH₂O— | 1668 | 2-F-4-(1,3-dioxan-2-yl)CH₂O— |
| 1669 | 2-F-5-(1,3-dioxan-2-yl)CH₂O— | 1670 | 2-F-6-(1,3-dioxan-2-yl)CH₂O— | 1671 | 2-Cl-3-(1,3-dioxan-2-yl)CH₂O— |
| 1672 | 2-Cl-4-(1,3-dioxan-2-yl)CH₂O— | 1673 | 2-Cl-5-(1,3-dioxan-2-yl)CH₂O— | 1674 | 2-Cl-6-(1,3-dioxan-2-yl)CH₂O— |
| 1675 | 2-Br-3-(1,3-dioxan-2-yl)CH₂O— | 1676 | 2-Br-4-(1,3-dioxan-2-yl)CH₂O— | 1677 | 2-Br-5-(1,3-dioxan-2-yl)CH₂O— |
| 1678 | 2-Br-6-(1,3-dioxan-2-yl)CH₂O— | 1679 | 2-I-3-(1,3-dioxan-2-yl)CH₂O— | 1680 | 2-I-4-(1,3-dioxan-2-yl)CH₂O— |
| 1681 | 2-I-5-(1,3-dioxan-2-yl)CH₂O— | 1682 | 2-I-6-(1,3-dioxan-2-yl)CH₂O— | 1683 | 2-Me-3-(1,3-dioxan-2-yl)CH₂O— |
| 1684 | 2-Me-4-(1,3-dioxan-2-yl)CH₂O— | 1685 | 2-Me-5-(1,3-dioxan-2-yl)CH₂O— | 1686 | 2-Me-6-(1,3-dioxan-2-yl)CH₂O— |
| 1687 | 2-F-3-(1,3-dioxan-2-yl)CH₂CH₂O— | 1688 | 2-F-4-(1,3-dioxan-2-yl)CH₂CH₂O— | 1689 | 2-F-5-(1,3-dioxan-2-yl)CH₂CH₂O— |
| 1690 | 2-F-6-(1,3-dioxan-2-yl)CH₂CH₂O— | 1691 | 2-Cl-3-(1,3-dioxan-2-yl)CH₂CH₂O— | 1692 | 2-Cl-4-(1,3-dioxan-2-yl)CH₂CH₂O— |
| 1693 | 2-Cl-5-(1,3-dioxan-2-yl)CH₂CH₂O— | 1694 | 2-Cl-6-(1,3-dioxan-2-yl)CH₂CH₂O— | 1695 | 2-Br-3-(1,3-dioxan-2-yl)CH₂CH₂O— |
| 1696 | 2-Br-4-(1,3-dioxan-2-yl)CH₂CH₂O— | 1697 | 2-Br-5-(1,3-dioxan-2-yl)CH₂CH₂O— | 1698 | 2-Br-6-(1,3-dioxan-2-yl)CH₂CH₂O— |
| 1699 | 2-I-3-(1,3-dioxan-2-yl)CH₂CH₂O— | 1700 | 2-I-4-(1,3-dioxan-2-yl)CH₂CH₂O— | 1701 | 2-I-5-(1,3-dioxan-2-yl)CH₂CH₂O— |
| 1702 | 2-I-6-(1,3-dioxan-2-yl)CH₂CH₂O— | 1703 | 2-Me-3-(1,3-dioxan-2-yl)CH₂CH₂O— | 1704 | 2-Me-4-(1,3-dioxan-2-yl)CH₂CH₂O— |
| 1705 | 2-Me-5-(1,3-dioxan-2-yl)CH₂CH₂O— | 1706 | 2-Me-6-(1,3-dioxan-2-yl)CH₂CH₂O— | 1707 | 2-F-3-cPrO— |
| 1708 | 2-F-4-cPrO— | 1709 | 2-F-5-cPrO— | 1710 | 2-F-6-cPrO— |
| 1711 | 2-Cl-3-cPrO— | 1712 | 2-Cl-4-cPrO— | 1713 | 2-Cl-5-cPrO— |
| 1714 | 2-Cl-6-cPrO— | 1715 | 2-Br-3-cPrO— | 1716 | 2-Br-4-cPrO— |
| 1717 | 2-Br-5-cPrO— | 1718 | 2-Br-6-cPrO— | 1719 | 2-I-3-cPrO— |
| 1720 | 2-I-4-cPrO— | 1721 | 2-I-5-cPrO— | 1722 | 2-I-6-cPrO— |
| 1723 | 2-Me-3-cPrO— | 1724 | 2-Me-4-cPrO— | 1725 | 2-Me-5-cPrO— |
| 1726 | 2-Me-6-cPrO— | 1727 | 2-F-3-cBuO— | 1728 | 2-F-4-cBuO— |
| 1729 | 2-F-5-cBuO— | 1730 | 2-F-6-cBuO— | 1731 | 2-Cl-3-cBuO— |
| 1732 | 2-Cl-4-cBuO— | 1733 | 2-Cl-5-cBuO— | 1734 | 2-Cl-6-cBuO— |
| 1735 | 2-Br-3-cBuO— | 1736 | 2-Br-4-cBuO— | 1737 | 2-Br-5-cBuO— |
| 1738 | 2-Br-6-cBuO— | 1739 | 2-I-3-cBuO— | 1740 | 2-I-4-cBuO— |
| 1741 | 2-I-5-cBuO— | 1742 | 2-I-6-cBuO— | 1743 | 2-Me-3-cBuO— |

TABLE 2-continued

| No. | (R2)n | No. | (R2)n | No. | (R2)n |
|---|---|---|---|---|---|
| 1744 | 2-Me-4-cBuO— | 1745 | 2-Me-5-cBuO— | 1746 | 2-Me-6-cBuO— |
| 1747 | 2-F-3-cPentylO— | 1748 | 2-F-4-cPentylO— | 1749 | 2-F-5-cPentylO— |
| 1750 | 2-F-6-cPentylO— | 1751 | 2-Cl-3-cPentylO— | 1752 | 2-Cl-4-cPentylO— |
| 1753 | 2-Cl-5-cPentylO— | 1754 | 2-Cl-6-cPentylO— | 1755 | 2-Br-3-cPentylO— |
| 1756 | 2-Br-4-cPentylO— | 1757 | 2-Br-5-cPentylO— | 1758 | 2-Br-6-cPentylO— |
| 1759 | 2-I-3-cPentylO— | 1760 | 2-I-4-cPentylO— | 1761 | 2-I-5-cPentylO— |
| 1762 | 2-I-6-cPentylO— | 1763 | 2-Me-3-cPentylO— | 1764 | 2-Me-4-cPentylO— |
| 1765 | 2-Me-5-cPentylO— | 1766 | 2-Me-6-cPentylO— | 1767 | 2-F-3-cHexylO— |
| 1768 | 2-F-4-cHexylO— | 1769 | 2-F-5-cHexylO— | 1770 | 2-F-6-cHexylO— |
| 1771 | 2-Cl-3-cHexylO— | 1772 | 2-Cl-4-cHexylO— | 1773 | 2-Cl-5-cHexylO— |
| 1774 | 2-Cl-6-cHexylO— | 1775 | 2-Br-3-cHexylO— | 1776 | 2-Br-4-cHexylO— |
| 1777 | 2-Br-5-cHexylO— | 1778 | 2-Br-6-cHexylO— | 1779 | 2-I-3-cHexylO— |
| 1780 | 2-I-4-cHexylO— | 1781 | 2-I-5-cHexylO— | 1782 | 2-I-6-cHexylO— |
| 1783 | 2-Me-3-cHexylO— | 1784 | 2-Me-4-cHexylO— | 1785 | 2-Me-5-cHexylO— |
| 1786 | 2-Me-6-cHexylO— | 1787 | 2-F-3-$F_3$CO— | 1788 | 2-F-4-$F_3$CO— |
| 1789 | 2-F-5-$F_3$CO— | 1790 | 2-F-6-$F_3$CO— | 1791 | 2-Cl-3-$F_3$CO— |
| 1792 | 2-Cl-4-F3CO— | 1793 | 2-Cl-5-$F_3$CO— | 1794 | 2-Cl-6-$F_3$CO— |
| 1795 | 2-Br-3-$F_3$CO— | 1796 | 2-Br-4-$F_3$CO— | 1797 | 2-Br-5-$F_3$CO— |
| 1798 | 2-Br-6-$F_3$CO— | 1799 | 2-I-3-$F_3$CO— | 1800 | 2-I-4-$F_3$CO— |
| 1801 | 2-I-5-$F_3$CO— | 1802 | 2-I-6-$F_3$CO— | 1803 | 2-Me-3-$F_3$CO— |
| 1804 | 2-Me-4-$F_3$CO— | 1805 | 2-Me-5-$F_3$CO— | 1806 | 2-Me-6-$F_3$CO— |
| 1807 | 2-F-3-$F_2$CHO— | 1808 | 2-F-4-$F_2$CHO— | 1809 | 2-F-5-$F_2$CHO— |
| 1810 | 2-F-6-$F_2$CHO— | 1811 | 2-Cl-3-$F_2$CHO— | 1812 | 2-Cl-4-$F_2$CHO— |
| 1813 | 2-Cl-5-$F_2$CHO— | 1814 | 2-Cl-6-$F_2$CHO— | 1815 | 2-Br-3-$F_2$CHO— |
| 1816 | 2-Br-4-$F_2$CHO— | 1817 | 2-Br-5-$F_2$CHO— | 1818 | 2-Br-6-$F_2$CHO— |
| 1819 | 2-I-3-$F_2$CHO— | 1820 | 2-I-4-$F_2$CHO— | 1821 | 2-I-5-$F_2$CHO— |
| 1822 | 2-I-6-$F_2$CHO— | 1823 | 2-Me-3-$F_2$CHO— | 1824 | 2-Me-4-$F_2$CHO— |
| 1825 | 2-Me-5-$F_2$CHO— | 1826 | 2-Me-6-$F_2$CHO— | 1827 | 2-F-3-$F_3$CCH$_2$O— |
| 1828 | 2-F-4-$F_3$CCH$_2$O— | 1829 | 2-F-5-$F_3$CCH$_2$O— | 1830 | 2-F-6-$F_3$CCH$_2$O— |
| 1831 | 2-Cl-3-$F_3$CCH$_2$O— | 1832 | 2-Cl-4-$F_3$CCH$_2$O— | 1833 | 2-Cl-5-$F_3$CCH$_2$O— |
| 1834 | 2-Cl-6-$F_3$CCH$_2$O— | 1835 | 2-Br-3-$F_3$CCH$_2$O— | 1836 | 2-Br-4-$F_3$CCH$_2$O— |
| 1837 | 2-Br-5-$F_3$CCH$_2$O— | 1838 | 2-Br-6-$F_3$CCH$_2$O— | 1839 | 2-I-3-$F_3$CCH$_2$O— |
| 1840 | 2-I-4-$F_3$CCH$_2$O— | 1841 | 2-I-5-$F_3$CCH$_2$O— | 1842 | 2-I-6-$F_3$CCH$_2$O— |
| 1843 | 2-Me-3-$F_3$CCH$_2$O— | 1844 | 2-Me-4-$F_3$CCH$_2$O— | 1845 | 2-Me-5-$F_3$CCH$_2$O— |
| 1846 | 2-Me-6-$F_3$CCH$_2$O— | 1847 | 2-F-3-$F_2$CHCH$_2$O— | 1848 | 2-F-4-$F_2$CHCH$_2$O— |
| 1849 | 2-F-5-$F_2$CHCH$_2$O— | 1850 | 2-F-6-$F_2$CHCH$_2$O— | 1851 | 2-Cl-3-$F_2$CHCH$_2$O— |
| 1852 | 2-Cl-4-$F_2$CHCH$_2$O— | 1853 | 2-Cl-5-$F_2$CHCH$_2$O— | 1854 | 2-Cl-6-$F_2$CHCH$_2$O— |
| 1855 | 2-Br-3-$F_2$CHCH$_2$O— | 1856 | 2-Br-4-$F_2$CHCH$_2$O— | 1857 | 2-Br-5-$F_2$CHCH$_2$O— |
| 1858 | 2-Br-6-$F_2$CHCH$_2$O— | 1859 | 2-I-3-$F_2$CHCH$_2$O— | 1860 | 2-I-4-$F_2$CHCH$_2$O— |
| 1861 | 2-I-5-$F_2$CHCH$_2$O— | 1862 | 2-I-6-$F_2$CHCH$_2$O— | 1863 | 2-Me-3-$F_2$CHCH$_2$O— |
| 1864 | 2-Me-4-$F_2$CHCH$_2$O— | 1865 | 2-Me-5-$F_2$CHCH$_2$O— | 1866 | 2-Me-6-$F_2$CHCH$_2$O— |
| 1867 | 2-F-3-H$_2$C=CHCH$_2$O— | 1868 | 2-F-4-H$_2$C=CHCH$_2$O— | 1869 | 2-F-5-H$_2$C=CHCH$_2$O— |
| 1870 | 2-F-6-H$_2$C=CHCH$_2$O— | 1871 | 2-Cl-3-H$_2$C=CHCH$_2$O— | 1872 | 2-Cl-4-H$_2$C=CHCH$_2$O— |
| 1873 | 2-Cl-5-H$_2$C=CHCH$_2$O— | 1874 | 2-Cl-6-H$_2$C=CHCH$_2$O— | 1875 | 2-Br-3-H$_2$C=CHCH$_2$O— |
| 1876 | 2-Br-4-H$_2$C=CHCH$_2$O— | 1877 | 2-Br-5-H$_2$C=CHCH$_2$O— | 1878 | 2-Br-6-H$_2$C=CHCH$_2$O— |
| 1879 | 2-I-3-H$_2$C=CHCH$_2$O— | 1880 | 2-I-4-H$_2$C=CHCH$_2$O— | 1881 | 2-I-5-H$_2$C=CHCH$_2$O— |
| 1882 | 2-I-6-H$_2$C=CHCH$_2$O— | 1883 | 2-Me-3-H$_2$C=CHCH$_2$O— | 1884 | 2-Me-4-H$_2$C=CHCH$_2$O— |
| 1885 | 2-Me-5-H$_2$C=CHCH$_2$O— | 1886 | 2-Me-6-H$_2$C=CHCH$_2$O— | 1887 | 2-F-3-HC≡CCH$_2$O— |
| 1888 | 2-F-4-HC≡CCH$_2$O— | 1889 | 2-F-5-HC≡CCH$_2$O— | 1890 | 2-F-6-HC≡CCH$_2$O— |
| 1891 | 2-Cl-3-HC≡CCH$_2$O— | 1892 | 2-Cl-4-HC≡CCH$_2$O— | 1893 | 2-Cl-5-HC≡CCH$_2$O— |
| 1894 | 2-Cl-6-HC≡CCH$_2$O— | 1895 | 2-Br-3-HC≡CCH$_2$O— | 1896 | 2-Br-4-HC≡CCH$_2$O— |
| 1897 | 2-Br-5-HC≡CCH$_2$O— | 1898 | 2-Br-6-HC≡CCH$_2$O— | 1899 | 2-I-3-HC≡CCH$_2$O— |
| 1900 | 2-I-4-HC≡CCH$_2$O— | 1901 | 2-I-5-HC≡CCH$_2$O— | 1902 | 2-I-6-HC≡CCH$_2$O— |
| 1903 | 2-Me-3-HC≡CCH$_2$O— | 1904 | 2-Me-4-HC≡CCH$_2$O— | 1905 | 2-Me-5-HC≡CCH$_2$O— |
| 1906 | 2-Me-6-HC≡CCH$_2$O— | 1907 | 2-F-3-Ac— | 1908 | 2-F-4-Ac— |
| 1909 | 2-F-5-Ac— | 1910 | 2-F-6-Ac— | 1911 | 2-Cl-3-Ac— |
| 1912 | 2-Cl-4-Ac— | 1913 | 2-Cl-5-Ac— | 1914 | 2-Cl-6-Ac— |
| 1915 | 2-Br-3-Ac— | 1916 | 2-Br-4-Ac— | 1917 | 2-Br-5-Ac— |
| 1918 | 2-Br-6-Ac— | 1919 | 2-I-3-Ac— | 1920 | 2-I-4-Ac— |
| 1921 | 2-I-5-Ac— | 1922 | 2-I-6-Ac— | 1923 | 2-Me-3-Ac— |
| 1924 | 2-Me-4-Ac— | 1925 | 2-Me-5-Ac— | 1926 | 2-Me-6-Ac— |
| 1927 | 2-F-3-MeOC(=O)— | 1928 | 2-F-4-MeOC(=O)— | 1929 | 2-F-5-MeOC(=O)— |
| 1930 | 2-F-6-MeOC(=O)— | 1931 | 2-Cl-3-MeOC(=O)— | 1932 | 2-Cl-4-MeOC(=O)— |
| 1933 | 2-Cl-5-MeOC(=O)— | 1934 | 2-Cl-6-MeOC(=O)— | 1935 | 2-Br-3-MeOC(=O)— |
| 1936 | 2-Br-4-MeOC(=O)— | 1937 | 2-Br-5-MeOC(=O)— | 1938 | 2-Br-6-MeOC(=O)— |
| 1939 | 2-I-3-MeOC(=O)— | 1940 | 2-I-4-MeOC(=O)— | 1941 | 2-I-5-MeOC(=O)— |
| 1942 | 2-I-6-MeOC(=O)— | 1943 | 2-Me-3-MeOC(=O)— | 1944 | 2-Me-4-MeOC(=O)— |
| 1945 | 2-Me-5-MeOC(=O)— | 1946 | 2-Me-6-MeOC(=O)— | 1947 | 2-F-3-EtOC(=O)— |
| 1948 | 2-F-4-EtOC(=O)— | 1949 | 2-F-5-EtOC(=O)— | 1950 | 2-F-6-EtOC(=O)— |
| 1951 | 2-Cl-3-EtOC(=O)— | 1952 | 2-Cl-4-EtOC(=O)— | 1953 | 2-Cl-5-EtOC(=O)— |
| 1954 | 2-Cl-6-EtOC(=O)— | 1955 | 2-Br-3-EtOC(=O)— | 1956 | 2-Br-4-EtOC(=O)— |
| 1957 | 2-Br-5-EtOC(=O)— | 1958 | 2-Br-6-EtOC(=O)— | 1959 | 2-I-3-EtOC(=O)— |
| 1960 | 2-I-4-EtOC(=O)— | 1961 | 2-I-5-EtOC(=O)— | 1962 | 2-I-6-EtOC(=O)— |
| 1963 | 2-Me-3-EtOC(=O)— | 1964 | 2-Me-4-EtOC(=O)— | 1965 | 2-Me-5-EtOC(=O)— |
| 1966 | 2-Me-6-EtOC(=O)— | 1967 | 2-F-3-AcO— | 1968 | 2-F-4-AcO— |
| 1969 | 2-F-5-AcO— | 1970 | 2-F-6-AcO— | 1971 | 2-Cl-3-AcO— |
| 1972 | 2-Cl-4-AcO— | 1973 | 2-Cl-5-AcO— | 1974 | 2-Cl-6-AcO— |
| 1975 | 2-Br-3-AcO— | 1976 | 2-Br-4-AcO— | 1977 | 2-Br-5-AcO— |

TABLE 2-continued

| No. | (R2)n | No. | (R2)n | No. | (R2)n |
|---|---|---|---|---|---|
| 1978 | 2-Br-6-AcO— | 1979 | 2-I-3-AcO— | 1980 | 2-I-4-AcO— |
| 1981 | 2-I-5-AcO— | 1982 | 2-I-6-AcO— | 1983 | 2-Me-3-AcO— |
| 1984 | 2-Me-4-AcO— | 1985 | 2-Me-5-AcO— | 1986 | 2-Me-6-AcO— |
| 1987 | 2-F-3-MeOC(=O)O— | 1988 | 2-F-4-MeOC(=O)O— | 1989 | 2-F-5-MeOC(=O)O— |
| 1990 | 2-F-6-MeOC(=O)O— | 1991 | 2-Cl-3-MeOC(=O)O— | 1992 | 2-Cl-4-MeOC(=O)O— |
| 1993 | 2-Cl-5-MeOC(=O)O— | 1994 | 2-Cl-6-MeOC(=O)O— | 1995 | 2-Br-3-MeOC(=O)O— |
| 1996 | 2-Br-4-MeOC(=O)O— | 1997 | 2-Br-5-MeOC(=O)O— | 1998 | 2-Br-6-MeOC(=O)O— |
| 1999 | 2-I-3-MeOC(=O)O— | 2000 | 2-I-4-MeOC(=O)O— | 2001 | 2-I-5-MeOC(=O)O— |
| 2002 | 2-I-6-MeOC(=O)O— | 2003 | 2-Me-3-MeOC(=O)— | 2004 | 2-Me-4-MeOC(=O)O— |
| 2005 | 2-Me-5-MeOC(=O)O— | 2006 | 2-Me-6-MeOC(=O)O— | 2007 | 2-F-3-EtOC(=O)O— |
| 2008 | 2-F-4-EtOC(=O)O— | 2009 | 2-F-5-EtOC(=O)O— | 2010 | 2-F-6-EtOC(=O)O— |
| 2011 | 2-Cl-3-EtOC(=O)O— | 2012 | 2-Cl-4-EtOC(=O)O— | 2013 | 2-Cl-5-EtOC(=O)O— |
| 2014 | 2-Cl-6-EtOC(=O)O— | 2015 | 2-Br-3-EtOC(=O)O— | 2016 | 2-Br-4-EtOC(=O)O— |
| 2017 | 2-Br-5-EtOC(=O)O— | 2018 | 2-Br-6-EtOC(=O)O— | 2019 | 2-I-3-EtOC(=O)O— |
| 2020 | 2-I-4-EtOC(=O)O— | 2021 | 2-I-5-EtOC(=O)O— | 2022 | 2-I-6-EtOC(=O)O— |
| 2023 | 2-Me-3-EtOC(=O)O— | 2024 | 2-Me-4-EtOC(=O)O— | 2025 | 2-Me-5-EtOC(=O)O— |
| 2026 | 2-Me-6-EtOC(=O)O— | 2027 | 2-F-3-(1,3-dioxolan-2-yl)- | 2028 | 2-F-4-(1,3-dioxolan-2-yl)- |
| 2029 | 2-F-5-(1,3-dioxolan-2-yl)- | 2030 | 2-F-6-(1,3-dioxolan-2-yl)- | 2031 | 2-Cl-3-(1,3-dioxolan-2-yl)- |
| 2032 | 2-Cl-4-(1,3-dioxolan-2-yl)- | 2033 | 2-Cl-5-(1,3-dioxolan-2-yl)- | 2034 | 2-Cl-6-(1,3-dioxolan-2-yl)- |
| 2035 | 2-Br-3-(1,3-dioxolan-2-yl)- | 2036 | 2-Br-4-(1,3-dioxolan-2-yl)- | 2037 | 2-Br-5-(1,3-dioxolan-2-yl)- |
| 2038 | 2-Br-6-(1,3-dioxolan-2-yl)- | 2039 | 2-I-3-(1,3-dioxolan-2-yl)- | 2040 | 2-I-4-(1,3-dioxolan-2-yl)- |
| 2041 | 2-I-5-(1,3-dioxolan-2-yl)- | 2042 | 2-I-6-(1,3-dioxolan-2-yl)- | 2043 | 2-Me-3-(1,3-dioxolan-2-yl)- |
| 2044 | 2-Me-4-(1,3-dioxolan-2-yl)- | 2045 | 2-Me-5-(1,3-dioxolan-2-yl)- | 2046 | 2-Me-6-(1,3-dioxolan-2-yl)- |
| 2047 | 2-F-3-(1,3-dioxan-2-yl)- | 2048 | 2-F-4-(1,3-dioxan-2-yl)- | 2049 | 2-F-5-(1,3-dioxan-2-yl)- |
| 2050 | 2-F-6-(1,3-dioxan-2-yl)- | 2051 | 2-Cl-3-(1,3-dioxan-2-yl)- | 2052 | 2-Cl-4-(1,3-dioxan-2-yl)- |
| 2053 | 2-Cl-5-(1,3-dioxan-2-yl)- | 2054 | 2-Cl-6-(1,3-dioxan-2-yl)- | 2055 | 2-Br-3-(1,3-dioxan-2-yl)- |
| 2056 | 2-Br-4-(1,3-dioxan-2-yl)- | 2057 | 2-Br-5-(1,3-dioxan-2-yl)- | 2058 | 2-Br-6-(1,3-dioxan-2-yl)- |
| 2059 | 2-I-3-(1,3-dioxan-2-yl)- | 2060 | 2-I-4-(1,3-dioxan-2-yl)- | 2061 | 2-I-5-(1,3-dioxan-2-yl)- |
| 2062 | 2-I-6-(1,3-dioxan-2-yl)- | 2063 | 2-Me-3-(1,3-dioxan-2-yl)- | 2064 | 2-Me-4-(1,3-dioxan-2-yl)- |
| 2065 | 2-Me-5-(1,3-dioxan-2-yl)- | 2066 | 2-Me-6-(1,3-dioxan-2-yl)- | 2067 | 2-F-3-MeS— |
| 2068 | 2-F-4-MeS— | 2069 | 2-F-5-MeS— | 2070 | 2-F-6-MeS— |
| 2071 | 2-Cl-3-MeS— | 2072 | 2-Cl-4-MeS— | 2073 | 2-Cl-5-MeS— |
| 2074 | 2-Cl-6-MeS— | 2075 | 2-Br-3-MeS— | 2076 | 2-Br-4-MeS— |
| 2077 | 2-Br-5-MeS— | 2078 | 2-Br-6-MeS— | 2079 | 2-I-3-MeS— |
| 2080 | 2-I-4-MeS— | 2081 | 2-I-5-MeS— | 2082 | 2-I-6-MeS— |
| 2083 | 2-Me-3-MeS— | 2084 | 2-Me-4-MeS— | 2085 | 2-Me-5-MeS— |
| 2086 | 2-Me-6-MeS— | 2087 | 2-F-3-MeS(O)— | 2088 | 2-F-4-MeS(O)— |
| 2089 | 2-F-5-MeS(O)— | 2090 | 2-F-6-MeS(O)— | 2091 | 2-Cl-3-MeS(O)— |
| 2092 | 2-Cl-4-MeS(O)— | 2093 | 2-Cl-5-MeS(O)— | 2094 | 2-Cl-6-MeS(O)— |
| 2095 | 2-Br-3-MeS(O)— | 2096 | 2-Br-4-MeS(O)— | 2097 | 2-Br-5-MeS(O)— |
| 2098 | 2-Br-6-MeS(O)— | 2099 | 2-I-3-MeS(O)— | 2100 | 2-I-4-MeS(O)— |
| 2101 | 2-I-5-MeS(O)— | 2102 | 2-I-6-MeS(O)— | 2103 | 2-Me-3-MeS(O)— |
| 2104 | 2-Me-4-MeS(O)— | 2105 | 2-Me-5-MeS(O)— | 2106 | 2-Me-6-MeS(O)— |
| 2107 | 2-F-3-MeSO$_2$— | 2108 | 2-F-4-MeSO$_2$— | 2109 | 2-F-5-MeSO$_2$— |
| 2110 | 2-F-6-MeSO$_2$— | 2111 | 2-Cl-3-MeSO$_2$— | 2112 | 2-Cl-4-MeSO$_2$— |
| 2113 | 2-Cl-5-MeSO$_2$— | 2114 | 2-Cl-6-MeSO$_2$— | 2115 | 2-Br-3-MeSO$_2$— |
| 2116 | 2-Br-4-MeSO$_2$— | 2117 | 2-Br-5-MeSO$_2$— | 2118 | 2-Br-6-MeSO$_2$— |
| 2119 | 2-I-3-MeSO$_2$— | 2120 | 2-I-4-MeSO$_2$— | 2121 | 2-I-5-MeSO$_2$— |
| 2122 | 2-I-6-MeSO$_2$— | 2123 | 2-Me-3-MeSO$_2$— | 2124 | 2-Me-4-MeSO$_2$— |
| 2125 | 2-Me-5-MeSO$_2$— | 2126 | 2-Me-6-MeSO$_2$— | 2127 | 2-F-3-ClCH$_2$S— |
| 2128 | 2-F-4-ClCH$_2$S— | 2129 | 2-F-5-ClCH$_2$S— | 2130 | 2-F-6-ClCH$_2$S— |
| 2131 | 2-Cl-3-ClCH$_2$S— | 2132 | 2-Cl-4-ClCH$_2$S— | 2133 | 2-Cl-5-ClCH$_2$S— |
| 2134 | 2-Cl-6-ClCH$_2$S— | 2135 | 2-Br-3-ClCH$_2$S— | 2136 | 2-Br-4-ClCH$_2$S— |
| 2137 | 2-Br-5-ClCH$_2$S— | 2138 | 2-Br-6-ClCH$_2$S— | 2139 | 2-I-3-ClCH$_2$S— |
| 2140 | 2-I-4-ClCH$_2$S— | 2141 | 2-I-5-ClCH$_2$S— | 2142 | 2-I-6-ClCH$_2$S— |
| 2143 | 2-Me-3-ClCH$_2$S— | 2144 | 2-Me-4-ClCH$_2$S— | 2145 | 2-Me-5-ClCH$_2$S— |
| 2146 | 2-Me-6-ClCH$_2$S— | 2147 | 2-F-3-ClCH$_2$S(O)— | 2148 | 2-F-4-ClCH$_2$S(O)— |
| 2149 | 2-F-5-ClCH$_2$S(O)— | 2150 | 2-F-6-ClCH$_2$S(O)— | 2151 | 2-Cl-3-ClCH$_2$S(O)— |
| 2152 | 2-Cl-4-ClCH$_2$S(O)— | 2153 | 2-Cl-5-ClCH$_2$S(O)— | 2154 | 2-Cl-6-ClCH$_2$S(O)— |
| 2155 | 2-Br-3-ClCH$_2$S(O)— | 2156 | 2-Br-4-ClCH$_2$S(O)— | 2157 | 2-Br-5-ClCH$_2$S(O)— |
| 2158 | 2-Br-6-ClCH$_2$S(O)— | 2159 | 2-I-3-ClCH$_2$S(O)— | 2160 | 2-I-4-ClCH$_2$S(O)— |
| 2161 | 2-I-5-ClCH$_2$S(O)— | 2162 | 2-I-6-ClCH$_2$S(O)— | 2163 | 2-Me-3-ClCH$_2$S(O)— |
| 2164 | 2-Me-4-ClCH$_2$S(O)— | 2165 | 2-Me-5-ClCH$_2$S(O)— | 2166 | 2-Me-6-ClCH$_2$S(O)— |
| 2167 | 2-F-3-ClCH$_2$SO$_2$— | 2168 | 2-F-4-ClCH$_2$SO$_2$— | 2169 | 2-F-5-ClCH$_2$SO$_2$— |
| 2170 | 2-F-6-ClCH$_2$SO$_2$— | 2171 | 2-Cl-3-ClCH$_2$SO$_2$— | 2172 | 2-Cl-4-ClCH$_2$SO$_2$— |
| 2173 | 2-Cl-5-ClCH$_2$SO$_2$— | 2174 | 2-Cl-6-ClCH$_2$SO$_2$— | 2175 | 2-Br-3-ClCH$_2$SO$_2$— |

TABLE 2-continued

| No. | (R2)n | No. | (R2)n | No. | (R2)n |
|---|---|---|---|---|---|
| 2176 | 2-Br-4-ClCH$_2$SO$_2$— | 2177 | 2-Br-5-ClCH$_2$SO$_2$— | 2178 | 2-Br-6-ClCH$_2$SO$_2$— |
| 2179 | 2-I-3-ClCH$_2$SO$_2$— | 2180 | 2-I-4-ClCH$_2$SO$_2$— | 2181 | 2-I-5-ClCH$_2$SO$_2$— |
| 2182 | 2-I-6-ClCH$_2$SO$_2$— | 2183 | 2-Me-3-ClCH$_2$SO$_2$— | 2184 | 2-Me-4-ClCH$_2$SO$_2$— |
| 2185 | 2-Me-5-ClCH$_2$SO$_2$— | 2186 | 2-Me-6-ClCH$_2$SO$_2$— | 2187 | 3,5-di-MeO— |
| 2188 | 3,5-di-EtO— | 2189 | 3,5-di-F— | 2190 | 3,5-di-Cl— |
| 2191 | 3,5-di-Br— | 2192 | 3,5-di-I— | 2193 | 3,5-di-Me— |
| 2194 | 3-F-5-Me— | 2195 | 3-Cl-5-Me— | 2196 | 3-Br-5-Me— |
| 2197 | 3-I-5-Me— | 2198 | 3-F-5-MeO— | 2199 | 3-Cl-5-MeO— |
| 2200 | 3-Br-5-MeO— | 2201 | 3-I-5-MeO— | 2202 | 5-F-3-EtO— |
| 2203 | 3-Cl-5-EtO— | 2204 | 3-Br-5-EtO— | 2205 | 5-I-3-EtO— |
| 2206 | 3-F-5-N≡CCH$_2$O— | 2207 | 3-Cl-5-N≡CCH$_2$O— | 2208 | 3-Br-5-N≡CCH$_2$O— |
| 2209 | 3-I-5-N≡CCH$_2$O— | 2210 | 3-F-5-MeOCH$_2$O— | 2211 | 3-Cl-5-MeOCH$_2$O— |
| 2212 | 3-Br-5-MeOCH$_2$O— | 2213 | 3-I-5-MeOCH$_2$O— | 2214 | 5-F-2-MeO— |
| 2215 | 5-Cl-2-MeO— | 2216 | 5-Br-2-MeO— | 2217 | 5-I-2-MeO— |
| 2218 | 5-Me-2-MeO— | 2219 | 2-F-3,5-di-MeO— | 2220 | 2-F-3,5-di-EtO— |
| 2221 | 2,3,5-tri-F— | 2222 | 2-F-3,5-di-Cl— | 2223 | 3,5-di-Br-2-F— |
| 2224 | 2-F-3,5-di-I— | 2225 | 2-F-3,5-di-Me— | 2226 | 2,3-di-F-5-Me— |
| 2227 | 2,5-di-F-3-Me— | 2228 | 3-Cl-2-F-5-Me— | 2229 | 5-Cl-2-F-3-Me— |
| 2230 | 3-Br-2-F-5-Me— | 2231 | 5-Br-2-F-3-Me— | 2232 | 2-F-3-I-5-Me— |
| 2233 | 2-F-5-I-3-Me— | 2234 | 2,3-di-F-5-MeO— | 2235 | 2,5-di-F-3-MeO— |
| 2236 | 3-Cl-2-F-5-MeO— | 2237 | 5-Cl-2-F-3-MeO— | 2238 | 3-Br-2-F-5-MeO— |
| 2239 | 5-Br-2-F-3-MeO— | 2240 | 2-F-3-I-5-MeO— | 2241 | 2-F-5-I-3-MeO— |
| 2242 | 2,3-di-F-5-EtO— | 2243 | 2,5-di-F-3-EtO— | 2244 | 3-Cl-2-F-5-EtO— |
| 2245 | 5-Cl-2-F-3-EtO— | 2246 | 3-Br-2-F-5-EtO— | 2247 | 5-Br-2-F-3-EtO— |
| 2248 | 2-F-3-I-5-EtO— | 2249 | 2-F-5-I-3-EtO— | 2250 | 2,3-di-F-5-N≡CCH$_2$O— |
| 2251 | 2,5-di-F-3-N≡CCH$_2$O— | 2252 | 3-Cl-2-F-5-N≡CCH$_2$O— | 2253 | 5-Cl-2-F-3-N≡CCH$_2$O— |
| 2254 | 3-Br-2-F-5-N≡CCH$_2$O— | 2255 | 5-Br-2-F-3-N≡CCH$_2$O— | 2256 | 2-F-3-I-5-N≡CCH$_2$O— |
| 2257 | 2-F-5-I-3-N≡CCH$_2$O— | 2258 | 2,3-di-F-5-MeOCH$_2$O— | 2259 | 2,5-di-F-3-MeOCH$_2$O— |
| 2260 | 3-Cl-2-F-5-MeOCH$_2$O— | 2261 | 5-Cl-2-F-3-MeOCH$_2$O— | 2262 | 3-Br-2-F-5-MeOCH$_2$O— |
| 2263 | 5-Br-2-F-3-MeOCH$_2$O— | 2264 | 2-F-3-I-5-MeOCH$_2$O— | 2265 | 2-F-5-I-3-MeOCH$_2$O— |
| 2266 | 2-Cl-3,5-di-MeO— | 2267 | 2-Cl-3,5-di-EtO— | 2268 | 2-Cl-3,5-di-F— |
| 2269 | 2,3,5-tri-Cl— | 2270 | 3,5-di-Br-2-Cl— | 2271 | 2-Cl-3,5-di-I— |
| 2272 | 2-Cl-3,5-di-Me— | 2273 | 2-Cl-3-F-5-Me— | 2274 | 2-Cl-5-F-3-Me— |
| 2275 | 2,3-di-Cl-5-Me— | 2276 | 2,5-di-Cl-3-Me— | 2277 | 3-Br-2-Cl-5-Me— |
| 2278 | 5-Br-2-Cl-3-Me— | 2279 | 2-Cl-3-I-5-Me— | 2280 | 2-Cl-5-I-3-Me— |
| 2281 | 2-Cl-3-F-5-MeO— | 2282 | 2-Cl-5-F-3-MeO— | 2283 | 2,3-di-Cl-5-MeO— |
| 2284 | 2,5-di-Cl-3-MeO— | 2285 | 3-Br-2-Cl-5-MeO— | 2286 | 5-Br-2-Cl-3-MeO— |
| 2287 | 2-Cl-3-I-5-MeO— | 2288 | 2-Cl-5-I-3-MeO— | 2289 | 2-Cl-3-F-5-EtO— |
| 2290 | 2-Cl-5-F-3-EtO— | 2291 | 2,3-di-Cl-5-EtO— | 2292 | 2,5-di-Cl-3-EtO— |
| 2293 | 3-Br-2-Cl-5-EtO— | 2294 | 5-Br-2-Cl-3-EtO— | 2295 | 2-Cl-3-I-5-EtO— |
| 2296 | 2-Cl-5-I-3-EtO— | 2297 | 2-Cl-3-F-5-N≡CCH$_2$O— | 2298 | 2-Cl-5-F-3-N≡CCH$_2$O— |
| 2299 | 2,3-di-Cl-5-N≡CCH$_2$O— | 2300 | 2,5-di-Cl-3-N≡CCH$_2$O— | 2301 | 3-Br-2-Cl-5-N≡CCH$_2$O— |
| 2302 | 5-Br-2-Cl-3-N≡CCH$_2$O— | 2303 | 2-Cl-3-I-5-N≡CCH$_2$O— | 2304 | 2-Cl-5-I-3-N≡CCH$_2$O— |
| 2305 | 2-Cl-3-F-5-MeOCH$_2$O— | 2306 | 2-Cl-5-F-3-MeOCH$_2$O— | 2307 | 2,3-di-Cl-5-MeOCH$_2$O— |
| 2308 | 2,5-di-Cl-3-MeOCH$_2$O— | 2309 | 3-Br-2-Cl-5-MeOCH$_2$O— | 2310 | 5-Br-2-Cl-3-MeOCH$_2$O— |
| 2311 | 2-Cl-3-I-5-MeOCH$_2$O— | 2312 | 2-Cl-5-I-3-MeOCH$_2$O— | 2313 | 2-Br-3,5-di-MeO— |
| 2314 | 2-Br-3,5-di-EtO— | 2315 | 2-Br-3,5-di-F— | 2316 | 2-Br-3,5-di-Cl— |
| 2317 | 2,3,5-tri-Br— | 2318 | 2-Br-3,5-di-I— | 2319 | 2-Br-3,5-di-Me— |
| 2320 | 2-Br-3-F-5-Me— | 2321 | 2-Br-5-F-3-Me— | 2322 | 2-Br-3-Cl-5-Me— |
| 2323 | 2-Br-5-Cl-3-Me— | 2324 | 2,3-di-Br-5-Me— | 2325 | 2,5-di-Br-3-Me— |
| 2326 | 2-Br-3-I-5-Me— | 2327 | 2-Br-5-I-3-Me— | 2328 | 2-Br-3-F-5-MeO— |
| 2329 | 2-Br-5-F-3-MeO— | 2330 | 2-Br-3-Cl-5-MeO— | 2331 | 2-Br-5-Cl-3-MeO— |
| 2332 | 2,3-di-Br-5-MeO— | 2333 | 2,5-di-Br-3-MeO— | 2334 | 2-Br-3-I-5-MeO— |
| 2335 | 2-Br-5-I-3-MeO— | 2336 | 2-Br-3-F-5-EtO— | 2337 | 2-Br-5-F-3-EtO— |
| 2338 | 2-Br-3-Cl-5-EtO— | 2339 | 2-Br-5-Cl-3-EtO— | 2340 | 2,3-di-Br-5-EtO— |
| 2341 | 2,5-di-Br-3-EtO— | 2342 | 2-Br-3-I-5-EtO— | 2343 | 2-Br-5-I-3-EtO— |
| 2344 | 2-Br-3-F-5-N≡CCH$_2$O— | 2345 | 2-Br-5-F-3-N≡CCH$_2$O— | 2346 | 2-Br-3-Cl-5-N≡CCH$_2$O— |
| 2347 | 2-Br-5-Cl-3-N≡CCH$_2$O— | 2348 | 2,3-di-Br-5-N≡CCH$_2$O— | 2349 | 2,5-di-Br-3-N≡CCH$_2$O— |
| 2350 | 2-Br-3-I-5-N≡CCH$_2$O— | 2351 | 2-Br-5-I-3-N≡CCH$_2$O— | 2352 | 2-Br-3-F-5-MeOCH$_2$O— |
| 2353 | 2-Br-5-F-3-MeOCH$_2$O— | 2354 | 2-Br-3-Cl-5-MeOCH$_2$O— | 2355 | 2-Br-5-Cl-3-MeOCH$_2$O— |
| 2356 | 2,3-di-Br-5-MeOCH$_2$O— | 2357 | 2,5-di-Br-3-MeOCH$_2$O— | 2358 | 2-Br-3-I-5-MeOCH$_2$O— |
| 2359 | 2-Br-5-I-3-MeOCH$_2$O— | 2360 | 2-I-3,5-di-MeO— | 2361 | 2-I-3,5-di-EtO— |
| 2362 | 3,5-di-F-2-I— | 2363 | 3,5-di-Cl-2-I— | 2364 | 3,5-di-Br-2-I— |
| 2365 | 2,3,5-Tri-I— | 2366 | 3,5-di-Me-2-I— | 2367 | 3-F-2-I-5-Me— |
| 2368 | 5-F-2-I-3-Me— | 2369 | 3-Cl-2-I-5-Me— | 2370 | 5-Cl-2-I-3-Me— |
| 2371 | 3-Br-2-I-5-Me— | 2372 | 5-Br-2-I-3-Me— | 2373 | 2,3-di-I-5-Me— |
| 2374 | 2,5-di-I-3-Me— | 2375 | 3-F-2-I-5-MeO— | 2376 | 5-F-2-I-3-MeO— |
| 2377 | 3-Cl-2-I-5-MeO— | 2378 | 5-Cl-2-I-3-MeO— | 2379 | 3-Br-2-I-5-MeO— |
| 2380 | 5-Br-2-I-3-MeO— | 2381 | 2,3-di-I-5-MeO— | 2382 | 2,5-di-I-3-MeO— |
| 2383 | 3-F-2-I-5-EtO— | 2384 | 5-F-2-I-3-EtO— | 2385 | 3-Cl-2-I-5-EtO— |
| 2386 | 5-Cl-2-I-3-EtO— | 2387 | 3-Br-2-I-5-EtO— | 2388 | 5-Br-2-I-3-EtO— |
| 2389 | 2,3-di-I-5-EtO— | 2390 | 2,5-di-I-3-EtO— | 2391 | 3-F-2-I-5-N≡CCH$_2$O— |
| 2392 | 5-F-2-I-3-N≡CCH$_2$O— | 2393 | 3-Cl-2-I-5-N≡CCH$_2$O— | 2394 | 5-Cl-2-I-3-N≡CCH$_2$O— |
| 2395 | 3-Br-2-I-5-N≡CCH$_2$O— | 2396 | 5-Br-2-I-3-N≡CCH$_2$O— | 2397 | 2,3-di-I-5-N≡CCH$_2$O— |
| 2398 | 2,5-di-I-3-N≡CCH$_2$O— | 2399 | 3-F-2-I-5-MeOCH$_2$O— | 2400 | 5-F-2-I-3-MeOCH$_2$O— |
| 2401 | 3-Cl-2-I-5-MeOCH$_2$O— | 2402 | 5-Cl-2-I-3-MeOCH$_2$O— | 2403 | 3-Br-2-I-5-MeOCH$_2$O— |
| 2404 | 5-Br-2-I-3-MeOCH$_2$O— | 2405 | 2,3-di-I-5-MeOCH$_2$O— | 2406 | 2,5-di-I-3-MeOCH$_2$O— |
| 2407 | 2-Me-3,5-di-MeO— | 2408 | 2-Me-3,5-di-EtO— | 2409 | 3,5-di-F-2-Me— |

TABLE 2-continued

| No. | (R2)n | No. | (R2)n | No. | (R2)n |
|---|---|---|---|---|---|
| 2410 | 3,5-di-Cl-2-Me— | 2411 | 3,5-di-Br-2-Me— | 2412 | 3,5-di-I-2-Me— |
| 2413 | 2,3,5-tri-Me— | 2414 | 3-F-2,5-di-Me— | 2415 | 5-F-2,3-di-Me— |
| 2416 | 3-Cl-2,5-di-Me— | 2417 | 5-Cl-2,3-di-Me— | 2418 | 3-Br-2,5-di-Me— |
| 2419 | 5-Br-2,3-di-Me— | 2420 | 3-I-2,5-di-Me— | 2421 | 5-I-2,3-di-Me— |
| 2422 | 3-F-2-Me-5-MeO— | 2423 | 5-F-2-Me-3-MeO— | 2424 | 3-Cl-2-Me-5-MeO— |
| 2425 | 5-Cl-2-Me-3-MeO— | 2426 | 3-Br-2-Me-5-MeO— | 2427 | 5-Br-2-Me-3-MeO— |
| 2428 | 3-I-2-Me-5-MeO— | 2429 | 5-I-2-Me-3-MeO— | 2430 | 3-F-2-Me-5-EtO— |
| 2431 | 5-F-2-Me-3-EtO— | 2432 | 3-Cl-2-Me-5-EtO— | 2433 | 5-O-2-Me-3-EtO— |
| 2434 | 3-Br-2-Me-5-EtO— | 2435 | 5-Br-2-Me-3-EtO— | 2436 | 3-I-2-Me-5-EtO— |
| 2437 | 5-I-2-Me-3-EtO— | 2438 | 3-F-2-Me-5-N≡CCH$_2$O— | 2439 | 5-F-2-Me-3-N≡CCH$_2$O— |
| 2440 | 3-Cl-2-Me-5-N≡CCH$_2$O— | 2441 | 5-Cl-2-Me-3-N≡CCH$_2$O— | 2442 | 3-Br-2-Me-5-N≡CCH$_2$O— |
| 2443 | 5-Br-2-Me-3-N≡CCH$_2$O— | 2444 | 3-I-2-Me-5-N≡CCH$_2$O— | 2445 | 5-I-2-Me-3-N≡CCH$_2$O— |
| 2446 | 3-F-2-Me-5-MeOCH$_2$O— | 2447 | 5-F-2-Me-3-MeOCH$_2$O— | 2448 | 3-Cl-2-Me-5-MeOCH$_2$O— |
| 2449 | 5-Cl-2-Me-3-MeOCH$_2$O— | 2450 | 3-Br-2-Me-5-MeOCH$_2$O— | 2451 | 5-Br-2-Me-3-MeOCH$_2$O— |
| 2452 | 3-I-2-Me-5-MeOCH$_2$O— | 2453 | 5-I-2-Me-3-MeOCH$_2$O— | 2454 | 2,3,6-Tri-F— |
| 2455 | 2,6-di-Cl-3-F— | 2456 | 2-Cl-3,6-di-F— | 2457 | 6-Cl-2,3-di-F— |
| 2458 | 3-Cl-2,6-di-F— | 2459 | 2,3,6-Tri-Cl— | 2460 | 2,3-di-O-6-F— |
| 2461 | 3,6-di-Cl-2-F— | 2462 | 3-Br-2,6-di-F— | 2463 | 3-Br-2,6-di-O— |
| 2464 | 3-Br-2-Cl-6-F— | 2465 | 3-Br-6-Cl-2-F— | 2466 | 2,6-di-F-3-I— |
| 2467 | 2,6-di-Cl-3-I— | 2468 | 2-Cl-6-F-3-I— | 2469 | 6-Cl-2-F-3-I— |
| 2470 | 2,6-di-F-3-Me— | 2471 | 2,6-di-Cl-3-Me— | 2472 | 2-Cl-6-F-3-Me— |
| 2473 | 6-Cl-2-F-3-Me— | 2474 | 2,6-di-F-3-MeO— | 2475 | 2,6-di-O-3-MeO— |
| 2476 | 2-Cl-6-F-3-MeO— | 2477 | 6-Cl-2-F-3-MeO— | 2478 | 2,6-di-F-3-EtO— |
| 2479 | 2,6-di-Cl-3-EtO— | 2480 | 2-Cl-6-F-3-EtO— | 2481 | 6-Cl-2-F-3-EtO— |
| 2482 | 2,6-di-F-3-N≡CCH$_2$O— | 2483 | 2,6-di-Cl-3-N≡CCH$_2$O— | 2484 | 2-Cl-6-F-3-N≡CCH$_2$O— |
| 2485 | 6-Cl-2-F-3-N≡CCH$_2$O— | 2486 | 2,6-di-F-3-MeOCH$_2$O— | 2487 | 2,6-di-Cl-3-MeOCH$_2$O— |
| 2488 | 2,6-di-F-3-MeOCH$_2$O— | 2489 | 6-Cl-2-F-3-MeOCH$_2$O— | 2490 | 3,4,5-tri-F— |
| 2491 | 4-Cl-3,5-di-F— | 2492 | 4-Br-3,5-di-F— | 2493 | 3,5-di-F-4-I— |
| 2494 | 3,5-di-F-4-Me— | 2495 | 3,5-di-Cl-4-F— | 2496 | 3,4,5-tri-Cl— |
| 2497 | 4-Br-3,5-di-Cl— | 2498 | 3,5-di-Cl-4-I— | 2499 | 3,5-di-Cl-4-Me— |
| 2500 | 3,5-di-Br-4-F— | 2501 | 3,5-di-Br-4-Cl— | 2502 | 3,4,5-tri-Br— |
| 2503 | 3,5-di-Br-4-I— | 2504 | 3,5-di-Br-4-Me— | 2505 | 4-F-3,5-di-I— |
| 2506 | 4-Cl-3,5-di-I— | 2507 | 4-Br-3,5-di-I— | 2508 | 3,4,5-tri-I— |
| 2509 | 4-Me-3,5-di-I— | 2510 | 4-F-3,5-di-Me— | 2511 | 4-Cl-3,5-di-Me— |
| 2512 | 4-Br-3,5-di-Me— | 2513 | 4-I-3,5-di-Me— | 2514 | 3,4,5-tri-Me— |
| 2515 | 4-F-3,5-di-Me— | 2516 | 4-Cl-3,5-di-Me— | 2517 | 4-Br-3,5-di-Me— |
| 2518 | 4-I-3,5-di-Me— | 2519 | 4-MeO-3,5-di-Me— | 2520 | 4-F-3,5-di-MeO— |
| 2521 | 4-Cl-3,5-di-MeO— | 2522 | 4-Br-3,5-di-MeO— | 2523 | 4-I-3,5-di-MeO— |
| 2524 | 4-Me-3,5-di-MeO— | 2525 | 4-F-3,5-di-EtO— | 2526 | 4-Cl-3,5-di-EtO— |
| 2527 | 4-Br-3,5-di-EtO— | 2528 | 4-I-3,5-di-EtO— | 2529 | 4-Me-3,5-di-EtO— |
| 2530 | 2,3,4-tri-F— | 2531 | 2-Cl-3,4-di-F— | 2532 | 2-Br-3,4-di-F— |
| 2533 | 3,4-di-F-2-I— | 2534 | 3,4-di-F-2-Me— | 2535 | 2,4,5-tri-F— |
| 2536 | 2-Cl-4,5-di-F— | 2537 | 2-Br-4,5-di-F— | 2538 | 4,5-di-F-2-I— |
| 2539 | 4,5-di-F-2-Me— | 2540 | 2,4-di-F-3-Cl— | 2541 | 2,3-di-Cl-4-F— |
| 2542 | 2-Br-3-Cl-4-F— | 2543 | 3-Cl-4-F-2-I— | 2544 | 3-Cl-4-F-2-Me— |
| 2545 | 2,4-di-F-5-Cl— | 2546 | 2,5-di-Cl-4-F— | 2547 | 2-Br-5-Cl-4-F— |
| 2548 | 5-Cl-4-F-2-I— | 2549 | 5-Cl-4-F-2-Me— | 2550 | 2-F-3,4-di-Cl— |
| 2551 | 2,3,4-tri-Cl— | 2552 | 2-Br-3,4-di-Cl— | 2553 | di-3,4-Cl-2-I— |
| 2554 | di-3,4-Cl-2-Me— | 2555 | 2-F-3,5-di-Cl— | 2556 | 2,3,5-tri-Cl— |
| 2557 | 2-Br-3,5-di-Cl— | 2558 | 3,5-di-Cl-2-I— | 2559 | 3,5-di-Cl-2-Me— |
| 2560 | 4-Cl-2,3-di-F— | 2561 | 2,4-di-Cl-3-F— | 2562 | 2-Br-4-Cl-3-F— |
| 2563 | 4-Cl-3-F-2-I— | 2564 | 4-Cl-3-F-2-Me— | 2565 | 4-Cl-2,5-di-F— |
| 2566 | 2,4-di-Cl-5-F— | 2567 | 2-Br-4-Cl-5-F— | 2568 | 4-Cl-5-F-2-I— |
| 2569 | 4-Cl-5-F-2-Me— | 2570 | 2,4-di-F-3-MeO— | 2571 | 2-Cl-4-F-3-MeO— |
| 2572 | 2-Br-4-F-3-MeO— | 2573 | 4-F-2-I-3-MeO— | 2574 | 4-F-2-Me-3-MeO— |
| 2575 | 2,4-F-5-MeO— | 2576 | 2-Cl-4-F-5-MeO— | 2577 | 2-Br-4-F-5-MeO— |
| 2578 | 4-F-2-I-5-MeO— | 2579 | 4-F-2-Me-5-MeO— | 2580 | 4-Cl-2-F-3-MeO— |
| 2581 | 2,4-di-Cl-3-MeO— | 2582 | 2-Br-4-Cl-3-MeO— | 2583 | 4-Cl-2-I-3-MeO— |
| 2584 | 4-Cl-2-Me-3-MeO— | 2585 | 4-Cl-2-F-5-MeO— | 2586 | 2,4-di-Cl-5-MeO— |
| 2587 | 2-Br-4-Cl-5-MeO— | 2588 | 4-Cl-2-I-5-MeO— | 2589 | 4-Cl-2-Me-5-MeO— |
| 2590 | 2,6-di-F-3,5-di-MeO— | 2591 | 2,6-di-Cl-3,5-di-MeO— | 2592 | 6-Cl-2-F-3,5-di-MeO— |
| 2593 | 6-Br-2-F-3,5-di-MeO— | 2594 | 2-Br-6-Cl-3,5-di-MeO— | 2595 | 2,3,4,5-tetra-F— |
| 2596 | 2,3,5,6,-tetra-F— | 2597 | 2,3,4,5,6-penta-F— | 2598 | 2-Me$_3$SiCH$_2$CH$_2$OCH$_2$O— |
| 2599 | 3-Me$_3$SiCH$_2$CH$_2$OCH$_2$O— | 2600 | 4-Me$_3$SiCH$_2$CH$_2$OCH$_2$O— | 2601 | 2-F-3-Me$_3$SiCH$_2$CH$_2$OCH$_2$O— |
| 2602 | 2-F-4-Me$_3$SiCH$_2$CH$_2$OCH$_2$O— | 2603 | 2-F-5-Me$_3$SiCH$_2$CH$_2$OCH$_2$O— | 2604 | 2-F-6-Me$_3$SiCH$_2$CH$_2$OCH$_2$O— |
| 2605 | 2-Cl-3-Me$_3$SiCH$_2$CH$_2$OCH$_2$O— | 2606 | 2-Cl-4-Me$_3$SiCH$_2$CH$_2$OCH$_2$O— | 2607 | 2-Cl-5-Me$_3$SiCH$_2$CH$_2$OCH$_2$O— |
| 2608 | 2-Cl-6-Me$_3$SiCH$_2$CH$_2$OCH$_2$O— | 2609 | 2-Br-3-Me$_3$SiCH$_2$CH$_2$OCH$_2$O— | 2610 | 2-Br-4-Me$_3$SiCH$_2$CH$_2$OCH$_2$O— |
| 2611 | 2-Br-5-Me$_3$SiCH$_2$CH$_2$OCH$_2$O— | 2612 | 2-Br-6-Me$_3$SiCH$_2$CH$_2$OCH$_2$O— | 2613 | 2-I-3-Me$_3$SiCH$_2$CH$_2$OCH$_2$O— |

TABLE 2-continued

| No. | (R2)n | No. | (R2)n | No. | (R2)n |
|---|---|---|---|---|---|
| 2614 | 2-I-4-Me$_3$SiCH$_2$CH$_2$OCH$_2$O— | 2615 | 2-I-5-Me$_3$SiCH$_2$CH$_2$OCH$_2$O— | 2616 | 2-I-6-Me$_3$SiCH$_2$CH$_2$OCH$_2$O— |
| 2617 | 2-Me-3-Me$_3$SiCH$_2$CH$_2$OCH$_2$O— | 2618 | 2-Me-4-Me$_3$SiCH$_2$CH$_2$OCH$_2$O— | 2619 | 2-Me-5-Me$_3$SiCH$_2$CH$_2$OCH$_2$O— |
| 2620 | 2-Me-6-Me$_3$SiCH$_2$CH$_2$OCH$_2$O— | | | | |

The methods for producing the compounds of Formula (1) is exemplified below.

[Production Method A]

[Chem. 15]

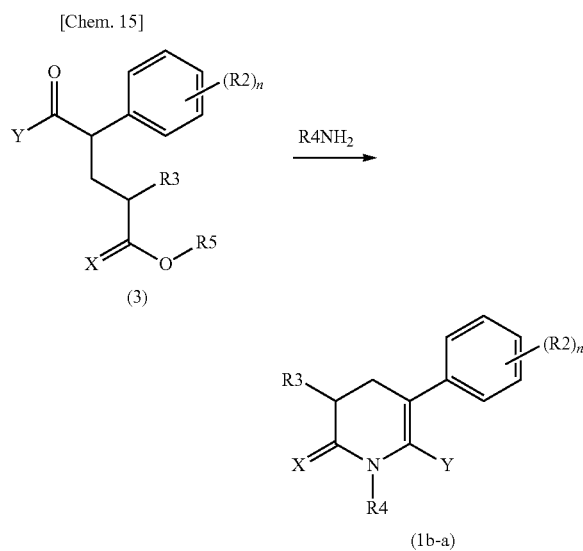

Production Method A produces a compound of Formula (1b-a) which is the inventive compound or the intermediate for the inventive compound. The production method includes reacting a compound of Formula (3) with R4NH$_2$ in the presence of an acid.

In the formula, R4 represents a hydrogen atom, a hydroxy group, a cyano group, a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, a C2-C6 haloalkynyl group, a C1-C6 alkoxy group optionally substituted with substituent A, a C1-C6 haloalkoxy group, a C3-C8 cycloalkoxy group optionally substituted with substituent A, a C2-C6 alkenyloxy group optionally substituted with substituent A, a C2-C6 haloalkenyloxy group, a C3-C6 alkynyloxy group optionally substituted with substituent A, a C3-C6 haloalkynyloxy group or an R10R11N— group (wherein R10 and R11 each independently represents a hydrogen atom or a C1-C6 alkyl group), R5 represents a hydrogen atom or a C1-C6 alkyl group, and n, R2, R3, X and Y are the same as defined hereinabove.

The R4NH$_2$ used in the reaction can be commercially available or produced by a known method. The R4NH$_2$ may be in the form of a salt with an acidic compound such as hydrochloric acid or acetic acid, and is not particularly limited as long as the objective reaction takes place.

The amount of the R4NH$_2$ used in the reaction is 1 equivalent weight or more relative to the compound of Formula (3). The amount is not particularly limited as long as the objective reaction takes place, and is preferably from 1 equivalent weight to 200 equivalent weight.

Examples of the acids used in the reaction include inorganic acids such as hydrochloric acid and sulfuric acid, and organic acids such as acetic acid, methanesulfonic acid and p-toluenesulfonic acid. The acid is not particularly limited as long as the objective reaction takes place, and acetic acid is preferable. The use of an acid is not an absolute necessity when the R4NH$_2$ is used as a salt with an acidic compound.

The amount of the acid used in the reaction is 1 equivalent weight or more relative to the R4NH$_2$. The amount is not particularly limited as long as the objective reaction takes place, and is preferably from 1 equivalent weight to 200 equivalent weight. When the acid used is liquid, the acid may also be used as a solvent.

The reaction may involve a solvent, which however is not an absolute necessity.

The solvent used in the reaction is not particularly limited as long as the objective reaction takes place. Examples include acidic solvents such as acetic acid and methanesulfonic acid, ether solvents such as diethyl ether, diisopropyl ether, methyl-t-butyl ether, dimethoxyethane, tetrahydrofuran and dioxane, alcohol solvents such as methanol, ethanol and isopropanol, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride. These solvents may be used singly, or two or more of these solvents may be used in combination in any ratio. As the solvents, among others, acidic solvents are preferable, and acetic acid is more preferable.

The amount of the solvent used in the reaction is not particularly limited as long as the objective reaction takes place, and is usually 3 to 200 times by weight relative to the amount of the compound of Formula (3).

The temperature of the reaction is not particularly limited as long as the objective reaction takes place, and is usually 50° C. to 180° C., or is not greater than the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane. These solvents may be used singly, or two or more of these solvents may be used in combination in any ratio. The liquid separation may be performed as many times as desired without limitation due to the desired purity and yield.

The above-obtained reaction mixture which includes the compound of Formula (1b-a) may be dried with a desiccant such as sodium sulfate or magnesium sulfate, but this dehydration may be omitted.

The above-obtained reaction mixture which includes the compound of Formula (1b-a) may be distilled to evaporate the solvent under reduced pressure as long as the compound is not decomposed.

The distilled reaction mixture which includes the compound of Formula (1b-a) may be purified with an appropriate solvent by a method such as washing, reprecipitation, recrystallization or column chromatography. The purification method may be selected appropriately due to the desired purity.

A compound produced by Production Method A that is represented by Formula (1b-a) in which R4 is a hydrogen atom, i.e. a compound of Formula (2), may be a useful intermediate for the production of a compound of Formula (1b) among the inventive compounds.

The specific examples of the production intermediates of Formula (2) are shown by the combinations of the structural formulae depicted in Table 3, (R2)n described in Table 2, and an oxygen atom or sulfur atom represented by X. Such compounds are only illustrative, and the scope of the invention is not limited thereto.

TABLE 3

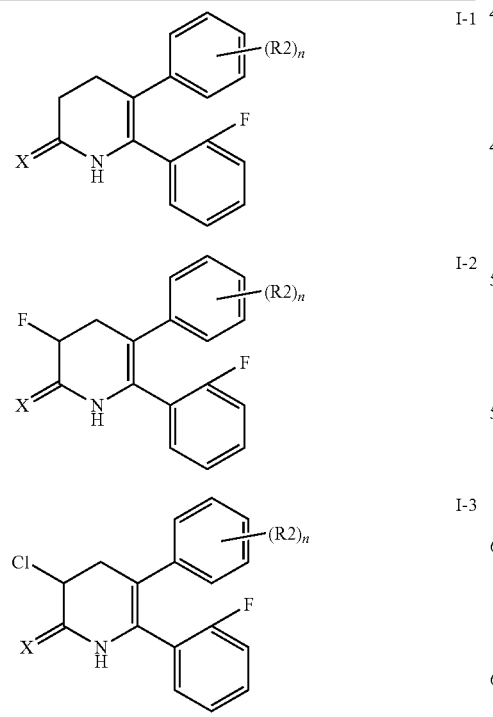

TABLE 3-continued

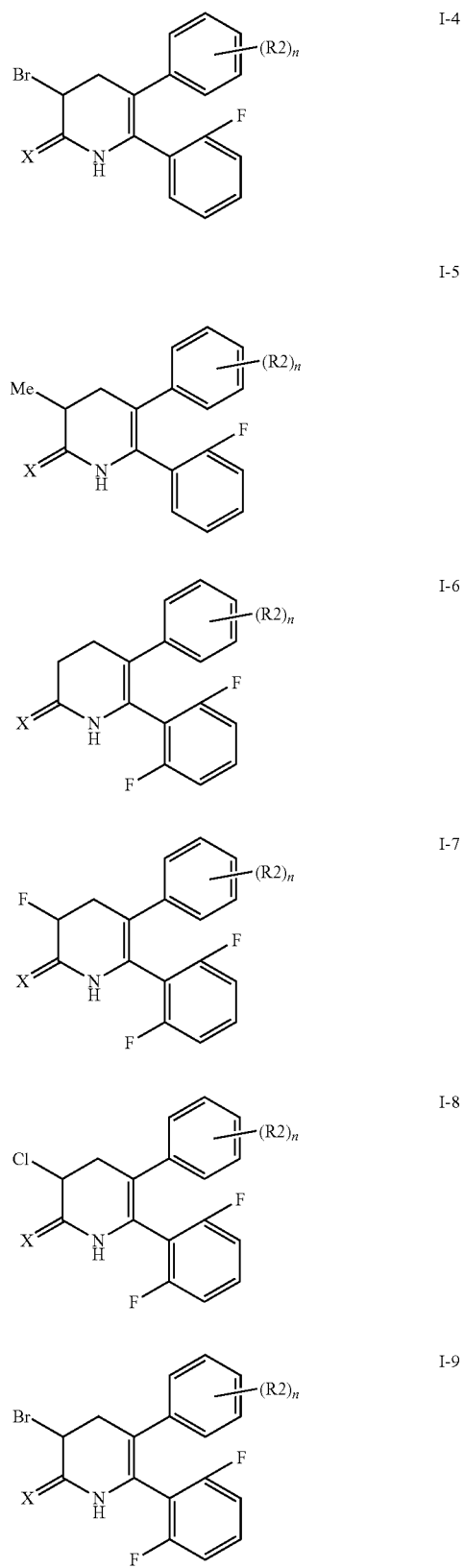

TABLE 3-continued
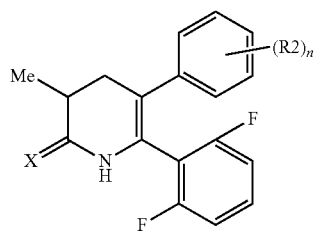
I-10
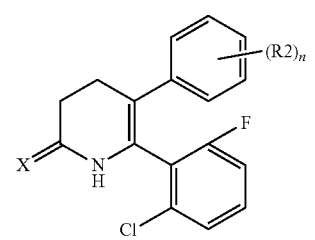
I-11
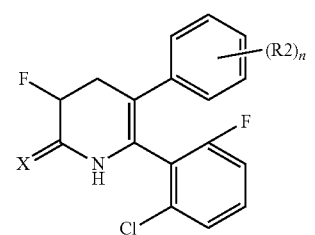
I-12
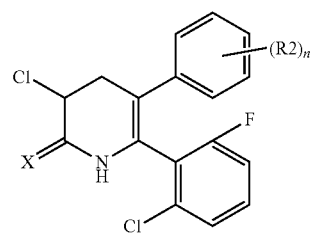
I-13
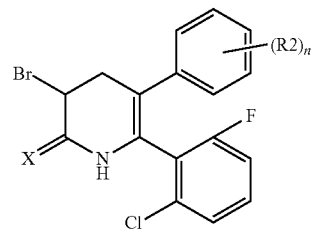
I-14
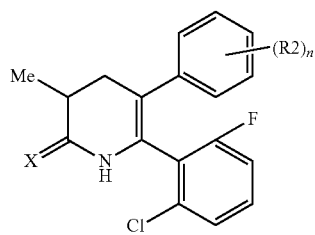
I-15
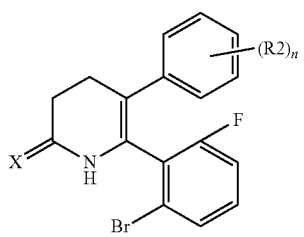
I-16
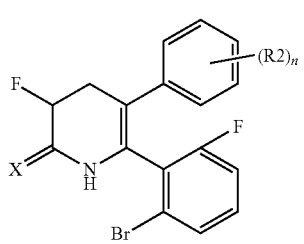
I-17
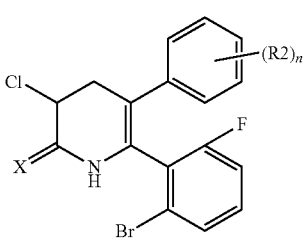
I-18
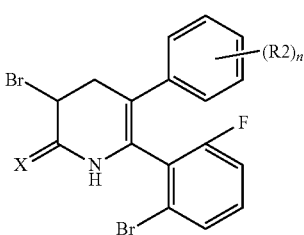
I-19
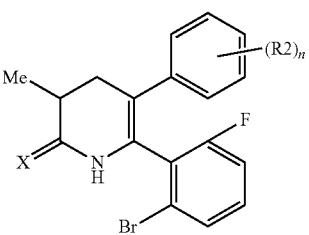
I-20
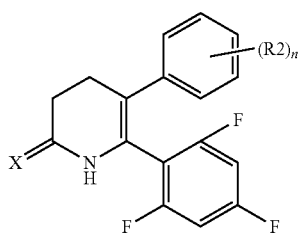
I-21

TABLE 3-continued
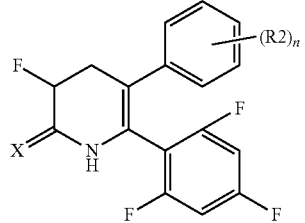 I-22
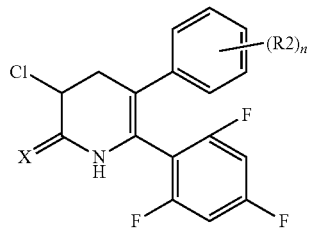 I-23
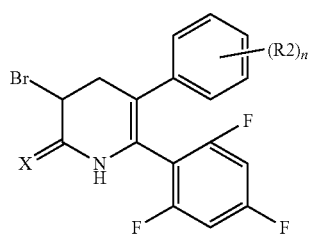 I-24
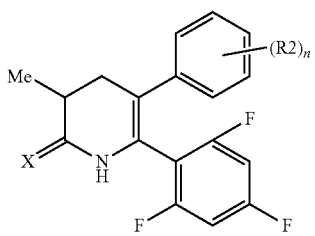 I-25
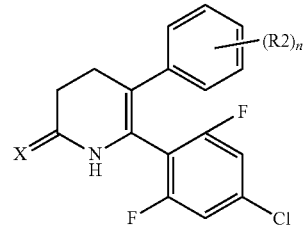 I-26
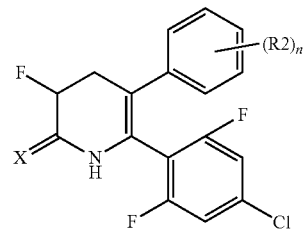 I-27
TABLE 3-continued
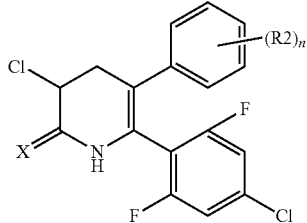 I-28
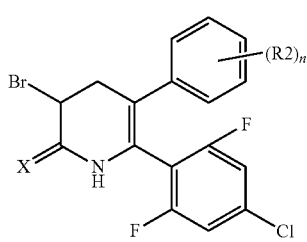 I-29
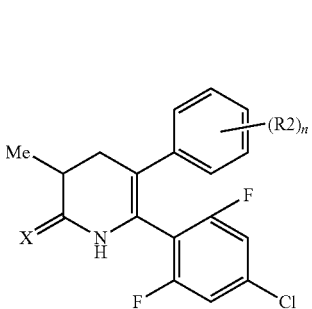 I-30
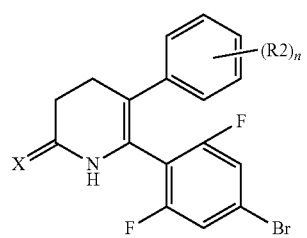 I-31
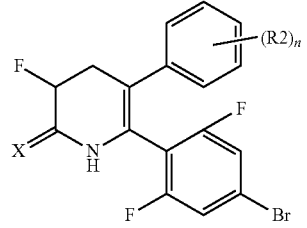 I-32
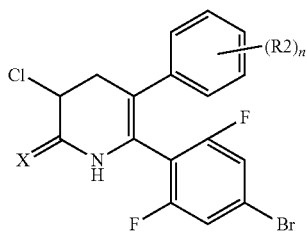 I-33

TABLE 3-continued
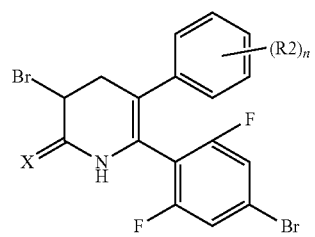  I-34
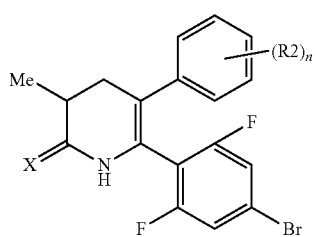  I-35
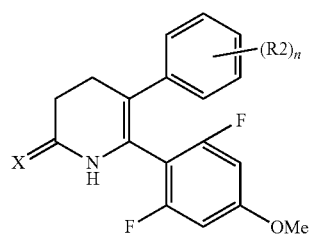  I-36
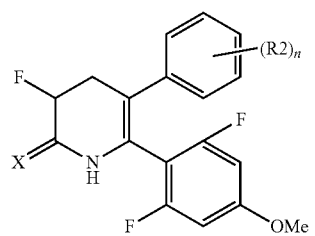  I-37
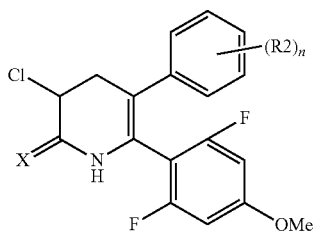  I-38
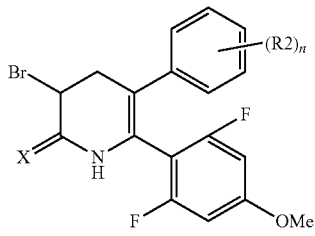  I-39
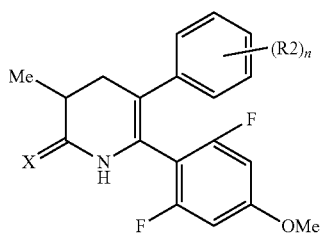  I-40
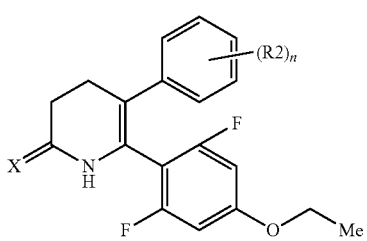  I-41
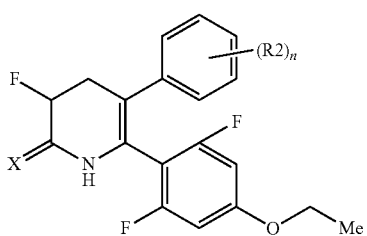  I-42
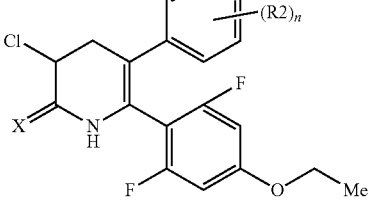  I-43
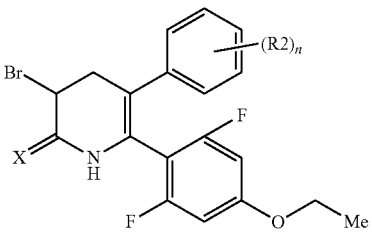  I-44
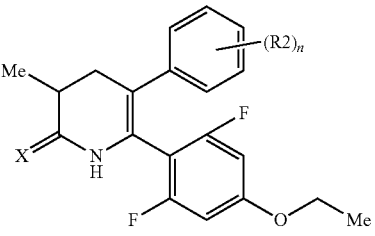  I-45

TABLE 3-continued

| Compound | Structure |
|---|---|
| I-46 | 3,4-dihydropyridin-2(1H)-one core with X=, 3-(R2)n-phenyl at 5-position, 3-chloropyridin-4-yl at 6-position |
| I-47 | 3-F substituted; 3-(R2)n-phenyl at 5; 3-chloropyridin-4-yl at 6 |
| I-48 | 3-Cl substituted; 3-(R2)n-phenyl at 5; 3-chloropyridin-4-yl at 6 |
| I-49 | 3-Br substituted; 3-(R2)n-phenyl at 5; 3-chloropyridin-4-yl at 6 |
| I-50 | 3-Me substituted; 3-(R2)n-phenyl at 5; 3-chloropyridin-4-yl at 6 |
| I-51 | 3-(R2)n-phenyl at 5; 3,5-dichloropyridin-2-yl at 6 |
| I-52 | 3-F; 3-(R2)n-phenyl at 5; 3,5-dichloropyridin-2-yl at 6 |
| I-53 | 3-Cl; 3-(R2)n-phenyl at 5; 3,5-dichloropyridin-2-yl at 6 |
| I-54 | 3-Br; 3-(R2)n-phenyl at 5; 3,5-dichloropyridin-2-yl at 6 |
| I-55 | 3-Me; 3-(R2)n-phenyl at 5; 3,5-dichloropyridin-2-yl at 6 |
| I-56 | 3-(R2)n-phenyl at 5; 3-chloro-5-methoxypyridin-2-yl at 6 |
| I-57 | 3-F; 3-(R2)n-phenyl at 5; 3-chloro-5-methoxypyridin-2-yl at 6 |
| I-58 | 3-Cl; 3-(R2)n-phenyl at 5; 3-chloro-5-methoxypyridin-2-yl at 6 |

TABLE 3-continued
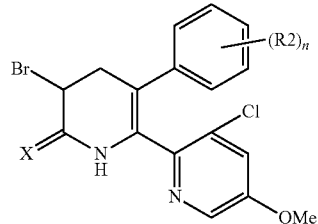
I-59
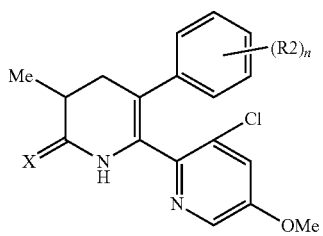
I-60
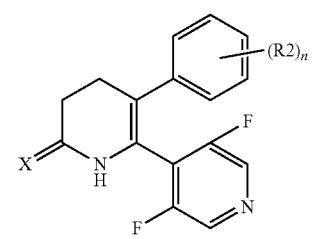
I-61
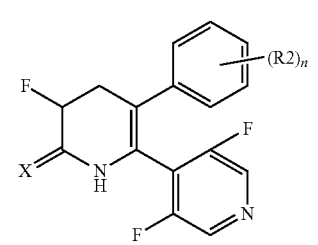
I-62
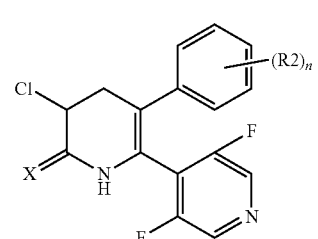
I-63
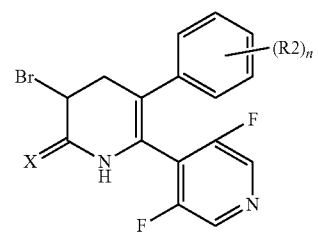
I-64
TABLE 3-continued
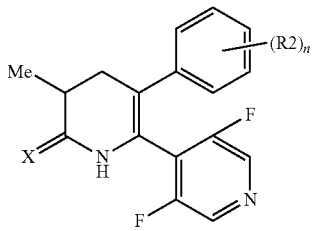
I-65
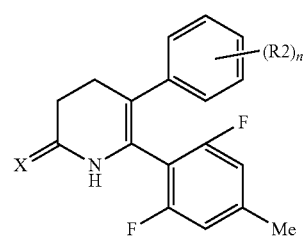
I-66
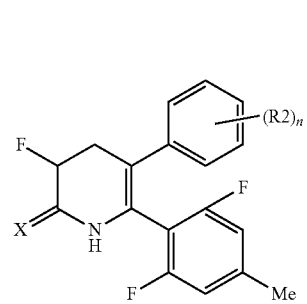
I-67
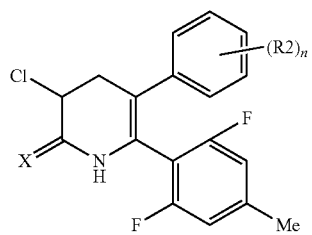
I-68
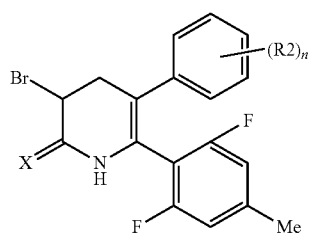
I-69
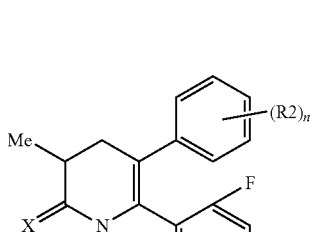
I-70

TABLE 3-continued
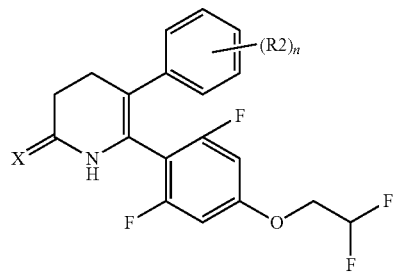 I-71
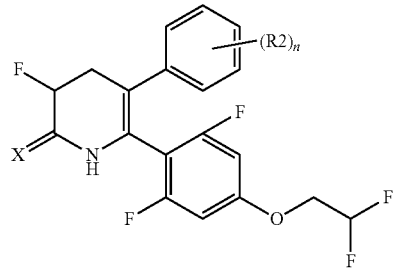 I-72
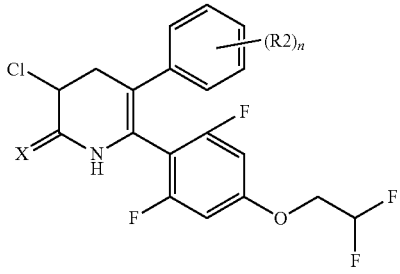 I-73
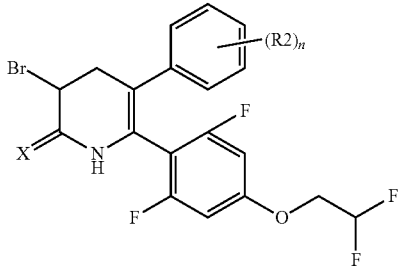 I-74
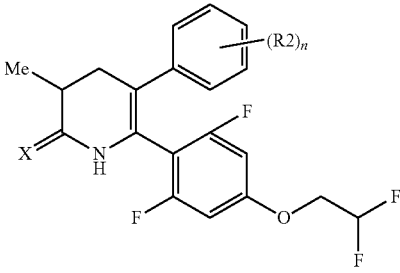 I-75
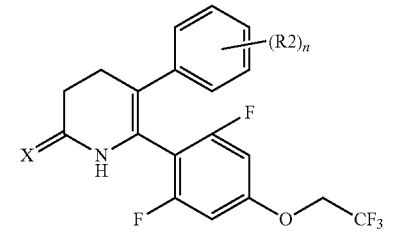 I-76
TABLE 3-continued
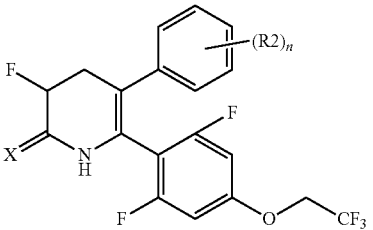 I-77
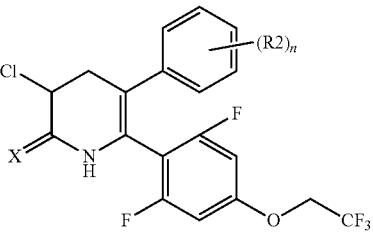 I-78
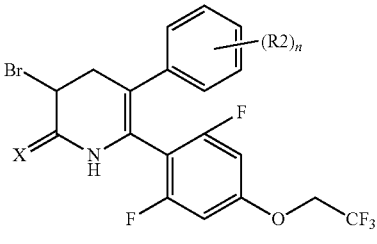 I-79
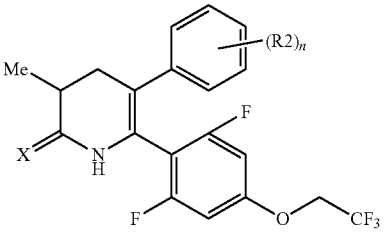 I-80
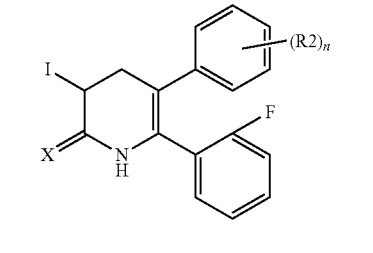 I-81
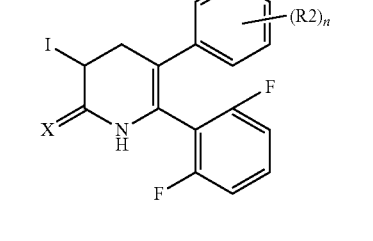 I-82

TABLE 3-continued
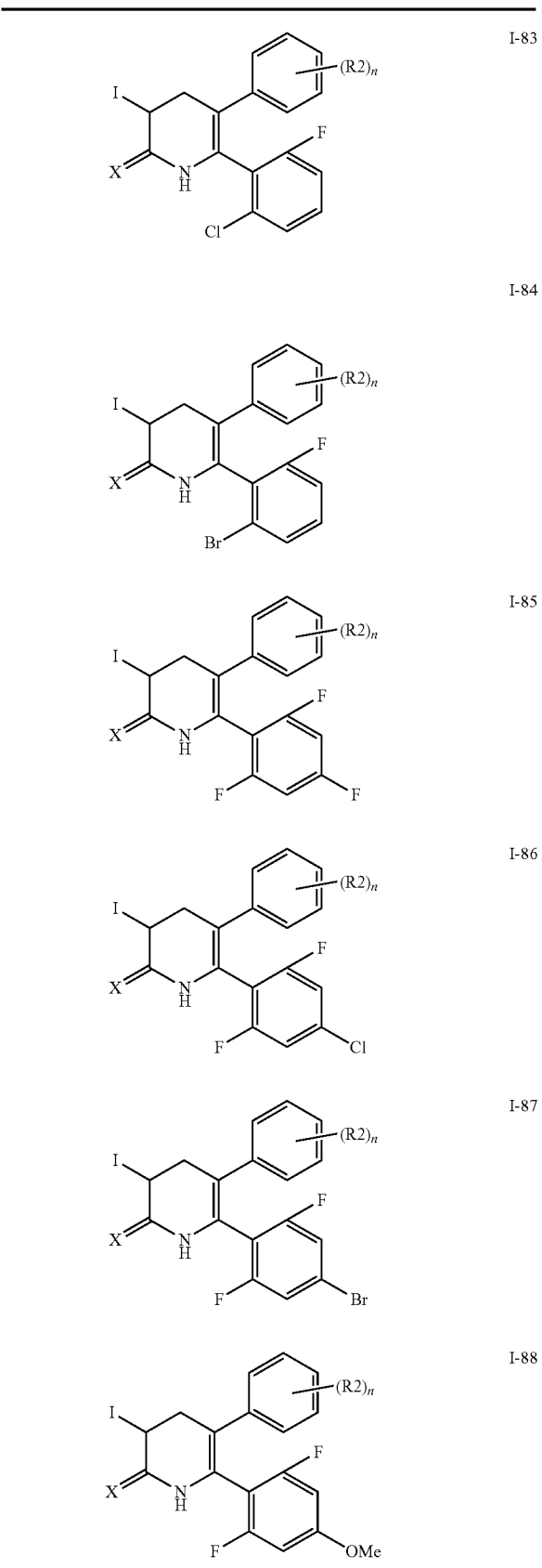
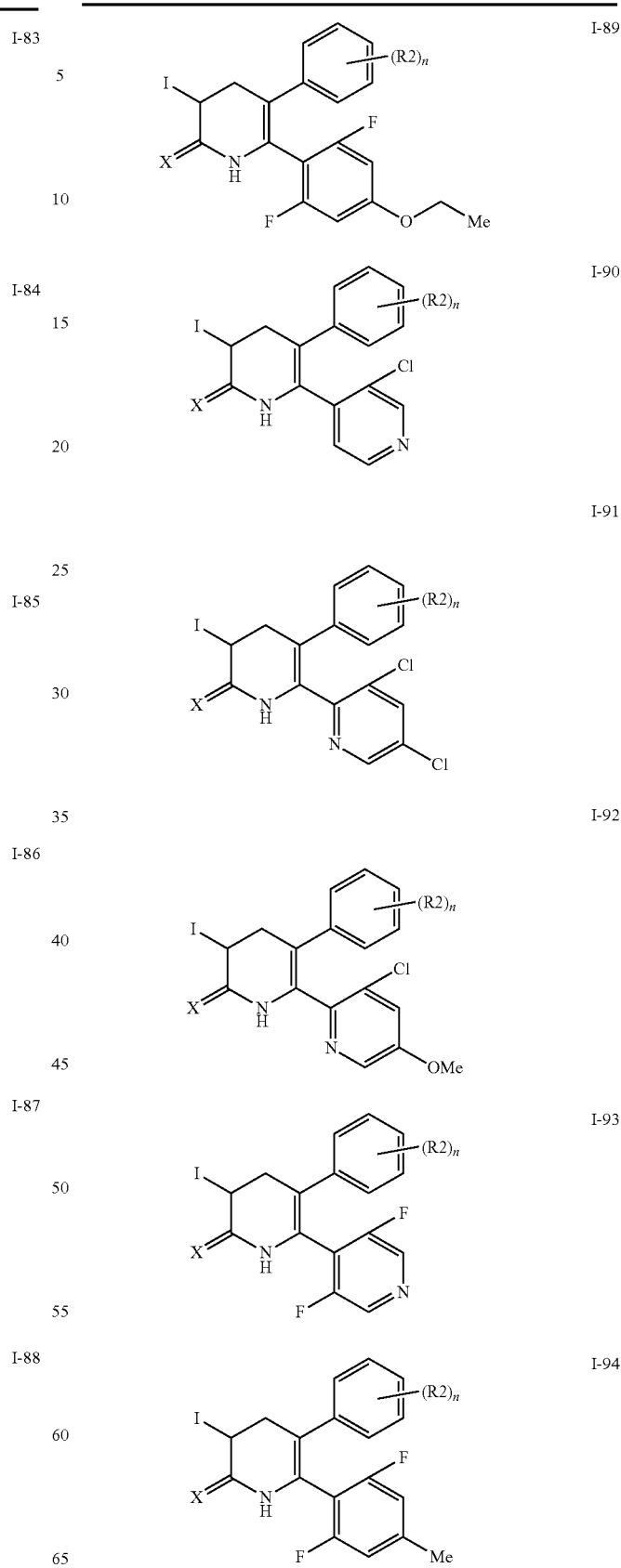

TABLE 3-continued

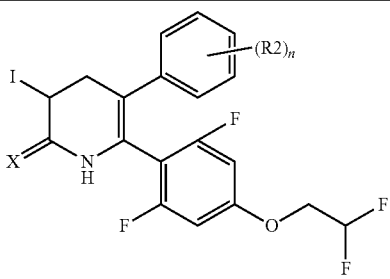

I-95

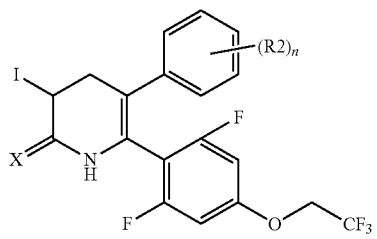

I-96

Illustrated below is the method for obtaining a compound of Formula (1b) of the invention using a compound of Formula (2) as an intermediate.

[Production Method B]

[Chem. 16]

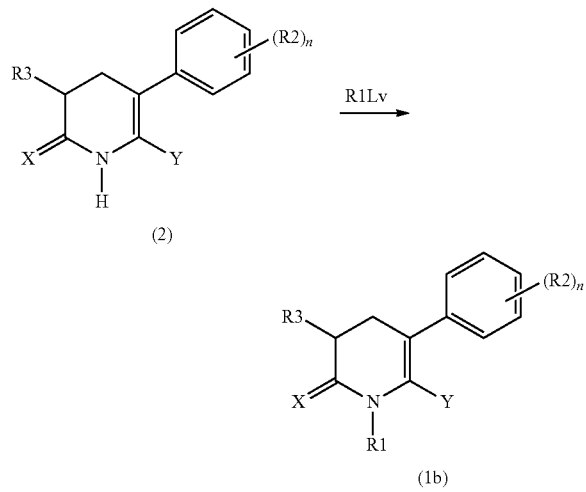

In the formula, Lv represents a leaving group such as methanesulfonyl, trifluoromethanesulfonyl, p-toluenesulfonyl or a halogen atom, and R1, R2, R3, X, Y and n are the same as defined hereinabove.

Production Method B produces a compound of Formula (1b). The production method includes reacting an intermediate of Formula (2) with R1Lv in a solvent in the presence of a base.

The R1Lv used in the reaction can be commercially available or produced by a known method.

The amount of the R1Lv used in the reaction is 1 equivalent amount or more relative to the compound of Formula (2). The amount is not particularly limited as long as the objective reaction takes place, and is preferably from 1 equivalent amount to 10 equivalent amount.

Examples of the bases used in the reaction include inorganic bases such as sodium hydroxide, potassium hydroxide, sodium carbonate, potassium carbonate, cesium carbonate and sodium hydride. The bases are not particularly limited thereto as long as the objective reaction takes place.

The amount of the base used in the reaction is 1 equivalent amount or more relative to the compound of Formula (2). The amount is not particularly limited as long as the objective reaction takes place, and is preferably from 1 equivalent amount to 10 equivalent amount.

The solvent used in the reaction is not particularly limited as long as the objective reaction takes place. Examples include ether solvents such as diethyl ether, diisopropyl ether, methyl-t-butyl ether, dimethoxyethane, tetrahydrofuran and dioxane, alcohol solvents such as methanol, ethanol and isopropanol, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethyl sulfoxide and sulfolane, ketone solvents such as acetone, methyl ethyl ketone and methyl isobutyl ketone. These solvents may be used singly, or two or more of these solvents may be used in combination in any ratio.

The amount of the solvent used in the reaction is not particularly limited as long as the objective reaction takes place, and is usually from 3 to 200 times by weight relative to the amount of the compound of Formula (2).

The temperature of the reaction is not particularly limited as long as the objective reaction takes place, and is usually from 0° C. to 150° C., or is not greater than the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, aqueous solutions of sulfur-containing salts such as sodium thiosulfate and sodium sulfite, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane. These solvents may be used singly, or two or more of these solvents may be used in combination in any ratio. The liquid separation may be performed as many times as desired without limitation due to the desired purity and yield.

The above-obtained reaction mixture which includes the compound of Formula (1b) may be dried with a desiccant such as sodium sulfate or magnesium sulfate, but this dehydration may be omitted.

The above-obtained reaction mixture which includes the compound of Formula (1b) may be distilled to evaporate the solvent under reduced pressure as long as the compound is not decomposed.

The distilled reaction mixture which includes the compound of Formula (1b) may be purified in an appropriate solvent by a method such as washing, reprecipitation, recrystallization or column chromatography. The purification method may be selected appropriately due to the desired purity.

[Production Method C]

[Chem. 17]

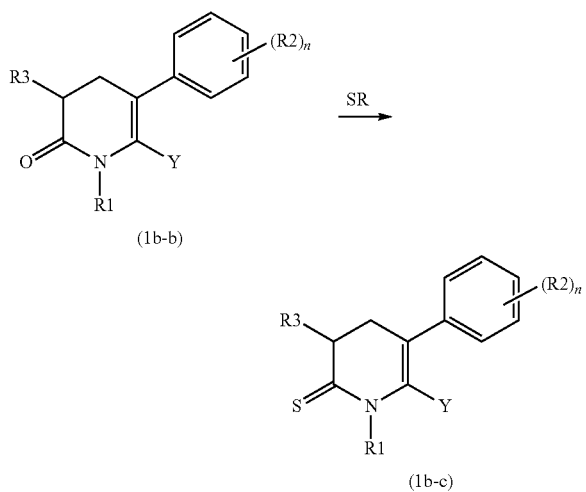

In the formulae, R represents a sulfurizing agent, and R1, R2, R3, Y and n are the same as defined hereinabove.

Production Method C produces a compound of Formula (1b-c), which belongs to the compounds of Formula (1b). The production method includes reacting a compound of Formula (1b-b) with a sulfurizing agent (SR) in a solvent.

An example of the sulfurizing agents used in the reaction includes Lawesson's reagent (2,4-bis(4-methoxyphenyl)-1,3-dithia-2,4-diphosphetane-2,4-disulfide).

The amount of the sulfurizing agent used in the reaction is 0.5 equivalent amount or more relative to the compound of Formula (1b-b). The amount is not particularly limited as long as the objective reaction takes place, and is preferably from 1 equivalent amount to 10 equivalent amount.

The solvent used in the reaction is not particularly limited as long as the objective reaction takes place. Examples include ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene. These solvents may be used singly, or two or more of these solvents may be used in combination in any ratio.

The amount of the solvent used in the reaction is not particularly limited as long as the objective reaction takes place, and is usually from 3 to 200 times by weight relative to the amount of the compound of Formula (1b-b).

The temperature of the reaction is not particularly limited as long as the objective reaction takes place, and is usually from 50° C. to 180° C., or is not greater than the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane. These solvents may be used singly, or two or more of these solvents may be used in combination in any ratio. The liquid separation may be performed as many times as desired without limitation due to the desired purity and yield. In the reaction, the liquid separation is not an absolute necessity.

The above-obtained reaction mixture which includes the compound of Formula (1b-c) may be dried with a desiccant such as sodium sulfate or magnesium sulfate, but this dehydration may be omitted.

The above-obtained reaction mixture which includes the compound of Formula (1b-c) may be distilled to evaporate the solvent under reduced pressure as long as the compound is not decomposed.

The distilled reaction mixture which includes the compound of Formula (1b-c) may be purified with an appropriate solvent by a method such as washing, reprecipitation, recrystallization or column chromatography. The purification method may be selected appropriately due to the desired purity.

[Production Method D]

[Chem. 18]

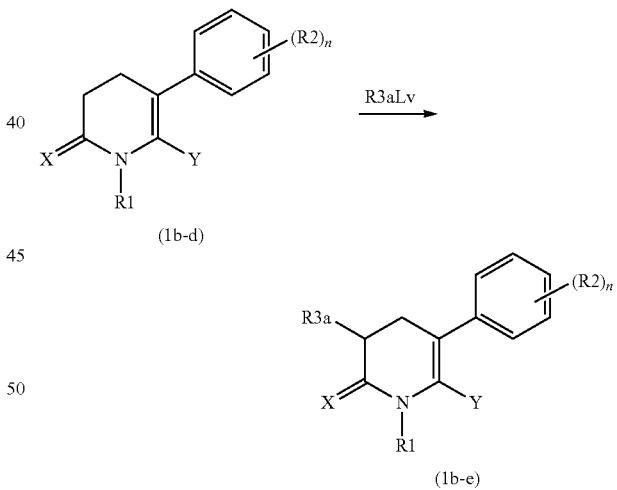

In the formula, R3a represents a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C2-C6 alkynyl group optionally substituted with substituent C, or a C2-C6 haloalkynyl group, and Lv, R1, R2, X, Y and n are the same as defined hereinabove.

Production Method D produces a compound of Formula (1b-e), which belongs to the compounds of Formula (1b), wherein R3a represents a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C2-C6 alkynyl group optionally substituted with substituent C, or a C2-C6 haloalkynyl group. The production method includes reacting a compound of Formula (1b-d) with R3aLv in a solvent in the presence of a base.

The R3aLv used in the reaction can be commercially available or produced by a known method.

The amount of the R3aLv used in the reaction is 1 equivalent amount or more relative to the compound of Formula (1b-d), and is preferably from 1 equivalent amount to 1.8 equivalent amount, although the amount is not particularly limited as long as the objective reaction takes place.

Examples of the bases used in the reaction include metal hydrides such as sodium hydride, organolithiums such as methyllithium, butyllithium, sec-butyllithium, t-butyllithium and hexyllithium, and metal amides such as lithium diisopropylamide, hexmethyldisilazane lithium, hexmethyldisilazane sodium and hexmethyldisilazane potassium.

The amount of the base used in the reaction is 1 equivalent amount or more relative to the compound of Formula (1b-d). The amount is not particularly limited as long as the objective reaction takes place, and is preferably from 1 equivalent amount to 10 equivalent amount.

The solvent used in the reaction is not particularly limited as long as the objective reaction takes place. Examples include ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene. These solvents may be used singly, or two or more of these solvents may be used in combination in any ratio.

The amount of the solvent used in the reaction is not particularly limited as long as the objective reaction takes place, and is usually from 3 to 200 times by weight relative to the amount of the compound of Formula (1b-d).

The temperature of the reaction is not particularly limited as long as the objective reaction takes place, and is usually from −80° C. to 100° C., or is not greater than the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, aqueous solutions of sulfur-containing salts such as sodium thiosulfate and sodium sulfite, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane and chloroform, hydrocarbon solvents such as hexane, heptane, cyclohexane and methylcyclohexane. These solvents may be used singly, or two or more of these solvents may be used in combination in any ratio. The liquid separation may be performed as many times as desired without limitation due to the desired purity and yield.

The above-obtained reaction mixture which includes the compound of Formula (1b-e) may be dried with a desiccant such as sodium sulfate or magnesium sulfate, but this dehydration may be omitted.

The above-obtained reaction mixture which includes the compound of Formula (1b-e) may be distilled to evaporate the solvent under reduced pressure as long as the compound is not decomposed.

The distilled reaction mixture which includes the compound of Formula (1b-e) may be purified with an appropriate solvent by a method such as washing, reprecipitation, recrystallization or column chromatography. The purification method may be selected appropriately due to the desired purity.

[Production Method E]

[Chem. 19]

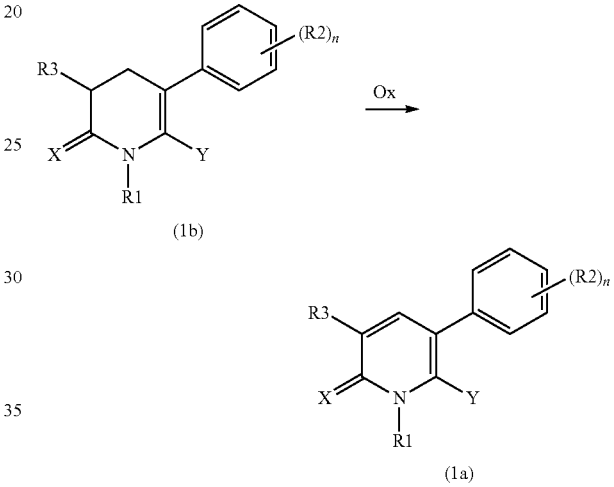

In the formula, Ox represents an oxidizer, and R1, R2, R3, X, Y and n are the same as defined hereinabove.

Production Method E produces a compound of Formula (1a). The production method includes reacting a compound of Formula (1b) with an oxidizer (Ox) in a solvent.

Examples of the oxidizers used in the reaction include metal oxides such as manganese dioxide, benzoquinones such as 2,3-dichloro-5,6-dicyano-p-benzoquinone, and combinations of radical initiators such as azobisisobutyronitrile or benzoyl peroxide with halogenating agents such as N-chlorosuccinimide, N-bromosuccinimide, N-iodosuccinimide, 1,3-dichloro-5,5-dimethylhydantoin, 1,3-dibromo-5,5-dimethylhydantoin or 1,3-diiodo-5,5-dimethylhydantoin.

The method wherein a metal oxide is used as the oxidizer is hereinafter described.

The amount of the oxidizer used in the reaction is 1 equivalent amount or more relative to the compound of Formula (1b). The amount is not particularly limited as long as the objective reaction takes place, and is usually from 1 equivalent amount to 200 equivalent amount.

The solvent used in the reaction is not particularly limited as long as the objective reaction takes place. Examples include benzene based solvents such as benzene, toluene, xylene, mesitylene, chlorobenzene and dichlorobenzene, halogen solvents such as dichloromethane, dichloroethane, chloroform and carbon tetrachloride. These solvents may be used singly, or two or more of these solvents may be used in combination in any ratio.

The amount of the solvent used in the reaction is not particularly limited as long as the objective reaction takes place, and is usually from 3 to 200 times by weight relative to the amount of the compound of Formula (1b).

The temperature of the reaction is not particularly limited as long as the objective reaction takes place, and is usually from 0° C. to 150° C., or is not greater than the boiling point of the solvent.

The reaction may be followed by a post treatment in which the undissolved metal is removed by filtration. Further, water or an appropriate aqueous solution may be added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane. These solvents may be used singly, or two or more of these solvents may be used in combination in any ratio. The liquid separation may be performed as many times as desired without limitation due to the desired purity and yield. In the reaction, the liquid separation is not an absolute necessity.

The above-obtained reaction mixture which includes the compound of Formula (1a) may be dried with a desiccant such as sodium sulfate or magnesium sulfate, but this dehydration may be omitted.

The above-obtained reaction mixture which includes the compound of Formula (1a) may be distilled to evaporate the solvent under reduced pressure as long as the compound is not decomposed.

The distilled reaction mixture which includes the compound of Formula (1a) may be purified in an appropriate solvent by a method such as washing, reprecipitation, recrystallization or column chromatography. The purification method may be selected appropriately due to the desired purity.

The method wherein benzoquinones is used as the oxidizer is described below.

The amount of the oxidizer used in the reaction is 1 equivalent amount or more relative to the compound of Formula (1b). The amount is not particularly limited as long as the objective reaction takes place, and is usually from 1 equivalent amount to 20 equivalent amount.

The solvent used in the reaction is not particularly limited as long as the objective reaction takes place. Examples include benzene based solvents such as benzene, toluene, xylene, mesitylene, chlorobenzene and dichlorobenzene, halogen solvents such as dichloromethane, dichloroethane, chloroform and carbon tetrachloride. These solvents may be used singly, or two or more of these solvents may be used in combination in any ratio.

The amount of the solvent used in the reaction is not particularly limited as long as the objective reaction takes place, and is usually from 3 to 200 times by weight relative to the amount of the compound of Formula (1b).

The temperature of the reaction is not particularly limited as long as the objective reaction takes place, and is usually from 0° C. to 150° C., or is not greater than the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane. These solvents may be used singly, or two or more of these solvents may be used in combination in any ratio. The liquid separation may be performed as many times as desired without limitation due to the desired purity and yield. In the reaction, the liquid separation is not an absolute necessity.

The above-obtained reaction mixture which includes the compound of Formula (1a) may be dried with a desiccant such as sodium sulfate or magnesium sulfate, but this dehydration may be omitted.

The above-obtained reaction mixture which includes the compound of Formula (1a) may be distilled to evaporate the solvent under reduced pressure as long as the compound is not decomposed.

The distilled reaction mixture which includes the compound of Formula (1a) may be purified in an appropriate solvent by a method such as washing, reprecipitation, recrystallization or column chromatography. The purification method may be selected appropriately due to the desired purity.

The method wherein a combination of a radical initiator and a halogenating agent is used as the oxidizer is illustrated below.

The amounts of the radical initiator and the halogenating agent used in the reaction are 0.01 equivalent amount or more and 1.0 equivalent amount or more, respectively, and their amounts are not particularly limited as long as the objective reaction takes place. Preferably, the radical initiator is from 0.01 equivalent amount to 1 equivalent amount and the halogenating agent is from 1 equivalent amount to 3 equivalent amount.

The solvent used in the reaction is not particularly limited as long as the objective reaction takes place. Examples include halogenated benzene based solvents such as chlorobenzene and dichlorobenzene, ester solvents such as ethyl acetate, isopropyl acetate and butyl acetate, halogen solvents such as dichloromethane, dichloroethane, chloroform and carbon tetrachloride, hydrocarbon solvents such as hexane, heptane, cyclohexane and methylcyclohexane. These solvents may be used singly, or two or more of these solvents may be used in combination in any ratio.

The amount of the solvent used in the reaction is not particularly limited as long as the objective reaction takes place, and is usually from 3 to 200 times by weight relative to the amount of the compound of Formula (1b).

The temperature of the reaction is not particularly limited as long as the objective reaction takes place, and is usually from 20° C. to 150° C., or is not greater than the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, aqueous solutions of sulfur-containing salts such as sodium thiosulfate and sodium sulfite, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane and chloroform, hydrocarbon solvents such as hexane, heptane, cyclohexane and methylcyclohexane. These solvents may be used singly, or two or more of these solvents may be used in combination in any ratio. The liquid separation may be performed as many times as desired without limitation due to the desired purity and yield.

The above-obtained reaction mixture which includes the compound of Formula (1a) may be dried with a desiccant such as sodium sulfate or magnesium sulfate, but this dehydration may be omitted.

The above-obtained reaction mixture which includes the compound of Formula (1a) may be distilled to evaporate the solvent under reduced pressure as long as the compound is not decomposed.

The distilled reaction mixture which includes the compound of Formula (1a) may be purified in an appropriate solvent by a method such as washing, reprecipitation, recrystallization or column chromatography. The purification method may be selected appropriately due to the desired purity.

[Production Method F]

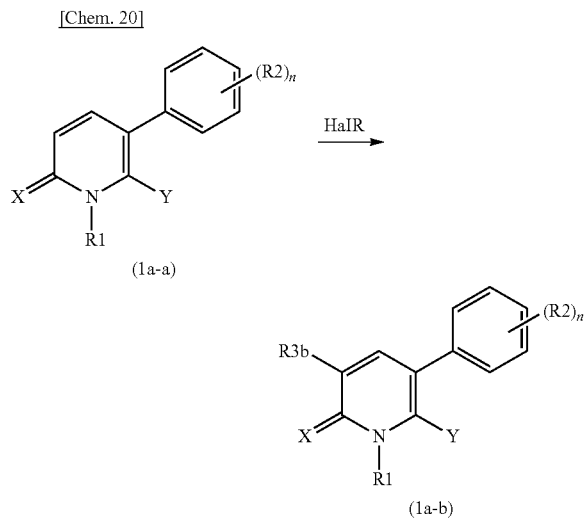

[Chem. 20]

(1a-a)

(1a-b)

In the formula, R3b represents a halogen atom, HalR represents a halogenating agent, and R1, R2, X, Y and n are the same as defined hereinabove.

Production Method F produces a compound of Formula (1a-b), which belongs to the compounds of Formula (1a), wherein R3b is a halogen atom. The production method includes reacting a compound of Formula (1a-a) with a halogenating agent (HalR) in a solvent.

Examples of the halogenating agents used in the reaction include Selectfluor (N-fluoro-N'-triethylenediamine bis(tetrafluoroborate)), N-chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin, bromine, iodine.

The amount of the halogenating agent used in the reaction is 1 equivalent amount or more relative to the compound of Formula (1a-a). The amount is not particularly limited as long as the objective reaction takes place, and is preferably from 1 equivalent amount to 10 equivalent amount. The halogenating agents including hydantoin may be used in at least 0.5 equivalent amounts, and their amount is not particularly limited as long as the objective reaction takes place. The amount is preferably from 1 equivalent amount to 5 equivalent amounts.

When the halogenating agent is an iodinating agent, the reaction may involve an acid, for example, an inorganic acid such as hydrochloric acid or sulfuric acid, or an organic acid such as acetic acid, trifluoroacetic acid, methanesulfonic acid or trifluoromethanesulfonic acid.

The amount of the acid, which is added when the halogenating agent is an iodinating agent, is at least 0.01 equivalent amount relative to the compound of Formula (1a-a). The amount is not particularly limited as long as the objective reaction takes place, and is preferably from 0.1 equivalent amount to 3 equivalent amount.

The solvent used in the reaction is not particularly limited as long as the objective reaction takes place. Examples include acidic solvents such as sulfuric acid, acetic acid, trifluoroacetic acid, methanesulfonic acid and trifluoromethanesulfonic acid, ether solvents such as diethyl ether, diisopropyl ether, methyl-t-butyl ether, dimethoxyethane, tetrahydrofuran and dioxane, alcohol solvents such as methanol, ethanol and isopropanol, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride. These solvents may be used singly, or two or more of these solvents may be used in combination in any ratio.

The amount of the solvent used in the reaction is not particularly limited as long as the objective reaction takes place, and is usually from 3 to 200 times by weight relative to the amount of the compound of Formula (1a-a).

The temperature of the reaction is not particularly limited as long as the objective reaction takes place, and is usually from 0° C. to 150° C., or is not greater than the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane. These solvents may be used singly, or two or more of these solvents may be used in combination in any ratio. The liquid separation may be performed as many times as desired without limitation due to the desired purity and yield.

The above-obtained reaction mixture which includes the compound of Formula (1a-b) may be dried with a desiccant such as sodium sulfate or magnesium sulfate, but this dehydration may be omitted.

The above-obtained reaction mixture which includes the compound of Formula (1a-b) may be distilled to evaporate the solvent under reduced pressure as long as the compound is not decomposed.

The distilled reaction mixture which includes the compound of Formula (1a-b) may be purified with an appropriate solvent by a method such as washing, reprecipitation, recrystallization or column chromatography. The purification method may be selected appropriately due to the desired purity.

[Production Method G]

[Chem. 21]

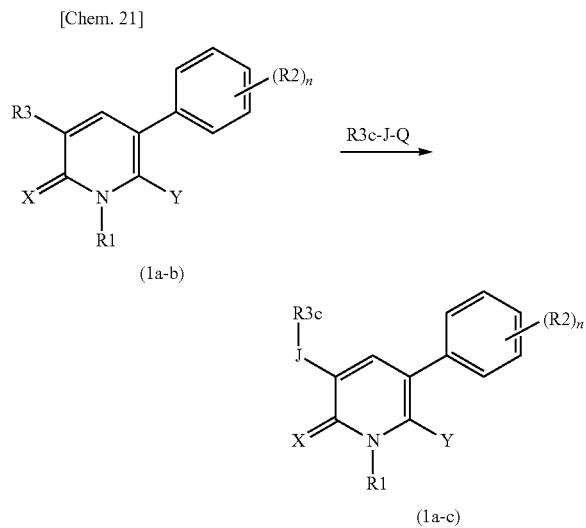

In the formula, R3c represents a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C2-C6 alkynyl group optionally substituted with substituent C or a C2-C6 haloalkynyl group, J represents an oxygen atom or a sulfur atom, Q represents a hydrogen atom or a metal, and R1, R2, R3b, X, Y and n are the same as defined hereinabove.

Production Method G produces a compound of Formula (1a-c), which belongs to the compounds of Formula (1a), wherein R3c represents C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C2-C6 alkynyl group optionally substituted with substituent C or a C2-C6 haloalkynyl group, and J represents an oxygen atom or a sulfur atom. The production method includes obtaining the compound by coupling reaction that reacts a compound of Formula (1a-b) with R3c-J-Q in the presence of a transition metal.

In the compound of Formula (1a-b), R3b is preferably chlorine atom, bromine atom or iodine atom.

The R3c-J-Q used in the reaction can be commercially available or produced by a known method. Preferably, Q is a hydrogen atom or an alkali metal such as sodium or potassium.

The amount of the R3c-J-Q used in the reaction is 1 equivalent amount or more relative to the compound of Formula (1a-b), and the amount is not particularly limited as long as the objective reaction takes place. When Q is a hydrogen atom, the reagent may also be used as a solvent.

The transition metal used in the reaction may have a ligand including palladium materials such as palladium acetate, [1,1'-bis(diphenylphosphino)ferrocene]palladium dichloride, tris(dibenzylideneacetone)dipalladium, tetrakis(triphenylphosphine)palladium and bis(triphenylphosphine) palladium dichloride.

The amount of the transition metal used in the reaction is from 0.001 equivalent amount to 1 equivalent amount relative to the compound of Formula (1a-b), but the amount is not particularly limited as long as the objective reaction takes place.

To allow the reaction to proceed efficiently, a phosphine ligand, for examples triphenylphosphine, 1,1'-bis(diphenylphosphino)ferrocene, 2-dicyclohexylphosphino-2'4'6'-triisopropylbiphenyl, 2-di-t-butylphosphino-2'4'6'-triisopropylbiphenyl, may be added.

The amount of the phosphine ligand used in the reaction is from 0.001 equivalent amount to 1 equivalent amount relative to the compound of Formula (1a-b), but the amount is not particularly limited as long as the objective reaction takes place.

Examples of the bases used in the reaction include inorganic bases such as sodium carbonate, potassium carbonate and cesium carbonate, and organic bases such as triethylamine, tributylamine and diisopropylethylamine.

The amount of the base used in the reaction is 1 equivalent amount or more relative to the compound of Formula (1a-b). The amount is not particularly limited as long as the objective reaction takes place, and is preferably from 1 equivalent amount to 50 equivalent amount.

The solvent used in the reaction is not particularly limited as long as the objective reaction takes place, and examples include alcohol solvents represented by R3c-J-H (wherein R3c is the same as defined hereinabove and J is an oxygen atom), ether-based solvents such as diethyl ether, diisopropyl ether, methyl-t-butyl ether, dimethoxyethane, tetrahydrofuran and dioxane and benzene-based solvents such as benzene, toluene, xylene, mesitylene, chlorobenzene and dichlorobenzene. These solvents may be used singly, or two or more of these solvents may be used as a mixture in any ratio.

The amount of the solvent used in the reaction is not particularly limited as long as the objective reaction takes place, and is usually from 3 to 200 times by weight relative to the amount of the compound of Formula (1a-b).

The temperature of the reaction is not particularly limited as long as the objective reaction takes place, and is usually from 30° C. to 200° C., or is not greater than the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane. These solvents may be used singly, or two or more of these solvents may be used in combination in any ratio. The liquid separation may be performed as many times as desired without limitation due to the desired purity and yield. Insolubles may be removed by filtration, which however is not an absolute necessity.

The above-obtained reaction mixture comprising the compound of Formula (1a-c) may be distilled to evaporate the solvent under reduced pressure as long as the compound is not decomposed.

The distilled reaction mixture which includes the compound of Formula (1a-c) may be purified with an appropriate solvent by a method such as washing, reprecipitation, recrystallization or column chromatography. The purification method may be selected appropriately due to the desired purity.

[Production Method H]

[Chem. 22]

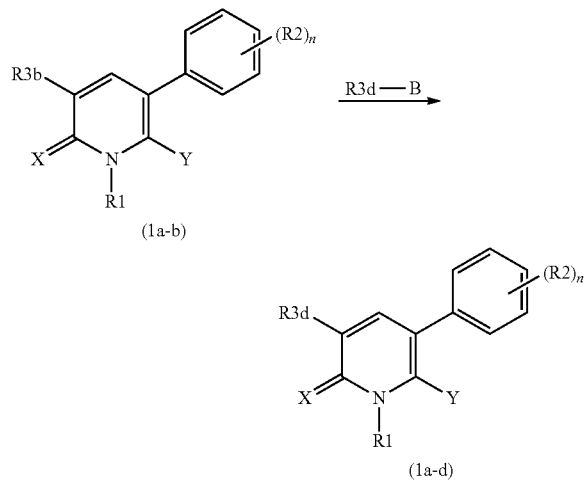

(1a-b)

(1a-d)

In the formula, R3d represents a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C or a C2-C6 haloalkenyl group, R3d-B represents an organoboronic acid, and R1, R2, R3b, X, Y and n are the same as defined hereinabove.

Production Method H produces a compound of Formula (1a-d), which belongs to the compounds of Formula (1a), wherein R3d is a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C or a C2-C6 haloalkenyl group, and includes obtaining the compound by the Suzuki-Miyaura coupling that reacts a compound of Formula (1a-b) with an organoboronic acid (R3d-B) in the presence of a transition metal and base.

In Formula (1a-b), R3b is preferably chlorine atom, bromine atom or iodine atom.

The R3d-B used in the reaction represents an organoboronic acid such as an organoboronic acid or an organoboronate ester, and can be commercially available or produced by a known method.

The amount of the R3d-B used in the reaction is 1 equivalent amount or more relative to the compound of Formula (1a-b), and is preferably from 1 equivalent amount to 10 equivalent amount, although the amount is not particularly limited as long as the objective reaction takes place.

The transition metal used in the reaction is, for example, palladium, nickel or ruthenium, and may have a ligand. Palladium materials, for examples palladium acetate, [1,1'-bis(diphenylphosphino)ferrocene]palladium dichloride, tris(dibenzylideneacetone)dipalladium, tetrakis(triphenylphosphine)palladium, bis(triphenylphosphine)palladium dichloride, is preferable.

The amount of the transition metal used in the reaction is from 0.001 equivalent amount to 1 equivalent amount relative to the compound of Formula (1a-b), but the amount is not particularly limited as long as the objective reaction takes place.

To allow the reaction to proceed efficiently, a phosphine ligand such as triphenylphosphine or tricyclohexylphosphine may be added.

The amount of the phosphine ligand used in the reaction is from 0.001 equivalent amount to 1 equivalent amount relative to the compound of Formula (1a-b), but the amount is not particularly limited as long as the objective reaction takes place.

Examples of the bases used in the reaction include, for example inorganic bases such as sodium carbonate, potassium carbonate, cesium carbonate and tripotassium phosphate, metal alkoxides such as sodium methoxide, sodium ethoxide and potassium t-butoxide.

The amount of the base used in the reaction is 1 equivalent amount or more relative to the compound of Formula (1a-b). The amount is not particularly limited as long as the objective reaction takes place, and is preferably from 1 equivalent amount to 50 equivalent amount.

The solvent used in the reaction is not particularly limited as long as the objective reaction takes place. Examples include aqueous solvents, ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene. These solvents may be used singly, or two or more of these solvents may be used in combination in any ratio.

The amount of the solvent used in the reaction is not particularly limited as long as the objective reaction takes place, and is usually from 3 to 200 times by weight relative to the amount of the compound of Formula (1a-b).

The temperature of the reaction is not particularly limited as long as the objective reaction takes place, and is usually from 30° C. to 200° C., or is not greater than the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane. These solvents may be used singly, or two or more of these solvents may be used in combination in any ratio. The liquid separation may be performed as many times as desired without limitation due to the desired purity and yield. Insolubles may be removed by filtration, which however is not an absolute necessity.

The above-obtained reaction mixture which includes the compound of Formula (1a-d) may be distilled to evaporate the solvent under reduced pressure as long as the compound is not decomposed.

The distilled reaction mixture which includes the compound of Formula (1a-d) may be purified with an appropriate solvent by a method such as washing, reprecipitation, recrystallization or column chromatography. The purification method may be selected appropriately due to the desired purity.

[Production Method I]

[Chem. 23]

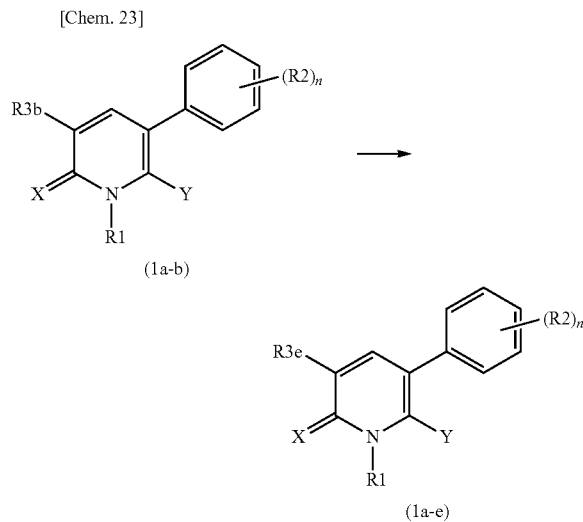

In the formula, R3e represents a C2-C6 alkynyl group optionally substituted with substituent C or a C2-C6 haloalkynyl group, and R1, R2, R3b, X, Y and n are the same as defined hereinabove.

Production Method I produces a compound of Formula (1a-e), which belongs to the compounds of Formula (1a), wherein R3e is a C2-C6 alkynyl group optionally substituted with substituent C or a C2-C6 haloalkynyl group, and the production method includes obtaining the compound by the Sonogashira coupling that reacts a compound of Formula (1a-b) with alkyne-terminated compound in the presence of a transition metal and a base.

In Formula (1a-b), R3b is preferably chlorine atom, bromine atom or iodine atom.

The alkyne-terminated compound used in the reaction can be commercially available or produced by a known method. Alternatively, trimethylsilylacetylene can also be used as the alkyne-terminated compound. In this case, desilylation needs to be performed after the introduction of the trimethylsilylethynyl into the compound of Formula (1a-b). The desilylation may be carried out with reference to non-patent literature such as the Journal of the American Chemical Society, Vol. 131, No. 2, pp. 634-643 (2009) and the Journal of Organometallic Chemistry, vol. 696, No. 25, pp 4039-4045 (2011).

The amount of the alkyne-terminated compound used in the reaction is 1 equivalent amount or more relative to the compound of Formula (1a-b), and is preferably from 1 equivalent amount to 10 equivalent amount, although the amount is not particularly limited as long as the objective reaction takes place.

The transition metal used in the reaction can have a ligand, and an example of such materials is palladium materials such as palladium acetate, [1,1'-bis(diphenylphosphino)ferrocene]palladium dichloride, tris(dibenzylideneacetone)dipalladium, tetrakis(triphenylphosphine)palladium or bis(triphenylphosphine)palladium dichloride. Further, copper materials such as copper chloride, copper bromide or copper iodide is used at the same time.

As for the amount of the transition metals used in the reaction, the amounts of the palladium material and the copper material are each at least 0.001 equivalent amounts relative to the compound of Formula (1a-b), and these amounts are not particularly limited as long as the objective reaction takes place. These amounts are each preferably from 0.001 equivalent amount to 1 equivalent amount.

Examples of the bases used in the reaction include organic amines such as triethylamine, tributylamine, isopropylamine, diethylamine, diisopropylamine or diisopropylethylamine, and inorganic bases such as sodium carbonate, potassium carbonate and cesium carbonate.

The amount of the base used in the reaction is 1 equivalent amount or more relative to the compound of Formula (1a-b). The amount is not particularly limited as long as the objective reaction takes place, and is preferably from 1 equivalent amount to 50 equivalent amount. The organic base that is liquid may also be used as a solvent.

To allow the reaction to proceed efficiently, a phosphine ligand such as tri-t-butylphosphine or 2-dicyclohexylphosphino-2'4'6'-triisopropylbiphenyl may be added. This addition, however, is not an absolute necessity.

The amount of the phosphine ligand used in the reaction is from 0.001 equivalent amount to 1 equivalent amount relative to the compound of Formula (1a-b), and the amount is not particularly limited as long as the objective reaction takes place.

The solvent used in the reaction is not particularly limited as long as the objective reaction takes place. Examples include ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, organic amine solvents such as triethylamine, tributylamine, isopropylamine, diethylamine, diisopropylamine and diisopropylethylamine. These solvents may be used singly, or two or more of these solvents may be used in combination in any ratio.

The amount of the solvent used in the reaction is not particularly limited as long as the objective reaction takes place, and is usually from 3 to 200 times by weight relative to the amount of the compound of Formula (1a-b).

The temperature of the reaction is not particularly limited as long as the objective reaction takes place, and is usually from 0° C. to 150° C., or is not greater than the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane. These solvents may be used singly, or two or more of these solvents may be used in combination in any ratio. The liquid separation may be performed as many times as desired without limitation due to the desired purity and yield. Insolubles may be removed by filtration, which however is not an absolute necessity.

The above-obtained reaction mixture which includes the compound of Formula (1a-e) may be distilled to evaporate the solvent under reduced pressure as long as the compound is not decomposed.

The distilled reaction mixture which includes the compound of Formula (1a-e) may be purified with an appropriate solvent by a method such as washing, reprecipitation, recrystallization or column chromatography. The purification method may be selected appropriately due to the desired purity.

[Production Method J]

[Chem. 24]

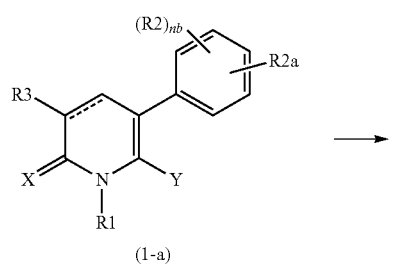

(1-a)

-continued

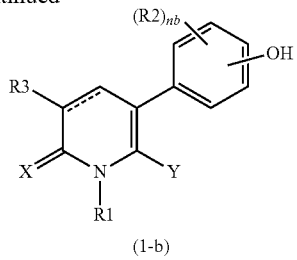

(1-b)

In the formula, R2a represents a C1-C6 alkoxy group, nb represents an integer of 0 to 4 (with the proviso that when nb is 2 or greater, the two or more R2 represent independent substituents), and R1, R2, R3, X, Y and the broken line are the same as defined hereinabove.

Production Method J produces a hydroxy group-containing compound of Formula (1-b), which belongs to the compounds of Formula (1). The production method includes reacting a compound of Formula (1-a) in which R2a is a C1-C6 alkoxy group with an acid.

Examples of the acids used in the reaction include boron halides such as boron trichloride or boron tribromide.

The amount of the acid used in the reaction is 1 equivalent amount or more relative to the compound of Formula (1-a). The amount is not particularly limited as long as the objective reaction takes place, and is preferably from 1 equivalent amount to 10 equivalent amount.

The solvent used in the reaction is not particularly limited as long as the objective reaction takes place. Examples include benzene based solvents such as benzene, toluene, xylene, mesitylene, chlorobenzene and dichlorobenzene, nitrile solvents such as acetonitrile, halogen solvents such as dichloromethane, dichloroethane, chloroform and carbon tetrachloride, hydrocarbon solvents such as hexane, heptane, cyclohexane and methylcyclohexane. These solvents may be used singly, or two or more of these solvents may be used in combination in any ratio.

The amount of the solvent used in the reaction is not particularly limited as long as the objective reaction takes place, and is usually from 3 to 200 times by weight relative to the amount of the compound of Formula (1-a).

The temperature of the reaction is not particularly limited as long as the objective reaction takes place, and is usually from −80° C. to 100° C., or is not greater than the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane. These solvents may be used singly, or two or more of these solvents may be used in combination in any ratio. The liquid separation may be performed as many times as desired without limitation due to the desired purity and yield.

The above-obtained reaction mixture which includes the compound of Formula (1-b) may be dried with a desiccant such as sodium sulfate or magnesium sulfate, but this dehydration may be omitted.

The above-obtained reaction mixture which includes the compound of Formula (1-b) may be distilled to evaporate the solvent under reduced pressure as long as the compound is not decomposed.

The distilled reaction mixture which includes the compound of Formula (1-b) may be purified with an appropriate solvent by a method such as washing, reprecipitation, recrystallization or column chromatography. The purification method may be selected appropriately due to the desired purity.

[Production Method K]

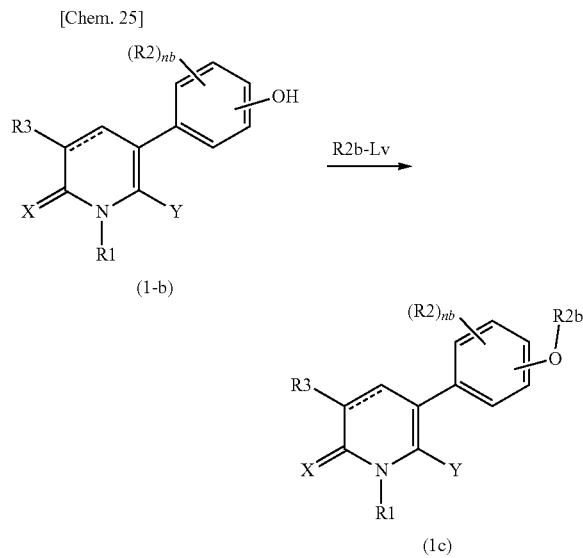

In the formula, R2b-O— represents a C1-C6 alkoxy group optionally substituted with substituent B, a C1-C6 haloalkoxy group, a C3-C8 cycloalkoxy group optionally substituted with substituent B, a C2-C6 alkenyloxy group optionally substituted with substituent B, a C2-C6 haloalkenyloxy group, a C3-C6 alkynyloxy group optionally substituted with substituent B, a C3-C6 haloalkynyloxy group or an R20C(=O)O— group, and Lv, R1, R2, R3, R20, X, Y, nb and the broken line are the same as defined hereinabove.

Production Method K produces a compound of Formula (1-c), which belongs to the compounds of Formula (1), wherein R2b-O— is a C1-C6 alkoxy group optionally substituted with substituent B, a C1-C6 haloalkoxy group, a C3-C8 cycloalkoxy group optionally substituted with substituent B, a C2-C6 alkenyloxy group optionally substituted with substituent B, a C2-C6 haloalkenyloxy group, a C3-C6 alkynyloxy group optionally substituted with substituent B, a C3-C6 haloalkynyloxy group or an R20C(=O)O— group (R20 is the same as defined hereinabove). The production method includes reacting a compound of Formula (1-b) with R2b-Lv in a solvent in the presence of a base.

The R2b-Lv used in the reaction can be commercially available or produced by a known method.

The amount of the R2b-Lv used in the reaction is 1 equivalent amount or more relative to the compound of Formula (1-b), and is preferably from 1 equivalent amount to 10 equivalent amount, although the amount is not particularly limited as long as the objective reaction takes place.

Examples of the bases used in the reaction include inorganic bases such as sodium carbonate, potassium carbonate, cesium carbonate and sodium hydride, and organic bases such as triethylamine, tributylamine, diisopropylethylamine, pyridine, 4-dimethylaminopyridine, collidine and lutidine. The bases are not particularly limited as long as the objective reaction takes place.

The amount of the base used in the reaction is 1 equivalent amount or more relative to the compound of Formula (1-b). The amount is not particularly limited as long as the objective reaction takes place, and is preferably from 1 equivalent amount to 10 equivalent amount.

The solvent used in the reaction is not particularly limited as long as the objective reaction takes place. Examples include ether solvents such as diethyl ether, diisopropyl ether, methyl-t-butyl ether, dimethoxyethane, tetrahydrofuran and dioxane, alcohol solvents such as methanol, ethanol and isopropanol, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethyl sulfoxide and sulfolane, ketone solvents such as acetone, methyl ethyl ketone and methyl isobutyl ketone. These solvents may be used singly, or two or more of these solvents may be used in combination in any ratio.

The amount of the solvent used in the reaction is not particularly limited as long as the objective reaction takes place, and is usually from 3 to 200 times by weight relative to the amount of the compound of Formula (1-b).

The temperature of the reaction is not particularly limited as long as the objective reaction takes place, and is usually from −20° C. to 150° C., or is not greater than the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane. These solvents may be used singly, or two or more of these solvents may be used in combination in any ratio. The liquid separation may be performed as many times as desired without limitation due to the desired purity and yield.

The above-obtained reaction mixture which includes the compound of Formula (1-c) may be dried with a desiccant such as sodium sulfate or magnesium sulfate, but this dehydration may be omitted.

The above-obtained reaction mixture which includes the compound of Formula (1-c) may be distilled to evaporate the solvent under reduced pressure as long as the compound is not decomposed.

The distilled reaction mixture which includes the compound of Formula (1-c) may be purified with an appropriate solvent by a method such as washing, reprecipitation, recrystallization or column chromatography. The purification method may be selected appropriately due to the desired purity.

[Production Method L]

[Chem. 26]

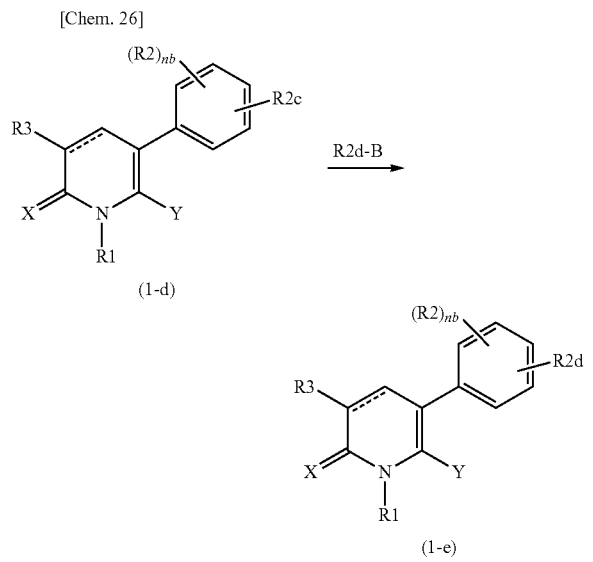

In the formula, R2c represents a halogen atom, R2d is a C1-C6 alkyl group optionally substituted with substituent B, a C1-C6 haloalkyl group, a C3-C8 cycloalkyl group optionally substituted with substituent B, a C2-C6 alkenyl group optionally substituted with substituent B or a C2-C6 haloalkenyl group, R2d-B is an organoboronic acid, and R1, R2, R3, nb, X, Y and the broken line are the same as defined hereinabove.

Production Method L produces a compound of Formula (1-e), which belongs to the compounds of Formula (1), wherein R2d is a C1-C6 alkyl group optionally substituted with substituent B, a C1-C6 haloalkyl group, a C3-C8 cycloalkyl group optionally substituted with substituent B, a C2-C6 alkenyl group optionally substituted with substituent B or a C2-C6 haloalkenyl group. The production method includes obtaining the compound by the Suzuki-Miyaura coupling that reacts a compound of Formula (1-d) with an organoboronic acid (R2d-B).

In Formula (1-d), R2c is preferably chlorine atom, bromine atom or iodine atom.

Production Method L may be performed in accordance with Production Method H, replacing the compound of Formula (1a-b) and the R3d-B in Production Method H by the compound of Formula (1-d) and the R2d-B, respectively.

[Production Method M]

[Chem. 27]

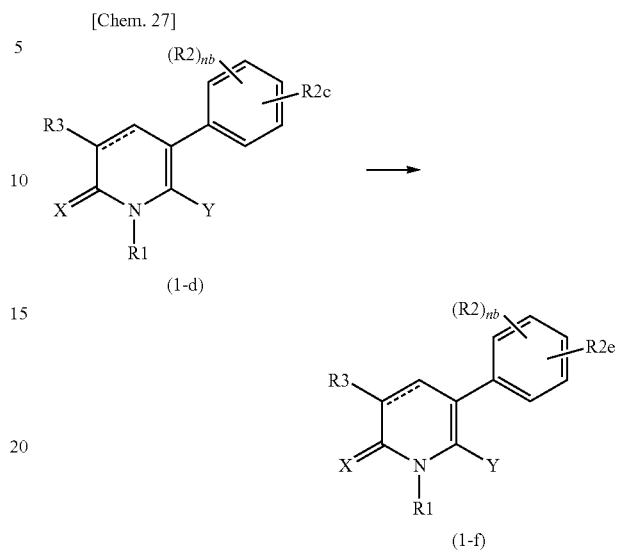

In the formula, R2e represents a C2-C6 alkynyl group optionally substituted with substituent B or a C2-C6 haloalkynyl group, and R1, R2, R2c, R3, nb, X, Y and the broken line are the same as defined hereinabove.

Production Method M produces a compound of Formula (1-f), which belongs to the compounds of Formula (1), wherein R2e is a C2-C6 alkynyl group optionally substituted with substituent B or a C2-C6 haloalkynyl group. The production method includes obtaining the compound by the Sonogashira coupling that reacts a compound of Formula (1-d) with an alkyne-terminated compound.

In the compound of Formula (1-d), R2c is preferably chlorine atom, bromine atom or iodine atom.

Production Method M may be performed in accordance with Production Method I, replacing the compound of Formula (1a-b) in Production Method I by the compound of Formula (1-d).

[Production Method N]

[Chem. 28]

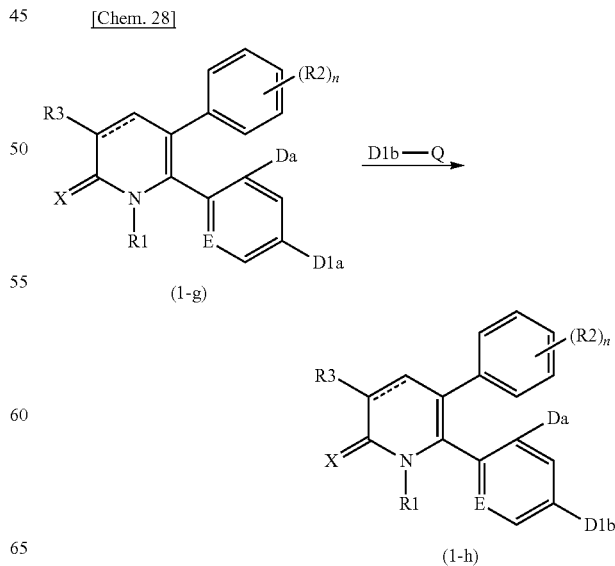

In the formula, Da represents a halogen atom, D1a represents a halogen atom, D1b represents a C1-C6 alkoxy group, a C1-C6 haloalkoxy group or a C3-C8 cycloalkoxy group, E represents a halogen-substituted carbon atom or a nitrogen atom, and R1, R2, R3, n, X, Q and the broken line are the same as defined hereinabove.

Production Method N produces a compound of Formula (1-h), which belongs to the compounds of Formula (1), wherein D1b is a C1-C6 alkoxy group, a C1-C6 haloalkoxy group or a C3-C8 cycloalkoxy group, and E is a halogen-substituted carbon atom or a nitrogen atom. The production method includes reacting a compound of Formula (1-g) with D1b-Q in a solvent.

The D1b-Q used in the reaction can be commercially available or produced by a known method. Preferably, Q is a hydrogen atom or an alkali metal such as sodium or potassium.

The amount of the D1b-Q used in the reaction is 1 equivalent amount or more relative to the compound of Formula (1-g). The amount is not particularly limited as long as the objective reaction takes place, and is preferably from 1 equivalent amount to 30 equivalent amount. When Q is a hydrogen atom, the reagent may also be used as a solvent.

The base used in the reaction is preferably an inorganic base such as sodium carbonate, potassium carbonate, cesium carbonate or sodium hydride. When Q is an alkali metal, the use of the base may be omitted.

The amount of the base used in the reaction is 1 equivalent weight or more relative to the compound of Formula (1-g). The amount is not particularly limited as long as the objective reaction takes place, and is preferably from 1 equivalent weight to 30 equivalent weight.

The solvent used in the reaction is not particularly limited as long as the objective reaction takes place. Examples include alcohol solvents represented by D1b-H, ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethyl sulfoxide and sulfolane, ketone solvents such as acetone, methyl ethyl ketone and methyl isobutyl ketone. These solvents may be used singly, or two or more of these solvents may be used in combination in any ratio.

The amount of the solvent used in the reaction is not particularly limited as long as the objective reaction takes place, and is usually from 3 to 200 times by weight relative to the amount of the compound of Formula (1-g).

The temperature of the reaction is not particularly limited as long as the objective reaction takes place, and is usually from 0° C. to 150° C., or is not greater than the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane. These solvents may be used singly, or two or more of these solvents may be used in combination in any ratio. The liquid separation may be performed as many times as desired without limitation due to the desired purity and yield.

The above-obtained reaction mixture which includes the compound of Formula (1-h) may be dried with a desiccant such as sodium sulfate or magnesium sulfate, but this dehydration may be omitted.

The above-obtained reaction mixture which includes the compound of Formula (1-h) may be distilled to evaporate the solvent under reduced pressure as long as the compound is not decomposed.

The distilled reaction mixture which includes the compound of Formula (1-h) may be purified with an appropriate solvent by a method such as washing, reprecipitation, recrystallization or column chromatography. The purification method may be selected appropriately due to the desired purity.

[Production Method O]

[Chem. 29]

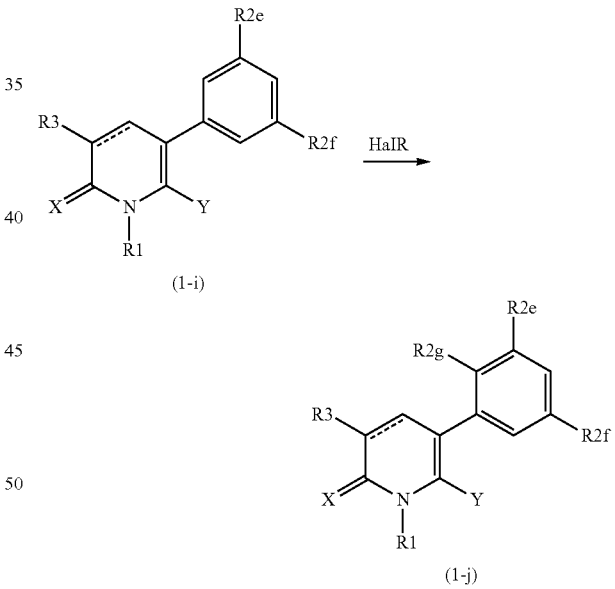

In the formula, R2e represents a C1-C6 alkoxy group optionally substituted with substituent B, R2f represents a C1-C6 alkoxy group optionally substituted with substituent B, R2g represents a halogen atom, and HalR, R1, R3, X, Y and the broken line are the same as defined hereinabove.

Production Method O produces a compound of Formula (1-j), which belongs to the compounds of Formula (1), wherein R2e is a C1-C6 alkoxy group optionally substituted with substituent B, R2f is a C1-C6 alkoxy group optionally substituted with substituent B, and R2g is a halogen atom. The production method includes reacting a compound of Formula (1-i) with a halogenating agent (HalR) in a solvent.

Examples of the halogenating agents used in the reaction include Selectfluor (N-fluoro-N'-triethylenediamine bis(tetrafluoroborate)), N-chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin, bromine, iodine.

The amount of the halogenating agent used in the reaction is 1 equivalent amount or more relative to the compound of Formula (1-i). The amount is not particularly limited as long as the objective reaction takes place, and is preferably from 1 equivalent amount to 10 equivalent amount. Those halogenating agents including hydantoin may be used in at least 0.5 equivalent amounts, and their amount is not particularly limited as long as the objective reaction takes place, and is preferably from 1 equivalent amount to 5 equivalent amounts.

When the halogenating agent is an iodinating agent, the reaction may involve an acid, for example an inorganic acid such as hydrochloric acid or sulfuric acid, or an organic acid such as acetic acid, trifluoroacetic acid, methanesulfonic acid or trifluoromethanesulfonic acid.

The amount of the acid, which is added when the halogenating agent is an iodinating agent, used in the reaction is at least 0.01 equivalent amount relative to the compound of Formula (1-i). The amount is not particularly limited as long as the objective reaction takes place, and is preferably from 0.1 equivalent amount to 3 equivalent amounts.

The solvent used in the reaction is not particularly limited as long as the objective reaction takes place. Examples include acidic solvents such as sulfuric acid, acetic acid, trifluoroacetic acid, methanesulfonic acid and trifluoromethanesulfonic acid, ether solvents such as diethyl ether, diisopropyl ether, methyl-t-butyl ether, dimethoxyethane, tetrahydrofuran and dioxane, alcohol solvents such as methanol, ethanol and isopropanol, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride. These solvents may be used singly, or two or more of these solvents may be used in combination in any ratio.

The amount of the solvent used in the reaction is not particularly limited as long as the objective reaction takes place, and is usually from 3 to 200 times by weight relative to the amount of the compound of Formula (1-i).

The temperature of the reaction is not particularly limited as long as the objective reaction takes place, and is usually from 0° C. to 150° C., or is not greater than the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, aqueous solutions of sulfur-containing salts such as sodium thiosulfate and sodium sulfite, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane. These solvents may be used singly, or two or more of these solvents may be used in combination in any ratio. The liquid separation may be performed as many times as desired without limitation due to the desired purity and yield.

The above-obtained reaction mixture which includes the compound of Formula (1-j) may be dried with a desiccant such as sodium sulfate or magnesium sulfate, but this dehydration may be omitted.

The above-obtained reaction mixture which includes the compound of Formula (1-j) may be distilled to evaporate the solvent under reduced pressure as long as the compound is not decomposed.

The distilled reaction mixture which includes the compound of Formula (1-j) may be purified with an appropriate solvent by a method such as washing, reprecipitation, recrystallization or column chromatography. The purification method may be selected appropriately due to the desired purity.

[Production Method P]

[Chem. 30]

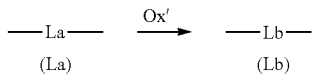

In the formula, La represents S, Lb represents SO or $SO_2$, and Ox' represents an oxidizer.

Production Method P produces a compound of Formula (1) wherein Lb in R1, R2 or R3 is SO or $SO_2$, which is of Formula (Lb). The production method includes reacting a compound of Formula (1) wherein La in R1, R2 or R3 is S, which is of Formula (La), with an oxidizer (Ox') in a solvent.

Examples of the oxidizers used in the reaction include peroxides such as hydrogen peroxide solution and meta-chloroperbenzoic acid. Transition metals such as sodium tungstate can also be added.

The amount of the oxidizer used in the reaction is usually from 1.0 equivalent amount to 1.2 equivalent amount relative to the compound of Formula (La) for the production of SO, and is usually from 2 equivalent amount to 10 equivalent amount for the production of $SO_2$. When a transition metal is added, the amount thereof is usually from 0.001 equivalent amount to 1 equivalent amount.

The solvent used in the reaction is not particularly limited as long as the objective reaction takes place. Examples include aqueous solvents, acidic solvents such as acetic acid, benzene based solvents such as benzene, toluene, xylene, mesitylene, chlorobenzene and dichlorobenzene, nitrile solvents such as acetonitrile, halogen solvents such as dichloromethane, dichloroethane, chloroform and carbon tetrachloride. These solvents may be used singly, or two or more of these solvents may be used in combination in any ratio.

The amount of the solvent used in the reaction is not particularly limited as long as the objective reaction takes place, and is usually from 3 to 200 times by weight relative to the amount of the compound of Formula (1) having Formula (La).

The temperature of the reaction is not particularly limited as long as the objective reaction takes place, and is usually from −10° C. to 120° C., or is not greater than the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane. These solvents may be used singly, or two or more of these solvents may be used in combination in any ratio. The liquid separation may be performed as many times as desired without limitation due to the desired purity and yield.

The above-obtained reaction mixture which includes the compound having Formula (Lb) may be dried with a desiccant such as sodium sulfate or magnesium sulfate, but this dehydration may be omitted.

The above-obtained reaction mixture which includes the compound having Formula (Lb) may be distilled to evaporate the solvent under reduced pressure as long as the compound is not decomposed.

The distilled reaction mixture which includes the compound having Formula (Lb) may be purified in an appropriate solvent by a method such as washing, reprecipitation, recrystallization or column chromatography. The purification method may be selected appropriately due to the desired purity.

The methods for synthesizing a compound of Formula (3) described in Production Method A is described below.

[Production Method Q]

[Chem. 31]

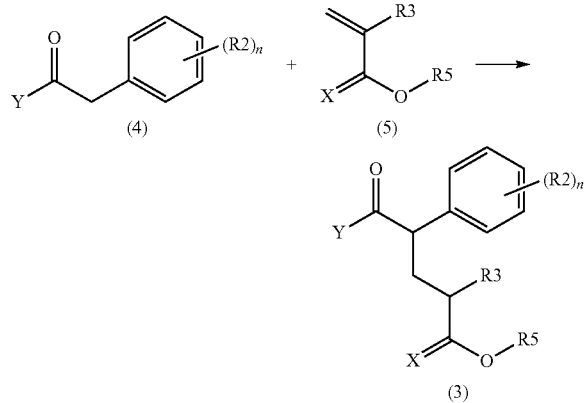

In the formula, R2, R3, R5, n, X and Y are the same as defined hereinabove.

Production Method Q produces an intermediate of Formula (3). The production method includes reacting a compound of Formula (4) with a compound of Formula (5) in a solvent in the presence of a base.

The compound of Formula (4) that is used in the reaction may be synthesized with reference to, for example Green Chemistry, vol. 41, pp. 580-585 or The Journal of Organic Chemistry, vol. 65, No. 20, pp. 6458-6461 (2000).

The compound of Formula (5) that is used in the reaction can be commercially available or produced by a known method.

The amount of the compound of Formula (5) used in the reaction is 1 equivalent amount or more relative to the compound of Formula (4), and is preferably from 1 equivalent amount to 3 equivalent amount, although the amount is not particularly limited as long as the objective reaction takes place.

Examples of the bases used in the reaction include inorganic bases such as sodium carbonate, potassium carbonate, cesium carbonate and tripotassium phosphate, metal alkoxides such as sodium methoxide, sodium ethoxide and potassium t-butoxide.

The amount of the base used in the reaction can be a catalytic amount, and is preferably from 0.01 equivalent amount to 3 equivalent amount relative to the compound of Formula (4), although the amount is not particularly limited as long as the objective reaction takes place.

Examples of the solvents used in the reaction include ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethyl sulfoxide and sulfolane, ketone solvents such as acetone, methyl ethyl ketone and methyl isobutyl ketone. These solvents may be used singly, or two or more of these solvents may be used in combination in any ratio.

The amount of the solvent used in the reaction is not particularly limited as long as the objective reaction takes place, and is usually from 3 to 200 times by weight relative to the amount of the compound of Formula (4).

The temperature of the reaction is not particularly limited as long as the objective reaction takes place, and is usually from −50° C. to 150° C., or is not greater than the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane. These solvents may be used singly, or two or more of these solvents may be used in combination in any ratio. The liquid separation may be performed as many times as desired without limitation due to the desired purity and yield.

The above-obtained reaction mixture which includes the compound of Formula (3) may be dried with a desiccant such as sodium sulfate or magnesium sulfate, but this dehydration may be omitted.

The above-obtained reaction mixture which includes the compound of Formula (3) may be distilled to evaporate the solvent under reduced pressure as long as the compound is not decomposed.

The distilled reaction mixture which includes the compound of Formula (3) may be purified with an appropriate solvent by a method such as washing, repreciptation, recrystallization or column chromatography. The purification method may be selected appropriately due to the desired purity.

[Production Method R]

[Chem. 32]

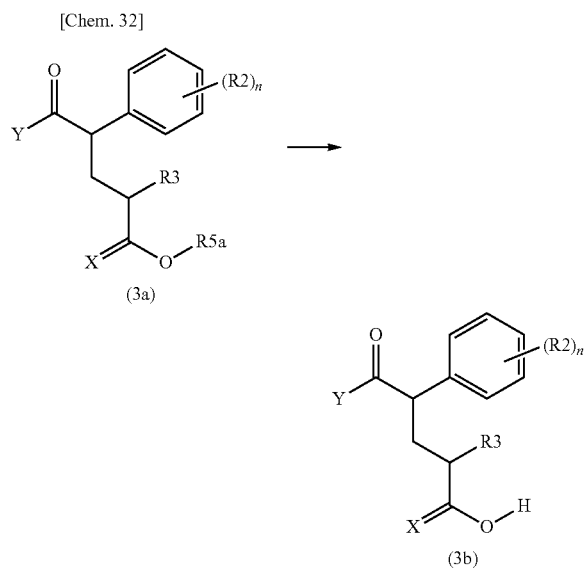

In the formula, R5a represents a C1-C6 alkyl group, and R2, R3, n, X and Y are the same as defined hereinabove.

Production Method R produces an intermediate of Formula (3b), which belongs to the compounds of Formula (3). The production method includes reacting a compound of Formula (3a) under acidic or basic conditions in a solvent.

First, the reaction under acidic conditions is described.

Examples of the acids used in the reaction include inorganic acids such as hydrochloric acid, hydrobromic acid and phosphoric acid, and organic acids such as acetic acid, methanesulfonic acid, p-toluenesulfonic acid and trifluoroacetic acid. The acids are not particularly limited as long as the objective reaction takes place.

The amount of the acid used in the reaction may be a catalytic amount. The amount is not particularly limited as long as the objective reaction takes place, and is preferably not less than 0.01 equivalent amount relative to the compound of Formula (3a). The acid which is liquid may be used also as solvents.

The solvent used in the reaction is not particularly limited as long as the objective reaction takes place. Examples include aqueous solvents, acidic solvents such as acetic acid and methanesulfonic acid, ether solvents such as diethyl ether, diisopropyl ether, methyl-t-butyl ether, dimethoxyethane, tetrahydrofuran and dioxane, alcohol solvents such as methanol, ethanol and isopropanol, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride. These solvents may be used singly, or two or more of these solvents may be used in combination in any ratio.

The amount of the solvent used in the reaction is not particularly limited as long as the objective reaction takes place, and is usually from 3 to 200 times by weight relative to the amount of the compound of Formula (3a).

The temperature of the reaction is not particularly limited as long as the objective reaction takes place, and is usually from 0° C. to 180° C., or is not greater than the boiling point of the solvent.

Next, the reaction under basic conditions is described.

Examples of the bases used in the reaction include inorganic bases such as lithium hydroxide, sodium hydroxide and potassium hydroxide. The bases are not particularly limited as long as the objective reaction takes place.

The amount of the base used in the reaction is 1 equivalent weight or more relative to the compound of Formula (3a). The amount is not particularly limited as long as the objective reaction takes place, and is preferably from 1 equivalent weight to 30 equivalent weight.

The solvent used in the reaction is not particularly limited as long as the objective reaction takes place. Examples include aqueous solvents, ether solvents such as diethyl ether, diisopropyl ether, methyl-t-butyl ether, dimethoxyethane, tetrahydrofuran and dioxane, alcohol solvents such as methanol, ethanol and isopropanol, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride. These solvents may be used singly, or two or more of these solvents may be used in combination in any ratio.

The amount of the solvent used in the reaction is not particularly limited as long as the objective reaction takes place, and is usually from 3 to 200 times by weight relative to the amount of the compound of Formula (3a).

The temperature of the reaction is not particularly limited as long as the objective reaction takes place, and is usually from −20° C. to 180° C., or is not greater than the boiling point of the solvent.

The reaction may be followed by a post treatment, which may be performed by a common method irrespective of whether the reaction condition is acidic or basic. Water or an appropriate aqueous solution may be added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane. These solvents may be used singly, or two or more of these solvents may be used in combination in any ratio. The liquid separation may be performed as many times as desired without limitation due to the desired purity and yield.

The above-obtained reaction mixture which includes the compound of Formula (3b) may be dried with a desiccant such as sodium sulfate or magnesium sulfate, but this dehydration may be omitted.

The above-obtained reaction mixture which includes the compound of Formula (3b) may be distilled to evaporate the solvent under reduced pressure as long as the compound is not decomposed.

The distilled reaction mixture which includes the compound of Formula (3b) may be purified in an appropriate solvent by a method such as washing, reprecipitation, recrystallization or column chromatography. The purification method may be selected appropriately due to the desired purity.

The compound of Formula (3b) may be an isomer of Formula (3b'):

[Chem. 33]

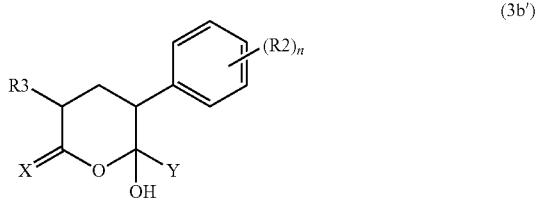

(3b')

wherein R2, R3, n, X and Y are the same as defined hereinabove.

The compound of Formula (3b') may be handled similarly to the compound of Formula (3b), and may be applied to Production Method A. The compound of Formula (3b') has an asymmetric carbon, and may be a single isomer or a mixture of isomers in an appropriate ratio. Further, a mixture of the compound of Formula (3b) and the compound of Formula (3b') may be used, and each of these compounds may be a single isomer or a mixture of isomers in an appropriate ratio.

The compounds of Formula (1) may be produced by appropriate combinations of Production Method A to Production Method R described hereinabove. Alternatively, the compounds of Formula (1) may be produced by appropriate combinations of known methods and Production Method A to Production Method R.

The compounds of the present invention exhibit good anti-parasitic pest effects and demonstrate control effects against parasitic pests effectively. A parasitic pest as herein referred to indicates those parasitically infests the bodies of animals externally or internally as well as plants.

Examples of animals to which the compounds of the present invention can be applied for the purpose of controlling parasitic pests include, but are not limited to, domestic animals such as horses, cows, pigs, sheep, goats, rabbits, camels, water buffalo, deer, minks or chinchillas, fowl such as chickens, ducks, geese or turkeys, pets such as dogs, cats, small birds or monkeys, and laboratory animals such as rats, mice, golden hamsters or guinea pigs. Animals are preferable with the exception of humans.

Examples of plants to which the compounds of the present invention can be applied for the purpose of controlling parasitic pests include, but are not limited to, agricultural crops such as corn, rice, wheat, barley, rye, oats, sorghum, cotton, soybeans, peanuts, buckwheat, sugar beets, rape, sunflowers, sugar cane or tobacco; vegetables such as solanaceous vegetables (such as eggplants, tomatoes, green peppers, red peppers or potatoes), cucurbitaceous vegetables (such as cucumbers, squash, zucchini, watermelons and melons), cruciferous vegetables (such as radishes, beets, horseradish, kohlrabi, Chinese cabbage, cabbage, Chinese mustard, broccoli or cauliflower), Asteraceae vegetables (such as burdock, garland chrysanthemum, artichokes or lettuce), Liliaceae vegetables (such as green onions, onions, garlic or asparagus), Apiaceae vegetables (such as carrots, parsley, celery or parsnips), Chenopodiaceae vegetables (such as spinach or Swiss chard), Lamiaceae vegetables (such as perilla, mint or basil), strawberries, sweet potatoes, yams or taro; fruits such as pome fruits (such as apples, pears, Japanese pears, Chinese quince or quince), stone fruits (such as peaches, Japanese plums, nectarines, plums, yellow peaches, apricots or prunes), citrus fruits (such as mandarin oranges, oranges, lemons, limes or grapefruit), nuts (such as chestnuts, walnuts, hazelnuts, almonds, pistachios, cashew nuts or macadamia nuts), berries (such as blueberries, cranberries, blackberries or raspberries), grapes, persimmons, olives, loquats, bananas, coffee, nutmeg, coconut palm or oil palm; trees other than fruit trees such as tea, mulberries, roadside trees (such as ash, birch, dogwood, eucalyptus, ginkgo, lilac, maple, oak, poplar, Judas tree, Formosan sweetgum, sycamore, zelkova, Japanese arborvitae, fir, hemlock, juniper, pine, spruce, yew, elm or horse chestnut tree), sweet viburnum, inumaki, cedar, cypress, croton, Japanese spindletree or Japanese photinia; grasses such as lawn grasses (such as Japanese lawn grass or Korean lawn grass), Bermuda grasses (such as Bermuda grass), bentgrasses (such as redtop grass, creeping bentgrass or colonial bentgrass), bluegrasses (such as Kentucky bluegrass or wildflowers), fescues (such as reed fescue, sheep fescue or red fescue), ryegrasses (such as Italian ryegrass or English ryegrass), orchard grass or timothy; oil crops such as oil palm or tungoil tree; flowering plants (such as roses, carnations, chrysanthemums, tulip gentians, baby's breath, gerbera, marigolds, salvias, petunias, verbena, tulips, asters, gentians, lilies, pansies, cyclamen, orchids, lily of the valley, lavender, stock, flowering kale, primrose, poinsettias, gladiolas, cattleyas, daisies, verbena, cymbidium or begonias); and foliage plants.

The following, but are not limited to, lists the specific examples of parasitic pests capable of being controlled using the compounds of the present invention.

Examples of parasitic pests that parasitically infest the bodies of animals externally include pests of the order Siphonaptera such as *Ctenocephalides felis, Ctenocephalides canis, Xenopsylla cheopis, Echidnophaga gallinacea* or *Pulex irritans*; pests of the order Acarina including ticks such as *Haemaphysalis longicornis, Haemaphysalis japonica, Rhipicephalus sanguineus, Boophilus macroplus, Dermacentor recticulatus, Dermacentor taiwanensis, Haemaphysalis flava, Ixodes ovatus, Ixodes persulcatus, Amblyomma americanum, Amblyomma maculatum, Dermacentor andersoni, Dermacentor occidentalis, Dermacentor variabilis, Haemaphysalis campanulata, Haemaphysalis* megaspinosa, Ixodes nipponensis, Ixodes pacifcus, Ixodes ricinus or Ixodes scapularis, Cheyletidaes such as Cheyletiella yasguri or Cheyletiella blakei, follicle mites such as Demodex canis or Demodex cati, Psoroptidaes such as Psoroptes ovis or itch mites such as Sarcoptes scabiei, Notoedres cati or Knemidocoptes spp.; pests of the order Diptera such as Musca hervei, Musca bezzii, Haematobia irritans, Stomoxys calcitrans, Hypderma lineatum, Oestrus ovis, Melophagus ovinus, Hypoderma bovis, Glossina palpalis, Glossina morsitans, Simulium iwatens, Culicoides oxystoma, Tabanus chrysurus, Culex pipiens, Aedes albopictus, Aedes aegypti, Anopheles hyracanus sinesis, Culex pipiens molestus or Prosimulium yezoensis; and pests of the order Anoplura such as Menacanthus stramineus, Bovicola bovis, Haematopinus eurysternus, Damalinia ovis, Haematopinus suis, Linognathus vituli or Solenoptes capillatus.

Examples of parasitic pests that parasitically infest the bodies of animals internally include:

nematodes of the order Enoplida such as Dioctophyma renale, Capillaria annulata, Capillaria contorta, Capillaria hepatica, Capillaria perforans, Capillaria philippinensis, Capillaria suis, Trichuris discolor, Trichuris ovis, Trichuris suis, Trichuris trichiura, Trichuris vulpis or Trichinella spiralis, nematodes of the order Rhabditida such as Strongyloides papillosus, Strongyloides planiceps, Strongyloides ransomi, Strongyloides stercoralis or Micronema spp., nematodes of the order Strongylida such as Ancylostoma braziliense, Ancylostoma caninum, Ancylostoma duodenale, Ancylostoma tubaeforme, Uncinaria stenocephala, Bunostomum phlebotomum, Bunostomum trigonocephalum, Necator americanus, Cyathostomum spp., Cylicocyclus spp., Cylicodontophorus spp., Cylicostephanus spp., Strongylus asini, Strongylus edentatus, Strongylus equinus, Strongylus vulgaris, Chabertia ovina, Oesophagostomum brevicaudatum, Oesophagostomum columbianum, Oesophagostomum dentatum, Oesophagostomum georgianum, Oesophagostomum maplestonei, Oesophagostomum quadrispinulatum, Oesophagostomum radiatum, Oesophagostomum venulosum, Syngamus skrjabinomorpha, Syngamus trachea, Stephanurus dentatus, Cooperia oncophora, Hyostrongylus rubidus, Trichostrongylus axei, Trichostrongylus colubriformis, Trichostrongylus orientalis, Haemonchus contortus, Mecistocirrus digitatus, Ostertagia ostertagi, Dictyocaulus filaria, Dictyocaulus viviparus, Nematodirus filicollis, Metastrongylus elongatus, Filaroides hirthi, Crenosoma aerophila, Crenosoma vulpis, Angiostrongylus cantonensis, Angiostrongylus vasorum or Protostrongylus spp., nematodes of the order Oxyurida such as Oxyuris equi, Passalurus ambiguus or Enterobius vermicularis, nematodes of the order Ascaridida such as Ascaris suum, Parascaris equorum, Toxascaris leonina, Toxocara canis, Toxocara cati, Toxocara vitulorum, Anisakis spp., Pseudoterranova spp., Heterakis gallinarum or Ascaridia galli, nematodes of the order Spirurida such as Dracunculus medinensis, Gnathostoma doloresi, Gnathostoma hispidum, Gnathostoma nipponicum, Gnathostoma spinigerum, Physaloptera canis, Physaloptera felidis, Physaloptera praeputialis, Physaloptera rara, Thelazia callipaeda, Thelazia rhodesi, Draschia megastoma, Habronema microstoma, Habronema muscae, Gongylonema pulchrum, Ascarops strongylina, Parafilaria bovicola, Parajilaria multipapillosa, Stephanofilaria okinawaensis, Wuchereria bancrofti, Brugia malayi, Onchocerca cervicalis, Onchocerca gibsoni, Onchocerca gutturosa, Onchocerca volvulus, Setaria digitate, Setaria equina, Setaria labiatopapillosa, Setaria marshalli, Dirofilaria immitis or Loa, Acanthocephalas such as Moniliformis or Macracanthorhynchus hirudinaceus, tapeworms such as Diphyllobothrium latum, Diphyllobothrium nihonkaiense, Spirometra erinaceieuropaei, Diplogonoporus grandis, Mesocestoides lineatus, Raillietina cesticillus, Raillietina chinobothrida, Raillietina tetragona, Taenia hydatigena, Taenia multiceps, Taenia ovis, Taenia pisiformis, Taenia saginata, Taenia serialis, Taenia solium, Taenia taeniaeformis, Echinococcus granulosus, Echinococcus multilocularis, Echinococcus oligarthrus, Echinococcus vogeli, Hymenolepis diminuta, Hymenolepis nana, Dipylidium caninum, Amoebotaenia sphenoides, Choanotaenia infundibulum, Metroliasthes coturnix, Anoplocephala magna, Anoplocephela perfoliata, Paranoplocephala mamillana, Moniezia benedeni, Moniezia, expansa or Stilesia spp., flukes such as Pharyngostomum cordatum, Schistosoma haematobium, Schistosoma japonicum, Schistosoma mansoni, Echinostoma cinetorchis, Echinostoma hortense, Fasciola gigantica, Fasciola hepatica, Fasciolopsis buski, Homalogaster paloniae, Dicrocoelium chinensis, Dicrocoelium dendriticum, Dicrocoelium hospes, Eurytrema coelomaticum, Eurytrema pancreaticum, Paragonimus miyazakii, Paragonimus ohirai, Paragonimus westermani, Amphimerus spp., Clonorchis sinensis, Opisthorchis felineus, Opisthorchis viverrini, Pseudamphistoma spp., Metorchis spp., Parametorchis spp., Heterophyes, Metagonimus yokokawai or Pygidiopsis summa, amoebas such as Entamoeba histolytica or Entamoeba invadens, sporozoans such as Babesia bigemina, Babesia bovis, Babesia caballi, Babesia canis, Babesia felis, Babesia gibsoni, Babesia ovata, Cytauxzoon felis, Theileria annulata, Theileria mutans, Theileria orientalis, Theileria parva, Haemoproteus mansoni, Leucocytozoon caulleryi, Plasmodium falciparum, Plasmodium malariae, Plasmodium ovale, Plasmodium vivax, Caryospora spp., Eimeria acervulina, Eimeria bovis, Eimeria brunetti, Eimeria maxima, Eimeria necatrix, Eimeria ovinoidalis, Eimeria stiedae, Eimeria tenella, Isospora canis, Isospora felis, Isospora suis, Tyzzeria alleni, Tyzzeria anseris, Tyzzeria perniciosa, Wenyonella anatis, Wenyonella gagari, Cryptosporidium canis, Cryptosporidium felis, Cryptosporidium hominis, Cryptosporidium meleagridis, Cryptosporidium muris, Cryptosporidium parvum, Sarcocystis canis, Sarcocystis cruzi, Sarcocystis felis, Sarcocystis hominis, Sarcocystis miescheriana, Sarcocystis neurona, Sarcocystis tenella, Sarcocystis ovalis, Toxoplasma gondii, Hepatozoon canis or Hepatozoon felis, flagellatas such as Histomanas meleagridis, Pentatrichomonas hominis, Trichomonas tenax, Giardia intestinalis, Giardia muris, Hexamita meleagridus, Hexamita parva, Leishmania donovani, Leishmania infantum, Leishmania major, Leishmania tropica, Trypanosoma brucei gambiense, Trypanosoma brucei rhodesiense, Trypanosoma cruzi, Trypanozoma equiperdum or Trypanosoma evansi, and ciliates such as Balantidium coli.

Examples of plant parasitic pests include insects of the order Lepidoptera such as Adoxophyes honmai, Adoxophyes orana faciata, Archips breviplicanus, Grapholita inopinata, Archips fuscocupreanus, Grapholita molesta, Choristoneura magnanima, Leguminavora glycinivorella, Olethreutes mori, Caloptilia zachrysa, Argyresthia conjugella, Spulerina astaurota, Matsumuraeses phaseoli, Pandemis heparana, Bucculatrix pyrivorella, Lyonetis clerkella, Carposina niponensis, Lyonetia prunifoliella malinella, Caloptilia

*theivora, Phyllonorycter ringoniella, Phyllocnistis citrella, Acrolepiopsis sapporensis, Acrolepiopsis suzukiella, Plutella xylostella, Stathmopoda masinissa, Helcystrogramma triannulella, Pectinophora gossypiella, Carposina sasakii, Chilo suppressalis, Cnaphalocrocis medinalis, Ephestia elutella, Conogethes punctiferalis, Diaphania indica, Etiella zinckenella, Glyphodes pyloalis, Scirpophaga incertulas, Hellula undalis, Ostrinia furnacalis, Ostrinia scapulalis, Parapediasia teterrella, Parnara guttata, Pieris brassicae, Pieris rapae crucivora, Papilio xuthus, Ascotis selenaria, Pseudoplusia includens, Euproctis pseudoconspersa, Lymantria dispar, Orgyia thyellina, Hyphantria cunea, Lemyra imparilis, Adris tyrannus, Aedia leucomelas, Agrotis ipsilon, Agrotis segetum, Autographa nigrisigna, Ctenoplusia agnata, Cydia pomenella, Helicoverpa armigera, Helicoverpa assulta, Helicoverpa zea, Heliothis virescens, Ostrinia nubilalis, Mamestra brassicae, Mythimna separata, Sesamia inferens, Naranga aenescens, Spodoptera eridania, Spodoptera exigua, Spodoptera frugiperda, Spodoptera littoralis, Spodoptera litura, Spodoptera depravata, Trichoplusia ni, Endopiza viteana, Manduca quinquemaculata* or *Manduca sexta,* insects of the order Hemiptera such as *Arboridia apacalis, Baklutha saltuella, Epiacanthus stramineus, Empoasca fabae, Empoasca nipponica, Empoasca onokii, Empoasca sakaii, Macrosteles striifrons, Nephotettix cinctinceps, Pseudatomoscelis seriatus, Laodelphax striatella, Nilaparvata lugens, Sogatella furcifera, Diaphorina citri, Psylla pyrisuga, Aleurocanthus spiniferus, Bemisia argentifolii, Bernisia tabaci, Dialeurodes citri, Trialeurodes vaporariorum, Aleurolobus taonabae, Viteus vitifolii, Lipaphis erysimi, Aphis gossypii, Aphis spiraecola, Myzus persicae, Toxoptera aurantii, Drosicha corpulenta, Icerya purchasi, Phenacoccus solani, Pulvinaria aurantii, Planococcus citri, Pseudaonidia duplex, Planococcus kuraunhiae, Pseudococcus comstocki, Comstockaspis perniciosa, Ceroplastes ceriferus, Ceroplastes rubens, Aonidiella aurantii, Fiorinia theae, Pseudaonidia paeoniae, Pseudaulacaspis pentagona, Pseudaulacaspis prunicola, Unaspis euonymi, Unaspis yanonensis, Cimex lectularius, Dolycoris baccarum, Eurydema rugosum, Eysarcoris aeneus, Eysarcoris lewisi, Eysarcoris ventralis, Glaucias subpunctatus, Halyomorpha halys, Nezara antennata, Nezara viridula, Piezodorus hybneri, Plautia crossota, Scotinophora lurida, Cletus punctiger, Leptocorisa chinensis, Riptortus clavatus, Rhopalus maculatus, Cavelerius saccharivorus, Togo hemipterus, Dysdercus cingulatus, Stephanitis pyrioides, Halticus insularis, Lygus lineolaris, Stenodema sibiricum, Stenotus rubrovittatus* or *Trigonotylus caelestialium,* insects of the order Coleoptera such as *Anomala cuprea, Anomala rufocuprea, Gametis jucunda, Heptophylla picea, Popillia japonica, Lepinotarsa decemlineata, Epilachna varivestis, Melanotus fortnumi, Melanotus tamsuyensis, Lasioderma serricorne, Lyctus brunneus, Tomicus piniperda, Rhizopertha dominica, Epuraea domina, Epilachna varivestis, Epilachna vigintioctopunctata, Tenebrio molitor, Tribolium castaneum, Anoplophora malasiaca, Monochamus alternatus, Psacothea hilaris, Xylotrechus pyrrhoderus, Callosobruchus chinensis, Aulacophora femoralis, Oulema oryzae, Chaetocnema concinna, Diabrotica undecimpunctata, Diabrotica virgifera, Diabrotica barberi, Phyllotreta striolata, Psylliodes angusticollis, Rhynchites heros, Cylas formicarius, Anthonomus grandis, Echinocnemus squameus, Euscepes postfasciatus, Hypera postica, Lissorhoptrus oryzophilus, Otiorhynchus sulcatus, Sitophilus granarius, Sitophilus zeamais, Sphenophorus venatus vestitus* or *Paederus fuscipes,* insects of the order Thysanoptera such as *Frankliniella intonsa, Thrips flavus, Frankliniella occidentalis, Heliothrips haemorrhoidalis, Scirtothrips dorsalis, Thrips palmi, Thrips tabaci* or *Ponticulothrips diospyrosi,* insects of the order Diptera such as *Asphondylia yushimai, Sitodiplosis mosellana, Bactrocera cucurbitae, Bactrocera dorsalis, Ceratitis capitata, Hydrellia griseola, Drosophila suzukii, Agromyza oryzae, Chromatomyia horticola, Liriomyza bryoniae, Liriomyza chinensis, Liriomyza sativae, Liriomyza trifolii, Delia platura, Delia antique, Pegomya cunicularia, Rhagoletis pomonella* or *Mayetiola destructor,* insects of the order Hymenoptera such as *Apethymus kuri, Athalia rosae, Arge pagana, Neodiprion sertifer* or *Dryocosmus kuriphilus,* insects of the order Orthoptera such as *Teleogryllus emma, Gryllotalpa orientalis, Locusta migratoria, Oxya yezoensis* or *Schistocerca gregaria,* insects of the order Collembola such as *Onychiurus folsomi, Onychiurus sibiricus* or *Bourletiella hortensis,* insects of the order Isoptera such as *Coptotermes formosanus, Reticulitermes speratus* or *Odontotermes formosanus,* nematodes for example root-knot nematodes such as *Meloidogyne incognita, Meloidogyne javanica, Meloidogyne hapla, Meloidogyne arenaria, Meloidogyne chitwoodi* or *Meloidogyne thamesi; Ditylenchus* spp. nematodes such as *Ditylenchus destructor, Ditylenchus dipsaci* or *Ditylenchus angustus; Pratylenchus* such as *Pratylenchus penetrans, Pratylenchus fallax, Pratylenchus coffeae* or *Pratylenchus vulnus;* cyst nematodes such as *Globodera rostochiensis, Globodera pallida, Heterodera glycines* or *Heterodera shachtii;* white-tip nematodes such as *Aphelenchoides besseyi; Radopholus similis* such as *Radopholus similis* or *Radopholus citrophilus; Nacobbus aberrans; Aphelenchus avenae; Bursaphelenchus xyiophilus; Xiphinema index; Paratylenchus curvitatus,* insects of the order Acarina for example Tarsonemidae such as *Phytonemus pallidus, Polyphagotarsonemus latus* or *Tarsonemus bilobatus;* Eupodidae such as *Penthaleus erythrocephalus* or *Penthaleus major;* spider mites such as *Oligonychus shinkajii, Panonychus citri, Panonychus mori, Panonychus ulmi, Panonychus kanzawai* or *Tetranychus urticae,* Eriophyidae such as *Acaphylla theavagrans, Aceria tulipae, Aculops lycopersici, Aculops pelekassi, Aculus schlechtendali, Eriophyes chibaensis* or *Phyllocoptrula oleivora,* or Acaridae such as *Rhizoglyphus robini, Tyrophagus putrescentiae* or *Tyrophagus similis,* crustaceans such as *Armadillidium vulgare;* and gastropods such as *Pomacea canaliculata, Achatina fulica, Meghimatium bilineatum, Limax valentiana, Acusta despecta sieboldiana* or *Euhadra peliomphala.*

The aforementioned parasitic pests are preferably pests of the order Acarina or nematodes, more preferably plant parasitic pests of the order Acarina, animal parasitic nematodes or plant parasitic nematodes, even more preferably spider mites, nematodes of the order Spirurida or root-knot nematodes, and most preferably two-spotted spider mites or southern root-knot nematodes.

The compounds of the present invention can be used in plants that have acquired characteristics such as pest resistance, disease resistance or herbicide resistance through, for example gene recombination or artificial crossing, and are effective against parasitic pests resistance to known insecticides, miticides and nematicides such as organophosphorous-based compounds, carbamate-based compounds, synthetic parathyroid-based compounds or acylurea-based compounds.

The present invention also relates to a method for controlling parasitic pests, wherein the method comprises the application of an effective amount of the compound of the present invention or a salt thereof to a subject in need thereof. The subject refers to the previously described plants and animals, and the application refers to, for example an administration to an animal or an application to a plant as indicated below.

The compounds of the present invention for controlling parasitic pests can be used to animals by oral administration or parenteral administration. In the case of oral administration, the compounds of the present invention can be used by incorporating in capsules, tablets, pills, powders, granules, grains, powders, syrups, enteric-coated agents, suspensions, pastes or liquid drinks for animals or feeds. In the case of parenteral administration, the compounds of the present invention can be used as injections, infusions, suppositories, emulsions, suspensions, drops, ointments, creams, solutions, lotions, sprays, aerosols, cataplasms, tapes or in a formulation form capable of maintaining absorption through a mucous membrane or a skin. With respect to applications to plants, the compounds of the present invention can be used as water-dispersible powders, water soluble powders, flowables, granulated water-dispersible powders, powders, emulsions, granules, fine granules, solutions, oils, aerosols, pastes, microcapsules, smoking agents, fumigants or coating agents. The compound of the present invention can be used, in addition to spraying various preparations onto stems and leaves, for protecting the roots or for being absorbed through the roots by treating soil, for example by whole soil treatment, whole soil layer treatment, applying to planting rows, mixing with bed soil, plug seedling treatment, planting hole treatment, plant base treatment, top dressing, nursery box treatment of rice paddy or applying to the water surface. In addition, the compounds of the present invention can also be used, for example by applying to a nutrient solution during nutrient solution (hydroponic) culturing, fumigating or stem infusion.

The parasitic pest control agent of the present invention can be in the aforementioned formulation forms.

Moreover, the compounds of the present invention are capable of not only controlling parasitic pests infesting animals and plants internally and externally, but also preventing infection of parasitic pests by applying to in an environment serving as the infection route. For example, soil-propagated infections from the soil of fields or parks, percutaneous infections from water systems such as rivers, lakes, marshes, wetlands or rice paddies, oral infections from the feces of dogs or cats, oral infections from, for example saltwater fish, freshwater fish, crustaceans, shellfish or the raw meat of domestic animals, or infections from, for example mosquitoes, gadflies, houseflies, cockroaches, mites, fleas, lice, assassin bugs or chiggers can be prevented.

In the case of using the compounds of the present invention to control parasitic pests of mammals or birds, the optimum dose varies due to factors, for example whether prevention or treatment, the type of parasitic pest causing parasitic infestation, the type or degree of infection or the formulation form. In the case of oral administration, the optimum dose of the active ingredient is generally within the range of from about 0.0001 mg/kg to 10000 mg/kg of body weight per day and preferably within the range of from about 0.001 mg/kg to 1000 mg/kg of body weight per day. In the case of parenteral administration, the optimum dose of active ingredient is within the range of from about 0.0001 mg/kg to 10000 mg/kg of body weight per day and preferably within the range of from about 0.001 mg/kg to 1000 mg/kg of body weight per day. Oral administration and parenteral administration are carried out either by a single administration or by divided administrations.

In the case of using the compounds of the present invention to control parasitic pests of plants, the optimum dose varies due to factors, for example the purpose of use, target pests, growth status of crops, pests incidence tendency, weather, environmental conditions, formulation forms, application method, application site or application timing. The optimum dose of the active ingredient is normally, appropriately selected from the range of from 0.1 g to 10000 g per are and preferably within the range of from 1 g to 1000 g per are.

The concentration of active ingredient in the parasitic pest control agent of the present invention is generally from 0.0001% by weight to 100% by weight, preferably from 0.001% by weight to 99% by weight, and even more preferably 0.005% by weight to 80% by weight. The pest control agent can be provided as a highly concentrated composition that is used by diluting to an appropriate concentration at the time of use.

The parasitic pest control agent of the present invention can further comprise, in addition to the compounds of formula (1) of the present invention, other commonly known insecticidal components. Examples of other insecticidal components include parathyroid compounds such as permethrin, d-phenothrin, allethrin, pyrethrum, prallethrin, cyphenothrin, cyfluthrin, fenvalerate, fenpropathrin, transfluthrin, metofluthrin, resmethrin, cypermethrin, alpha-cypermethrin, bifenthrin, deltamethrin, lambda cyhalothrin, d,d-trans-cyphenothrin, tetramethrin or etofenprox; organophosphorous-based compounds such as dichlorvos, tetrachlorvinphos, fenthion, chlorpyrifos, chlorpyrifos methyl, malathion, primiphos methyl, fenitrothion, diazinon, piraclophos or cadusafos; N-phenylpyrazol-based compounds such as fipronil; caramabate-based compounds such as propoxyl, carbaryl, bendiocarb, metoxadiazon, fenocarb or oxamyl; neonicotinoid-based compounds such as imidacloprid, clothianidin, thiamethoxam, acetamiprid, nitenpyram or dinotefuran; diamide-based compounds such as chlorantraniliprole, cyantraniliprole or flubendiamide; insect growth regulators such as methoprene, piriproxyfen, lefenuron, phenoxycarb, triflumuron or chromafenozide; milbemycin oxime; milbemectin; lepimectin; abamectin; ivermectin; selamectin; spinosad; rotenone; etoxazole; broflanilide; fluralaner; afoxalaner; sarolaner; amitraz; pyflubumide; fluensulfone; fluazaindolizine; and tioxazafen.

In the case the parasitic pest control agent of the present invention further comprises the above-described another insecticidal components, the weight ratio between the pyridone compound of the present invention and the above-described another insecticidal component is normally from 0.02 parts by weight to 50 parts by weight, and preferably from 0.1 parts by weight to 20 parts by weight of the above-described another insecticidal component to 1 part by weight of the compound of formula (1) of the present invention.

The parasitic pest control agent of the present invention may also comprises, in addition to a compound of the present invention and the aforementioned insecticidal component, commonly used additives.

Although the following illustrates the specific preparation examples, the present invention is not limited thereto.

Preparation Example 1

Emulsions

Ten parts of the pyridone compound of the present invention, 6 parts of polyoxyethylene styryl phenyl ether and 84 parts of solvent naphtha are stirred and mixed homogeneously to obtain an emulsions.

Preparation Example 2

Ointments

One part of the pyridone compound of the present invention, 50 parts by weight of white beeswax and 49 parts of white Vaseline are mixed well to obtain an ointments.

Preparation Example 3

Tablets

Two parts of the pyridone compound of the present invention, 10 parts of vegetable oil (olive oil), 3 parts of crystalline cellulose, 20 parts of white carbon and 65 parts of kaolin are mixed well and compressed into tablets.

Preparation Example 4

Injections

Ten parts of the pyridone compound of the present invention, 10 parts of propylene glycol for food additives and 80 parts of vegetable oil (corn oil) are mixed to obtain an injections.

Preparation Example 5

Aqueous Solutions

Five parts of the pyridone compound of the present invention, 20 parts of surfactant and 75 parts of ion exchange water are mixed well to obtain the aqueous solutions.

Preparation Example 6

Granules

Ten parts of the pyridone compound of the present invention, 0.5 parts of dioctylsulfosuccinate, 3 parts of enzyme-modified dextrin, 15 parts of talc and 71.5 parts of clay are mixed, added water, and then molded with a granulator. The resulting molded product is dried followed by sizing to obtain granules.

Production Example 7

Flowables

Ten parts of the pyridone compound of the present invention, 5 parts of a sodium salt of naphthalene sulfonate formaldehyde condensate, 1 part of polyoxyethylene aryl phenyl ether, 5 parts of propylene glycol, 0.1 parts of a silicone-based antifoaming agent, 0.2 parts of xanthan gum and 78.7 parts of ion exchange water are mixed to obtain a slurry followed by wet milling using Dyno-Mill KDL with glass beads having a diameter of 1.0 mm to obtain a flowables.

Preparation Example 8

Water-Dispersible Powders

Ten parts of the pyridone compound of the present invention, 10 parts of white carbon, 2 parts of polyvinyl alcohol, 0.5 parts of sodium dioctylsulfosuccinate, 5 parts of sodium alkylbenzene sulfonate, 10 parts of calcined diatomaceous earth and 62.5 parts of kaolinite clay are mixed well and milled with an air mill to obtain water-dispersible powders.

A method for controlling parasitic pests can be provided by using the pyridone compound of the present invention, a salt thereof, or a parasitic pest control agent comprising the compound or a salt thereof as an active ingredient. Preferably, the method for controlling parasitic pests wherein the parasitic pest is nematodes or an insect pest of the order Acarina is provided. More preferably, the method for controlling parasitic pests wherein the nematodes is a heartworm or a southern root-knot nematode, or an insect pest of the order Acarina is a two-spotted spider mite is provided.

The above-described another insecticidal components may also be used in combination therewith.

Examples

Although a more detailed explanation of the present invention is illustrated by synthesis examples, reference examples and test examples, the present invention is not limited thereto.

Synthesis Example 1

Step 1: Synthesis of 5-(2-chloro-5-methoxyphenyl)-6-(2,6-difluorophenyl)-3,4-dihydropyridine-2(1H)-one

[Chem. 34]

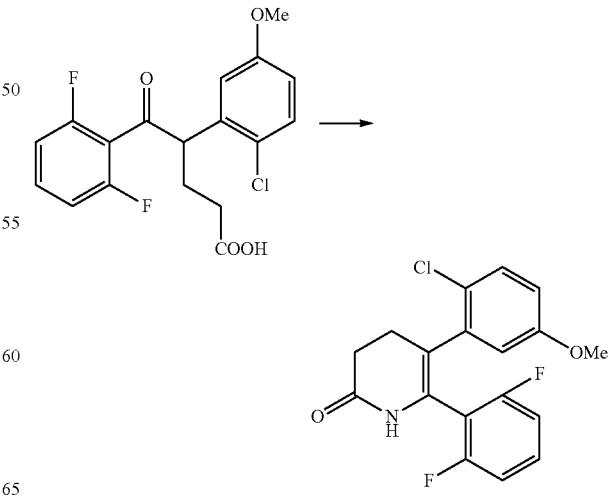

First, 10 ml of the acetic acid solution containing 1.47 g of 4-(2-chloro-5-methoxyphenyl)-5-(2,6-difluorophenyl)-5-oxopentanoic acid and 6.75 g of ammonium acetate was allowed to react at 130° C. for 14 hours. After cooling to room temperature, the reaction mixture was separated by adding ethyl acetate and water. The obtained organic layer was added water, potassium carbonate was further added until bubble releasing subsided, and then the resulting mixture was separated. Subsequently, the organic layer was washed with brine and dried over sodium sulfate. After the solvent was distilled off under reduced pressure, the precipitate was washed with diisopropyl ether. The resulting purple solid was the title compound (0.98 g).

$^1$H-NMR (CDCl$_3$) δ: 7.25-7.21 (1H, m), 7.19 (1H, d, J=8.8 Hz), 6.83-6.76 (3H, m), 6.65 (1H, dd, J=8.8, 3.4 Hz), 6.53 (1H, d, J=3.4 Hz), 3.61 (3H, s), 2.91-2.76 (4H, m).

Step 2: Synthesis of 5-(2-chloro-5-methoxyphenyl)-6-(2,6-difluorophenyl)-1-ethyl-3,4-dihydropyridine-2(1H)-one (Compound No. 52)

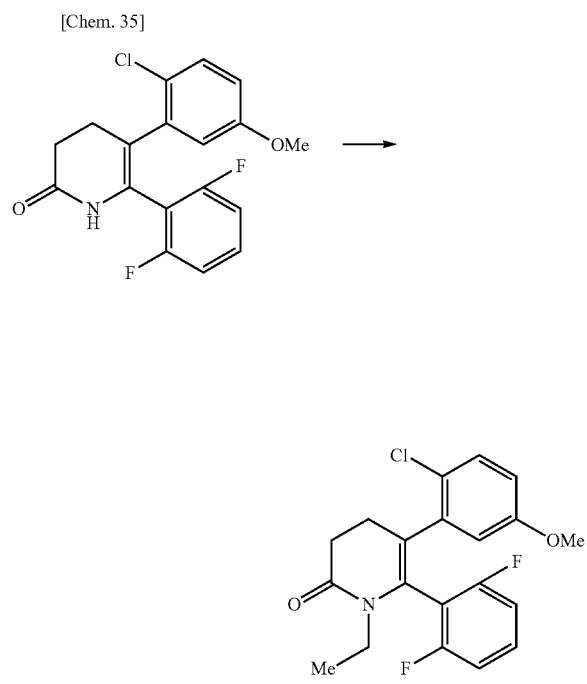

[Chem. 35]

To 5 ml of the DMF solution containing 0.50 g of 5-(2-chloro-5-methoxyphenyl)-6-(2,6-difluorophenyl)-3,4-dihydropyridine-2(1H)-one were added 346 µl of ethyl iodide and 1.41 g of cesium carbonate, and the mixture was stirred at 60° C. for 2 hours. After cooling to room temperature, the reaction mixture was separated by adding water and ethyl acetate. The obtained organic layer was sequentially washed with aqueous sodium thiosulfate solution and brine and dried over sodium sulfate. After the solvent was distilled off under reduced pressure, the resulting residue was purified by silica gel column chromatography. The title compound was obtained as a white solid (0.54 g).

Synthesis Example 2

Synthesis of 5-(2-chloro-5-methoxyphenyl)-6-(2,6-difluorophenyl)-1-ethylpyridine-2(1H)-one (Compound No. 53)

[Chem. 36]

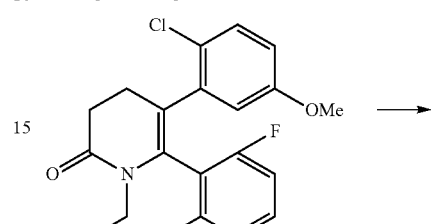

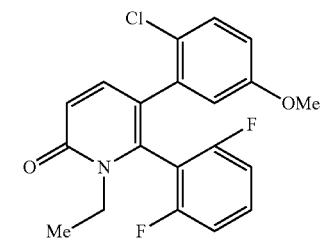

To 20 ml of the carbon tetrachloride solution containing 520 mg of 5-(2-chloro-5-methoxyphenyl)-6-(2,6-difluorophenyl)-1-ethyl-3,4-dihydropyridine-2(1H)-one were added 258 mg of N-bromosuccinimide and 23 mg of azobisisobutyronitrile, and the mixture was stirred at 80° C. for 90 minutes. After cooling to room temperature, the reaction mixture was added water, and carbon tetrachloride was distilled off under reduced pressure. After the resulting mixture was separated by adding ethyl acetate, the obtained organic layer was sequentially washed with aqueous sodium thiosulfate solution and brine and dried over sodium sulfate. After the solvent was distilled off under reduced pressure, the resulting residue was purified by silica gel column chromatography. The title compound was obtained as a white solid (467 mg).

Synthesis Example 3

Synthesis of 3-chloro-5-(2-chloro-5-methoxyphenyl)-6-(2,6-difluorophenyl)-1-ethylpyridine-2(1H)-one (Compound No. 54)

[Chem. 37]

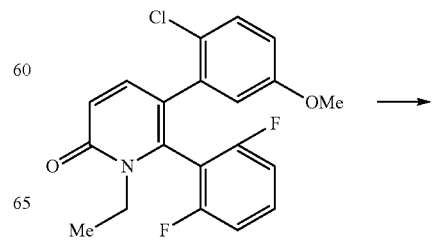

161
-continued

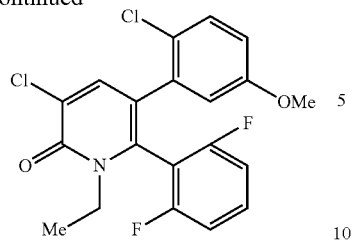

To 2 ml of the DMF solution containing 110 mg of 5-(2-chloro-5-methoxyphenyl)-6-(2,6-difluorophenyl)-1-ethylpyridine-2(1H)-one was added 43 mg of N-chlorosuccinimide, and the mixture was stirred at 70° C. for 1 hour. After cooling to room temperature, the reaction mixture was separated by adding ethyl acetate and water. The obtained organic layer was washed with brine and then dried over sodium sulfate. After the solvent was distilled off under reduced pressure, the resulting residue was purified by silica gel column chromatography. The title compound was obtained as a white solid (114 mg).

Synthesis Example 4

Synthesis of 5-(2-chloro-5-hydroxyphenyl)-6-(2,6-difluorophenyl)-1-ethylpyridine-2(1H)-one (Compound No. 234)

[Chem. 38]

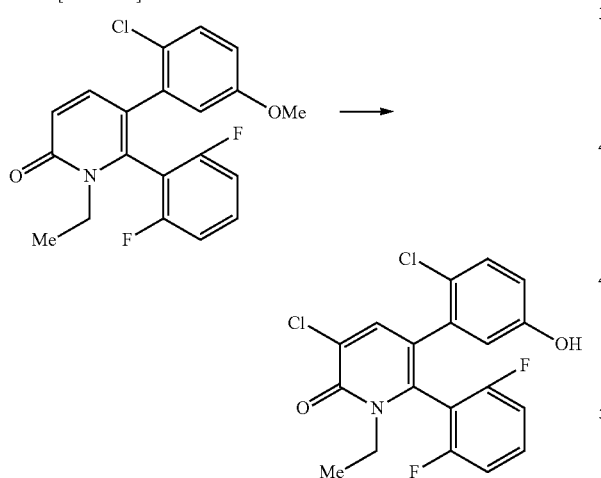

First, 40 ml of the dichloromethane solution containing 4.0 g of 5-(2-chloro-5-methoxyphenyl)-6-(2,6-difluorophenyl)-1-ethylpyridine-2(1H)-one was ice-cooled, and 23.4 ml of a 1.0 mol/l solution of boron tribromide in dichloromethane was added dropwise. After stirring for 30 minutes under ice cooling, the reaction mixture was separated by adding water. The obtained organic layer was sequentially washed with aqueous sodium thiosulfate solution and the aqueous saturated sodium bicarbonate solution and dried over sodium sulfate. After the solvent was distilled off under reduced pressure, the resulting residue was washed with hexane. The title compound was obtained as a white solid (3.9 g.

162

Synthesis Example 5

Synthesis of 5-(2-chloro-5-(methoxymethoxy)phenyl)-6-(2,6-difluorophenyl)-1-ethylpyridine-2(1H)-one (Compound No. 97)

[Chem. 39]

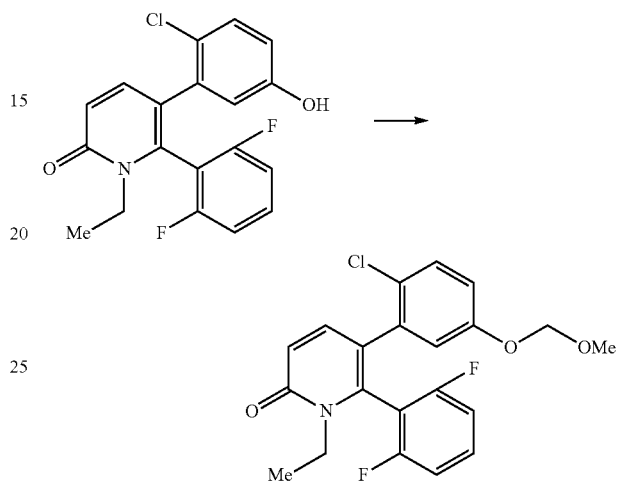

The THF solution containing 0.08 g of sodium hydride (about 60% by weight, dispersed in liquid paraffin) and 0.62 g of 5-(2-chloro-5-hydroxyphenyl)-6-(2,6-difluorophenyl)-1-ethylpyridine-2(1H)-one was added 0.08 g of chloromethyl methyl ether, and the mixture was stirred at room temperature for 3 hours. After the reaction mixture was separated by adding water and ethyl acetate, the obtained organic layer was dried over magnesium sulfate. After the solvent was distilled off under reduced pressure, the resulting residue was purified by silica gel column chromatography. The title compound was obtained as a white solid (0.46 g).

Synthesis Example 6

Synthesis of 3-chloro-5-(2-chloro-5-(methoxymethoxy)phenyl)-6-(2,6-difluorophenyl)-1-ethylpyridine-2(1H)-one (Compound No. 127)

[Chem. 40]

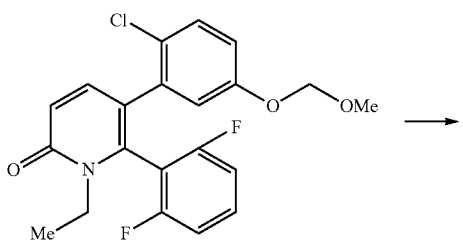

-continued

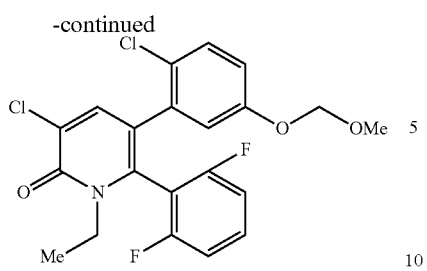

First, 3 ml of the DMF solution containing 219 mg of 5-(2-chloro-5-(methoxymethoxy)phenyl)-6-(2,6-difluorophenyl)-1-ethylpyridine-2(1H)-one and 79 mg of N-chlorosuccinimide was stirred at 70° C. for 1 hour. After cooling to room temperature, the reaction mixture was separated by adding the aqueous saturated sodium bicarbonate solution and ethyl acetate. The resulting organic layer was sequentially washed with aqueous sodium thiosulfate solution and brine and dried over sodium sulfate. After the solvent was distilled off under reduced pressure, the resulting residue was purified by silica gel column chromatography. The title compound was obtained as a yellow gum (203 mg).

Synthesis Example 7

Synthesis of 5-(2-chloro-5-methoxyphenyl)-1-(2,2-difluoroethyl)-6-(2,6-difluorophenyl)-3,4-dihydropyridine-2(1H)-one (Compound No. 192)

[Chem. 41]

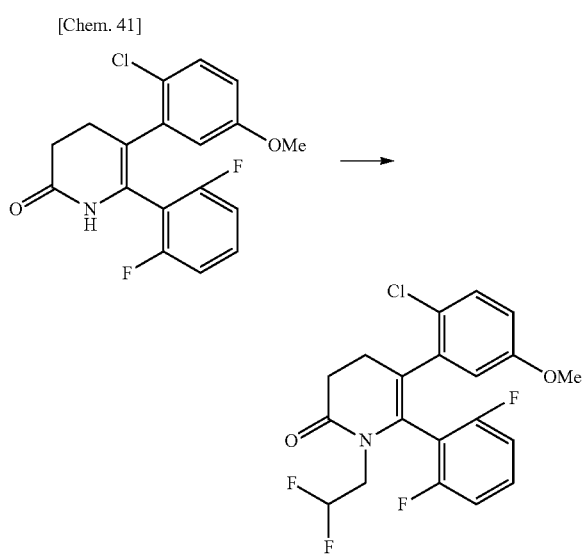

First, 10 ml of the DMF solution containing 0.50 g of 5-(2-chloro-5-methoxyphenyl)-6-(2,6-difluorophenyl)-3,4-dihydropyridine-2(1H)-one, 0.68 g of 2,2-difluoroethyl p-toluenesulfonate, and 1.40 g of cesium carbonate was stirred at 80° C. for 4 hours. After the reaction mixture was separated by adding water and ethyl acetate, the obtained organic layer was sequentially washed with 1N hydrochloric acid, the aqueous saturated sodium bicarbonate solution and brine and dried over sodium sulfate. After the solvent was distilled off under reduced pressure, the resulting residue was purified by silica gel column chromatography. The title compound was obtained as a white solid (0.48 g).

Synthesis Example 8

Synthesis of 5-(2-chloro-5-methoxyphenyl)-1-(2,2-difluoroethyl)-6-(2,6-difluorophenyl)pyridine-2(1H)-one (Compound No. 194)

[Chem. 42]

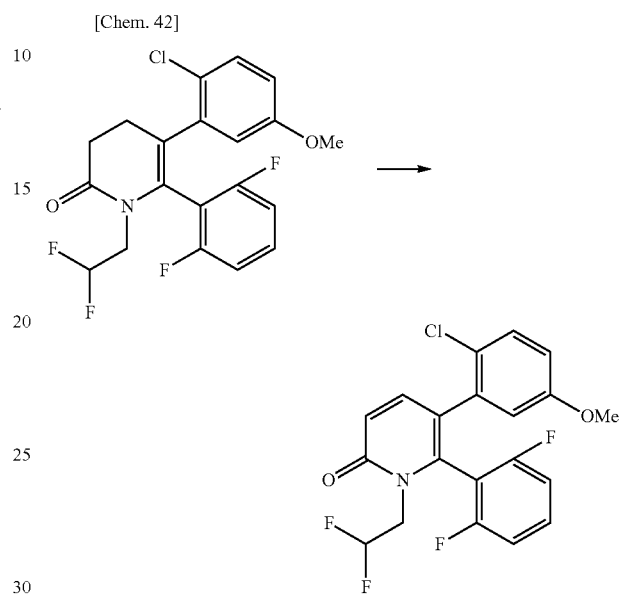

To 15 ml of the carbon tetrachloride solution containing 0.42 g of 5-(2-chloro-5-methoxyphenyl)-1-(2,2-difluoroethyl)-6-(2,6-difluorophenyl)-3,4-dihydropyridine-2(1H)-one were added 190 mg of N-bromosuccinimide and 16 mg of azobisisobutyronitrile, and the mixture was stirred at 80° C. for 15 minutes. After cooling to room temperature, the reaction mixture was added water, and carbon tetrachloride was distilled off under reduced pressure. After the resulting mixture was separated by adding ethyl acetate, the obtained organic layer was sequentially washed with aqueous sodium thiosulfate solution and brine, and dried over sodium sulfate. After the solvent was distilled off under reduced pressure, the resulting residue was purified by silica gel column chromatography. The title compound was obtained as a white solid (0.38 g).

Synthesis Example 9

Synthesis of 3-bromo-5-(2-chloro-5-methoxyphenyl)-1-(2,2-difluoroethyl)-6-(2,6-difluorophenyl)pyridine-2(1H)-one (Compound No. 198)

[Chem. 43]

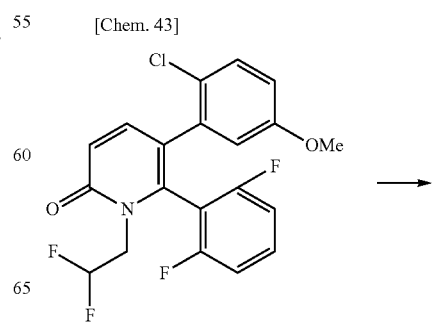

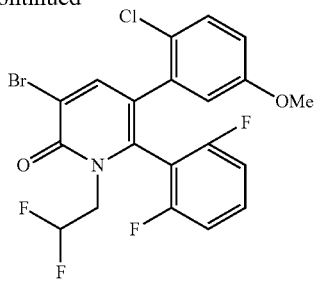

First, 5 ml of the DMF solution containing 125 mg of 5-(2-chloro-5-methoxyphenyl)-1-(2,2-difluoroethyl)-6-(2,6-difluorophenyl)pyridine-2(1H)-one and 65 mg of N-bromosuccinimide was stirred at 70° C. for 2 hours. 27 mg of N-bromosuccinimide was additionally added, and the mixture was further stirred at 70° C. for 2 hours. After cooling to room temperature, the reaction mixture was separated by adding water and ethyl acetate. The obtained organic layer was sequentially washed with aqueous sodium thiosulfate solution and brine and dried over sodium sulfate. After the solvent was distilled off under reduced pressure, the resulting residue was purified by silica gel column chromatography. The title compound was obtained as an off-white solid (109 mg).

Synthesis Example 10

Synthesis of 5-(2-chloro-5-methoxyphenyl)-6-(2,6-difluorophenyl)-1-ethyl-3-methyl-3,4-dihydropyridine-2(1H)-one

[Chem. 44]

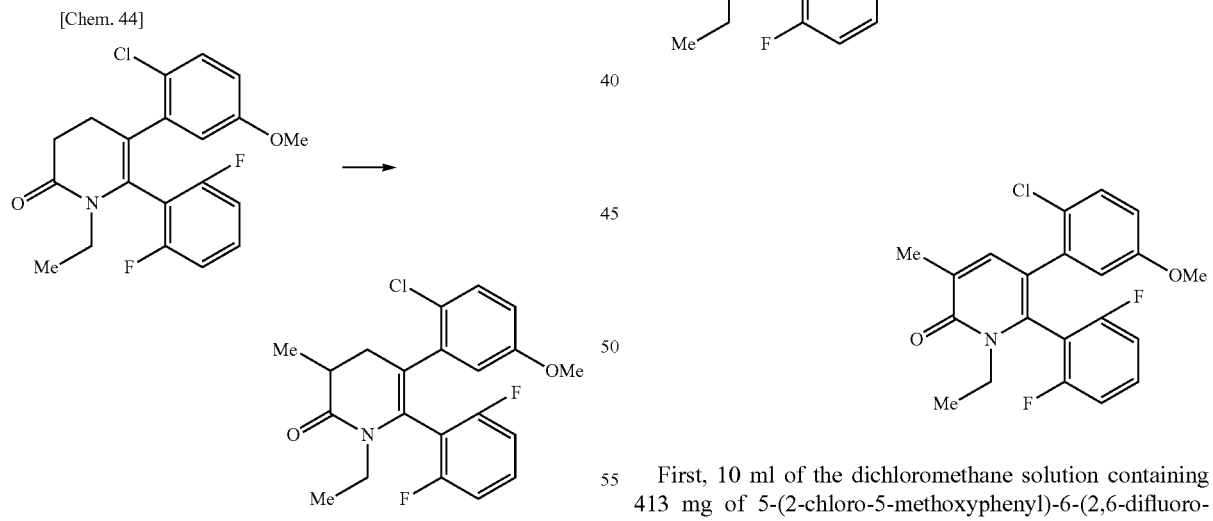

First, 10 ml of the THF solution containing 500 mg of 5-(2-chloro-5-methoxyphenyl)-6-(2,6-difluorophenyl)-1-ethyl-3,4-dihydropyridine-2(1H)-one was cooled to −78° C., 1.33 ml of a 1.09 mol/l solution of lithium diisopropylamide in THF was added dropwise, and the mixture was stirred at the same temperature for 30 minutes. Subsequently, 2 ml of the THF solution containing 82 μl of methyl iodide was added dropwise, the mixture was stirred at −78° C. for 2 hours, and then the temperature was raised to room temperature. After further stirring at room temperature for 2 hours, the reaction mixture was separated by adding the saturated aqueous ammonium chloride solution and ethyl acetate. The obtained organic layer was washed with brine and dried over sodium sulfate. After the solvent was distilled off under reduced pressure, the resulting residue was purified by silica gel column chromatography. The title compound was obtained as a white solid (101 mg). The resulting title compound was a stereoisomeric mixture.

$^1$H-NMR (CDCl$_3$) δ: 7.24-7.17 (1H, m:mixture), 7.15-7.13 (1H, m:mixture), 6.87-6.71 (2H, m:mixture), 6.57-6.49 (2H, m:mixture), 3.70-3.14 (2H, m:mixture), 3.65 (3H, s:major), 3.58 (3H, s:minor), 2.98-2.70 (2H, m:mixture), 2.46-2.37 (1H, m:mixture), 1.35 (3H, d, J=6.7 Hz:minor), 1.33 (3H, d, J=7.0 Hz:major), 1.00-0.96 (3H, m). Stereoisomeric mixture ratio: about 57:43

Synthesis Example 11

Synthesis of 5-(2-chloro-5-methoxyphenyl)-6-(2,6-difluorophenyl)-1-ethyl-3-methylpyridine-2(1H)-one (Compound No. 329)

[Chem. 45]

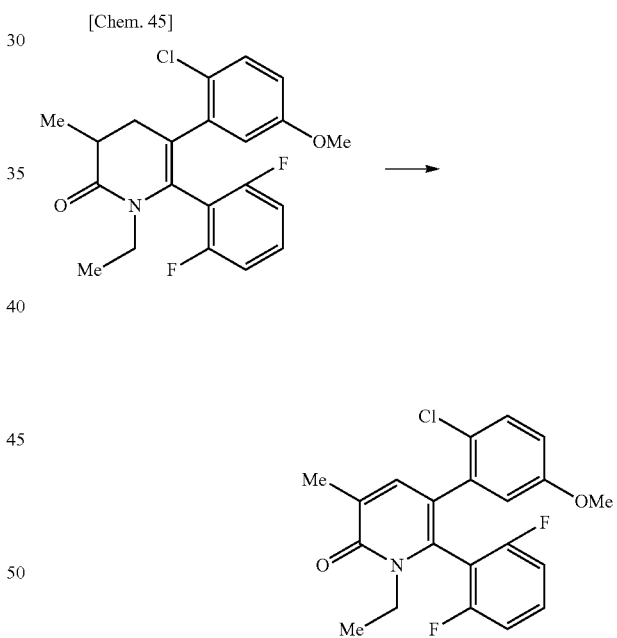

First, 10 ml of the dichloromethane solution containing 413 mg of 5-(2-chloro-5-methoxyphenyl)-6-(2,6-difluorophenyl)-1-ethyl-3-methyl-3,4-dihydropyridine-2(1H)-one and 5.48 g of manganese dioxide was stirred for 11 hours under heating at reflux. Then, 1.83 g of manganese dioxide was further added, and the mixture was stirred under heating at reflux for 3 hours. After cooling to room temperature, the reaction mixture was filtered through Celite. After the solvent was distilled off from the filtrate under reduced pressure, the resulting residue was purified by silica gel column chromatography. The title compound was obtained as a white solid (291 mg).

Synthesis Example 12

Step 1: Synthesis of 5-(2-chloro-5-fluorophenyl)-6-(2,4,6-trifluorophenyl)-3,4-dihydropyridine-2(1H)-one

[Chem. 46]

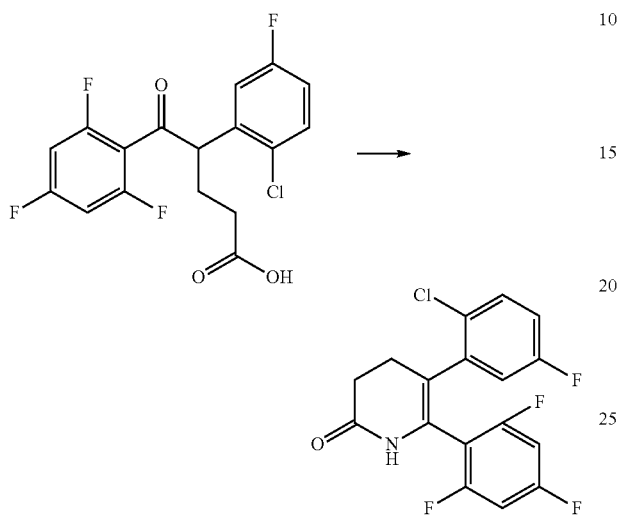

First, 25 ml of the acetic acid solution containing 4.46 g of 4-(2-chloro-5-fluorophenyl)-5-oxo-5-(2,4,6-trifluorophenyl)pentanoic acid and 45.9 g of ammonium acetate was stirred at 130° C. for 2 hours. After cooling to room temperature, the reaction mixture was separated by adding ethyl acetate and water. The obtained organic layer was added water, and potassium carbonate was further added until bubbling was subsided, and the resulting mixture was separated. Subsequently, the organic layer was washed with brine and dried over sodium sulfate. The solvent was distilled off under reduced pressure, and the precipitate was washed with diisopropyl ether. The resulting white solid was the title compound (2.24 g). The filtrate formed after washing the precipitate was distilled off under reduced pressure, and the resulting residue was purified by silica gel column chromatography. The white solid obtained from the filtrate was also the title compound (0.46 g).

$^1$H-NMR (CDCl$_3$) δ: 7.28-7.26 (1H, m), 7.18 (1H, br s), 6.86-6.83 (1H, m), 6.74-6.72 (1H, m), 6.61-6.59 (2H, br m), 2.85-2.74 (4H, br m).

Step 2: Synthesis of 5-(2-chloro-5-fluorophenyl)-1-ethyl-6-(2,4,6-trifluorophenyl)-3,4-dihydropyridine-2(1H)-one (Compound No. 320)

[Chem. 47]

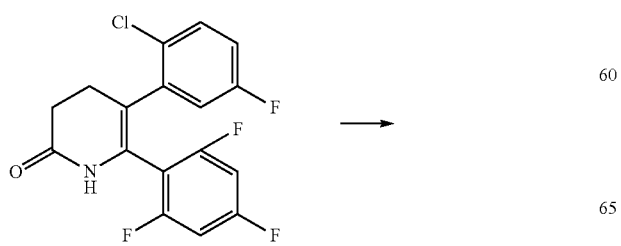

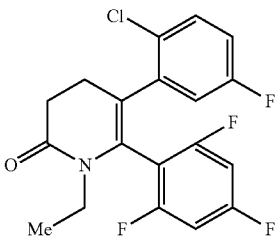

First, 32 ml of the DMF solution containing 2.70 g of 5-(2-chloro-5-fluorophenyl)-6-(2,4,6-trifluorophenyl)-3,4-dihydropyridine-2(1H)-one, 7.42 g of cesium carbonate and 3.55 g of ethyl iodide was stirred at 55° C. for 2 hours. After cooling to room temperature, the reaction mixture was separated by adding ethyl acetate and water. The obtained organic layer was washed with brine and dried over sodium sulfate. After the solvent was distilled off under reduced pressure, the resulting residue was purified by silica gel column chromatography. The title compound was obtained as a reddish purple gum (2.47 g).

Synthesis Example 13

Synthesis of 5-(2-chloro-5-fluorophenyl)-1-ethyl-6-(2,4,6-trifluorophenyl)pyridine-2(1H)-one (Compound No. 321)

[Chem. 48]

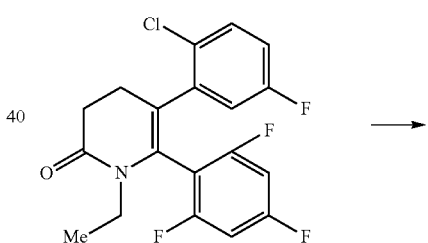

First, 5 ml of toluene solution containing 0.21 g of 5-(2-chloro-5-fluorophenyl)-1-ethyl-6-(2,4,6-trifluorophenyl)-3,4-dihydropyridine-2(1H)-one and 1.42 g of manganese dioxide was stirred at 90° C. for 5 hours. After cooling to room temperature, the reaction mixture was filtered through Celite. The solvent was distilled off from the filtrate under reduced pressure, and then the resulting residue was purified by silica gel column chromatography. The title compound was obtained as a white solid (0.14 g).

Synthesis Example 14

Synthesis of 3-bromo-5-(2-chloro-5-fluorophenyl)-1-ethyl-6-(2,4,6-trifluorophenyl)pyridine-2(1H)-one (Compound No. 381)

[Chem. 49]

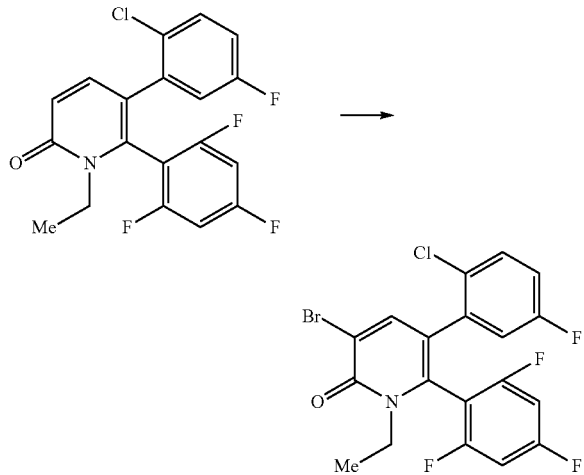

First, 30 ml of the DMF solution containing 0.60 g of 5-(2-chloro-5-fluorophenyl)-1-ethyl-6-(2,4,6-trifluorophenyl)pyridine-2(1H)-one and 0.33 g of N-bromosuccinimide was stirred at 75° C. for 2.5 hours. 0.10 g of N-bromosuccinimide was further added, and the mixture was stirred at 75° C. for 1.5 hours. After cooling to room temperature, the reaction mixture was separated by adding water and ethyl acetate. The obtained organic layer was washed with brine and then dried over sodium sulfate. After the solvent was distilled off under reduced pressure, the resulting residue was purified by silica gel column chromatography. The title compound was obtained as a white solid (0.64 g).

Synthesis Example 15

Synthesis of 5-(2-chloro-5-fluorophenyl)-1-ethyl-3-methyl-6-(2,4,6-trifluorophenyl)pyridine-2(1H)-one (Compound No. 461)

[Chem. 50]

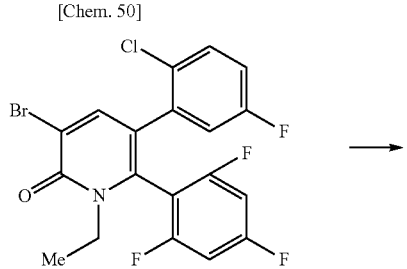

-continued

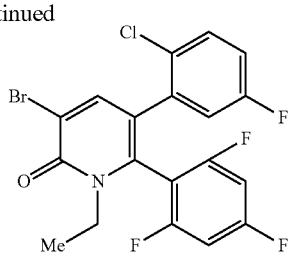

A mixed solution of 8 ml of toluene and 0.8 ml of water containing 250 mg of 3-bromo-5-(2-chloro-5-fluorophenyl)-1-ethyl-6-(2,4,6-trifluorophenyl)pyridine-2(1H)-one, 49 mg of methylboronic acid, 6 mg of palladium(II) acetate, 403 mg of tripotassium phosphate, and 15 mg of tricyclohexylphosphine was stirred at 100° C. for 7 hours. After cooling to room temperature, the reaction mixture was separated by adding water and ethyl acetate. The obtained organic layer was washed with brine and then dried over sodium sulfate. After the solvent was distilled off under reduced pressure, the resulting residue was purified by silica gel column chromatography. The title compound was obtained as a white solid (116 mg).

Synthesis Example 16

Synthesis of 3-bromo-5-(2-chloro-5-fluorophenyl)-6-(2,6-difluoro-4-methoxyphenyl)-1-ethylpyridine-2(1H)-one (Compound No. 476)

[Chem. 51]

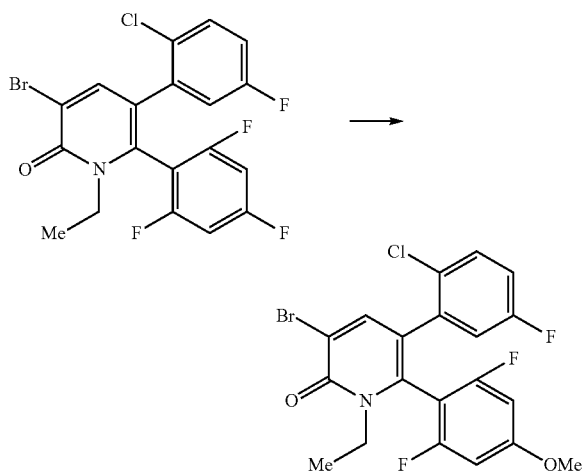

First, 8 ml of methanol solution of 300 mg of 3-bromo-5-(2-chloro-5-fluorophenyl)-1-ethyl-6-(2,4,6-trifluorophenyl)pyridine-2(1H)-one was added 0.63 ml of sodium methoxide (in methanol, 28% by weight), and the mixture was stirred under heating at reflux for 13 hours. After cooling to room temperature, the reaction mixture was separated by adding the saturated aqueous ammonium chloride solution and ethyl acetate. The obtained organic layer was washed with brine and dried over sodium sulfate. After the solvent was distilled off under reduced pressure, the resulting residue was purified by silica gel column chromatography. The title compound was obtained as a white solid (271 mg).

Synthesis Example 17

Step 1: Synthesis of 5-(3,5-dimethoxyphenyl)-6-(2,4,6-trifluorophenyl)-3,4-dihydropyridine-2(1H)-one

[Chem.52]

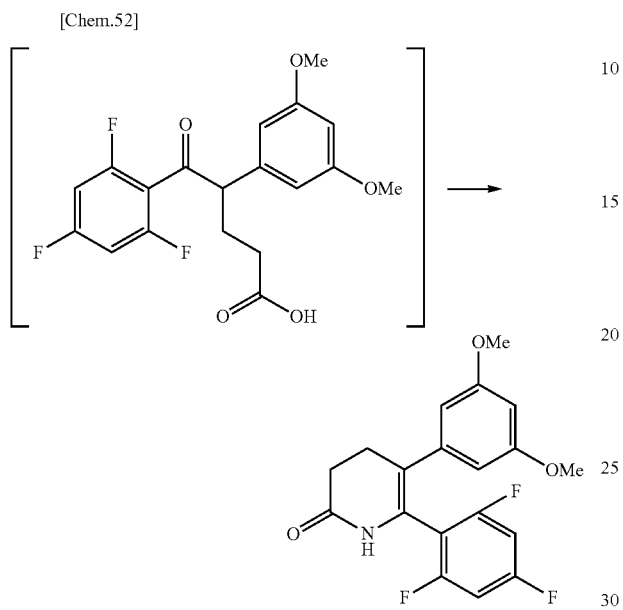

The unpurified 4-(3,5-dimethoxyphenyl)-5-oxo-5-(2,4,6-trifluorophenyl)pentanoic acid obtained in Reference Example 3 were added 14.18 g of ammonium acetate and 15 ml of acetic acid, and the mixture was stirred at 120° C. for 10 hours. After cooling to room temperature, the reaction mixture was separated by adding water and ethyl acetate. The obtained organic layer was sequentially washed with the aqueous saturated sodium bicarbonate solution and brine and dried over sodium sulfate. After the solvent was distilled off under reduced pressure, the resulting solid was added isopropyl ether, and the solution was washed. The title compound was obtained as a brown solid (0.99 g).
$^1$H-NMR (CDCl$_3$) δ: 6.68 (1H, s), 6.62 (2H, td, J=8.7, 1.4 Hz), 6.26 (1H, t, J=2.1 Hz), 6.16 (2H, d, J=2.1 Hz), 3.65 (6H, s), 2.87-2.86 (2H, m), 2.73-2.71 (2H, m).

Step 2: Synthesis of 5-(3,5-dimethoxyphenyl)-1-methyl-6-(2,4,6-trifluorophenyl)-3,4-dihydropyridine-2(1H)-one

[Chem.53]

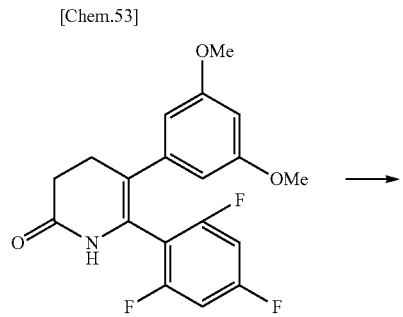

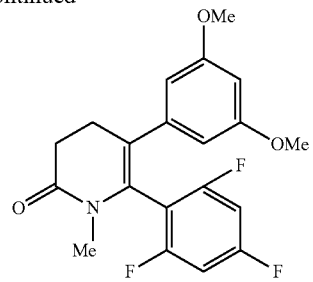

First, 6 ml of the DMF solution containing 343 mg of 5-(3,5-dimethoxyphenyl)-6-(2,4,6-trifluorophenyl)-3,4-dihydropyridine-2(1H)-one, 176 μl of methyl iodide, and 1.85 g of cesium carbonate was stirred at room temperature for 3 hours. The reaction mixture was separated by adding water and ethyl acetate. The obtained organic layer was sequentially washed with water, aqueous sodium thiosulfate solution and brine, and dried over sodium sulfate. After the solvent was distilled off under reduced pressure, the resulting residue was purified by silica gel column chromatography. The title compound was obtained as a white solid (346 mg).
$^1$H-NMR (CDCl$_3$) δ: 6.62-6.60 (2H, m), 6.23 (1H, t, J=2.1 Hz), 6.13 (2H, d, J=2.1 Hz), 3.65 (6H, s), 2.87 (3H, s), 2.76-2.74 (4H, m).

Synthesis Example 18

Synthesis of 5-(3,5-dimethoxyphenyl)-1-methyl-6-(2,4,6-trifluorophenyl)pyridine-2(1H)-one (Compound No. 134)

[Chem. 54]

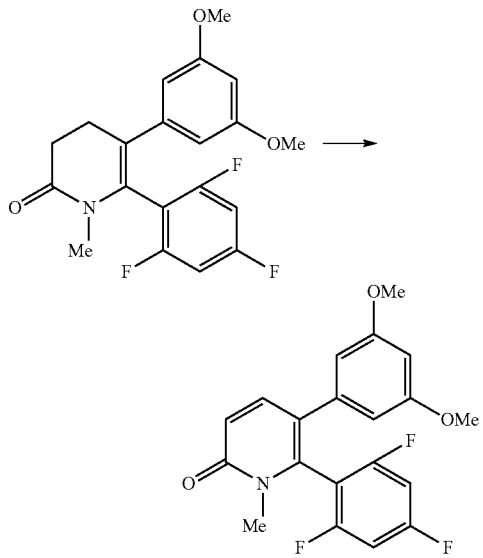

First, 12 ml of the dichloromethane solution containing 320 mg of 5-(3,5-dimethoxyphenyl)-1-methyl-6-(2,4,6-trifluorophenyl)-3,4-dihydropyridine-2(1H)-one and 4.42 g of manganese dioxide was stirred under heating at reflux for 5 hours. After cooling to room temperature, the reaction mixture was filtered through Celite. After the solvent was distilled off from the filtrate under reduced pressure, the resulting residue was purified by silica gel column chromatography. The title compound was obtained as a white solid (263 mg).

Synthesis Example 19

Synthesis of 5-(2-chloro-3,5-dimethoxyphenyl)-1-methyl-6-(2,4,6-trifluorophenyl)pyridine-2(1H)-one (Compound No. 136)

[Chem. 55]

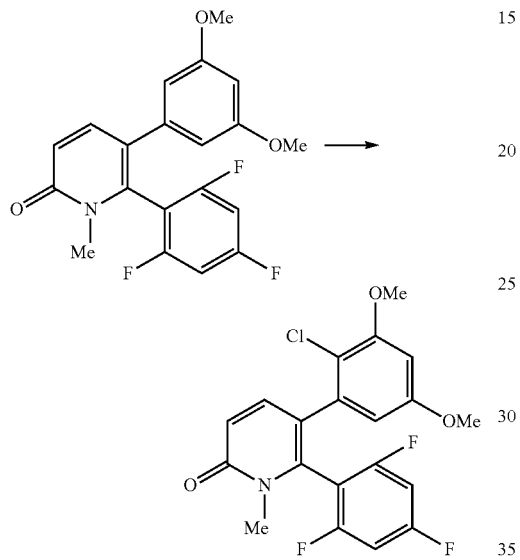

First, 6 ml of the DMF solution containing 163 mg of 5-(3,5-dimethoxyphenyl)-1-methyl-6-(2,4,6-trifluorophenyl)pyridine-2(1H)-one and 64 mg of N-chlorosuccinimide was stirred at 80° C. for 5 hours. 45 mg of N-chlorosuccinimide was further added, and the mixture was stirred at 100° C. for 4 hours. After cooling to room temperature, the reaction mixture was separated by adding water and ethyl acetate. The obtained organic layer was sequentially washed with aqueous sodium thiosulfate solution and brine, and dried over sodium sulfate. After the solvent was distilled off under reduced pressure, the resulting residue was purified by silica gel column chromatography. The title compound was obtained as a white solid (150 mg).

Reference Example 1

Step 1: Synthesis of 2-(2-chloro-5-methoxyphenyl)-1-(2,6-difluorophenyl)ethanone

[Chem. 56]

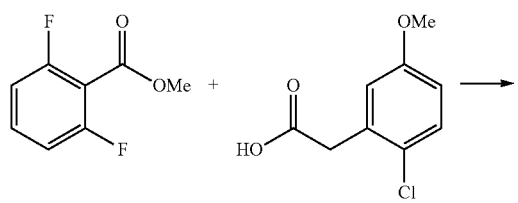

-continued

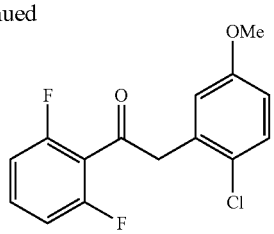

After 30 ml of the THF solution containing 2.05 g of 2-(2-chloro-5-methoxyphenyl)acetic acid was cooled to −78° C., 17.21 ml of the solution of hexmethyldisilazane sodium in THF (1.9 mol/L) was added dropwise at −50° C. or lower, and the mixture was stirred at −78° C. for 40 minutes. After 10 ml of the THF solution containing 1.76 g of methyl 2,6-difluorobenzoate was added dropwise at −78° C., the temperature was allowed to warm to room temperature, and the mixture was stirred for 1.5 hours. The reaction mixture was added the saturated aqueous ammonium chloride solution, the mixture was stirred, and was separated by adding ethyl acetate. The obtained organic layer was washed with brine and dried over sodium sulfate. After the solvent was distilled off under reduced pressure, the resulting residue was purified by silica gel column chromatography to obtain the title compound as a yellow oil (2.58 g).
$^1$H-NMR (CDCl$_3$) δ: 7.40-7.38 (1H, m), 7.28-7.27 (1H, m), 6.96-6.94 (2H, m), 6.83 (1H, d, J=3.1 Hz), 6.78 (1H, dd, J=8.9, 3.1 Hz), 4.27 (2H, s), 3.79 (3H, s).

Step 2: Synthesis of ethyl 4-(2-chloro-5-methoxyphenyl)-5-(2,6-difluorophenyl)-5-oxopentanoate

[Chem. 57]

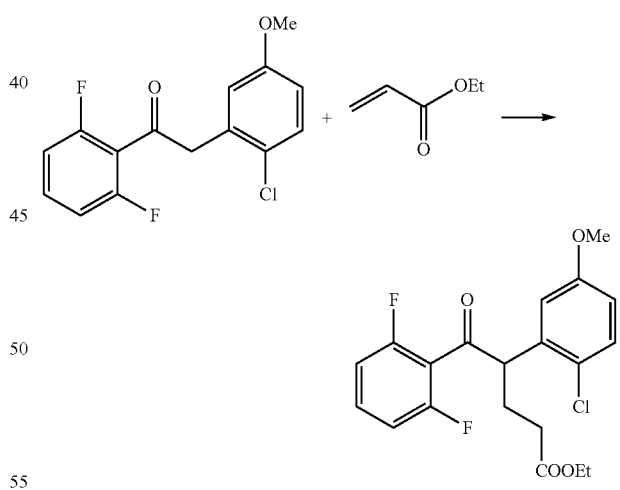

To 15 ml of the THF solution containing 1.30 g of 2-(2-chloro-5-methoxyphenyl)-1-(2,6-difluorophenyl)ethanone were added 98 mg of potassium t-butoxide and 525 μl of ethyl acrylate, and the mixture was stirred overnight under ice cooling. After the reaction mixture was separated by adding 1N hydrochloric acid and ethyl acetate, the obtained organic layer was washed with brine and dried over sodium sulfate. After the solvent was distilled off under reduced pressure, the title compound was obtained as a yellow oil (1.69 g), which was used in the next step without further purification.

$^1$H-NMR (CDCl$_3$) δ: 7.36-7.25 (1H, m), 7.19 (1H, d, J=8.9 Hz), 6.83 (2H, t, J=8.1 Hz), 6.74-6.71 (2H, m), 4.91 (1H, t, J=7.2 Hz), 4.13 (2H, q, J=7.1 Hz), 3.76 (3H, s), 2.57-2.53 (1H, m), 2.42-2.29 (2H, m), 2.16-2.07 (1H, m), 1.25 (3H, t, J=7.1 Hz).

Step 3: Synthesis of 4-(2-chloro-5-methoxyphenyl)-5-(2,6-difluorophenyl)-5-oxopentanoic acid

[Chem. 58]

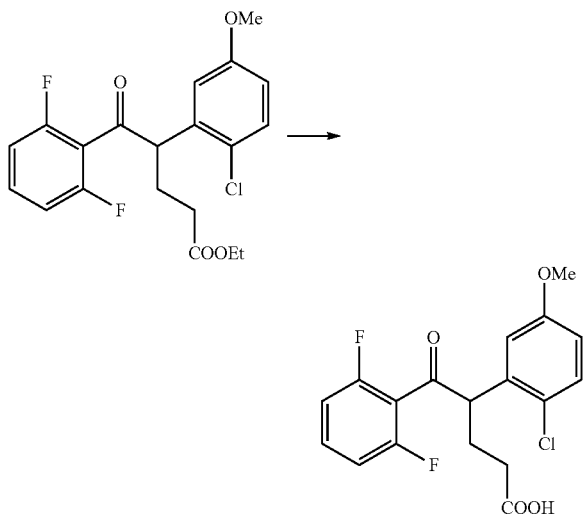

The mixed solution of 40 ml of THF and 10 ml of water containing 1.69 g of ethyl 4-(2-chloro-5-methoxyphenyl)-5-(2,6-difluorophenyl)-5-oxopentanoate was added 0.74 g of lithium hydroxide monohydrate, and the mixture was stirred at 60° C. for 3 hours. After cooling to room temperature, the solvent of the reaction mixture was distilled off until the liquid volume was reduced by half. The resulting mixture was separated by adding water and diethyl ether. The obtained aqueous layer was separated by adding concentrated hydrochloric acid and ethyl acetate. The obtained organic layer was washed with brine and dried over sodium sulfate. Subsequently, after the solvent was distilled off under reduced pressure, the title compound was obtained as a yellow gum (1.47 g), which was used in the next step without further purification.

$^1$H-NMR (CDCl$_3$) δ: 7.28-7.27 (1H, m), 7.19 (1H, d, J=8.6 Hz), 6.83 (2H, t, J=8.3 Hz), 6.75-6.74 (1H, m), 6.71 (1H, dd, J=8.6, 3.1 Hz), 4.92 (1H, t, J=7.3 Hz), 3.75 (3H, s), 2.60-2.34 (3H, m), 2.15-2.12 (1H, m).

Reference Example 2

Step 1: Synthesis of N'-(2-chloro-5-fluorobenzylidene)-4-methylbenzenesulfonylhydrazide

[Chem. 59]

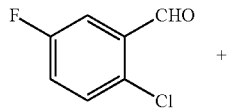
+

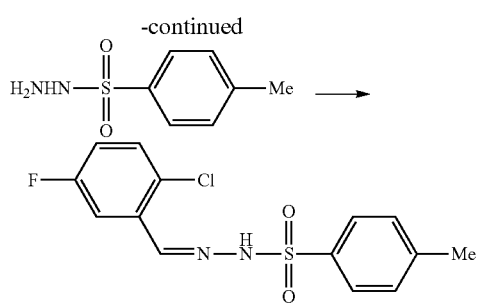

First, 250 ml of ethanol solution containing 25.43 g of 2-chloro-5-fluorobenzaldehyde and 29.87 g of 4-methylbenzenesulfonylhydrazide was stirred at room temperature for 4 hours. Subsequently, the reaction mixture was stirred under ice cooling for 1 hour, and then the precipitate was filtered to obtain the title compound as a white solid (40.74 g).

$^1$H-NMR (CDCl$_3$) δ: 8.27 (1H, s), 8.10 (1H, d, J=1.8 Hz), 7.88 (2H, d, J=8.2 Hz), 7.58 (1H, dd, J=9.2, 3.1 Hz), 7.34 (2H, d, J=8.2 Hz), 7.30-7.28 (1H, m), 7.02-6.99 m), 2.43 (3H, s).

Step 2: Synthesis of 2-(2-chloro-5-fluorophenyl)-1-(2,4,6-trifluorophenyl)ethanone

[Chem. 60]

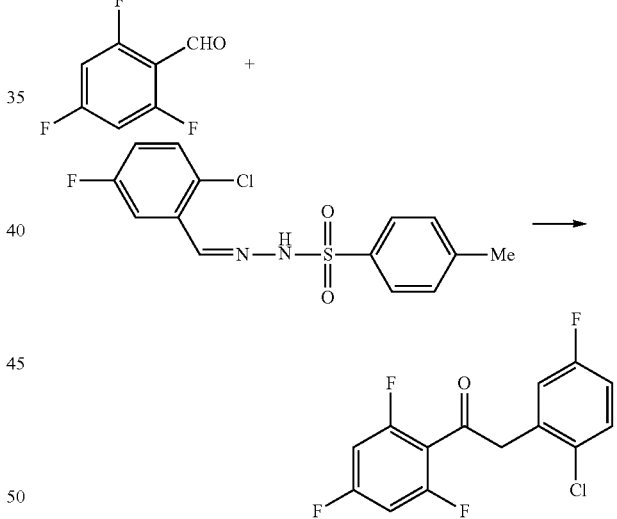

First, 600 ml of the aqueous solution containing 4.0 g of sodium hydroxide were added 32.7 g of N'-(2-chloro-5-fluorobenzylidene)-4-methylbenzenesulfonylhydrazide and 8.0 g of 2,4,6-trifluorobenzaldehyde, and the mixture was stirred at 80° C. for 1 hour. After cooling to room temperature, the reaction mixture were added ethyl acetate and 15.0 g of ammonium chloride, and the resulting mixture was stirred and separated. The obtained organic layer was washed with brine and dried over sodium sulfate. The solvent was distilled off under reduced pressure, and the resulting residue was purified by silica gel column chromatography. The title compound was obtained as a pale yellow solid (6.13 g).

$^1$H-NMR (CDCl$_3$) δ: 7.36-7.34 (1H, m), 7.04-7.02 (1H, m), 6.98-6.96 (1H, m), 6.76-6.72 (2H, m) 4.26 (2H, s).

Step 3: Synthesis of ethyl 4-(2-chloro-5-fluorophenyl)-5-oxo-5-(2,4,6-trifluorophenyl)pentanoate

[Chem. 61]

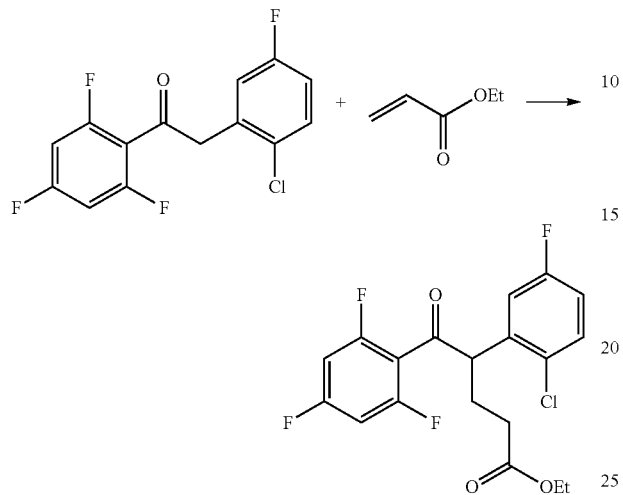

To 75 ml of the THF solution containing 6.13 g of 2-(2-chloro-5-fluorophenyl)-1-(2,4,6-trifluorophenyl)ethanone was ice-cooled, 0.45 g of potassium t-butoxide and 2.23 g of ethyl acrylate were added, and the mixture was stirred at room temperature for 8 hours. After the reaction mixture was added 10% hydrochloric acid, the resulting mixture was separated by adding water and ethyl acetate. The obtained organic layer was washed with brine and then dried over sodium sulfate. The solvent was distilled off under reduced pressure, and the resulting residue was purified by silica gel column chromatography. The title compound was obtained as a pale yellow oil (4.97 g).

$^1$H-NMR (CDCl$_3$) δ: 7.30 (1H, dd, J=8.9, 5.2 Hz), 7.01-6.98 (1H, m), 6.92-6.90 (1H, m), 6.66-6.60 (2H, m), 4.89 (1H, t, J=7.2 Hz), 4.13 (2H, q, J=7.2 Hz), 2.54-2.52 (1H, m), 2.35-2.31 (2H, m), 2.12-2.09 (1H, m), 1.25 (3H, t, J=7.2 Hz).

Step 4: Synthesis of 4-(2-chloro-5-fluorophenyl)-5-oxo-5-(2,4,6-trifluorophenyl)pentanoic acid

[Chem. 62]

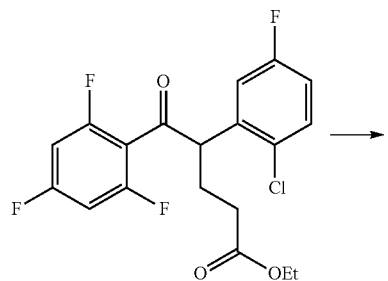

→

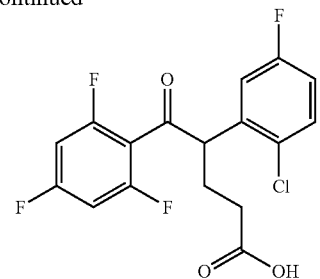

To 100 ml of the THF solution containing 4.97 g of ethyl 4-(2-chloro-5-fluorophenyl)-5-oxo-5-(2,4,6-trifluorophenyl)pentanoate were added 25 ml of water and 2.59 g of lithium hydroxide monohydrate, and the mixture was stirred at 60° C. for 2 hours. After cooling to room temperature, the solvent of the reaction mixture was distilled off under reduced pressure. The resulting mixture was separated by adding water and diethyl ether. Subsequently, the obtained aqueous layer was acidified by adding concentrated hydrochloric acid and then extracted with ethyl acetate. The obtained organic layer was washed with brine and dried over sodium sulfate. The solvent was distilled off under reduced pressure, and the title compound was obtained as a colorless transparent gum (4.46 g), which was used in the next step without further purification.

$^1$H-NMR (CDCl$_3$) δ: 7.32-7.29 (1H, m), 7.00-6.97 (1H, m), 6.94-6.89 (1H, m), 6.64-6.60 (2H, m), 4.89 (1H, t, J=7.2 Hz), 2.58-2.06 (4H, m).

Reference Example 3

Step 1: Synthesis of N'—(3,5-dimethoxybenzylidene)-4-methylbenzenesulfonylhydrazide

[Chem. 63]

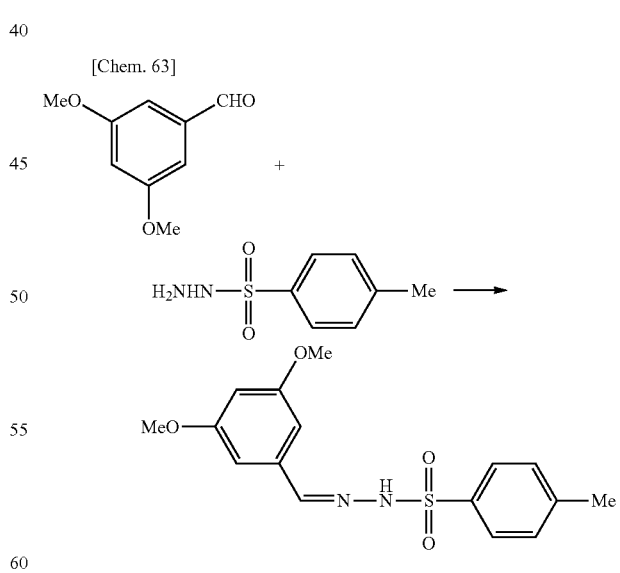

First, 100 ml of ethanol solution containing 10.0 g of 3,5-dimethoxybenzaldehyde and 11.2 g of 4-methylbenzenesulfonylhydrazide was stirred at room temperature for 5 hours. After the solvent of the resulting reaction mixture was distilled off under reduced pressure, the title compound was obtained as a yellow solid (20.0 g).

$^1$H-NMR (CDCl$_3$) δ: 8.13 (1H, s), 7.87 (2H, d, J=7.8 Hz), 7.68 (1H, s), 7.30 (2H, d, J=7.8 Hz), 6.72 (2H, d, J=2.4 Hz), 6.46 (1H, t, J=2.4 Hz), 3.79 (6H, s), 2.40 (3H, s).

Step 2: Synthesis of 2-(3,5-dimethoxyphenyl)-1-(2,4,6-trifluorophenyl)ethanone

[Chem. 64]

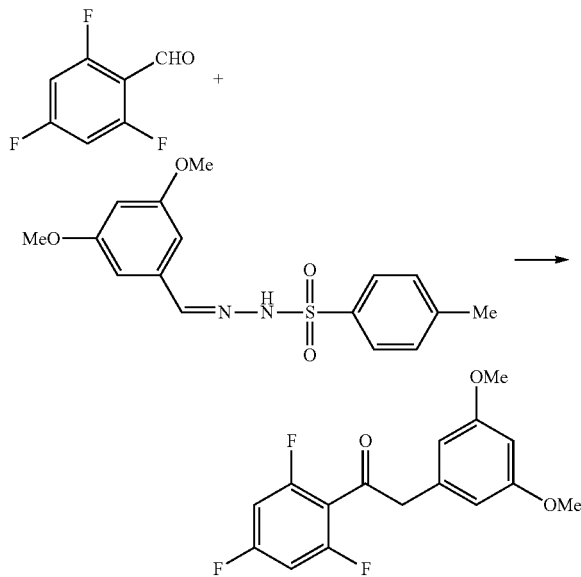

To 100 ml of the aqueous solution containing 6.68 g of N'—(3,5-dimethoxybenzylidene)-4-methylbenzenesulfonylhydrazide were added 20 ml of the solution of 0.80 g of sodium hydroxide dissolved in water and 1.60 g of 2,4,6-trifluorobenzaldehyde, and the mixture was stirred at 80° C. for 90 minutes. After cooling to room temperature, the reaction mixture was separated by adding ethyl acetate. The obtained organic layer was sequentially washed with the saturated aqueous ammonium chloride solution and brine and dried over sodium sulfate. The solvent was distilled off under reduced pressure, and the resulting residue was purified by silica gel column chromatography. The title compound was obtained as a yellow oil (1.85 g).
$^1$H-NMR (CDCl$_3$) δ: 6.68-6.66 (2H, m), 6.35 (3H, s),4.06 (2H,s), 3.75 (6H, s).

Step 3: Synthesis of ethyl 4-(3,5-dimethoxyphenyl)-5-oxo-5-(2,4,6-trifluorophenyl)pentanoate

[Chem. 65]

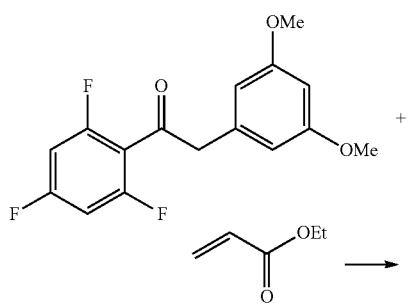

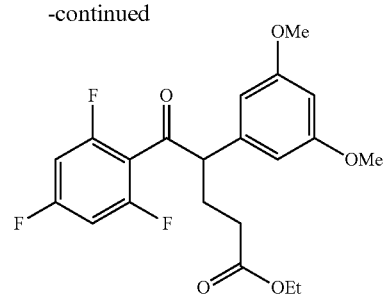

First, 18 ml of the THF solution containing 1.85 g of 2-(3,5-dimethoxyphenyl)-1-(2,4,6-trifluorophenyl)ethanone were added 67 mg of potassium t-butoxide and 714 μl of ethyl acrylate, and the mixture was stirred under ice cooling for overnight. The reaction mixture was separated by adding the saturated aqueous ammonium chloride solution and ethyl acetate. The obtained organic layer was washed with brine and then dried over sodium sulfate. The solvent was distilled off under reduced pressure, and the resulting residue was purified by silica gel column chromatography. The title compound was obtained as a brown oil (1.51 g).
$^1$H-NMR (CDCl$_3$) δ: 6.61-6.57 (2H, m), 6.31-6.29 (3H, m), 4.19 (1H, t, J=7.3 Hz), 4.13 (2H, q, J=7.1 Hz), 3.73 (6H, s), 2.49-2.47 (1H, m), 2.30 (2H, t, J=7.5 Hz), 2.09-2.07 (1H, m), 1.25 (3H, t, J=7.1 Hz)

Step 4: Synthesis of 4-(3,5-dimethoxyphenyl)-5-oxo-5-(2,4,6-trifluorophenyl)pentanoic acid

[Chem. 66]

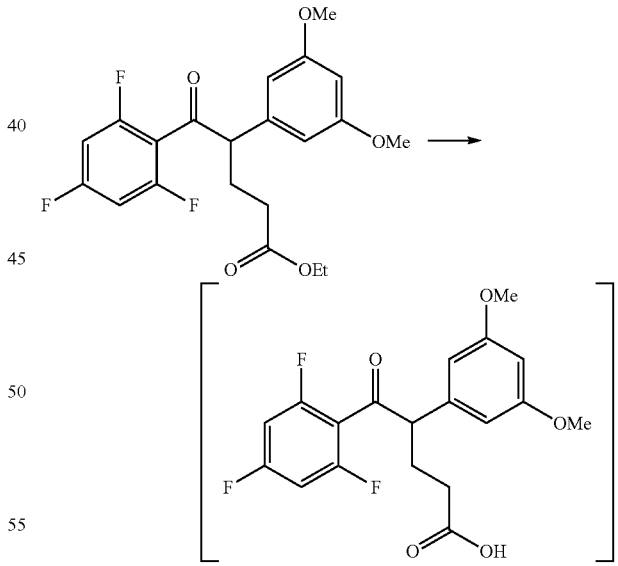

First, 15 ml of the acetic acid solution containing 1.51 g of ethyl 4-(3,5-dimethoxyphenyl)-5-oxo-5-(2,4,6-trifluorophenyl)pentanoate and 3 ml of concentrated hydrochloric acid was stirred at 60° C. for 3 hours. After cooling to room temperature, the reaction mixture was separated by adding water and ethyl acetate. The obtained organic layer was sequentially washed with water and brine and dried over sodium sulfate. The solvent was distilled off under reduced pressure, and the title compound was obtained, which was used in the next step without further purification.

Although Table 4 illustrates the compounds synthesized according to the previously described examples, the compounds of the present invention are not limited thereto.

Structure A is as follows:

[Chem. 67]

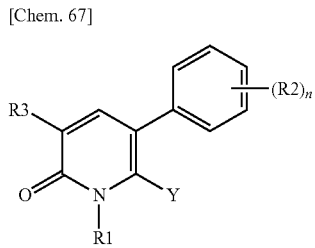

Structure B is as follows:

[Chem. 68]

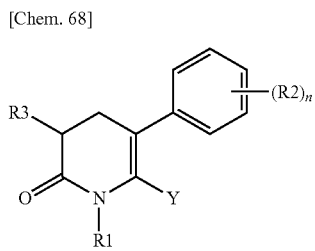

Structure C is as follows:

[Chem. 69]

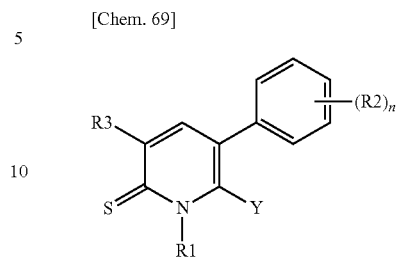

Structure D is as follows:

[Chem. 70]

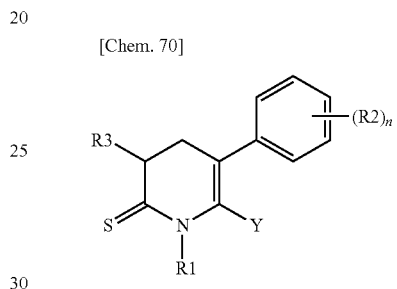

TABLE 4

| Compound | Structure | R1 | Y | (R2)n | R3 |
|---|---|---|---|---|---|
| 1 | B | Me | 3,5-di-Cl-2-Py | — | H |
| 2 | A | Me | 3,5-di-Cl-2-Py | — | H |
| 3 | B | Me | 3,5-di-Cl-2-Py | 2,6-di-F— | H |
| 4 | B | Et | 3,5-di-Cl-2-Py | 2,6-di-F— | H |
| 5 | A | Me | 3,5-di-Cl-2-Py | 2,6-di-F— | H |
| 6 | A | Et | 3,5-di-Cl-2-Py | 2,6-di-F— | H |
| 7 | A | Me | 3-Cl-5-MeO-2-Py | 2,6-di-F— | H |
| 8 | A | Et | 3-Cl-5-MeO-2-Py | 2,6-di-F— | H |
| 9 | A | Me | 3-Cl-5-MeO-2-Py | — | H |
| 10 | A | Et | 3,5-di-Cl-2-Py | — | H |
| 11 | A | Et | 3-Cl-5-MeO-2-Py | — | H |
| 12 | A | Me | 3-Cl-4-Py | — | H |
| 13 | A | Et | 3-Cl-4-Py | — | H |
| 14 | A | Et | 2,6-di-F—Ph | 3,5-di-MeO— | H |
| 15 | B | Et | 2,6-di-F—Ph | 3,5-di-MeO— | H |
| 16 | A | Et | 2,6-di-F—Ph | 2-Br-3,5-di-MeO— | H |
| 17 | B | Me | 2,6-di-F—Ph | 4-F— | H |
| 18 | B | Et | 2,6-di-F—Ph | 4-F— | H |
| 19 | A | Me | 2,6-di-F—Ph | 4-F— | H |
| 20 | A | Et | 2,6-di-F—Ph | 4-F— | H |
| 21 | B | Me | 3,5-di-Cl-2-Py | 4-F— | H |
| 22 | A | Me | 3,5-di-Cl-2-Py | 4-F— | Br |
| 23 | A | Me | 3,5-di-Cl-2-Py | 4-F— | H |
| 24 | B | Et | 3,5-di-Cl-2-Py | 4-F— | H |
| 25 | A | Et | 3,5-di-Cl-2-Py | 4-F— | Br |
| 26 | A | Et | 3,5-di-Cl-2-Py | 4-F— | H |
| 27 | B | Me | 2,6-di-F—Ph | 3,5-di-MeO— | H |
| 28 | A | Me | 2,6-di-F—Ph | 3,5-di-MeO— | H |
| 29 | A | Me | 2,6-di-F—Ph | 2-Br-3,5-di-MeO— | H |
| 30 | A | Me | 2,6-di-F—Ph | 2-Cl-3,5-di-MeO— | H |
| 31 | A | Me | 2,6-di-F—Ph | 4-Cl-3,5-di-MeO— | H |
| 32 | A | Et | 2,6-di-F—Ph | 2-Cl-3,5-di-MeO— | H |
| 33 | B | Et | 2,6-di-F-4-MeO—Ph | 2-Cl-4-F— | H |
| 34 | A | Et | 2,6-di-F-4-MeO—Ph | 2-Cl-4-F— | Br |
| 35 | A | Et | 2,6-di-F-4-MeO—Ph | 2-Cl-4-F— | H |
| 36 | B | Me | 2,6-di-F-4-MeO—Ph | 2-Cl-4-F— | H |
| 37 | A | Me | 2,6-di-F-4-MeO—Ph | 2-Cl-4-F— | H |
| 38 | A | Me | 2,6-di-F-4-MeO—Ph | 2-Cl-4-F— | Br |

TABLE 4-continued

| Compound | Structure | R1 | Y | (R2)n | R3 |
|---|---|---|---|---|---|
| 39 | A | Et | 2,6-di-F—Ph | 4-Br-3,5-di-MeO— | H |
| 40 | A | Et | 2,6-di-F—Ph | 4-Cl-3,5-di-MeO— | H |
| 41 | A | Pr | 2,6-di-F—Ph | 3,5-di-MeO— | H |
| 42 | A | Pr | 2,6-di-F—Ph | 2-Br-3,5-di-MeO— | H |
| 43 | B | CH$_2$=CHCH$_2$— | 2,6-di-F-4-MeO—Ph | 2-Cl-4-F— | H |
| 44 | A | CH$_2$=CHCH$_2$— | 2,6-di-F-4-MeO—Ph | 2-Cl-4-F— | H |
| 45 | A | FCH$_2$CH$_2$— | 2,6-di-F-4-MeO—Ph | 2-Cl-4-F— | H |
| 46 | A | Et | 2,6-di-F—Ph | — | H |
| 47 | A | Me | 2,6-di-F—Ph | — | H |
| 48 | A | Et | 2,6-di-F—Ph | — | Cl |
| 49 | A | Me | 2,6-di-F—Ph | — | Cl |
| 50 | A | Et | 2,6-di-F—Ph | — | Br |
| 51 | A | Me | 2,6-di-F—Ph | — | Br |
| 52 | B | Et | 2,6-di-F—Ph | 2-Cl-5-MeO— | H |
| 53 | A | Et | 2,6-di-F—Ph | 2-Cl-5-MeO— | H |
| 54 | A | Et | 2,6-di-F—Ph | 2-Cl-5-MeO— | Cl |
| 55 | A | Et | 2,6-di-F—Ph | 2-Cl-5-MeO— | Br |
| 56 | B | Me | 2,6-di-F—Ph | 2-Cl-5-MeO— | H |
| 57 | A | Me | 2,6-di-F—Ph | 2-Cl-5-MeO— | H |
| 58 | B | Et | 2,6-di-F—Ph | 2-Cl-4-F— | H |
| 59 | A | Et | 2,6-di-F—Ph | 2-Cl-4-F— | H |
| 60 | A | Me | 2,6-di-F—Ph | 2-Cl-5-MeO— | Cl |
| 61 | A | Me | 2,6-di-F—Ph | 2-Cl-5-MeO— | Br |
| 62 | A | Et | 2,6-di-F—Ph | 2-Cl-4-F— | Cl |
| 63 | A | Et | 2,6-di-F—Ph | 2-Cl-4-F— | Br |
| 64 | A | Me | 2,6-di-F—Ph | 2-Cl-4-F— | H |
| 65 | A | Et | 2,6-di-F—Ph | 2-Cl-3-MeO— | H |
| 66 | A | Et | 2,6-di-F—Ph | 2-Cl-3-MeO— | Br |
| 67 | A | Et | 2,6-di-F—Ph | 2-Br-6-Cl-3,5-di-MeO— | H |
| 68 | A | Et | 2,6-di-F—Ph | 2,6-di-Cl-3,5-di-MeO— | H |
| 69 | A | Et | 2,6-di-F—Ph | 2-Br-6-Cl-3,5-di-MeO— | Cl |
| 70 | A | Et | 2,6-di-F—Ph | 2-Br-6-Cl-3,5-di-MeO— | Br |
| 71 | A | Et | 2,6-di-F-4-MeO—Ph | 3,5-di-MeO— | H |
| 72 | A | Et | 2,6-di-F-4-MeO—Ph | 2-Br-3,5-di-MeO— | H |
| 73 | A | Et | 2,6-di-F-4-MeO—Ph | 2-Cl-3,5-di-MeO— | H |
| 74 | A | Et | 2,6-di-F—Ph | 2-Cl— | H |
| 75 | A | Et | 2,6-di-F—Ph | 2-Cl— | Cl |
| 76 | A | Et | 2,6-di-F—Ph | 2-Cl— | Br |
| 77 | A | Me | 2,6-di-F—Ph | 2-Cl— | H |
| 78 | A | Me | 2,6-di-F—Ph | 2-Cl— | Cl |
| 79 | A | Me | 2,6-di-F—Ph | 2-Cl— | Br |
| 80 | A | Me | 2,6-di-F-4-MeO—Ph | 3,5-di-MeO— | H |
| 81 | A | Me | 2,6-di-F-4-MeO—Ph | 2-Br-3,5-di-MeO— | H |
| 82 | A | Me | 2,6-di-F-4-MeO—Ph | 2-Cl-3,5-di-MeO— | H |
| 83 | A | Et | 2,6-di-F—Ph | 2,6-di-Cl-3,5-di-MeO— | Br |
| 84 | A | Et | 2,6-di-F—Ph | 2,6-di-Cl-3,5-di-MeO— | Cl |
| 85 | A | Et | 2,6-di-F—Ph | 2-Br— | H |
| 86 | A | Et | 2,6-di-F—Ph | 2-Br— | Cl |
| 87 | A | Et | 2,6-di-F—Ph | 2-Br— | Br |
| 88 | A | Et | 2,6-di-F—Ph | 2-F-5-MeO— | Br |
| 89 | A | Et | 2,6-di-F—Ph | 2-F-5-MeO— | H |
| 90 | A | Me | 2,6-di-F—Ph | 2-F-5-MeO— | Br |
| 91 | A | Me | 2,6-di-F—Ph | 2-F-5-MeO— | H |
| 92 | A | Et | 2,6-di-F—Ph | 2-F-5-MeO— | Cl |
| 93 | A | Me | 2,6-di-F—Ph | 2-F-5-MeO— | Cl |
| 94 | A | Me | 2,6-di-F—Ph | 2-Br— | H |
| 95 | A | Me | 2,6-di-F—Ph | 2-Br— | Cl |
| 96 | A | Me | 2,6-di-F—Ph | 2-Br— | Br |
| 97 | A | Et | 2,6-di-F—Ph | 2-Cl-5-MeOCH$_2$O— | H |
| 98 | A | Et | 2,6-di-F—Ph | 2-Cl-5-N=CCH$_2$O— | H |
| 99 | A | Et | 2,6-di-F—Ph | 2-Cl-5-EtO— | H |
| 100 | A | Et | 2,6-di-F—Ph | 3-MeO— | H |
| 101 | A | Et | 2,6-di-F—Ph | 3-MeOCH$_2$O— | H |
| 102 | A | Et | 2,6-di-F—Ph | 3-N=CCH$_2$O— | H |
| 103 | A | Et | 2,6-di-F—Ph | 3-EtO— | H |
| 104 | A | Et | 2,6-di-F—Ph | 2,6-di-F-3-MeO— | H |
| 105 | A | Et | 2,6-di-F—Ph | 2,6-di-F-3-MeO— | Br |
| 106 | A | Et | 2,6-di-F—Ph | 2,6-di-F-3-MeO— | Cl |
| 107 | A | Et | 2,6-di-F—Ph | 2-Cl-5-AcO— | H |
| 108 | A | Me | 2,6-di-F—Ph | 2,6-di-F-3-MeO— | H |
| 109 | A | Me | 2,6-di-F—Ph | 2,6-di-F-3-MeO— | Br |
| 110 | A | Me | 2,6-di-F—Ph | 2,6-di-F-3-MeO— | Cl |
| 111 | A | Et | 2,6-di-F—Ph | 2-I— | H |
| 112 | A | Et | 2,6-di-F—Ph | 2-I— | Cl |
| 113 | A | Et | 2,6-di-F—Ph | 2-I— | Br |
| 114 | A | Me | 2,6-di-F—Ph | 2-I— | H |
| 115 | A | Me | 2,6-di-F—Ph | 2-I— | Cl |
| 116 | A | Me | 2,6-di-F—Ph | 2-I— | Br |

TABLE 4-continued

| Compound | Structure | R1 | Y | (R2)n | R3 |
|---|---|---|---|---|---|
| 117 | B | Et | 2,6-di-F—Ph | 2-Cl-3,5-di-MeO— | H |
| 118 | B | Et | 4-Cl-2,6-di-F—Ph | 3,5-di-MeO— | H |
| 119 | A | Et | 4-Cl-2,6-di-F—Ph | 3,5-di-MeO— | H |
| 120 | A | Et | 4-Cl-2,6-di-F—Ph | 2-Br-3,5-di-MeO— | H |
| 121 | A | Et | 4-Cl-2,6-di-F—Ph | 2-Cl-3,5-di-MeO— | H |
| 122 | A | Et | 4-Cl-2,6-di-F—Ph | 4-Cl-3,5-di-MeO— | H |
| 123 | A | Et | 2,6-di-F—Ph | 2-MeO— | H |
| 124 | A | Et | 2,6-di-F—Ph | 5-Cl-2-MeO— | Cl |
| 125 | A | Et | 2,6-di-F—Ph | 5-Br-2-MeO— | Br |
| 126 | A | Et | 2,6-di-F—Ph | 2-Cl-5-MeOCH$_2$O— | Br |
| 127 | A | Et | 2,6-di-F—Ph | 2-Cl-5-MeOCH$_2$O— | Cl |
| 128 | A | Et | 2,6-di-F—Ph | 2-Cl-5-N≡CCH$_2$O— | Br |
| 129 | A | Et | 2,6-di-F—Ph | 2-Cl-5-N≡CCH$_2$O— | Cl |
| 130 | B | Et | 2,4,6-tri-F—Ph | 3,5-di-MeO— | H |
| 131 | A | Et | 2,4,6-tri-F—Ph | 3,5-di-MeO— | H |
| 132 | A | Et | 2,4,6-tri-F—Ph | 2-Br-3,5-di-MeO— | H |
| 133 | A | Et | 2,4,6-tri-F—Ph | 2-Cl-3,5-di-MeO— | H |
| 134 | A | Me | 2,4,6-tri-F—Ph | 3,5-di-MeO— | H |
| 135 | A | Me | 2,4,6-tri-F—Ph | 2-Br-3,5-di-MeO— | H |
| 136 | A | Me | 2,4,6-tri-F—Ph | 2-Cl-3,5-di-MeO— | H |
| 137 | A | Me | 2,6-di-F—Ph | 2-MeO— | H |
| 138 | A | Me | 2,6-di-F—Ph | 5-Cl-2-MeO— | Cl |
| 139 | A | Me | 2,6-di-F—Ph | 5-Br-2-MeO— | Br |
| 140 | A | Et | 2,6-di-F—Ph | 2-F— | H |
| 141 | A | Et | 2,6-di-F—Ph | 2-F— | Cl |
| 142 | A | Et | 2,6-di-F—Ph | 2-F— | Br |
| 143 | A | Me | 2,6-di-F—Ph | 2-F— | H |
| 144 | A | Me | 2,6-di-F—Ph | 2-F— | Cl |
| 145 | A | Me | 2,6-di-F—Ph | 2-F— | Br |
| 146 | A | Et | 2,6-di-F—Ph | 2-F$_3$C— | H |
| 147 | A | Et | 2,6-di-F—Ph | 2-F$_3$C— | Cl |
| 148 | A | Et | 2,6-di-F—Ph | 2-F$_3$C— | Br |
| 149 | B | Et | 2-Cl-6-F—Ph | 3,5-di-MeO— | H |
| 150 | A | Et | 2-Cl-6-F—Ph | 3,5-di-MeO— | H |
| 151 | A | Et | 2-Cl-6-F—Ph | 2-Br-3,5-di-MeO— | H |
| 152 | A | Et | 2-Cl-6-F—Ph | 2-Cl-3,5-di-MeO— | H |
| 153 | A | Et | 2,6-di-F—Ph | 3-F— | H |
| 154 | A | Et | 2,6-di-F—Ph | 3-F— | Cl |
| 155 | A | Et | 2,6-di-F—Ph | 3-F— | Br |
| 156 | B | Et | 2,6-di-F—Ph | 3-F— | H |
| 157 | A | Me | 2,6-di-F—Ph | 2-F$_3$C— | H |
| 158 | A | Me | 2,6-di-F—Ph | 2-F$_3$C— | Cl |
| 159 | A | Me | 2,6-di-F—Ph | 2-F$_3$C— | Br |
| 160 | A | Et | 2,6-di-F—Ph | 2-Me— | H |
| 161 | A | Et | 2,6-di-F—Ph | 2-Me— | Cl |
| 162 | A | Et | 2,6-di-F—Ph | 2-Me— | Br |
| 163 | B | Me | 2-Cl-6-F—Ph | 3,5-di-MeO— | H |
| 164 | A | Me | 2-Cl-6-F—Ph | 3,5-di-MeO— | H |
| 165 | A | Me | 2-Cl-6-F—Ph | 2-Br-3,5-di-MeO— | H |
| 166 | A | Me | 2-Cl-6-F—Ph | 2-Cl-3,5-di-MeO— | H |
| 167 | A | Et | 2-Cl-6-F—Ph | 2,6-di-Cl-3,5-di-MeO— | Cl |
| 168 | A | Me | 2,6-di-F—Ph | 3-F— | H |
| 169 | A | Me | 2,6-di-F—Ph | 3-F— | Cl |
| 170 | A | Me | 2,6-di-F—Ph | 3-F— | Br |
| 171 | A | Et | 2,6-di-F—Ph | 3-Cl— | H |
| 172 | B | Me | 2,6-di-F—Ph | 3-F— | H |
| 173 | B | Et | 2,6-di-F—Ph | 3-Cl— | H |
| 174 | B | Et | 2-Br-6-F—Ph | 3,5-di-MeO— | H |
| 175 | A | Et | 2-Br-6-F—Ph | 3,5-di-MeO— | H |
| 176 | A | Et | 2-Br-6-F—Ph | 2-Br-3,5-di-MeO— | H |
| 177 | A | Et | 2-Br-6-F—Ph | 2-Cl-3,5-di-MeO— | H |
| 178 | A | Et | 2,6-di-F—Ph | 3-Cl— | Cl |
| 179 | A | Et | 2,6-di-F—Ph | 3-Cl— | Br |
| 180 | A | Me | 2,6-di-F—Ph | 2-Me— | H |
| 181 | A | Me | 2,6-di-F—Ph | 2-Me— | Cl |
| 182 | A | Me | 2,6-di-F—Ph | 2-Me— | Br |
| 183 | A | Me | 2-Br-6-F—Ph | 3,5-di-MeO— | H |
| 184 | A | Me | 2-Br-6-F—Ph | 2-Br-3,5-di-MeO— | H |
| 185 | A | Me | 2-Br-6-F—Ph | 2-Cl-3,5-di-MeO— | H |
| 186 | B | Et | 4-Br-2,6-di-F—Ph | 3,5-di-MeO— | H |
| 187 | B | Me | 4-Br-2,6-di-F—Ph | 3,5-di-MeO— | H |
| 188 | A | Me | 2,6-di-F—Ph | 3-Cl— | H |
| 189 | A | Me | 2,6-di-F—Ph | 3-Cl— | Cl |
| 190 | A | Me | 2,6-di-F—Ph | 3-Cl— | Br |
| 191 | B | Me | 2,6-di-F—Ph | 3-Cl— | H |
| 192 | B | F$_2$CHCH$_2$— | 2,6-di-F—Ph | 2-Cl-5-MeO— | H |
| 193 | A | Et | 2,6-di-F—Ph | 2-Cl-5-MeOCH$_2$O— | H |
| 194 | A | F$_2$CHCH$_2$— | 2,6-di-F—Ph | 2-Cl-5-MeO— | H |

TABLE 4-continued

| Compound | Structure | R1 | Y | (R2)n | R3 |
|---|---|---|---|---|---|
| 195 | A | Et | 2,6-di-F—Ph | 2-Cl-5-MeOCH$_2$CH$_2$O— | Cl |
| 196 | A | Et | 2,6-di-F—Ph | 2-Cl-5-MeOCH$_2$CH$_2$O— | Br |
| 197 | A | F$_2$CHCH$_2$— | 2,6-di-F—Ph | 2-Cl-5-MeO— | Cl |
| 198 | A | F$_2$CHCH$_2$— | 2,6-di-F—Ph | 2-Cl-5-MeO— | Br |
| 199 | A | Et | 4-Br-2,6-di-F—Ph | 3,5-di-MeO— | H |
| 200 | A | Et | 4-Br-2,6-di-F—Ph | 2-Br-3,5-di-MeO— | H |
| 201 | A | Et | 4-Br-2,6-di-F—Ph | 2-Cl-3,5-di-MeO— | H |
| 202 | A | Et | 4-Br-2,6-di-F—Ph | 4-Cl-3,5-di-MeO— | H |
| 203 | A | Me | 4-Br-2,6-di-F—Ph | 3,5-di-MeO— | H |
| 204 | A | Me | 4-Br-2,6-di-F—Ph | 2-Br-3,5-di-MeO— | H |
| 205 | A | Me | 4-Br-2,6-di-F—Ph | 2-Cl-3,5-di-MeO— | H |
| 206 | A | Me | 4-Br-2,6-di-F—Ph | 4-Cl-3,5-di-MeO— | H |
| 207 | B | Et | 2,6-di-F—Ph | 3-Me— | H |
| 208 | B | Et | 2,6-di-F—Ph | 3-F$_3$CO— | H |
| 209 | A | Et | 2,6-di-F—Ph | 2-MeS— | H |
| 210 | A | Et | 2,6-di-F—Ph | 2-ClCH$_2$S— | Cl |
| 211 | A | Et | 2,6-di-F—Ph | 2-MeSO$_2$— | H |
| 212 | A | Et | 2,6-di-F—Ph | 2-Cl-5-cPrCH$_2$O— | H |
| 213 | A | F$_2$CHCH$_2$— | 2,6-di-F—Ph | 2-Cl-5-MeOCH$_2$O— | H |
| 214 | A | F$_2$CHCH$_2$— | 2,6-di-F—Ph | 2-Cl-5-EtO— | H |
| 215 | A | Et | 3,5-di-F-4-Py | 3,5-di-MeO— | H |
| 216 | A | Et | 3,5-di-F-4-Py | 2-Br-3,5-di-MeO— | H |
| 217 | A | Et | 2,6-di-F—Ph | 3-F$_3$CO— | H |
| 218 | A | Et | 2,6-di-F—Ph | 3-F$_3$CO— | Cl |
| 219 | A | Et | 2,6-di-F—Ph | 3-Me— | H |
| 220 | A | Et | 2,6-di-F—Ph | 3-Me— | Cl |
| 221 | A | Et | 2,6-di-F—Ph | 2-Cl-5-cPrCH$_2$O— | Cl |
| 222 | A | F$_2$CHCH$_2$— | 2,6-di-F—Ph | 2-Cl-5-MeOCH$_2$O— | Cl |
| 223 | A | F$_2$CHCH$_2$— | 2,6-di-F—Ph | 2-Cl-5-EtO— | Cl |
| 224 | A | Et | 3,5-di-F-4-Py | 2-Cl-3,5-di-MeO— | H |
| 225 | B | Et | 2-F—Ph | 3,5-di-MeO— | H |
| 226 | B | Me | 2-F—Ph | 3,5-di-MeO— | H |
| 227 | A | Me | 2-F—Ph | 3,5-di-MeO— | H |
| 228 | A | Me | 2-F—Ph | 2-Br-3,5-di-MeO— | H |
| 229 | A | Me | 2-F—Ph | 2-Cl-3,5-di-MeO— | H |
| 230 | A | Et | 2-F—Ph | 3,5-di-MeO— | H |
| 231 | A | Et | 2-F—Ph | 2-Br-3,5-di-MeO— | H |
| 232 | A | Et | 2-F—Ph | 2-Cl-3,5-di-MeO— | H |
| 233 | A | Me | 2-F—Ph | 2,6-di-Cl-3,5-di-MeO— | H |
| 234 | A | Et | 2,6-di-F—Ph | 2-Cl-5-HO— | H |
| 235 | A | Me | 2,6-di-F—Ph | 2-Cl-5-HO— | H |
| 236 | A | Me | 2,6-di-F—Ph | 2-Cl-5-N≡CCH$_2$O— | H |
| 237 | A | Me | 2,6-di-F—Ph | 2-Cl-5-EtO— | H |
| 238 | A | Me | 2,6-di-F—Ph | 2-Cl-5-cPrCH$_2$O— | H |
| 239 | A | Me | 2,6-di-F—Ph | 2-Cl-5-MeOCH$_2$O— | H |
| 240 | A | Me | 2,6-di-F—Ph | 2-Cl-5-MeOCH$_2$CH$_2$O— | H |
| 241 | A | Me | 2,6-di-F—Ph | 2-Cl-5-PrO— | H |
| 242 | A | Et | 2,6-di-F—Ph | 2-Cl-5-PrO— | H |
| 243 | A | Me | 2,6-di-F—Ph | 2-Cl-5-HC≡CCH$_2$O— | H |
| 244 | A | Et | 2,6-di-F—Ph | 2-Cl-5-HC≡CCH$_2$O— | H |
| 245 | A | Et | 2,6-di-F—Ph | 2-Cl-5-Me$_3$SiCH$_2$CH$_2$OCH$_2$O— | H |
| 246 | A | Me | 2,6-di-F—Ph | 2-Cl-5-Me$_3$SiCH$_2$CH$_2$OCH$_2$O— | H |
| 247 | A | Me | 4-EtO-2,6-di-F—Ph | 2-Cl-3,5-di-MeO— | H |
| 248 | A | Me | 4-tBuO-2,6-di-F—Ph | 2-Cl-3,5-di-MeO— | H |
| 249 | A | Me | 2,6-di-F-4-HO—Ph | 2-Cl-3,5-di-MeO— | H |
| 250 | A | Et | 2,6-di-F—Ph | 2-Cl-5-N≡CCH$_2$CH$_2$O— | H |
| 251 | A | Me | 2,6-di-F—Ph | 2-Cl-5-N≡CCH$_2$CH$_2$O— | H |
| 252 | A | Et | 2,6-di-F—Ph | 2-Cl-5-BuO— | H |
| 253 | A | Me | 2,6-di-F—Ph | 2-Cl-5-BuO— | H |
| 254 | A | Et | 2,6-di-F—Ph | 2-Cl-5-PentylO— | H |
| 255 | A | Me | 2,6-di-F—Ph | 2-Cl-5-PentylO— | H |
| 256 | A | Et | 2,6-di-F—Ph | 2-Cl-5-iPrO— | H |
| 257 | A | Me | 2,6-di-F—Ph | 2-Cl-5-iPrO— | H |
| 258 | A | Et | 2,6-di-F—Ph | 2-Cl-5-iBuO— | H |
| 259 | A | Me | 2,6-di-F—Ph | 2-Cl-5-iBuO— | H |
| 260 | A | Et | 2,6-di-F—Ph | 2-Cl-5-Me$_3$SiCH$_2$O— | H |
| 261 | A | Me | 2,6-di-F—Ph | 2-Cl-5-Me$_3$SiCH$_2$O— | H |
| 262 | A | Et | 2,6-di-F—Ph | 2-Cl-5-F$_3$CCH$_2$O— | H |
| 263 | A | Me | 2,6-di-F—Ph | 2-Cl-5-F$_3$CCH$_2$O— | H |
| 264 | A | Et | 2,6-di-F—Ph | 2-MeS(O)— | H |
| 265 | A | Et | 2,6-di-F—Ph | 4-Cl— | H |
| 266 | A | Et | 2,6-di-F—Ph | 4-Cl— | Cl |
| 267 | B | Et | 2,6-di-F—Ph | 4-Me— | H |
| 268 | B | Me | 2,6-di-F—Ph | 4-Me— | H |
| 269 | A | Et | 2,6-di-F—Ph | 4-Me— | H |
| 270 | A | Me | 2,6-di-F—Ph | 4-Me— | H |

TABLE 4-continued

| Compound | Structure | R1 | Y | (R2)n | R3 |
|---|---|---|---|---|---|
| 271 | A | Et | 2,6-di-F—Ph | 4-Me— | Br |
| 272 | A | Et | 2,6-di-F—Ph | 4-Me— | Cl |
| 273 | A | Me | 2,6-di-F—Ph | 4-Me— | Br |
| 274 | A | Me | 2,6-di-F—Ph | 4-Me— | Cl |
| 275 | A | Et | 2,6-di-F—Ph | 2-Cl-5-Me$_3$SiCH$_2$CH$_2$O— | H |
| 276 | A | Me | 2,6-di-F—Ph | 2-Cl-5-Me$_3$SiCH$_2$CH$_2$O— | H |
| 277 | A | Et | 2,6-di-F—Ph | 2-Cl-5-F$_2$CHCH$_2$O— | H |
| 278 | A | Me | 2,6-di-F—Ph | 2-Cl-5-F$_2$CHCH$_2$O— | H |
| 279 | A | Et | 2,6-di-F—Ph | 4-Cl— | Br |
| 280 | A | Me | 2,6-di-F—Ph | 4-Cl— | H |
| 281 | A | Me | 2,6-di-F-4-PrO—Ph | 2-Cl-3,5-di-MeO— | H |
| 282 | A | Me | 4-BuO-2,6-di-F—Ph | 2-Cl-3,5-di-MeO— | H |
| 283 | B | Et | 2,6-di-F—Ph | 3-F$_3$C— | H |
| 284 | A | Et | 2,6-di-F—Ph | 3-F$_3$C— | H |
| 285 | A | Me | 2,6-di-F—Ph | 4-Cl— | Cl |
| 286 | A | Me | 2,6-di-F—Ph | 4-Cl— | Br |
| 287 | A | Et | 2,6-di-F—Ph | 2-Cl-5-cPentylO— | H |
| 288 | A | Me | 2,6-di-F—Ph | 2-Cl-5-cPentylO— | H |
| 289 | A | Me | 2,6-di-F—Ph | 4-Br— | H |
| 290 | A | Me | 2,6-di-F—Ph | 4-Br— | Br |
| 291 | A | Me | 2,6-di-F—Ph | 4-Br— | Cl |
| 292 | A | Et | 2,6-di-F—Ph | 4-Br— | H |
| 293 | A | Et | 2,6-di-F—Ph | 4-Br— | Br |
| 294 | A | Et | 2,6-di-F—Ph | 4-Br— | Cl |
| 295 | A | Et | 2,6-di-F—Ph | 2-Cl-5-cHexylO— | H |
| 296 | A | Me | 2,6-di-F—Ph | 2-Cl-5-cHexylO— | H |
| 297 | A | Et | 2,6-di-F—Ph | 2-Cl-5-MeOC(=O)O— | H |
| 298 | A | Me | 2,6-di-F—Ph | 2-Cl-5-MeOC(=O)O— | H |
| 299 | A | Et | 2,6-di-F—Ph | 3-F$_3$C— | Cl |
| 300 | B | Et | 2,6-di-F—Ph | 4-MeO— | H |
| 301 | A | Et | 2,6-di-F—Ph | 4-MeO— | H |
| 302 | A | Et | 2,6-di-F—Ph | 4-MeO— | Cl |
| 303 | A | Et | 2,6-di-F—Ph | 2-Cl-5-AcCH$_2$O— | H |
| 304 | A | Me | 2,6-di-F—Ph | 2-Cl-5-AcCH$_2$O— | H |
| 305 | A | Et | 2,6-di-F—Ph | 2-Cl-5-MeSCH$_2$O— | H |
| 306 | A | Me | 2,6-di-F—Ph | 2-Cl-5-MeSCH$_2$O— | H |
| 307 | A | Et | 2,6-di-F—Ph | 2-Cl-5-EtOC(=O)CH$_2$O— | H |
| 308 | A | Me | 2,6-di-F—Ph | 2-Cl-5-EtOC(=O)CH$_2$O— | H |
| 309 | A | Et | 2,6-di-F—Ph | 2-Cl-5-MeSO$_2$CH$_2$O— | H |
| 310 | A | Et | 2,6-di-F—Ph | 2-Cl-5-MeOCH$_2$CH$_2$O— | H |
| 311 | A | Me | 2,6-di-F—Ph | 2-Cl-5-MeOCH$_2$CH$_2$O— | H |
| 312 | A | Me | 2,6-di-F—Ph | 2-Cl-5-MeSO$_2$CH$_2$O— | H |
| 313 | A | Et | 2,6-di-F—Ph | 2-Cl-5-H$_2$C=CHCH$_2$O— | H |
| 314 | A | Me | 2,6-di-F—Ph | 2-Cl-5-H$_2$C=CHCH$_2$O— | H |
| 315 | A | Et | 2,6-di-F—Ph | 2-Cl-5-(1,3-dioxolan-2-yl)CH$_2$O— | H |
| 316 | A | Me | 2,6-di-F—Ph | 2-Cl-5-(1,3-dioxolan-2-yl)CH$_2$O— | H |
| 317 | A | Et | 2,6-di-F—Ph | 2-Cl-5-(1,3-dioxan-2-yl)CH$_2$CH$_2$O— | H |
| 318 | A | Me | 2,6-di-F—Ph | 2-Cl-5-(1,3-dioxan-2-yl)CH$_2$CH$_2$O— | H |
| 319 | A | Me | 4-(F$_3$CCH$_2$O)-2,6-di-F—Ph | 2-Cl-3,5-di-MeO— | H |
| 320 | B | Et | 2,4,6-tri-F—Ph | 2-Cl-5-F— | H |
| 321 | A | Et | 2,4,6-tri-F—Ph | 2-Cl-5-F— | H |
| 322 | A | Et | 2,4,6-tri-F—Ph | 2-Cl-5-F— | Cl |
| 323 | A | Et | 2,6-di-F—Ph | 2-Cl-5-cPentylCH$_2$O— | H |
| 324 | A | Me | 2,6-di-F—Ph | 2-Cl-5-cPentylCH$_2$O— | H |
| 325 | A | Et | 2,6-di-F—Ph | 2-Cl-5-EtOCH$_2$O— | H |
| 326 | A | Me | 2,6-di-F—Ph | 2-Cl-5-EtOCH$_2$O— | H |
| 327 | A | Et | 2,6-di-F—Ph | 3-Br— | H |
| 328 | A | Et | 2,6-di-F—Ph | 3-Br— | Cl |
| 329 | A | Et | 2,6-di-F—Ph | 2-Cl-5-MeO— | Me |
| 330 | A | Et | 2,6-di-F—Ph | 2-Cl-5-MeOCH$_2$OCH$_2$O— | H |
| 331 | A | Me | 2,6-di-F—Ph | 2-Cl-5-MeOCH$_2$OCH$_2$O— | H |
| 332 | A | Et | 2,6-di-F—Ph | 2,4-di-Cl— | H |
| 333 | A | Et | 2,6-di-F—Ph | 2,4-di-Cl— | Cl |
| 334 | B | F$_3$CCH$_2$— | 2,6-di-F—Ph | 2-Cl-3,5-di-MeO— | H |
| 335 | A | F$_3$CCH$_2$— | 2,6-di-F—Ph | 2-Cl-3,5-di-MeO— | H |
| 336 | B | F$_2$CHCH$_2$— | 2,6-di-F—Ph | 2-Cl-3,5-di-MeO— | H |
| 337 | A | F$_2$CHCH$_2$— | 2,6-di-F—Ph | 2-Cl-3,5-di-MeO— | H |
| 338 | A | Me | 4-(F$_2$CHCH$_2$O)-2,6-di-F—Ph | 2-Cl-3,5-di-MeO— | H |

TABLE 4-continued

| Compound | Structure | R1 | Y | (R2)n | R3 |
|---|---|---|---|---|---|
| 339 | A | Me | 2,4,6-tri-F—Ph | 2-Cl-5-F— | H |
| 340 | A | Me | 2,4,6-tri-F—Ph | 2-Cl-5-F— | Cl |
| 341 | A | Et | 2,6-di-F—Ph | 3-N≡C— | H |
| 342 | B | Et | 2,4,6-tri-F—Ph | 2-Cl-3,5-di-MeO— | H |
| 343 | A | F$_2$CHCH$_2$— | 2,4,6-tri-F—Ph | 2-Cl-3,5-di-MeO— | H |
| 344 | A | Me | 2,6-di-F—Ph | 2-Et— | H |
| 345 | A | F$_2$CHCH$_2$— | 2,6-di-F—Ph | 2,4-di-Cl— | H |
| 346 | A | Me | 2,6-di-F—Ph | 2,4-di-Cl— | H |
| 347 | A | F$_2$CHCH$_2$— | 2,6-di-F—Ph | 2,4-di-Cl— | Cl |
| 348 | A | Me | 2,6-di-F—Ph | 2,4-di-Cl— | Cl |
| 349 | A | Et | 2,6-di-F—Ph | 2,3-di-Cl— | H |
| 350 | A | Et | 2,6-di-F—Ph | 2,3-di-Cl— | Cl |
| 351 | A | Et | 2,6-di-F—Ph | 2-Cl-5-MeO— | HC≡C— |
| 352 | A | Et | 2,6-di-F—Ph | 2-Cl-5-MeO— | cPr |
| 353 | A | Et | 2,6-di-F—Ph | 3-N≡C— | Cl |
| 354 | A | Et | 2,4,6-tri-F—Ph | 2,5-di-Cl— | H |
| 355 | A | Et | 2,4,6-tri-F—Ph | 2,5-di-Cl— | Cl |
| 356 | B | Et | 2,6-di-F—Ph | 2-Cl-5-F— | H |
| 357 | B | Me | 2,6-di-F—Ph | 2-Cl-5-F— | H |
| 358 | A | Et | 2,6-di-F—Ph | 2-Cl-5-F— | H |
| 359 | A | Me | 2,6-di-F—Ph | 2-Cl-5-F— | H |
| 360 | A | Et | 2,6-di-F—Ph | 2-Cl-5-F— | Cl |
| 361 | A | Et | 2,6-di-F—Ph | 2-Cl-5-F— | Br |
| 362 | A | Me | 2,6-di-F—Ph | 2-Cl-5-F— | Cl |
| 363 | A | Me | 2,6-di-F—Ph | 2-Cl-5-F— | Br |
| 364 | A | Me | 2,6-di-F—Ph | 2,3-di-Cl— | H |
| 365 | A | Me | 2,6-di-F—Ph | 2,3-di-Cl— | Cl |
| 366 | A | F$_2$CHCH$_2$— | 2,6-di-F—Ph | 2,3-di-Cl— | H |
| 367 | A | F$_2$CHCH$_2$— | 2,6-di-F—Ph | 2,3-di-Cl— | Cl |
| 368 | A | Et | 2,6-di-F—Ph | 2,3,4,5,6-penta-F— | H |
| 369 | A | Et | 2,6-di-F—Ph | 2-Cl-5-MeO— | Et |
| 370 | A | Et | 2,6-di-F—Ph | 2-Cl-5-MeO— | Pr |
| 371 | A | Et | 2,6-di-F—Ph | 2-Cl-5-MeO— | MeO |
| 372 | A | Et | 2,6-di-F—Ph | 2,3,4,5,6-penta-F— | Cl |
| 373 | A | Me | 2,6-di-F—Ph | 2,3,4,5,6-penta-F— | H |
| 374 | A | Me | 2,6-di-F—Ph | 2,3,4,5,6-penta-F— | Cl |
| 375 | A | Et | 2,6-di-F—Ph | 2-Cl-5-MeO— | MeS |
| 376 | A | Et | 2,6-di-F—Ph | 2-Cl-5-EtO— | Cl |
| 377 | A | F$_3$CCH$_2$— | 2,4,6-tri-F—Ph | 2-Cl-3,5-di-MeO— | H |
| 378 | A | Et | 4-EtO-2,6-di-F—Ph | 2-Cl-3,5-di-MeO— | H |
| 379 | A | (E) FCH═CH— | 2,4,6-tri-F—Ph | 2-Cl-3,5-di-MeO— | H |
| 380 | A | (Z) FCH═CH— | 2,4,6-tri-F—Ph | 2-Cl-3,5-di-MeO— | H |
| 381 | A | Et | 2,4,6-tri-F—Ph | 2-Cl-5-F— | Br |
| 382 | A | Et | 2,6-di-F-4-MeO—Ph | 2-Cl-5-F— | H |
| 383 | A | F$_2$CHCH$_2$— | 2,6-di-F—Ph | 2,3,4,5,6-penta-F— | H |
| 384 | A | F$_2$CHCH$_2$— | 2,6-di-F—Ph | 2,3,4,5,6-penta-F— | Cl |
| 385 | A | Et | 2,6-di-F—Ph | 2-Cl-6-F— | H |
| 386 | A | Et | 2,6-di-F-4-MeO—Ph | 2-Cl-5-F— | Cl |
| 387 | A | Et | 2,6-di-F—Ph | 2-Cl-5-MeO— | MeSO$_2$ |
| 388 | B | F$_2$CHCH$_2$— | 2,6-di-F—Ph | 2-Cl-5-F— | H |
| 389 | B | Pr | 2,6-di-F—Ph | 2-Cl-5-MeO— | H |
| 390 | B | Bu | 2,6-di-F—Ph | 2-Cl-5-MeO— | H |
| 391 | A | F$_2$CHCH$_2$— | 2,6-di-F—Ph | 2-Cl-5-F— | H |
| 392 | A | F$_2$CHCH$_2$— | 2,6-di-F—Ph | 2-Cl-5-F— | Cl |
| 393 | A | F$_2$CHCH$_2$— | 2,6-di-F—Ph | 2-Cl-5-F— | Br |
| 394 | A | Bu | 2,6-di-F—Ph | 2-Cl-5-MeO— | H |
| 395 | A | Bu | 2,6-di-F—Ph | 2-Cl-5-MeO— | Cl |
| 396 | A | Bu | 2,6-di-F—Ph | 2-Cl-5-MeO— | Br |
| 397 | A | Et | 2,6-di-F—Ph | 2-Cl-6-F— | Cl |
| 398 | A | Me | 2,6-di-F—Ph | 2-Cl-6-F— | H |
| 399 | A | Pr | 2,6-di-F—Ph | 2-Cl-5-MeO— | H |
| 400 | A | Pr | 2,6-di-F—Ph | 2-Cl-5-MeO— | Cl |
| 401 | A | Pr | 2,6-di-F—Ph | 2-Cl-5-MeO— | Br |
| 402 | A | MeOCH$_2$— | 2,6-di-F—Ph | 2-Cl-5-MeO— | H |
| 403 | A | Et | 2,4,6-tri-F—Ph | 2-Cl-5-MeO— | H |
| 404 | A | Et | 2,4,6-tri-F—Ph | 2-Cl-5-MeO— | Cl |
| 405 | A | Me | 2,6-di-F—Ph | 2-Cl-6-F— | Cl |
| 406 | A | F$_2$CHCH$_2$— | 2,6-di-F—Ph | 2-Cl-6-F— | H |
| 407 | A | F$_2$CHCH$_2$— | 2,6-di-F—Ph | 2-Cl-6-F— | Cl |
| 408 | A | Et | 2,6-di-F—Ph | 4-Cl-2-F— | H |
| 409 | A | F$_3$CCH$_2$— | 2,6-di-F—Ph | 2-Cl-5-MeO— | H |
| 410 | A | F$_3$CCH$_2$— | 2,6-di-F—Ph | 2-Cl-5-MeO— | Cl |
| 411 | A | F$_3$CCH$_2$— | 2,6-di-F—Ph | 2-Cl-5-MeO— | Br |
| 412 | A | iPr | 2,6-di-F—Ph | 2-Cl-5-MeO— | H |
| 413 | A | iPr | 2,6-di-F—Ph | 2-Cl-5-MeO— | Cl |
| 414 | A | MeOCH$_2$— | 2,6-di-F—Ph | 2-Cl-5-MeO— | Cl |
| 415 | A | Me | 2,4,6-tri-F—Ph | 2-Cl-5-MeO— | H |
| 416 | A | Me | 2,4,6-tri-F—Ph | 2-Cl-5-MeO— | Cl |

TABLE 4-continued

| Compound | Structure | R1 | Y | (R2)n | R3 |
|---|---|---|---|---|---|
| 417 | A | Et | 2,6-di-F—Ph | 4-Cl-2-F— | Cl |
| 418 | A | Me | 2,6-di-F—Ph | 4-Cl-2-F— | H |
| 419 | A | Me | 2,6-di-F—Ph | 4-Cl-2-F— | Cl |
| 420 | A | Et | 2,4,6-tri-F—Ph | 2-Cl— | H |
| 421 | A | Et | 2,4,6-tri-F—Ph | 2-Cl— | Cl |
| 422 | A | $H_2N$— | 2,6-di-F—Ph | 2-Cl-5-MeO— | H |
| 423 | A | $H_2N$— | 2,6-di-F—Ph | 2-Cl-5-MeO— | Cl |
| 424 | A | Et | 2,4,6-tri-F—Ph | 2,5-di-F— | H |
| 425 | A | Et | 2,4,6-tri-F—Ph | 2,5-di-F— | Cl |
| 426 | A | Me | 2,4,6-tri-F—Ph | 2,5-di-F— | H |
| 427 | A | Me | 2,4,6-tri-F—Ph | 2,5-di-F— | Cl |
| 428 | A | $F_2CHCH_2$— | 2,6-di-F—Ph | 4-Cl-2-F— | H |
| 429 | A | $F_2CHCH_2$— | 2,6-di-F—Ph | 4-Cl-2-F— | Cl |
| 430 | A | Et | 2,6-di-F-4-MeO—Ph | 2-Cl— | H |
| 431 | A | Me | 2,4,6-tri-F—Ph | 2-Cl— | H |
| 432 | A | Me | 2,4,6-tri-F—Ph | 2-Cl— | Cl |
| 433 | A | Me | 2,6-di-F-4-MeO—Ph | 2-Cl— | H |
| 434 | A | Et | 2,6-di-F-4-MeO—Ph | 2-Cl— | Cl |
| 435 | A | Me | 2,6-di-F-4-MeO—Ph | 2-Cl— | Cl |
| 436 | B | Et | 2,6-di-F—Ph | 2,3,5-tri-F— | H |
| 437 | B | Me | 2,6-di-F—Ph | 2,3,5-tri-F— | H |
| 438 | A | Et | 2,6-di-F—Ph | 2,3,5-tri-F— | H |
| 439 | A | Me | 2,6-di-F—Ph | 2,3,5-tri-F— | H |
| 440 | A | Et | 2,6-di-F—Ph | 2,3,5-tri-F— | Cl |
| 441 | A | Et | 2,6-di-F—Ph | 2,3,5-tri-F— | Br |
| 442 | A | Me | 2,6-di-F—Ph | 2,3,5-tri-F— | Cl |
| 443 | A | Me | 2,6-di-F—Ph | 2,3,5-tri-F— | Br |
| 444 | A | Et | 2,6-di-F—Ph | 2,5-di-Cl— | H |
| 445 | A | Et | 2,6-di-F—Ph | 2,5-di-Cl— | Cl |
| 446 | A | Me | 2,6-di-F—Ph | 2,5-di-Cl— | H |
| 447 | A | Me | 2,6-di-F—Ph | 2,5-di-Cl— | Cl |
| 448 | A | $F_2CHCH_2$— | 2,6-di-F—Ph | 2,5-di-Cl— | H |
| 449 | A | $F_2CHCH_2$— | 2,6-di-F—Ph | 2,5-di-Cl— | Cl |
| 450 | A | Et | 2,6-di-F—Ph | 2,3,5-tri-Cl— | H |
| 451 | A | Et | 2,6-di-F—Ph | 2,3,5-tri-Cl— | Cl |
| 452 | A | Me | 2,6-di-F—Ph | 2,3,5-tri-Cl— | H |
| 453 | A | Me | 2,6-di-F—Ph | 2,3,5-tri-Cl— | Cl |
| 454 | A | $F_2CHCH_2$— | 2,6-di-F—Ph | 2,3,5-tri-Cl— | H |
| 455 | A | $F_2CHCH_2$— | 2,6-di-F—Ph | 2,3,5-tri-Cl— | Cl |
| 456 | B | HC≡C—$CH_2$— | 2,6-di-F—Ph | 2-Cl-5-MeO— | H |
| 457 | A | Me | 2,6-di-F—Ph | 2,3,5-tri-F— | Me |
| 458 | A | HC≡C—$CH_2$— | 2,6-di-F—Ph | 2-Cl-5-MeO— | H |
| 459 | A | Et | 2,6-di-F—Ph | 2,3,5-tri-F— | Me |
| 460 | A | N≡C—$CH_2$— | 2,6-di-F—Ph | 2-Cl-5-MeO— | H |
| 461 | A | Et | 2,4,6-tri-F—Ph | 2-Cl-5-F— | Me |
| 462 | A | HC≡C—$CH_2$— | 2,6-di-F—Ph | 2-Cl-5-MeO— | Cl |
| 463 | A | N≡C—$CH_2$— | 2,6-di-F—Ph | 2-Cl-5-MeO— | Cl |
| 464 | A | Et | 2,4,6-tri-F—Ph | 2,3,5-tri-F— | H |
| 465 | A | Et | 2,4,6-tri-F—Ph | 2,3,5-tri-F— | Cl |
| 466 | A | Me | 2,4,6-tri-F—Ph | 2,3,5-tri-F— | H |
| 467 | A | Me | 2,4,6-tri-F—Ph | 2,3,5-tri-F— | Cl |
| 468 | A | Et | 2,6-di-F-4-MeO—Ph | 2,5-di-F— | H |
| 469 | A | Et | 2,6-di-F-4-MeO—Ph | 2,5-di-F— | Cl |
| 470 | A | Et | 2,6-di-F—Ph | 2,5-di-Cl— | Me |
| 471 | A | Me | 2,6-di-F—Ph | 2,5-di-Cl— | Me |
| 472 | A | Et | 2,6-di-F—Ph | 3-Cl-2-F— | H |
| 473 | A | Et | 2,6-di-F—Ph | 3-Cl-2-F— | Cl |
| 474 | A | Me | 2,6-di-F—Ph | 3-Cl-2-F— | H |
| 475 | A | Me | 2,6-di-F—Ph | 3-Cl-2-F— | Cl |
| 476 | A | Et | 2,6-di-F-4-MeO—Ph | 2-Cl-5-F— | Br |
| 477 | B | Et | 2,6-di-F—Ph | 2,5-di-F— | H |
| 478 | A | Et | 2,6-di-F—Ph | 2,5-di-F— | H |
| 479 | A | Et | 2,6-di-F-4-MeO—Ph | 2-Cl-5-F— | Me |
| 480 | B | Me | 2,6-di-F—Ph | 2,5-di-F— | H |
| 481 | A | Et | 2,6-di-F—Ph | 2,5-di-F— | Cl |
| 482 | A | Et | 2,6-di-F—Ph | 2,5-di-F— | Br |
| 483 | A | Me | 2,6-di-F—Ph | 2,5-di-F— | H |
| 484 | A | Me | 2,6-di-F—Ph | 2,5-di-F— | Cl |
| 485 | A | Me | 2,6-di-F—Ph | 2,5-di-F— | Br |
| 486 | A | Et | 2,4,6-tri-F—Ph | 2-Cl-3-F— | H |
| 487 | A | Et | 2,4,6-tri-F—Ph | 2-Cl-3-F— | Br |
| 488 | A | Et | 2,4,6-tri-F—Ph | 2-Cl-3-F— | Cl |
| 489 | A | Et | 2,6-di-F-4-MeO—Ph | 2-Cl-3-F— | H |
| 490 | A | Et | 2,6-di-F-4-MeO—Ph | 2-Cl-3-F— | Cl |
| 491 | A | Me | 2,4,6-tri-F—Ph | 2-Cl-3-F— | H |
| 492 | A | Me | 2,6-di-F-4-MeO—Ph | 2-Cl-3-F— | H |
| 493 | A | Et | 2,6-di-F—Ph | 3-Cl-2-F— | Me |
| 494 | A | $F_2CHCH_2$— | 2,6-di-F—Ph | 3-Cl-2-F— | H |

TABLE 4-continued

| Compound | Structure | R1 | Y | (R2)n | R3 |
|---|---|---|---|---|---|
| 495 | A | F$_2$CHCH$_2$— | 2,6-di-F—Ph | 3-Cl-2-F— | Cl |
| 496 | A | cPr | 2,6-di-F—Ph | 2-Cl-5-MeO— | H |
| 497 | A | Et | 2,6-di-F—Ph | 2,5-di-F— | Me |
| 498 | A | cPr | 2,6-di-F—Ph | 2-Cl-5-MeO— | Cl |
| 499 | A | Me | 2,6-di-F—Ph | 2,5-di-F— | Me |
| 500 | A | Me | 2,4,6-tri-F—Ph | 2-Cl-3-F— | Cl |
| 501 | A | Et | 2,4,6-tri-F—Ph | 2-Cl-3-F— | Me |
| 502 | A | Et | 2,4,6-tri-F—Ph | 3-F-2-Me— | Me |
| 503 | A | Me | 2,4,6-tri-F—Ph | 2-Cl-3-F— | Br |
| 504 | A | Me | 2,6-di-F-4-MeO—Ph | 2-Cl-3-F— | Cl |
| 505 | A | Me | 2,4,6-tri-F—Ph | 2-Cl-3-F— | Me |
| 506 | A | Et | 2,6-di-F—Ph | 2-Cl-3-F— | H |
| 507 | A | Et | 2,6-di-F—Ph | 2-Cl-3-F— | Cl |
| 508 | A | Me | 2,6-di-F—Ph | 2-Cl-3-F— | H |
| 509 | A | Me | 2,6-di-F—Ph | 2-Cl-3-F— | Cl |
| 510 | A | F$_2$CHCH$_2$— | 2,6-di-F—Ph | 2-Cl-3-F— | H |
| 511 | A | F$_2$CHCH$_2$— | 2,6-di-F—Ph | 2-Cl-3-F— | Cl |
| 512 | A | Et | 2,6-di-F—Ph | 2-Cl-5-F— | F |
| 513 | A | Me | 2,6-di-F—Ph | 2-Cl-5-F— | F |
| 514 | B | Et | 2,4,6-tri-F—Ph | 2-F— | H |
| 515 | A | Et | 2,6-di-F-4-MeO—Ph | 2-Cl-3-F— | Me |
| 516 | A | Et | 2,6-di-F-4-MeO—Ph | 3-F-2-Me— | Me |
| 517 | A | Me | 2,6-di-F-4-MeO—Ph | 2-Cl-3-F— | Me |
| 518 | A | Et | 2,6-di-F—Ph | 2,3-di-F— | H |
| 519 | A | Et | 2,6-di-F—Ph | 2,3-di-F— | Cl |
| 520 | A | Et | 2,6-di-F—Ph | 2,3-di-F— | Br |
| 521 | A | F$_2$CHCH$_2$— | 2,6-di-F—Ph | 3-Cl-2-F— | Me |
| 522 | A | Et | 2,6-di-F—Ph | 5-Cl-2-F— | H |
| 523 | A | Et | 2,6-di-F—Ph | 5-Cl-2-F— | Cl |
| 524 | A | Me | 2,6-di-F—Ph | 5-Cl-2-F— | H |
| 525 | A | Me | 2,6-di-F—Ph | 5-Cl-2-F— | Cl |
| 526 | B | Me | 2,4,6-tri-F—Ph | 2-F— | H |
| 527 | A | Et | 2,4,6-tri-F—Ph | 2-F— | H |
| 528 | A | Me | 2,4,6-tri-F—Ph | 2-F— | H |
| 529 | A | Et | 2,4,6-tri-F—Ph | 2-F— | Cl |
| 530 | A | Et | 2,6-di-F-4-MeO—Ph | 2-F— | H |
| 531 | A | Et | 2,6-di-F-4-MeO—Ph | 2-F— | Cl |
| 532 | A | Et | 2,4,6-tri-F—Ph | 2-F— | Br |
| 533 | A | Et | 2,6-di-F—Ph | 2-Cl-5-MeO— | F |
| 534 | A | Et | 2,6-di-F—Ph | 2,3-di-F— | Me |
| 535 | A | Me | 2,6-di-F—Ph | 2,3-di-F— | H |
| 536 | A | Me | 2,6-di-F—Ph | 2,3-di-F— | Br |
| 537 | A | Me | 2,6-di-F—Ph | 2,3-di-F— | Cl |
| 538 | A | Me | 2,6-di-F—Ph | 2,3-di-F— | Me |
| 539 | A | F$_2$CHCH$_2$— | 2,6-di-F—Ph | 5-Cl-2-F— | H |
| 540 | A | F$_2$CHCH$_2$— | 2,6-di-F—Ph | 5-Cl-2-F— | Cl |
| 541 | A | Et | 2,6-di-F-4-MeO—Ph | 2-F— | Br |
| 542 | A | Et | 2,4,6-tri-F—Ph | 2-F— | Me |
| 543 | A | Me | 2,4,6-tri-F—Ph | 2-F— | Cl |
| 544 | A | Me | 2,6-di-F-4-MeO—Ph | 2-F— | H |
| 545 | A | Me | 2,4,6-tri-F—Ph | 2-F— | Br |
| 546 | A | Et | 2,6-di-F-4-MeO—Ph | 2,3,5-tri-F— | Cl |
| 547 | A | Et | 4-EtO-2,6-di-F—Ph | 2-Cl-5-F— | Cl |
| 548 | A | Et | 2,6-di-F-4-MeO—Ph | 2,3,5-tri-F— | H |
| 549 | A | Me | 2,6-di-F-4-MeO—Ph | 2,3,5-tri-F— | Cl |
| 550 | A | Me | 2,6-di-F-4-MeO—Ph | 2,3,5-tri-F— | H |
| 551 | A | Et | 2,6-di-F—Ph | 2-Cl-3,5-di-F— | H |
| 552 | A | Et | 2,6-di-F—Ph | 2-Cl-3,5-di-F— | Cl |
| 553 | A | Me | 2,6-di-F—Ph | 2-Cl-3,5-di-F— | H |
| 554 | A | Me | 2,6-di-F—Ph | 2-Cl-3,5-di-F— | Cl |
| 555 | A | F$_2$CHCH$_2$— | 2,6-di-F—Ph | 2-Cl-3,5-di-F— | H |
| 556 | A | F$_2$CHCH$_2$— | 2,6-di-F—Ph | 2-Cl-3,5-di-F— | Cl |
| 557 | A | Me | 2,4,6-tri-F—Ph | 2,3-di-F— | H |
| 558 | A | Et | 2,4,6-tri-F—Ph | 2,3-di-F— | H |
| 559 | A | Me | 2,4,6-tri-F—Ph | 2,3-di-F— | Cl |
| 560 | A | Me | 2,4,6-tri-F—Ph | 2,3-di-F— | Br |
| 561 | A | Me | 2,6-di-F-4-MeO—Ph | 2,3-di-F— | H |
| 562 | A | Me | 2,6-di-F-4-MeO—Ph | 2,3-di-F— | Cl |
| 563 | A | Me | 2,6-di-F-4-MeO—Ph | 2,3-di-F— | Br |
| 564 | A | Me | 2,4,6-tri-F—Ph | 2,3-di-F— | Me |
| 565 | A | Me | 2,6-di-F-4-MeO—Ph | 2,3-di-F— | Me |
| 566 | A | Et | 2,4,6-tri-F—Ph | 2,3-di-F— | Cl |
| 567 | A | Et | 2,4,6-tri-F—Ph | 2,3-di-F— | Br |
| 568 | A | Et | 2,4,6-tri-F—Ph | 2-F— | F |
| 569 | A | Et | 2,6-di-F-4-MeO—Ph | 2-F— | Me |
| 570 | A | Me | 2,6-di-F-4-MeO—Ph | 2-F— | Cl |
| 571 | A | Me | 2,4,6-tri-F—Ph | 2-F— | Me |
| 572 | A | Me | 2,6-di-F-4-MeO—Ph | 2-F— | Br |

TABLE 4-continued

| Compound | Structure | R1 | Y | (R2)n | R3 |
|---|---|---|---|---|---|
| 573 | B | Et | 2,4,6-tri-F—Ph | 2-Cl-4-F— | H |
| 574 | B | Me | 2,4,6-tri-F—Ph | 2-Cl-4-F— | H |
| 575 | A | Et | 2,4,6-tri-F—Ph | 2-Cl-4-F— | H |
| 576 | A | Me | 2,4,6-tri-F—Ph | 2-Cl-4-F— | H |
| 577 | A | Et | 2,4,6-tri-F—Ph | 2-Cl-4-F— | Cl |
| 578 | A | Et | 2,4,6-tri-F—Ph | 2-Cl-4-F— | Br |
| 579 | A | Et | 4-EtO-2,6-di-F—Ph | 2,3,5-tri-F— | H |
| 580 | A | Et | 4-EtO-2,6-di-F—Ph | 2,3,5-tri-F— | Cl |
| 581 | D | Et | 2,6-di-F—Ph | 2-Cl-5-MeO— | H |
| 582 | C | Et | 2,6-di-F—Ph | 2-Cl-5-MeO— | H |
| 583 | B | Et | 2,4,6-tri-F—Ph | 2-Cl-3,5-di-F— | H |
| 584 | A | Et | 2,4,6-tri-F—Ph | 2-Cl-3,5-di-F— | H |
| 585 | A | Et | 2,4,6-tri-F—Ph | 2-Cl-3,5-di-F— | Cl |
| 586 | A | Me | 2,4,6-tri-F—Ph | 2-Cl-3,5-di-F— | H |
| 587 | A | Me | 2,4,6-tri-F—Ph | 2-Cl-3,5-di-F— | Cl |
| 588 | A | Et | 2,6-di-F-4-MeO—Ph | 2,3-di-F— | H |
| 589 | A | Et | 2,6-di-F-4-MeO—Ph | 2,3-di-F— | Br |
| 590 | A | Et | 2,6-di-F-4-MeO—Ph | 2,3-di-F— | Cl |
| 591 | A | Me | 4-EtO-2,6-di-F—Ph | 2-F— | H |
| 592 | A | Et | 2,4,6-tri-F—Ph | 2-Cl-4-F— | F |
| 593 | A | Et | 2,6-di-F-4-MeO—Ph | 2-Cl-4-F— | Cl |
| 594 | A | Et | 2,4,6-tri-F—Ph | 2-Cl-4-F— | Me |
| 595 | A | Et | 4-EtO-2,6-di-F—Ph | 2-Cl-4-F— | Cl |
| 596 | A | Me | 2,4,6-tri-F—Ph | 2-Cl-4-F— | Cl |
| 597 | A | Me | 2,4,6-tri-F—Ph | 2-Cl-4-F— | Br |
| 598 | A | Me | 4-EtO-2,6-di-F—Ph | 2-F— | Cl |
| 599 | A | Et | 2,6-di-F-4-MeO—Ph | 2-Cl-4-F— | Me |
| 600 | A | Me | 2,6-di-F-4-MeO—Ph | 2-Cl-4-F— | Cl |
| 601 | A | Et | 4-Cl-2,6-di-F—Ph | 2-Cl-5-F— | H |
| 602 | A | Et | 4-Cl-2,6-di-F—Ph | 2-Cl-5-F— | Cl |
| 603 | A | Et | 4-Cl-2,6-di-F—Ph | 2-Cl-5-F— | Br |
| 604 | A | Me | 4-Cl-2,6-di-F—Ph | 2-Cl-5-F— | H |
| 605 | A | Me | 4-Cl-2,6-di-F—Ph | 2-Cl-5-F— | Cl |
| 606 | A | Me | 4-Cl-2,6-di-F—Ph | 2-Cl-5-F— | Br |
| 607 | A | F$_2$CHCH$_2$— | 2,4,6-tri-F—Ph | 2-Cl-3,5-di-F— | H |
| 608 | A | F$_2$CHCH$_2$— | 2,4,6-tri-F—Ph | 2-Cl-3,5-di-F— | Cl |
| 609 | A | Et | 2,4,6-tri-F—Ph | 2,3-di-F— | Me |
| 610 | A | Et | 2,6-di-F-4-MeO—Ph | 2,3-di-F— | Me |
| 611 | A | Et | 4-EtO-2,6-di-F—Ph | 2,3-di-F— | Me |
| 612 | A | Me | 4-EtO-2,6-di-F—Ph | 2-Cl-4-F— | H |
| 613 | A | Me | 2,4,6-tri-F—Ph | 2-Cl-4-F— | Me |
| 614 | B | Et | 2,4,6-tri-F—Ph | 2-Cl-3-F-5-MeO— | H |
| 615 | A | Et | 2,4,6-tri-F—Ph | 2-Cl-3-F-5-MeO— | H |
| 616 | A | Me | 4-EtO-2,6-di-F—Ph | 2-Cl-4-F— | Cl |
| 617 | A | Et | 2,4,6-tri-F—Ph | 2-Cl-3-F-5-MeO— | Cl |
| 618 | A | Et | 2,4,6-tri-F—Ph | 2-Cl-3-MeO— | H |
| 619 | A | Et | 2,4,6-tri-F—Ph | 2-Cl-3-MeO— | Cl |
| 620 | A | Et | 2,4,6-tri-F—Ph | 2-Cl-3-MeO— | Br |
| 621 | A | Me | 2,6-di-F-4-MeO—Ph | 2-Cl-4-F— | Me |
| 622 | B | Et | 2,4,6-tri-F—Ph | 4-Br-2-Cl— | H |
| 623 | A | Et | 2,6-di-F-4-MeO—Ph | 2-Cl-3-F-5-MeO— | H |
| 624 | A | Et | 2,4,6-tri-F—Ph | 4-Br-2-Cl— | H |
| 625 | A | Et | 2,4,6-tri-F—Ph | 4-Br-2-Cl— | Cl |
| 626 | A | Et | 2,4,6-tri-F—Ph | 2-Cl-4-Me— | H |
| 627 | A | Et | 2,6-di-F-4-MeO—Ph | 2-Cl-3-F-5-MeO— | Cl |
| 628 | A | Et | 2,4,6-tri-F—Ph | 2-Cl-4-Me— | Cl |
| 629 | A | Et | 2,6-di-F—Ph | 2,4-di-F— | H |
| 630 | A | Et | 2,6-di-F—Ph | 2,4-di-F— | Cl |
| 631 | A | Me | 2,6-di-F—Ph | 2,4-di-F— | H |
| 632 | A | Et | 2,4,6-tri-F—Ph | 2-Cl-3-MeO— | Me |
| 633 | A | Et | 2,6-di-F-4-MeO—Ph | 2-Cl-3-MeO— | H |
| 634 | A | Et | 4-EtO-2,6-di-F—Ph | 2-Cl-3-MeO— | H |
| 635 | A | Et | 2,4,6-tri-F—Ph | 2,4,5-tri-F— | H |
| 636 | A | Et | 2,4,6-tri-F—Ph | 2,4,5-tri-F— | Cl |
| 637 | A | Et | 2,6-di-F-4-MeO—Ph | 2,4,5-tri-F— | Cl |
| 638 | A | Et | 2,6-di-F-4-MeO—Ph | 2,4,5-tri-F— | H |
| 639 | A | Me | 2,4,6-tri-F—Ph | 2,4,5-tri-F— | H |
| 640 | A | Et | 2,6-di-F-4-MeO—Ph | 2-Cl-3-MeO— | Cl |
| 641 | A | Et | 4-EtO-2,6-di-F—Ph | 2-Cl-3-MeO— | Cl |
| 642 | A | Et | 2,6-di-F-4-MeO—Ph | 2-Cl-3-MeO— | Br |
| 643 | A | Et | 4-EtO-2,6-di-F—Ph | 2-Cl-3-MeO— | Br |
| 644 | A | Et | 2,6-di-F-4-MeO—Ph | 2-Cl-3-MeO— | Me |
| 645 | A | Et | 4-EtO-2,6-di-F—Ph | 2-Cl-3-MeO— | Me |
| 646 | A | Me | 2,6-di-F—Ph | 2,4-di-F— | Cl |
| 647 | A | F$_2$CHCH$_2$— | 2,6-di-F—Ph | 2,4-di-F— | H |
| 648 | A | F$_2$CHCH$_2$— | 2,6-di-F—Ph | 2,4-di-F— | Cl |
| 649 | C | Et | 2,4,6-tri-F—Ph | 2-Cl-3,5-di-F— | H |
| 650 | B | Et | 2,4,6-tri-F—Ph | 2-Br— | H |

TABLE 4-continued

| Compound | Structure | R1 | Y | (R2)n | R3 |
|---|---|---|---|---|---|
| 651 | A | Et | 2,4,6-tri-F—Ph | 2-Br— | H |
| 652 | A | Et | 2,4,6-tri-F—Ph | 2-Br— | Cl |
| 653 | A | Me | 2,4,6-tri-F—Ph | 2,4,5-tri-F— | Cl |
| 654 | A | Me | 2,6-di-F-4-MeO—Ph | 2,4,5-tri-F— | H |
| 655 | A | Me | 2,6-di-F-4-MeO—Ph | 2,4,5-tri-F— | Cl |
| 656 | A | Et | 2,6-di-F-4-MeO—Ph | 2-Cl-3-F— | Br |
| 657 | A | Et | 4-EtO-2,6-di-F—Ph | 2-Cl-3-F— | H |
| 658 | A | Et | 4-EtO-2,6-di-F—Ph | 2-Cl-3-F— | Cl |
| 659 | A | Et | 4-EtO-2,6-di-F—Ph | 2-Cl-3-F— | Br |
| 660 | A | Et | 4-EtO-2,6-di-F—Ph | 2-Cl-3-F— | Me |
| 661 | A | Me | 2,4,6-tri-F—Ph | 2-Cl-3-MeO— | H |
| 662 | A | Me | 2,4,6-tri-F—Ph | 2-Cl-3-MeO— | Br |
| 663 | A | Me | 2,6-di-F-4-MeO—Ph | 2-Cl-3-MeO— | H |
| 664 | A | Me | 4-EtO-2,6-di-F—Ph | 2-Cl-3-MeO— | H |
| 665 | A | Et | 2,6-di-F-4-MeO—Ph | 2-Cl-3,5-di-F— | H |
| 666 | A | Et | 2,6-di-F-4-MeO—Ph | 2-Cl-3,5-di-F— | Cl |
| 667 | A | Et | 2,6-di-F-4-MeO—Ph | 2-Br— | H |
| 668 | A | Et | 2,6-di-F-4-MeO—Ph | 2-Br— | Cl |
| 669 | A | Me | 2,6-di-F-4-MeO—Ph | 2-Cl-3-MeO— | Br |
| 670 | A | Me | 4-EtO-2,6-di-F—Ph | 2-Cl-3-MeO— | Br |
| 671 | A | Me | 2,4,6-tri-F—Ph | 2-Cl-3-MeO— | Me |
| 672 | A | Me | 2,6-di-F-4-MeO—Ph | 2-Cl-3-MeO— | Me |
| 673 | A | Me | 4-EtO-2,6-di-F—Ph | 2-Cl-3-MeO— | Me |
| 674 | A | Et | 2,4,6-tri-F—Ph | 3-F-2-Me— | H |
| 675 | A | Et | 2,4,6-tri-F—Ph | 3-F-2-Me— | Cl |
| 676 | A | Me | 2,6-di-F-4-MeO—Ph | 2-Cl-3,5-di-F— | H |
| 677 | A | Me | 2,6-di-F-4-MeO—Ph | 2-Cl-3,5-di-F— | Cl |
| 678 | A | F$_2$CHCH$_2$— | 2,6-di-F-4-MeO—Ph | 2-Cl-3,5-di-F— | H |
| 679 | A | F$_2$CHCH$_2$— | 2,6-di-F-4-MeO—Ph | 2-Cl-3,5-di-F— | Cl |
| 680 | A | Me | 4-Br-2,6-di-F—Ph | 2-Cl-5-F— | H |
| 681 | A | Me | 4-Br-2,6-di-F—Ph | 2-Cl-5-F— | Cl |
| 682 | A | Et | 2,4,6-tri-F—Ph | 3-F-2-Me— | Br |
| 683 | A | Et | 2,4,6-tri-F—Ph | 2-Cl— | Br |
| 684 | A | Et | 4-EtO-2,6-di-F—Ph | 2-Cl— | Cl |
| 685 | A | Et | 4-EtO-2,6-di-F—Ph | 2-Cl— | H |
| 686 | A | Et | 2,6-di-F-4-MeO—Ph | 2-Cl— | Br |
| 687 | A | Et | 2,4,6-tri-F—Ph | 2-Cl— | Me |
| 688 | A | Et | 2,4,6-tri-F—Ph | 2-Cl-3,5-di-F— | Br |
| 689 | A | Et | 2,4,6-tri-F—Ph | 2-Cl-3,5-di-F— | Me |
| 690 | A | Me | 2,6-di-F-4-Me—Ph | 2-Cl-5-F— | H |
| 691 | A | Me | 2,6-di-F-4-Me—Ph | 2-Cl-5-F— | Cl |
| 692 | A | Et | 4-Br-2,6-di-F—Ph | 2-Cl-5-F— | H |
| 693 | C | Et | 2,6-di-F-4-MeO—Ph | 2-Cl-3,5-di-F— | H |
| 694 | A | Me | 2,4,6-tri-F—Ph | 2-Cl-3,5-di-F— | Me |
| 695 | A | Et | 2,6-di-F-4-MeO—Ph | 2-Cl-3,5-di-F— | Br |
| 696 | C | Et | 2,4,6-tri-F—Ph | 2-Cl-3,5-di-MeO— | H |
| 697 | A | Et | 2,6-di-F-4-MeO—Ph | 3-F-2-Me— | H |
| 698 | A | Et | 4-EtO-2,6-di-F—Ph | 3-F-2-Me— | H |
| 699 | A | Et | 2,6-di-F-4-MeO—Ph | 3-F-2-Me— | Cl |
| 700 | A | Et | 4-EtO-2,6-di-F—Ph | 3-F-2-Me— | Cl |
| 701 | A | Et | 2,6-di-F-4-MeO—Ph | 2-Cl— | Me |
| 702 | A | Et | 4-EtO-2,6-di-F—Ph | 2-Cl— | Me |
| 703 | A | Et | 4-EtO-2,6-di-F—Ph | 2-Cl— | Br |
| 704 | B | N≡C— | 2,6-di-F—Ph | 2-Cl-5-MeO— | H |
| 705 | B | Me | 2,4,6-tri-F—Ph | 2-Cl— | H |
| 706 | A | Et | 4-Br-2,6-di-F—Ph | 2-Cl-5-F— | Cl |
| 707 | A | Et | 2,6-di-F-4-Me—Ph | 2-Cl-5-F— | H |
| 708 | A | Et | 2,6-di-F-4-Me—Ph | 2-Cl-5-F— | Cl |
| 709 | A | Et | 2,6-di-F-4-Me—Ph | 2-Cl-5-F— | Br |
| 710 | A | Et | 2,6-di-F-4-Me—Ph | 2-Cl-5-F— | Me |
| 711 | A | Et | 2,6-di-F-4-MeO—Ph | 3-F-2-Me— | Br |
| 712 | A | Et | 4-EtO-2,6-di-F—Ph | 3-F-2-Me— | Br |
| 713 | A | Et | 4-EtO-2,6-di-F—Ph | 3-F-2-Me— | Me |
| 714 | A | Et | 2,6-di-F-4-MeO—Ph | 2-Cl-3,5-di-F— | Me |
| 715 | C | Et | 2,4,6-tri-F—Ph | 2-Cl— | H |
| 716 | C | Et | 2,6-di-F-4-MeO—Ph | 2-Cl-3,5-di-MeO— | H |
| 717 | A | Me | 2,6-di-F-4-MeO—Ph | 2-Cl-3,5-di-F— | Br |
| 718 | C | Et | 2,6-di-F-4-MeO—Ph | 2-Cl— | H |
| 719 | A | N≡C— | 2,6-di-F—Ph | 2-Cl-5-MeO— | H |
| 720 | A | Me | 2,4,6-tri-F—Ph | 2-Cl— | Br |
| 721 | A | Me | 2,6-di-F-4-MeO—Ph | 2-Cl-5-MeO— | H |
| 722 | A | Me | 2,6-di-F-4-MeO—Ph | 2-Cl-5-MeO— | Cl |
| 723 | A | Me | 2,6-di-F-4-MeO—Ph | 2-Cl-5-MeO— | Br |
| 724 | A | Me | 2,6-di-F-4-MeO—Ph | 2-Cl-5-MeO— | Me |
| 725 | A | Me | 2,4,6-tri-F—Ph | 2-Cl-5-MeO— | Br |
| 726 | A | Me | 2,4,6-tri-F—Ph | 2-Cl-5-MeO— | Me |
| 727 | A | Et | 4-(F$_3$CCH$_2$O)-2,6-di-F—Ph | 2-Cl-3-F— | Cl |
| 728 | C | Et | 2,6-di-F—Ph | 2-Cl-3,5-di-MeO— | H |

TABLE 4-continued

| Compound | Structure | R1 | Y | (R2)n | R3 |
|---|---|---|---|---|---|
| 729 | C | Et | 2,6-di-F—Ph | 2,3,5-tri-F— | H |
| 730 | A | Me | 4-EtO-2,6-di-F—Ph | 2-Cl— | H |
| 731 | A | Me | 2,4,6-tri-F—Ph | 2-Cl— | Me |
| 732 | A | Me | 2,6-di-F-4-MeO—Ph | 2-Cl— | Br |
| 733 | A | Me | 2,6-di-F-4-MeO—Ph | 2-Cl— | Me |
| 734 | A | Me | 4-EtO-2,6-di-F—Ph | 2-Cl— | Cl |
| 735 | A | Et | 2,6-di-F—Ph | 2-Cl-4-MeO— | H |
| 736 | A | Et | 2,6-di-F—Ph | 2-Cl-4-MeO— | Cl |
| 737 | A | Et | 2,6-di-F—Ph | 2-Cl-4-MeO— | Br |
| 738 | C | Et | 2,4,6-tri-F—Ph | 2-Cl-5-F— | H |
| 739 | C | Et | 2,6-di-F-4-MeO—Ph | 2-Cl-5-F— | H |
| 740 | A | Me | 2,6-di-F—Ph | 2-Cl-4-MeO— | H |
| 741 | A | Et | 2,6-di-F—Ph | 2-Cl-4-MeO— | Me |
| 742 | A | Et | 2,4,6-tri-F—Ph | 2-Cl-4-MeO— | H |
| 743 | A | Me | 2,6-di-F—Ph | 2-Cl-4-MeO— | Cl |
| 744 | A | Me | 2,6-di-F—Ph | 2-Cl-4-MeO— | Br |
| 745 | A | Et | 2,6-di-F—Ph | 2-Cl-3-F— | Br |
| 746 | A | Et | 2,4,6-tri-F—Ph | 2-Cl-4-MeO— | Cl |
| 747 | A | Et | 2,4,6-tri-F—Ph | 2-Cl-4-MeO— | Br |
| 748 | A | Et | 2,6-di-F-4-MeO—Ph | 2-Cl-4-MeO— | Cl |
| 749 | A | Me | 2,6-di-F—Ph | 2-Cl-4-MeO— | Me |
| 750 | A | Et | 2,4,6-tri-F—Ph | 2-Cl-4-MeO— | Me |
| 751 | A | Et | 2,6-di-F-4-MeO—Ph | 2-Cl-4-MeO— | Me |
| 752 | A | Et | 2,6-di-F—Ph | 2-Cl-3-F— | Me |
| 753 | A | Me | 2,6-di-F—Ph | 2-Cl-3-F— | Br |
| 754 | A | Me | 2,6-di-F—Ph | 2-Cl-3-F— | Me |
| 755 | A | Et | 2,6-di-F-4-MeO—Ph | 2-Cl-4-MeO— | H |
| 756 | A | Me | 2,4,6-tri-F—Ph | 2-Cl-4-MeO— | H |
| 757 | A | Me | 2,4,6-tri-F—Ph | 2-Cl-5-F— | Br |
| 758 | A | Me | 2,4,6-tri-F—Ph | 2-Cl-5-F— | Me |
| 759 | A | Me | 2,6-di-F-4-MeO—Ph | 2-Cl-5-F— | Me |
| 760 | A | Me | 2,6-di-F-4-MeO—Ph | 2-Cl-5-F— | H |
| 761 | A | Me | 2,6-di-F-4-MeO—Ph | 2-Cl-5-F— | Cl |
| 762 | A | Et | 2,4,6-tri-F—Ph | — | H |
| 763 | A | Et | 2,6-di-F-4-MeO—Ph | — | H |
| 764 | A | Et | 2,4,6-tri-F—Ph | MeO— | Cl |
| 765 | A | Me | 2,6-di-F-4-MeO—Ph | 2-Cl-4-MeO— | H |
| 766 | A | Me | 2,4,6-tri-F—Ph | 2-Cl-4-MeO— | Cl |
| 767 | A | Me | 2,4,6-tri-F—Ph | 2-Cl-4-MeO— | Br |
| 768 | A | Et | 2,4,6-tri-F—Ph | 2-Cl-5-MeO— | Br |
| 769 | A | Et | 2,4,6-tri-F—Ph | 2-Cl-5-MeO— | Me |
| 770 | A | Et | 2,6-di-F-4-MeO—Ph | 2-Cl-5-MeO— | H |
| 771 | A | Et | 2,6-di-F-4-MeO—Ph | 2-Cl-5-MeO— | Me |
| 772 | A | Et | 2,6-di-F-4-MeO—Ph | 2-Cl-5-MeO— | Cl |
| 773 | A | Et | 2,6-di-F-4-MeO—Ph | — | Cl |
| 774 | A | Et | 2,4,6-tri-F—Ph | — | Br |
| 775 | A | Et | 2,6-di-F-4-MeO—Ph | — | Br |
| 776 | A | Me | 2,6-di-F-4-MeO—Ph | 2-Cl-4-MeO— | Cl |
| 777 | A | Me | 2,4,6-tri-F—Ph | — | H |
| 778 | A | Me | 2,6-di-F-4-MeO—Ph | — | H |
| 779 | A | Me | 2,4,6-tri-F—Ph | — | Cl |
| 780 | A | Me | 2,4,6-tri-F—Ph | — | Br |
| 781 | A | Me | 2,6-di-F-4-MeO—Ph | — | Cl |
| 782 | A | Me | 2,6-di-F-4-MeO—Ph | — | Br |
| 783 | A | Et | 2,6-di-F—Ph | 2-Cl-3-MeO— | Cl |
| 784 | A | Me | 2,6-di-F—Ph | 2-Cl-3-MeO— | H |
| 785 | A | Me | 2,6-di-F—Ph | 2-Cl-3-MeO— | Cl |
| 786 | A | Me | 2,6-di-F—Ph | 2-Cl-3-MeO— | Br |
| 787 | A | Me | 2,4,6-tri-F—Ph | 2-Cl-3-MeO— | Cl |
| 788 | A | Me | 2,6-di-F-4-MeO—Ph | 2-Cl-3-MeO— | Cl |
| 789 | A | Et | 2,4,6-tri-F—Ph | 3,5-di-F— | H |
| 790 | A | Et | 2,6-di-F-4-MeO—Ph | 3,5-di-F— | H |
| 791 | A | Et | 2,4,6-tri-F—Ph | 3,5-di-F— | Cl |
| 792 | A | Et | 2,4,6-tri-F—Ph | 2-Cl-5-HO— | Cl |
| 793 | A | Et | 2,4,6-tri-F—Ph | 2-Cl-5-EtO— | Cl |
| 794 | A | Et | 2,4,6-tri-F—Ph | 2-Cl-5-N≡CCH$_2$O— | Cl |
| 795 | A | Et | 2,4,6-tri-F—Ph | 2-Cl-5-MeOCH$_2$O— | Cl |
| 796 | A | Et | 2,6-di-F-4-MeO—Ph | 2-Cl-5-EtO— | Cl |
| 797 | A | Et | 2,4,6-tri-F—Ph | 3,5-di-F— | Br |
| 798 | A | Et | 2,6-di-F-4-MeO—Ph | 3,5-di-F— | Cl |
| 799 | A | Et | 2,6-di-F-4-MeO—Ph | 3,5-di-F— | Br |
| 800 | A | Me | 2,4,6-tri-F—Ph | 3,5-di-F— | H |
| 801 | A | Et | 2,6-di-F—Ph | 2-Cl-5-N≡CCH$_2$O— | Me |
| 802 | A | Et | 2,6-di-F—Ph | 2-Cl-5-EtO— | Me |
| 803 | A | Me | 2,6-di-F-4-MeO—Ph | 3,5-di-F— | H |
| 804 | A | Me | 2,4,6-tri-F—Ph | 3,5-di-F— | Cl |
| 805 | A | Me | 2,4,6-tri-F—Ph | 3,5-di-F— | Br |
| 806 | A | Et | 2,4,6-tri-F—Ph | 2-Cl-3-HO— | Cl |

TABLE 4-continued

| Compound | Structure | R1 | Y | (R2)n | R3 |
|---|---|---|---|---|---|
| 807 | A | Me | 2,6-di-F-4-MeO—Ph | 3,5-di-F— | Cl |
| 808 | A | Me | 2,6-di-F-4-MeO—Ph | 3,5-di-F— | Br |
| 809 | A | Et | 2,4,6-tri-F—Ph | 2-Cl-3-EtO— | Cl |
| 810 | A | Et | 2,4,6-tri-F—Ph | 2-Cl-3-N=CCH$_2$O— | Cl |
| 811 | A | Et | 2,4,6-tri-F—Ph | 2-Cl-3-MeOCH$_2$O— | Cl |
| 812 | A | Et | 2,4,6-tri-F—Ph | 2-Br-3,5-di-F— | H |
| 813 | A | Et | 2,4,6-tri-F—Ph | 2-Br-3,5-di-F— | Cl |
| 814 | A | Et | 2,4,6-tri-F—Ph | 2-Br-3,5-di-F— | Br |
| 815 | A | Me | 2,4,6-tri-F—Ph | 2-Br-3,5-di-F— | H |
| 816 | A | Me | 2,4,6-tri-F—Ph | 2-Br-3,5-di-F— | Cl |
| 817 | A | Me | 2,4,6-tri-F—Ph | 2-Br-3,5-di-F— | Br |
| 818 | A | Et | 2,6-di-F-4-MeO—Ph | 2-Br-3,5-di-F— | H |
| 819 | A | Et | 2,6-di-F-4-MeO—Ph | 2-Br-3,5-di-F— | Cl |
| 820 | A | Et | 2,6-di-F-4-MeO—Ph | 2-Br-3,5-di-F— | Br |
| 821 | A | Et | 2,4,6-tri-F—Ph | 2-Cl— | I |
| 822 | A | Et | 2,6-di-F-4-MeO—Ph | 2-Cl— | I |
| 823 | A | Me | 2,6-di-F-4-MeO—Ph | 2-Br-3,5-di-F— | H |
| 824 | A | Me | 2,6-di-F-4-MeO—Ph | 2-Br-3,5-di-F— | Cl |
| 825 | A | Me | 2,6-di-F-4-MeO—Ph | 2-Br-3,5-di-F— | Br |

The $^1$H-NMR data for the compounds listed in Table 4 are shown in Table 5.

TABLE 5

| Compound | $^1$H-NMR |
|---|---|
| 1 | $^1$H-NMR (CDCl$_3$) δ: 8.46 (1H, d, J = 2.1 Hz), 7.64 (1H, d, J = 2.1 Hz), 7.13-7.11 (3H, m), 6.92-6.92 (2H, m), 2.84-2.77 (4H, m), 2.79 (3H, s). |
| 2 | $^1$H-NMR (CDCl$_3$) δ: 8.54 (1H, d, J = 2.1 Hz), 7.66 (1H, d, J = 2.1 Hz), 7.45 (1H, d, J = 9.5 Hz), 7.18-7.18 (3H, m), 7.04-7.02 (2H, m), 6.78 (1H, d, J = 9.5 Hz), 3.28 (3H, s). |
| 3 | $^1$H-NMR (CDCl$_3$) δ: 8.36 (1H, d, J = 2.1 Hz), 7.65 (1H, d, J = 2.1 Hz), 7.12-7.09 (1H, m), 6.76-6.70 (2H, m), 2.84 (3H, s), 2.78-2.69 (4H, m). |
| 4 | $^1$H-NMR (CDCl$_3$) δ: 8.39 (1H, d, J = 2.1 Hz), 7.62 (1H, d, J = 2.1 Hz), 7.11-7.09 (1H, m), 6.73-6.70 (2H, m), 3.60 (1H, dd, J = 14.1, 7.0 Hz), 3.19 (1H, dd, J = 14.1, 7.0 Hz), 2.78-2.68 (4H, m), 1.00 (3H, t, J = 7.0 Hz). |
| 5 | $^1$H-NMR (CDCl$_3$) δ: 8.47 (1H, d, J = 2.0 Hz), 7.71 (1H, d, J = 2.0 Hz), 7.33 (1H, d, J = 9.8 Hz), 7.19-7.16 (1H, m), 6.82-6.73 (3H, m), 3.32 (3H, s). |
| 6 | $^1$H-NMR (CDCl$_3$) δ: 8.52 (1H, d, J = 2.1 Hz), 7.65 (1H, d, J = 2.1 Hz), 7.30 (1H, dd, J = 9.5, 1.1 Hz), 7.20-7.17 (1H, m), 6.85-6.82 (1H, m), 6.77 (1H, d, J = 9.5 Hz), 6.70-6.68 (1H, m), 4.06 (1H, dd, J = 13.5, 7.0 Hz), 3.68 (1H, dd, J = 13.5, 7.0 Hz), 1.16 (3H, t, J = 7.0 Hz). |
| 7 | $^1$H-NMR (CDCl$_3$) δ: 8.20 (1H, d, J = 2.4 Hz), 7.32 (1H, d, J = 9.2 Hz), 7.17-7.14 (2H, m), 6.78-6.74 (3H, m), 3.85 (3H, s), 3.32 (3H, s). |
| 8 | $^1$H-NMR (CDCl$_3$) δ: 8.25 (1H, d, J = 2.8 Hz), 7.30 (1H, dd, J = 9.5, 0.9 Hz), 7.17-7.14 (1H, m), 7.10 (1H, d, J = 2.8 Hz), 6.83 (1H, t, J = 8.6 Hz), 6.74 (1H, d, J = 9.5 Hz), 6.68 (1H, t, J = 8.6 Hz), 4.05-4.02 (1H, m), 3.86 (3H, s), 3.77-3.75 (1H, m), 1.15 (3H, t, J = 7.0 Hz). |
| 9 | $^1$H-NMR (CDCl$_3$) δ: 8.26 (1H, d, J = 2.4 Hz), 7.45 (1H, d, J = 9.3 Hz), 7.19-7.13 (3H, m), 7.05-7.03 (2H, m), 6.75 (1H, d, J = 9.3 Hz), 3.86 (3H, s), 3.28 (3H, s). |
| 10 | $^1$H-NMR (CDCl$_3$) δ: 8.56 (1H, d, J = 2.1 Hz), 7.62 (1H, d, J = 2.1 Hz), 7.42 (1H, d, J = 9.2 Hz), 7.17-7.16 (3H, m), 7.03-7.00 (2H, m), 6.76 (1H, d, J = 9.2 Hz), 4.04-4.02 (1H, m), 3.63-3.60 (1H, m), 1.17 (3H, t, J = 7.0 Hz). |
| 11 | $^1$H-NMR (CDCl$_3$) δ: 8.29 (1H, d, J = 2.4 Hz), 7.42 (1H, d, J = 9.3 Hz), 7.16-7.14 (3H, m), 7.08 (1H, d, J = 2.4 Hz), 7.02-7.01 (2H, m), 6.74 (1H, d, J = 9.3 Hz), 4.04-3.97 (1H, m), 3.86 (3H, s), 3.70-3.67 (1H, m), 1.16 (3H, t, J = 7.1 Hz). |
| 12 | $^1$H-NMR (CDCl$_3$) δ: 8.66 (1H, s), 8.42 (1H, d, J = 4.6 Hz), 7.44 (1H, d, J = 9.5 Hz), 7.17-7.16 (3H, m), 7.02-6.99 (3H, m), 6.76 (1H, d, J = 9.5 Hz), 3.31 (3H, s). |
| 13 | $^1$H-NMR (CDCl$_3$) δ: 8.61 (1H, s), 8.44 (1H, d, J = 4.9 Hz), 7.41 (1H, d, J = 9.5 Hz), 7.16-7.16 (3H, m), 7.12 (1H, d, J = 4.9 Hz), 7.01-6.99 (2H, m), 6.74 (1H, d, J = 9.2 Hz), 4.25-4.22 (1H, m), 3.46-3.43 (1H, m), 1.12 (3H, t, J = 7.0 Hz). |
| 14 | $^1$H-NMR (CDCl$_3$) δ: 7.40 (1H, d, J = 9.5 Hz), 7.34 (1H, tt, J = 8.6, 6.1 Hz), 6.89 (2H, dd, J = 8.6, 7.2 Hz), 6.72 (1H, d, J = 9.5 Hz), 6.26 (1H, t, J = 2.3 Hz), 6.22 (2H, d, J = 2.3 Hz), 3.90 (2H, q, J = 7.1 Hz), 3.66 (6H, s), 1.14 (3H, t, J = 7.1 Hz). |
| 15 | $^1$H-NMR (CDCl$_3$) δ: 7.30-7.23 (1H, m), 6.83 (2H, dd, J = 8.6, 7.3 Hz), 6.20 (1H, t, J = 2.3 Hz), 6.13 (2H, d, J = 2.3 Hz), 3.62 (6H, s), 3.41 (2H, q, J = 7.1 Hz), 2.78-2.70 (4H, m), 0.96 (3H, t, J = 7.1 Hz). |
| 16 | $^1$H-NMR (CDCl$_3$) δ: 7.34-7.28 (2H, m), 6.90 (1H, t, J = 8.4 Hz), 6.83 (1H, t, J = 8.4 Hz), 6.73 (1H, d, J = 9.5 Hz), 6.30 (1H, d, J = 2.8 Hz), 6.28-6.27 (1H, m), 3.94-3.84 (2H, m), 3.81 (3H, s), 3.65 (3H, s), 1.16 (3H, t, J = 7.2 Hz). |
| 17 | $^1$H-NMR (CDCl$_3$) δ: 7.26 (1H, tt, J = 8.3, 6.4 Hz), 6.96-6.93 (2H, m), 6.84-6.79 (4H, m), 2.87 (3H, s), 2.78-2.73 (4H, m). |
| 18 | $^1$H-NMR (CDCl$_3$) δ: 7.26 (1H, tt, J = 8.3, 6.4 Hz), 6.95-6.92 (2H, m), 6.83-6.78 (4H, m), 3.41 (2H, q, J = 7.2 Hz), 2.74-2.72 (4H, m), 0.96 (3H, t, J = 7.2 Hz). |
| 19 | $^1$H-NMR (CDCl$_3$) δ: 7.38 (1H, d, J = 9.2 Hz), 7.34 (1H, tt, J = 8.3, 6.4 Hz), 7.02-7.00 (2H, m), 6.90-6.85 (4H, m), 6.75 (1H, d, J = 9.2 Hz), 3.38 (3H, s). |

TABLE 5-continued

| Compound | ¹H-NMR |
|---|---|
| 20 | ¹H-NMR (CDCl₃) δ: 7.36 (1H, d, J = 9.2 Hz), 7.33 (1H, tt, J = 8.4, 6.4 Hz), 7.03-7.01 (2H, m), 6.88-6.84 (4H, m), 6.73 (1H, d, J = 9.2 Hz), 3.90 (2H, q, J = 7.0 Hz), 1.14 (3H, t, J = 7.0 Hz). |
| 21 | ¹H-NMR (CDCl₃) δ: 8.47 (1H, d, J = 2.1 Hz), 7.66 (1H, d, J = 2.1 Hz), 6.91-6.88 (2H, m), 6.82 (2H, t, J = 8.6 Hz), 2.79-2.77 (7H, m). |
| 22 | ¹H-NMR (CDCl₃) δ: 8.55 (1H, d, J = 2.1 Hz), 7.84 (1H, s), 7.69 (1H, d, J = 2.1 Hz), 7.02-6.99 (2H, m), 6.88 (2H, t, J = 8.6 Hz), 3.34 (3H, s). |
| 23 | ¹H-NMR (CDCl₃) δ: 8.55 (1H, d, J = 2.1 Hz), 7.68 (1H, d, J = 2.1 Hz), 7.40 (1H, d, J = 9.5 Hz), 7.00 (2H, dd, J = 8.7, 5.4 Hz), 6.87 (2H, t, J = 8.7 Hz), 6.77 (1H, d, J = 9.5 Hz), 3.27 (3H, s). |
| 24 | ¹H-NMR (CDCl₃) δ: 8.47 (1H, d, J = 2.1 Hz), 7.63 (1H, d, J = 2.1 Hz), 6.89-6.87 (2H, m), 6.82-6.80 (2H, m), 3.46 (1H, dq, J = 14.1, 7.0 Hz), 3.22 (1H, dq, J = 14.1, 7.0 Hz), 2.82-2.71 (4H, m), 0.98 (3H, t, J = 7.2 Hz). |
| 25 | ¹H-NMR (CDCl₃) δ: 8.57 (1H, d, J = 2.1 Hz), 7.82 (1H, s), 7.64 (1H, d, J = 2.1 Hz), 6.99-6.98 (2H, m), 6.88-6.86 (2H, m), 4.07 (1H, dq, J = 13.5, 7.2 Hz), 3.64 (1H, dq, J = 13.5, 7.2 Hz), 1.19 (3H, t, J = 7.2 Hz). |
| 26 | ¹H-NMR (CDCl₃) δ: 8.57 (1H, d, J = 2.1 Hz), 7.64 (1H, d, J = 2.1 Hz), 7.38 (1H, d, J = 9.5 Hz), 6.99-6.97 (2H, m), 6.88-6.84 (2H, m), 6.75 (1H, d, J = 9.5 Hz), 4.01 (1H, dq, J = 13.5, 7.0 Hz), 3.60 (1H, dq, J = 13.5, 7.0 Hz), 1.17 (3H, t, J = 7.0 Hz). |
| 27 | ¹H-NMR (CDCl₃) δ: 7.28-7.26 (1H, m), 6.84 (2H, dd, J = 8.6, 7.0 Hz), 6.21 (1H, t, J = 2.3 Hz), 6.14 (2H, d, J = 2.3 Hz), 3.61 (6H, s), 2.87 (3H, s), 2.80-2.72 (4H, m). |
| 28 | ¹H-NMR (CDCl₃) δ: 7.43 (1H, d, J = 9.2 Hz), 7.36-7.34 (1H, m), 6.90 (2H, dd, J = 8.3, 7.0 Hz), 6.74 (1H, d, J = 9.2 Hz), 6.27 (1H, t, J = 2.3 Hz), 6.21 (2H, d, J = 2.3 Hz), 3.65 (6H, s), 3.37 (3H, s). |
| 29 | ¹H-NMR (CDCl₃) δ: 7.34 (1H, d, J = 9.2 Hz), 7.31-7.29 (1H, m), 6.91 (1H, t, J = 8.4 Hz), 6.83 (1H, t, J = 8.4 Hz), 6.75 (1H, d, J = 9.2 Hz), 6.31 (1H, d, J = 2.8 Hz), 6.23 (1H, dd, J = 2.8, 1.5 Hz), 3.81 (3H, s), 3.63 (3H, s), 3.37 (3H, s). |
| 30 | ¹H-NMR (CDCl₃) δ: 7.36 (1H, d, J = 9.5 Hz), 7.32-7.30 (1H, m), 6.90 (1H, t, J = 8.4 Hz), 6.83 (1H, t, J = 8.4 Hz), 6.75 (1H, d, J = 9.5 Hz), 6.34 (1H, d, J = 2.8 Hz), 6.19 (1H, dd, J = 2.8, 1.2 Hz), 3.81 (3H, s), 3.63 (3H, s), 3.38 (3H, s). |
| 31 | ¹H-NMR (CDCl₃) δ: 7.44 (1H, d, J = 9.3 Hz), 7.38-7.36 (1H, m), 6.93-6.88 (2H, m), 6.76 (1H, d, J = 9.3 Hz), 6.30 (2H, s), 3.74 (6H, s), 3.38 (3H, s). |
| 32 | ¹H-NMR (CDCl₃) δ: 7.35-7.28 (2H, m), 6.90 (1H, t, J = 8.6 Hz), 6.83 (1H, t, J = 8.6 Hz), 6.73 (1H, d, J = 9.2 Hz), 6.32 (1H, d, J = 2.8 Hz), 6.24 (1H, dd, J = 2.8, 1.4 Hz), 3.96-3.94 (1H, m), 3.88-3.85 (1H, m), 3.80 (3H, s), 3.58 (3H, s), 1.15 (3H, t, J = 7.2 Hz). |
| 33 | ¹H-NMR (CDCl₃) δ: 7.03 (1H, dd, J = 8.6, 2.8 Hz), 7.00-6.98 (1H, m), 6.74 (1H, td, J = 8.6, 2.8 Hz), 6.36-6.34 (1H, m), 6.30-6.28 (1H, m), 3.74 (3H, s), 3.52-3.49 (1H, m), 3.35-3.32 (1H, m), 2.84-2.73 (2H, m), 2.70-2.65 (1H, m), 2.55-2.49 (1H, m), 0.98 (3H, t, J = 7.0 Hz). |
| 34 | ¹H-NMR (CDCl₃) δ: 7.71 (1H, s), 7.07-7.05 (2H, m), 6.80 (1H, td, J = 8.3, 2.4 Hz), 6.42-6.40 (1H, m), 6.38-6.35 (1H, m), 3.96 (2H, q, J = 7.1 Hz), 3.77 (3H, s), 1.17 (3H, t, J = 7.1 Hz). |
| 35 | ¹H-NMR (CDCl₃) δ: 7.27 (1H, d, J = 9.5 Hz), 7.06-7.04 (2H, m), 6.79 (1H, td, J = 8.3, 2.5 Hz), 6.71 (1H, d, J = 9.5 Hz), 6.42-6.40 (1H, m), 6.37-6.35 (1H, m), 3.93-3.90 (2H, m), 3.77 (3H, s), 1.15 (3H, t, J = 7.2 Hz). |
| 36 | ¹H-NMR (CDCl₃) δ: 7.04 (1H, dd, J = 8.6, 2.8 Hz), 6.98-6.97 (1H, m), 6.75-6.73 (1H, m), 6.38-6.35 (1H, m), 6.30-6.27 (1H, m), 3.74 (3H, s), 2.89 (3H, s), 2.85-2.77 (2H, m), 2.72-2.66 (1H, m), 2.55-2.52 (1H, m). |
| 37 | ¹H-NMR (CDCl₃) δ: 7.30 (1H, d, J = 9.2 Hz), 7.07 (1H, dd, J = 8.4, 2.6 Hz), 7.04-7.00 (1H, m), 6.80 (1H, td, J = 8.4, 2.6 Hz), 6.73 (1H, d, J = 9.2 Hz), 6.43-6.41 (1H, m), 6.37-6.35 (1H, m), 3.77 (3H, s), 3.39 (3H, s). |
| 38 | ¹H-NMR (CDCl₃) δ: 7.73 (1H, s), 7.07 (1H, dd, J = 8.6, 2.4 Hz), 7.04-7.02 (1H, m), 6.84-6.80 (1H, m), 6.41-6.37 (2H, m), 3.77 (3H, s), 3.45 (3H, s). |
| 39 | ¹H-NMR (CDCl₃) δ: 7.41 (1H, d, J = 9.5 Hz), 7.37-7.35 (1H, m), 6.91-6.89 (2H, m), 6.75 (1H, d, J = 9.5 Hz), 6.28 (2H, s), 3.92-3.88 (2H, m), 3.75 (6H, s), 1.16 (3H, t, J = 7.2 Hz). |
| 40 | ¹H-NMR (CDCl3) δ: 7.41 (1H, d, J = 9.5 Hz), 7.37-7.35 (1H, m), 6.91-6.89 (2H, m), 6.75 (1H, d, J = 9.5 Hz), 6.31 (2H, s), 3.93-3.88 (2H, m), 3.76 (6H, s), 1.15 (3H, t, J = 7.0 Hz). |
| 41 | ¹H-NMR (CDCl₃) δ: 7.39 (1H, d, J = 9.3 Hz), 7.35-7.33 (1H, m), 6.89-6.87 (2H, m), 6.71 (1H, d, J = 9.3 Hz), 6.26 (1H, t, J = 2.4 Hz), 6.21 (2H, d, J = 2.4 Hz), 3.78-3.76 (2H, m), 3.66 (6H, s), 1.59-1.53 (2H, m), 0.74 (3H, t, J = 7.3 Hz). |
| 42 | ¹H-NMR (CDCl₃) δ: 7.32-7.30 (2H, m), 6.92-6.87 (1H, m), 6.84-6.80 (1H, m), 6.72 (1H, d, J = 9.3 Hz), 6.30 (1H, d, J = 2.9 Hz), 6.27-6.26 (1H, m), 3.85-3.83 (1H, m), 3.81 (3H, s), 3.72-3.66 (1H, m), 3.64 (3H, s), 1.61-1.57 (2H, m), 0.75 (3H, t, J = 7.3 Hz). |
| 43 | ¹H-NMR (CDCl₃) δ: 7.03 (1H, dd, J = 8.6, 2.8 Hz), 7.00-6.96 (1H, m), 6.74 (1H, td, J = 8.6, 2.8 Hz), 6.33-6.31 (1H, m), 6.25-6.23 (1H, m), 5.64-5.62 (1H, m), 4.97-4.95 (1H, m), 4.86-4.83 (1H, m), 4.18-4.15 (1H, m), 3.91-3.88 (1H, m), 3.73 (3H, s), 2.89-2.78 (2H, m), 2.74-2.69 (1H, m), 2.56-2.53 (1H, m). |
| 44 | ¹H-NMR (CDCl₃) δ: 7.29 (1H, d, J = 9.3 Hz), 7.06-7.03 (2H, m), 6.80-6.78 (1H, m), 6.73 (1H, d, J = 9.3 Hz), 6.39-6.37 (1H, m), 6.33-6.30 (1H, m), 5.81-5.71 (1H, m), 5.04-5.02 (1H, m), 4.79 (1H, d, J = 17.1 Hz), 4.59-4.56 (1H, m), 4.49-4.45 (1H, m), 3.76 (3H, s). |
| 45 | ¹H-NMR (CDCl₃) δ: 7.32 (1H, d, J = 9.3 Hz), 7.08-7.04 (2H, m), 6.81 (1H, td, J = 8.3, 2.6 Hz), 6.73 (1H, d, J = 9.3 Hz), 6.39-6.35 (2H, m), 4.62 (2H, dt, J = 47.3, 5.1 Hz), 4.19 (2H, dt, J = 24.1, 5.1 Hz), 3.76 (3H, s). |
| 46 | ¹H-NMR (CDCl₃) δ: 7.40 (1H, d, J = 9.5 Hz), 7.32-7.29 (1H, m), 7.17-7.15 (3H, m), 7.06-7.04 (2H, m), 6.85 (2H, dd, J = 8.5, 7.1 Hz), 6.73 (1H, d, J = 9.5 Hz), 3.91 (2H, q, J = 7.0 Hz), 1.14 (3H, t, J = 7.0 Hz). |
| 47 | ¹H-NMR (CDCl₃) δ: 7.43 (1H, d, J = 9.5 Hz), 7.33-7.30 (1H, m), 7.18-7.16 (3H, m), 7.05-7.04 (2H, m), 6.88-6.84 (2H, m), 6.75 (1H, d, J = 9.5 Hz), 3.38 (3H, s). |
| 48 | ¹H-NMR (CDCl₃) δ: 7.63 (1H, s), 7.32 (1H, tt, J = 8.6, 6.7 Hz), 7.18-7.16 (3H, m), 7.06-7.04 (2H, m), 6.86-6.85 (2H, m), 3.96 (2H, q, J = 7.0 Hz), 1.17 (3H, t, J = 7.0 Hz). |

TABLE 5-continued

| Compound | ¹H-NMR |
|---|---|
| 49 | ¹H-NMR (CDCl₃) δ: 7.66 (1H, s), 7.34 (1H, tt, J = 8.6, 6.7 Hz), 7.19-7.17 (3H, m), 7.05-7.03 (2H, m), 6.87-6.86 (2H, m), 3.45 (3H, s). |
| 50 | ¹H-NMR (CDCl₃) δ: 7.84 (1H, s), 7.32 (1H, tt, J = 8.6, 6.7 Hz), 7.18-7.16 (3H, m), 7.06-7.04 (2H, m), 6.86-6.85 (2H, m), 3.96 (2H, q, J = 7.0 Hz), 1.17 (3H, t, J = 7.0 Hz). |
| 51 | ¹H-NMR (CDCl₃) δ: 7.86 (1H, s), 7.34 (1H, tt, J = 8.4, 6.7 Hz), 7.19-7.16 (3H, m), 7.05-7.03 (2H, m), 6.88-6.84 (2H, m), 3.45 (3H, s). |
| 52 | ¹H-NMR (CDCl₃) δ: 7.22-7.21 (1H, m), 7.14 (1H, d, J = 8.9 Hz), 6.83 (1H, t, J = 8.6 Hz), 6.75 (1H, t, J = 8.6 Hz), 6.61 (1H, dd, J = 8.9, 3.1 Hz), 6.57-6.57 (1H, m), 3.63 (3H, s), 3.52-3.49 (1H, m), 3.35-3.32 (1H, m), 2.85-2.83 (2H, m), 2.72-2.69 (1H, m), 2.58-2.56 (1H, m), 0.99 (3H, t, J = 7.2 Hz). |
| 53 | ¹H-NMR (CDCl₃) δ: 7.33 (1H, d, J = 9.5 Hz), 7.31-7.30 (1H, m), 7.18 (1H, d, J = 8.9 Hz), 6.90 (1H, t, J = 8.4 Hz), 6.83 (1H, t, J = 8.4 Hz), 6.73 (1H, d, J = 9.5 Hz), 6.66 (1H, dd, J = 8.9, 3.1 Hz), 6.61-6.61 (1H, m), 3.94-3.87 (2H, m), 3.65 (3H, s), 1.16 (3H, t, J = 7.0 Hz). |
| 54 | ¹H-NMR (CDCl₃) δ: 7.57 (1H, s), 7.34-7.31 (1H, m), 7.18 (1H, d, J = 8.6 Hz), 6.90 (1H, t, J = 8.3 Hz), 6.84 (1H, t, J = 8.3 Hz), 6.68 (1H, dd, J = 8.6, 3.1 Hz), 6.61 (1H, dd, J = 3.1, 1.5 Hz), 3.96-3.95 (2H, m), 3.65 (3H, s), 1.18 (3H, t, J = 7.0 Hz). |
| 55 | ¹H-NMR (CDCl₃) δ: 7.77 (1H, s), 7.34-7.32 (1H, m), 7.17 (1H, d, J = 8.9 Hz), 6.90 (1H, t, J = 8.4 Hz), 6.84 (1H, t, J = 8.4 Hz), 6.68 (1H, dd, J = 8.9, 2.8 Hz), 6.61-6.61 (1H, m), 3.97-3.94 (2H, m), 3.65 (3H, s), 1.18 (3H, t, J = 7.0 Hz). |
| 56 | ¹H-NMR (CDCl₃) δ: 7.24-7.20 (1H, m), 7.15 (1H, d, J = 8.9 Hz), 6.84 (1H, t, J = 8.6 Hz), 6.76 (1H, t, J = 8.6 Hz), 6.61 (1H, dd, J = 8.9, 3.2 Hz), 6.56-6.55 (1H, m), 3.62 (3H, s), 2.89 (3H, s), 2.88-2.85 (2H, m), 2.75-2.69 (1H, m), 2.59-2.56 (1H, m). |
| 57 | ¹H-NMR (CDCl₃) δ: 7.36 (1H, d, J = 9.5 Hz), 7.34-7.30 (1H, m), 7.18 (1H, d, J = 8.9 Hz), 6.90 (1H, t, J = 8.4 Hz), 6.84 (1H, t, J = 8.4 Hz), 6.75 (1H, d, J = 9.5 Hz), 6.68 (1H, dd, J = 8.9, 3.1 Hz), 6.58 (1H, dd, J = 3.1, 1.5 Hz), 3.64 (3H, s), 3.39 (3H, s). |
| 58 | ¹H-NMR (CDCl₃) δ: 7.24-7.20 (1H, m), 7.02 (1H, dd, J = 8.6, 2.4 Hz), 7.00-6.97 (1H, m), 6.81 (1H, t, J = 8.4 Hz), 6.75 (1H, t, J = 8.4 Hz), 6.73-6.69 (1H, m), 3.52-3.49 (1H, m), 3.34-3.31 (1H, m), 2.87-2.76 (2H, m), 2.72-2.70 (1H, m), 2.56-2.53 (1H, m), 0.98 (3H, t, J = 7.0 Hz). |
| 59 | ¹H-NMR (CDCl₃) δ: 7.32-7.31 (2H, m), 7.05-7.04 (2H, m), 6.89 (1H, t, J = 8.4 Hz), 6.83 (1H, t, J = 8.4 Hz), 6.76-6.73 (2H, m), 3.97-3.83 (2H, m), 1.15 (3H, t, J = 7.0 Hz). |
| 60 | ¹H-NMR (CDCl₃) δ: 7.59 (1H, s), 7.35-7.32 (1H, m), 7.18 (1H, d, J = 8.9 Hz), 6.90 (1H, t, J = 8.6 Hz), 6.85 (1H, t, J = 8.6 Hz), 6.69 (1H, dd, J = 8.9, 3.1 Hz), 6.59-6.58 (1H, m), 3.65 (3H, s), 3.45 (3H, s). |
| 61 | ¹H-NMR (CDCl₃) δ: 7.79 (1H, s), 7.35-7.32 (1H, m), 7.18 (1H, d, J = 8.9 Hz), 6.90 (1H, t, J = 8.4 Hz), 6.85 (1H, t, J = 8.4 Hz), 6.69 (1H, dd, J = 8.9, 3.1 Hz), 6.58 (1H, dd, J = 3.1, 1.5 Hz), 3.65 (3H, s), 3.45 (3H, s). |
| 62 | ¹H-NMR (CDCl₃) δ: 7.53 (1H, s), 7.34-7.33 (1H, m), 7.07-7.04 (2H, m), 6.91-6.88 (1H, m), 6.86-6.84 (1H, m), 6.79-6.76 (1H, m), 3.97-3.94 (2H, m), 1.18 (3H, t, J = 7.2 Hz). |
| 63 | ¹H-NMR (CDCl₃) δ: 7.73 (1H, s), 7.34-7.32 (1H, m), 7.06-7.04 (2H, m), 6.91-6.87 (1H, m), 6.86-6.84 (1H, m), 6.79-6.75 (1H, m), 3.97-3.94 (2H, m), 1.18 (3H, t, J = 7.2 Hz). |
| 64 | ¹H-NMR (CDCl₃) δ: 7.34-7.31 (2H, m), 7.06 (1H, dd, J = 8.4, 2.6 Hz), 7.04-7.00 (1H, m), 6.89 (1H, t, J = 8.6 Hz), 6.84 (1H, t, J = 8.6 Hz), 6.78-6.75 (2H, m), 3.38 (3H, s). |
| 65 | ¹H-NMR (CDCl₃) δ: 7.32 (1H, d, J = 9.2 Hz), 7.29-7.25 (1H, m), 6.98 (1H, t, J = 8.1 Hz), 6.88 (1H, t, J = 8.4 Hz), 6.80 (1H, t, J = 8.4 Hz), 6.76-6.72 (2H, m), 6.69-6.67 (1H, m), 3.98-3.95 (1H, m), 3.88-3.80 (1H, m), 3.85 (3H, s), 1.16 (3H, t, J = 7.0 Hz). |
| 66 | ¹H-NMR (CDCl₃) δ: 7.75 (1H, s), 7.33-7.26 (1H, m), 6.99 (1H, t, J = 7.9 Hz), 6.90-6.85 (1H, m), 6.82-6.80 (1H, m), 6.78-6.76 (1H, m), 6.69-6.67 (1H, m), 3.97-3.92 (2H, m), 3.84 (3H, s), 1.18 (3H, t, J = 7.0 Hz). |
| 67 | ¹H-NMR (CDCl₃) δ: 7.34-7.25 (1H, m), 7.15 (1H, d, J = 9.5 Hz), 6.87-6.83 (1H, m), 6.82-6.80 (1H, m), 6.76 (1H, d, J = 9.5 Hz), 6.43 (1H, s), 4.02 (1H, dq, J = 14.5, 7.2 Hz), 3.90 (1H, dq, J = 14.5, 7.2 Hz), 3.86 (3H, s), 3.85 (3H, s), 1.14 (3H, t, J = 7.2 Hz). |
| 68 | ¹H-NMR (CDCl₃) δ: 7.31-7.28 (1H, m), 7.17 (1H, d, J = 9.5 Hz), 6.84-6.82 (2H, m), 6.76 (1H, d, J = 9.5 Hz), 6.45 (1H, s), 3.96 (2H, q, J = 7.0 Hz), 3.85 (6H, s), 1.14 (3H, t, J = 7.0 Hz). |
| 69 | ¹H-NMR (CDCl₃) δ: 7.39 (1H, s), 7.33-7.30 (1H, m), 6.88-6.80 (2H, m), 6.43 (1H, s), 4.05-3.96 (2H, m), 3.86-3.85 (6H, m), 1.16 (3H, t, J = 7.0 Hz). |
| 70 | ¹H-NMR (CDCl₃) δ: 7.59 (1H, s), 7.33-7.30 (1H, m), 6.88-6.80 (2H, m), 6.43 (1H, s), 4.07 (1H, dq, J = 13.9, 6.9 Hz), 3.94 (1H, dq, J = 13.9, 6.9 Hz), 3.86 (3H, s), 3.85 (3H, s), 1.16 (3H, t, J = 6.9 Hz). |
| 71 | ¹H-NMR (CDCl₃) δ: 7.38 (1H, d, J = 9.5 Hz), 6.70 (1H, d, J = 9.5 Hz), 6.43-6.40 (2H, m), 6.28 (1H, t, J = 2.1 Hz), 6.23 (2H, d, J = 2.1 Hz), 3.90 (2H, q, J = 7.1 Hz), 3.78 (3H, s), 3.68 (6H, s), 1.14 (3H, t, J = 7.1 Hz). |
| 72 | ¹H-NMR (CDCl₃) δ: 7.30 (1H, d, J = 9.5 Hz), 6.71 (1H, d, J = 9.5 Hz), 6.44-6.41 (1H, m), 6.36-6.34 (1H, m), 6.32 (1H, d, J = 2.8 Hz), 6.28 (1H, dd, J = 2.8, 1.7 Hz), 3.92-3.87 (2H, m), 3.82 (3H, s), 3.77 (3H, s), 3.67 (3H, s), 1.16 (3H, t, J = 7.0 Hz). |
| 73 | ¹H-NMR (CDCl₃) δ: 7.30 (1H, d, J = 9.2 Hz), 6.71 (1H, d, J = 9.2 Hz), 6.43-6.41 (1H, m), 6.37-6.34 (2H, m), 6.24 (1H, dd, J = 2.7, 1.5 Hz), 3.95-3.93 (1H, m), 3.88-3.86 (1H, m), 3.82 (3H, s), 3.76 (3H, s), 3.66 (3H, s), 1.16 (3H, t, J = 7.2 Hz). |
| 74 | ¹H-NMR (CDCl₃) δ: 7.33 (1H, d, J = 9.5 Hz), 7.31-7.25 (2H, m), 7.13-7.09 (1H, m), 7.09-7.04 (1H, m), 7.03-7.00 (1H, m), 6.88 (1H, t, J = 8.4 Hz), 6.80 (1H, t, J = 8.4 Hz), 6.73 (1H, d, J = 9.5 Hz), 3.99-3.92 (1H, m), 3.90-3.83 (1H, m), 1.16 (3H, t, J = 7.0 Hz). |
| 75 | ¹H-NMR (CDCl₃) δ: 7.57 (1H, s), 7.33-7.28 (2H, m), 7.14-7.11 (1H, m), 7.07-7.01 (2H, m), 6.88 (1H, t, J = 8.4 Hz), 6.82 (1H, t, J = 8.4 Hz), 4.02-3.90 (2H, m), 1.18 (3H, t, J = 7.0 Hz). |
| 76 | ¹H-NMR (CDCl₃) δ: 7.77 (1H, s), 7.33-7.27 (2H, m), 7.14-7.11 (1H, m), 7.07-7.01 (2H, m), 6.88 (1H, t, J = 8.4 Hz), 6.81 (1H, t, J = 8.4 Hz), 4.02-3.88 (2H, m), 1.18 (3H, t, J = 7.0 Hz). |
| 77 | ¹H-NMR (CDCl₃) δ: 7.36 (1H, d, J = 9.5 Hz), 7.32-7.26 (2H, m), 7.14-7.10 (1H, m), 7.03 (2H, d, J = 4.6 Hz), 6.88 (1H, t, J = 8.4 Hz), 6.81 (1H, t, J = 8.4 Hz), 6.75 (1H, d, J = 9.5 Hz), 3.39 (3H, s). |

TABLE 5-continued

| Compound | ¹H-NMR |
|---|---|
| 78 | ¹H-NMR (CDCl₃) δ: 7.59 (1H, s), 7.34-7.26 (2H, m), 7.16-7.12 (1H, m), 7.05-7.04 (2H, m), 6.88 (1H, t, J = 8.4 Hz), 6.82 (1H, t, J = 8.4 Hz), 3.45 (3H, s). |
| 79 | ¹H-NMR (CDCl₃) δ: 7.79 (1H, s), 7.34-7.28 (2H, m), 7.15-7.12 (1H, m), 7.05-7.03 (2H, m), 6.88 (1H, t, J = 8.4 Hz), 6.82 (1H, t, J = 8.4 Hz), 3.46 (3H, s). |
| 80 | ¹H-NMR (CDCl₃) δ: 7.41 (1H, d, J = 9.5 Hz), 6.72 (1H, d, J = 9.5 Hz), 6.44-6.41 (2H, m), 6.29 (1H, t, J = 2.1 Hz), 6.22 (2H, d, J = 2.1 Hz), 3.78 (3H, s), 3.67 (6H, s), 3.37 (3H, s). |
| 81 | ¹H-NMR (CDCl₃) δ: 7.32 (1H, d, J = 9.5 Hz), 6.72 (1H, d, J = 9.5 Hz), 6.45-6.42 (1H, m), 6.37-6.35 (1H, m), 6.33 (1H, d, J = 2.8 Hz), 6.24 (1H, dd, J = 2.8, 1.7 Hz), 3.83 (3H, s), 3.76 (3H, s), 3.66 (3H, s), 3.38 (3H, s). |
| 82 | ¹H-NMR (CDCl₃) δ: 7.33 (1H, d, J = 9.5 Hz), 6.72 (1H, d, J = 9.5 Hz), 6.44-6.42 (1H, m), 6.37-6.36 (2H, m), 6.21 (1H, dd, J = 2.6, 1.4 Hz), 3.83 (3H, s), 3.77 (3H, s), 3.66 (3H, s), 3.38 (3H, s). |
| 83 | ¹H-NMR (CDCl₃) δ: 7.61 (1H, s), 7.32-7.29 (1H, m), 6.85-6.83 (2H, m), 6.45 (1H, s), 4.01 (2H, q, J = 7.2 Hz), 3.85 (6H, s), 1.16 (3H, t, J = 7.2 Hz). |
| 84 | ¹H-NMR (CDCl₃) δ: 7.41 (1H, s), 7.32-7.29 (1H, m), 6.85-6.84 (2H, m), 6.45 (1H, s), 4.00 (2H, q, J = 7.0 Hz), 3.85 (6H, s), 1.16 (3H, t, J = 7.0 Hz). |
| 85 | ¹H-NMR (CDCl₃) δ: 7.50 (1H, d, J = 7.6 Hz), 7.33 (1H, d, J = 9.5 Hz), 7.31-7.25 (1H, m), 7.07 (2H, d, J = 4.3 Hz), 7.05-7.00 (1H, m), 6.89 (1H, t, J = 8.4 Hz), 6.80 (1H, t, J = 8.4 Hz), 6.73 (1H, d, J = 9.5 Hz), 3.99-3.91 (1H, m), 3.89-3.81 (1H, m), 1.16 (3H, t, J = 7.2 Hz). |
| 86 | ¹H-NMR (CDCl₃) δ: 7.56 (1H, s), 7.51 (1H, d, J = 7.3), 7.32-7.28 (1H, m), 7.08-7.03 (3H, m), 6.89 (1H, t, J = 8.4 Hz), 6.81 (1H, t, J = 8.4 Hz), 4.01-3.88 (2H, m), 1.19 (3H, t, J = 7.0 Hz). |
| 87 | ¹H-NMR (CDCl₃) δ: 7.77 (1H, s), 7.50 (1H, d, J = 7.6 Hz), 7.33-7.28 (1H, m), 7.08-7.03 (3H, m), 6.89 (1H, t, J = 8.4 Hz), 6.81 (1H, t, J = 8.4 Hz), 4.02-3.89 (2H, m), 1.19 (3H, t, J = 7.2 Hz). |
| 88 | ¹H-NMR (CDCl₃) δ: 7.80 (1H, d, J = 0.9 Hz), 7.37-7.32 (1H, m), 6.89-6.87 (2H, m), 6.83 (1H, t, J = 9.0 Hz), 6.70-6.66 (1H, m), 6.54 (1H, dd, J = 5.8, 3.1 Hz), 3.97 (2H, q, J = 7.0 Hz), 3.66 (3H, s), 1.17 (3H, t, J = 7.0 Hz). |
| 89 | ¹H-NMR (CDCl₃) δ: 7.37-7.31 (2H, m), 6.89-6.80 (3H, m), 6.73 (1H, d, J = 9.2 Hz), 6.68-6.66 (1H, m), 6.54 (1H, dd, J = 6.1, 3.1 Hz), 3.92 (2H, q, J = 7.0 Hz), 3.65 (3H, s), 1.15 (3H, t, J = 7.0 Hz). |
| 90 | ¹H-NMR (CDCl₃) δ: 7.82 (1H, d, J = 0.9 Hz), 7.37-7.34 (1H, m), 6.89-6.87 (2H, m), 6.83 (1H, t, J = 9.0 Hz), 6.71-6.68 (1H, m), 6.54-6.53 (1H, m), 3.66 (3H, s), 3.47 (3H, s). |
| 91 | ¹H-NMR (CDCl₃) δ: 7.39 (1H, dd, J = 9.2, 1.1 Hz), 7.35-7.32 (1H, m), 6.89-6.87 (2H, m), 6.83 (1H, t, J = 9.0 Hz), 6.75 (1H, d, J = 9.2 Hz), 6.69-6.67 (1H, m), 6.53 (1H, dd, J = 5.8, 3.1 Hz), 3.65 (3H, s), 3.40 (3H, s). |
| 92 | ¹H-NMR (CDCl₃) δ: 7.60 (1H, d, J = 0.9 Hz), 7.37-7.32 (1H, m), 6.89-6.87 (2H, m), 6.83 (1H, t, J = 9.0 Hz), 6.70-6.66 (1H, m), 6.54 (1H, dd, J = 5.8, 3.1 Hz), 3.97 (2H, q, J = 7.1 Hz), 3.66 (3H, s), 1.17 (3H, t, J = 7.1 Hz). |
| 93 | ¹H-NMR (CDCl₃) δ: 7.62 (1H, d, J = 0.9 Hz), 7.37-7.33 (1H, m), 6.89-6.87 (2H, m), 6.83 (1H, t, J = 9.0 Hz), 6.71-6.68 (1H, m), 6.54-6.53 (1H, m), 3.65 (3H, s), 3.46 (3H, s). |
| 94 | ¹H-NMR (CDCl₃) δ: 7.51 (1H, d, J = 9.2 Hz), 7.36 (1H, d, J = 9.5 Hz), 7.32-7.27 (1H, m), 7.09-7.02 (3H, m), 6.89 (1H, t, J = 8.4 1 Hz), 6.80 (1H, t, J = 8.4 Hz), 6.75 (1H, d, J = 9.5 Hz), 3.38 (3H, s). |
| 95 | ¹H-NMR (CDCl₃) δ: 7.58 (1H, s), 7.51 (1H, dd, J = 7.6, 1.2 Hz), 7.34-7.28 (1H, m), 7.10-7.02 (3H, m), 6.89 (1H, t, J = 8.4 Hz), 6.82 (1H, t, J = 8.4 Hz), 3.45 (3H, s). |
| 96 | ¹H-NMR (CDCl₃) δ: 7.79 (1H, s), 7.51 (1H, dd, J = 7.6, 1.5 Hz), 7.33-7.27 (1H, m), 7.10-7.02 (3H, m), 6.89 (1H, t, J = 8.4 Hz), 6.82 (1H, t, J = 8.4 Hz), 3.45 (3H, t, J = 7.2 Hz). |
| 97 | ¹H-NMR (CDCl₃) δ: 7.34(1H, d, J = 9.2 Hz), 7.33-7.28(1H, m), 7.18(1H, d, J = 9.2 Hz), 6.90(1H, t, J = 8.3 Hz), 6.82(1H, t, J = 8.3 Hz), 6.79-6.76(2H, m), 6.73(1H, d.J = 9.2 Hz), 5.01(1H, d, J = 7.0 Hz), 4.96(1H, d, J = 7.0 Hz), 4.00-3.81(2H, m), 3.38(3H, s), 1.16(3H, t, J = 7.0 Hz). |
| 98 | ¹H-NMR (CDCl₃) δ: 7.33-7.28 (3H, m), 6.94 (1H, t, J = 8.6 Hz), 6.85 (1H, t, J = 8.6 Hz), 6.78 (1H, dd, J = 8.9, 3.1 Hz), 6.75-6.72 (2H, m), 4.65 (1H, d, J = 16.2 Hz), 4.61 (1H, d, J = 16.2 Hz), 3.91 (2H, q, J = 7.1 Hz), 1.16 (3H, t, J = 7.1 Hz). |
| 99 | ¹H-NMR (CDCl₃) δ: 7.33 (1H, d, J = 9.5 Hz), 7.35-7.27(1H, m), 7.16(1H, d, J = 8.9 Hz), 6.89(1H, t, J = 8.6 Hz), 6.84(1H, t, J = 8.3 Hz), 6.73 (1H, d, J = 9.2 Hz), 6.65(1H, dd, J = 8.9 Hz, J = 3.1 Hz), 6.61-6.59(1H, m), 3.98-3.74(4H, m), 1.33(3H, t, J = 6.7 Hz), 1.16(3H, t, J = 7.0 Hz). |
| 100 | ¹H-NMR (CDCl₃) δ: 7.40(1H, d, J = 9.4 Hz), 7.37-7.28(1H, m), 7.07(1H, t, J = 7.9 Hz), 6.90-6.83(2H, m), 6.73(1H, d, J = 9.2 Hz), 6.72-6.58(3H, m), 3.90(2H, q.J = 7.3 Hz), 3.68(3H, s), 1.14(3H, t, J = 7.3 Hz). |
| 101 | ¹H-NMR (CDCl₃) δ: 7.40 (1H, d, J = 9.2 Hz), 7.39-7.28(2H, m), 7.09(1H, t, J = 8.0 Hz), 6.92-6.79(3H, m), 6.76-6.69(2H, m), 5.03 (2H, s), 3.90(2H, q, J = 7.0 Hz), 3.40(3H, s), 1.14(3H, t, J = 7.0 Hz). |
| 102 | ¹H-NMR (CDCl₃) δ: 7.38 (1H, d, J = 9.5 Hz), 7.38-7.30(1H, m), 7.15(1H, t, J = 8.3 Hz), 6.91-6.85(2H, m), 6.81-6.77(2H, m), 6.74 (1H, d, J = 9.2 Hz), 6.70-6.68(1H, m), 4.66(2H, s), 3.90(2H, q, J = 7.0 Hz), 1.15(3H, t, J = 7.0 Hz). |
| 103 | ¹H-NMR (CDCl₃) δ: 7.39 (1H, d, J = 9.2 Hz), 7.38-7.29(1H, m), 7.05(1H, t, J = 8.0 Hz), 6.92-6.81(2H, m), 6.72(1H, d, J = 9.5 Hz), 6.71-6.67(1H, m), 6.63-6.58 (2H, m), 3.93-3.85(4H, m), 1.35(3H, t, J = 7.0 Hz), 1.14(3H, t, J = 7.0 Hz). |
| 104 | ¹H-NMR (CDCl₃) δ: 7.35-7.33 (1H, m), 7.30 (1H, d, J = 9.5 Hz), 6.87-6.86 (2H, m), 6.77-6.75 (2H, m), 6.66 (1H, td, J = 8.8, 1.9 Hz), 3.98-3.93 (2H, m), 3.78 (3H, s), 1.14 (3H, t, J = 7.0 Hz). |
| 105 | ¹H-NMR (CDCl₃) δ: 7.74 (1H, s), 7.36-7.32 (1H, m), 6.88-6.86 (2H, m), 6.78-6.76 (1H, m), 6.67 (1H, td, J = 8.8, 2.0 Hz), 4.01-3.99 (2H, m), 3.78 (3H, s), 1.17 (3H, t, J = 7.0 Hz). |
| 106 | ¹H-NMR (CDCl₃) δ: 7.54 (1H, s), 7.35-7.33 (1H, m), 6.87 (2H, t, J = 8.0 Hz), 6.79-6.77 (1H, m), 6.67 (1H, td, J = 8.7, 1.8 Hz), 4.03-3.98 (2H, m), 3.78 (3H, s), 1.17 (3H, t, J = 7.2 Hz). |

TABLE 5-continued

| Compound | ¹H-NMR |
|---|---|
| 107 | ¹H-NMR (CDCl₃) δ: 7.36-7.28(1H, m), 7.32 (1H, d, J = 9.5 Hz), 7.29(1H, d, J = 8.6 Hz), 6.92(1Ht,J = 8.6 Hz), 6.87-6.81(2H, m), 6.73(1H, d, J = 9.5 Hz), 3.97-3.84(2H, m), 2.24 (3H, s), 1.16(3H, t, J = 7.0 Hz). |
| 108 | ¹H-NMR (CDCl₃) δ: 7.37-7.29 (2H, m), 6.89-6.84 (2H, m), 6.78-6.76 (2H, m), 6.67 (1H, td, J = 8.9, 1.8 Hz), 3.78 (3H, s), 3.42 (3H, s). |
| 109 | ¹H-NMR (CDCl₃) δ: 7.77 (1H, s), 7.36-7.34 (1H, m), 6.89-6.87 (2H, m), 6.80-6.78 (1H, m), 6.68 (1H, td, J = 8.9, 2.1 Hz), 3.78 (3H, s), 3.49 (3H, s). |
| 110 | ¹H-NMR (CDCl₃) δ: 7.57 (1H, s), 7.37-7.33 (1H, m), 6.89-6.87 (2H, m), 6.80-6.78 (1H, m), 6.68 (1H, td, J = 8.9, 1.8 Hz), 3.78 (3H, s), 3.48 (3H, s). |
| 111 | ¹H-NMR (CDCl₃) δ: 7.79 (1H, dd, J = 7.8, 1.1 Hz), 7.30 (1H, d, J = 9.5 Hz), 7.28-7.26 (1H, m), 7.11 (1H, dd, J = 7.6, 1.2 Hz), 7.07 (1H, ddd, J = 9.6, 4.8, 2.2 Hz), 6.89 (1H, t, J = 8.6 Hz), 6.85 (1H, ddd, J = 8.4, 6.6, 1.4 Hz), 6.8 (1H, t, J = 8.3 Hz), 6.74 (1H, d. J = 9.5 Hz), 3.94 (1H, td, J = 13.8, 6.9 Hz), 3.85 (1H, td, J = 13.8, 6.9 Hz), 1.17 (3H, t, J = 7.2 Hz). |
| 112 | ¹H-NMR (CDCl₃) δ: 7.79 (1H, dd, J = 8.1, 1.1 Hz), 7.31 (1H, ddd, J = 12.1, 6.9, 3.6 Hz), 7.11 (1H, td, J = 7.3, 1.2 Hz), 7.07 (1H, dt, J = 7.6, 1.8 Hz), 6.92-6.84 (2H, m), 6.84 (1H, tt, J = 8.4, 1.1 Hz), 3.94 (2H, dq, J = 27.0, 6.8 Hz), 1.19 (3H, t, J = 7.0 Hz). |
| 113 | ¹H-NMR (CDCl₃) δ: 7.79 (1H, dd, J = 8.0, 1.2 Hz), 7.30 (1H, tt, J = 8.4, 3.5 Hz), 7.11 (1H, td, J = 7.3, 1.2 Hz), 7.06 (1H, dt, J = 7.6, 1.8 Hz), 6.92-6.85 (2H, m), 6.81 (1H, t, J = 8.3 Hz), 3.95 (2H, m), 1.19 (3H, t, J = 7.0 Hz). |
| 114 | ¹H-NMR (CDCl₃) δ: 7.80 (1H, dd, J = 8.0, 1.2 Hz), 7.33 (1H, d, J = 9.5 Hz), 7.27-7.31 (1H, m), 7.10 (1H, td, J = 7.5, 1.2 Hz), 7.03 (1H, dt, J = 7.6, 1.7 Hz), 6.91-6.94 (2H, m), 6.80 (1H, t, J = 8.4 Hz), 6.76 (1H, d, J = 9.5 Hz), 3.38 (3H, s). |
| 115 | ¹H-NMR (CDCl₃) δ: 7.80 (1H, dd, J = 7.9, 1.2 Hz), 7.56 (1H, s), 7.31 (1H, tt, J = 8.5, 3.6 Hz), 7.12 (1H, td, J = 7.5, 1.2 Hz), 7.04 (1H, dt, J = 7.7, 1.7 Hz), 6.93-6.89 (m, 1H), 6.87 (1H, dd, J = 7.8, 1.7 Hz), 6.81 (1H, tt, J = 8.5, 1.0 Hz), 3.45 (3H, s). |
| 116 | ¹H-NMR (CDCl₃) δ: 7.80 (1H, dd, J = 7.9, 1.2 Hz), 7.76 (1H, s), 7.31 (1H, tt, J = 8.5, 3.6 Hz), 7.11 (1H, td, J = 7.5, 1.2 Hz), 7.03 (1H, dt, J = 7.7, 1.8 Hz), 6.92-6.89 (m, 1H), 6.88-6.85 (1H, m), 6.81 (1H, tt, J = 8.4, 1.0 Hz), 3.45 (3H, s). |
| 117 | ¹H-NMR (CDCl₃) δ: 7.21 (1H, tt, J = 8.3, 6.4 Hz), 6.83-6.81 (1H, m), 6.77-6.73 (1H, m), 6.28 (1H, d, J = 2.7 Hz), 6.20 (1H, dd, J = 2.7, 1.5 Hz), 3.79 (3H, s), 3.63 (3H, s), 3.50 (1H, dd, J = 14.3, 7.2 Hz), 3.32 (1H, dd, J = 14.3, 7.2 Hz), 2.91-2.80 (2H, m), 2.71-2.67 (1H, m), 2.59-2.51 (1H, m), 0.99 (3H, t, J = 7.2 Hz). |
| 118 | ¹H-NMR (CDCl₃) δ: 6.88 (2H, dd, J = 9.6, 2.9 Hz), 6.23 (1H, t, J = 2.3 Hz), 6.12 (2H, d, J = 2.3 Hz), 3.65 (6H, s), 3.40 (2H, q, J = 7.0 Hz), 2.73-2.71 (4H, m), 0.97 (3H, t, J = 7.0 Hz). |
| 119 | ¹H-NMR (CDCl₃) δ: 7.37 (1H, d, J = 9.5 Hz), 6.94-6.93 (2H, m), 6.72 (1H, d, J = 9.5 Hz), 6.30 (1H, t, J = 2.1 Hz), 6.20 (2H, d, J = 2.1 Hz), 3.87 (2H, q, J = 7.0 Hz), 3.69 (6H, s), 1.14 (3H, t, J = 7.0 Hz). |
| 120 | ¹H-NMR (CDCl₃) δ: 7.29 (1H, d, J = 9.5 Hz), 6.94 (1H, dt, J = 8.6, 1.8 Hz), 6.88 (1H, dt, J = 8.6, 1.8 Hz), 6.73 (1H, d, J = 9.5 Hz), 6.34 (1H, d, J = 2.1 Hz), 6.27-6.26 (1H, m), 3.88-3.86 (2H, m), 3.83 (3H, s), 3.68 (3H, s), 1.16 (3H, t, J = 7.2 Hz). |
| 121 | ¹H-NMR (CDCl₃) δ: 7.30 (1H, d, J = 9.5 Hz), 6.93 (1H, dt, J = 8.4, 1.8 Hz), 6.89 (1H, dt, J = 8.4, 1.8 Hz), 6.73 (1H, d, J = 9.5 Hz), 6.38 (1H, d, J = 2.7 Hz), 6.23 (1H, dd, J = 2.7, 1.8 Hz), 3.90-3.86 (2H, m), 3.83 (3H, s), 3.67 (3H, s), 1.16 (3H, t, J = 7.2 Hz). |
| 122 | ¹H-NMR (CDCl₃) δ: 7.39 (1H, d, J = 9.5 Hz), 6.96-6.94 (2H, m), 6.75 (1H, d, J = 9.5 Hz), 6.29 (2H, s), 3.87 (2H, q, J = 7.0 Hz), 3.77 (6H, s), 1.15 (3H, t, J = 7.0 Hz). |
| 123 | ¹H-NMR (CDCl₃) δ: 7.33 (1H, d, J = 9.5 Hz), 7.29-7.21 (1H, m), 7.14 (1H, ddd, J = 8.8, 7.1, 1.3 Hz), 6.99 (1H, d, J = 7.0 Hz), 6.82-6.74 (3H, m), 6.71-6.67 (2H, m), 4.05-3.79 (2H, brm), 3.63 (3H, s), 1.14 (3H, t, J = 7.0 Hz). |
| 124 | ¹H-NMR (CDCl₃) δ: 7.53 (1H, s), 7.32 (1H, tt, J = 8.5, 3.5 Hz), 7.10 (1H, dd, J = 8.9, 2.7 Hz), 6.99 (1H, d, J = 2.7 Hz), 6.85 (2H, t, J = 7.9 Hz), 6.61 (1H, d, J = 8.9 Hz), 4.00 (2H, brs), 3.62 (3H, s), 1.16 (3H, t, J = 7.2 Hz). |
| 125 | ¹H-NMR (CDCl₃) δ: 7.73 (1H, s), 7.32 (1H, tt, J = 8.4, 3.5 Hz), 7.24 (1H, dd, J = 8.9, 2.4 Hz), 7.13 (1H, d, J = 2.4 Hz), 6.85 (2H, t, J = 7.9 Hz), 6.56 (1H, d, J = 8.9 Hz), 3.96 (2H, brs), 3.62 (3H, s), 1.16 (3H, t, J = 7.0 Hz). |
| 126 | ¹H-NMR (CDCl₃) δ: 7.78 (1H, s), 7.34-7.30 (1H, m), 7.20-7.18 (1H, m), 6.91-6.89 (1H, m), 6.86-6.81 (1H, m), 6.80-6.78 (2H, m), 5.01 (1H, d, J = 7.0 Hz), 4.96 (1H, d, J = 7.0 Hz), 3.97-3.94 (2H, m), 3.38 (3H, s), 1.18 (3H, t, J = 7.2 Hz). |
| 127 | ¹H-NMR (CDCl₃) δ: 7.57 (1H, s), 7.34-7.30 (1H, m), 7.20-7.18 (1H, m), 6.90 (1H, t, J = 8.4 Hz), 6.84 (1H, t, J = 8.4 Hz), 6.80-6.79 (2H, m), 5.01 (1H, d, J = 7.0 Hz), 4.96 (1H, d, J = 7.0 Hz), 3.97-3.94 (2H, m), 3.38 (3H, s), 1.18 (3H, t, J = 7.0 Hz). |
| 128 | ¹H-NMR (CDCl₃) δ: 7.74 (1H, s), 7.36-7.34 (1H, m), 7.27 (2H, d, J = 8.9 Hz), 6.94 (1H, t, J = 8.4 Hz), 6.86 (1H, t, J = 8.4 Hz), 6.79 (1H, dd, J = 8.9, 3.1 Hz), 6.73 (1H, dd, J = 3.1, 1.5 Hz), 4.66 (1H, d, J = 16.2 Hz), 4.62 (1H, d, J = 16.2 Hz), 3.98-3.93 (2H, m), 1.18 (3H, t, J = 7.0 Hz). |
| 129 | ¹H-NMR (CDCl₃) δ: 7.54 (1H, s), 7.35-7.33 (1H, m), 7.27 (1H, d, J = 8.9 Hz), 6.94 (1H, t, J = 8.6 Hz), 6.86 (1H, t, J = 8.6 Hz), 6.79 (1H, dd, J = 8.9, 3.1 Hz), 6.73 (1H, dd, J = 3.1, 1.5 Hz), 4.66 (1H, d, J = 16.2 Hz), 4.62 (1H, d, J = 16.2 Hz), 3.97-3.94 (2H, m), 1.19 (3H, t, J = 7.2 Hz). |
| 130 | ¹H-NMR (CDCl₃) δ: 6.62-6.59 (2H, m), 6.23 (1H, t, J = 2.1 Hz), 6.12 (2H, d, J = 2.1 Hz), 3.65 (6H, s), 3.40 (2H, q, J = 7.1 Hz), 2.73-2.71 (4H, m), 0.97 (3H, t, J = 7.1 Hz). |
| 131 | ¹H-NMR (CDCl₃) δ: 7.38 (1H, d, J = 9.5 Hz), 6.72 (1H, d, J = 9.5 Hz), 6.67-6.65 (2H, m), 6.29 (1H, t, J = 2.1 Hz), 6.20 (2H, d, J = 2.1 Hz), 3.88 (2H, q, J = 7.1 Hz), 3.69 (6H, s), 1.15 (3H, t, J = 7.1 Hz). |
| 132 | ¹H-NMR (CDCl₃) δ: 7.30 (1H, d, J = 9.5 Hz), 6.73 (1H, d, J = 9.5 Hz), 6.67 (1H, tt, J = 8.7, 2.1 Hz), 6.61 (1H, tt, J = 8.7, 2.1 Hz), 6.33 (1H, d, J = 2.8 Hz), 6.26 (1H, dd, J = 2.8, 1.8 Hz), 3.91-3.84 (2H, m), 3.82 (3H, s), 3.67 (3H, s), 1.17 (3H, t, J = 7.0 Hz). |

TABLE 5-continued

| Compound | ¹H-NMR |
|---|---|
| 133 | ¹H-NMR (CDCl₃) δ: 7.31 (1H, d, J = 9.5 Hz), 6.73 (1H, d, J = 9.5 Hz), 6.67 (1H, tt, J = 8.9, 2.1 Hz), 6.62 (1H, tt, J = 8.9, 2.1 Hz), 6.37 (1H, d, J = 2.8 Hz), 6.22 (1H, tt, J = 8.9, 2.1 Hz), 3.92-3.84 (2H, m), 3.83 (3H, s), 3.67 (3H, s), 1.16 (3H, t, J = 7.2 Hz). |
| 134 | ¹H-NMR (CDCl₃) δ: 7.41 (1H, d, J = 9.5 Hz), 6.74 (1H, d, J = 9.5 Hz), 6.68-6.66 (2H, m), 6.30 (1H, t, J = 2.3 Hz), 6.19 (2H, d, J = 2.3 Hz), 3.68 (6H, s), 3.37 (3H, s). |
| 135 | ¹H-NMR (CDCl₃) δ: 7.33 (1H, d, J = 9.5 Hz), 6.75 (1H, d, J = 9.5 Hz), 6.68 (1H, tt, J = 8.7, 2.1 Hz), 6.61 (1H, tt, J = 8.7, 2.1 Hz), 6.35 (1H, d, J = 2.7 Hz), 6.23 (1H, dd, J = 2.7, 1.8 Hz), 3.83 (3H, s), 3.67 (3H, s), 3.37 (3H, s). |
| 136 | ¹H-NMR (CDCl₃) δ: 7.33 (1H, d, J = 9.5 Hz), 6.75 (1H, d, J = 9.5 Hz), 6.68-6.66 (1H, m), 6.63-6.62 (1H, m), 6.38 (1H, d, J = 2.8 Hz), 6.19 (1H, dd, J = 2.8, 1.8 Hz), 3.83 (3H, s), 3.67 (3H, s). |
| 137 | ¹H-NMR (CDCl₃) δ: 7.37 (1H, d, J = 9.5 Hz), 7.29-7.23 (1H, m), 7.17-7.13 (1H, m), 6.99-6.97 (1H, m), 6.81-6.76 (3H, m), 6.73 (1H, d, J = 9.5 Hz), 6.70 (1H, d, J = 8.3 Hz), 3.62 (3H, s), 3.39 (3H, s). |
| 138 | ¹H-NMR (CDCl₃) δ: 7.31 (1H, tt, J = 8.4, 3.4 Hz), 7.26 (1H, s), 7.14 (1H, dd, J = 8.9, 2.8 Hz), 7.0 (1H, t, J = 2.3 Hz), 6.88-6.81 (2H, m), 6.64 (1H, d, J = 8.9 Hz), 3.66 (3H, s), 3.42 (3H, s). |
| 139 | ¹H-NMR (CDCl₃) δ: 7.76 (1H, s), 7.36-7.29 (1H, m), 7.27-7.24 (1H, m), 7.12 (1H, d, J = 2.4 Hz), 6.86 (2H, dd, J = 8.2, 7.6 Hz), 6.56 (1H, d, J = 8.9 Hz), 3.60 (3H, s), 3.46 (3H, s). |
| 140 | ¹H-NMR (CDCl₃) δ: 7.36 (H, d, J = 9.5 Hz), 7.31 (1H, tt, J = 8.4, 3.5 Hz), 7.18-7.13 (1H, m), 7.04-7.01 (1H, m), 6.96-6.93 (1H, m), 6.92-6.89 (1H, m), 6.86-6.83 (2H, m), 6.74 (1H, d, J = 9.5 Hz), 3.93 (2H, q, J = 7.0 Hz), 1.15 (3H, t, J = 7.0 Hz). |
| 141 | ¹H-NMR (CDCl₃) δ: 7.59 (1H, s), 7.32 (1H, tt, J = 8.4, 3.5 Hz), 7.20-7.15 (1H, m), 7.05-7.01 (1H, m), 6.97-6.94 (1H, m), 6.93-6.90 (1H, m), 6.85 (2H, dd, J = 8.5, 7.3 Hz), 3.98 (2H, q, J = 7.1 Hz), 1.17 (3H, t, J = 7.1 Hz). |
| 142 | ¹H-NMR (CDCl₃) δ: 7.80 (1H, s), 7.32 (1H, tt, J = 8.4, 3.5 Hz), 7.20-7.15 (1H, m), 7.05-7.01 (1H, m), 6.97-6.94 (1H, m), 6.93-6.89 (1H, m), 6.87-6.83 (2H, m), 3.98 (2H, q, J = 7.0 Hz), 1.17 (3H, t, J = 7.0 Hz). |
| 143 | ¹H-NMR (CDCl₃) δ: 7.38 (1H, dd, J = 9.3, 0.8 Hz), 7.31 (1H, tt, J = 8.4, 3.5 Hz), 7.20-7.14 (1H, m), 7.04-7.00 (1H, m), 6.97-6.94 (1H, m), 6.93-6.89 (1H, m), 6.87-6.83 (2H, m), 6.75 (1H, d, J = 9.2 Hz), 3.40 (3H, s). |
| 144 | ¹H-NMR (CDCl₃) δ: 7.62 (1H, s), 7.33 (1H, tt, J = 8.6, 3.5 Hz), 7.21-7.17 (1H, m), 7.05-7.01 (1H, m), 6.98-6.95 (1H, m), 6.94-6.91 (1H, m), 6.86 (2H, t, J = 8.0 Hz), 3.47 (3H, s). |
| 145 | ¹H-NMR (CDCl₃) δ: 7.82 (1H, s), 7.36-7.30 (1H, m), 7.21-7.16 (1H, m), 7.04-7.01 (1H, m), 6.98-6.95 (1H, m), 6.92 (1H, t, J = 8.9 Hz), 6.86 (2H, t, J = 8.0 Hz), 3.47 (3H, s). |
| 146 | ¹H-NMR (CDCl₃) δ: 7.60-7.59 (1H, m), 7.33-7.25 (4H, m), 7.22-7.18 (1H, m), 6.88 (1H, t, J = 8.4 Hz), 6.78 (1H, t, J = 8.4 Hz), 6.7 (1H, d, J = 9.5 Hz), 3.88 (2H, q, J = 7.1 Hz), 1.16 (3H, t, J = 7.1 Hz). |
| 147 | ¹H-NMR (CDCl₃) δ: 7.60-7.57 (1H, m), 7.55 (1H, s), 7.35-7.32 (2H, m), 7.31-7.28 (1H, m), 7.22-7.18 (1H, m), 6.88 (1H, t, J = 8.4 Hz), 6.80 (1H, t, J = 8.4 Hz), 3.98-3.88 (2H, m), 1.18 (3H, t, J = 7.2 Hz). |
| 148 | ¹H-NMR (CDCl₃) δ: 7.75 (1H, s), 7.60-7.57 (1H, m), 7.35-7.32 (2H, m), 7.31-7.28 (1H, m), 7.22-7.18 (1H, m), 6.88 (1H, t, J = 8.4 Hz), 6.80 (1H, t, J = 8.4 Hz), 3.9-3.87 (2H, m), 1.18 (3H, t, J = 7.0 Hz). |
| 149 | ¹H-NMR (CDCl₃) δ: 7.25-7.21 (1H, m), 7.18-7.16 (1H, m), 6.92-6.91 (1H, m), 6.20 (1H, t, J = 2.1 Hz), 6.14 (2H, d, J = 2.1 Hz), 3.66 (1H, dq, J = 14.1, 7.0 Hz), 3.61 (6H, s), 3.05 (1H, dq, J = 14.1, 7.0 Hz), 2.89-2.63 (4H, m), 0.97 (3H, t, J = 7.0 Hz). |
| 150 | ¹H-NMR (CDCl₃) δ: 7.40 (1H, d, J = 9.5 Hz), 7.33-7.27 (1H, m), 7.19 (1H, d, J = 8.0 Hz), 7.01-6.98 (1H, m), 6.73 (1H, d, J = 9.5 Hz), 6.25 (3H, s), 4.12 (1H, dq, J = 13.8, 7.0 Hz), 3.66 (6H, s), 3.61 (1H, dq, J = 13.8, 7.0 Hz), 1.14 (3H, t, J = 7.0 Hz). |
| 151 | Diastereomer-A (major) ¹H-NMR (CDCl₃) δ: 7.35 (1H, d, J = 9.5 Hz), 7.31-7.25 (1H, m), 7.23-7.21 (1H, m), 6.93-6.91 (1H, m), 6.73 (1H, d, J = 9.5 Hz), 6.36 (1H, d, J = 2.8 Hz), 6.30-6.29 (1H, m), 3.81 (3H, s), 3.76-3.71 (1H, m), 3.61 (3H, s), 3.40 (1H, dq, J = 13.4, 7.0 Hz), 1.15 (3H, t, J = 7.0 Hz).<br>Diastereomer-B (minor) ¹H-NMR (CDCl₃) δ: 7.40 (1H, d, J = 9.5 Hz), 7.31-7.25 (1H, m), 7.14-7.12 (1H, m), 7.05-7.03 (1H, m), 6.73 (1H, d, J = 9.5 Hz), 6.30-6.29 (1H, m), 6.27-6.25 (1H, m), 4.35 (1H, dq, J = 13.8, 7.0 Hz), 3.95-3.88 (1H, m), 3.81 (3H, s), 3.62 (3H, s), 1.19 (3H, t, J = 7.0 Hz).<br>Diastero ratio = 55/45 |
| 152 | Diastereomer-A (major) ¹H-NMR (CDCl₃) δ: 7.35 (1H, d, J = 9.5 Hz), 7.31-7.25 (1H, m), 7.23-7.22 (1H, m), 6.93-6.91 (1H, m), 6.73 (1H, d, J = 9.5 Hz), 6.34-6.31 (2H, m), 3.82 (3H, s), 3.76 (1H, dq, J = 13.6, 6.9 Hz), 3.61 (3H, s), 3.43 (1H, dq, J = 13.6, 6.9 Hz), 1.14 (3H, t, J = 6.9 Hz).<br>Diastereomer-B (minor) ¹H-NMR (CDCl₃) δ: 7.39 (1H, d, J = 9.5 Hz), 7.31-7.25 (1H, m), 7.13 (1H, d, J = 8.2 Hz), 7.05-7.03 (1H, m), 6.73 (1H, d, J = 9.5 Hz), 6.34-6.31 (1H, m), 6.22 (1H, dd, J = 2.7, 1.2 Hz), 4.34 (1H, dq, J = 13.6, 6.9 Hz), 3.91 (1H, dq, J = 13.6, 6.9 Hz), 3.82 (3H, s), 3.61 (3H, s), 1.18 (3H, t, J = 6.9 Hz).<br>Diastero ratio = 55/45 |
| 153 | ¹H-NMR (CDCl₃) δ: 7.36-7.34 (2H, m), 7.14-7.12 (1H, m), 6.88-6.85 (4H, m), 6.77 (1H, dt, J = 9.8, 2.1 Hz), 6.74 (1H, d, J = 9.2 Hz), 3.90 (2H, q, J = 7.0 Hz), 1.14 (3H, t, J = 7.0 Hz). |
| 154 | ¹H-NMR (CDCl₃) δ: 7.61 (1H, s), 7.37-7.35 (1H, m), 7.15-7.14 (1H, m), 6.91-6.83 (4H, m), 6.78 (1H, dt, J = 9.6, 2.1 Hz), 3.95 (2H, q, J = 7.0 Hz), 1.17 (3H, t, J = 7.0 Hz). |
| 155 | ¹H-NMR (CDCl₃) δ: 7.82 (1H, s), 7.37-7.35 (1H, m), 7.15-7.14 (1H, m), 6.91-6.83 (4H, m), 6.77 (1H, dt, J = 9.6, 2.1 Hz), 3.95 (2H, q, J = 7.0 Hz), 1.17 (3H, t, J = 7.0 Hz). |
| 156 | ¹H-NMR (CDCl₃) δ: 7.29-7.27 (1H, m), 7.08-7.07 (1H, m), 6.81-6.76 (4H, m), 6.67 (1H, dt, J = 10.0, 2.0 Hz), 3.42 (2H, q, J = 7.1 Hz), 2.78-2.71 (4H, m), 0.96 (3H, t, J = 7.1 Hz). |
| 157 | ¹H-NMR (CDCl₃) δ: 7.62-7.57 (1H, m), 7.34-7.30 (3H, m), 7.29-7.24 (1H, m), 7.18-7.16 (1H, m), 6.90-6.86 (1H, m), 6.80-6.76 (1H, m), 6.72 (1H, d, J = 9.5 Hz), 3.37 (3H, s). |

TABLE 5-continued

| Compound | ¹H-NMR |
|---|---|
| 158 | ¹H-NMR (CDCl₃) δ: 7.61-7.58 (1H, m), 7.56 (1H, s), 7.36-7.33 (2H, m), 7.32-7.27 (1H, m), 7.19-7.17 (1H, m), 6.88 (1H, t, J = 8.4 Hz), 6.80 (H, t, J = 8.4 Hz), 3.43 (3H, s). |
| 159 | ¹H-NMR (CDCl₃) δ: 7.76 (1H, s), 7.16-7.57 (1H, m), 7.36-7.32 (2H, m), 7.31-7.26 (1H, m), 7.20-7.16 (1H, m), 6.88 (1H, t, J = 8.3 Hz). 6.80 (1H, t, J = 8.3 Hz), 3.43 (3H, s). |
| 160 | ¹H-NMR (CDCl₃) δ: 7.28-7.21 (2H, m), 7.10-7.08 (1H, m), 7.07-7.04 (1H, m), 6.96-6.90 (2H, m), 6.88 (1H, t, J = 8.4 Hz), 6.76 (1H, d, J = 8.6 Hz), 6.72 (1H, d, J = 9.5 Hz), 3.99-3.92 (1H, m), 3.87-3.80 (1H, m), 2.16 (3H, s), 1.16 (3H, t, J = 7.0 Hz). |
| 161 | ¹H-NMR (CDCl₃) δ: 7.51 (1H, s), 7.30-7.23 (1H, m), 7.10-7.05 (2H, m), 6.96-6.91 (2H, m), 6.90-6.85 (1H, m), 6.79-6.75 (1H, m), 4.04-3.86 (2H, m), 2.17 (3H, s), 1.19 (3H, t, J = 7.0 Hz). |
| 162 | ¹H-NMR (CDCl₃) δ: 7.72 (1H, s), 7.30-7.23 (1H, m), 7.10-7.04 (2H, m), 6.96-6.91 (2H, m), 6.90-6.86 (1H, m), 6.79-6.75 (1H, m), 4.04-3.86 (2H, m), 2.17 (3H, s), 1.18 (3H, t, J = 7.0 Hz). |
| 163 | ¹H-NMR (CDCl₃) δ: 7.25-7.22 (1H, m), 7.18 (1H, d, J = 8.5 Hz), 6.93-6.92 (1H, m), 6.20 (1H, t, J = 2.3 Hz), 6.15 (2H, d, J = 2.3 Hz), 3.61 (6H, s), 2.88-2.86 (1H, m), 2.82 (3H, s), 2.78-2.66 (3H, m). |
| 164 | ¹H-NMR (CDCl₃) δ: 7.43 (1H, d, J = 9.5 Hz), 7.31 (1H, td, J = 8.2, 5.8 Hz), 7.21 (1H, dt, J = 8.2, 1.0 Hz), 6.99 (1H, td, J = 8.2, 1.1 Hz), 6.74 (1H, d, J = 9.5 Hz), 6.27-6.25 (3H, m), 3.66 (6H, s), 3.33 (3H, s). |
| 165 | Diastereomer-A(major) ¹H-NMR (CDCl₃) δ: 7.38 (1H, d, J = 9.5 Hz), 7.29-7.25 (2H, m), 6.92 (1H, td, J = 8.0, 1.6 Hz), 6.74 (1H, d, J = 9.5 Hz), 6.32 (1H, d, J = 3.1 Hz), 6.30 (1H, d, J = 3.1 Hz), 3.82 (3H, s), 3.60 (3H, s), 3.34 (3H, s).<br>Diastereomer-B (minor) ¹H-NMR (CDCl₃) δ: 7.41 (1H, d, J = 9.5 Hz), 7.31-7.27 (1H, m), 7.14-7.13 (1H, m), 7.04 (1H, td, J = 8.5, 0.9 Hz), 6.74 (1H, d, J = 9.5 Hz), 6.30 (1H, d, J = 2.7 Hz), 6.25 (1H, dd, J = 2.7, 1.2 Hz), 3.82 (3H, s), 3.61 (3H, s), 3.32 (3H, s).<br>Diastero ratio = 59/41 |
| 166 | Diastereomer-A(major) ¹H-NMR (CDCl₃) δ: 7.38 (1H, d, J = 9.5 Hz), 7.32-7.23 (2H, m), 6.92 (1H, td, J = 8.1, 1.6 Hz), 6.75 (1H, dd, J = 9.5, 1.2 Hz), 6.34 (1H, d, J = 2.7 Hz), 6.28 (1H, d, J = 2.7 Hz), 3.82 (3H, s), 3.60 (3H, s), 3.35 (3H, s).<br>Diastereomer-B(minor) ¹H-NMR (CDCl₃) δ: 7.41 (1H, d, J = 9.5 Hz), 7.32-7.23 (1H, m), 7.15-7.13 (1H, m), 7.04 (1H, t, J = 8.5 Hz), 6.75 (1H, dd, J = 9.5, 1.2 Hz), 6.34 (1H, d, J = 2.4 Hz), 6.21 (1H, m), 3.82 (3H, s), 3.61 (3H, s), 3.32 (3H, s).<br>Diastero ratio = 58/42 |
| 167 | ¹H-NMR (CDCl₃) δ: 7.42 (1H, s), 7.29-7.25 (1H, m), 7.15-7.14 (1H, m), 6.95 (1H, td, J = 8.5, 1.1 Hz), 6.47 (1H, s), 4.16 (1H, dq, J = 13.8, 7.0 Hz), 3.86 (6H, s), 3.82 (1H, dq, J = 13.8, 7.0 Hz), 1.16 (3H, t, J = 7.0 Hz). |
| 168 | ¹H-NMR (CDCl₃) δ: 7.40 (1H, d, J = 9.5 Hz), 7.38-7.33 (1H, m), 7.15-7.13 (1H, m), 6.91-6.85 (3H, m), 6.82 (1H, d, J = 8.0 Hz), 6.77-6.75 (2H, m), 3.38 (3H, s). |
| 169 | ¹H-NMR (CDCl₃) δ: 7.63 (1H, s), 7.38-7.37 (1H, m), 7.16-7.14 (1H, m), 6.92-6.87 (3H, m), 6.83 (1H, d, J = 8.0 Hz), 6.77 (1H, dt, J = 9.6, 2.1 Hz), 3.44 (3H, s). |
| 170 | ¹H-NMR (CDCl₃) δ: 7.84 (1H, s), 7.40-7.35 (1H, m), 7.16-7.14 (1H, m), 6.90-6.88 (3H, m), 6.83 (1H, d, J = 8.0 Hz), 6.77 (1H, dt, J = 9.6, 2.1 Hz), 3.45 (3H, s). |
| 171 | ¹H-NMR (CDCl₃) δ: 7.36-7.34 (2H, m), 7.13-7.07 (3H, m), 6.92-6.89 (3H, m), 6.74 (1H, d, J = 9.5 Hz), 3.90 (2H, q, J = 7.1 Hz), 1.14 (3H, t, J = 7.1 Hz). |
| 172 | ¹H-NMR (CDCl₃) δ: 7.32-7.24 (1H, m), 7.09-7.07 (1H, m), 6.86-6.74 (4H, m), 6.70-6.67 (1H, m), 2.87 (3H, s), 2.81-2.72 (4H, m). |
| 173 | ¹H-NMR (CDCl₃) δ: 7.29-7.28 (1H, m), 7.07-7.02 (2H, m), 6.97 (1H, t, J = 1.7 Hz), 6.84-6.82 (3H, m), 3.42 (2H, q, J = 7.1 Hz), 2.77-2.71 (4H, m), 0.96 (3H, t, J = 7.1 Hz). |
| 174 | ¹H-NMR (CDCl₃) δ: 7.36 (1H, d, J = 8.3 Hz), 7.17 (1H, td, J = 8.3, 5.8 Hz), 6.95 (1H, td, J = 8.3, 0.9 Hz), 6.20 (1H, t, J = 2.1 Hz), 6.16 (2H, d, J = 2.1 Hz), 3.73 (1H, dd, J = 14.2, 7.0 Hz), 3.62 (6H, s), 2.98 (1H, dd, J = 14.2, 7.0 Hz), 2.91-2.86 (1H, m), 2.80-2.74 (1H, m), 2.69-2.63 (2H, m), 0.98 (3H, t, J = 7.0 Hz). |
| 175 | ¹H-NMR (CDCl₃) δ: 7.40 (1H, d, J = 9.2 Hz), 7.36 (1H, d, J = 8.3 Hz), 7.23 (1H, td, J = 8.3, 6.0 Hz), 7.04 (1H, td, J = 8.3, 0.9 Hz), 6.73 (1H, d, J = 9.2 Hz), 6.27 (2H, d, J = 2.1 Hz), 6.26 (1H, t, J = 2.1 Hz), 4.18 (1H, dq, J = 13.6, 7.0 Hz), 3.66 (6H, s), 3.54 (1H, dq, J = 13.6, 7.0 Hz), 1.15 (3H, t, J = 7.0 Hz). |
| 176 | Diastereoisomer-A(major) ¹H-NMR (CDCl₃) δ: 7.42-7.39 (1H, m), 7.35 (1H, d, J = 9.5 Hz), 7.21-7.19 (1H, m), 6.96-6.94 (1H, m), 6.73 (1H, d, J = 9.5 Hz), 6.42 (1H, d, J = 2.7 Hz), 6.29 (1H, d, J = 2.7 Hz), 4.44 (1H, dq, J = 13.4, 7.0 Hz), 3.81 (3H, s), 3.61 (3H, s), 3.34 (1H, dq, J = 13.4, 7.0 Hz), 1.14 (3H, t, J = 7.0 Hz).<br>Diastereoisomer-B(minor) ¹H-NMR (CDCl₃) δ: 7.41 (1H, d, J = 9.5 Hz), 7.33-7.30 (1H, m), 7.24-7.17 (1H, m), 7.10-7.08 (1H, m), 6.73 (1H, d, J = 9.5 Hz), 6.30-6.29 (1H, m), 6.28-6.27 (1H, m), 3.99 (1H, dq, J = 13.6, 7.0 Hz), 3.82 (3H, s), 3.67 (1H, dq, J = 13.6, 7.0 Hz), 3.61 (3H, s), 1.20 (3H, t, J = 7.0 Hz).<br>Diastero ratio = 62/38 |
| 177 | Diatereomer-A(major) ¹H-NMR (CDCl₃) δ: 7.41-7.40 (1H, m), 7.36 (1H, d, J = 9.5 Hz), 7.22-7.20 (1H, m), 6.97-6.95 (1H, m), 6.74 (1H, d, J = 9.5 Hz), 6.38 (1H, d, J = 2.8 Hz), 6.32 (1H, d, J = 2.8 Hz), 4.43 (1H, dq, J = 13.6, 6.9 Hz), 3.82 (3H, s), 3.61 (3H, s), 3.36 (1H, dq, J = 13.6, 6.9 Hz), 1.14 (3H, t, J = 6.9 Hz).<br>Diastereomer-B(minor) ¹H-NMR (CDCl₃) δ: 7.41 (1H, d, J = 9.5 Hz), 7.33-7.31 (1H, m), 7.22-7.19 (1H, m), 7.11-7.07 (1H, m), 6.73 (1H, d, J = 9.5 Hz), 6.33 (1H, d, J = 2.8 Hz), 6.22 (1H, d, J = 2.8 Hz), 3.96 (1H, dd, J = 13.6, 7.0 Hz), 3.82 (3H, s), 3.71-3.66 (1H, m), 3.61 (3H, s), 1.20 (3H, t, J = 7.0 Hz).<br>Diastero ratio = 59/41 |
| 178 | ¹H-NMR (CDCl₃) δ: 7.60 (1H, s), 7.38-7.36 (1H, m), 7.16 (1H, dq, J = 8.1, 1.1 Hz), 7.10 (1H, t, J = 7.8 Hz), 7.07 (1H, t, J = 1.7 Hz), 6.94-6.88 (3H, m), 3.95 (2H, q, J = 7.1 Hz), 1.17 (3H, t, J = 7.1 Hz). |

TABLE 5-continued

| Compound | ¹H-NMR |
|---|---|
| 179 | ¹H-NMR (CDCl₃) δ: 7.81 (1H, s), 7.38-7.36 (1H, m), 7.16-7.15 (1H, m), 7.10 (1H, t, J = 7.8 Hz), 7.06 (1H, t, J = 1.8 Hz), 6.94-6.88 (3H, m), 3.95 (2H, q, J = 7.1 Hz), 1.17 (3H, t, J = 7.1 Hz). |
| 180 | ¹H-NMR (CDCl₃) δ: 7.30 (1H, d, J = 9.2 Hz), 7.28-7.23 (1H, m), 7.11-7.05 (2H, m), 6.95-6.86 (3H, m), 6.78-3.73 (2H, m), 3.38 (3H, s), 2.16 (3H, s). |
| 181 | ¹H-NMR (CDCl₃) δ: 7.53 (1H, s), 7.30-7.24 (1H, m), 7.11-7.07 (2H, m), 6.96-6.87 (3H, m), 6.77 (1H, t, J = 8.6 Hz), 3.45 (3H, s), 2.17 (3H, s). |
| 182 | ¹H-NMR (CDCl₃) δ: 7.73 (1H, s), 7.30-7.24 (1H, m), 7.11-7.07 (2H, m), 6.96-6.87 (3H, m), 6.77 (1H, t, J = 8.6 Hz), 3.45 (3H, s), 2.17 (3H, s). |
| 183 | ¹H-NMR (CDCl₃) δ: 7.43 (1H, d, J = 9.5 Hz), 7.39-7.37 (1H, m), 7.27-7.21 (1H, m), 7.05-7.03 (1H, m), 6.75 (1H, d, J = 9.5 Hz), 6.28-6.26 (3H, m), 3.66 (6H, s), 3.33 (3H, s). |
| 184 | Diastereomer-A(major) ¹H-NMR (CDCl₃) δ: 7.42 (1H, d, J = 8.0 Hz), 7.38 (1H, d, J = 9.5 Hz), 7.23-7.20 (1H, m), 6.96-6.95 (1H, m), 6.75 (1H, d, J = 9.5 Hz), 6.40 (1H, d, J = 2.8 Hz), 6.30 (1H, d, J = 2.8 Hz), 3.82 (3H, s), 3.61 (3H, s), 3.35 (3H, s).<br>Diastereomixture-B(minor) ¹H-NMR (CDCl₃) δ: 7.44 (1H, d, J = 9.5 Hz), 7.32 (1H, d, J = 8.3 Hz), 7.25-7.19 (1H, m), 7.11-7.07 (1H, m), 6.75 (1H, d, J = 9.5 Hz), 6.31 (1H, d, J = 2.8 Hz), 6.26 (1H, d, J = 2.8 Hz), 3.82 (3H, s), 3.61 (3H, s), 3.31 (3H, s).<br>Diastero ratio = 64/36 |
| 185 | Diastereomer-A(major) ¹H-NMR (CDCl₃) δ: 7.42 (1H, d, J = 8.0 Hz), 7.38 (1H, d, J = 9.5 Hz), 7.23-7.21 (1H, m), 6.97-6.95 (1H, m), 6.76 (1H, d, J = 9.5 Hz), 6.36 (1H, d, J = 2.8 Hz), 6.33 (1H, d, J = 2.8 Hz), 3.82 (3H, s), 3.60 (3H, s), 3.35 (3H, s).<br>Diastereomer-B(minor) ¹H-NMR (CDCl₃) δ: 7.43 (1H, d, J = 9.5 Hz), 7.32 (1H, d, J = 8.0 Hz), 7.23-7.21 (1H, m), 7.10-7.08 (1H, m), 6.75 (1H, d, J = 9.5 Hz), 6.34 (1H, d, J = 2.8 Hz), 6.21 (1H, d, J = 2.8 Hz), 3.83 (3H, s), 3.60 (3H, s), 3.31 (3H, s).<br>Diastero ratio = 63/37 |
| 186 | ¹H-NMR (CDCl₃) δ: 7.04-7.02 (2H, m), 6.23 (1H, t, J = 2.3 Hz), 6.11 (2H, d, J = 2.3 Hz), 3.65 (6H, s), 3.39 (2H, q, J = 7.0 Hz), 2.75-2.69 (4H, m), 0.96 (3H, t, J = 7.0 Hz). |
| 187 | ¹H-NMR (CDCl₃) δ: 7.06-7.03 (2H, m), 6.24 (1H, t, J = 2.3 Hz), 6.12 (2H, d, J = 2.3 Hz), 3.65 (6H, s), 2.86 (3H, s), 2.77-2.72 (4H, m). |
| 188 | ¹H-NMR (CDCl₃) δ: 7.38-7.35 (2H, m), 7.15 (1H, dt, J = 8.3, 1.6 Hz), 7.10 (1H, t, J = 7.8 Hz), 7.06 (1H, t, J = 1.8 Hz), 6.93-6.87 (3H, m), 6.75 (1H, d, J = 9.5 Hz), 3.38 (3H, s). |
| 189 | ¹H-NMR (CDCl₃) δ: 7.63 (1H, s), 7.39-7.37 (1H, m), 7.18-7.16 (1H, m), 7.11 (1H, t, J = 7.8 Hz), 7.06 (1H, t, J = 1.8 Hz), 6.92-6.90 (3H, m), 3.45 (3H, s). |
| 190 | ¹H-NMR (CDCl₃) δ: 7.83 (1H, s), 7.39-7.37 (1H, m), 7.17-7.16 (1H, m), 7.11 (1H, t, J = 7.8 Hz), 7.06 (1H, t, J = 1.8 Hz), 6.92-6.90 (3H, m), 3.45 (3H, s). |
| 191 | ¹H-NMR (CDCl₃) δ: 7.32-7.26 (1H, m), 7.06-7.04 (2H, m), 6.97 (1H, t, J = 1.8 Hz), 6.85-6.82 (3H, m), 2.87 (3H, s), 2.77-2.75 (4H, m). |
| 192 | ¹H-NMR (CDCl₃) δ: 7.26-7.24 (1H, m), 7.15 (1H, d, J = 8.9 Hz), 6.83 (1H, t, J = 8.6 Hz), 6.77 (1H, t, J = 8.6 Hz), 6.62 (1H, dd, J = 8.9, 3.1 Hz), 6.58 (1H, dd, J = 3.1, 1.4 Hz), 5.93 (1H, tt, J = 56.6, 4.4 Hz), 3.74-3.65 (2H, m), 3.64 (3H, s), 2.95-2.89 (1H, m), 2.87-2.81 (1H, m), 2.76-2.73 (1H, m), 2.67-2.61 (1H, m). |
| 193 | ¹H-NMR (CDCl₃) δ: 7.32-7.29 (2H, m), 7.16 (1H, d, J = 8.9 Hz), 6.89 (1H, t, J = 8.6 Hz), 6.83 (1H, t, J = 8.6 Hz), 6.74-6.70 (2H, m), 6.63-6.62 (1H, m), 4.00-3.97 (1H, m), 3.92-3.87 (3H, m), 3.71-3.64 (2H, m), 3.43 (3H, s), 1.16 (3H, t, J = 7.2 Hz). |
| 194 | ¹H-NMR (CDCl₃) δ: 7.41 (1H, d, J = 9.5 Hz), 7.36-7.33 (1H, m), 7.18 (1H, d, J = 8.9 Hz), 6.90 (1H, t, J = 8.6 Hz), 6.84 (1H, t, J = 8.6 Hz), 6.76 (1H, d, J = 9.5 Hz), 6.68 (1H, dd, J = 8.9, 3.1 Hz), 6.62 (1H, dd, J = 3.1, 1.5 Hz), 6.18 (1H, tt, J = 56.7, 4.5 Hz), 4.17 (2H, td, J = 12.9, 4.5 Hz), 3.65 (3H, s). |
| 195 | ¹H-NMR (CDCl₃) δ: 7.55 (1H, s), 7.34-7.30 (1H, m), 7.17 (1H, d, J = 8.9 Hz), 6.89 (1H, t, J = 8.4 Hz), 6.85 (1H, t, J = 8.4 Hz), 6.73 (1H, dd, J = 8.9, 3.1 Hz), 6.63 (1H, dd, J = 3.1, 1.7 Hz), 3.98-3.94 (3H, m), 3.89-3.86 (1H, m), 3.69-3.67 (2H, m), 3.43 (3H, s), 1.18 (3H, t, J = 7.0 Hz). |
| 196 | ¹H-NMR (CDCl₃) δ: 7.75 (1H, s), 7.33-7.30 (1H, m), 7.16 (1H, d, J = 8.9 Hz), 6.89 (1H, t, J = 7.9 Hz), 6.85 (1H, t, J = 7.9 Hz), 6.73 (1H, dd, J = 8.9, 3.1 Hz), 6.63 (1H, dd, J = 3.1, 1.5 Hz), 4.01-3.92 (3H, m), 3.89-3.85 (1H, m), 3.69-3.67 (2H, m), 3.43 (3H, s), 1.18 (3H, t, J = 7.0 Hz). |
| 197 | ¹H-NMR (CDCl₃) δ: 7.63 (1H, s), 7.36-7.33 (1H, m), 7.18 (1H, d, J = 8.9 Hz), 6.92-6.84 (2H, m), 6.70 (1H, dd, J = 8.9, 3.1 Hz), 6.62 (1H, dd, J = 3.1, 1.7 Hz), 6.20 (1H, tt, J = 56.6, 4.6 Hz), 4.23-4.19 (2H, m), 3.66 (3H, s). |
| 198 | ¹H-NMR (CDCl₃) δ: 7.84 (1H, s), 7.37-7.35 (1H, m), 7.18 (1H, d, J = 8.9 Hz), 6.91-6.84 (2H, m), 6.70 (1H, dd, J = 8.9, 2.9 Hz), 6.62 (1H, dd, J = 2.9, 1.7 Hz), 6.20 (1H, tt, J = 56.6, 4.4 Hz), 4.26-4.17 (2H, m), 3.66 (3H, s). |
| 199 | ¹H-NMR (CDCl₃) δ: 7.37 (1H, d, J = 9.5 Hz), 7.10-7.08 (2H, m), 6.72 (1H, d, J = 9.5 Hz), 6.30 (1H, t, J = 2.3 Hz), 6.20 (2H, d, J = 2.3 Hz), 3.86 (2H, q, J = 7.2 Hz), 3.69 (6H, s), 1.14 (3H, t, J = 7.2 Hz). |
| 200 | ¹H-NMR (CDCl₃) δ: 7.29 (1H, d, J = 9.2 Hz), 7.09 (1H, dt, J = 8.1, 1.6 Hz), 7.04 (1H, dt, J = 8.1, 1.6 Hz), 6.73 (1H, d, J = 9.2 Hz), 6.34 (1H, d, J = 2.8 Hz), 6.26-6.26 (1H, m), 3.88-3.86 (2H, m), 3.83 (3H, s), 3.68 (3H, s), 1.16 (3H, t, J = 7.0 Hz). |
| 201 | ¹H-NMR (CDCl₃) δ: 7.29 (1H, d, J = 9.5 Hz), 7.09 (1H, dt, J = 8.3, 1.8 Hz), 7.05 (1H, dt, J = 8.3, 1.8 Hz), 6.73 (1H, d, J = 9.5 Hz), 6.38 (1H, d, J = 2.8 Hz), 6.23-6.22 (1H, m), 3.88-3.86 (2H, m), 3.83 (3H, s), 3.68 (3H, s), 1.15 (3H, t, J = 7.0 Hz). |
| 202 | ¹H-NMR (CDCl₃) δ: 7.39 (1H, d, J = 9.5 Hz), 7.11-7.10 (2H, m), 6.75 (1H, d, J = 9.5 Hz), 6.29 (2H, s), 3.86 (2H, q, J = 7.0 Hz), 3.77 (6H, s), 1.15 (3H, t, J = 7.0 Hz). |
| 203 | ¹H-NMR (CDCl₃) δ: 7.40 (1H, d, J = 9.2 Hz), 7.11-7.10 (2H, m), 6.74 (1H, d, J = 9.2 Hz), 6.31 (1H, t, J = 2.1 Hz), 6.19 (2H, d, J = 2.1 Hz), 3.68 (6H, s), 3.36 (3H, s). |
| 204 | ¹H-NMR (CDCl₃) δ: 7.31 (1H, d, J = 9.5 Hz), 7.10 (1H, dt, J = 8.3, 1.5 Hz), 7.04 (1H, dt, J = 8.3, 1.5 Hz), 6.74 (1H, d, J = 9.5 Hz), 6.35 (1H, d, J = 2.8 Hz), 6.23 (1H, m), 3.84 (3H, s), 3.67 (3H, s), 3.36 (3H, s). |

TABLE 5-continued

| Compound | $^1$H-NMR |
|---|---|
| 205 | $^1$H-NMR (CDCl$_3$) δ: 7.32 (1H, d, J = 9.5 Hz), 7.10 (1H, dt, J = 8.1, 1.7 Hz), 7.05 (1H, dt, J = 8.1, 1.7 Hz), 6.75 (1H, d, J = 9.5 Hz), 6.39 (1H, d, J = 2.7 Hz), 6.20 (1H, dd, J = 2.7, 1.5 Hz), 3.84 (3H, s), 3.67 (3H, s), 3.36 (3H, s). |
| 206 | $^1$H-NMR (CDCl$_3$) δ: 7.42 (1H, d, J = 9.5 Hz), 7.13-7.11 (2H, m), 6.76 (1H, d, J = 9.5 Hz), 6.28 (2H, s), 3.76 (6H, s), 3.37 (3H, s). |
| 207 | $^1$H-NMR (CDCl$_3$) δ: 7.27-7.21 (1H, m), 6.99 (1H, t, J = 7.5 Hz), 6.89 (1H, d, J = 7.3 Hz), 6.81-6.78 (3H, m), 6.75 (1H, d, J = 7.6 Hz), 3.42 (2H, q, J = 7.1 Hz), 2.78-2.70 (4H, m), 2.18 (3H, s), 0.96 (3H, t, J = 7.1 Hz). |
| 208 | $^1$H-NMR (CDCl$_3$) δ: 7.30-7.24 (1H, m), 7.17 (1H, t, J = 8.1 Hz), 6.95-6.93 (2H, m), 6.84-6.79 (3H, m), 3.42 (2H, q, J = 7.1 Hz), 2.79-2.72 (4H, m), 0.96 (3H, t, J = 7.1 Hz). |
| 209 | $^1$H-NMR (CDCl$_3$) δ: 7.37 (1H, d, J = 9.5 Hz), 7.30-7.23 (1H, m), 7.17-7.12 (1H, m), 7.11-7.08 (1H, m), 6.97-6.94 (1H, m), 6.91-6.89 (1H, m), 6.87-6.85 (1H, m), 6.79 (1H, t, J-8.4 Hz), 6.72 (1H, d, J = 9.5 Hz), 3.90-3.81 (2H, m), 2.39 (3H, s), 1.16 (3H, t, J = 7.2 Hz). |
| 210 | $^1$H-NMR (CDCl$_3$) δ: 7.58 (1H, s), 7.51 (1H, d, J = 8.0 Hz), 7.32-7.23 (2H, m), 7.07-7.06 (2H, m), 6.88 (1H, t, J = 8.4 Hz), 6.80 (1H, t, J = 8.4 Hz), 4.94 (2H, dd, J = 19.3, 12.2 Hz), 3.94 (2H, q, J = 7.0 Hz), 1.18 (3H, t, J = 7.0 Hz). |
| 211 | $^1$H-NMR (CDCl$_3$) δ: 8.08 (1H, dd, J = 7.9, 1.5 Hz), 7.63 (1H, d, J = 9.5 Hz), 7.41-7.30 (3H, m), 7.20-7.17 (1H, m), 7.00-6.95 (1H, m), 6.79 (1H, t, J = 8.5 Hz), 6.73 (1H, d, J = 9.5 Hz), 4.02-3.94 (1H, m), 3.82-3.73 (1H, m), 2.98 (3H, s), 1.16 (3H, t, J = 7.0 Hz). |
| 212 | $^1$H-NMR (CDCl$_3$) δ: 7.32-7.31 (2H, m), 7.16 (1H, d, J = 8.6 Hz), 6.88 (1H, t, J = 8.6 Hz), 6.83 (1H, t, J = 8.6 Hz), 6.72 (1H, d, J = 9.5 Hz), 6.68 (1H, dd, J = 8.6, 3.1 Hz), 6.59 (1H, dd, J = 3.1, 1.4 Hz), 3.96-3.83 (2H, m), 3.65-3.63 (1H, m), 3.58-3.56 (1H, m), 1.17-1.13 (4H, m), 0.62-0.61 (2H, m), 0.29-0.28 (2H, m). |
| 213 | $^1$H-NMR (CDCl$_3$) δ: 7.42 (1H, d, J = 9.5 Hz), 7.37-7.31 (1H, m), 7.19 (1H, d, J = 8.9 Hz), 6.90 (1H, t, J = 8.4 Hz), 6.83 (1H, t, J = 8.4 Hz), 6.81-6.74 (3H, m), 6.17 (1H, tt, J = 56.6, 4.6 Hz), 5.01-4.96 (2H, m), 4.23-4.11 (2H, m), 3.37 (3H, s). |
| 214 | $^1$H-NMR (CDCl$_3$) δ: 7.40 (1H, d, J = 9.5 Hz), 7.36-7.30 (1H, m), 7.16 (1H, d, J = 8.9 Hz), 6.91-6.83 (2H, m), 6.75 (1H, d, J = 9.5 Hz), 6.69-6.67 (1H, m), 6.61-6.60 (1H, m), 6.18 (1H, tt, J = 56.6, 4.5 Hz), 4.21-4.11 (2H, m), 3.93-3.89 (1H, m), 3.80-3.77 (1H, m), 1.33 (3H, t, J = 6.9 Hz). |
| 215 | $^1$H-NMR (CDCl$_3$) δ: 8.37 (2H, s), 7.39 (1H, d, J = 9.5 Hz), 6.75 (1H, d, J = 9.5 Hz), 6.28 (1H, t, J = 2.4 Hz), 6.19 (2H, d, J = 2.4 Hz), 3.85 (2H, q, J = 7.1 Hz), 3.67 (6H, s), 1.15 (3H, t, J = 7.1 Hz). |
| 216 | $^1$H-NMR (CDCl$_3$) δ: 8.37 (1H, s), 8.32 (1H, s), 7.31 (1H, d, J = 9.5 Hz), 6.76 (1H, d, J = 9.5 Hz), 6.32 (1H, d, J = 2.4 Hz), 6.26-6.26 (1H, m), 3.85 (2H, q, J = 7.2 Hz), 3.82 (3H, s), 3.67 (3H, s), 1.17 (3H, t, J = 7.2 Hz). |
| 217 | $^1$H-NMR (CDCl$_3$) δ: 7.37-7.33 (2H, m), 7.22 (1H, t, J = 8.1 Hz), 7.03-7.01 (2H, m), 6.90-6.86 (3H, m), 6.75 (1H, d, J = 9.5 Hz), 3.91 (2H, q, J = 7.1 Hz), 1.14 (3H, t, J = 7.1 Hz). |
| 218 | $^1$H-NMR (CDCl$_3$) δ: 7.62 (1H, s), 7.38-7.32 (1H, m), 7.24 (1H, t, J = 8.1 Hz), 7.05-7.02 (2H, m), 6.91-6.87 (3H, m), 3.96 (2H, q, J = 7.0 Hz), 1.17 (3H, t, J = 7.0 Hz). |
| 219 | $^1$H-NMR (CDCl$_3$) δ: 7.39 (1H, d, J = 9.5 Hz), 7.32-7.30 (1H, m), 7.03 (1H, t, J = 7.5 Hz), 6.96 (1H, d, J = 7.3 Hz), 6.87-6.82 (4H, m), 6.72 (1H, d, J = 9.5 Hz), 3.91 (2H, q, J = 7.1 Hz), 2.21 (3H, s), 1.14 (3H, t, J = 7.1 Hz). |
| 220 | $^1$H-NMR (CDCl$_3$) δ: 7.63 (1H, s), 7.34-7.32 (1H, m), 7.04 (1H, t, J = 7.6 Hz), 6.97 (1H, d, J = 7.3 Hz), 6.88-6.82 (4H, m), 3.95 (2H, q, J = 7.0 Hz), 2.22 (3H, s), 1.17 (3H, t, J = 7.0 Hz). |
| 221 | $^1$H-NMR (CDCl$_3$) δ: 7.55 (1H, s), 7.34-7.31 (1H, m), 7.16 (1H, d, J = 8.9 Hz), 6.90-6.83 (2H, m), 6.69 (1H, dd, J = 8.9, 2.9 Hz), 6.60 (1H, dd, J = 2.8, 1.5 Hz), 3.95 (2H, q, J = 7.0 Hz), 3.65-3.63 (1H, m), 3.59-3.57 (1H, m), 1.19-1.17 (4H, m), 0.63-0.61 (2H, m), 0.30-0.28 (2H, m). |
| 222 | $^1$H-NMR (CDCl$_3$) δ: 7.64 (1H, s), 7.36-7.35 (1H, m), 7.19 (1H, d, J = 8.6 Hz), 6.90 (1H, t, J = 8.6 Hz), 6.85 (1H, t, J = 8.6 Hz), 6.83-6.79 (2H, m), 6.19 (1H, tt, J = 56.6, 4.5 Hz), 5.02 (1H, d, J = 7.0 Hz), 4.97 (1H, d, J = 7.0 Hz), 4.25-4.17 (2H, m), 3.38 (3H, s). |
| 223 | $^1$H-NMR (CDCl$_3$) δ: 7.62 (1H, s), 7.37-7.35 (1H, m), 7.16 (1H, d, J = 8.9 Hz), 6.90-6.86 (2H, m), 6.70-6.68 (1H, m), 6.62-6.61 (1H, m), 6.20 (1H, tt, J = 56.6, 4.4 Hz), 4.27-4.16 (2H, m), 3.93-3.88 (1H, m), 3.82-3.78 (1H, m), 1.34 (3H, t, J = 7.0 Hz). |
| 224 | $^1$H-NMR (CDCl$_3$) δ: 8.37 (1H, s), 8.33 (1H, s), 7.31 (1H, d, J = 9.5 Hz), 6.76 (1H, d, J = 9.5 Hz), 6.36 (1H, d, J = 2.8 Hz), 6.22-6.22 (1H, m), 3.86 (2H, q, J = 7.0 Hz), 3.82 (3H, s), 3.67 (3H, s), 1.16 (3H, t, J = 7.0 Hz). |
| 225 | $^1$H-NMR (CDCl$_3$) δ: 7.30-7.28 (1H, m), 7.09-7.01 (3H, m), 6.17 (1H, t, J = 2.4 Hz), 6.06 (2H, d, J = 2.4 Hz), 3.61-3.54 (7H, m), 3.28-3.25 (1H, m), 2.84-2.67 (4H, m), 0.95 (3H, t, J = 7.2 Hz). |
| 226 | $^1$H-NMR (CDCl$_3$) δ: 7.30-7.27 (1H, m), 7.06-7.01 (3H, m), 6.17 (1H, t, J = 2.3 Hz), 6.07 (2H, d, J = 2.3 Hz), 3.57 (6H, s), 2.88-2.86 (4H, m), 2.72-2.69 (3H, m). |
| 227 | $^1$H-NMR (CDCl$_3$) δ: 7.45 (1H, d, J = 9.5 Hz), 7.39-7.34 (1H, m), 7.13-7.11 (1H, m), 7.07 (1H, td, J = 7.3, 1.2 Hz), 7.01 (1H, td, J = 7.3, 1.7 Hz), 6.71 (1H, d, J = 9.5 Hz), 6.23 (1H, t, J = 2.3 Hz), 6.15 (2H, d, J = 2.3 Hz), 3.62 (6H, s), 3.36 (3H, s). |
| 228 | Diastereomer-A(major) $^1$H-NMR (CDCl$_3$) δ: 7.32-7.30 (2H, m), 7.11-7.06 (2H, m), 7.01 (1H, td, J = 7.5, 1.2 Hz), 6.71 (1H, d, J = 9.5 Hz), 6.27 (1H, d, J = 2.8 Hz), 6.14 (1H, d, J = 2.8 Hz), 3.82 (3H, s), 3.59 (3H, s), 3.35 (3H, s).<br>Diastereomer-B (minor) $^1$H-NMR (CDCl$_3$) δ: 7.33-7.30 (2H, m), 7.11-7.06 (2H, m), 7.01 (1H, td, J = 7.5, 1.2 Hz), 6.71 (1H, d, J = 9.5 Hz), 6.30 (1H, d, J = 2.8 Hz), 6.21 (1H, d, J = 2.8 Hz), 3.79 (3H, s), 3.66 (3H, s), 3.37 (3H, s).<br>Diastero ratio = 82/18 |
| 229 | Diastereomer-A(major) $^1$H-NMR (CDCl$_3$) δ: 7.33-7.30 (2H, m), 7.09-7.00 (3H, m), 6.71 (1H, d, J = 9.5 Hz), 6.31 (1H, d, J = 2.8 Hz), 6.10 (1H, d, J = 2.8 Hz), 3.82 (3H, s), 3.58 (3H, s), 3.35 (3H, s). |

TABLE 5-continued

| Compound | ¹H-NMR |
|---|---|
| | Diastereomer-B (minor) ¹H-NMR (CDCl₃) δ: 7.33-7.30 (2H, m), 7.09-7.00 (3H, m), 6.71 (1H, d, J = 9.5 Hz), 6.33 (1H, d, J = 2.8 Hz), 6.19 (1H, d, J = 2.8 Hz), 3.79 (3H, s), 3.66 (3H, s), 3.37 (3H, s).<br>Diastero ratio = 79/21 |
| 230 | ¹H-NMR (CDCl₃) δ: 7.41 (1H, d, J = 9.5 Hz), 7.38-7.33 (1H, m), 7.11-7.06 (3H, m), 6.69 (1H, d, J = 9.5 Hz), 6.22 (1H, t, J = 2.8 Hz), 6.16 (2H, d, J = 2.8 Hz), 4.04 (1H, dd, J = 13.6, 7.0 Hz), 3.76 (1H, dd, J = 13.6, 7.0 Hz), 3.63 (6H, s), 1.13 (3H, t, J = 7.0 Hz). |
| 231 | Diastereomer-A(major) ¹H-NMR (CDCl₃) δ: 7.31-7.27 (2H, m), 7.17-7.16 (1H, m), 7.08-7.03 (2H, m), 6.69 (1H, d, J = 9.2 Hz), 6.27-6.25 (2H, m), 4.03-3.97 (1H, m), 3.80 (3H, s), 3.74 (1H, dd, J = 13.9, 7.0 Hz), 3.63 (3H, s), 1.15 (3H, t, J = 7.0 Hz).<br>Diastereomer-B (minor) ¹H-NMR (CDCl₃) δ: 7.31-7.27 (2H, m), 7.17-7.16 (1H, m), 7.08-7.03 (2H, m), 6.74 (1H, d, J = 9.5 Hz), 6.27-6.27 (1H, m), 6.14 (1H, d, J = 2.8 Hz), 4.03-3.97 (1H, m), 3.88 (3H, s), 3.81 (3H, s), 3.75-3.72 (1H, m), 1.12 (3H, t, J = 7.0 Hz).<br>Diastero ratio = 86/14 |
| 232 | Diastereomer-A(major) ¹H-NMR (CDCl₃) δ: 7.33-7.24 (2H, m), 7.14-7.08 (1H, m), 7.06-6.98 (2H, m), 6.69 (1H, d, J = 9.5 Hz), 6.30 (1H, d, J = 2.8 Hz), 6.21 (1H, dd, J = 2.8, 1.2 Hz), 4.06-3.94 (1H, m), 3.80 (3H, s), 3.77-3.70 (1H, m), 3.62 (3H, s), 1.15 (3H, t, J = 7.0 Hz).<br>Diastereomer-B (minor) ¹H-NMR (CDCl₃) δ: 7.33-7.25 (2H, m), 7.13-7.11 (1H, m), 7.06-6.99 (2H, m), 6.69 (1H, d, J = 9.5 Hz), 6.30 (1H, d, J = 2.8 Hz), 6.11 (1H, d, J = 2.8 Hz), 4.02-3.99 (1H, m), 3.87 (3H, s), 3.82 (3H, s), 3.76-3.72 (1H, m), 1.13 (3H, t, J = 7.0 Hz).<br>Diastero ratio = 82/18 |
| 233 | ¹H-NMR (CDCl₃) δ: 7.32-7.29 (1H, m), 7.18-7.15 (1H, m), 7.14 (1H, d, J = 9.5 Hz), 7.08-7.06 (1H, m), 6.97 (1H, td, J = 7.6, 1.2 Hz), 6.74 (1H, d, J = 9.5 Hz), 6.42 (1H, s), 3.90 (3H, s), 3.81 (3H, s), 3.39 (3H, d, J = 1.2 Hz). |
| 234 | ¹H-NMR (DMSO-D₆) δ: 9.66 (1H, br s), 7.54-7.51 (1H, m), 7.41 (1H, d, J = 9.5 Hz), 7.22 (1H, t, J = 8.7 Hz), 7.15 (1H, d, J = 8.9 Hz), 7.12 (1H, t, J = 8.7 Hz), 6.63-6.58 (2H, m), 6.47 (1H, dd, J = 3.1, 1.5 Hz), 3.78-3.73 (2H, m), 1.01 (3H, t, J = 7.0 Hz). |
| 235 | ¹H-NMR (DMSO-D₆) δ: 9.64 (1H, br s), 7.53-7.51 (1H, m), 7.43 (1H, d, J = 9.2 Hz), 7.20 (1H, t, J = 8.7 Hz), 7.16-7.09 (2H, m), 6.64-6.59 (2H, m), 6.46-6.45 (1H, m), 3.22 (3H, s). |
| 236 | ¹H-NMR (CDCl₃) δ: 7.33-7.29 (3H, m), 6.93 (1H, t, J = 8.4 Hz), 6.85 (1H, t, J = 8.4 Hz), 6.79 (1H, dd, J = 8.9, 3.1 Hz), 6.76 (1H, d, J = 9.5 Hz), 6.70 (1H, dd, J = 3.1, 1.2 Hz), 4.64 (1H, d, J = 15.9 Hz), 4.60 (1H, d, J = 15.9 Hz), 3.39 (3H, s). |
| 237 | ¹H-NMR (CDCl₃) δ: 7.35 (1H, d, J = 9.2 Hz), 7.33-7.30 (1H, m), 7.17 (1H, d, J = 8.9 Hz), 6.90 (1H, t, J = 8.6 Hz), 6.84 (1H, t, J = 8.6 Hz), 6.75 (1H, d, J = 9.2 Hz), 6.67 (1H, dd, J = 8.9, 3.1 Hz), 6.57 (1H, dd, J = 3.1, 1.4 Hz), 3.91-3.89 (1H, m), 3.77-3.75 (1H, m), 3.38 (3H, s), 1.32 (3H, t, J = 7.0 Hz). |
| 238 | ¹H-NMR (CDCl₃) δ: 7.35-7.30 (2H, m), 7.17 (1H, d, J = 8.9 Hz), 6.88 (1H, t, J = 8.6 Hz), 6.84 (1H, t, J = 8.6 Hz), 6.74 (1H, d, J = 9.5 Hz), 6.69 (1H, dd, J = 8.9, 3.1 Hz), 6.57 (1H, m), 3.63 (1H, dd, J = 10.1, 7.0 Hz), 3.57-3.55 (1H, m), 3.38 (3H, s), 1.18-1.13 (1H, m), 0.62-0.60 (2H, m), 0.29-0.27 (2H, m). |
| 239 | ¹H-NMR (CDCl₃) δ: 7.37 (1H, d, J = 9.5 Hz), 7.33-7.30 (1H, m), 7.20 (1H, d, J = 8.9 Hz), 6.91 (1H, t, J = 8.4 Hz), 6.83 (1H, t, J = 8.4 Hz), 6.79 (1H, dd, J = 8.9, 2.9 Hz), 6.75-6.74 (2H, m), 5.00 (1H, d, J = 6.7 Hz), 4.94 (1H, d, J = 6.7 Hz), 3.38 (3H, s), 3.36 (3H, s). |
| 240 | ¹H-NMR (CDCl₃) δ: 7.33-7.30 (2H, m), 7.17 (1H, d, J = 8.9 Hz), 6.89 (1H, t, J = 8.4 Hz), 6.84 (1H, t, J = 8.4 Hz), 6.75-6.71 (2H, m), 6.60-6.60 (1H, m), 3.99-3.97 (1H, m), 3.87-3.83 (1H, m), 3.69-3.66 (2H, m), 3.42 (3H, s), 3.38 (3H, s). |
| 241 | ¹H-NMR (CDCl₃) δ: 7.36 (1H, d, J = 9.5 Hz), 7.33-7.30 (1H, m), 7.16 (1H, d, J = 8.6 Hz), 6.89 (1H, t, J = 8.4 Hz), 6.84 (1H, t, J = 8.4 Hz), 6.75 (1H, d, J = 9.5 Hz), 6.67 (1H, dd, J = 8.6, 3.1 Hz), 6.57 (1H, dd, J = 3.1, 1.2 Hz), 3.78-3.76 (1H, m), 3.67-3.66 (1H, m), 3.39 (3H, s), 1.72-1.69 (2H, m), 0.97 (3H, t, J = 7.5 Hz). |
| 242 | ¹H-NMR (CDCl₃) δ: 7.33-7.30 (2H, m), 7.16 (1H, d, J = 8.9 Hz), 6.89 (1H, t, J = 8.4 Hz), 6.83 (1H, t, J = 8.4 Hz), 6.73 (1H, d, J = 9.2 Hz), 6.65 (1H, dd, J = 8.9, 2.9 Hz), 6.60 (1H, dd, J = 2.9, 1.4 Hz), 3.93-3.88 (2H, m), 3.80-3.77 (1H, m), 3.68-3.66 (1H, m), 1.72-1.70 (2H, m), 1.16 (3H, t, J = 7.2 Hz), 0.98 (3H, t, J = 7.3 Hz). |
| 243 | ¹H-NMR (CDCl₃) δ: 7.36-7.29 (2H, m), 7.21 (1H, d, J = 8.6 Hz), 6.90 (1H, t, J = 8.6 Hz), 6.84 (1H, t, J = 8.6 Hz), 6.77-6.75 (2H, m), 6.69-6.68 (1H, m), 4.51 (2H, d, J = 2.3 Hz), 3.38 (3H, s), 2.50 (1H, t, J = 2.3 Hz). |
| 244 | ¹H-NMR (CDCl₃) δ: 7.33-7.29 (2H, m), 7.20 (1H, d, J = 8.9 Hz), 6.90 (1H, t, J = 8.6 Hz), 6.83 (1H, t, J = 8.6 Hz), 6.74-6.72 (3H, m), 4.51 (2H, d, J = 2.4 Hz), 3.92-3.89 (2H, m), 2.51 (1H, t, J = 2.4 Hz), 1.16 (3H, t, J = 7.2 Hz). |
| 245 | ¹H-NMR (CDCl₃) δ: 7.33 (1H, d, J = 9.2 Hz), 7.31-7.28 (1H, m), 7.17 (1H, d, J = 9.2 Hz), 6.88 (1H, t, J = 8.3 Hz), 6.82 (1H, t, J = 8.3 Hz), 6.79-6.78 (2H, m), 6.72 (1H, d, J = 9.2 Hz), 5.04-5.00 (2H, m), 3.92-3.88 (2H, m), 3.68-3.64 (2H, m), 1.15 (3H, t, J = 7.0 Hz), 0.93-0.91 (2H, m), −0.01 (9H, s). |
| 246 | ¹H-NMR (CDCl₃) δ: 7.36 (1H, d, J = 9.5 Hz), 7.33-7.29 (1H, m), 7.19 (1H, d, J = 8.9 Hz), 6.89 (1H, t, J = 8.4 Hz), 6.84 (1H, t, J = 8.4 Hz), 6.81 (1H, dd, J = 8.9, 3.1 Hz), 6.76-6.75 (2H, m), 5.04 (1H, d, J = 7.0 Hz), 5.00 (1H, d, J = 7.0 Hz), 3.68-3.64 (2H, m), 3.39 (3H, s), 0.93-0.91 (2H, m), −0.01 (9H, s). |
| 247 | ¹H-NMR (CDCl₃) δ: 7.33 (1H, d, J = 9.2 Hz), 6.72 (1H, d, J = 9.2 Hz), 6.41 (1H, d, J = 10.7 Hz), 6.36 (1H, d, J = 2.8 Hz), 6.34 (1H, d, J = 10.7 Hz), 6.20 (1H, d, J = 2.8 Hz), 3.95 (2H, q, J = 7.0 Hz), 3.83 (3H, s), 3.65 (3H, s), 3.38 (3H, s), 1.40 (3H, t, J = 7.0 Hz). |
| 248 | ¹H-NMR (CDCl₃) δ: 7.35 (1H, d, J = 9.5 Hz), 6.73 (1H, d, J = 9.5 Hz), 6.51 (1H, dt, J = 10.7, 1.8 Hz), 6.43 (1H, dt, J = 10.7, 1.8 Hz), 6.34 (1H, d, J = 2.8 Hz), 6.16 (1H, dd, J = 2.8, 1.4 Hz), 3.82 (3H, s), 3.63 (3H, s), 3.41 (3H, s), 1.35 (9H, s). |
| 249 | ¹H-NMR (DMSO-D₆) δ: 7.39 (1H, d, J = 9.5 Hz), 6.59 (1H, d, J = 9.5 Hz), 6.57 (1H, d, J = 2.8 Hz), 6.53-6.51 (1H, m), 6.40-6.39 (1H, m), 6.15 (1H, d, J = 2.8 Hz), 3.80 (3H, s), 3.63 (3H, s), 3.23 (3H, s). |

TABLE 5-continued

| Compound | ¹H-NMR |
|---|---|
| 250 | ¹H-NMR (CDCl₃) δ: 7.35-7.31 (2H, m), 7.21 (1H, d, J = 8.9 Hz), 6.92 (1H, t, J = 8.4 Hz), 6.85 (1H, t, J = 8.4 Hz), 6.74 (1H, d, J = 9.5 Hz), 6.69 (1H, dd, J = 8.9, 2.9 Hz), 6.62 (1H, m), 4.08-4.06 (1H, m), 3.97-3.87 (3H, m), 2.76 (2H, t, J = 6.3 Hz), 1.16 (3H, t, J = 7.0 Hz). |
| 251 | ¹H-NMR (CDCl₃) δ: 7.35-7.34 (2H, m), 7.22 (1H, d, J = 8.9 Hz), 6.93 (1H, t, J = 8.4 Hz), 6.86 (1H, t, J = 8.4 Hz), 6.75 (1H, dd, J = 9.5, 0.9 Hz), 6.71 (1H, dd, J = 8.9, 3.1 Hz), 6.60-6.59 (1H, m), 4.08-4.06 (1H, m), 3.95-3.93 (1H, m), 3.39 (3H, s), 2.76 (2H, t, J = 6.3 Hz). |
| 252 | ¹H-NMR (CDCl₃) δ: 7.33 (1H, d, J = 9.2 Hz), 7.32-7.30 (1H, m), 7.15 (1H, d, J = 8.9 Hz), 6.88 (1H, t, J = 8.4 Hz), 6.83 (1H, t, J = 8.4 Hz), 6.73 (1H, d, J = 9.2 Hz), 6.65 (1H, dd, J = 8.9, 3.1 Hz), 6.60 (1H, dd, J = 3.1, 1.5 Hz), 3.91-3.84 (3H, m), 3.73-3.69 (1H, m), 1.69-1.64 (2H, m), 1.43-1.41 (2H, m), 1.16 (3H, t, J = 7.0 Hz), 0.95 (3H, t, J = 7.3 Hz). |
| 253 | ¹H-NMR (CDCl₃) δ: 7.36 (1H, d, J = 9.2 Hz), 7.32-7.29 (1H, m), 7.16 (1H, d, J = 8.9 Hz), 6.89 (1H, t, J = 8.4 Hz), 6.84 (1H, t, J = 8.4 Hz), 6.74 (1H, d, J = 9.2 Hz), 6.66 (1H, dd, J = 8.9, 3.1 Hz), 6.56 (1H, dd, J = 3.1, 1.5 Hz), 3.83-3.80 (1H, m), 3.71-3.68 (1H, m), 3.38 (3H, s), 1.70-1.63 (2H, m), 1.44-1.40 (2H, m), 0.94 (3H, t, J = 7.3 Hz). |
| 254 | ¹H-NMR (CDCl₃) δ: 7.33 (1H, d, J = 9.2 Hz), 7.32-7.28 (1H, m), 7.15 (1H, d, J = 8.9 Hz), 6.88 (1H, t, J = 8.4 Hz), 6.83 (1H, t, J = 8.4 Hz), 6.73 (1H, d, J = 9.2 Hz), 6.65 (1H, dd, J = 8.9, 3.1 Hz), 6.59 (1H, dd, J = 3.1, 1.4 Hz), 3.93-3.88 (2H, m), 3.83-3.80 (1H, m), 3.71-3.68 (1H, m), 1.72-1.66 (2H, m), 1.37-1.35 (4H, m), 1.16 (3H, t, J = 7.2 Hz), 0.93 (3H, t, J = 7.2 Hz). |
| 255 | ¹H-NMR (CDCl₃) δ: 7.36 (1H, d, J = 9.2 Hz), 7.33-7.30 (1H, m), 7.16 (1H, d, J = 8.9 Hz), 6.89 (1H, t, J = 8.4 Hz), 6.84 (1H, t, J = 8.4 Hz), 6.75 (1H, d, J = 9.2 Hz), 6.66 (1H, dd, J = 8.9, 3.1 Hz), 6.57-6.56 (1H, m), 3.82-3.80 (1H, m), 3.69-3.67 (1H, m), 3.39 (3H, s), 1.69-1.67 (2H, m), 1.37-1.35 (4H, m), 0.92 (3H, t, J = 7.0 Hz). |
| 256 | ¹H-NMR (CDCl₃) δ: 7.32 (2H, d, J = 9.2 Hz), 7.31-7.29 (1H, m), 7.15 (1H, d, J = 8.9 Hz), 6.88 (1H, t, J = 8.4 Hz), 6.84 (1H, t, J = 8.4 Hz), 6.73 (1H, d, J = 9.2 Hz), 6.65 (1H, dd, J = 8.9, 3.1 Hz), 6.60 (1H, dd, J = 3.1, 1.5 Hz), 4.34-4.28 (1H, m), 3.92-3.88 (2H, m), 1.24 (3H, d, J = 6.1 Hz), 1.18 (3H, d, J = 6.1 Hz), 1.16 (3H, t, J = 7.0 Hz). |
| 257 | ¹H-NMR (CDCl₃) δ: 7.35 (1H, d, J = 9.5 Hz), 7.33-7.29 (1H, m), 7.16 (1H, d, J = 8.9 Hz), 6.88 (1H, t, J = 8.4 Hz), 6.85 (1H, t, J = 8.4 Hz), 6.74 (1H, d, J = 9.5 Hz), 6.66 (1H, dd, J = 8.9, 3.1 Hz), 6.57 (1H, dd, J = 3.1, 1.5 Hz), 4.31-4.29 (1H, m), 3.38 (3H, s), 1.23 (3H, d, J = 6.1 Hz), 1.16 (3H, d, J = 6.1 Hz). |
| 258 | ¹H-NMR (CDCl₃) δ: 7.33 (1H, d, J = 9.2 Hz), 7.32-7.28 (1H, m), 7.15 (1H, d, J = 8.6 Hz), 6.88 (1H, t, J = 8.6 Hz), 6.83 (1H, t, J = 8.6 Hz), 6.73 (1H, d, J = 9.5 Hz), 6.65 (1H, dd, J = 8.6, 3.1 Hz), 6.60 (1H, dd, J = 3.1, 1.4 Hz), 3.93-3.89 (2H, m), 3.58 (1H, dd, J = 9.0, 6.6 Hz), 3.47 (1H, dd, J = 9.0, 6.6 Hz), 2.00-1.95 (1H, m), 1.16 (3H, t, J = 7.0 Hz), 0.96 (6H, d, J = 6.7 Hz). |
| 259 | ¹H-NMR (CDCl₃) δ: 7.36 (1H, d, J = 9.5 Hz), 7.32-7.30 (1H, m), 7.16 (1H, d, J = 8.9 Hz), 6.89 (1H, t, J = 8.6 Hz), 6.84 (1H, t, J = 8.6 Hz), 6.75 (1H, d, J = 9.5 Hz), 6.67 (1H, dd, J = 8.9, 3.1 Hz), 6.56 (1H, dd, J = 3.1, 1.2 Hz), 3.57 (1H, dd, J = 9.0, 6.6 Hz), 3.45 (1H, dd, J = 9.0, 6.6 Hz), 3.39 (3H, s), 1.99-1.94 (1H, m), 0.95 (6H, d, J = 6.7 Hz). |
| 260 | ¹H-NMR (CDCl₃) δ: 7.33 (1H, d, J = 9.5 Hz), 7.31-7.29 (1H, m), 7.14 (1H, d, J = 8.6 Hz), 6.87 (1H, t, J = 8.4 Hz), 6.83 (1H, t, J = 8.4 Hz), 6.72 (1H, d, J = 9.5 Hz), 6.70-6.67 (2H, m), 3.92-3.89 (2H, m), 3.44 (1H, d, J = 12.5 Hz), 3.31 (1H, d, J = 12.5 Hz), 1.16 (3H, t, J = 7.0 Hz), 0.10 (9H, s). |
| 261 | ¹H-NMR (CDCl₃) δ: 7.36 (1H, d, J = 9.5 Hz), 7.32-7.30 (1H, m), 7.15 (1H, d, J = 8.9 Hz), 6.88 (1H, t, J = 8.6 Hz), 6.83 (1H, t, J = 8.6 Hz), 6.74 (1H, d, J = 9.5 Hz), 6.71 (1H, dd, J = 8.9, 3.1 Hz), 6.64 (1H, dd, J = 3.1, 1.2 Hz), 3.44 (1H, d, J = 12.5 Hz), 3.39 (3H, s), 3.29 (1H, d, J = 12.5 Hz), 0.10 (9H, s). |
| 262 | ¹H-NMR (CDCl₃) δ: 7.36-7.30 (1H, m), 7.31 (1H, d, J = 9.5 Hz), 7.23 (1H, d, J = 8.9 Hz), 6.91 (1H, t, J = 8.4 Hz), 6.84 (1H, t, J = 8.4 Hz), 6.75-6.73 (2H, m), 6.66 (1H, dd, J = 3.1, 1.2 Hz), 4.23-4.19 (1H, m), 4.15-4.12 (1H, m), 3.92-3.89 (2H, m), 1.16 (3H, t, J = 7.2 Hz). |
| 263 | ¹H-NMR (CDCl₃) δ: 7.34-7.33 (2H, m), 7.24 (1H, d, J = 8.9 Hz), 6.91 (1H, t, J = 8.4 Hz), 6.85 (1H, t, J = 8.4 Hz), 6.76-6.74 (2H, m), 6.64 (1H, dd, J = 3.1, 1.2 Hz), 4.22-4.19 (1H, m), 4.14-4.11 (1H, m), 3.39 (3H, s). |
| 264 | ¹H-NMR (CDCl₃), mixture of 2 diastereoisomers, δ: 8.05-8.02 (1H, m, one diastereoisomer), 7.90 (1H, dd, J = 8.0, 0.9 Hz, one diastereoisomer), 7.52 (1H, d, J = 9.2 Hz, one diastereoisomer), 7.47-7.15 (7H, m, two diastereoisomers), 7.13 (1H, d, J = 9.2 Hz, one diastereoisomer), 7.06-7.01 (2H, m, two diastereoisomers), 6.91 (1H, t, J = 8.4 Hz, one diastereoisomer), 6.81-6.72 (4H, m, two diastereoisomers), 4.14-4.07 (1H, m, one diastereoisomer), 4.01-.95 (1H, m, one diastereoisomer), 3.81-3.72 (2H, m, two diastereoisomers), 2.63 (3H, s, one diastereoisomer), 2.60 (3H, s, one diastereoisomer.), 1.15 (6H, t, J = 7.0 Hz, two diastereoisomers). Diastero ratio = 50/50 |
| 265 | ¹H-NMR (CDCl₃) δ 7.39-7.31 (2H, m), 7.14 (2H, d, J = 8.9 Hz), 6.98 (2H, d, J = 8.9 Hz), 6.88 (2H, td, J = 8.9, 1.9 Hz), 6.73 (1H, d, J = 9.2 Hz), 3.90 (2H, q, J = 7.0 Hz), 1.14 (3H, t, J = 7.0 Hz). |
| 266 | ¹H-NMR (CDCl₃) δ: 7.58 (1H, s), 7.37 (1H, tt, J = 8.4, 7.2 Hz), 7.15 (2H, d, J = 8.5 Hz), 6.98 (2H, d, J = 8.5 Hz), 6.89 (2H, dd, J = 8.4, 7.2 Hz), 3.95 (2H, q, J = 7.0 Hz), 1.16 (3H, t, J = 7.0 Hz). |
| 267 | ¹H-NMR (CDCl₃) δ: 7.26-7.24 (1H, m), 6.92 (2H, d, J = 8.0 Hz), 6.85 (2H, d, J = 8.0 Hz), 6.81-6.79 (2H, m), 3.41 (2H, q, J = 7.0 Hz), 2.77-2.69 (4H, m), 2.23 (3H, s), 0.96 (3H, t, J = 7.0 Hz). |
| 268 | ¹H-NMR (CDCl₃) δ: 7.26-7.24 (1H, m), 6.93 (2H, d, J = 8.0 Hz), 6.86 (2H, d, J = 8.0 Hz), 6.82-6.80 (2H, m), 2.86 (3H, s), 2.78-2.73 (4H, m), 2.23 (3H, s). |
| 269 | ¹H-NMR (CDCl₃) δ: 7.38 (1H, d, J = 9.5 Hz), 7.33-7.30 (1H, m), 6.96 (2H, d, J = 8.3 Hz), 6.93 (2H, d, J = 8.3 Hz), 6.86 (2H, dd, J = 8.4, 7.2 Hz), 6.72 (1H, d, J = 9.5 Hz), 3.90 (2H, q, J = 7.0 Hz), 2.24 (3H, s), 1.14 (3H, t, J = 7.0 Hz). |
| 270 | ¹H-NMR (CDCl₃) δ: 7.41 (1H, d, J = 9.5 Hz), 7.33 (1H, tt, J = 8.4, 6.4 Hz), 6.97 (2H, d, J = 8.0 Hz), 6.92 (2H, d, J = 8.0 Hz), 6.89-6.85 (2H, m), 6.74 (1H, d, J = 9.5 Hz), 3.37 (3H, s), 2.25 (3H, s). |

TABLE 5-continued

| Compound | ¹H-NMR |
|---|---|
| 271 | ¹H-NMR (CDCl₃) δ: 7.82 (1H, s), 7.33 (1H, tt, J = 8.4, 6.4 Hz), 6.98-6.91 (4H, m), 6.86 (2H, dd, J = 8.4, 7.0 Hz), 3.95 (2H, q, J = 7.1 Hz), 2.25 (3H, s), 1.16 (3H, t, J = 7.1 Hz). |
| 272 | ¹H-NMR (CDCl₃) δ: 7.61 (1H, s), 7.33-7.31 (1H, m), 6.98-6.91 (4H, m), 6.86 (2H, dd, J = 8.4, 7.2 Hz), 3.95 (2H, q, J = 7.1 Hz), 2.25 (3H, s), 1.16 (3H, t, J = 7.1 Hz). |
| 273 | ¹H-NMR (CDCl₃) δ: 7.85 (1H, s), 7.35-7.33 (1H, m), 6.98-6.92 (4H, m), 6.87 (2H, dd, J = 8.6, 7.1 Hz), 3.44 (3H, s), 2.25 (3H, s). |
| 274 | 1H-NMR (CDCl3) δ: 7.64 (1H, s), 7.34 (1H, tt, J = 8.6, 7.0 Hz), 6.98 (2H, d, J = 8.2 Hz), 6.92 (2H, d, J = 8.2 Hz), 6.88 (2H, dd, J = 8.6, 7.0 Hz), 3.44 (3H, s), 2.25 (3H, s). |
| 275 | ¹H-NMR (CDCl₃) δ: 7.32 (1H, d, J = 9.5 Hz), 7.31-7.29 (1H, m), 7.15 (1H, d, J = 8.9 Hz), 6.88 (1H, t, J = 8.4 Hz), 6.83 (1H, t, J = 8.4 Hz), 6.72 (1H, d, J = 9.5 Hz), 6.65 (1H, dd, J = 8.9, 3.1 Hz), 6.59 (1H, dd, J = 3.1, 1.5 Hz), 3.92-3.88 (2H, m), 3.79-3.75 (1H, m), 3.66-3.63 (1H, m), 1.71-1.69 (2H, m), 1.16 (3H, t, J = 7.2 Hz), 0.56-0.52 (2H, m), 0.01 (9H, s). |
| 276 | ¹H-NMR (CDCl₃) δ: 7.35 (1H, d, J = 9.5 Hz), 7.33-7.30 (1H, m), 7.16 (1H, d, J = 8.9 Hz), 6.88 (1H, t, J = 8.6 Hz), 6.84 (1H, t, J = 8.6 Hz), 6.74 (1H, d, J = 9.5 Hz), 6.66 (1H, dd, J = 8.9, 3.1 Hz), 6.57 (1H, dd, J = 3.1, 1.5 Hz), 3.77-3.76 (1H, m), 3.64-3.63 (1H, m), 3.38 (3H, s), 1.70-1.69 (2H, m), 0.56-0.51 (2H, m), 0.01 (9H, s). |
| 277 | ¹H-NMR (CDCl₃) δ: 7.33-7.31 (2H, m), 7.21 (1H, d, J = 8.9 Hz), 6.91 (1H, t, J = 8.4 Hz), 6.84 (1H, t, J = 8.4 Hz), 6.75-6.69 (2H, m), 6.64-6.63 (1H, m), 5.98 (1H, tt, J = 55.1, 4.1 Hz), 4.08-3.87 (4H, m), 1.16 (3H, t, J = 7.2 Hz). |
| 278 | ¹H-NMR (CDCl₃) δ: 7.35-7.32 (1H, m), 7.34 (1H, d, J = 9.5 Hz), 7.22 (1H, d, J = 8.9 Hz), 6.92 (1H, t, J = 8.4 Hz), 6.85 (1H, t, J = 8.4 Hz), 6.75 (1H, d, J = 9.5 Hz), 6.72 (1H, dd, J = 8.9, 3.1 Hz), 6.60 (1H, dd, J = 3.1, 1.5 Hz), 5.98 (1H, tt, J = 54.9, 4.1 Hz), 4.07-3.90 (2H, m), 3.39 (3H, s). |
| 279 | ¹H-NMR (CDCl₃) δ: 7.79 (1H, s), 7.37 (1H, tt, J = 8.6, 3.5 Hz), 7.15 (2H, d, J = 8.3 Hz), 6.98 (2H, d, J = 8.6 Hz), 6.89 (2H, dd, J = 8.4, 7.2 Hz), 3.95 (2H, q, J = 7.0 Hz), 1.16 (3H, t, J = 7.0 Hz). |
| 280 | ¹H-NMR (CDCl₃) δ: 7.39-7.33 (2H, m), 7.15 (2H, d, J = 8.6 Hz), 6.98 (2H, d, J = 8.3 Hz), 6.89 (2H, dt, J = 12.4, 4.8 Hz), 6.75 (1H, d, J = 9.2 Hz), 3.37 (3H, s). |
| 281 | ¹H-NMR (CDCl₃) δ: 7.33 (1H, d, J = 9.5 Hz), 6.72 (1H, d, J = 9.5 Hz), 6.42-6.41 (1H, m), 6.37 (1H, d, J = 2.8 Hz), 6.35-6.33 (1H, m), 6.21 (1H, dd, J = 2.8, 1.2 Hz), 3.85-3.84 (5H, m), 3.65 (3H, s), 3.38 (3H, s), 1.79-1.78 (2H, m), 1.02 (3H, t, J = 7.3 Hz). |
| 282 | ¹H-NMR (CDCl₃) δ: 7.33 (1H, d, J = 9.5 Hz), 6.72 (1H, d, J = 9.5 Hz), 6.42-6.40 (1H, m), 6.37 (1H, d, J = 2.8 Hz), 6.35-6.33 (1H, m), 6.21 (1H, dd, J = 2.8, 1.2 Hz), 3.88 (2H, t, J = 6.6 Hz), 3.83 (3H, s), 3.65 (3H, s), 3.38 (3H, s), 1.75-1.72 (2H, m), 1.47-1.44 (2H, m), 0.97 (3H, t, J = 7.3 Hz). |
| 283 | ¹H-NMR (CDCl₃) δ: 7.32-7.26 (3H, m), 7.18-7.17 (2H, m), 6.83-6.80 (2H, m), 3.44 (2H, q, J = 7.1 Hz), 2.82-2.73 (4H, m), 0.97 (3H, t, J = 7.1 Hz). |
| 284 | ¹H-NMR (CDCl₃) δ: 7.43-7.26 (6H, m), 6.87 (2H, dd, J = 8.4, 7.2 Hz), 6.76 (1H, d, J = 9.2 Hz), 3.92 (2H, q, J = 7.2 Hz), 1.15 (3H, t, J = 7.2 Hz). |
| 285 | ¹H-NMR (CDCl₃) δ: 7.61 (1H, s), 7.38 (1H, tt, J = 8.6, 3.5 Hz), 7.16 (2H, d, J = 8.6 Hz), 6.98 (2H, dd, J = 8.6 Hz), 6.90 (2H, dd, J = 8.4, 7.2 Hz), 3.44 (3H, s). |
| 286 | ¹H-NMR (CDCl₃) δ: 7.81 (1H, s), 7.38 (1H, tt, J = 8.5, 3.5 Hz), 7.16 (2H, dt, J = 8.7, 2.3 Hz), 6.98 (2H, dt, J = 8.9, 2.3 Hz), 6.89 (2H, tt, J = 10.1, 1.8 Hz), 3.44 (3H, s). |
| 287 | ¹H-NMR (CDCl₃) δ: 7.34-7.28 (1H, m), 7.32 (1H, d, J = 8.6 Hz), 6.89 (1H, t, J = 8.4 Hz), 6.84 (1H, t, J = 8.4 Hz), 6.73 (1H, d, J = 9.5 Hz), 6.63 (1H, dd, J = 8.6, 3.1 Hz), 6.57 (1H, dd, J = 3.1, 1.5 Hz), 4.53-4.52 (1H, m), 3.94-3.86 (2H, m), 1.82-1.57 (8H, m), 1.16 (3H, t, J = 7.2 Hz). |
| 288 | ¹H-NMR (CDCl₃) δ: 7.35 (1H, d, J = 9.5 Hz), 7.32-7.30 (1H, m), 7.15 (1H, d, J = 8.6 Hz), 6.89 (1H, t, J = 8.4 Hz), 6.84 (1H, t, J = 8.4 Hz), 6.75 (1H, d, J = 9.2 Hz), 6.64 (1H, dd, J = 8.6, 3.1 Hz), 6.54 (1H, dd, J = 3.1, 1.4 Hz), 4.53-4.51 (1H, m), 3.38 (3H, s), 1.81-1.56 (8H, m). |
| 289 | ¹H-NMR (CDCl₃) δ: 7.37-7.36 (2H, m), 7.30 (2H, d, J = 8.6 Hz), 6.91-6.89 (4H, m), 6.75 (1H, d, J = 9.2 Hz), 3.37 (3H, s). |
| 290 | ¹H-NMR (CDCl₃) δ: 7.81 (1H, s), 7.40-7.36 (1H, m), 7.31 (2H, d, J = 8.6 Hz), 6.91-6.89 (4H, m), 3.44 (3H, s). |
| 291 | ¹H-NMR (CDCl₃) δ: 7.60 (1H, s), 7.40-7.36 (1H, m), 7.31 (2H, d, J = 8.3 Hz), 6.93-6.88 (4H, m), 3.44 (3H, s). |
| 292 | ¹H-NMR (CDCl₃) δ: 7.39-7.28 (4H, m), 6.94-6.86 (4H, m), 6.73 (1H, d, J = 9.5 Hz), 3.89 (2H, q, J = 7.1 Hz), 1.14 (3H, t, J = 7.1 Hz). |
| 293 | ¹H-NMR (CDCl₃) δ: 7.79 (1H, s), 7.38-7.36 (1H, m), 7.31 (2H, d, J = 8.3 Hz), 6.94-6.87 (4H, m), 3.94 (2H, q, J = 7.1 Hz), 1.16 (3H, t, J = 7.1 Hz). |
| 294 | ¹H-NMR (CDCl₃) δ: 7.58 (1H, s), 7.41-7.34 (1H, m), 7.31 (2H, d, J = 8.6 Hz), 6.92-6.89 (4H, m), 3.94 (2H, q, J = 7.1 Hz), 1.16 (3H, t, J = 7.1 Hz). |
| 295 | ¹H-NMR (CDCl₃) δ: 7.33 (1H, d, J = 9.5 Hz), 7.32-7.30 (1H, m), 7.15 (1H, d, J = 8.7 Hz), 6.88 (1H, t, J = 8.4 Hz), 6.84 (1H, t, J = 8.4 Hz), 6.73 (1H, d, J = 9.5 Hz), 6.66 (1H, dd, J = 8.7, 2.9 Hz), 6.60 (1H, dd, J = 2.9, 1.4 Hz), 3.95-3.89 (3H, m), 1.76-1.40 (10H, m), 1.16 (3H, t, J = 7.0 Hz). |
| 296 | ¹H-NMR (CDCl₃) δ: 7.36 (1H, d, J = 9.5 Hz), 7.32-7.30 (1H, m), 7.16 (1H, d, J = 8.9 Hz), 6.89 (1H, t, J = 8.6 Hz), 6.84 (1H, t, J = 8.6 Hz), 6.75 (1H, d, J = 9.5 Hz), 6.67 (1H, dd, J = 8.9, 3.1 Hz), 6.57 (1H, dd, J = 3.1, 1.2 Hz), 3.99-3.96 (1H, m), 3.38 (3H, s), 1.74-1.37 (10H, m). |
| 297 | ¹H-NMR (CDCl₃) δ: 7.31 (3H, tt, J = 9.6, 3.0 Hz), 6.96-6.90 (3H, m), 6.83 (1H, t, J = 8.4 Hz), 6.74 (1H, d, J = 9.5 Hz), 3.93-3.88 (2H, m), 3.88 (3H, s), 1.16 (3H, t, J = 7.2 Hz). |
| 298 | ¹H-NMR (CDCl₃) δ: 7.36-7.30 (3H, m), 6.97 (1H, dd, J = 8.9, 2.8 Hz), 6.92-6.90 (2H, m), 6.84 (1H, t, J = 8.4 Hz), 6.75 (1H, d, J = 9.5 Hz), 3.87 (3H, s), 3.39 (3H, s). |
| 299 | ¹H-NMR (CDCl₃) δ: 7.64 (1H, s), 7.44 (1H, d, J = 7.3 Hz), 7.35-7.31 (4H, m), 6.90-6.86 (2H, m), 3.97 (2H, q, J = 7.2 Hz), 1.18 (3H, t, J = 7.2 Hz). |
| 300 | ¹H-NMR (CDCl₃) δ: 7.26-7.23 (1H, m), 6.89 (2H, d, J = 8.6 Hz), 6.80 (2H, t, J = 7.8 Hz), 6.65 (2H, d, J = 8.9 Hz), 3.72 (3H, s), 3.41 (2H, q, J = 7.0 Hz), 2.74-2.71 (4H, m), 0.95 (3H, t, J = 7.0 Hz). |

TABLE 5-continued

| Compound | ¹H-NMR |
|---|---|
| 301 | ¹H-NMR (CDCl₃) δ: 7.37 (1H, d, J = 9.2 Hz), 7.32-7.31 (1H, m), 6.97-6.96 (2H, m), 6.86 (2H, dd, J = 8.4, 7.2 Hz), 6.72-6.69 (3H, m), 3.90 (2H, q, J = 7.2 Hz), 3.73 (3H, s), 1.14 (3H, t, J = 7.2 Hz). |
| 302 | ¹H-NMR (CDCl₃) δ: 7.61 (1H, s), 7.34-7.32 (1H, m), 6.96 (2H, dt, J = 9.4, 2.5 Hz), 6.88-6.86 (2H, m), 6.69 (2H, dt, J = 9.3, 2.6 Hz), 3.94 (2H, q, J = 7.2 Hz), 3.73 (3H, s), 1.16 (3H, t, J = 7.2 Hz). |
| 303 | ¹H-NMR (CDCl₃) δ: 7.32-7.31 (1H, m), 7.31 (1H, d, J = 9.5 Hz), 7.20 (1H, d, J = 8.9 Hz), 6.91 (1H, t, J = 8.4 Hz), 6.84 (1H, t, J = 8.4 Hz), 6.73 (1H, d, J = 9.5 Hz), 6.69 (1H, dd, J = 8.9, 3.1 Hz), 6.55 (1H, dd, J = 3.1, 1.5 Hz), 4.42 (1H, d, J = 16.8 Hz), 4.37 (1H, d, J = 16.8 Hz), 3.92-3.87 (2H, m), 2.20 (3H, s), 1.16 (3H, t, J = 7.0 Hz). |
| 304 | ¹H-NMR (CDCl₃) δ: 7.34-7.32 (2H, m), 7.21 (1H, d, J = 8.9 Hz), 6.92 (1H, t, J = 8.4 Hz), 6.85 (1H, t, J = 8.4 Hz), 6.75 (1H, d, J = 9.2 Hz), 6.70 (1H, dd, J = 8.9, 3.1 Hz), 6.53 (1H, dd, J = 3.1, 1.4 Hz), 4.41 (1H, d, J = 16.8 Hz), 4.35 (1H, d, J = 16.8 Hz), 3.38 (3H, s), 2.19 (3H, s). |
| 305 | ¹H-NMR (CDCl₃) δ: 7.33 (1H, d, J = 9.2 Hz), 7.33-7.30 (1H, m), 7.21 (1H, d, J = 8.9 Hz), 6.91 (1H, t, J = 8.4 Hz), 6.84 (1H, t, J = 8.4 Hz), 6.73-6.72 (2H, m), 6.68-6.67 (1H, m), 4.98 (1H, d, J = 11.9 Hz), 4.96 (1H, d, J = 11.9 Hz), 3.93-3.87 (2H, m), 2.17 (3H, s), 1.16 (3H, t, J = 7.2 Hz). |
| 306 | ¹H-NMR (CDCl₃) δ: 7.36 (1H, d, J = 9.5 Hz), 7.33-7.30 (1H, m), 1.12 (1H, d, J = 8.5 Hz), 6.91 (1H, t, J = 8.4 Hz), 6.84 (1H, t, J = 8.4 Hz), 6.74 (1H, dd, J = 9.0, 3.4 Hz), 6.65 (1H, m), 4.98 (1H, d, J = 11.9 Hz), 4.94 (1H, d, J = 11.9 Hz), 3.38 (3H, s), 2.16 (3H, s). |
| 307 | ¹H-NMR (CDCl₃) δ: 7.33-7.31 (2H, m), 7.19 (1H, d, J = 8.9 Hz), 6.91 (1H, t, J = 8.4 Hz), 6.84 (1H, t, J = 8.4 Hz), 6.73-6.71 (2H, m), 6.59 (1H, dd, J = 3.1, 1.5 Hz), 4.43 (2H, s), 4.27 (2H, q, J = 7.1 Hz), 3.91-3.89 (2H, m), 1.30 (3H, t, J = 7.1 Hz), 1.16 (3H, t, J = 7.1 Hz). |
| 308 | ¹H-NMR (CDCl₃) δ: 7.34-7.31 (1H, m), 7.34 (1H, d, J = 9.5 Hz), 7.20 (1H, d, J = 8.9 Hz), 6.91 (1H, t, J = 8.6 Hz), 6.84 (1H, t, J = 8.6 Hz), 6.76-6.71 (2H, m), 6.57 (1H, dd, J = 3.1, 1.5 Hz), 4.42 (2H, s), 4.26 (2H, q, J = 7.2 Hz), 3.38 (3H, s), 1.30 (3H, t, J = 7.2 Hz). |
| 309 | ¹H-NMR (CDCl₃) δ: 7.34-7.32 (1H, m), 7.31 (1H, d, J = 9.5 Hz), 7.26 (3H, d, J = 8.9 Hz), 6.93 (1H, t, J = 8.4 Hz), 6.87-6.83 (2H, m), 6.78 (1H, dd, J = 2.9, 1.4 Hz), 6.74 (1H, d, J = 9.5 Hz), 4.80 (1H, d, J = 12.2 Hz), 4.73 (1H, d, J = 12.2 Hz), 3.93-3.87 (2H, m), 2.96 (3H, s), 1.16 (3H, t, J = 7.2 Hz). |
| 310 | ¹H-NMR (CDCl₃) δ: 7.33-7.27 (1H, m), 7.33 (1H, d, J = 9.2 Hz), 7.16 (1H, d, J = 8.9 Hz), 6.89 (1H, t, J = 8.4 Hz), 6.83 (1H, t, J = 8.4 Hz), 6.73 (1H, d, J = 9.2 Hz), 6.66 (1H, dd, J = 8.9, 3.1 Hz), 6.61 (1H, dd, J = 3.1, 1.2 Hz), 3.96-3.78 (4H, m), 3.49-3.48 (2H, m), 3.34 (3H, s), 1.98-1.93 (2H, m), 1.16 (3H, t, J = 7.0 Hz). |
| 311 | ¹H-NMR (CDCl₃) δ: 7.35 (1H, d, J = 9.5 Hz), 7.32-7.30 (1H, m), 7.17 (1H, d, J = 8.9 Hz), 6.90 (1H, t, J = 8.4 Hz), 6.84 (1H, t, J = 8.4 Hz), 6.75 (1H, d, J = 9.5 Hz), 6.67 (1H, dd, J = 8.9, 3.1 Hz), 6.58 (1H, dd, J = 3.1, 1.4 Hz), 3.93-3.90 (1H, m), 3.80-3.78 (1H, m), 3.48 (2H, t, J = 6.1 Hz), 3.39 (3H, s), 3.34 (3H, s), 1.97-1.92 (2H, m). |
| 312 | ¹H-NMR (CDCl₃) δ: 7.36-7.32 (2H, m), 7.27-7.26 (1H, m), 6.93 (1H, t, J = 8.4 Hz), 6.88-6.84 (2H, m), 6.76-6.75 (2H, m), 4.79 (1H, d, J = 12.2 Hz), 4.72 (1H, d, J = 12.2 Hz), 3.39 (3H, s), 2.95 (3H, s). |
| 313 | ¹H-NMR (CDCl₃) δ: 7.32 (1H, d, J = 9.5 Hz), 7.32-7.30 (1H, m), 7.17 (1H, d, J = 8.9 Hz), 6.89 (1H, t, J = 8.4 Hz), 6.83 (1H, t, J = 8.4 Hz), 6.73 (1H, d, J = 9.5 Hz), 6.68 (1H, dd, J = 8.9, 3.1 Hz), 6.62 (1H, dd, J = 3.1, 1.5 Hz), 5.99-5.91 (1H, m), 5.34-5.30 (1H, m), 5.27-5.25 (1H, m), 4.40-4.38 (1H, m), 4.32-4.31 (1H, m), 3.94-3.88 (2H, m), 1.16 (3H, t, J = 7.0 Hz). |
| 314 | ¹H-NMR (CDCl₃) δ: 7.35 (1H, d, J = 9.2 Hz), 7.32-7.31 (1H, m), 7.18 (1H, d, J = 8.9 Hz), 6.90 (1H, t, J = 8.6 Hz), 6.84 (1H, t, J = 8.6 Hz), 6.75 (1H, d, J = 9.2 Hz), 6.69 (1H, dd, J = 8.9, 3.1 Hz), 6.59 (1H, dd, J = 3.1, 1.4 Hz), 5.98-5.90 (1H, m), 5.34-5.29 (1H, m), 5.26-5.24 (1H, m), 4.40-4.37 (1H, m), 4.32-4.29 (1H, m), 3.38 (3H, s). |
| 315 | ¹H-NMR (CDCl₃) δ: 7.33-7.29 (1H, m), 7.31 (1H, d, J = 9.5 Hz), 7.17 (1H, d, J = 8.9 Hz), 6.89 (1H, t, J = 8.4 Hz), 6.83 (1H, t, J = 8.4 Hz), 6.73-6.71 (2H, m), 6.64-6.63 (1H, m), 5.19 (1H, t, J = 4.0 Hz), 4.05-4.00 (2H, m), 3.99-3.87 (5H, m), 3.77 (1H, dd, J = 10.2, 4.0 Hz), 1.16 (3H, t, J = 7.2 Hz). |
| 316 | ¹H-NMR (CDCl₃) δ: 7.34-7.29 (1H, m), 7.34 (1H, d, J = 9.5 Hz), 7.18 (1H, d, J = 8.9 Hz), 6.89 (1H, t, J = 8.6 Hz), 6.84 (1H, t, J = 8.6 Hz), 6.75-6.72 (2H, m), 6.62-6.61 (1H, m), 5.19 (1H, t, J = 4.0 Hz), 4.03-4.01 (2H, m), 3.98-3.94 (2H, m), 3.89 (1H, dd, J = 10.1, 4.0 Hz), 3.76 (1H, dd, J = 10.1, 4.0 Hz), 3.38 (3H, s). |
| 317 | ¹H-NMR (CDCl₃) δ: 7.33 (1H, d, J = 9.2 Hz), 7.32-7.29 (1H, m), 7.16 (1H, d, J = 8.9 Hz), 6.90 (1H, t, J = 8.4 Hz), 6.83 (1H, t, J = 8.4 Hz), 6.73 (1H, d, J = 9.2 Hz), 6.66 (1H, dd, J = 8.9, 2.9 Hz), 6.61 (1H, dd, J = 2.9, 1.4 Hz), 4.70 (1H, t, J = 5.2 Hz), 4.12-4.10 (2H, m), 3.96-3.75 (6H, m), 2.12-2.05 (1H, m), 1.99-1.97 (2H, m), 1.38-1.35 (6H, m), 1.16 (3H, t, J = 7.0 Hz). |
| 318 | ¹H-NMR (CDCl₃) δ: 7.35 (1H, d, J = 9.5 Hz), 7.32-7.30 (1H, m), 7.17 (1H, d, J = 8.9 Hz), 6.90 (1H, t, J = 8.6 Hz), 6.83 (1H, t, J = 8.6 Hz), 6.74 (1H, d, J = 9.5 Hz), 6.67 (1H, dd, J = 8.9, 3.1 Hz), 6.58 (1H, dd, J = 3.1, 1.2 Hz), 4.70 (1H, t, J = 5.2 Hz), 4.12-4.09 (2H, m), 3.94-3.92 (1H, m), 3.79-3.77 (3H, m), 3.39 (3H, s), 1.98-1.96 (2H, m), 1.38-1.35 (6H, m). |
| 319 | ¹H-NMR (CDCl₃) δ: 7.32 (1H, d, J = 9.5 Hz), 6.74 (1H, d, J = 9.5 Hz), 6.51 (1H, dt, J = 10.0, 2.0 Hz), 6.42 (1H, dt, J = 10.0, 2.0 Hz), 6.38 (1H, d, J = 2.8 Hz), 6.21 (1H, dd, J = 2.8, 1.7 Hz), 4.29 (2H, q, J = 7.8 Hz), 3.83 (3H, s), 3.67 (3H, s), 3.37 (3H, s). |
| 320 | ¹H-NMR (CDCl₃) δ: 7.24 (1H, dd, J = 8.9, 5.2 Hz), 6.83-6.81 (1H, m), 6.76-6.74 (1H, m), 6.63-6.61 (1H, m), 6.56-6.54 (1H, m), 3.44-3.39 (2H, m), 2.89-2.54 (4H, m), 0.99 (3H, t, J = 7.0 Hz). |
| 321 | ¹H-NMR (CDCl₃) δ: 7.30-7.27 (2H, m), 6.90-6.61 (5H, m), 3.90 (2H, q, J = 6.9 Hz), 1.16 (3H, t, J = 6.9 Hz). |
| 322 | ¹H-NMR (CDCl₃) δ: 7.53 (1H, s), 7.29 (1H, dd, J = 8.9, 5.2 Hz), 6.92-6.90 (1H, m), 6.82-6.80 (1H, m), 6.71 (1H, tt, J = 8.7, 2.0 Hz), 6.64 (1H, tt, J = 8.7, 2.0 Hz), 3.99-3.90 (2H, m), 1.19 (3H, t, J = 7.0 Hz). |
| 323 | ¹H-NMR (CDCl₃) δ: 7.34-7.28 (1H, m), 7.33 (1H, d, J = 9.5 Hz), 7.15 (1H, d, J = 8.9 Hz), 6.88 (1H, t, J = 8.6 Hz), 6.83 (1H, t, J = 8.6 Hz), 6.73 (1H, d, J = 9.5 Hz), 6.65 (1H, dd, J = 8.9, |

TABLE 5-continued

| Compound | ¹H-NMR |
|---|---|
| | 3.1 Hz), 6.60 (1H, dd, J = 3.1, 1.4 Hz), 3.97-3.84 (2H, m), 3.69 (1H, dd, J = 9.0, 7.0 Hz), 3.57 (1H, dd, J = 9.0, 7.0 Hz), 2.27-2.22 (1H, m), 1.79-1.74 (2H, m), 1.64-1.54 (4H, m), 1.28-1.26 (2H, m), 1.16 (3H, t, J = 7.0 Hz). |
| 324 | ¹H-NMR (CDCl₃) δ: 7.36 (1H, d, J = 9.5 Hz), 7.33-7.30 (1H, m), 7.16 (1H, d, J = 8.9 Hz), 6.89 (1H, t, J = 8.6 Hz), 6.84 (1H, t, J = 8.6 Hz), 6.74 (1H, d, J = 9.5 Hz), 6.67 (1H, dd, J = 8.9, 2.8 Hz), 6.57 (1H, dd, J = 2.8, 1.2 Hz), 3.68 (1H, dd, J = 9.0, 6.9 Hz), 3.55 (1H, dd, J = 9.0, 6.9 Hz), 3.39 (3H, s), 2.24 (1H, t, J = 7.3 Hz), 1.78-1.77 (2H, m), 1.63-1.56 (4H, m), 1.29-1.25 (2H, m). |
| 325 | ¹H-NMR (CDCl₃) δ: 7.33 (1H, d, J = 9.2 Hz), 7.33-7.27 (1H, m), 7.19-7.17 (1H, m), 6.89 (1H, t, J = 8.4 Hz), 6.83 (1H, t, J = 8.4 Hz), 6.80-6.77 (2H, m), 6.73 (1H, d, J = 9.2 Hz), 5.05 (1H, d, J = 7.0 Hz), 5.02 (1H, d, J = 7.0 Hz), 3.92-3.88 (2H, m), 3.63 (2H, q, J = 7.1 Hz), 1.20-1.14 (6H, m). |
| 326 | ¹H-NMR (CDCl₃) δ: 7.36 (1H, d, J = 9.5 Hz), 7.32-7.30 (1H, m), 7.19 (1H, d, J = 8.9 Hz), 6.89 (1H, t, J = 8.4 Hz), 6.83 (1H, t, J = 8.4 Hz), 6.80 (1H, dd, J = 8.9, 2.9 Hz), 6.76-6.74 (2H, m), 5.05 (1H, d, J = 7.0 Hz), 5.01 (1H, d, J = 7.0 Hz), 3.62 (2H, q, J = 7.0 Hz), 3.38 (3H, s), 1.18 (3H, t, J = 7.0 Hz). |
| 327 | ¹H-NMR (CDCl₃) δ: 7.37-7.35 (2H, m), 7.30-7.28 (1H, m), 7.22 (1H, t, J = 1.7 Hz), 7.03 (1H, t, J = 7.6 Hz), 6.98-6.97 (1H, m), 6.92-6.87 (2H, m), 6.73 (1H, d, J = 9.5 Hz), 3.90 (2H, q, J = 7.1 Hz), 1.14 (3H, t, J = 7.1 Hz). |
| 328 | ¹H-NMR (CDCl₃) δ: 7.60 (1H, s), 7.38-7.36 (1H, m), 7.32-7.30 (1H, m), 7.22 (1H, t, J = 1.7 Hz), 7.05-7.03 (1H, m), 6.99-6.97 (1H, m), 6.93-6.88 (2H, m), 3.95 (2H, q, J = 7.1 Hz), 1.17 (3H, t, J = 7.1 Hz). |
| 329 | 1H-NMR (CDCl3) δ: 7.30-7.28 (1H, m), 7.23 (1H, s), 7.17 (1H, d, J = 8.9 Hz), 6.88 (1H, t, J = 8.3 Hz), 6.82 (1H, t, J = 8.3 Hz), 6.65 (1H, dd, J = 8.9, 3.1 Hz), 6.63-6.61 (1H, m), 3.93-3.90 (2H, m), 3.65 (3H, s), 2.25 (3H, s), 1.16 (3H, t, J = 7.0 Hz). |
| 330 | ¹H-NMR (CDCl₃) δ: 7.32 (1H, d, J = 9.5 Hz), 7.31-7.28 (1H, m), 7.18 (1H, d, J = 8.5 Hz), 6.89 (1H, t, J = 8.5 Hz), 6.85-6.78 (3H, m), 6.73 (1H, d, J = 9.5 Hz), 5.10 (1H, d, J = 7.0 Hz), 5.07 (1H, d, J = 7.0 Hz), 3.91-3.89 (2H, m), 3.74-3.71 (2H, m), 3.54-3.51 (2H, m), 3.37 (3H, s), 1.16 (3H, t, J = 7.0 Hz). |
| 331 | ¹H-NMR (CDCl₃) δ: 7.35 (1H, d, J = 9.5 Hz), 7.33-7.29 (1H, m), 7.19 (1H, d, J = 8.9 Hz), 6.89 (1H, t, J = 8.4 Hz), 6.85-6.81 (2H, m), 6.75-6.74 (2H, m), 5.09 (1H, d, J = 7.0 Hz), 5.06 (1H, d, J = 7.0 Hz), 3.73-3.71 (2H, m), 3.53-3.51 (2H, m), 3.38 (3H, s), 3.36 (3H, s). |
| 332 | ¹H-NMR (CDCl₃)δ: 7.36-7.30 (2H, m), 7.28 (1H, d, J = 9.5 Hz), 7.03-6.97 (2H, m), 6.90 (1H, t, J = 8.5 Hz), 6.85 (1H, t, J = 8.5 Hz), 3.96-3.83 (2H, m), 1.15 (3H, t, J = 7.0 Hz). |
| 333 | ¹H-NMR (CDCl₃) δ: 7.51 (1H, s), 7.37-7.31 (2H, m), 7.08-6.99 (2H, m), 6.91-6.83 (2H, m), 4.01-3.91 (2H, m), 1.18 (3H, t, J = 7.0 Hz). |
| 334 | ¹H-NMR (CDCl₃) δ: 7.27-7.23 (1H, m), 6.82 (1H, t, J = 8.4 Hz), 6.77 (1H, t, J = 8.4 Hz), 6.31 (1H, d, J = 2.4 Hz), 6.19-6.17 (1H, br m), 4.07 (2H, br s), 3.80 (3H, s), 3.63 (3H, s), 2.97-2.91 (1H, m), 2.87-2.82 (1H, m), 2.78-2.72 (1H, m), 2.67-2.61 (1H, m). |
| 335 | ¹H-NMR (CDCl₃) δ: 7.38-7.30 (2H, m), 6.90-6.82 (2H, m), 6.77 (1H, d, J = 9.5 Hz), 6.35 (1H, d, J = 2.7 Hz), 6.24-6.21 (1H, br m), 4.62 (2H, br s), 3.81 (3H, s), 3.65 (3H, s). |
| 336 | ¹H-NMR (CDCl₃) δ: 7.26-7.22 (1H, m), 6.82 (1H, tt, J = 8.4, 1.5 Hz), 6.77 (1H, tt, J = 8.4, 1.5 Hz), 6.30 (1H, d, J = 2.7 Hz), 6.21 (1H, dd, J = 2.7, 1.8 Hz), 5.92 (1H, tt, J = 56.6, 4.6 Hz), 3.79 (3H, s), 3.68 (2H, tt, J = 13.4, 4.6 Hz), 3.63 (3H, s), 2.98-2.59 (4H, m). |
| 337 | ¹H-NMR (CDCl₃) δ: 7.39 (1H, d, J = 9.5 Hz), 7.38-7.30 (1H, m), 6.89 (1H, t, J = 8.5 Hz), 6.84 (1H, t, J = 8.5 Hz), 6.75 (1H, d, J = 9.5 Hz), 6.35 (1H, d, J = 2.7 Hz), 6.24 (1H, dd, J = 2.7, 1.5 Hz), 6.18 (1H, tt, J = 56.8, 4.5 Hz), 4.19-4.10 (2H, m), 3.81 (3H, s), 3.64 (3H, s). |
| 338 | ¹H-NMR (CDCl₃) δ: 7.32 (1H, d, J = 9.5 Hz), 6.73 (1H, d, J = 9.5 Hz), 6.47 (1H, dt, J = 10.5, 2.0 Hz), 6.42-6.39 (1H, m), 6.37 (1H, d, J = 2.7 Hz), 6.21 (1H, dd, J = 2.7, 1.5 Hz), 6.06 (1H, tt, J = 55.2, 4.0 Hz), 4.12 (2H, dt, J = 4.0, 12.8 Hz), 3.83 (3H, s), 3.66 (3H, s), 3.37 (3H, s). |
| 339 | ¹H-NMR (CDCl₃) δ: 7.32-7.29 (2H, m), 6.91-6.88 (1H, m), 6.79-6.77 (2H, m), 6.73-6.61 (2H, m), 3.38 (3H, s). |
| 340 | ¹H-NMR (CDCl₃) δ: 7.54 (1H, s), 7.29 (1H, dd, J = 9.0, 5.0 Hz), 6.93-6.91 (1H, m), 6.81-6.79 (1H, m), 6.73-6.62 (2H, m), 3.45 (3H, s). |
| 341 | ¹H-NMR (CDCl₃) δ: 7.46-7.45 (1H, m), 7.40-7.33 (3H, m), 7.30-7.29 (2H, m), 6.90 (2H, dd, J = 8.4, 7.2 Hz), 6.76 (1H, d, J = 9.5 Hz), 3.91 (2H, q, J = 7.2 Hz), 1.15 (3H, t, J = 7.2 Hz). |
| 342 | ¹H-NMR (CDCl₃) δ: 6.61-6.51 (2H, m), 6.31 (1H, d, J = 2.7 Hz), 6.19 (1H, m), 3.81 (3H, s), 3.67 (3H, s), 3.46 (1H, dq, J = 14.3, 7.2 Hz), 3.35 (1H, dq, J = 14.3, 7.2 Hz), 2.91-2.52 (4H, m), 0.99 (3H, t, J = 7.2 Hz). |
| 343 | ¹H-NMR (CDCl₃) δ: 7.37 (1H, d, J = 9.5 Hz), 6.76 (1H, d, J = 9.5 Hz), 6.69-6.59 (2H, m), 6.38 (1H, d, J = 2.7 Hz), 6.23 (1H, dd, J = 2.7, 2.0 Hz), 6.17 (1H, tt, J = 56.8, 4.6 Hz), 4.16-4.12 (2H, m), 3.83 (3H, s), 3.68 (3H, s). |
| 344 | ¹H-NMR (CDCl₃) δ: 7.29 (1H, d, J = 9.2 Hz), 7.26-7.22 (1H, m), 7.16-7.11 (2H, m), 6.95 (2H, d, J = 3.7 Hz), 6.86 (1H, t, J = 8.4 Hz), 6.78-6.72 (2H, m), 3.37 (3H, s), 2.56-2.41 (2H, m), 1.14 (3H, t, J = 7.5 Hz). |
| 345 | ¹H-NMR (CDCl₃) δ: 7.33-7.32 (3H, m), 7.04 (1H, dd, J = 8.3, 2.1 Hz), 7.00 (1H, dd, J = 8.3, 1.5 Hz), 6.89 (1H, t, J = 8.6 Hz), 6.85 (1H, t, J = 8.6 Hz), 6.75 (1H, d, J = 9.5 Hz), 6.16 (1H, tt, J = 56.7, 4.5 Hz), 4.23-4.10 (2H, m). |
| 346 | ¹H-NMR (CDCl₃) δ: 7.36-7.29 (3H, m), 7.03 (1H, dd, J = 8.3, 2.1 Hz), 6.97 (1H, dd, J = 8.3, 1.2 Hz), 6.90 (1H, t, J = 8.4 Hz), 6.85 (1H, t, J = 8.4 Hz), 6.75 (1H, d, J = 9.5 Hz), 3.38 (3H, s). |
| 347 | ¹H-NMR (CDCl₃) δ: 7.58 (1H, s), 7.38 (1H, tt, J = 8.4, 3.5 Hz), 7.33 (1H, d, J = 2.1 Hz), 7.06 (1H, dd, J = 8.3, 2.1 Hz), 7.01 (1H, dd, J = 8.3, 1.8 Hz), 6.92-6.85 (2H, m), 6.18 (1H, tt, J = 56.4, 4.4 Hz), 4.21 (2H, m). |
| 348 | ¹H-NMR (CDCl₃) δ: 7.53 (1H, s), 7.38-7.32 (2H, m), 7.04 (1H, dd, J = 8.4, 2.0 Hz), 6.98 (1H, dd, J = 8.4, 1.5 Hz), 6.88 (2H, dt, J = 21.0, 8.4 Hz), 3.44 (3H, s). |

TABLE 5-continued

| Compound | ¹H-NMR |
|---|---|
| 349 | ¹H-NMR (CDCl₃) δ: 7.33-7.27 (3H, m), 7.00-6.94 (2H, m), 6.88 (1H, t, J = 8.4 Hz), 6.83 (1H, t, J = 8.3 Hz), 6.73 (1H, d, J = 9.5 Hz), 3.99-3.90 (1H, m), 3.89-3.82 (1H, m), 1.16 (3H, t, J = 7.0 Hz). |
| 350 | ¹H-NMR (CDCl₃) δ: 7.54 (1H, s), 7.35-7.29 (2H, m), 7.01-6.96 (2H, m), 6.91-6.83 (2H, m), 4.00-3.88 (2H, m), 1.18 (3H, t, J = 7.2 Hz). |
| 351 | ¹H-NMR (CDCl₃) δ: 7.61 (1H, s), 7.34-7.31 (1H, m), 7.17 (1H, d, J = 8.9 Hz), 6.89 (1H, t, J = 8.4 Hz), 6.84 (1H, t, J = 8.4 Hz), 6.67 (1H, dd, J = 8.9, 3.1 Hz), 6.61 (1H, dd, J = 3.1, 1.5 Hz), 3.94-3.92 (2H, m), 3.65 (3H, s), 3.38 (1H, s), 1.18 (3H, t, J = 7.2 Hz). |
| 352 | ¹H-NMR (CDCl₃) δ: 7.31-7.28 (1H, m), 7.16 (1H, d, J = 8.9 Hz), 6.88 (1H, t, J = 8.4 Hz), 6.83 (1H, s), 6.81 (1H, t, J = 8.4 Hz), 6.65 (1H, dd, J = 8.9, 3.1 Hz), 6.59 (1H, dd, J = 3.1, 1.2 Hz), 3.95-3.90 (2H, m), 3.64 (3H, s), 2.31-2.28 (1H, m), 1.17 (3H, t, J = 7.0 Hz), 1.01-1.00 (2H, m), 0.72-0.67 (2H, m). |
| 353 | ¹H-NMR (CDCl₃) δ: 7.58 (1H, s), 7.49-7.47 (1H, m), 7.41-7.38 (1H, m), 7.34 (1H, m), 7.32-7.31 (2H, m), 6.92-6.89 (2H, m), 3.96 (2H, q, J = 7.2 Hz), 1.17 (3H, t, J = 7.2 Hz). |
| 354 | ¹H-NMR (CDCl₃) δ: 7.28 (1H, d, J = 9.2 Hz), 7.25 (1H, d, J = 8.5 Hz), 7.13 (1H, dd, J = 8.5, 2.7 Hz), 7.06 (1H, dd, J = 2.4, 1.5 Hz), 6.75-6.69 (2H, m), 6.63-6.61 (1H, m), 3.90 (2H, q, J = 7.0 Hz), 1.16 (3H, t, J = 7.0 Hz). |
| 355 | ¹H-NMR (CDCl₃) δ: 7.52 (1H, s), 7.26 (1H, d, J = 8.3 Hz), 7.16 (1H, dd, J = 8.6, 2.8 Hz), 7.07 (1H, t, J = 2.0 Hz), 6.72 (1H, tt, J = 8.6, 2.1 Hz), 6.64 (1H, tt, J = 8.6, 2.1 Hz), 4.01-3.89 (2H, m), 1.19 (3H, t, J = 7.0 Hz). |
| 356 | ¹H-NMR (CDCl₃) δ: 7.23-7.22 (2H, m), 6.86-6.83 (1H, m), 6.78-6.76 (3H, m), 3.51-3.33 (2H, m), 2.78-2.65 (4H, m), 0.98 (3H, t, J = 7.2 Hz). |
| 357 | ¹H-NMR (CDCl₃) δ: 7.27-7.21 (2H, m), 6.86 (1H, t, J = 8.6 Hz), 6.80-6.73 (3H, m), 2.89 (3H, s), 2.87-2.82 (2H, m), 2.73-2.70 (1H, m), 2.61-2.55 (1H, m). |
| 358 | ¹H-NMR (CDCl₃) δ: 7.33 (1H, tt, J = 8.4, 6.7 Hz), 7.30 (1H, d, J = 9.5 Hz), 7.25 (1H, dd, J = 8.6, 4.9 Hz), 6.92 (1H, t, J = 8.4 Hz), 6.86-6.79 (3H, m), 6.74 (1H, d, J = 9.5 Hz), 3.93-3.88 (2H, m), 1.16 (3H, t, J = 7.0 Hz). |
| 359 | ¹H-NMR (CDCl₃) δ: 7.34 (1H, tt, J = 8.6, 6.7 Hz), 7.33 (1H, d, J = 9.5 Hz), 7.26 (1H, dd, J = 8.9, 5.2 Hz), 6.92 (1H, t, J = 8.6 Hz), 6.87-6.83 (2H, m), 6.79-6.77 (1H, m), 6.75 (1H, d, J = 9.5 Hz), 3.38 (3H, s). |
| 360 | ¹H-NMR (CDCl₃) δ: 7.54 (1H, s), 7.35 (1H, tt, J = 8.6, 6.7 Hz), 7.26 (1H, dd, J = 8.4, 5.5 Hz), 6.93 (1H, t, J = 8.6 Hz), 6.88-6.80 (3H, m), 3.95 (2H, q, J = 7.0 Hz), 1.18 (3H, t, J = 7.0 Hz). |
| 361 | ¹H-NMR (CDCl₃) δ: 7.74 (1H, s), 7.35 (1H, tt, J = 8.5, 6.7 Hz), 7.26 (1H, dd, J = 8.9, 4.9 Hz), 6.95-6.90 (1H, m), 6.88-6.80 (3H, m), 3.95 (2H, q, J = 7.2 Hz), 1.18 (3H, t, J = 7.2 Hz). |
| 362 | ¹H-NMR (CDCl₃) δ: 7.56 (1H, s), 7.36 (1H, tt, J = 8.4, 6.7 Hz), 7.27 (1H, dd, J = 9.3, 4.7 Hz), 6.92-6.87 (3H, m), 6.81-6.79 (1H, m), 3.45 (3H, s). |
| 363 | ¹H-NMR (CDCl₃) δ: 7.76 (1H, s), 7.35 (1H, tt, J = 8.9, 6.7 Hz), 7.26 (1H, dd, J = 8.6, 5.2 Hz), 6.94-6.84 (3H, m), 6.79 (1H, ddd, J = 8.6, 3.1, 1.5 Hz), 3.45 (3H, s). |
| 364 | ¹H-NMR (CDCl₃) δ: 7.35-7.26 (3H, m), 7.00-6.95 (2H, m), 6.89 (1H, tt, J = 8.5, 1.1 Hz), 6.84 (1H, tt, J = 8.4, 1.1 Hz), 6.76 (1H, d, J = 9.5 Hz), 3.38 (3H, s). |
| 365 | ¹H-NMR (CDCl₃) δ: 7.56 (1H, s), 7.36-7.30 (2H, m), 7.01-6.95 (2H, m), 6.92-6.83 (2H, m), 3.45 (3H, s). |
| 366 | ¹H-NMR (CDCl₃) δ: 7.38-7.29 (3H, m), 6.99 (2H, dd, J = 4.3, 1.2 Hz), 6.91-6.83 (2H, m), 6.77 (1H, d, J = 9.5 Hz), 6.17 (1H, tt, J = 56.6, 4.5 Hz), 4.21-4.11 (2H, m). |
| 367 | ¹H-NMR (CDCl₃) δ: 7.60 (1H, s), 7.39-7.31 (2H, m), 7.03-6.99 (2H, m), 6.91-6.85 (2H, m), 6.19 (1H, tt, J = 56.4, 4.5 Hz), 4.21 (2H, td, J = 12.8, 4.4 Hz). |
| 368 | ¹H-NMR (CDCl₃) δ: 7.41 (1H, tt, J = 8.5, 3.6 Hz), 7.24 (1H, d, J = 9.5 Hz), 6.94 (2H, dd, J = 8.5, 7.3 Hz), 6.77 (1H, d, J = 9.5 Hz), 3.95 (2H, q, J = 7.2 Hz), 1.14 (3H, t, J = 7.2 Hz). |
| 369 | ¹H-NMR (CDCl₃) δ: 7.31-7.28 (1H, m), 7.19 (1H, s), 7.17 (1H, d, J = 8.9 Hz), 6.88 (1H, t, J = 8.4 Hz), 6.82 (1H, t, J = 8.4 Hz), 6.66 (1H, dd, J = 8.9, 3.1 Hz), 6.63 (1H, dd, J = 3.1, 1.2 Hz), 3.93-3.90 (2H, m), 3.65 (3H, s), 2.68 (2H, q, J = 7.4 Hz), 1.25 (3H, t, J = 7.4 Hz), 1.16 (3H, t, J = 7.0 Hz). |
| 370 | ¹H-NMR (CDCl₃) δ: 7.31-7.28 (1H, m), 7.18 (1H, s), 7.17 (1H, d, J = 8.6 Hz), 6.88 (1H, t, J = 8.6 Hz), 6.81 (1H, t, J = 8.6 Hz), 6.65 (1H, dd, J = 8.6, 3.1 Hz), 6.62 (1H, dd, J = 3.1, 1.2 Hz), 3.93-3.88 (2H, m), 3.64 (3H, s), 2.65-2.59 (2H, m), 1.71-1.68 (2H, m), 1.15 (3H, t, J = 7.0 Hz), 1.02 (3H, t, J = 7.5 Hz). |
| 371 | ¹H-NMR (CDCl₃) δ: 7.30-7.27 (1H, m), 7.18 (1H, dd, J = 8.1, 1.1 Hz), 6.88 (1H, t, J = 8.4 Hz), 6.81 (1H, t, J = 8.4 Hz), 6.68-6.63 (3H, m), 3.95-3.91 (2H, m), 3.87 (3H, s), 3.65 (3H, s), 1.16 (3H, t, J = 7.2 Hz). |
| 372 | ¹H-NMR (CDCl₃) δ: 7.49 (1H, s), 7.43 (1H, tt, J = 8.4, 3.5 Hz), 6.95 (2H, dd, J = 8.5, 7.3 Hz), 4.00 (2H, q, J = 7.1 Hz), 1.17 (3H, t, J = 7.2 Hz). |
| 373 | ¹H-NMR (CDCl₃) δ: 7.42 (1H, tt, J = 8.5, 3.6 Hz), 7.27 (1H, d, J = 9.5 Hz), 6.94 (2H, dd, J = 8.4, 7.5 Hz), 6.79 (1H, d, J = 9.5 Hz), 3.42 (3H, s). |
| 374 | ¹H-NMR (CDCl₃) δ: 7.51 (1H, s), 7.44 (1H, tt, J = 8.6, 3.5 Hz), 6.95 (2H, t, J = 8.0 Hz), 3.48 (3H, s). |
| 375 | ¹H-NMR (CDCl₃) δ: 7.31-7.29 (1H, m), 7.18 (1H, d, J = 8.6 Hz), 6.96 (1H, s), 6.88 (1H, t, J = 8.4 Hz), 6.82 (1H, t, J = 8.4 Hz), 6.67 (1H, dd, J = 8.6, 3.1 Hz), 6.65 (1H, dd, J = 2.9, 1.4 Hz), 3.95-3.90 (2H, m), 3.65 (3H, s), 2.38 (3H, s), 1.17 (3H, t, J = 7.0 Hz). |
| 376 | ¹H-NMR (CDCl₃) δ: 7.56 (1H, s), 7.34-7.31 (1H, m), 7.16 (1H, d, J = 8.6 Hz), 6.89 (1H, t, J = 8.6 Hz), 6.85 (1H, t, J = 8.6 Hz), 6.67 (1H, dd, J = 8.6, 3.1 Hz), 6.60 (1H, dd, J = 3.1, 1.5 Hz), 3.96-3.91 (3H, m), 3.79-3.77 (1H, m), 1.33 (3H, t, J = 6.9 Hz), 1.18 (3H, t, J = 7.2 Hz). |
| 377 | ¹H-NMR (CDCl₃) δ: 7.34 (1H, d, J = 9.5 Hz), 6.78 (1H, d, J = 9.5 Hz), 6.65-6.62 (2H, m), 6.39 (1H, d, J = 2.7 Hz), 6.23 (1H, br s), 4.66 (1H, br s), 4.53 (1H, br s), 3.83 (3H, s), 3.68 (3H, s). |
| 378 | ¹H-NMR (CDCl₃) δ: 7.30 (1H, d, J = 9.5 Hz), 6.70 (1H, d, J = 9.5 Hz), 6.40 (1H, dt, J = 10.8, 1.9 Hz), 6.35 (1H, d, J = 2.8 Hz), 6.33 (1H, dd, J = 10.8, 1.9 Hz), 6.24 (1H, dd, J = 2.8, 1.5 Hz), 3.96-3.95 (1H, m), 3.85 (1H, dd, J = 13.8, 7.0 Hz), 3.82 (3H, s), 3.65 (3H, s), 1.40 (3H, t, J = 7.0 Hz), 1.16 (3H, t, J = 7.0 Hz). |

TABLE 5-continued

| Compound | ¹H-NMR |
|---|---|
| 379 | ¹H-NMR (CDCl₃) δ: 7.34 (1H, d, J = 9.5 Hz), 7.26 (1H, dd, J = 80.2, 11.0 Hz), 6.75 (1H, d, J = 9.5 Hz), 6.64-6.61 (2H, m), 6.41 (1H, t, J = 11.0 Hz), 6.39 (1H, d, J = 2.8 Hz), 6.19 (1H, dd, J = 2.8, 1.5 Hz), 3.83 (3H, s), 3.67 (3H, s). |
| 380 | ¹H-NMR (CDCl₃) δ: 7.38 (1H, d, J = 9.5 Hz), 6.75 (1H, d, J = 9.5 Hz), 6.57-6.55 (2H, m), 6.45 (1H, dd, J = 76.3, 3.7 Hz), 6.40 (1H, d, J = 2.8 Hz), 6.24-6.23 (1H, m), 6.01 (1H, dd, J = 30.2, 3.7 Hz), 3.83 (3H, s), 3.67 (3H, s). |
| 381 | ¹H-NMR (CDCl₃) δ: 7.73 (1H, s), 7.29 (1H, dd, J = 8.9, 5.2 Hz), 6.92-6.90 (1H, m), 6.82-6.80 (1H, m), 6.70 (1H, tt, J = 8.7, 2.0 Hz), 6.64 (1H, tt, J = 8.7, 2.0 Hz), 3.98-3.90 (2H, m), 1.18 (3H, t, J = 7.2 Hz). |
| 382 | ¹H-NMR (CDCl₃) δ: 7.28-7.26 (2H, m), 6.89-6.83 (1H, m), 6.83-6.78 (1H, m), 6.72 (1H, d, J = 9.5 Hz), 6.45 (1H, dt, J = 10.5, 2.0 Hz), 6.36 (1H, dt, J = 10.5, 2.0 Hz), 3.93-3.88 (2H, m), 3.77 (3H, s), 1.16 (3H, t, J = 7.0 Hz). |
| 383 | ¹H-NMR (CDCl₃) δ: 7.44 (1H, tt, J = 8.6, 3.5 Hz), 7.32 (1H, d, J = 9.5 Hz), 6.94 (2H, dd, J = 8.6, 7.6 Hz), 6.81 (1H, d, J = 9.5 Hz), 6.12 (1H, tt, J = 56.6, 4.5 Hz), 4.22 (2H, td, J = 12.8, 4.5 Hz). |
| 384 | ¹H-NMR (CDCl₃) δ: 7.56 (1H, s), 7.47 (1H, tt, J = 8.4, 3.5 Hz), 6.96 (2H, dd, J = 8.6, 7.6 Hz), 6.14 (1H, tt, J = 56.4, 4.5 Hz), 4.27 (2H, td, J = 12.6, 4.5 Hz). |
| 385 | ¹H-NMR (CDCl₃) δ: 7.32-7.26 (2H, m), 7.13-7.07 (2H, m), 6.89 (1H, t, J = 8.4 Hz), 6.82-6.78 (2H, m), 6.76 (1H, d, J = 9.5 Hz), 4.10-4.03 (1H, m), 3.88-3.81 (1H, m), 1.15 (3H, t, J = 7.0 Hz). |
| 386 | ¹H-NMR (CDCl₃) δ: 7.52 (1H, s), 7.29-7.28 (1H, m), 6.89-6.87 (1H, m), 6.83-6.81 (1H, m), 6.45 (1H, dt, J = 10.8, 1.8 Hz), 6.37 (1H, dt, J = 10.8, 1.8 Hz), 3.96 (2H, q, J = 7.2 Hz), 3.77 (3H, s), 1.18 (3H, t, J = 7.2 Hz). |
| 387 | ¹H-NMR (CDCl₃) δ: 8.20 (1H, s), 7.39-7.36 (1H, m), 7.18 (1H, d, J = 8.9 Hz), 6.94-6.87 (2H, m), 6.70 (1H, dd, J = 8.9, 3.1 Hz), 6.61 (1H, dd, J = 2.9, 1.7 Hz), 3.99 (2H, dt, J = 21.7, 7.0 Hz), 3.67 (3H, s), 3.42 (3H, s), 1.21 (3H, t, J = 7.2 Hz). |
| 388 | ¹H-NMR (CDCl₃) δ: 7.29-7.26 (1H, m), 7.22 (1H, dd, J = 8.6, 5.2 Hz), 6.86 (1H, t, J = 8.6 Hz), 6.82-6.76 (3H, m), 5.92 (1H, tt, J = 56.4, 4.5 Hz), 3.74-3.63 (2H, m), 2.95-2.89 (1H, m), 2.85-2.82 (1H, m), 2.77-2.74 (1H, m), 2.67-2.61 (1H, m). |
| 389 | ¹H-NMR (CDCl₃) δ: 7.21 (1H, tt, J = 8.5, 6.4 Hz), 7.14 (1H, d, J = 8.9 Hz), 6.82 (1H, t, J = 8.5 Hz), 6.74 (1H, t, J = 8.5 Hz), 6.60 (1H, dd, J = 8.9, 3.1 Hz), 6.54 (1H, dd, J = 3.1, 1.2 Hz), 3.62 (3H, s), 3.47-3.43 (1H, m), 3.21-3.17 (1H, m), 2.87-2.83 (2H, m), 2.73-2.69 (1H, m), 2.60-2.52 (1H, m), 1.45-1.38 (2H, m), 0.74 (3H, t, J = 7.5 Hz). |
| 390 | ¹H-NMR (CDCl₃) δ: 7.21 (1H, tt, J = 8.5, 6.4 Hz), 7.14 (1H, d, J = 8.9 Hz), 6.82 (1H, t, J = 8.5 Hz), 6.74 (1H, t, J = 8.5 Hz), 6.60 (1H, dd, J = 8.5, 3.1 Hz), 6.55 (1H, dd, J = 3.1, 1.2 Hz), 3.62 (3H, s), 3.50-3.43 (1H, m), 3.27-3.20 (1H, m), 2.90-2.51 (4H, m), 1.43-1.32 (2H, m), 1.14 (2H, td, J = 14.8, 7.3 Hz), 0.74 (3H, t, J = 7.3 Hz). |
| 391 | ¹H-NMR (CDCl₃) δ: 7.40-7.32 (2H, m), 7.28-7.24 (1H, m), 6.93-6.91 (1H, m), 6.89-6.80 (3H, m), 6.76 (1H, d, J = 9.5 Hz), 6.16 (1H, tt, J = 56.6, 4.5 Hz), 4.17 (2H, td, J = 13.0, 4.5 Hz). |
| 392 | ¹H-NMR (CDCl₃) δ: 7.60 (1H, s), 7.38 (1H, tt, J = 8.5, 6.4 Hz), 7.27 (1H, dd, J = 9.3, 4.7 Hz), 6.94-6.81 (4H, m), 6.18 (1H, tt, J = 56.5, 4.5 Hz), 4.26-4.17 (2H, m). |
| 393 | ¹H-NMR (CDCl₃) δ: 7.80 (1H, s), 7.38 (1H, tt, J = 8.5, 6.4 Hz), 7.27 (1H, dd, J = 9.3, 4.9 Hz), 6.94-6.81 (4H, m), 6.18 (1H, tt, J = 56.5, 4.5 Hz), 4.26-4.16 (2H, m). |
| 394 | ¹H-NMR (CDCl₃) δ: 7.33-7.30 (2H, m), 7.17 (1H, d, J = 8.5 Hz), 6.89 (1H, t, J = 8.5 Hz), 6.82 (1H, t, J = 8.5 Hz), 6.72 (1H, d, J = 9.5 Hz), 6.66 (1H, dd, J = 8.5, 3.1 Hz), 6.60 (1H, dd, J = 3.1, 1.4 Hz), 3.85-3.75 (2H, m), 3.64 (3H, s), 1.59-1.49 (2H, m), 1.18-1.15 (2H, m), 0.72 (3H, t, J = 7.5 Hz). |
| 395 | ¹H-NMR (CDCl₃) δ: 7.56 (1H, s), 7.32 (1H, tt, J = 8.4, 6.4 Hz), 7.17 (1H, d, J = 8.9 Hz), 6.89 (1H, t, J = 8.4 Hz), 6.84 (1H, t, J = 8.4 Hz), 6.68 (1H, dd, J = 8.9, 3.1 Hz), 6.61 (1H, dd, J = 3.1, 1.5 Hz), 3.88-3.84 (2H, m), 3.65 (3H, s), 1.59-1.52 (2H, m), 1.19-1.15 (2H, m), 0.73 (3H, t, J = 7.3 Hz). |
| 396 | ¹H-NMR (CDCl₃) δ: 7.76 (1H, s), 7.32 (1H, tt, J = 8.5, 6.4 Hz), 7.17 (1H, d, J = 8.9 Hz), 6.89 (1H, t, J = 8.5 Hz), 6.84 (1H, t, J = 8.5 Hz), 6.68 (1H, dd, J = 8.9, 3.1 Hz), 6.61 (1H, dd, J = 3.1, 1.5 Hz), 3.89-3.85 (2H, m), 3.65 (3H, s), 1.58-1.55 (2H, m), 1.20-1.12 (2H, m), 0.73 (3H, t, J = 7.3 Hz). |
| 397 | ¹H-NMR (CDCl₃) δ: 7.52 (1H, s), 7.32 (1H, tt, J = 8.4, 3.6 Hz), 7.15-7.10 (2H, m), 6.90 (1H, t, J = 8.4 Hz), 6.83-6.78 (2H, m), 4.14-4.07 (1H, m), 3.95-3.87 (1H, m), 1.18 (3H, t, J = 7.2 Hz). |
| 398 | ¹H-NMR (CDCl₃) δ: 7.34-7.28 (2H, m), 7.15-7.10 (2H, m), 6.89 (1H, tt, J = 8.6, 1.0 Hz), 6.83-6.79 (2H, m), 6.77 (1H, d, J = 9.2 Hz), 3.42 (3H, s). |
| 399 | ¹H-NMR (CDCl₃) δ: 7.35-7.29 (2H, m), 7.17 (1H, d, J = 8.9 Hz), 6.89 (1H, t, J = 8.5 Hz), 6.82 (1H, t, J = 8.5 Hz), 6.72 (1H, d, J = 9.2 Hz), 6.66 (1H, dd, J = 8.9, 3.1 Hz), 6.60 (1H, dd, J = 3.1, 1.5 Hz), 3.86-3.82 (1H, m), 3.77-3.70 (1H, m), 3.64 (3H, s), 1.62-1.53 (2H, m), 0.75 (3H, t, J = 7.5 Hz). |
| 400 | ¹H-NMR (CDCl₃) δ: 7.56 (1H, s), 7.36-7.30 (1H, m), 7.17 (1H, d, J = 8.9 Hz), 6.89 (1H, t, J = 8.4 Hz), 6.84 (1H, t, J = 8.4 Hz), 6.68 (1H, dd, J = 8.9, 3.1 Hz), 6.60 (1H, dd, J = 3.1, 1.4 Hz), 3.87-3.79 (2H, m), 3.65 (3H, s), 1.62-1.58 (2H, m), 0.76 (3H, t, J = 7.3 Hz). |
| 401 | ¹H-NMR (CDCl₃) δ: 7.76 (1H, s), 7.33 (1H, tt, J = 8.5, 6.4 Hz), 7.17 (1H, d, J = 8.9 Hz), 6.89 (1H, t, J = 8.5 Hz), 6.84 (1H, t, J = 8.5 Hz), 6.68 (1H, dd, J = 8.5, 3.1 Hz), 6.60 (1H, dd, J = 3.1, 1.5 Hz), 3.83 (2H, q, J = 7.6 Hz), 3.65 (3H, s), 1.63-1.56 (2H, m), 0.76 (3H, t, J = 7.3 Hz). |
| 402 | ¹H-NMR (CDCl₃) δ: 7.36 (1H, d, J = 9.5 Hz), 7.30-7.27 (1H, m), 7.19 (1H, d, J = 8.9 Hz), 6.86 (1H, t, J = 8.4 Hz), 6.78 (1H, t, J = 8.4 Hz), 6.73 (1H, d, J = 9.5 Hz), 6.68 (1H, dd, J = 8.9, 3.1 Hz), 6.63 (1H, dd, J = 3.1, 0.9 Hz), 5.30-5.29 (2H, m), 3.65 (3H, s), 3.33 (3H, s). |
| 403 | ¹H-NMR (CDCl₃) δ: 7.31 (1H, d, J = 9.5 Hz), 7.20 (1H, d, J = 8.9 Hz), 6.75-6.60 (5H, m), 3.90 (2H, q, J = 7.2 Hz), 3.68 (3H, s), 1.16 (3H, t, J = 7.2 Hz). |
| 404 | ¹H-NMR (CDCl₃) δ: 7.55 (1H, s), 7.20 (1H, d, J = 8.9 Hz), 6.72 (1H, dd, J = 8.9, 3.1 Hz), 6.69-6.60 (3H, m), 3.97-3.92 (2H, m), 3.68 (3H, s), 1.19 (3H, t, J = 7.0 Hz). |

TABLE 5-continued

| Compound | ¹H-NMR |
|---|---|
| 405 | ¹H-NMR (CDCl₃) δ: 7.54 (1H, s), 7.36-7.29 (1H, m), 7.16-7.14 (2H, m), 6.91-6.88 (1H, m), 6.85-6.80 (2H, m), 3.49 (3H, s). |
| 406 | ¹H-NMR (CDCl₃) δ: 7.37-7.30 (2H, m), 7.16-7.11 (2H, m), 6.91-6.87 (1H, m), 6.84-6.77 (3H, m), 6.14 (1H, tdd, J = 56.6, 4.9, 3.9 Hz), 4.42-4.33 (1H, m), 4.13-4.05 (1H, m). |
| 407 | ¹H-NMR (CDCl₃) δ: 7.59 (1H, s), 7.35 (1H, tt, J = 8.5, 3.7 Hz), 7.17-7.14 (2H, m), 6.90 (1H, t, J = 8.2 Hz), 6.85-6.81 (2H, m), 6.16 (1H, tt, J = 56.9, 4.4 Hz), 4.43-4.37 (1H, m), 4.20-4.10 (1H, m). |
| 408 | ¹H-NMR (CDCl₃) δ: 7.35 (1H, tt, J = 8.4, 3.5 Hz), 7.30 (1H, dd, J = 9.5, 0.9 Hz), 6.97-6.94 (3H, m), 6.88 (2H, dd, J = 8.6, 7.3 Hz), 6.73 (1H, d, J = 9.2 Hz), 3.91 (2H, q, J = 7.0 Hz), 1.14 (3H, t, J = 6.9 Hz). |
| 409 | ¹H-NMR (CDCl₃) δ: 7.37 (1H, d, J = 9.5 Hz), 7.35-7.33 (1H, m), 7.17 (1H, d, J = 8.9 Hz), 6.88 (1H, t, J = 8.6 Hz), 6.84 (1H, t, J = 8.6 Hz), 6.78 (1H, d, J = 9.5 Hz), 6.69 (1H, dd, J = 8.9, 3.1 Hz), 6.62-6.60 (1H, m), 4.63 (2H, s), 3.66 (3H, s). |
| 410 | ¹H-NMR (CDCl₃) δ: 7.60 (1H, s), 7.36 (1H, tt, J = 8.6, 6.4 Hz), 7.17 (1H, d, J = 8.9 Hz), 6.91-6.84 (2H, m), 6.71 (1H, dd, J = 8.9, 3.1 Hz), 6.63-6.61 (1H, m), 4.73 (1H, s), 4.61 (1H, s), 3.66 (3H, s). |
| 411 | ¹H-NMR (CDCl₃) δ: 7.81 (1H, s), 7.36 (1H, tt, J = 8.6, 6.4 Hz), 7.17 (1H, d, J = 8.9 Hz), 6.88-6.86 (2H, m), 6.70 (1H, dd, J = 8.9, 3.1 Hz), 6.63-6.61 (1H, m), 4.73 (1H, s), 4.61 (1H, s), 3.66 (3H, s). |
| 412 | ¹H-NMR (CDCl₃) δ: 7.29-7.27 (2H, m), 7.15 (1H, d, J = 8.9 Hz), 6.87 (1H, t, J = 8.6 Hz), 6.81 (1H, t, J = 8.6 Hz), 6.65-6.63 (2H, m), 6.61 (1H, dd, J = 3.1, 1.7 Hz), 4.13-3.95 (1H, m), 3.65 (3H, s), 1.60-1.59 (6H, m). |
| 413 | ¹H-NMR (CDCl₃) δ: 7.52 (1H, s), 7.32-7.29 (1H, m), 7.16 (1H, d, J = 8.9 Hz), 6.87 (1H, t, J = 8.5 Hz), 6.82 (1H, t, J = 8.5 Hz), 6.66 (1H, dd, J = 8.9, 3.1 Hz), 6.61 (1H, dd, J = 3.1, 1.8 Hz), 4.09-4.06 (1H, m), 3.65 (3H, s), 1.61-1.59 (6H, m). |
| 414 | ¹H-NMR (CDCl₃) δ: 7.59 (1H, s), 7.30-7.28 (1H, m), 7.19 (1H, d, J = 8.9 Hz), 6.86 (1H, t, J = 8.4 Hz), 6.79 (1H, t, J = 8.4 Hz), 6.69 (1H, dd, J = 8.9, 3.1 Hz), 6.64 (1H, dd, J = 3.1, 1.2 Hz), 5.38 (1H, d, J = 10.4 Hz), 5.32 (1H, d, J = 10.4 Hz), 3.65 (3H, s), 3.36 (3H, s). |
| 415 | ¹H-NMR (CDCl₃) δ: 7.34 (1H, d, J = 9.5 Hz), 7.20 (1H, d, J = 8.9 Hz), 6.75 (1H, d, J = 9.5 Hz), 6.71 (1H, dd, J = 8.9, 3.1 Hz), 6.67-6.62 (2H, m), 6.58 (1H, dd, J = 2.9, 1.7 Hz), 3.68 (3H, s), 3.38 (3H, s). |
| 416 | ¹H-NMR (CDCl₃) δ: 7.57 (1H, s), 7.20 (1H, d, J = 8.9 Hz), 6.73 (1H, dd, J = 8.9, 3.1 Hz), 6.70-6.61 (2H, m), 6.59 (1H, dd, J = 3.1, 1.5 Hz), 3.68 (3H, s), 3.45 (3H, s). |
| 417 | ¹H-NMR (CDCl₃) δ: 7.54 (1H, s), 7.37 (1H, tt, J = 8.6, 3.6 Hz), 6.99-6.94 (3H, m), 6.89 (2H, dd, J = 8.6, 7.3 Hz), 3.97 (2H, q, J = 7.1 Hz), 1.16 (3H, t, J = 7.0 Hz). |
| 418 | ¹H-NMR (CDCl₃) δ: 7.39-7.32 (2H, m), 6.98-6.95 (3H, m), 6.88 (2H, dd, J = 8.5, 7.3 Hz), 6.75 (1H, d, J = 9.5 Hz), 3.39 (3H, s). |
| 419 | ¹H-NMR (CDCl₃) δ: 7.57 (1H, d, J = 0.6 Hz), 7.38 (1H, tt, J = 8.6, 3.5 Hz), 6.99-6.96 (3H, m), 6.89 (2H, dd, J = 8.4, 7.5 Hz), 3.46 (3H, s). |
| 420 | ¹H-NMR (CDCl₃) δ: 7.33-7.30 (2H, m), 7.16-7.14 (1H, m), 7.09-7.02 (2H, m), 6.74 (1H, d, J = 9.5 Hz), 6.65 (1H, tt, J = 8.9, 2.1 Hz), 6.58 (1H, tt, J = 8.9, 2.1 Hz), 3.93-3.87 (2H, m), 1.16 (3H, t, J = 7.0 Hz). |
| 421 | ¹H-NMR (CDCl₃) δ: 7.56 (1H, s), 7.33-7.32 (1H, m), 7.18-7.16 (1H, m), 7.10-7.04 (2H, m), 6.67-6.63 (1H, m), 6.61-6.59 (1H, m), 3.95 (2H, q, J = 7.1 Hz), 1.19 (3H, t, J = 7.1 Hz). |
| 422 | ¹H-NMR (CDCl₃) δ: 7.41 (1H, d, J = 9.5 Hz), 7.31 (1H, tt, J = 8.6, 6.4 Hz), 7.20 (1H, d, J = 8.9 Hz), 6.88 (1H, t, J = 8.6 Hz), 6.83-6.82 (2H, m), 6.70 (1H, dd, J = 8.9, 3.1 Hz), 6.59 (1H, dd, J = 3.1, 1.2 Hz), 5.10 (2H, s), 3.64 (3H, s). |
| 423 | ¹H-NMR (CDCl₃) δ: 7.62 (1H, s), 7.32 (1H, tt, J = 8.5, 6.4 Hz), 7.20 (1H, d, J = 8.9 Hz), 6.87-6.83 (2H, m), 6.72 (1H, dd, J = 8.9, 3.1 Hz), 6.60 (1H, dd, J = 3.1, 1.2 Hz), 5.16 (2H, s), 3.65 (3H, s). |
| 424 | ¹H-NMR (CDCl₃) δ: 7.32 (1H, dd, J = 9.5, 0.6 Hz), 6.91-6.88 (2H, m), 6.77-6.74 (2H, m), 6.70-6.64 (2H, m), 3.91 (2H, q, J = 7.1 Hz), 1.15 (3H, t, J = 7.1 Hz). |
| 425 | ¹H-NMR (CDCl₃) δ: 7.56 (1H, d, J = 0.9 Hz), 6.93-6.90 (2H, m), 6.78-6.76 (1H, m), 6.70-6.65 (2H, m), 3.96 (2H, q, J = 7.1 Hz), 1.17 (3H, t, J = 7.1 Hz). |
| 426 | ¹H-NMR (CDCl₃) δ: 7.35 (1H, dd, J = 9.5, 0.9 Hz), 6.91-6.89 (2H, m), 6.78-6.76 (2H, m), 6.69-6.66 (1H, m), 3.39 (3H, s). |
| 427 | ¹H-NMR (CDCl₃) δ: 7.58 (1H, s), 6.94-6.90 (2H, m), 6.79-6.77 (1H, m), 6.70-6.66 (2H, m), 3.46 (3H, s). |
| 428 | ¹H-NMR (CDCl₃) δ: 7.41-7.37 (2H, m), 6.98-6.96 (3H, m), 6.88 (2H, dd, J = 8.4, 7.5 Hz), 6.77 (1H, d, J = 9.5 Hz), 6.14 (1H, tt, J = 56.6, 4.5 Hz), 4.19 (2H, td, J = 12.8, 4.5 Hz). |
| 429 | ¹H-NMR (CDCl₃) δ: 7.61 (1H, s), 7.40 (1H, tt, J = 8.5, 3.5 Hz), 7.01-6.96 (3H, m), 6.89 (2H, t, J = 7.9 Hz), 6.16 (1H, tt, J = 56.6, 4.4 Hz), 4.23 (2H, td, J = 12.7, 4.4 Hz). |
| 430 | ¹H-NMR (CDCl₃) δ: 7.32-7.29 (2H, m), 7.14-7.12 (1H, m), 7.06-7.05 (2H, m), 6.72 (1H, d, J = 9.2 Hz), 6.42-6.39 (1H, m), 6.34-6.32 (1H, m), 3.98-3.95 (1H, m), 3.89-3.87 (1H, m), 3.75 (3H, s), 1.16 (3H, t, J = 7.0 Hz). |
| 431 | ¹H-NMR (CDCl₃) δ: 7.35 (1H, d, J = 9.5 Hz), 7.33-7.32 (1H, m), 7.16 (1H, td, J = 7.6, 1.8 Hz), 7.08 (1H, td, J = 7.6, 1.2 Hz), 7.03-7.02 (1H, m), 6.76 (1H, d, J = 9.5 Hz), 6.67-6.63 (1H, m), 6.61-6.57 (1H, m), 3.39 (3H, s). |
| 432 | ¹H-NMR (CDCl₃) δ: 7.58 (1H, s), 7.34-7.32 (1H, m), 7.18 (1H, td, J = 7.6, 1.8 Hz), 7.10 (1H, td, J = 7.6, 1.2 Hz), 7.05-7.03 (1H, m), 6.68-6.58 (2H, m), 3.45 (3H, s). |
| 433 | ¹H-NMR (CDCl₃) δ: 7.35-7.31 (2H, m), 7.16-7.13 (1H, m), 7.08-7.02 (2H, m), 6.73 (1H, d, J = 9.2 Hz), 6.42-6.40 (1H, m), 6.35-6.32 (1H, m), 3.75 (3H, s), 3.39 (3H, s). |
| 434 | ¹H-NMR (CDCl₃) δ: 7.55 (1H, s), 7.33-7.31 (1H, m), 7.16-7.14 (1H, m), 7.07-7.06 (2H, m), 6.41-6.39 (1H, m), 6.35-6.32 (1H, m), 3.98-3.96 (2H, m), 3.75 (3H, s), 1.18 (3H, t, J = 7.0 Hz). |
| 435 | ¹H-NMR (CDCl₃) δ: 7.57 (1H, s), 7.33-7.31 (1H, m), 7.18-7.14 (1H, m), 7.09-7.07 (1H, m), 7.05-7.04 (1H, m), 6.42-6.39 (1H, m), 6.36-6.33 (1H, m), 3.75 (3H, s), 3.46 (3H, s). |

TABLE 5-continued

| Compound | ¹H-NMR |
|---|---|
| 436 | ¹H-NMR (CDCl₃) δ: 7.29 (1H, tt, J = 8.6, 6.4 Hz), 6.86-6.82 (2H, m), 6.70-6.68 (1H, m), 6.43-6.41 (1H, m), 3.43 (2H, q, J = 7.1 Hz), 2.77-2.69 (4H, m), 0.97 (3H, t, J = 7.1 Hz). |
| 437 | ¹H-NMR (CDCl₃) δ: 7.30 (1H, tt, J = 8.6, 6.4 Hz), 6.86-6.83 (2H, m), 6.72-6.67 (1H, m), 6.43-6.41 (1H, m), 2.89 (3H, s), 2.78-2.71 (4H, m) |
| 438 | ¹H-NMR (CDCl₃) δ: 7.38 (1H, tt, J = 8.6, 6.4 Hz), 7.31 (1H, dd, J = 9.5, 0.9 Hz), 6.92-6.91 (2H, m), 6.79-6.72 (2H, m), 6.58-6.55 (1H, m), 3.92 (2H, q, J = 7.0 Hz), 1.14 (3H, t, J = 7.0 Hz). |
| 439 | ¹H-NMR (CDCl₃) δ: 7.39 (1H, tt, J = 8.4, 6.4 Hz), 7.34 (1H, dd, J = 9.5, 0.9 Hz), 6.93-6.91 (2H, m), 6.80-6.75 (2H, m), 6.57-6.55 (1H, m), 3.40 (3H, s). |
| 440 | ¹H-NMR (CDCl₃) δ: 7.55 (1H, s), 7.40 (1H, tt, J = 8.4, 6.4 Hz), 6.94-6.92 (2H, m), 6.82-6.75 (1H, m), 6.59-6.56 (1H, m), 3.97 (2H, q, J = 7.0 Hz), 1.17 (3H, t, J = 7.0 Hz). |
| 441 | ¹H-NMR (CDCl₃) δ: 7.76 (1H, s), 7.40 (1H, tt, J = 8.4, 6.4 Hz), 6.93-6.91 (2H, m), 6.82-6.75 (1H, m), 6.59-6.56 (1H, m), 3.97 (2H, q, J = 7.1 Hz), 1.17 (3H, t, J = 7.1 Hz). |
| 442 | ¹H-NMR (CDCl₃) δ: 7.57 (1H, s), 7.41 (1H, tt, J = 8.4, 6.4 Hz), 6.94-6.92 (2H, m), 6.84-6.77 (1H, m), 6.59-6.56 (1H, m), 3.46 (3H, s). |
| 443 | ¹H-NMR (CDCl₃) δ: 7.78 (1H, s), 7.41 (1H, tt, J = 8.6, 6.4 Hz), 6.94-6.92 (2H, m), 6.83-6.77 (1H, m), 6.59-6.57 (1H, m), 3.46 (3H, s). |
| 444 | ¹H-NMR (CDCl₃) δ: 7.37-7.29 (2H, m), 7.23 (1H, d, J = 8.2 Hz), 7.10-7.06 (2H, m), 6.94 (1H, t, J = 8.4 Hz), 6.83 (1H, t, J = 8.4 Hz), 6.74 (1H, d, J = 9.5 Hz), 3.98-3.93 (2H, m), 1.16 (3H, t, J = 7.3 Hz). |
| 445 | ¹H-NMR (CDCl₃) δ: 7.54 (1H, s), 7.35 (1H, tt, J = 8.6, 3.5 Hz), 7.23 (1H, d, J = 8.6 Hz), 7.11 (1H, dd, J = 8.6, 2.4 Hz), 7.08-7.06 (1H, m), 6.95 (1H, t, J = 8.4 Hz), 6.85 (1H, t, J = 8.4 Hz), 3.96 (2H, q, J = 7.1 Hz), 1.18 (3H, t, J = 7.1 Hz). |
| 446 | ¹H-NMR (CDCl₃) δ: 7.37-7.31 (2H, m), 7.23 (1H, d, J = 8.6 Hz), 7.10 (1H, dd, J = 8.6, 2.4 Hz), 7.05-7.03 (1H, m), 6.94 (1H, t, J = 8.4 Hz), 6.85 (1H, t, J = 8.4 Hz), 6.76 (1H, d, J = 9.2 Hz), 3.39 (3H, s). |
| 447 | ¹H-NMR (CDCl₃) δ: 7.55 (1H, s), 7.36 (1H, tt, J = 8.4, 3.5 Hz), 7.24 (1H, d, J = 8.6 Hz), 7.13 (1H, dd, J = 8.6, 2.8 Hz), 7.06-7.04 (1H, m), 6.94 (1H, t, J = 8.6 Hz), 6.86 (1H, t, J = 8.6 Hz), 3.45 (3H, s). |
| 448 | ¹H-NMR (CDCl₃) δ: 7.40-7.33 (2H, m), 7.23 (1H, d, J = 8.5 Hz), 7.11 (1H, dd, J = 8.5, 2.7 Hz), 7.10-7.06 (1H, m), 6.96-6.91 (1H, m), 6.87-6.82 (1H, m), 6.77 (1H, d, J = 9.5 Hz), 6.16 (1H, tt, J = 56.6, 4.5 Hz), 4.26-4.11 (2H, m). |
| 449 | ¹H-NMR (CDCl₃) δ: 7.60 (1H, s), 7.39 (1H, tt, J = 8.4, 3.5 Hz), 7.24 (1H, d, J = 8.9 Hz), 7.14 (1H, dd, J = 8.6, 2.4 Hz), 7.10-7.08 (1H, m), 6.94 (1H, t, J = 8.4 Hz), 6.87 (1H, t, J = 8.4 Hz), 6.19 (1H, tt, J = 56.4, 4.5 Hz), 4.26-4.18 (2H, m). |
| 450 | ¹H-NMR (CDCl₃) δ: 7.41-7.32 (1H, m), 7.30 (1H, d, J = 2.4 Hz), 7.28-7.25 (1H, m), 7.00 (1H, dd, J = 2.4, 1.2 Hz), 6.99-6.93 (1H, m), 6.90-6.84 (1H, m), 6.74 (1H, d, J = 9.5 Hz), 3.97-3.82 (2H, m), 1.16 (3H, t, J = 7.2 Hz). |
| 451 | ¹H-NMR (CDCl₃) δ: 7.51 (1H, s), 7.43-7.34 (1H, m), 7.32 (1H, d, J = 2.4 Hz), 7.01 (1H, dd, J = 2.4, 1.5 Hz), 6.96 (1H, t, J = 8.4 Hz), 6.89 (1H, t, J = 8.4 Hz), 3.95 (2H, q, J = 7.0 Hz), 1.18 (3H, t, J = 7.0 Hz). |
| 452 | ¹H-NMR (CDCl₃) δ: 7.40-7.33 (1H, m), 7.32 (1H, d, J = 2.4 Hz), 7.29 (1H, d, J = 9.5 Hz), 6.98-6.94 (2H, m), 6.88 (1H, t, J = 8.4 Hz), 6.76 (1H, d, J = 9.5 Hz), 3.38 (3H, s). |
| 453 | ¹H-NMR (CDCl₃) δ: 7.53 (1H, s), 7.42-7.35 (1H, m), 7.34 (1H, d, J = 2.4 Hz), 6.99 (1H, dd, J = 2.4, 1.5 Hz), 6.98-6.94 (1H, m), 6.92-6.87 (1H, m), 3.45 (3H, s). |
| 454 | ¹H-NMR (CDCl₃) δ: 7.42-7.36 (1H, m), 7.35-7.33 (2H, m), 7.01 (1H, dd, J = 2.3, 1.7 Hz), 6.95 (1H, t, J = 8.4 Hz), 6.88 (1H, t, J = 8.4 Hz), 6.77 (1H, d, J = 9.5 Hz), 6.16 (1H, tt, J = 56.6, 4.5 Hz), 4.16 (2H, td, J = 12.9, 4.5 Hz). |
| 455 | ¹H-NMR (CDCl₃) δ: 7.58 (1H, s), 7.45-7.38 (1H, m), 7.35 (1H, d, J = 2.4 Hz), 7.03 (1H, dd, J = 2.4, 1.5 Hz), 6.96 (1H, t, J = 8.6 Hz), 6.90 (1H, t, J = 8.6 Hz), 6.18 (1H, tt, J = 56.4, 4.4 Hz), 4.28-4.13 (2H, m). |
| 456 | ¹H-NMR (CDCl₃) δ: 7.27-7.21 (1H, m), 7.15 (1H, d, J = 8.6 Hz), 6.83 (1H, t, J = 8.4 Hz), 6.75 (1H, t, J = 8.4 Hz), 6.62 (1H, dd, J = 8.6, 3.1 Hz), 6.61-6.60 (1H, m), 4.26 (1H, dd, J = 17.7, 2.4 Hz), 4.17 (1H, dd, J = 17.7, 2.4 Hz), 3.64 (3H, s), 2.93-2.83 (2H, m), 2.78-2.72 (1H, m), 2.65-2.59 (1H, m), 2.03 (1H, t, J = 2.4 Hz). |
| 457 | ¹H-NMR (CDCl₃) δ: 7.37 (1H, tt, J = 8.5, 6.4 Hz), 7.23 (1H, m), 6.91 (2H, dd, J = 8.5, 7.3 Hz), 6.80-6.73 (1H, m), 6.58-6.55 (1H, m), 3.40 (3H, s), 2.26 (3H, d, J = 1.2 Hz). |
| 458 | ¹H-NMR (CDCl₃) δ: 7.37 (1H, d, J = 9.5 Hz), 7.34 (1H, tt, J = 8.6, 6.4 Hz), 7.19 (1H, d, J = 8.9 Hz), 6.90 (1H, t, J = 8.6 Hz), 6.83 (1H, t, J = 8.6 Hz), 6.77 (1H, d, J = 9.5 Hz), 6.68 (1H, dd, J = 8.9, 3.1 Hz), 6.62 (1H, dd, J = 3.1, 1.2 Hz), 4.70-4.70 (2H, m), 3.65 (3H, s), 2.11 (1H, t, J = 2.6 Hz). |
| 459 | ¹H-NMR (CDCl₃) δ: 7.36 (1H, tt, J = 8.6, 6.4 Hz), 7.21 (1H, m), 6.90 (2H, dd, J = 8.6, 7.2 Hz), 6.76-6.74 (1H, m), 6.58-6.55 (1H, m), 3.92 (2H, q, J = 7.0 Hz), 2.25 (3H, d, J = 1.2 Hz), 1.14 (3H, t, J = 7.0 Hz). |
| 460 | ¹H-NMR (CDCl₃) δ: 7.43 (1H, d, J = 9.5 Hz), 7.41 (1H, tt, J = 8.6, 6.4 Hz), 7.20 (1H, d, J = 8.9 Hz), 6.98 (1H, t, J = 8.6 Hz), 6.91 (1H, t, J = 8.6 Hz), 6.80 (1H, d, J = 9.5 Hz), 6.71 (1H, dd, J = 8.9, 3.1 Hz), 6.61 (1H, dd, J = 3.1, 1.5 Hz), 4.85 (1H, d, J = 17.1 Hz), 4.72 (1H, d, J = 17.1 Hz), 3.66 (3H, s). |
| 461 | ¹H-NMR (CDCl₃) δ: 7.27 (1H, dd, J = 8.6, 5.5 Hz), 7.18 (1H, m), 6.87 (1H, td, J = 8.6, 3.3 Hz), 6.80 (1H, ddd, J = 8.9, 3.3, 1.2 Hz), 6.68 (1H, tt, J = 8.6, 2.1 Hz), 6.61 (1H, tt, J = 8.6, 2.1 Hz), 3.93-3.89 (2H, m), 2.25 (3H, d, J = 0.9 Hz), 1.16 (3H, t, J = 7.0 Hz). |
| 462 | ¹H-NMR (CDCl₃) δ: 7.59 (1H, s), 7.39-7.32 (1H, m), 7.19 (1H, d, J = 8.9 Hz), 6.90 (1H, t, J = 8.4 Hz), 6.85 (1H, t, J = 8.4 Hz), 6.70 (1H, dd, J = 8.9, 3.1 Hz), 6.63 (1H, dd, J = 3.1, 1.5 Hz), 4.78 (1H, dd, J = 17.4, 2.6 Hz), 4.72 (1H, dd, J = 17.4, 2.6 Hz), 3.66 (3H, s), 2.14 (1H, t, J = 2.6 Hz). |
| 463 | ¹H-NMR (CDCl₃) δ: 7.64 (1H, s), 7.43 (1H, tt, J = 8.4, 6.4 Hz), 7.20 (1H, d, J = 8.9 Hz), 6.98 (1H, t, J = 8.4 Hz), 6.92 (1H, t, J = 8.4 Hz), 6.74-6.71 (1H, m), 6.62 (1H, dd, J = 3.1, 1.5 Hz), 4.91 (1H, d, J = 17.1 Hz), 4.74 (1H, d, J = 17.1 Hz), 3.66 (3H, s). |

TABLE 5-continued

| Compound | ¹H-NMR |
|---|---|
| 464 | ¹H-NMR (CDCl₃) δ: 7.30 (1H, dd, J = 9.3, 0.8 Hz), 6.84-6.79 (1H, m), 6.76 (1H, d, J = 9.3 Hz), 6.72-6.68 (2H, m), 6.58-6.56 (1H, m), 3.91 (2H, q, J = 7.0 Hz), 1.15 (3H, t, J = 7.0 Hz). |
| 465 | ¹H-NMR (CDCl₃) δ: 7.54 (1H, d, J = 0.9 Hz), 6.87-6.80 (1H, m), 6.74-6.68 (2H, m), 6.60-6.57 (1H, m), 3.96 (2H, q, J = 7.0 Hz), 1.17 (3H, t, J = 7.0 Hz). |
| 466 | ¹H-NMR (CDCl₃) δ: 7.33 (1H, dd, J = 9.5, 0.6 Hz), 6.85-6.79 (1H, m), 6.78 (1H, d, J = 9.5 Hz), 6.73-6.68 (2H, m), 6.59-6.57 (1H, m), 3.39 (3H, s). |
| 467 | ¹H-NMR (CDCl₃) δ: 7.56 (1H, s), 6.87-6.82 (1H, m), 6.74-6.69 (2H, m), 6.61-6.58 (1H, m), 3.46 (3H, s). |
| 468 | ¹H-NMR (CDCl₃) δ: 7.31 (1H, dd, J = 9.5, 0.9 Hz), 6.93-6.83 (2H, m), 6.77-6.75 (1H, m), 6.72 (1H, d, J = 9.2 Hz), 6.41 (2H, d, J = 9.2 Hz), 3.93 (2H, q, J = 7.2 Hz), 3.78 (3H, s), 1.14 (3H, t, J = 7.2 Hz). |
| 469 | 1H-NMR (CDCl3) δ: 7.55 (1H, d, J = 0.9 Hz), 6.92-6.89 (2H, m), 6.79-6.74 (1H, m), 6.42 (2H, d, J = 9.2 Hz), 3.98 (2H, q, J = 7.1 Hz), 3.78 (3H, s), 1.17 (3H, t, J = 7.1 Hz). |
| 470 | ¹H-NMR (CDCl₃) δ: 7.32 (1H, tt, J = 8.4, 3.5 Hz), 7.21 (1H, d, J = 9.2 Hz), 7.19 (1H, d, J = 1.2 Hz), 7.09-7.06 (2H, m), 6.92 (1H, t, J = 8.4 Hz), 6.83 (1H, t, J = 8.4 Hz), 3.92 (2H, q, J = 7.0 Hz), 2.26-2.24 (3H, m), 1.16 (3H, t, J = 7.0 Hz). |
| 471 | ¹H-NMR (CDCl₃) δ: 7.32 (1H, tt, J = 8.6, 3.5 Hz), 7.22-7.19 (2H, m), 7.09 (1H, dd, J = 8.6, 2.4 Hz), 7.06-7.03 (1H, m), 6.91 (1H, t, J = 8.4 Hz), 6.84 (1H, t, J = 8.4 Hz), 3.40 (3H, s), 2.26-2.25 (3H, m). |
| 472 | ¹H-NMR (CDCl₃) δ: 7.37-7.31 (2H, m), 7.23-7.20 (1H, m), 6.95-6.91 (1H, m), 6.88 (3H, t, J = 8.0 Hz), 6.74 (1H, d, J = 9.5 Hz), 3.92 (2H, q, J = 7.0 Hz), 1.15 (3H, t, J = 7.0 Hz). |
| 473 | ¹H-NMR (CDCl₃) δ: 7.57 (1H, s), 7.35 (1H, tt, J = 8.4, 3.5 Hz), 7.26-7.21 (1H, m), 6.96-6.86 (4H, m), 3.97 (2H, q, J = 7.0 Hz), 1.17 (3H, t, J = 7.0 Hz). |
| 474 | ¹H-NMR (CDCl₃) δ: 7.38-7.31 (2H, m), 7.25-7.21 (1H, m), 6.94-6.90 (2H, m), 6.88-6.85 (2H, m), 6.76 (1H, d, J = 9.2 Hz), 3.40 (3H, s). |
| 475 | ¹H-NMR (CDCl₃) δ: 7.59 (1H, s), 7.36 (1H, tt, J = 8.4, 3.5 Hz), 7.27-7.23 (1H, m), 6.94-6.87 (4H, m), 3.46 (3H, s). |
| 476 | ¹H-NMR (CDCl₃) δ: 7.72 (1H, s), 7.29-7.27 (1H, m), 6.88 (1H, ddd, J = 8.9, 8.0, 3.1 Hz), 6.82 (1H, ddd, J = 8.9, 3.1, 1.5 Hz), 6.45 (1H, dt, J = 10.8, 1.9 Hz), 6.37 (1H, dt, J = 10.8, 1.9 Hz), 3.96 (2H, q, J = 7.2 Hz), 3.77 (3H, s), 1.18 (3H, t, J = 7.2 Hz). |
| 477 | ¹H-NMR (CDCl₃) δ: 7.27 (1H, tt, J = 8.6, 6.4 Hz), 6.90-6.74 (4H, m), 6.63-6.59 (1H, m), 3.43 (2H, q, J = 7.0 Hz), 2.77-2.69 (4H, m), 0.97 (3H, t, J = 7.0 Hz). |
| 478 | ¹H-NMR (CDCl₃) δ: 7.37-7.33 (2H, m), 6.91-6.82 (4H, m), 6.77-6.73 (2H, m), 3.92 (2H, q, J = 7.1 Hz), 1.14 (3H, t, J = 7.1 Hz). |
| 479 | ¹H-NMR (CDCl₃) δ: 7.27-7.25 (1H, m), 7.17 (1H, d, J = 1.2 Hz), 6.87-6.80 (2H, m), 6.43 (1H, dt, J = 10.7, 2.0 Hz), 6.36 (1H, dt, J = 10.7, 2.0 Hz), 3.92 (2H, q, J = 7.1 Hz), 3.77 (3H, s), 2.24 (3H, d, J = 1.2 Hz), 1.15 (3H, t, J = 7.1 Hz). |
| 480 | ¹H-NMR (CDCl₃) δ: 7.27 (1H, tt, J = 8.5, 6.4 Hz), 6.90-6.75 (4H, m), 6.63-6.59 (1H, m), 2.89 (3H, s), 2.76-2.73 (4H, m). |
| 481 | ¹H-NMR (CDCl₃) δ: 7.57 (1H, d, J = 0.9 Hz), 7.37 (1H, tt, J = 8.6, 6.4 Hz), 6.92-6.86 (4H, m), 6.78-6.74 (1H, m), 3.97 (2H, q, J = 7.1 Hz), 1.17 (3H, t, J = 7.1 Hz). |
| 482 | ¹H-NMR (CDCl₃) δ: 7.78 (1H, d, J = 0.9 Hz), 7.37 (1H, tt, J = 8.4, 6.4 Hz), 6.90-6.87 (4H, m), 6.78-6.75 (1H, m), 3.97 (2H, q, J = 7.2 Hz), 1.17 (3H, t, J = 7.2 Hz). |
| 483 | ¹H-NMR (CDCl₃) δ: 7.38-7.34 (2H, m), 6.91-6.85 (4H, m), 6.77-6.74 (2H, m), 3.40 (3H, s). |
| 484 | ¹H-NMR (CDCl₃) δ: 7.59 (1H, d, J = 0.9 Hz), 7.38 (1H, tt, J = 8.6, 6.4 Hz), 6.90-6.89 (4H, m), 6.77-6.75 (1H, m), 3.46 (3H, s). |
| 485 | ¹H-NMR (CDCl₃) δ: 7.80 (1H, d, J = 0.6 Hz), 7.38 (1H, tt, J = 8.6, 6.4 Hz), 6.90-6.88 (4H, m), 6.78-6.74 (1H, m), 3.47 (3H, s). |
| 486 | ¹H-NMR (CDCl₃) δ: 7.30 (1H, d, J = 9.5 Hz), 7.07-7.00 (2H, m), 6.87-6.85 (1H, m), 6.75 (1H, d, J = 9.5 Hz), 6.66 (1H, tt, J = 8.7, 2.0 Hz), 6.61 (1H, tt, J = 8.7, 2.0 Hz), 3.97-3.83 (2H, m), 1.16 (3H, t, J = 7.0 Hz). |
| 487 | ¹H-NMR (CDCl₃) δ: 7.74 (1H, s), 7.09-7.02 (2H, m), 6.88-6.85 (1H, m), 6.69-6.61 (2H, m), 3.97-3.93 (2H, m), 1.19 (3H, t, J = 7.0 Hz). |
| 488 | ¹H-NMR (CDCl₃) δ: 7.53 (1H, s), 7.09-7.02 (2H, m), 6.88-6.86 (1H, m), 6.69-6.61 (2H, m), 3.96-3.94 (2H, m), 1.19 (3H, t, J = 7.0 Hz). |
| 489 | ¹H-NMR (CDCl₃) δ: 7.29 (1H, d, J = 9.5 Hz), 7.05-6.98 (2H, m), 6.88-6.86 (1H, m), 6.72 (1H, d, J = 9.5 Hz), 6.43-6.40 (1H, m), 6.36-6.34 (1H, m), 3.99-3.84 (2H, m), 3.76 (3H, s), 1.16 (3H, t, J = 7.0 Hz). |
| 490 | ¹H-NMR (CDCl₃) δ: 7.52 (1H, s), 7.07-6.99 (2H, m), 6.89-6.87 (1H, m), 6.42-6.39 (1H, m), 6.37-6.34 (1H, m), 4.01-3.93 (2H, m), 3.76 (3H, s), 1.18 (3H, t, J = 7.2 Hz). |
| 491 | ¹H-NMR (CDCl₃) δ: 7.32 (1H, d, J = 9.5 Hz), 7.08-7.01 (2H, m), 6.85-6.83 (1H, m), 6.77 (1H, d, J = 9.5 Hz), 6.69-6.60 (2H, m), 3.39 (3H, s). |
| 492 | ¹H-NMR (CDCl₃) δ: 7.31 (1H, d, J = 9.2 Hz), 7.07-6.98 (2H, m), 6.86-6.83 (1H, m), 6.74 (1H, d, J = 9.2 Hz), 6.43-6.40 (1H, m), 6.37-6.34 (1H, m), 3.76 (3H, s), 3.39 (3H, s). |
| 493 | ¹H-NMR (CDCl₃) δ: 7.35-7.28 (1H, m), 7.25-7.19 (2H, m), 6.95-6.91 (1H, m), 6.89-6.80 (3H, m), 3.93 (2H, q, J = 7.0 Hz), 2.26-2.24(3H, m), 1.14 (3H, t, J = 7.0 Hz). |
| 494 | ¹H-NMR (CDCl₃) δ: 7.42-7.33 (2H, m), 7.25-7.22 (1H, m), 6.96-6.85 (4H, m), 6.77 (1H, d, J = 9.5 Hz), 6.15 (1H, tt, J = 56.6, 4.5 Hz), 4.22-4.15 (2H, m). |
| 495 | ¹H-NMR (CDCl₃) δ: 7.64 (1H, s), 7.39 (1H, tt, J = 8.6, 3.6 Hz), 7.28-7.25 (1H, m), 6.97-6.87 (4H, m), 6.17 (1H, tt, J = 56.6, 4.5 Hz), 4.26-4.20 (2H, m). |
| 496 | ¹H-NMR (CDCl₃) δ: 7.33-7.25 (2H, m), 7.18 (1H, d, J = 8.9 Hz), 6.86 (1H, t, J = 8.6 Hz), 6.80 (1H, t, J = 8.6 Hz), 6.69-6.67 (2H, m), 6.53 (1H, dd, J = 3.1, 1.5 Hz), 3.62 (3H, s), 2.93-2.91 (1H, m), 0.90-0.61 (4H, m). |
| 497 | ¹H-NMR (CDCl₃) δ: 7.33 (1H, tt, J = 8.4, 6.4 Hz), 7.23 (1H, m), 6.89-6.81 (4H, m), 6.77-6.74 (1H, m), 3.93 (2H, q, J = 7.0 Hz), 2.25 (3H, d, J = 1.2 Hz), 1.14 (3H, t, J = 7.0 Hz). |
| 498 | ¹H-NMR (CDCl₃) δ: 7.54 (1H, s), 7.31 (1H, tt, J = 8.6, 6.4 Hz), 7.18 (1H, d, J = 8.9 Hz), 6.86 (1H, t, J = 8.6 Hz), 6.81 (1H, t, J = 8.6 Hz), 6.69 (1H, dd, J = 8.9, 3.1 Hz), 6.54 (1H, dd, J = 3.1, 1.7 Hz), 3.63 (3H, s), 3.00-2.99 (1H, m), 0.90-0.66 (4H, m). |

TABLE 5-continued

| Compound | ¹H-NMR |
| --- | --- |
| 499 | ¹H-NMR (CDCl₃) δ: 7.34 (1H, tt, J = 8.4, 6.4 Hz), 7.25 (1H, m), 6.89-6.83 (4H, m), 6.76-6.74 (1H, m), 3.40 (3H, s), 2.26 (3H, d, J = 1.2 Hz). |
| 500 | ¹H-NMR (CDCl₃) δ: 7.55 (1H, s), 7.10-7.03 (2H, m), 6.87-6.84 (1H, m), 6.69-6.61 (2H, m), 3.45 (3H, s). |
| 501 | ¹H-NMR (CDCl₃) δ: 7.19-7.18 (1H, m), 7.06-6.99 (2H, m), 6.87-6.85 (1H, m), 6.66-6.58 (2H, m), 3.96-3.85 (2H, m), 2.25 (3H, d, J = 1.2 Hz), 1.16 (3H, t, J = 7.0 Hz). |
| 502 | ¹H-NMR (CDCl₃) δ: 7.13 (1H, m), 6.93 (1H, td, J = 7.8, 5.9 Hz), 6.88-6.83 (1H, m), 6.74 (1H, d, J = 7.8 Hz), 6.64 (1H, tt, J = 8.7, 2.1 Hz), 6.56 (1H, tt, J = 8.7, 2.1 Hz), 3.99-3.81 (2H, m), 2.25 (3H, d, J = 0.9 Hz), 2.06 (3H, d, J = 1.8 Hz), 1.16 (3H, t, J = 7.2 Hz). |
| 503 | ¹H-NMR (CDCl₃) δ: 7.76 (1H, s), 7.09-7.03 (2H, m), 6.86-6.84 (1H, m), 6.69-6.61 (2H, m), 3.46 (3H, s). |
| 504 | ¹H-NMR (CDCl₃) δ: 7.55 (1H, s), 7.10-7.01 (2H, m), 6.88-6.85 (1H, m), 6.43-6.35 (2H, m), 3.77 (3H, s), 3.46 (3H, s). |
| 505 | ¹H-NMR (CDCl₃) δ: 7.21 (1H, d, J = 1.2 Hz), 7.07-7.00 (2H, m), 6.85-6.83 (1H, m), 6.66-6.59 (2H, m), 3.39 (3H, s), 2.26 (3H, d, J = 1.2 Hz). |
| 506 | ¹H-NMR (CDCl₃) δ: 7.34-7.28 (2H, m), 7.03-6.95 (2H, m), 6.91-6.80 (3H, m), 6.74 (1H, d, J = 9.2 Hz), 3.98-3.83 (2H, m), 1.16 (3H, t, J = 7.2 Hz). |
| 507 | ¹H-NMR (CDCl₃) δ: 7.54 (1H, s), 7.32 (1H, m), 7.05-6.97 (2H, m), 6.91-6.81 (3H, m), 4.01-3.90 (2H, m), 1.18 (3H, t, J = 7.0 Hz). |
| 508 | ¹H-NMR (CDCl₃) δ: 7.35-7.28 (2H, m), 7.03-6.96 (2H, m), 6.91-6.86 (1H, m), 6.85-6.80 (2H, m), 6.76 (1H, d, J = 9.5 Hz), 3.39 (3H, s). |
| 509 | ¹H-NMR (CDCl₃) δ: 7.56 (1H, s), 7.34 (1H, m), 7.05-6.98 (2H, m), 6.91-6.88 (1H, m), 6.86-6.82 (2H, m), 3.45 (3H, s). |
| 510 | ¹H-NMR (CDCl₃) δ: 7.38 (1H, d, J = 9.2 Hz), 7.37-7.30 (1H, m), 7.05-6.98 (2H, m), 6.90-6.86 (2H, m), 6.85-6.82 (1H, m), 6.77 (1H, d, J = 9.2 Hz), 6.17 (1H, tt, J = 56.6, 4.5 Hz), 4.25-4.10 (2H, m). |
| 511 | ¹H-NMR (CDCl₃) δ: 7.61 (1H, s), 7.36 (1H, m), 7.07-6.99 (2H, m), 6.91-6.83 (3H, m), 6.19 (1H, tt, J = 56.5, 4.6 Hz), 4.25-4.17 (2H, m). |
| 512 | ¹H-NMR (CDCl₃) δ: 7.35 (1H, tt, J = 8.5, 6.4 Hz), 7.27 (1H, dd, J = 8.9, 5.0 Hz), 7.13 (1H, d, J = 9.5 Hz), 6.93 (1H, t, J = 8.4 Hz), 6.89-6.80 (3H, m), 3.98-3.92 (2H, m), 1.17 (3H, t, J = 7.0 Hz). |
| 513 | ¹H-NMR (CDCl₃) δ: 7.35 (1H, tt, J = 8.5, 6.4 Hz), 7.27 (1H, dd, J = 8.9, 5.2 Hz), 7.15 (1H, d, J = 9.5 Hz), 6.93 (1H, t, J = 8.5 Hz), 6.88-6.86 (2H, m), 6.80 (1H, ddd, J = 8.9, 3.1, 1.2 Hz), 3.44 (3H, s). |
| 514 | ¹H-NMR (CDCl₃) δ: 7.14-7.09 (1H, m), 6.94-6.90 (3H, m), 6.57-6.55 (2H, m), 3.42 (2H, q, J = 7.2 Hz), 2.75-2.69 (4H, m), 0.98 (3H, t, J = 7.2 Hz). |
| 515 | ¹H-NMR (CDCl₃) δ: 7.18 (1H, d, J = 1.2 Hz), 7.05-6.96 (2H, m), 6.88-6.86 (1H, m), 6.41-6.38 (1H, m), 6.36-6.33 (1H, m), 3.99-3.86 (2H, m), 3.76 (3H, s), 2.24 (3H, d, J = 1.2 Hz), 1.15 (3H, t, J = 7.0 Hz). |
| 516 | ¹H-NMR (CDCl₃) δ: 7.12 (1H, d, J = 1.2 Hz), 6.93 (1H, td, J = 7.7, 5.9 Hz), 6.85-6.82 (1H, m), 6.76 (1H, d, J = 7.7 Hz), 6.41-6.38 (1H, m), 6.33-6.30 (1H, m), 3.98-3.85 (2H, m), 3.74 (3H, s), 2.24 (3H, d, J = 1.2 Hz), 2.06-2.05 (3H, m), 1.16 (3H, t, J = 7.2 Hz). |
| 517 | ¹H-NMR (CDCl₃) δ: 7.20 (1H, d, J = 1.1 Hz), 7.06-6.98 (2H, m), 6.86-6.84 (1H, m), 6.41-6.39 (1H, m), 6.36-6.33 (1H, m), 3.76 (3H, s), 3.40 (3H, s), 2.25 (3H, d, J = 1.1 Hz). |
| 518 | ¹H-NMR (CDCl₃) δ: 7.37-7.31 (2H, m), 7.02-6.96 (1H, m), 6.90-6.85 (3H, m), 6.79 (1H, dd, J = 7.6, 6.1 Hz), 6.75 (1H, d, J = 9.2 Hz), 3.93 (2H, q, J = 7.1 Hz), 1.15 (3H, t, J = 7.1 Hz). |
| 519 | ¹H-NMR (CDCl₃) δ: 7.58 (1H, d, J = 0.9 Hz), 7.38-7.32 (1H, m), 7.04-6.98 (1H, m), 6.92-6.87 (3H, m), 6.82-6.79 (1H, m), 3.98 (2H, q, J = 7.1 Hz), 1.17 (3H, t, J = 7.1 Hz). |
| 520 | ¹H-NMR (CDCl₃) δ: 7.78 (1H, d, J = 0.6 Hz), 7.38-7.32 (1H, m), 7.04-6.98 (1H, m), 6.92-6.86 (3H, m), 6.82-6.79 (1H, m), 3.98 (2H, q, J = 7.1 Hz), 1.17 (3H, t, J = 7.1 Hz). |
| 521 | ¹H-NMR (CDCl₃) δ: 7.35 (1H, m), 7.30-7.28 (1H, m), 7.25-7.21 (1H, m), 6.96-6.85 (4H, m), 6.16 (1H, tt, J = 56.6, 4.5 Hz), 4.23-4.15 (2H, m), 2.26 (3H, d, J = 1.2 Hz). |
| 522 | ¹H-NMR (CDCl₃) δ: 7.38-7.31 (2H, m), 7.13-7.09 (1H, m), 7.04-7.01 (1H, m), 6.91-6.84 (3H, m), 6.74 (1H, d, J = 9.5 Hz), 3.92 (2H, q, J = 7.1 Hz), 1.14 (3H, t, J = 7.1 Hz). |
| 523 | ¹H-NMR (CDCl₃) δ: 7.56 (1H, s), 7.37 (1H, m), 7.15-7.12 (1H, m), 7.05-7.03 (1H, m), 6.92-6.85 (3H, m), 3.97 (2H, q, J = 7.0 Hz), 1.17 (3H, t, J = 7.0 Hz). |
| 524 | ¹H-NMR (CDCl₃) δ: 7.39-7.33 (2H, m), 7.14-7.11 (1H, m), 7.04-7.01 (1H, m), 6.91-6.84 (3H, m), 6.76 (1H, d, J = 9.5 Hz), 3.40 (3H, s). |
| 525 | ¹H-NMR (CDCl₃) δ: 7.58 (1H, s), 7.38 (1H, m), 7.17-7.13 (1H, m), 7.05-7.02 (1H, m), 6.92-6.84 (3H, m), 3.46 (3H, s). |
| 526 | ¹H-NMR (CDCl₃) δ: 7.16-7.10 (1H, m), 6.95-6.93 (1H, m), 6.90-6.89 (2H, m), 6.58-6.56 (2H, m), 2.89 (3H, s), 2.75-2.73 (4H, br m). |
| 527 | ¹H-NMR (CDCl₃) δ: 7.35 (1H, dd, J = 9.2, 0.8 Hz), 7.22-7.17 (1H, m), 7.03 (1H, td, J = 7.5, 1.9 Hz), 6.99 (1H, td, J = 7.5, 1.1 Hz), 6.96-6.92 (1H, m), 6.75 (1H, d, J = 9.2 Hz), 6.65-6.60 (2H, m), 3.92 (2H, q, J = 7.0 Hz), 1.15 (3H, t, J = 7.0 Hz). |
| 528 | ¹H-NMR (CDCl₃) δ: 7.37 (1H, dd, J = 9.5, 0.9 Hz), 7.22-7.19 (1H, m), 7.03-7.00 (2H, m), 6.95-6.93 (1H, m), 6.76 (1H, d, J = 9.5 Hz), 6.66-6.60 (2H, m), 3.40 (3H, s). |
| 529 | ¹H-NMR (CDCl₃) δ: 7.59 (1H, d, J = 0.6 Hz), 7.22-7.21 (1H, m), 7.05-7.03 (1H, m), 7.00 (1H, td, J = 7.3, 1.2 Hz), 6.96-6.93 (1H, m), 6.65-6.61 (2H, m), 3.97 (2H, q, J = 7.0 Hz), 1.17 (3H, t, J = 7.0 Hz). |
| 530 | ¹H-NMR (CDCl₃) δ: 7.34 (1H, dd, J = 9.5, 0.9 Hz), 7.20-7.15 (1H, m), 7.04-7.02 (1H, m), 6.98-6.96 (1H, m), 6.95-6.93 (1H, m), 6.72 (1H, d, J = 9.5 Hz), 6.39-6.37 (2H, m), 3.94 (2H, q, J = 7.0 Hz), 3.76 (3H, s), 1.14 (3H, t, J = 7.0 Hz). |
| 531 | ¹H-NMR (CDCl₃) δ: 7.58 (1H, d, J = 0.7 Hz), 7.22-7.17 (1H, m), 7.05-7.02 (1H, m), 6.99-6.97 (1H, m), 6.96-6.93 (1H, m), 6.39-6.36 (2H, m), 3.99 (2H, q, J = 7.1 Hz), 3.76 (3H, s), 1.17 (3H, t, J = 7.1 Hz). |
| 532 | ¹H-NMR (CDCl₃) δ: 7.79 (1H, s), 7.24-7.19 (1H, m), 7.04-6.99 (2H, m), 6.95-6.93 (1H, m), 6.66-6.60 (2H, m), 3.97 (2H, q, J = 7.0 Hz), 1.17 (3H, t, J = 7.0 Hz). |

TABLE 5-continued

| Compound | ¹H-NMR |
|---|---|
| 533 | ¹H-NMR (CDCl₃) δ: 7.33 (1H, tt, J = 8.3, 6.4 Hz), 7.18 (1H, d, J = 8.9 Hz), 7.15 (1H, d, J = 9.5 Hz), 6.90 (1H, t, J = 8.3 Hz), 6.84 (1H, t, J = 8.3 Hz), 6.68 (1H, dd, J = 8.9, 3.1 Hz), 6.62 (1H, dd, J = 3.1, 1.5 Hz), 4.02-3.87 (2H, m), 3.65 (3H, s), 1.18 (3H, t, J = 7.1 Hz). |
| 534 | ¹H-NMR (CDCl₃) δ: 7.35-7.28 (1H, m), 7.23 (1H, t, J = 0.9 Hz), 7.01-6.94 (1H, m), 6.89-6.84 (3H, m), 6.81-6.77 (1H, m), 3.93 (2H, q, J = 7.0 Hz), 2.25 (3H, d, J = 0.9 Hz), 1.14 (3H, t, J = 7.0 Hz). |
| 535 | ¹H-NMR (CDCl₃) δ: 7.38-7.31 (2H, m), 7.03-6.96 (1H, m), 6.92-6.86 (3H, m), 6.81-6.75 (2H, m), 3.40 (3H, s). |
| 536 | ¹H-NMR (CDCl₃) δ: 7.80 (1H, d, J = 0.7 Hz), 7.40-7.33 (1H, m), 7.06-6.99 (1H, m), 6.94-6.87 (3H, m), 6.82-6.78 (1H, m), 3.47 (3H, s). |
| 537 | ¹H-NMR (CDCl₃) δ: 7.60 (1H, br s), 7.39-7.34 (1H, m), 7.05-7.00 (1H, m), 6.93-6.87 (3H, m), 6.82-6.78 (1H, m), 3.47 (3H, s). |
| 538 | ¹H-NMR (CDCl₃) δ: 7.36-7.30 (1H, m), 7.26 (1H, m), 7.02-6.96 (1H, m), 6.90-6.85 (3H, m), 6.81-6.77 (1H, m), 3.41 (3H, s), 2.26 (3H, d, J = 0.9 Hz). |
| 539 | ¹H-NMR (CDCl₃) δ: 7.41-7.35 (2H, m), 7.15-7.12 (1H, m), 7.05-7.02 (1H, m), 6.91-6.85 (3H, m), 6.77 (1H, d, J = 9.5 Hz), 6.14 (1H, tt, J = 56.6, 4.5 Hz), 4.22-4.16 (2H, m). |
| 540 | ¹H-NMR (CDCl₃) δ: 7.63 (1H, s), 7.44-7.36 (1H, m), 7.18-7.14 (1H, m), 7.06-7.03 (1H, m), 6.93-6.85 (3H, m), 6.16 (1H, tt, J = 56.4, 4.5 Hz), 4.27-4.20 (2H, m). |
| 541 | ¹H-NMR (CDCl₃) δ: 7.78 (1H, d, J = 0.9 Hz), 7.21-7.17 (1H, m), 7.04 (1H, td, J = 7.6, 1.6 Hz), 6.98 (1H, td, J = 7.6, 1.1 Hz), 6.96-6.92 (1H, m), 6.39-6.37 (2H, m), 3.99 (2H, q, J = 7.0 Hz), 3.76 (3H, s), 1.17 (3H, t, J = 7.0 Hz). |
| 542 | ¹H-NMR (CDCl₃) δ: 7.24 (1H, t, J = 1.2 Hz), 7.21-7.16 (1H, m), 7.03 (1H, td, J = 7.5, 1.6 Hz), 6.98 (1H, td, J = 7.5, 1.2 Hz), 6.95-6.91 (1H, m), 6.63-6.59 (2H, m), 3.92 (2H, q, J = 7.1 Hz), 2.25 (3H, d, J = 1.2 Hz), 1.15 (3H, t, J = 7.1 Hz). |
| 543 | ¹H-NMR (CDCl₃) δ: 7.60 (1H, d, J = 0.7 Hz), 7.25-7.20 (1H, m), 7.03-7.00 (2H, m), 6.97-6.92 (1H, m), 6.67-6.61 (2H, m), 3.46 (3H, s). |
| 544 | ¹H-NMR (CDCl₃) δ: 7.37 (1H, dd, J = 9.5, 1.0 Hz), 7.21-7.15 (1H, m), 7.05-7.01 (1H, m), 7.00-6.96 (1H, m), 6.96-6.92 (1H, m), 6.73 (1H, d, J = 9.5 Hz), 6.40-6.37 (2H, m), 3.76 (3H, s), 3.40 (3H, s). |
| 545 | ¹H-NMR (CDCl₃) δ: 7.81 (1H, d, J = 0.7 Hz), 7.25-7.20 (1H, m), 7.03-7.01 (2H, m), 6.95-6.93 (1H, m), 6.66-6.61 (2H, m), 3.47 (3H, s). |
| 546 | ¹H-NMR (CDCl₃) δ: 7.53 (1H, d, J = 0.9 Hz), 6.83-6.78 (1H, m), 6.59-6.57 (1H, m), 6.44 (2H, dd, J = 11.9, 2.8 Hz), 3.98 (2H, q, J = 7.1 Hz), 3.80 (3H, s), 1.17 (3H, t, J = 7.1 Hz). |
| 547 | ¹H-NMR (CDCl₃) δ: 7.52 (1H, s), 7.29-7.27 (1H, m), 6.89-6.87 (1H, m), 6.82 (1H, dq, J = 8.7, 1.4 Hz), 6.43 (1H, dt, J = 10.8, 1.9 Hz), 6.35 (1H, dt, J = 10.8, 1.9 Hz), 3.96 (4H, q, J = 7.0 Hz), 1.40 (3H, t, J = 7.0 Hz), 1.18 (3H, t, J = 7.0 Hz). |
| 548 | ¹H-NMR (CDCl₃) δ: 7.29 (1H, dd, J = 9.5, 0.9 Hz), 6.81-6.76 (1H, m), 6.73 (1H, d, J = 9.2 Hz), 6.58-6.56 (1H, m), 6.44 (2H, dd, J = 11.9, 2.8 Hz), 3.93 (2H, q, J = 7.1 Hz), 3.80 (3H, s), 1.14 (3H, t, J = 7.1 Hz). |
| 549 | ¹H-NMR (CDCl₃) δ: 7.55 (1H, d, J = 0.9 Hz), 6.84-6.79 (1H, m), 6.59-6.57 (1H, m), 6.45 (2H, dd, J = 11.9, 2.8 Hz), 3.80 (3H, s), 3.46 (3H, s). |
| 550 | ¹H-NMR (CDCl₃) δ: 7.32 (1H, dd, J = 9.5, 0.9 Hz), 6.82-6.77 (1H, m), 6.74 (1H, d, J = 9.5 Hz), 6.58-6.55 (1H, m), 6.44 (2H, dd, J = 12.2, 2.8 Hz), 3.80 (3H, s), 3.40 (3H, s). |
| 551 | ¹H-NMR (CDCl₃) δ: 7.38-7.32 (1H, m), 7.27 (1H, d, J = 9.8 Hz), 6.94 (1H, t, J = 8.4 Hz), 6.87 (1H, t, J = 8.4 Hz), 6.78-6.73 (2H, m), 6.68-6.65 (1H, m), 3.96-3.84 (2H, m), 1.16 (3H, t, J = 7.0 Hz). |
| 552 | ¹H-NMR (CDCl₃) δ: 7.51 (1H, s), 7.41-7.33 (1H, m), 6.95 (1H, t, J = 8.4 Hz), 6.88 (1H, t, J = 8.4 Hz), 6.81-6.76 (1H, m), 6.69-6.66 (1H, m), 3.95 (2H, q, J = 7.1 Hz), 1.18 (3H, t, J = 7.1 Hz). |
| 553 | ¹H-NMR (CDCl₃) δ: 7.40-7.32 (1H, m), 7.30 (1H, d, J = 9.3 Hz), 6.94 (1H, t, J = 8.4 Hz), 6.87 (1H, t, J = 8.4 Hz), 6.80-6.75 (2H, m), 6.66-6.62 (1H, m), 3.38 (3H, s). |
| 554 | ¹H-NMR (CDCl₃) δ: 7.53 (1H, s), 7.42-7.34 (1H, m), 6.94 (1H, t, J = 8.4 Hz), 6.89 (1H, t, J = 8.4 Hz), 6.82-6.75 (1H, m), 6.67-6.64 (1H, m), 3.45 (3H, s). |
| 555 | ¹H-NMR (CDCl₃) δ: 7.41-7.37 (1H, m), 7.35 (1H, d, J = 9.5 Hz), 6.94 (1H, t, J = 8.4 Hz), 6.88 (1H, t, J = 8.4 Hz), 6.81-6.77 (2H, m), 6.69-6.66 (1H, m), 6.16 (1H, tt, J = 56.6, 4.4 Hz), 4.19-4.13 (2H, m). |
| 556 | ¹H-NMR (CDCl₃) δ: 7.58 (1H, s), 7.44-7.37 (1H, m), 6.96-6.87 (2H, m), 6.83-6.78 (1H, m), 6.71-6.67 (1H, m), 6.18 (1H, tt, J = 56.5, 4.5 Hz), 4.26-4.16 (2H, m). |
| 557 | ¹H-NMR (CDCl₃) δ: 7.35 (1H, dd, J = 9.3, 0.8 Hz), 7.07-7.01 (1H, m), 6.96-6.92 (1H, m), 6.81-6.76 (2H, m), 6.68-6.64 (2H, m), 3.40 (3H, s). |
| 558 | ¹H-NMR (CDCl₃) δ: 7.33 (1H, dd, J = 9.2, 0.9 Hz), 7.06-7.00 (1H, m), 6.95-6.90 (1H, m), 6.81-6.77 (1H, m), 6.75 (1H, d, J = 9.2 Hz), 6.68-6.63 (2H, m), 3.91 (2H, q, J = 7.2 Hz), 1.15 (3H, t, J = 7.2 Hz). |
| 559 | ¹H-NMR (CDCl₃) δ: 7.59 (1H, d, J = 0.6 Hz), 7.09-7.04 (1H, m), 6.98-6.94 (1H, m), 6.83-6.79 (1H, m), 6.69-6.65 (2H, m), 3.46 (3H, s). |
| 560 | ¹H-NMR (CDCl₃) δ: 7.79 (1H, s), 7.09-7.04 (1H, m), 6.98-6.94 (1H, m), 6.83-6.79 (1H, m), 6.69-6.65 (2H, m), 3.47 (3H, s). |
| 561 | ¹H-NMR (CDCl₃) δ: 7.35 (1H, dd, J = 9.3, 1.0 Hz), 7.05-6.98 (1H, m), 6.95-6.89 (1H, m), 6.81-6.77 (1H, m), 6.74 (1H, d, J = 9.3 Hz), 6.42-6.38 (2H, m), 3.78 (3H, s), 3.40 (3H, s). |
| 562 | ¹H-NMR (CDCl₃) δ: 7.58 (1H, d, J = 0.7 Hz), 7.07-7.00 (1H, m), 6.96-6.91 (1H, m), 6.82-6.78 (1H, m), 6.43-6.39 (2H, m), 3.78 (3H, s), 3.47 (3H, s). |
| 563 | ¹H-NMR (CDCl₃) δ: 7.78 (1H, d, J = 0.6 Hz), 7.07-7.01 (1H, m), 6.96-6.91 (1H, m), 6.82-6.79 (1H, m), 6.41 (2H, dd, J = 12.2, 2.8 Hz), 3.78 (3H, s), 3.47 (3H, s). |
| 564 | ¹H-NMR (CDCl₃) δ: 7.25-7.24 (1H, m), 7.06-6.99 (1H, m), 6.96-6.90 (1H, m), 6.81-6.77 (1H, m), 6.67-6.62 (2H, m), 3.40 (3H, s), 2.26 (3H, d, J = 1.2 Hz). |
| 565 | ¹H-NMR (CDCl₃) δ: 7.25-7.23 (1H, m), 7.04-6.97 (1H, m), 6.93-6.88 (1H, m), 6.81-6.77 (1H, m), 6.41-6.37 (2H, m), 3.77 (3H, s), 3.41 (3H, s), 2.25 (3H, d, J = 1.2 Hz). |

TABLE 5-continued

| Compound | ¹H-NMR |
|---|---|
| 566 | ¹H-NMR (CDCl₃) δ: 7.57 (1H, d, J = 0.6 Hz), 7.08-7.03 (1H, m), 6.97-6.92 (1H, m), 6.82-6.79 (1H, m), 6.69-6.64 (2H, m), 3.97 (2H, q, J = 7.0 Hz), 1.18 (3H, t, J = 7.0 Hz). |
| 567 | ¹H-NMR (CDCl₃) δ: 7.77 (1H, s), 7.08-7.03 (1H, m), 6.97-6.92 (1H, m), 6.82-6.79 (1H, m), 6.68-6.64 (2H, m), 3.97 (2H, q, J = 7.0 Hz), 1.17 (3H, t, J = 7.0 Hz). |
| 568 | ¹H-NMR (CDCl₃) δ: 7.25-7.19 (1H, m), 7.16 (1H, d, J = 9.3 Hz), 7.01-6.97 (3H, m), 6.66-6.60 (2H, m), 3.96 (2H, q, J = 7.1 Hz), 1.17 (3H, t, J = 7.1 Hz). |
| 569 | ¹H-NMR (CDCl₃) δ: 7.24 (1H, m), 7.19-7.13 (1H, m), 7.03 (1H, td, J = 7.5, 1.8 Hz), 6.98-6.91 (2H, m), 6.38-6.35 (2H, m), 3.94 (2H, q, J = 7.1 Hz), 3.75 (3H, s), 2.24 (3H, d, J = 1.0 Hz), 1.14 (3H, t, J = 7.1 Hz). |
| 570 | ¹H-NMR (CDCl₃) δ: 7.60 (1H, d, J = 0.7 Hz), 7.23-7.18 (1H, m), 7.04 (1H, td, J = 7.6, 1.8 Hz), 7.01-6.98 (1H, m), 6.97-6.92 (1H, m), 6.40-6.37 (2H, m), 3.76 (3H, s), 3.47 (3H, s). |
| 571 | ¹H-NMR (CDCl₃) δ: 7.28-7.25 (1H, m), 7.21-7.18 (1H, m), 7.03 (1H, td, J = 7.4, 2.0 Hz), 6.99 (1H, td, J = 7.4, 1.2 Hz), 6.93 (1H, ddd, J = 9.7, 8.2, 1.2 Hz), 6.64-6.59 (2H, m), 3.41 (3H, s), 2.26 (3H, d, J = 1.0 Hz). |
| 572 | ¹H-NMR (CDCl₃) δ: 7.80 (1H, d, J = 1.0 Hz), 7.23-7.17 (1H, m), 7.04 (1H, td, J = 7.4, 2.1 Hz), 7.01-6.97 (1H, m), 6.94 (1H, ddd, J = 9.7, 8.3, 1.2 Hz), 6.40-6.37 (2H, m), 3.76 (3H, s), 3.47 (3H, s). |
| 573 | ¹H-NMR (CDCl₃) δ: 7.04 (1H, dd, J = 8.6, 2.8 Hz), 6.98 (1H, ddd, J = 7.9, 6.1, 1.8 Hz), 6.76 (1H, td, J = 7.9, 2.8 Hz), 6.59 (1H, tt, J = 8.9, 2.1 Hz), 6.54 (1H, tt, J = 8.9, 2.1 Hz), 3.47 (1H, dq, J = 14.1, 7.0 Hz), 3.35 (1H, dq, J = 14.1, 7.0 Hz), 2.87-2.52 (4H, m), 0.99 (3H, t, J = 7.0 Hz). |
| 574 | ¹H-NMR (CDCl₃) δ: 7.05 (1H, dd, J = 8.6, 2.8 Hz), 6.97 (1H, ddd, J = 8.3, 6.1, 1.8 Hz), 6.76 (1H, td, J = 8.3, 2.8 Hz), 6.60 (1H, tt, J = 8.7, 2.1 Hz), 6.54 (1H, tt, J = 8.7, 2.1 Hz), 2.89 (3H, s), 2.87-2.77 (2H, m), 2.72-2.69 (1H, m), 2.59-2.55 (1H, m). |
| 575 | ¹H-NMR (CDCl₃) δ: 7.28 (1H, d, J = 9.2 Hz), 7.07 (1H, dd, J = 8.6, 2.8 Hz), 7.05-7.02 (1H, m), 6.81 (1H, ddd, J = 8.6, 8.0, 2.8 Hz), 6.74 (1H, d, J = 9.2 Hz), 6.67-6.62 (2H, m), 3.91-3.88 (2H, m), 1.16 (3H, t, J = 7.0 Hz). |
| 576 | ¹H-NMR (CDCl₃) δ: 7.30 (1H, d, J = 9.5 Hz), 7.08 (1H, dd, J = 8.5, 2.5 Hz), 7.02 (1H, ddd, J = 8.5, 6.0, 1.8 Hz), 6.82 (1H, ddd, J = 8.6, 8.0, 2.5 Hz), 6.76 (1H, d, J = 9.5 Hz), 6.69-6.61 (2H, m), 3.38 (3H, s). |
| 577 | ¹H-NMR (CDCl₃) δ: 7.52 (1H, s), 7.08 (1H, dd, J = 8.4, 2.6 Hz), 7.05 (1H, ddd, J = 8.6, 6.1, 1.8 Hz), 6.82 (1H, ddd, J = 8.6, 8.0, 2.6 Hz), 6.69-6.62 (2H, m), 3.96-3.93 (2H, m), 1.18 (3H, t, J = 7.0 Hz). |
| 578 | ¹H-NMR (CDCl₃) δ: 7.72 (1H, s), 7.08 (1H, dd, J = 8.6, 2.6 Hz), 7.04 (1H, ddd, J = 8.6, 6.1, 1.8 Hz), 6.82 (1H, ddd, J = 8.6, 8.0, 2.6 Hz), 6.69-6.62 (2H, m), 3.96-3.93 (2H, m), 1.18 (3H, t, J = 7.0 Hz). |
| 579 | ¹H-NMR (CDCl₃) δ: 7.29 (1H, dd, J = 9.5, 0.9 Hz), 6.81-6.75 (1H, m), 6.73 (1H, d, J = 9.5 Hz), 6.58-6.55 (1H, m), 6.43-6.40 (2H, m), 3.99 (2H, q, J = 7.0 Hz), 3.93 (2H, q, J = 7.0 Hz), 1.42 (3H, t, J = 7.0 Hz), 1.14 (3H, t, J = 7.0 Hz). |
| 580 | ¹H-NMR (CDCl₃) δ: 7.53 (1H, d, J = 0.6 Hz), 6.83-6.78 (1H, m), 6.59-6.57 (1H, m), 6.43-6.41 (2H, m), 4.01-3.96 (4H, m), 1.42 (3H, t, J = 7.0 Hz), 1.17 (3H, t, J = 7.0 Hz). |
| 581 | ¹H-NMR (CDCl₃) δ: 7.23-7.21 (1H, m), 7.15 (1H, d, J = 8.8 Hz), 6.84 (1H, t, J = 8.5 Hz), 6.78 (1H, t, J = 8.5 Hz), 6.62 (1H, dd, J = 8.8, 3.2 Hz), 6.56-6.54 (1H, m), 4.19-4.11 (1H, m), 3.97-3.90 (1H, m), 3.64 (3H, s), 3.44-3.36 (1H, m), 3.31-3.23 (1H, m), 2.75-2.68 (1H, m), 2.50-2.42 (1H, m), 1.10 (3H, t, J = 7.1 Hz). |
| 582 | ¹H-NMR (CDCl₃) δ: 7.85 (1H, d, J = 9.0 Hz), 7.38-7.30 (1H, m), 7.18 (1H, d, J = 9.0 Hz), 7.14 (1H, d, J = 9.0 Hz), 6.94-6.89 (1H, m), 6.88-6.83 (1H, m), 6.69 (1H, dd, J = 8.9, 3.1 Hz), 6.59-6.58 (1H, m), 4.64-4.52 (2H, m), 3.65 (3H, s), 1.28 (3H, t, J = 7.2 Hz). |
| 583 | ¹H-NMR (CDCl₃) δ: 6.74 (1H, td, J = 8.5, 2.9 Hz), 6.66-6.55 (3H, m), 3.49-3.42 (1H, m), 3.40-3.33 (1H, m), 2.88-2.82 (1H, m), 2.79-2.74 (1H, m), 2.72-2.67 (1H, m), 2.60-2.54 (1H, m), 0.99 (3H, t, J = 7.2 Hz). |
| 584 | ¹H-NMR (CDCl₃) δ: 7.26 (1H, d, J = 9.5 Hz), 6.81 (1H, td, J = 8.5, 2.9 Hz), 6.75 (1H, d, J = 9.5 Hz), 6.73-6.69 (1H, m), 6.67-6.63 (2H, m), 3.89 (2H, q, J = 7.0 Hz), 1.16 (3H, t, J = 7.0 Hz). |
| 585 | ¹H-NMR (CDCl₃) δ: 7.50 (1H, s), 6.83 (1H, td, J = 8.4, 3.0 Hz), 6.74-6.69 (1H, m), 6.69-6.65 (2H, m), 3.98-3.90 (2H, m), 1.19 (3H, t, J = 7.0 Hz). |
| 586 | ¹H-NMR (CDCl₃) δ: 7.28 (1H, d, J = 9.5 Hz), 6.82 (1H, td, J = 8.4, 2.9 Hz), 6.77 (1H, d, J = 9.5 Hz), 6.74-6.62 (3H, m), 3.38 (3H, s). |
| 587 | ¹H-NMR (CDCl₃) δ: 7.52 (1H, s), 6.84 (1H, td, J = 8.4, 2.8 Hz), 6.74-6.64 (3H, m), 3.45 (3H, s). |
| 588 | ¹H-NMR (CDCl₃) δ: 7.32 (1H, dd, J = 9.4, 0.9 Hz), 7.03-6.98 (1H, m), 6.93-6.88 (1H, m), 6.81-6.78 (1H, m), 6.73 (1H, d, J = 9.4 Hz), 6.41-6.38 (2H, m), 3.93 (2H, q, J = 7.1 Hz), 3.78 (3H, s), 1.14 (3H, t, J = 7.1 Hz). |
| 589 | ¹H-NMR (CDCl₃) δ: 7.76 (1H, d, J = 0.9 Hz), 7.06-7.00 (1H, m), 6.95-6.90 (1H, m), 6.82-6.79 (1H, m), 6.42-6.39 (2H, m), 3.99 (2H, q, J = 7.0 Hz), 3.78 (3H, s), 1.17 (3H, t, J = 7.0 Hz). |
| 590 | ¹H-NMR (CDCl₃) δ: 7.56 (1H, d, J = 0.6 Hz), 7.06-7.00 (1H, m), 6.95-6.90 (1H, m), 6.82-6.79 (1H, m), 6.42-6.39 (2H, m), 3.98 (2H, q, J = 7.1 Hz), 3.78 (3H, s), 1.17 (3H, t, J = 7.1 Hz). |
| 591 | ¹H-NMR (CDCl₃) δ: 7.37 (1H, dd, J = 9.5, 0.9 Hz), 7.20-7.16 (1H, m), 7.03 (1H, td, J = 7.6, 2.1 Hz), 6.98-6.94 (2H, m), 6.73 (1H, d, J = 9.5 Hz), 6.37-6.35 (2H, m), 3.95 (2H, q, J = 7.0 Hz), 3.40 (3H, s), 1.39 (3H, t, J = 7.0 Hz). |
| 592 | ¹H-NMR (CDCl₃) δ: 7.10 (1H, d, J = 9.3 Hz), 7.07-7.04 (2H, m), 6.82 (1H, ddd, J = 8.8, 8.1, 2.8 Hz), 6.67 (1H, tt, J = 8.6, 2.1 Hz), 6.63 (1H, tt, J = 8.6, 2.1 Hz), 3.94 (2H, q, J = 7.1 Hz), 1.17 (3H, t, J = 7.1 Hz). |
| 593 | ¹H-NMR (CDCl₃) δ: 7.51 (1H, s), 7.08-7.03 (2H, m), 6.81 (1H, ddd, J = 8.8, 8.1, 2.8 Hz), 6.43-6.39 (1H, m), 6.39-6.34 (1H, m), 3.96 (2H, q, J = 7.2 Hz), 3.77 (3H, s), 1.17 (3H, t, J = 7.2 Hz). |
| 594 | ¹H-NMR (CDCl₃) δ: 7.17 (1H, q, J = 0.9 Hz), 7.06-7.03 (2H, m), 6.80 (1H, td, J = 8.3, 2.7 Hz), 6.66-6.59 (2H, m), 3.90 (2H, q, J = 7.2 Hz), 2.25 (3H, d, J = 0.9 Hz), 1.15 (3H, t, J = 7.2 Hz). |

TABLE 5-continued

| Compound | ¹H-NMR |
|---|---|
| 595 | ¹H-NMR (CDCl₃) δ: 7.51 (1H, s), 7.08-7.03 (2H, m), 6.80 (1H, ddd, J = 8.8, 8.0, 2.8 Hz), 6.39 (1H, dt, J = 10.8, 2.0 Hz), 6.34 (1H, dt, J = 10.8, 2.0 Hz), 3.97-3.95 (4H, m), 1.40 (3H, t, J = 7.1 Hz), 1.17 (3H, t, J = 7.1 Hz). |
| 596 | ¹H-NMR (CDCl₃) δ: 7.54 (1H, s), 7.08 (1H, dd, J = 8.4, 2.8 Hz), 7.04 (1H, ddd, J = 8.0, 6.1, 1.8 Hz), 6.84 (1H, ddd, J = 8.8, 8.0, 2.8 Hz), 6.67-6.65 (2H, m), 3.45 (3H, s). |
| 597 | ¹H-NMR (CDCl₃) δ: 7.74 (1H, s), 7.08 (1H, dd, J = 8.3, 2.8 Hz), 7.06-7.01 (1H, m), 6.84 (1H, ddd, J = 8.9, 8.0, 2.8 Hz), 6.68 (1H, dt, J = 8.5, 2.1 Hz), 6.63 (1H, dt, J = 8.5, 2.1 Hz), 3.45 (3H, s). |
| 598 | ¹H-NMR (CDCl₃) δ: 7.60 (1H, d, J = 1.0 Hz), 7.21-7.17 (1H, m), 7.04-6.92 (3H, m), 6.38-6.35 (2H, m), 3.95 (2H, q, J = 7.0 Hz), 3.47 (3H, s), 1.39 (3H, t, J = 7.0 Hz). |
| 599 | ¹H-NMR (CDCl₃) δ: 7.16 (1H, q, J = 0.9 Hz), 7.06-7.03 (2H, m), 6.78 (1H, td, J = 8.3, 2.7 Hz), 6.40 (1H, dt, J = 10.7, 1.8 Hz), 6.35 (1H, dt, J = 10.6, 1.9 Hz), 3.93-3.90 (2H, m), 3.77 (3H, s), 2.24 (3H, d, J = 0.9 Hz), 1.15 (3H, t, J = 7.0 Hz). |
| 600 | ¹H-NMR (CDCl₃) δ: 7.53 (1H, s), 7.08 (1H, dd, J = 8.4, 2.8 Hz), 7.03 (1H, ddd, J = 8.0, 6.0, 1.7 Hz), 6.82 (1H, ddd, J = 8.8, 8.0, 2.8 Hz), 6.41 (1H, dt, J = 10.8, 1.9 Hz), 6.37 (1H, dt, J = 10.8, 1.9 Hz), 3.77 (3H, s), 3.45 (3H, s). |
| 601 | ¹H-NMR (CDCl₃) δ: 7.30-7.27 (2H, m), 6.97 (1H, dt, J = 8.4, 1.8 Hz), 6.92-6.88 (2H, m), 6.80 (1H, m), 6.74 (1H, d, J = 9.2 Hz), 3.92-3.85 (2H, m), 1.16 (3H, t, J = 7.0 Hz). |
| 602 | ¹H-NMR (CDCl₃) δ: 7.52 (1H, s), 7.29 (1H, dd, J = 8.8, 5.1 Hz), 6.97 (1H, dt, J = 8.5, 1.8 Hz), 6.93-6.90 (2H, m), 6.82 (1H, m), 4.01-3.86 (2H, m), 1.18 (3H, t, J = 7.1 Hz). |
| 603 | ¹H-NMR (CDCl₃) δ: 7.73 (1H, s), 7.29 (1H, dd, J = 8.9, 5.2 Hz), 6.97 (1H, dt, J = 8.4, 1.8 Hz), 6.94-6.90 (2H, m), 6.81 (1H, m), 4.00-3.87 (2H, m), 1.18 (3H, t, J = 7.2 Hz). |
| 604 | ¹H-NMR (CDCl₃) δ: 7.31-7.28 (2H, m), 6.97 (1H, dt, J = 8.6, 1.7 Hz), 6.93-6.89 (2H, m), 6.79 (1H, m), 6.76 (1H, d, J = 9.5 Hz), 3.37 (3H, s). |
| 605 | ¹H-NMR (CDCl₃) δ: 7.54 (1H, s), 7.29 (1H, dd, J = 8.9, 5.2 Hz), 6.97 (1H, m), 6.95-6.91 (2H, m), 6.81 (1H, m), 3.44 (3H, s). |
| 606 | ¹H-NMR (CDCl₃) δ: 7.74 (1H, s), 7.29 (1H, dd, J = 8.8, 5.1 Hz), 6.98-6.90 (3H, m), 6.81 (1H, m), 3.44 (3H, s). |
| 607 | ¹H-NMR (CDCl₃) δ: 7.33 (1H, d, J = 9.5 Hz), 6.83 (1H, td, J = 8.4, 2.8 Hz), 6.78 (1H, d, J = 9.5 Hz), 6.74-6.63 (3H, m), 6.15 (1H, tt, J = 56.6, 4.5 Hz), 4.22-4.09 (2H, m). |
| 608 | ¹H-NMR (CDCl₃) δ: 7.57 (1H, s), 6.86 (1H, td, J = 8.3, 2.9 Hz), 6.73-6.65 (3H, m), 6.17 (1H, tt, J = 56.4, 4.5 Hz), 4.29-4.10 (2H, m). |
| 609 | ¹H-NMR (CDCl₃) δ: 7.23-7.22 (1H, m), 7.05-6.99 (1H, m), 6.94-6.89 (1H, m), 6.81-6.78 (1H, m), 6.66-6.62 (2H, m), 3.92 (2H, q, J = 7.0 Hz), 2.25 (3H, d, J = 0.9 Hz), 1.15 (3H, t, J = 7.0 Hz). |
| 610 | ¹H-NMR (CDCl₃) δ: 7.22-7.21 (1H, m), 7.03-6.96 (1H, m), 6.92-6.86 (1H, m), 6.82-6.77 (1H, m), 6.41-6.37 (2H, m), 3.94 (2H, q, J = 7.1 Hz), 3.77 (3H, s), 2.24 (3H, d, J = 1.2 Hz), 1.14 (3H, t, J = 7.1 Hz). |
| 611 | ¹H-NMR (CDCl₃) δ: 7.22-7.21 (1H, m), 7.03-6.96 (1H, m), 6.92-6.86 (1H, m), 6.82-6.77 (1H, m), 6.39-6.35 (2H, m), 3.99-3.91 (4H, m), 2.24 (3H, d, J = 1.0 Hz), 2.05 (1H, s), 1.40 (3H, t, J = 7.0 Hz), 1.14 (3H, t, J = 7.1 Hz). |
| 612 | ¹H-NMR (CDCl₃) δ: 7.30 (1H, d, J = 9.5 Hz), 7.07 (1H, dd, J = 8.6, 2.8 Hz), 7.03-7.00 (1H, m), 6.80 (1H, td, J = 8.3, 2.8 Hz), 6.73 (1H, d, J = 9.5 Hz), 6.40 (1H, dt, J = 11.0, 1.8 Hz), 6.34 (1H, dt, J = 11.0, 1.8 Hz), 3.96 (2H, q, J = 7.0 Hz), 3.39 (3H, s), 1.40 (3H, t, J = 7.0 Hz). |
| 613 | ¹H-NMR (CDCl₃) δ: 7.19 (1H, d, J = 1.2 Hz), 7.07 (1H, dd, J = 8.3, 2.8 Hz), 7.04-7.00 (1H, m), 6.81 (1H, ddd, J = 8.6, 8.0, 2.8 Hz), 6.66-6.64 (1H, m), 6.61-6.60 (1H, m), 3.39 (3H, s), 2.25 (3H, d, J = 1.2 Hz). |
| 614 | ¹H-NMR (CDCl₃) δ: 6.61 (1H, tt, J = 8.3, 2.8 Hz), 6.58-6.55 (1H, m), 6.53 (1H, dd, J = 10.5, 2.9 Hz), 6.39-6.38 (1H, m), 3.67 (3H, s), 3.47-3.44 (1H, m), 3.39-3.34 (1H, m), 2.89-2.82 (1H, m), 2.79-2.75 (1H, m), 2.71-2.68 (1H, m), 2.59-2.53 (1H, m), 0.99 (3H, t, J = 7.2 Hz). |
| 615 | ¹H-NMR (CDCl₃) δ: 7.29 (1H, d, J = 9.5 Hz), 6.74 (1H, d, J = 9.5 Hz), 6.71-6.62 (2H, m), 6.59 (1H, dd, J = 10.4, 3.1 Hz), 6.44-6.43 (1H, m), 3.91-3.85 (2H, m), 3.68 (3H, s), 1.16 (3H, t, J = 7.0 Hz). |
| 616 | ¹H-NMR (CDCl₃) δ: 7.53 (1H, s), 7.07 (1H, dd, J = 8.6, 2.8 Hz), 7.03 (1H, ddd, J = 8.6, 6.1, 1.7 Hz), 6.82 (1H, ddd, J = 8.6, 8.0, 2.8 Hz), 6.39 (1H, dt, J = 10.8, 1.8 Hz), 6.35 (1H, dt, J = 10.8, 1.8 Hz), 3.96 (2H, q, J = 7.0 Hz), 3.45 (3H, s), 1.40 (3H, t, J = 7.0 Hz). |
| 617 | ¹H-NMR (CDCl₃) δ: 7.52 (1H, s), 6.71-6.64 (2H, m), 6.61 (1H, dd, J = 10.4, 2.8 Hz), 6.45-6.44 (1H, m), 3.98-3.92 (2H, m), 3.69 (3H, s), 1.19 (3H, t, J = 7.0 Hz). |
| 618 | ¹H-NMR (CDCl₃) δ: 7.31 (1H, d, J = 9.2 Hz), 7.03 (1H, dd, J = 8.3, 8.0 Hz), 6.79 (1H, dd, J = 8.3, 1.4 Hz), 6.74 (1H, d, J = 9.2 Hz), 6.67-6.63 (2H, m), 6.58 (1H, tt, J = 8.7, 2.1 Hz), 3.96-3.83 (5H, m), 1.16 (3H, t, J = 7.0 Hz). |
| 619 | ¹H-NMR (CDCl₃) δ: 7.54 (1H, s), 7.04 (1H, dd, J = 8.3, 7.6 Hz), 6.81 (1H, dd, J = 8.3, 1.2 Hz), 6.68-6.63 (2H, m), 6.59 (1H, tt, J = 8.6, 2.0 Hz), 3.99-3.90 (2H, m), 3.86 (3H, s), 1.18 (3H, t, J = 7.0 Hz). |
| 620 | ¹H-NMR (CDCl₃) δ: 7.74 (1H, s), 7.04 (1H, dd, J = 8.3, 7.8 Hz), 6.81 (1H, dd, J = 8.3, 1.2 Hz), 6.68-6.57 (3H, m), 4.01-3.89 (2H, m), 3.86 (3H, s), 1.18 (3H, t, J = 7.1 Hz). |
| 621 | ¹H-NMR (CDCl₃) δ: 7.19 (1H, d, J = 1.2 Hz), 7.06 (1H, dd, J = 8.6, 2.8 Hz), 7.04-7.01 (1H, m), 6.80 (1H, td, J = 8.3, 2.5 Hz), 6.40 (1H, dt, J = 10.7, 1.8 Hz), 6.36 (1H, dt, J = 10.5, 1.9 Hz), 3.76 (3H, s), 3.39 (3H, s), 2.25 (3H, d, J = 1.2 Hz). |
| 622 | ¹H-NMR (CDCl₃) δ: 7.46 (1H, d, J = 2.0 Hz), 7.16 (1H, dd, J = 8.3, 2.0 Hz), 6.87 (1H, dd, J = 8.3, 2.0 Hz), 6.63-6.52 (2H, m), 3.51-3.44 (1H, m), 3.38-3.31 (1H, m), 2.75-2.62 (4H, m), 0.98 (3H, t, J = 7.1 Hz). |
| 623 | ¹H-NMR (CDCl₃) δ: 7.28 (1H, d, J = 9.5 Hz), 6.72 (1H, d, J = 9.5 Hz), 6.57 (1H, dd, J = 10.4, 3.1 Hz), 6.46-6.42 (2H, m), 6.38 (1H, dt, J = 10.4, 2.0 Hz), 3.92-3.87 (2H, m), 3.78 (3H, s), 3.68 (3H, s), 1.16 (3H, t, J = 7.0 Hz). |
| 624 | ¹H-NMR (CDCl₃) δ: 7.50 (1H, d, J = 2.0 Hz), 7.26 (1H, d, J = 9.5 Hz), 7.21 (1H, dd, J = 8.3, 2.0 Hz), 6.92 (1H, dd, J = 8.3, 2.0 Hz), 6.74 (1H, d, J = 9.5 Hz), 6.70-6.60 (2H, m), 3.90-3.87 (2H, m), 1.15 (3H, t, J = 7.1 Hz). |

TABLE 5-continued

| Compound | ¹H-NMR |
|---|---|
| 625 | ¹H-NMR (CDCl₃) δ: 7.51 (1H, d, J = 1.8 Hz), 7.50 (1H, s), 7.23 (1H, dd, J = 8.3, 1.8 Hz), 6.93 (1H, dd, J = 8.3, 1.8 Hz), 6.70-6.62 (2H, m), 3.94 (2H, q, J = 7.0 Hz), 1.18 (3H, t, J = 7.0 Hz). |
| 626 | ¹H-NMR (CDCl₃) δ: 7.30 (1H, d, J = 9.5 Hz), 7.13 (1H, dd, J = 1.7, 0.9 Hz), 6.91 (1H, dd, J = 7.8, 1.7 Hz), 6.86 (1H, ddd, J = 7.8, 1.7, 0.9 Hz), 6.72 (1H, d, J = 9.5 Hz), 6.65 (1H, tt, J = 8.7, 2.1 Hz), 6.59 (1H, tt, J = 8.7, 2.1 Hz), 3.94-3.84 (2H, m), 2.26 (3H, s), 1.15 (3H, t, J = 7.0 Hz). |
| 627 | ¹H-NMR (CDCl₃) δ: 7.51 (1H, s), 6.59 (1H, dd, J = 10.4, 2.8 Hz), 6.47-6.45 (1H, m), 6.43-6.39 (2H, m), 3.96 (2H, q, J = 7.1 Hz), 3.78 (3H, s), 3.68 (3H, s), 1.18 (3H, t, J = 7.1 Hz). |
| 628 | ¹H-NMR (CDCl₃) δ: 7.53 (1H, s), 7.14 (1H, m), 6.92 (1H, dd, J = 8.0, 1.8 Hz), 6.88-6.86 (1H, m), 6.66 (1H, tt, J = 8.7, 2.1 Hz), 6.61 (1H, tt, J = 8.7, 2.1 Hz), 3.96-3.93 (2H, m), 2.27 (3H, s), 1.18 (3H, t, J = 7.0 Hz). |
| 629 | ¹H-NMR (CDCl₃) δ: 7.37-7.30 (2H, m), 7.04-6.98 (1H, m), 6.87 (2H, dd, J = 8.4, 7.2 Hz), 6.73 (1H, d, J = 9.3 Hz), 6.71-6.65 (2H, m), 3.92 (2H, q, J = 7.1 Hz), 1.14 (3H, t, J = 7.1 Hz). |
| 630 | ¹H-NMR (CDCl₃) δ: 7.55 (1H, s), 7.38-7.31 (1H, m), 7.04-6.98 (1H, m), 6.88 (2H, dd, J = 8.5, 7.3 Hz), 6.73-6.66 (2H, m), 3.97 (2H, q, J = 7.1 Hz), 1.17 (3H, t, J = 7.1 Hz). |
| 631 | ¹H-NMR (CDCl₃) δ: 7.38-7.31 (2H, m), 7.03-6.97 (1H, m), 6.87 (2H, dd, J = 8.3, 7.3 Hz), 6.75 (1H, d, J = 9.3 Hz), 6.73-6.65 (2H, m), 3.39 (3H, s). |
| 632 | ¹H-NMR (CDCl₃) δ: 7.20-7.19 (1H, m), 7.02 (1H, dd, J = 8.3, 7.6 Hz), 6.78 (1H, dd, J = 8.3, 1.5 Hz), 6.67 (1H, ddd, J = 7.6, 1.7, 1.5 Hz), 6.63 (1H, tt, J = 8.9, 2.1 Hz), 6.57 (1H, tt, J = 8.7, 2.1 Hz), 3.96-3.85 (5H, m), 2.24 (3H, d, J = 1.2 Hz), 1.16 (3H, t, J = 7.2 Hz). |
| 633 | ¹H-NMR (CDCl₃) δ: 7.30 (1H, d, J = 9.3 Hz), 7.02 (1H, dd, J = 8.4, 7.6 Hz), 6.78 (1H, dd, J = 8.4, 1.5 Hz), 6.72 (1H, d, J = 9.3 Hz), 6.68 (1H, dt, J = 7.6, 1.5 Hz), 6.42-6.39 (1H, m), 6.34-6.31 (1H, m), 4.00-3.93 (1H, m), 3.90-3.82 (4H, m), 3.75 (3H, s), 1.16 (3H, t, J = 7.0 Hz). |
| 634 | ¹H-NMR (CDCl₃) δ: 7.30 (1H, d, J = 9.5 Hz), 7.01 (1H, dd, J = 8.3, 7.6 Hz), 6.78 (1H, dd, J = 8.3, 1.5 Hz), 6.71 (1H, d, J = 9.5 Hz), 6.68 (1H, dt, J = 7.6, 1.5 Hz), 6.40-6.37 (1H, m), 6.32-6.29 (1H, m), 4.00-3.92 (3H, m), 3.90-3.82 (4H, m), 1.38 (3H, t, J = 7.0 Hz), 1.15 (3H, t, J = 7.2 Hz). |
| 635 | ¹H-NMR (CDCl₃) δ: 7.28 (1H, dd, J = 9.5, 0.6 Hz), 6.91-6.88 (1H, m), 6.83-6.81 (1H, m), 6.75 (1H, d, J = 9.5 Hz), 6.71-6.67 (2H, m), 3.90 (2H, q, J = 7.1 Hz), 1.14 (3H, t, J = 7.1 Hz). |
| 636 | ¹H-NMR (CDCl₃) δ: 7.53 (1H, d, J = 0.5 Hz), 6.93-6.89 (1H, m), 6.85-6.82 (1H, m), 6.73-6.67 (2H, m), 3.95 (2H, q, J = 7.1 Hz), 1.17 (3H, t, J = 7.1 Hz). |
| 637 | ¹H-NMR (CDCl₃) δ: 7.52 (1H, d, J = 0.7 Hz), 6.93-6.80 (2H, m), 6.45-6.42 (2H, m), 3.97 (2H, q, J = 7.1 Hz), 3.80 (3H, s), 1.16 (3H, t, J = 7.1 Hz). |
| 638 | ¹H-NMR (CDCl₃) δ: 7.28-7.27 (1H, m), 6.91-6.79 (2H, m), 6.72 (1H, d, J = 9.5 Hz), 6.44-6.42 (2H, m), 3.92 (2H, q, J = 7.1 Hz), 3.80 (3H, s), 1.14 (3H, t, J = 7.1 Hz). |
| 639 | ¹H-NMR (CDCl₃) δ: 7.31 (1H, dd, J = 9.5, 0.6 Hz), 6.93-6.79 (2H, m), 6.76 (1H, d, J = 9.2 Hz), 6.72-6.68 (2H, m), 3.39 (3H, s). |
| 640 | ¹H-NMR (CDCl₃) δ: 7.53 (1H, s), 7.03 (1H, dd, J = 8.3, 7.6 Hz), 6.79 (1H, dd, J = 8.3, 1.5 Hz), 6.70-6.67 (1H, m), 6.42-6.39 (1H, m), 6.35-6.32 (1H, m), 4.03-3.89 (2H, m), 3.86 (3H, s), 3.75 (3H, s), 1.18 (3H, t, J = 7.0 Hz). |
| 641 | ¹H-NMR (CDCl₃) δ: 7.53 (1H, s), 7.03 (1H, dd, J = 8.3, 7.8 Hz), 6.79 (1H, dd, J = 8.3, 1.2 Hz), 6.69-6.67 (1H, m), 6.40-6.37 (1H, m), 6.33-6.30 (1H, m), 4.03-3.90 (4H, m), 3.86 (3H, s), 1.38 (3H, t, J = 7.0 Hz), 1.18 (3H, t, J = 7.2 Hz). |
| 642 | ¹H-NMR (CDCl₃) δ: 7.73 (1H, s), 7.03 (1H, dd, J = 8.3, 7.7 Hz), 6.79 (1H, dd, J = 8.3, 1.5 Hz), 6.69-6.67 (1H, m), 6.42-6.39 (1H, m), 6.35-6.32 (1H, m), 4.02-3.90 (2H, m), 3.86 (3H, s), 3.75 (3H, s), 1.18 (3H, t, J = 7.0 Hz). |
| 643 | ¹H-NMR (CDCl₃) δ: 7.73 (1H, s), 7.03 (1H, dd, J = 8.3, 7.6 Hz), 6.79 (1H, dd, J = 8.3, 1.5 Hz), 6.68 (1H, dt, J = 7.6, 1.5 Hz), 6.40-6.37 (1H, m), 6.33-6.30 (1H, m), 4.03-3.89 (4H, m), 3.86 (3H, s), 1.38 (3H, t, J = 7.0 Hz), 1.17 (3H, t, J = 7.0 Hz). |
| 644 | ¹H-NMR (CDCl₃) δ: 7.19 (1H, m), 7.01 (1H, dd, J = 8.3, 7.7 Hz), 6.77 (1H, dd, J = 8.3, 1.5 Hz), 6.69 (1H, ddd, J = 7.7, 1.6, 1.5 Hz), 6.40-6.37 (1H, m), 6.34-6.31 (1H, m), 3.99-3.84 (5H, m), 3.75 (3H, s), 2.24 (3H, d, J = 0.9 Hz), 1.15 (3H, t, J = 7.2 Hz). |
| 645 | ¹H-NMR (CDCl₃) δ: 7.19 (1H, d, J = 1.2 Hz), 7.01 (1H, dd, J = 8.3, 7.9 Hz), 6.77 (1H, dd, J = 8.3, 1.2 Hz), 6.69 (1H, ddd, J = 7.9, 1.4, 1.2 Hz), 6.39-6.36 (1H, m), 6.31-6.29 (1H, m), 3.98-3.86 (7H, m), 2.23 (3H, d, J = 0.9 Hz), 1.38 (3H, t, J = 7.0 Hz), 1.15 (3H, t, J = 7.0 Hz). |
| 646 | ¹H-NMR (CDCl₃) δ: 7.57 (1H, d, J = 0.7 Hz), 7.39-7.32 (1H, m), 7.04-6.98 (1H, m), 6.88 (2H, dd, J = 8.4, 7.4 Hz), 6.74-6.66 (2H, m), 3.46 (3H, s). |
| 647 | ¹H-NMR (CDCl₃) δ: 7.40-7.34 (2H, m), 7.04-6.99 (1H, m), 6.88 (2H, dd, J = 8.6, 7.3 Hz), 6.76 (1H, d, J = 9.2 Hz), 6.73-6.66 (2H, m), 6.15 (1H, tt, J = 56.6, 4.5 Hz), 4.21-4.15 (2H, m). |
| 648 | ¹H-NMR (CDCl₃) δ: 7.62 (1H, d, J = 0.7 Hz), 7.42-7.35 (1H, m), 7.06-7.00 (1H, m), 6.89 (2H, dd, J = 8.4, 7.4 Hz), 6.76-6.66 (2H, m), 6.17 (1H, tt, J = 56.5, 4.5 Hz), 4.26-4.19 (2H, m). |
| 649 | ¹H-NMR (CDCl₃) δ: 7.85 (1H, d, J = 9.2 Hz), 7.05 (1H, d, J = 9.2 Hz), 6.86-6.82 (1H, m), 6.76-6.72 (1H, m), 6.71-6.64 (2H, m), 4.59-4.91 (2H, m), 1.27 (3H, t, J = 7.0 Hz). |
| 650 | ¹H-NMR (CDCl₃) δ: 7.47 (1H, dd, J = 8.2, 1.3 Hz), 7.10-6.99 (3H, m), 6.60-6.49 (2H, m), 3.50-3.43 (1H, m), 3.40-3.33 (1H, m), 2.95-2.79 (2H, m), 2.71-2.68 (1H, m), 2.61-2.53 (1H, m), 0.99 (3H, t, J = 7.1 Hz). |
| 651 | ¹H-NMR (CDCl₃) δ: 7.52 (1H, ddd, J = 7.5, 1.5, 0.7 Hz), 7.32 (1H, d, J = 9.3 Hz), 7.11-7.06 (3H, m), 6.74 (1H, d, J = 9.3 Hz), 6.66 (1H, tt, J = 8.8, 2.1 Hz), 6.58 (1H, tt, J = 8.8, 2.1 Hz), 3.93-3.86 (2H, m), 1.17 (3H, t, J = 7.1 Hz). |
| 652 | ¹H-NMR (CDCl₃) δ: 7.55 (1H, s), 7.54-7.52 (1H, m), 7.15-7.04 (3H, m), 6.66 (1H, tt, J = 8.8, 2.1 Hz), 6.60 (1H, tt, J = 8.8, 2.1 Hz), 3.96-3.93 (2H, m), 1.19 (3H, t, J = 7.1 Hz). |
| 653 | ¹H-NMR (CDCl₃) δ: 7.55 (1H, s), 6.93-6.91 (1H, m), 6.85-6.82 (1H, m), 6.73-6.69 (2H, m), 3.46 (3H, s). |
| 654 | ¹H-NMR (CDCl₃) δ: 7.30 (1H, dd, J = 9.5, 0.9 Hz), 6.90-6.87 (1H, m), 6.83-6.80 (1H, m), 6.73 (1H, d, J = 9.5 Hz), 6.45-6.42 (2H, m), 3.80 (3H, s), 3.39 (3H, s). |
| 655 | ¹H-NMR (CDCl₃) δ: 7.53 (1H, d, J = 0.7 Hz), 6.93-6.80 (2H, m), 6.45-6.42 (2H, m), 3.80 (3H, s), 3.46 (3H, s). |

TABLE 5-continued

| Compound | ¹H-NMR |
|---|---|
| 656 | ¹H-NMR (CDCl₃) δ: 7.73 (1H, s), 7.07-6.99 (2H, m), 6.88-6.87 (1H, m), 6.42-6.34 (2H, m), 4.01-3.93 (2H, m), 3.76 (3H, s), 1.18 (3H, t, J = 7.0 Hz). |
| 657 | ¹H-NMR (CDCl₃) δ: 7.29 (1H, d, J = 9.3 Hz), 7.06-6.97 (2H, m), 6.88-6.85 (1H, m), 6.72 (1H, d, J = 9.3 Hz), 6.41-6.31 (2H, m), 4.00-3.84 (4H, m), 1.39 (3H, t, J = 7.0 Hz), 1.15 (3H, t, J = 7.1 Hz). |
| 658 | ¹H-NMR (CDCl₃) δ: 7.52 (1H, s), 7.08-6.99 (2H, m), 6.89-6.86 (1H, m), 6.41-6.32 (2H, m), 4.04-3.90 (4H, m), 1.39 (3H, t, J = 7.0 Hz), 1.18 (3H, t, J = 7.1 Hz). |
| 659 | ¹H-NMR (CDCl₃) δ: 7.72 (1H, s), 7.08-6.99 (2H, m), 6.89-6.86 (1H, m), 6.40-6.32 (2H, m), 4.04-3.90 (4H, m), 1.39 (3H, t, J = 7.0 Hz), 1.18 (3H, t, J = 7.1 Hz). |
| 660 | ¹H-NMR (CDCl₃) δ: 7.18 (1H, d, J = 1.2 Hz), 7.05-6.96 (2H, m), 6.88-6.86 (1H, m), 6.39-6.31 (2H, m), 3.99-3.86 (4H, m), 2.24 (3H, d, J = 1.2 Hz), 1.39 (3H, t, J = 7.0 Hz), 1.15 (3H, t, J = 7.0 Hz). |
| 661 | ¹H-NMR (CDCl₃) δ: 7.33 (1H, d, J = 9.4 Hz), 7.04 (1H, dd, J = 8.4, 8.0 Hz), 6.80 (1H, dd, J = 8.4, 1.4 Hz), 6.75 (1H, d, J = 9.4 Hz), 6.68-6.63 (2H, m), 6.59 (1H, tt, J = 8.9, 2.1 Hz), 3.87 (3H, s), 3.38 (3H, s). |
| 662 | ¹H-NMR (CDCl₃) δ: 7.76 (1H, s), 7.07-7.03 (1H, m), 6.82 (1H, dd, J = 8.3, 1.5 Hz), 6.68-6.57 (3H, m), 3.87 (3H, s), 3.45 (3H, s). |
| 663 | ¹H-NMR (CDCl₃) δ: 7.32 (1H, d, J = 9.4 Hz), 7.04-7.00 (1H, m), 6.79 (1H, dd, J = 8.3, 1.2 Hz), 6.72 (1H, d, J = 9.4 Hz), 6.65 (1H, dt, J = 7.7, 1.5 Hz), 6.43-6.39 (1H, m), 6.35-6.31 (1H, m), 3.87 (3H, s), 3.75 (3H, s), 3.38 (3H, s). |
| 664 | ¹H-NMR (CDCl₃) δ: 7.32 (1H, d, J = 9.5 Hz), 7.02 (1H, dd, J = 8.3, 7.8 Hz), 6.78 (1H, dd, J = 8.3, 1.4 Hz), 6.72 (1H, d, J = 9.5 Hz), 6.65 (1H, dt, J = 7.8, 1.4 Hz), 6.41-6.37 (1H, m), 6.33-6.29 (1H, m), 3.94 (2H, q, J = 7.0 Hz), 3.86 (3H, s), 3.38 (3H, s), 1.38 (3H, t, J = 7.0 Hz). |
| 665 | ¹H-NMR (CDCl₃) δ: 7.25 (1H, d, J = 9.5 Hz), 6.79 (1H, td, J = 8.5, 3.1 Hz), 6.73 (1H, d, J = 9.5 Hz), 6.68-6.65 (1H, m), 6.47-6.44 (1H, m), 6.40-6.37 (1H, m), 3.95-3.87 (2H, m), 3.79 (3H, s), 1.15 (3H, t, J = 7.2 Hz). |
| 666 | ¹H-NMR (CDCl₃) δ: 7.49 (1H, s), 6.81 (1H, td, J = 8.5, 3.0 Hz), 6.69-6.66 (1H, m), 6.47-6.44 (1H, m), 6.41-6.38 (1H, m), 3.96 (2H, q, J = 7.0 Hz), 3.79 (3H, s), 1.18 (3H, t, J = 7.0 Hz). |
| 667 | ¹H-NMR (CDCl₃) δ: 7.53-7.50 (1H, m), 7.31 (1H, d, J = 9.3 Hz), 7.10-7.03 (3H, m), 6.72 (1H, d, J = 9.3 Hz), 6.41 (1H, dt, J = 10.7, 2.0 Hz), 6.33 (1H, dt, J = 10.7, 2.0 Hz), 3.95-3.88 (2H, m), 3.75 (3H, s), 1.16 (3H, t, J = 7.1 Hz). |
| 668 | ¹H-NMR (CDCl₃) δ: 7.54 (1H, s), 7.53-7.51 (1H, m), 7.13-7.04 (3H, m), 6.41 (1H, dt, J = 10.7, 2.0 Hz), 6.34 (1H, dt, J = 10.7, 2.0 Hz), 3.98-3.94 (2H, m), 3.75 (3H, s), 1.18 (3H, t, J = 7.1 Hz). |
| 669 | ¹H-NMR (CDCl₃) δ: 7.75 (1H, s), 7.04 (1H, dd, J = 8.4, 7.8 Hz), 6.80 (1H, dd, J = 8.4, 1.6 Hz), 6.66 (1H, dt, J = 7.8, 1.6 Hz), 6.42-6.39 (1H, m), 6.36-6.33 (1H, m), 3.86 (3H, s), 3.75 (3H, s), 3.45 (3H, s). |
| 670 | ¹H-NMR (CDCl₃) δ: 7.75 (1H, s), 7.04 (1H, dd, J = 8.3, 7.6 Hz), 6.80 (1H, dd, J = 8.3, 1.4 Hz), 6.66 (1H, dt, J = 7.6, 1.4 Hz), 6.40-6.37 (1H, m), 6.33-6.30 (1H, m), 3.94 (2H, q, J = 7.0 Hz), 3.86 (3H, s), 3.45 (3H, s), 1.38 (3H, t, J = 7.0 Hz). |
| 671 | ¹H-NMR (CDCl₃) δ: 7.22 (1H, q, J = 1.2 Hz), 7.03 (1H, dd, J = 8.3, 7.6 Hz), 6.79 (1H, dd, J = 8.3, 1.5 Hz), 6.66-6.56 (3H, m), 3.86 (3H, s), 3.39 (3H, s), 2.25 (3H, d, J = 1.2 Hz). |
| 672 | ¹H-NMR (CDCl₃) δ: 7.21-7.21 (1H, m), 7.02 (1H, dd, J = 8.3, 7.7 Hz), 6.78 (1H, dd, J = 8.3, 1.5 Hz), 6.66 (1H, dt, J = 7.7, 1.5 Hz), 6.41-6.38 (1H, m), 6.34-6.31 (1H, m), 3.86 (3H, s), 3.75 (3H, s), 3.39 (3H, s), 2.24 (3H, d, J = 1.2 Hz). |
| 673 | ¹H-NMR (CDCl₃) δ: 7.21 (1H, m), 7.02 (1H, dd, J = 8.3, 7.7 Hz), 6.77 (1H, dd, J = 8.3, 1.2 Hz), 6.66 (1H, ddd, J = 7.7, 1.4, 1.2 Hz), 6.39-6.36 (1H, m), 6.32-6.29 (1H, m), 3.94 (2H, q, J = 7.0 Hz), 3.86 (3H, s), 3.39 (3H, s), 2.24 (3H, d, J = 0.9 Hz), 1.38 (3H, t, J = 7.0 Hz). |
| 674 | ¹H-NMR (CDCl₃) δ: 7.23 (1H, d, J = 9.2 Hz), 6.96-6.92 (1H, m), 6.89-6.85 (1H, m), 6.75-6.73 (2H, m), 6.66 (1H, tt, J = 8.7, 2.1 Hz), 6.57 (1H, tt, J = 8.9, 2.1 Hz), 3.98-3.91 (1H, m), 3.86-3.79 (1H, m), 2.06 (3H, d, J = 1.8 Hz), 1.16 (3H, t, J = 7.2 Hz). |
| 675 | ¹H-NMR (CDCl₃) δ: 7.47 (1H, s), 7.00-6.86 (2H, m), 6.76-6.73 (1H, m), 6.66 (1H, tt, J = 8.7, 2.1 Hz), 6.59 (1H, tt, J = 8.8, 2.1 Hz), 4.02-3.85 (2H, m), 2.07 (3H, d, J = 1.7 Hz), 1.19 (3H, t, J = 7.1 Hz). |
| 676 | ¹H-NMR (CDCl₃) δ: 7.28 (1H, d, J = 9.3 Hz), 6.80 (1H, td, J = 8.5, 2.9 Hz), 6.74 (1H, d, J = 9.3 Hz), 6.66-6.63 (1H, m), 6.47-6.43 (1H, m), 6.41-6.37 (1H, m), 3.79 (3H, s), 3.39 (3H, s). |
| 677 | ¹H-NMR (CDCl₃) δ: 7.51 (1H, s), 6.82 (1H, td, J = 8.4, 3.2 Hz), 6.67-6.65 (1H, m), 6.46-6.44 (1H, m), 6.41-6.39 (1H, m), 3.79 (3H, s), 3.45 (3H, s). |
| 678 | ¹H-NMR (CDCl₃) δ: 7.32 (1H, d, J = 9.5 Hz), 6.83-6.78 (1H, m), 6.75 (1H, d, J = 9.5 Hz), 6.70-6.66 (1H, m), 6.46-6.43 (1H, m), 6.41-6.37 (1H, m), 6.16 (1H, tt, J = 56.6, 4.5 Hz), 4.22-4.11 (2H, m), 3.79 (3H, s). |
| 679 | ¹H-NMR (CDCl₃) δ: 7.56 (1H, s), 6.85-6.81 (1H, m), 6.71-6.68 (1H, m), 6.46-6.43 (1H, dt, J = 10.8, 1.8 Hz), 6.42-6.39 (1H, m), 6.18 (1H, tt, J = 56.6, 4.5 Hz), 4.28-4.17 (2H, m), 3.80 (3H, s). |
| 680 | ¹H-NMR (CDCl₃) δ: 7.30-7.28 (2H, m), 7.12 (1H, dt, J = 8.1, 1.7 Hz), 7.07 (1H, dt, J = 8.1, 1.6 Hz), 6.92-6.90 (1H, m), 6.79 (1H, m), 6.76 (1H, d, J = 9.5 Hz), 3.37 (3H, s). |
| 681 | ¹H-NMR (CDCl₃) δ: 7.54 (1H, s), 7.29 (1H, dd, J = 8.9, 5.2 Hz), 7.12 (1H, dt, J = 8.2, 1.6 Hz), 7.08 (1H, dt, J = 8.2, 1.6 Hz), 6.94-6.92 (1H, m), 6.81 (1H, m), 3.44 (3H, s). |
| 682 | ¹H-NMR (CDCl₃) δ: 7.68 (1H, s), 6.98-6.93 (1H, m), 6.90-6.86 (1H, m), 6.75-6.73 (1H, m), 6.66 (1H, tt, J = 8.7, 2.1 Hz), 6.59 (1H, tt, J = 8.9, 2.1 Hz), 4.01-3.87 (2H, m), 2.07 (3H, d, J = 1.8 Hz), 1.19 (3H, t, J = 7.0 Hz). |
| 683 | ¹H-NMR (CDCl₃) δ: 7.76 (1H, s), 7.32 (1H, dd, J = 8.0, 1.2 Hz), 7.17 (1H, ddd, J = 8.0, 7.3, 1.8 Hz), 7.08 (1H, td, J = 7.3, 1.2 Hz), 7.05 (1H, dt, J = 7.3, 1.8 Hz), 6.65 (1H, tt, J = 8.9, 2.1 Hz), 6.60 (1H, tt, J = 8.9, 2.1 Hz), 3.95 (2H, q, J = 7.0 Hz), 1.19 (3H, t, J = 7.0 Hz). |
| 684 | ¹H-NMR (CDCl₃) δ: 7.55 (1H, s), 7.33-7.31 (1H, m), 7.16-7.14 (1H, m), 7.07-7.06 (2H, m), 6.38 (1H, dt, J = 10.8, 1.8 Hz), 6.32 (1H, dt, J = 10.8, 1.8 Hz), 3.98-3.94 (4H, m), 1.38 (3H, t, J = 7.0 Hz), 1.18 (3H, t, J = 7.0 Hz). |

TABLE 5-continued

| Compound | ¹H-NMR |
|---|---|
| 685 | ¹H-NMR (CDCl₃) δ: 7.32-7.30 (2H, m), 7.14-7.12 (1H, m), 7.06-7.05 (2H, m), 6.71 (1H, d, J = 9.5 Hz), 6.39 (1H, dt, J = 10.7, 2.0 Hz), 6.31 (1H, dt, J = 10.7, 2.0 Hz), 3.94-3.90 (4H, m), 1.38 (3H, t, J = 7.1 Hz), 1.16 (3H, t, J = 7.1 Hz). |
| 686 | ¹H-NMR (CDCl₃) δ: 7.75 (1H, s), 7.32 (1H, dd, J = 7.8, 1.2 Hz), 7.16-7.14 (1H, m), 7.07-7.06 (2H, m), 6.40 (1H, dt, J = 10.7, 1.8 Hz), 6.34 (1H, dt, J = 10.7, 1.8 Hz), 4.00-3.94 (2H, m), 3.75 (3H, s), 1.18 (3H, t, J = 7.2 Hz). |
| 687 | ¹H-NMR (CDCl₃) δ: 7.32-7.30 (1H, m), 7.21 (1H, q, J = 1.1 Hz), 7.15-7.13 (1H, m), 7.08-7.06 (2H, m), 6.65-6.55 (2H, m), 3.92-3.89 (2H, m), 2.25 (3H, d, J = 1.1 Hz), 1.16 (3H, t, J = 7.1 Hz). |
| 688 | ¹H-NMR (CDCl₃) δ: 7.71 (1H, s), 6.83 (1H, td, J = 8.4, 3.1 Hz), 6.74-6.69 (1H, m), 6.69-6.65 (2H, m), 3.98-3.90 (2H, m), 1.18 (3H, t, J = 7.2 Hz). |
| 689 | ¹H-NMR (CDCl₃) δ: 7.15 (1H, d, J = 1.2 Hz), 6.80 (1H, td, J = 8.5, 2.8 Hz), 6.72-6.61 (3H, m), 3.94-3.85 (2H, m), 2.25 (3H, d, J = 1.2 Hz), 1.16 (3H, t, J = 7.1 Hz). |
| 690 | ¹H-NMR (CDCl₃) δ: 7.31 (1H, d, J = 9.2 Hz), 7.28-7.26 (1H, m), 6.88-6.86 (1H, m), 6.79 (1H, m), 6.74-6.72 (2H, m), 6.65 (1H, d, J = 9.2 Hz), 3.38 (3H, s), 2.32 (3H, s). |
| 691 | ¹H-NMR (CDCl₃) δ: 7.54 (1H, s), 7.29-7.26 (1H, m), 6.90-6.88 (1H, m), 6.80 (1H, m), 6.73 (1H, d, J = 9.5 Hz), 6.66 (1H, d, J = 9.5 Hz), 3.44 (3H, s), 2.33 (3H, s). |
| 692 | ¹H-NMR (CDCl₃) δ: 7.30-7.27 (2H, m), 7.13 (1H, dt, J = 8.1, 1.7 Hz), 7.06 (1H, dt, J = 8.0, 1.6 Hz), 6.91-6.89 (1H, m), 6.80 (1H, m), 6.74 (1H, d, J = 9.5 Hz), 3.92-3.83 (2H, m), 1.16 (3H, t, J = 7.1 Hz). |
| 693 | ¹H-NMR (CDCl₃) δ: 7.84 (1H, d, J = 8.9 Hz), 7.05 (1H, d, J = 8.9 Hz), 6.82 (1H, td, J = 8.4, 2.8 Hz), 6.67-6.64 (1H, m), 6.48-6.46 (1H, m), 6.42-6.39 (1H, m), 4.60-4.54 (2H, m), 3.80 (3H, s), 1.27 (3H, t, J = 7.0 Hz). |
| 694 | ¹H-NMR (CDCl₃) δ: 7.17 (1H, d, J = 1.2 Hz), 6.81 (1H, td, J = 8.5, 3.0 Hz), 6.71-6.63 (3H, m), 3.39 (3H, s), 2.26 (3H, d, J = 1.2 Hz). |
| 695 | ¹H-NMR (CDCl₃) δ: 7.69 (1H, s), 6.81 (1H, td, J = 8.4, 3.2 Hz), 6.69-6.67 (1H, m), 6.47-6.44 (1H, m), 6.39-6.37 (1H, m), 3.96 (2H, q, J = 7.0 Hz), 3.79 (3H, s), 1.18 (3H, t, J = 7.0 Hz). |
| 696 | ¹H-NMR (CDCl₃) δ: 7.84 (1H, d, J = 8.9 Hz), 7.11 (1H, d, J = 8.9 Hz), 6.71-6.62 (2H, m), 6.38 (1H, d, J = 2.8 Hz), 6.19-6.18 (1H, m), 4.60-4.51 (2H, m), 3.83 (3H, s), 3.68 (3H, s), 1.28 (3H, t, J = 7.1 Hz). |
| 697 | ¹H-NMR (CDCl₃) δ: 7.22 (1H, d, J = 9.4 Hz), 6.96-6.91 (1H, m), 6.87-6.83 (1H, m), 6.77-6.75 (1H, m), 6.71 (1H, d, J = 9.4 Hz), 6.42-6.39 (1H, m), 6.33-6.30 (1H, m), 3.99-3.83 (2H, m), 3.75 (3H, s), 2.06 (3H, d, J = 2.1 Hz), 1.16 (3H, t, J = 7.2 Hz). |
| 698 | ¹H-NMR (CDCl₃) δ: 7.21 (1H, d, J = 9.5 Hz), 6.96-6.91 (1H, m), 6.87-6.83 (1H, m), 6.77-6.75 (1H, m), 6.71 (1H, d, J = 9.5 Hz), 6.40-6.37 (1H, m), 6.31-6.28 (1H, m), 3.99-3.83 (4H, m), 2.05 (3H, d, J = 2.1 Hz), 1.38 (3H, t, J = 7.0 Hz), 1.16 (3H, t, J = 7.2 Hz). |
| 699 | ¹H-NMR (CDCl₃) δ: 7.46 (1H, s), 6.98-6.92 (1H, m), 6.89-6.84 (1H, m), 6.78-6.75 (1H, m), 6.40 (1H, m), 6.33 (1H, m), 4.03-3.89 (2H, m), 3.75 (3H, s), 2.06 (3H, d, J = 2.0 Hz), 1.18 (3H, t, J = 7.1 Hz). |
| 700 | ¹H-NMR (CDCl₃) δ: 7.45 (1H, s), 6.98-6.92 (1H, m), 6.89-6.84 (1H, m), 6.78-6.75 (1H, m), 6.40-6.36 (1H, m), 6.32-6.29 (1H, m), 4.03-3.91 (4H, m), 2.06 (3H, d, J = 2.0 Hz), 1.38 (3H, t, J = 7.0 Hz), 1.18 (3H, t, J = 7.1 Hz). |
| 701 | ¹H-NMR (CDCl₃) δ: 7.32-7.29 (1H, m), 7.21 (1H, q, J = 1.1 Hz), 7.13-7.11 (1H, m), 7.07-7.04 (2H, m), 6.39 (1H, ddd, J = 10.5, 2.4, 1.4 Hz), 6.32 (1H, ddd, J = 10.5, 2.4, 1.4 Hz), 3.96-3.90 (2H, m), 3.74 (3H, s), 2.24 (3H, d, J = 1.1 Hz), 1.15 (3H, t, J = 7.1 Hz). |
| 702 | ¹H-NMR (CDCl₃) δ: 7.31-7.29 (1H, m), 7.20 (1H, q, J = 1.0 Hz), 7.13-7.11 (1H, m), 7.07-7.04 (2H, m), 6.37 (1H, dt, J = 10.6, 2.0 Hz), 6.30 (1H, dt, J = 10.6, 2.0 Hz), 3.94-3.92 (4H, m), 2.24 (3H, d, J = 1.0 Hz), 1.38 (3H, t, J = 7.1 Hz), 1.15 (3H, t, J = 7.1 Hz). |
| 703 | ¹H-NMR (CDCl₃) δ: 7.75 (1H, s), 7.33-7.30 (1H, m), 7.16-7.14 (1H, m), 7.07-7.06 (2H, m), 6.38 (1H, dt, J = 10.6, 1.9 Hz), 6.31 (1H, dt, J = 10.6, 1.9 Hz), 3.97-3.94 (4H, m), 1.38 (3H, t, J = 7.0 Hz), 1.18 (3H, t, J = 7.1 Hz). |
| 704 | ¹H-NMR (CDCl₃) δ: 7.25-7.19 (2H, m), 6.78 (2H, t, J = 8.5 Hz), 6.69 (1H, dd, J = 8.9, 3.1 Hz), 6.62 (1H, d, J = 3.2 Hz), 3.64 (3H, s), 2.93-2.65 (4H, m). |
| 705 | ¹H-NMR (CDCl₃) δ: 7.29 (1H, dd, J = 8.0, 1.2 Hz), 7.10 (1H, ddd, J = 8.0, 7.3, 1.7 Hz), 7.03 (1H, td, J = 7.3, 1.2 Hz), 6.98 (1H, dt, J = 7.3, 1.7 Hz), 6.59 (1H, tt, J = 8.9, 2.1 Hz), 6.51 (1H, tt, J = 8.9, 2.1 Hz), 2.89 (3H, s), 2.89-2.81 (2H, m), 2.73-2.70 (1H, m), 2.62-2.55 (1H, m). |
| 706 | ¹H-NMR (CDCl₃) δ: 7.52 (1H, s), 7.29 (1H, dd, J = 8.8, 5.1 Hz), 7.13 (1H, dt, J = 8.1, 1.7 Hz), 7.07 (1H, dt, J = 8.0, 1.6 Hz), 6.93-6.91 (1H, m), 6.82 (1H, dq, J = 8.5, 1.5 Hz), 4.01-3.85 (2H, m), 1.18 (3H, t, J = 7.1 Hz). |
| 707 | ¹H-NMR (CDCl₃) δ: 7.29-7.26 (2H, m), 6.88-6.79 (2H, m), 6.74-6.71 (2H, m), 6.64 (1H, d, J = 9.3 Hz), 3.95-3.85 (2H, m), 2.32 (3H, s), 1.15 (3H, t, J = 7.1 Hz). |
| 708 | ¹H-NMR (CDCl₃) δ: 7.52 (1H, s), 7.29-7.26 (1H, m), 6.88-6.86 (1H, m), 6.82 (1H, dq, J = 8.9, 1.4 Hz), 6.73 (1H, d, J = 9.5 Hz), 6.65 (1H, d, J = 9.2 Hz), 3.95 (2H, q, J = 7.0 Hz), 2.32 (3H, s), 1.17 (3H, t, J = 7.0 Hz). |
| 709 | ¹H-NMR (CDCl₃) δ: 7.73 (1H, s), 7.28-7.26 (1H, m), 6.88-6.86 (1H, m), 6.83-6.80 (1H, m), 6.73 (1H, d, J = 9.5 Hz), 6.65 (1H, d, J = 9.3 Hz), 3.95 (2H, q, J = 7.1 Hz), 2.32 (3H, s), 1.17 (3H, t, J = 7.1 Hz). |
| 710 | ¹H-NMR (CDCl₃) δ: 7.26-7.24 (1H, m), 7.18 (1H, d, J = 1.0 Hz), 6.85-6.81 (2H, m), 6.70 (1H, d, J = 9.3 Hz), 6.63 (1H, d, J = 9.3 Hz), 3.90 (2H, q, J = 7.1 Hz), 2.31 (3H, s), 2.24 (3H, d, J = 1.0 Hz), 1.15 (3H, t, J = 7.1 Hz). |
| 711 | ¹H-NMR (CDCl₃) δ: 7.67 (1H, s), 6.97-6.93 (1H, m), 6.88-6.85 (1H, m), 6.77-6.75 (1H, m), 6.42-6.39 (1H, m), 6.34-6.31 (1H, m), 4.02-3.90 (2H, m), 3.75 (3H, s), 2.07 (3H, d, J = 2.1 Hz), 1.18 (3H, t, J = 7.0 Hz). |
| 712 | ¹H-NMR (CDCl₃) δ: 7.66 (1H, s), 6.95 (1H, td, J = 7.9, 6.0 Hz), 6.88-6.84 (1H, m), 6.77-6.75 (1H, m), 6.39-6.36 (1H, m), 6.32-6.29 (1H, m), 4.01-3.90 (4H, m), 2.06 (3H, d, J = 2.1 Hz), 1.38 (3H, t, J = 7.0 Hz), 1.18 (3H, t, J = 7.0 Hz). |

TABLE 5-continued

| Compound | ¹H-NMR |
|---|---|
| 713 | ¹H-NMR (CDCl₃) δ: 7.11 (1H, m), 6.93 (1H, td, J = 7.9, 5.9 Hz), 6.86-6.81 (1H, m), 6.77-6.75 (1H, m), 6.39-6.35 (1H, m), 6.30-6.27 (1H, m), 3.99-3.84 (4H, m), 2.24 (3H, d, J = 1.2 Hz), 2.05-2.05 (3H, m), 1.38 (3H, t, J = 7.0 Hz), 1.15 (3H, t, J = 7.1 Hz). |
| 714 | ¹H-NMR (CDCl₃) δ: 7.14 (1H, d, J = 1.2 Hz), 6.77 (1H, td, J = 8.5, 2.8 Hz), 6.69-6.65 (1H, m), 6.45-6.42 (1H, m), 6.39-6.35 (1H, m), 3.91 (2H, q, J = 7.1 Hz), 3.78 (3H, s), 2.24 (3H, d, J = 1.2 Hz), 1.15 (3H, t, J = 7.1 Hz). |
| 715 | ¹H-NMR (CDCl₃) δ: 7.85 (1H, d, J = 8.8 Hz), 7.33 (1H, m), 7.19 (1H, m), 7.13 (1H, d, J = 8.8 Hz), 7.09 (1H, m), 7.04-7.01 (1H, m), 6.70-6.59 (2H, m), 4.61-4.54 (2H, m), 1.28 (3H, t, J = 7.1 Hz). |
| 716 | ¹H-NMR (CDCl₃) δ: 7.83 (1H, d, J = 8.9 Hz), 7.11 (1H, d, J = 8.9 Hz), 6.44-6.41 (1H, m), 6.39-6.36 (2H, m), 6.21-6.20 (1H, m), 4.65-4.50 (2H, m), 3.83 (3H, s), 3.78 (3H, s), 3.67 (3H, s), 1.28 (3H, t, J = 7.5 Hz). |
| 717 | ¹H-NMR (CDCl₃) δ: 7.71 (1H, s), 6.82 (1H, td, J = 8.4, 2.9 Hz), 6.68-6.64 (1H, m), 6.46-6.43 (1H, m), 6.42-6.38 (1H, m), 3.79 (3H, s), 3.45 (3H, s). |
| 718 | ¹H-NMR (CDCl₃) δ: 7.84 (1H, d, J = 8.8 Hz), 7.33 (1H, dd, J = 7.9, 1.1 Hz), 7.18-7.14 (1H, m), 7.12 (1H, d, J = 8.8 Hz), 7.10-7.06 (1H, m), 7.0-5-7.02 (1H, m), 6.43-6.39 (1H, m), 6.36-6.33 (1H, m), 4.66-4.55 (2H, m), 3.76 (3H, s), 1.28 (3H, t, J = 7.1 Hz). |
| 719 | ¹H-NMR (CDCl₃) δ: 7.45 (1H, d, J = 9.5 Hz), 7.33 (1H, tt, J = 8.4, 6.4 Hz), 7.27 (1H, d, J = 8.7 Hz), 6.85 (2H, t, J = 8.7 Hz), 6.77 (1H, dd, J = 8.7, 3.1 Hz), 6.61 (1H, d, J = 3.1 Hz), 6.46 (1H, d, J = 9.5 Hz), 3.64 (3H, s). |
| 720 | ¹H-NMR (CDCl₃) δ: 7.78 (1H, s), 7.33 (1H, dd, J = 8.1, 1.2 Hz), 7.18 (1H, td, J = 7.6, 2.0 Hz), 7.10 (1H, td, J = 7.6, 1.2 Hz), 7.03 (1H, dt, J = 7.6, 2.0 Hz), 6.67-6.58 (2H, m), 3.46 (3H, s). |
| 721 | ¹H-NMR (CDCl₃) δ: 7.34 (1H, d, J = 9.3 Hz), 7.20 (1H, d, J = 8.8 Hz), 6.73-6.70 (2H, m), 6.59 (1H, dd, J = 2.9, 1.5 Hz), 6.43 (1H, dt, J = 10.8, 2.0 Hz), 6.37 (1H, dt, J = 10.6, 1.9 Hz), 3.77 (3H, s), 3.66 (3H, s), 3.39 (3H, s). |
| 722 | ¹H-NMR (CDCl₃) δ: 7.57 (1H, s), 7.20 (1H, d, J = 8.6 Hz), 6.71 (1H, dd, J = 8.9, 3.1 Hz), 6.60-6.59 (1H, m), 6.44-6.41 (1H, m), 6.39-6.37 (1H, m), 3.77 (3H, s), 3.67 (3H, s), 3.45 (3H, s). |
| 723 | ¹H-NMR (CDCl₃) δ: 7.77 (1H, s), 7.20 (1H, d, J = 8.8 Hz), 6.71 (1H, dd, J = 8.9, 3.1 Hz), 6.60-6.59 (1H, m), 6.42-6.38 (2H, m), 3.77 (3H, s), 3.67 (3H, s), 3.45 (3H, s). |
| 724 | ¹H-NMR (CDCl₃) δ: 7.23 (1H, d, J = 1.0 Hz), 7.19 (1H, d, J = 8.8 Hz), 6.69 (1H, dd, J = 8.8, 3.2 Hz), 6.60-6.59 (1H, m), 6.41-6.36 (2H, m), 3.76 (3H, s), 3.66 (3H, s), 3.39 (3H, s), 2.25 (3H, d, J = 1.2 Hz). |
| 725 | ¹H-NMR (CDCl₃) δ: 7.77 (1H, s), 7.20 (1H, d, J = 8.9 Hz), 6.73 (1H, dd, J = 8.9, 3.1 Hz), 6.67-6.64 (2H, m), 6.59 (1H, m), 3.69 (3H, s), 3.45 (3H, s). |
| 726 | ¹H-NMR (CDCl₃) δ: 7.23 (1H, d, J = 1.0 Hz), 7.19 (1H, d, J = 8.8 Hz), 6.70 (1H, dd, J = 8.9, 3.1 Hz), 6.68-6.58 (3H, m), 3.68 (3H, s), 3.39 (3H, s), 2.26 (3H, d, J = 1.0 Hz). |
| 727 | ¹H-NMR (CDCl₃) δ: 7.53 (1H, s), 7.09-7.01 (2H, m), 6.88 (1H, dq, J = 7.4, 1.5 Hz), 6.51-6.48 (1H, m), 6.45-6.42 (1H, m), 4.29 (2H, q, J = 7.8 Hz), 3.95 (2H, q, J = 7.1 Hz), 1.18 (3H, t, J = 7.1 Hz). |
| 728 | ¹H-NMR (CDCl₃) δ: 7.85 (1H, d, J = 8.9 Hz), 7.37-7.32 (1H, m), 7.13 (1H, d, J = 8.9 Hz), 6.92 (1H, t, J = 8.4 Hz), 6.86 (1H, t, J = 8.4 Hz), 6.35 (1H, d, J = 2.8 Hz), 6.21-6.20 (1H, m), 4.65-4.60 (1H, m), 4.55-4.48 (1H, m), 3.81 (3H, s), 3.65 (3H, s), 1.28 (3H, t, J = 7.2 Hz). |
| 729 | ¹H-NMR (CDCl₃) δ: 7.85 (1H, d, J = 9.0 Hz), 7.45-7.37 (1H, m), 7.10 (1H, d, J = 9.0 Hz), 6.94 (2H, dd, J = 8.9, 7.0 Hz), 6.83-6.77 (1H, m), 6.58-6.55 (1H, m), 4.61-4.55 (2H, m), 1.25 (3H, t, J = 7.1 Hz). |
| 730 | ¹H-NMR (CDCl₃) δ: 7.34-7.32 (2H, m), 7.16-7.12 (1H, m), 7.08-7.02 (2H, m), 6.73 (1H, d, J = 9.5 Hz), 6.39 (1H, dt, J = 10.9, 1.8 Hz), 6.31 (1H, dt, J = 10.9, 1.8 Hz), 3.94 (2H, q, J = 7.0 Hz), 3.39 (3H, s), 1.38 (3H, t, J = 7.0 Hz). |
| 731 | ¹H-NMR (CDCl₃) δ: 7.31 (1H, dd, J = 8.0, 1.2 Hz), 7.23 (1H, d, J = 1.2 Hz), 7.15 (1H, ddd, J = 8.0, 7.5, 1.8 Hz), 7.08 (1H, td, J = 7.5, 1.2 Hz), 7.03 (1H, dt, J = 7.5, 1.8 Hz), 6.65-6.56 (2H, m), 3.40 (3H, s), 2.26 (3H, d, J = 1.2 Hz). |
| 732 | ¹H-NMR (CDCl₃) δ: 7.77 (1H, s), 7.32 (1H, dd, J = 8.1, 1.2 Hz), 7.17-7.15 (1H, m), 7.08 (1H, td, J = 7.6, 1.2 Hz), 7.04 (1H, dt, J = 7.6, 1.8 Hz), 6.40 (1H, dt, J = 10.6, 2.0 Hz), 6.35 (1H, dt, J = 10.6, 2.0 Hz), 3.75 (3H, s), 3.46 (3H, s). |
| 733 | ¹H-NMR (CDCl₃) δ: 7.31 (1H, dd, J = 8.1, 1.2 Hz), 7.23 (1H, d, J = 1.0 Hz), 7.14-7.12 (1H, m), 7.07-7.04 (2H, m), 6.39 (1H, dt, J = 10.6, 2.0 Hz), 6.33 (1H, dt, J = 10.6, 2.0 Hz), 3.74 (3H, s), 3.40 (3H, s), 2.25 (3H, d, J = 1.0 Hz). |
| 734 | ¹H-NMR (CDCl₃) δ: 7.57 (1H, s), 7.32 (1H, dd, J = 8.1, 1.2 Hz), 7.17-7.15 (1H, m), 7.08 (1H, td, J = 7.6, 1.2 Hz), 7.04 (1H, dt, J = 7.6, 1.7 Hz), 6.38 (1H, dt, J = 10.7, 2.0 Hz), 6.32 (1H, dt, J = 10.7, 2.0 Hz), 3.94 (2H, q, J = 7.0 Hz), 3.46 (3H, s), 1.38 (3H, t, J = 7.0 Hz). |
| 735 | ¹H-NMR (CDCl₃) δ: 7.32-7.27 (2H, m), 6.95 (1H, dd, J = 8.6, 1.5 Hz), 6.88 (1H, t, J = 8.4 Hz), 6.84-6.80 (2H, m), 6.71 (1H, d, J = 9.5 Hz), 6.57 (1H, dd, J = 8.6, 2.8 Hz), 3.92-3.90 (1H, m), 3.89-3.82 (1H, m), 3.73 (3H, s), 1.15 (3H, t, J = 7.0 Hz). |
| 736 | ¹H-NMR (CDCl₃) δ: 7.54 (1H, s), 7.34-7.21 (1H, m), 6.95 (1H, dd, J = 8.5, 1.7 Hz), 6.89 (1H, t, J = 8.4 Hz), 6.85-6.81 (2H, m), 6.57 (1H, dd, J = 8.5, 2.7 Hz), 4.00-3.89 (2H, m), 3.73 (3H, s), 1.17 (3H, t, J = 7.1 Hz). |
| 737 | ¹H-NMR (CDCl₃) δ: 7.75 (1H, s), 7.34-7.28 (1H, m), 6.95 (1H, dd, J = 8.6, 1.8 Hz), 6.84-6.81 (1H, m), 6.83 (2H, dd, J = 9.5, 7.0 Hz), 6.57 (1H, dd, J = 8.6, 2.8 Hz), 3.99-3.90 (2H, m), 3.73 (3H, s), 1.17 (3H, t, J = 7.2 Hz). |
| 738 | ¹H-NMR (CDCl₃) δ: 7.85 (1H, d, J = 9.0 Hz), 7.30 (1H, dd, J = 9.0, 5.1 Hz), 7.09 (1H, d, J = 9.0 Hz), 6.94-6.89 (1H, m), 6.80-6.77 (1H, m), 6.72 (1H, tt, J = 8.7, 2.1 Hz), 6.65 (1H, tt, J = 8.7, 2.1 Hz), 4.61-4.51 (2H, m), 1.27 (3H, t, J = 7.0 Hz). |
| 739 | ¹H-NMR (CDCl₃) δ: 7.84 (1H, d, J = 8.9 Hz), 7.29 (1H, dd, J = 8.9, 5.2 Hz), 7.09 (1H, d, J = 8.9 Hz), 6.91-6.87 (1H, m), 6.81-6.78 (1H, m), 6.47-6.49 (1H, m), 6.39-6.36 (1H, m), 4.61-4.56 (2H, m), 3.78 (3H, s), 1.27 (3H, t, J = 7.0 Hz). |
| 740 | ¹H-NMR (CDCl₃) δ: 7.34-7.28 (2H, m), 6.94-6.86 (2H, m), 6.84-6.80 (2H, m), 6.73 (1H, d, J = 9.3 Hz), 6.58 (1H, dd, J = 8.5, 2.7 Hz), 3.73 (3H, s), 3.38 (3H, s). |

TABLE 5-continued

| Compound | ¹H-NMR |
|---|---|
| 741 | ¹H-NMR (CDCl₃) δ: 7.31-7.20 (2H, m), 6.96 (1H, d, J = 8.5 Hz), 6.88-6.79 (3H, m), 6.57 (1H, d, J = 8.5 Hz), 3.96-3.85 (2H, m), 3.72 (3H, s), 2.25 (3H, s), 1.15 (3H, t, J = 7.0 Hz). |
| 742 | ¹H-NMR (CDCl₃) δ: 7.30 (1H, d, J = 9.2 Hz), 6.94 (1H, dd, J = 8.6, 1.8 Hz), 6.86 (1H, d, J = 2.4 Hz), 6.72 (1H, d, J = 9.2 Hz), 6.67-6.63 (1H, m), 6.62-6.58 (2H, m), 3.93-3.84 (2H, m), 3.75 (3H, s), 1.15 (3H, t, J = 7.0 Hz). |
| 743 | ¹H-NMR (CDCl₃) δ: 7.56 (1H, s), 7.35-7.29 (1H, m), 6.93 (1H, dd, J = 8.6, 1.5 Hz), 6.89 (1H, t, J = 8.4 Hz), 6.85-6.82 (2H, m), 6.59 (1H, dd, J = 8.6, 2.4 Hz), 3.73 (3H, s), 3.44 (3H, s). |
| 744 | ¹H-NMR (CDCl₃) δ: 7.77 (1H, s), 7.35-7.29 (1H, m), 6.93 (1H, dd, J = 8.6, 1.8 Hz), 6.89 (1H, t, J = 8.4 Hz), 6.85-6.82 (2H, m), 6.59 (1H, dd, J = 8.6, 2.8 Hz), 3.73 (3H, s), 3.45 (3H, s). |
| 745 | ¹H-NMR (CDCl₃) δ: 7.75 (1H, s), 7.35-7.29 (1H, m), 7.05-6.97 (2H, m), 6.91-6.82 (3H, m), 4.02-3.90 (2H, m), 1.18 (3H, t, J = 7.0 Hz). |
| 746 | ¹H-NMR (CDCl₃) δ: 7.53 (1H, s), 6.94 (1H, dd, J = 8.5, 2.0 Hz), 6.85 (1H, d, J = 2.4 Hz), 6.69-6.59 (3H, m), 3.94 (2H, q, J = 7.1 Hz), 3.75 (3H, s), 1.18 (3H, t, J = 7.1 Hz). |
| 747 | ¹H-NMR (CDCl₃) δ: 7.74 (1H, s), 6.94 (1H, dd, J = 8.6, 1.8 Hz), 6.85 (1H, d, J = 2.8 Hz), 6.67-6.60 (3H, m), 3.94 (2H, q, J = 7.1 Hz), 3.75 (3H, s), 1.18 (3H, t, J = 7.1 Hz). |
| 748 | ¹H-NMR (CDCl₃) δ: 7.52 (1H, s), 6.96 (1H, dd, J = 8.6, 1.8 Hz), 6.85 (1H, d, J = 2.8 Hz), 6.61 (1H, dd, J = 8.6, 2.8 Hz), 6.42-6.39 (1H, m), 6.37-6.34 (1H, m), 4.00-3.91 (2H, m), 3.77 (3H, s), 3.75 (3H, s), 1.17 (3H, t, J = 7.0 Hz). |
| 749 | ¹H-NMR (CDCl₃) δ: 7.31-7.25 (1H, m), 7.22 (1H, d, J = 1.2 Hz), 6.93 (1H, dd, J = 8.6, 1.5 Hz), 6.88-6.80 (3H, m), 6.58 (1H, dd, J = 8.6, 2.8 Hz), 3.73 (3H, s), 3.39 (3H, s), 2.25 (3H, s). |
| 750 | ¹H-NMR (CDCl₃) δ: 7.19 (1H, m), 6.94 (1H, dd, J = 8.6, 1.8 Hz), 6.85 (1H, d, J = 2.8 Hz), 6.66-6.58 (3H, m), 3.90 (2H, q, J = 7.1 Hz), 3.75 (3H, s), 2.24 (3H, d, J = 1.2 Hz), 1.15 (3H, t, J = 7.1 Hz). |
| 751 | ¹H-NMR (CDCl₃) δ: 7.18 (1H, m), 6.96 (1H, dd, J = 8.6, 1.5 Hz), 6.85 (1H, d, J = 2.8 Hz), 6.60 (1H, dd, J = 8.6, 2.8 Hz), 6.40-6.38 (1H, m), 6.35-6.33 (1H, m), 3.95-3.87 (2H, m), 3.76 (3H, s), 3.75 (3H, s), 2.23 (3H, d, J = 0.9 Hz), 1.15 (3H, t, J = 7.0 Hz). |
| 752 | ¹H-NMR (CDCl₃) δ: 7.32-7.25 (1H, m), 7.20-7.19 (1H, m), 7.02-6.94 (2H, m), 6.88-6.79 (3H, m), 3.99-3.84 (2H, m), 2.26 (3H, d, J = 1.2 Hz), 1.16 (3H, t, J = 7.1 Hz). |
| 753 | ¹H-NMR (CDCl₃) δ: 7.77 (1H, s), 7.37-7.30 (1H, m), 7.06-6.98 (2H, m), 6.91-6.82 (3H, m), 3.46 (3H, s). |
| 754 | ¹H-NMR (CDCl₃) δ: 7.33-7.28 (1H, m), 7.22 (1H, d, J = 0.9 Hz), 7.03-6.96 (2H, m), 6.89-6.80 (3H, m), 3.40 (3H, s), 2.26 (3H, d, J = 0.9 Hz). |
| 755 | ¹H-NMR (CDCl₃) δ: 7.29 (1H, d, J = 9.3 Hz), 6.95 (1H, dd, J = 8.5, 1.5 Hz), 6.85 (1H, d, J = 2.4 Hz), 6.69 (1H, d, J = 9.3 Hz), 6.60 (1H, dd, J = 8.5, 2.7 Hz), 6.43-6.39 (1H, m), 6.36-6.33 (1H, m), 3.97-3.84 (2H, m), 3.76 (3H, s), 3.75 (3H, s), 1.15 (3H, t, J = 7.1 Hz). |
| 756 | ¹H-NMR (CDCl₃) δ: 7.32 (1H, d, J = 9.3 Hz), 6.92 (1H, dd, J = 8.5, 1.7 Hz), 6.86 (1H, d, J = 2.7 Hz), 6.74 (1H, d, J = 9.3 Hz), 6.64-6.62 (1H, m), 3.75 (3H, s), 3.38 (3H, s). |
| 757 | ¹H-NMR (CDCl₃) δ: 7.75 (1H, s), 7.29 (1H, dd, J = 8.9, 4.9 Hz), 6.93-6.91 (1H, m), 6.80 (1H, dq, J = 8.6, 1.5 Hz), 6.72-6.63 (2H, m), 3.45 (3H, s). |
| 758 | ¹H-NMR (CDCl₃) δ: 7.28-7.26 (1H, m), 7.20 (1H, d, J = 1.2 Hz), 6.89-6.88 (1H, m), 6.79 (1H, dq, J = 8.8, 1.5 Hz), 6.69-6.60 (2H, m), 3.39 (3H, s), 2.26 (3H, d, J = 1.2 Hz). |
| 759 | ¹H-NMR (CDCl₃) δ: 7.27-7.26 (1H, m), 7.19 (1H, m), 6.87-6.85 (1H, m), 6.80-6.79 (1H, m), 6.43 (1H, dt, J = 10.6, 1.9 Hz), 6.37 (1H, dt, J = 10.6, 1.9 Hz), 3.77 (3H, s), 3.40 (3H, s), 2.25 (3H, d, J = 0.9 Hz). |
| 760 | ¹H-NMR (CDCl₃) δ: 7.31 (1H, d, J = 9.5 Hz), 7.29-7.26 (1H, m), 6.89-6.87 (1H, m), 6.80-6.78 (1H, m), 6.74 (1H, d, J = 9.5 Hz), 6.46-6.44 (1H, m), 6.38-6.36 (1H, m), 3.78 (3H, s), 3.39 (3H, s). |
| 761 | ¹H-NMR (CDCl₃) δ: 7.54 (1H, s), 7.29 (1H, m), 6.91-6.89 (1H, m), 6.81-6.79 (1H, m), 6.46-6.43 (1H, m), 6.39-6.37 (1H, m), 3.78 (3H, s), 3.45 (3H, s). |
| 762 | ¹H-NMR (CDCl₃) δ: 7.39 (1H, d, J = 9.4 Hz), 7.21-7.18 (3H, m), 7.05-7.02 (2H, m), 6.74 (1H, d, J = 9.4 Hz), 6.65-6.60 (2H, m), 3.90 (2H, q, J = 7.1 Hz), 1.15 (3H, t, J = 7.1 Hz). |
| 763 | ¹H-NMR (CDCl₃) δ: 7.38 (1H, d, J = 9.2 Hz), 7.21-7.15 (3H, m), 7.06-7.04 (2H, m), 6.72 (1H, d, J = 9.2 Hz), 6.40-6.37 (2H, m), 3.92 (2H, q, J = 7.1 Hz), 3.76 (3H, s), 1.14 (3H, t, J = 7.1 Hz). |
| 764 | ¹H-NMR (CDCl₃) δ: 7.62 (1H, s), 7.22-7.19 (3H, m), 7.05-7.03 (2H, m), 6.66-6.61 (2H, m), 3.95 (2H, q, J = 7.1 Hz), 1.17 (3H, t, J = 7.1 Hz). |
| 765 | ¹H-NMR (CDCl₃) δ: 7.31 (1H, d, J = 9.5 Hz), 6.93 (1H, dd, J = 8.6, 1.5 Hz), 6.86 (1H, d, J = 2.8 Hz), 6.71 (1H, d, J = 9.5 Hz), 6.61 (1H, dd, J = 8.6, 2.8 Hz), 6.42-6.40 (1H, m), 6.36-6.34 (1H, m), 3.77 (3H, s), 3.75 (3H, s), 3.38 (3H, s). |
| 766 | ¹H-NMR (CDCl₃) δ: 7.55 (1H, s), 6.93 (1H, dd, J = 8.5, 1.7 Hz), 6.86 (1H, d, J = 2.7 Hz), 6.69-6.60 (3H, m), 3.76 (3H, s), 3.44 (3H, s). |
| 767 | ¹H-NMR (CDCl₃) δ: 7.75 (1H, s), 6.93 (1H, dd, J = 8.6, 1.8 Hz), 6.85 (1H, d, J = 2.4 Hz), 6.67-6.60 (3H, m), 3.76 (3H, s), 3.45 (3H, s). |
| 768 | ¹H-NMR (CDCl₃) δ: 7.76 (1H, s), 7.20 (1H, d, J = 8.8 Hz), 6.73-6.60 (4H, m), 3.97-3.92 (2H, m), 3.69 (3H, s), 1.18 (3H, t, J = 7.1 Hz). |
| 769 | ¹H-NMR (CDCl₃) δ: 7.20-7.19 (2H, m), 6.70-6.59 (4H, m), 3.91-3.89 (2H, m), 3.68 (3H, s), 2.25 (3H, d, J = 1.2 Hz), 1.16 (3H, t, J = 7.0 Hz). |
| 770 | ¹H-NMR (CDCl₃) δ: 7.31 (1H, d, J = 9.5 Hz), 7.19 (1H, d, J = 8.9 Hz), 6.71-6.69 (2H, m), 6.62-6.61 (1H, m), 6.44-6.42 (1H, m), 6.37-6.35 (1H, m), 3.98-3.85 (2H, m), 3.77 (3H, s), 3.67 (3H, s), 1.16 (3H, t, J = 7.0 Hz). |
| 771 | ¹H-NMR (CDCl₃) δ: 7.20-7.18 (2H, m), 6.68 (1H, dd, J = 8.8, 3.2 Hz), 6.63-6.62 (1H, m), 6.42-6.40 (1H, m), 6.37-6.34 (1H, m), 3.92 (2H, q, J = 7.1 Hz), 3.76 (3H, s), 3.67 (3H, s), 2.24 (3H, d, J = 1.0 Hz), 1.16 (3H, t, J = 7.1 Hz). |
| 772 | ¹H-NMR (CDCl₃) δ: 7.55 (1H, s), 7.19 (1H, d, J = 8.6 Hz), 6.70 (1H, dd, J = 8.9, 3.1 Hz), 6.62 (1H, dd, J = 2.9, 1.4 Hz), 6.43 (1H, dt, J = 10.6, 2.0 Hz), 6.37 (1H, dt, J = 10.6, 1.9 Hz), 3.96 (2H, q, J = 7.1 Hz), 3.77 (3H, s), 3.68 (3H, s), 1.18 (3H, t, J = 7.1 Hz). |

TABLE 5-continued

| Compound | ¹H-NMR |
|---|---|
| 773 | ¹H-NMR (CDCl₃) δ: 7.62 (1H, s), 7.23-7.17 (3H, m), 7.08-7.03 (2H, m), 6.41-6.36 (2H, m), 3.97 (2H, q, J = 7.1 Hz), 3.76 (3H, s), 1.17 (3H, t, J = 7.1 Hz). |
| 774 | ¹H-NMR (CDCl₃) δ: 7.83 (1H, s), 7.22-7.19 (3H, m), 7.05-7.02 (2H, m), 6.66-6.60 (2H, m), 3.95 (2H, q, J = 7.1 Hz), 1.17 (3H, t, J = 7.1 Hz). |
| 775 | ¹H-NMR (CDCl₃) δ: 7.82 (1H, s), 7.23-7.17 (3H, m), 7.07-7.04 (2H, m), 6.41-6.36 (2H, m), 3.97 (2H, q, J = 7.1 Hz), 3.76 (3H, s), 1.16 (3H, t, J = 7.1 Hz). |
| 776 | ¹H-NMR (CDCl₃) δ: 7.54 (1H, s), 6.94 (1H, dd, J = 8.6, 1.5 Hz), 6.86 (1H, d, J = 2.4 Hz), 6.62 (1H, dd, J = 8.6, 2.4 Hz), 6.42-6.39 (1H, m), 6.37-6.34 (1H, m), 3.77 (3H, s), 3.76 (3H, s), 3.45 (3H, s). |
| 777 | ¹H-NMR (CDCl₃) δ: 7.42 (1H, d, J = 9.3 Hz), 7.22-7.19 (3H, m), 7.04-7.02 (2H, m), 6.76 (1H, d, J = 9.3 Hz), 6.67-6.61 (2H, m), 3.38 (3H, s). |
| 778 | ¹H-NMR (CDCl₃) δ: 7.42 (1H, d, J = 9.2 Hz), 7.22-7.16 (3H, m), 7.06-7.04 (2H, m), 6.74 (1H, d, J = 9.2 Hz), 6.41-6.37 (2H, m), 3.76 (3H, s), 3.39 (3H, s). |
| 779 | ¹H-NMR (CDCl₃) δ: 7.65 (1H, s), 7.23-7.20 (3H, m), 7.04-7.02 (2H, m), 6.68-6.61 (2H, m), 3.45 (3H, s). |
| 780 | ¹H-NMR (CDCl₃) δ: 7.85 (1H, s), 7.23-7.20 (3H, m), 7.05-7.01 (2H, m), 6.67-6.62 (2H, m), 3.45 (3H, s). |
| 781 | ¹H-NMR (CDCl₃) δ: 7.64 (1H, s), 7.22-7.19 (3H, m), 7.06-7.04 (2H, m), 6.42-6.38 (2H, m), 3.77 (3H, s), 3.45 (3H, s). |
| 782 | ¹H-NMR (CDCl₃) δ: 7.85 (1H, s), 7.23-7.17 (3H, m), 7.07-7.03 (2H, m), 6.41-6.37 (2H, m), 3.77 (3H, s), 3.46 (3H, s). |
| 783 | ¹H-NMR (CDCl₃) δ: 7.55 (1H, s), 7.33-7.27 (1H, m), 7.01-6.98 (1H, m), 6.90-6.86 (1H, m), 6.83-6.80 (1H, m), 6.77 (1H, dd, J = 8.4, 1.4 Hz), 6.69-6.67 (1H, m), 4.02-3.87 (2H, m), 3.85 (3H, s), 1.18 (3H, t, J = 7.2 Hz). |
| 784 | ¹H-NMR (CDCl₃) δ: 7.35 (1H, d, J = 9.3 Hz), 7.32-7.25 (1H, m), 7.01-6.97 (1H, m), 6.91-6.86 (1H, m), 6.82-6.73 (3H, m), 6.66-6.63 (1H, m), 3.85 (3H, s), 3.38 (3H, s). |
| 785 | ¹H-NMR (CDCl₃) δ: 7.57 (1H, s), 7.34-7.28 (1H, m), 7.02-6.99 (1H, m), 6.90-6.87 (1H, m), 6.84-6.80 (1H, m), 6.79-6.77 (1H, m), 6.66-6.64 (1H, m), 3.85 (3H, s), 3.44 (3H, s). |
| 786 | ¹H-NMR (CDCl₃) δ: 7.77 (1H, s), 7.35-7.27 (1H, m), 7.03-6.99 (1H, m), 6.91-6.86 (1H, m), 6.84-6.77 (2H, m), 6.65 (1H, dt, J = 7.7, 1.5 Hz), 3.85 (3H, s), 3.45 (3H, s). |
| 787 | ¹H-NMR (CDCl₃) δ: 7.56 (1H, s), 7.05 (1H, dd, J = 8.3, 7.6 Hz), 6.82 (1H, dd, J = 8.3, 1.2 Hz), 6.68-6.58 (3H, m), 3.87 (3H, s), 3.44 (3H, s). |
| 788 | ¹H-NMR (CDCl₃) δ: 7.55 (1H, s), 7.06-7.02 (1H, m), 6.80 (1H, dd, J = 8.4, 1.4 Hz), 6.67-6.65 (1H, m), 6.42-6.39 (1H, m), 6.36-6.33 (1H, m), 3.87 (3H, s), 3.75 (3H, s), 3.45 (3H, s). |
| 789 | ¹H-NMR (CDCl₃) δ: 7.33 (1H, d, J = 9.5 Hz), 6.75-6.63 (4H, m), 6.61-6.55 (2H, m), 3.88 (2H, q, J = 7.1 Hz), 1.15 (3H, t, J = 7.1 Hz). |
| 790 | ¹H-NMR (CDCl₃) δ: 7.32 (1H, d, J = 9.5 Hz), 6.72 (1H, d, J = 9.5 Hz), 6.67-6.57 (3H, m), 6.47-6.42 (2H, m), 3.90 (2H, q, J = 7.1 Hz), 3.80 (3H, s), 1.14 (3H, t, J = 7.1 Hz). |
| 791 | ¹H-NMR (CDCl₃) δ: 7.57 (1H, s), 6.74-6.66 (3H, m), 6.62-6.57 (2H, m), 3.93 (2H, q, J = 7.0 Hz), 1.17 (3H, t, J = 7.0 Hz). |
| 792 | ¹H-NMR (CDCl₃) δ: 7.56 (1H, s), 7.15 (1H, d, J = 8.6 Hz), 6.71 (1H, dd, J = 8.6, 3.1 Hz), 6.69-6.62 (2H, m), 6.53 (1H, dd, J = 3.1, 1.8 Hz), 5.91 (1H, brs), 3.97-3.94 (2H, m), 1.18 (3H, t, J = 7.2 Hz). |
| 793 | ¹H-NMR (CDCl₃) δ: 7.54 (1H, s), 7.18 (1H, d, J = 8.8 Hz), 6.72-6.59 (4H, m), 3.96-3.89 (3H, m), 3.83-3.81 (1H, m), 1.36 (3H, t, J = 7.0 Hz), 1.18 (3H, t, J = 7.2 Hz). |
| 794 | ¹H-NMR (CDCl₃) δ: 7.52 (1H, s), 7.30 (1H, d, J = 8.8 Hz), 6.83 (1H, dd, J = 8.8, 3.1 Hz), 6.74-6.62 (3H, m), 4.70 (1H, d, J = 16.4 Hz), 4.65 (1H, d, J = 16.4 Hz), 3.99-3.92 (2H, m), 1.19 (3H, t, J = 7.1 Hz). |
| 795 | ¹H-NMR (CDCl₃) δ: 7.56 (1H, s), 7.21 (1H, d, J = 8.8 Hz), 6.83 (1H, dd, J = 8.8, 3.1 Hz), 6.76 (1H, dd, J = 3.1, 1.6 Hz), 6.70-6.60 (2H, m), 5.06 (1H, d, J = 7.0 Hz), 4.98 (1H, d, J = 7.0 Hz), 3.96-3.93 (2H, m), 3.39 (3H, s), 1.18 (3H, t, J = 7.1 Hz). |
| 796 | ¹H-NMR (CDCl₃) δ: 7.54 (1H, s), 7.18 (1H, d, J = 8.8 Hz), 6.69 (1H, dd, J = 8.8, 2.9 Hz), 6.60 (1H, dd, J = 2.9, 1.7 Hz), 6.41-6.37 (2H, m), 3.96-3.94 (3H, m), 3.83-3.80 (1H, m), 3.76 (3H, s), 1.35 (3H, t, J = 7.0 Hz), 1.18 (3H, t, J = 7.2 Hz). |
| 797 | ¹H-NMR (CDCl₃) δ: 7.78 (1H, s), 6.73-6.66 (3H, m), 6.62-6.57 (2H, m), 3.93 (2H, q, J = 7.1 Hz), 1.17 (3H, t, J = 7.1 Hz). |
| 798 | ¹H-NMR (CDCl₃) δ: 7.56 (1H, s), 6.69-6.57 (3H, m), 6.47-6.42 (2H, m), 3.95 (2H, q, J = 7.1 Hz), 3.80 (3H, s), 1.16 (3H, t, J = 7.1 Hz). |
| 799 | ¹H-NMR (CDCl₃) δ: 7.77 (1H, s), 6.66 (1H, tt, J = 9.0, 2.3 Hz), 6.63-6.58 (2H, m), 6.46-6.43 (2H, m), 3.96 (2H, q, J = 7.1 Hz), 3.80 (3H, s), 1.16 (3H, t, J = 7.1 Hz). |
| 800 | ¹H-NMR (CDCl₃) δ: 7.36 (1H, d, J = 9.5 Hz), 6.77-6.64 (4H, m), 6.61-6.55 (2H, m), 3.37 (3H, s). |
| 801 | ¹H-NMR (CDCl₃) δ: 7.34-7.28 (1H, m), 7.26-7.25 (1H, m), 7.20-7.19 (1H, m), 6.93-6.90 (1H, m), 6.86-6.82 (1H, m), 6.76 (1H, dd, J = 8.6, 3.1 Hz), 6.73-6.72 (1H, m), 4.66-4.59 (2H, m), 3.95-3.88 (2H, m), 2.26 (3H, d, J = 1.2 Hz), 1.16 (3H, t, J = 7.1 Hz). |
| 802 | ¹H-NMR (CDCl₃) δ: 7.33-7.25 (1H, m), 7.22 (1H, d, J = 1.2 Hz), 7.15 (1H, d, J = 8.5 Hz), 6.89-6.80 (2H, m), 6.64 (1H, dd, J = 8.5, 2.9 Hz), 6.61-6.60 (1H, m), 3.96-3.87 (1H, m), 3.82-3.74 (1H, m), 2.25 (3H, d, J = 1.2 Hz), 1.33 (3H, t, J = 7.1 Hz), 1.16 (3H, t, J = 7.1 Hz). |
| 803 | ¹H-NMR (CDCl₃) δ: 7.35 (1H, d, J = 9.5 Hz), 6.74 (1H, d, J = 9.5 Hz), 6.67-6.56 (3H, m), 6.48-6.43 (2H, m), 3.80 (3H, s), 3.38 (3H, s). |
| 804 | ¹H-NMR (CDCl₃) δ: 7.59 (1H, s), 6.75-6.67 (3H, m), 6.61-6.56 (2H, m), 3.44 (3H, s). |
| 805 | ¹H-NMR (CDCl₃) δ: 7.81 (1H, s), 6.76-6.68 (3H, m), 6.62-6.57 (2H, m), 3.45 (3H, s). |
| 806 | ¹H-NMR (CDCl₃) δ: 7.54 (1H, s), 7.01-6.98 (1H, m), 6.91 (1H, dd, J = 8.2, 1.6 Hz), 6.70-6.58 (3H, m), 5.66 (1H, s), 4.02-3.87 (2H, m), 1.19 (3H, t, J = 7.1 Hz). |
| 807 | ¹H-NMR (CDCl₃) δ: 7.59 (1H, s), 6.67 (1H, tt, J = 8.9, 2.3 Hz), 6.63-6.57 (2H, m), 6.48-6.43 (2H, m), 3.80 (3H, s), 3.44 (3H, s). |
| 808 | ¹H-NMR (CDCl₃) δ: 7.79 (1H, s), 6.67 (1H, tt, J = 8.9, 2.3 Hz), 6.62-6.56 (2H, m), 6.48-6.43 (2H, m), 3.80 (3H, s), 3.44 (3H, s). |

TABLE 5-continued

| Compound | $^1$H-NMR |
|---|---|
| 809 | $^1$H-NMR (CDCl$_3$) δ: 7.54 (1H, s), 7.00 (1H, dd, J = 8.3, 7.8 Hz), 6.79 (1H, dd, J = 8.3, 1.5 Hz), 6.68-6.57 (3H, m), 4.08-3.86 (4H, m), 1.45 (3H, t, J = 7.0 Hz), 1.18 (3H, t, J = 7.1 Hz). |
| 810 | $^1$H-NMR (CDCl$_3$) δ: 7.53 (1H, s), 7.12 (1H, dd, J = 8.3, 7.8 Hz), 6.97 (1H, dd, J = 8.3, 1.5 Hz), 6.85 (1H, dt, J = 7.8, 1.5 Hz), 6.69-6.60 (2H, m), 4.85-4.78 (2H, m), 3.99-3.91 (2H, m), 1.19 (3H, t, J = 7.1 Hz). |
| 811 | $^1$H-NMR (CDCl$_3$) δ: 7.55 (1H, s), 7.07-6.99 (2H, m), 6.73 (1H, dt, J = 7.3, 1.8 Hz), 6.68-6.57 (2H, m), 5.22 (1H, d, J = 6.8 Hz), 5.19 (1H, d, J = 6.8 Hz), 3.99-3.90 (2H, m), 3.49 (3H, s), 1.19 (3H, t, J = 7.1 Hz). |
| 812 | $^1$H-NMR (CDCl$_3$) δ: 7.26 (1H, d, J = 9.5 Hz), 6.80-6.63 (5H, m), 3.92-3.85 (2H, m), 1.16 (3H, t, J = 7.2 Hz). |
| 813 | $^1$H-NMR (CDCl$_3$) δ: 7.49 (1H, s), 6.81 (1H, td, J = 8.3, 3.1 Hz), 6.76-6.64 (3H, m), 3.96-3.91 (2H, m), 1.19 (3H, t, J = 7.0 Hz). |
| 814 | $^1$H-NMR (CDCl$_3$) δ: 7.70 (1H, s), 6.80 (1H, td, J = 8.2, 2.8 Hz), 6.76-6.63 (3H, m), 3.95-3.92 (2H, m), 1.19 (3H, t, J = 7.1 Hz). |
| 815 | $^1$H-NMR (CDCl$_3$) δ: 7.28 (1H, d, J = 10.0 Hz), 6.82-6.70 (3H, m), 6.68-6.63 (2H, m), 3.38 (3H, s). |
| 816 | $^1$H-NMR (CDCl$_3$) δ: 7.51 (1H, s), 6.82 (1H, td, J = 8.3, 3.1 Hz), 6.73 (1H, tt, J = 8.7, 2.1 Hz), 6.68-6.66 (2H, m), 3.44 (3H, s). |
| 817 | $^1$H-NMR (CDCl$_3$) δ: 7.71 (1H, s), 6.81 (1H, td, J = 8.3, 2.8 Hz), 6.74-6.72 (1H, m), 6.69-6.65 (2H, m), 3.45 (3H, s). |
| 818 | $^1$H-NMR (CDCl$_3$) δ: 7.25 (1H, d, J = 9.5 Hz), 6.76-6.70 (3H, m), 6.48-6.46 (1H, m), 6.39-6.37 (1H, m), 3.93-3.88 (2H, m), 3.79 (3H, s), 1.16 (3H, t, J = 7.0 Hz). |
| 819 | $^1$H-NMR (CDCl$_3$) δ: 7.48 (1H, s), 6.78 (1H, td, J = 8.3, 3.1 Hz), 6.71-6.68 (1H, m), 6.48-6.46 (1H, m), 6.40-6.38 (1H, m), 3.95 (2H, q, J = 7.1 Hz), 3.79 (3H, s), 1.18 (3H, t, J = 7.1 Hz). |
| 820 | $^1$H-NMR (CDCl$_3$) δ: 7.69 (1H, s), 6.78 (1H, td, J = 8.3, 2.8 Hz), 6.71-6.68 (1H, m), 6.47 (1H, dt, J = 10.7, 1.8 Hz), 6.39 (1H, dt, J = 10.5, 2.0 Hz), 3.96 (2H, q, J = 7.1 Hz), 3.79 (3H, s), 1.18 (3H, t, J = 7.1 Hz). |
| 821 | $^1$H-NMR (CDCl$_3$) δ: 7.99 (1H, s), 7.32 (1H, dd, J = 8.1, 1.2 Hz), 7.18-7.16 (1H, m), 7.08-7.04 (2H, m), 6.67-6.57 (2H, m), 3.95 (2H, q, J = 7.1 Hz), 1.18 (3H, t, J = 7.1 Hz). |
| 822 | $^1$H-NMR (CDCl$_3$) δ: 7.98 (1H, s), 7.32-7.30 (1H, m), 7.15-7.14 (1H, m), 7.08-7.05 (2H, m), 6.40 (1H, ddd, J = 10.7, 2.5, 1.6 Hz), 6.34 (1H, ddd, J = 10.4, 2.5, 1.6 Hz), 4.00-3.94 (2H, m), 3.75 (3H, s), 1.17 (3H, t, J = 7.2 Hz). |
| 823 | $^1$H-NMR (CDCl$_3$) δ: 7.27 (1H, d, J = 6.1 Hz), 6.79-6.73 (2H, m), 6.68-6.65 (1H, m), 6.48-6.45 (1H, m), 6.40-6.37 (1H, m), 3.79 (3H, s), 3.38 (3H, s). |
| 824 | $^1$H-NMR (CDCl$_3$) δ: 7.50 (1H, s), 6.79 (1H, td, J = 8.3, 3.1 Hz), 6.69-6.66 (1H, m), 6.48-6.45 (1H, m), 6.41-6.39 (1H, m), 3.79 (3H, s), 3.45 (3H, s). |
| 825 | $^1$H-NMR (CDCl$_3$) δ: 7.70 (1H, s), 6.79 (1H, td, J = 8.2, 2.8 Hz), 6.69-6.66 (1H, m), 6.48-6.45 (1H, m), 6.41-6.38 (1H, m), 3.79 (3H, s), 3.45 (3H, s). |

The following specifically demonstrates that the parasitic pest control agent of the present invention is effective against parasitic pests, although the present invention is not limited to these examples.

Test Example 1

Heartworm

Compound Nos. 32, 53, 54 and 55 were each dissolved in dimethyl sulfoxide to 10 mg/ml. These dimethyl sulfoxide solutions were diluted 100-fold to a final concentration of 100 μg/ml with the culture broth containing heartworm microfillaria collected from dogs infected with heartworm. The mortality rate of heartworm microfillaria was investigated after culturing for 7 days.

As a result, the mortality rate was 100% in each of the treatment groups.

Test Example 2

Southern Root-Knot Nematode

The dimethyl sulfoxide solution comprising Compound No. 340, 362, 427, 428, 432, 438, 439, 486, 487, 488, 491, 500, 543, 553, 554, 559, 566, 577, 584, 585, 586, 649, 720, 753, 800, 812, 813, 814, 815, 816 or 817 at 25000 ppm were mixed with a suspension of the second-stage larva of southern root-knot nematode to prepare 20 ppm solutions. The prepared solutions were allowed to stand overnight in dark followed by treating the bases of cucumber seedlings grown in 90 ml of 0.5% agar per plant at 2 ml/plant. The number of root knots formed on the roots 7 days after treatment was counted, and compared with the number of root knots of an untreated group.

As a result, the ratio of the number of root knots of the treated group to that of the untreated group was 30 or less in all the treatment groups.

Test Example 3

Two-Spotted Spider Mite

A sponge was placed into a 9 cm Petri dish containing water, a piece of filter paper was spread out over the sponge, and a leaf disk from a black-eyed pea was placed on the filter paper. Four female adult two-spotted spider mites were released onto the leaf disk and allowed to spawn overnight, the adults were removed prior to the test, and the number of eggs spawned was counted.

The dimethyl sulfoxide solution comprising Compound No. 428, 430, 455, 513, 577, 583, 584, 585, 587, 593, 607, 622, 624, 649, 668, 679, 683, 689, 715, 733, 812, 813, 814 or 815 at 25000 ppm was added to the distilled water containing Gramin S (from Mitsui Chemicals Agro, Inc.) to prepare the 500 ppm solutions. The solutions were sprayed at 1 ml per Petri dish. After 9 days, the Petri dishes were observed with a stereomicroscope, and the mortality rates of the eggs and hatched larva were investigated. Unhatched larva were counted as dead.

As a result, the mortality rate was 70% or more in each of the treatment groups.

INDUSTRIAL APPLICABILITY

Because the novel pyridone compounds of the present invention can control pests parasitically infesting animals and plants, the compounds are useful as parasitic pest control agents.

The invention claimed is:

1. A method for controlling parasitic pests, wherein the method comprises administering a parasitic pest control agent to an animal in need thereof, wherein the parasitic pest control agent comprises a compound of Formula (1) or a salt thereof as an active ingredient:

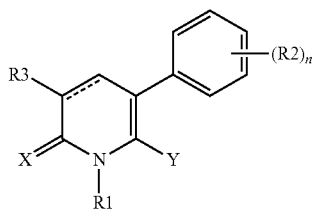
(1)

wherein
R1 represents a hydroxyl group,
  a cyano group,
  a C1-C6 alkyl group optionally substituted with substituent A,
  a C1-C6 haloalkyl group,
  a C3-C8 cycloalkyl group optionally substituted with substituent A,
  a C2-C6 alkenyl group optionally substituted with substituent A,
  a C2-C6 haloalkenyl group,
  a C2-C6 alkynyl group optionally substituted with substituent A,
  a C2-C6 haloalkynyl group,
  a C1-C6 alkoxy group optionally substituted with substituent A,
  a C1-C6 haloalkoxy group,
  a C3-C8 cycloalkoxy group optionally substituted with substituent A,
  a C2-C6 alkenyloxy group optionally substituted with substituent A,
  a C2-C6 haloalkenyloxy group,
  a C3-C6 alkynyloxy group optionally substituted with substituent A,
  a C3-C6 haloalkynyloxy group, or
  a R10R11N— group wherein R10 and R11 each independently represents a hydrogen atom or a C1-C6 alkyl group;
R2 represents a halogen atom,
  a hydroxyl group,
  a cyano group,
  a nitro group,
  a C1-C6 alkyl group optionally substituted with substituent B,
  a C1-C6 haloalkyl group,
  a C3-C8 cycloalkyl group optionally substituted with substituent B,
  a C2-C6 alkenyl group optionally substituted with substituent B,
  a C2-C6 haloalkenyl group,
  a C2-C6 alkynyl group optionally substituted with substituent B,
  a C2-C6 haloalkynyl group,
  a C1-C6 alkoxy group optionally substituted with substituent B,
  a C1-C6 haloalkoxy group,
  a C3-C8 cycloalkoxy group optionally substituted with substituent B,
  a C2-C6 alkenyloxy group optionally substituted with substituent B,
  a C2-C6 haloalkenyloxy group,
  a C3-C6 alkynyloxy group optionally substituted with substituent B,
  a C3-C6 haloalkynyloxy group,
  a R20C(=O)— group wherein R20 represents a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or a R21R22N— group wherein R21 and R22 each independently represents a hydrogen atom, a C1-C6 alkyl group optionally substituted with substituent B1, a C1-C6 haloalkyl group or a C3-C8 cycloalkyl group, or R21 and R22 together with the nitrogen atom to which they are bonded form aziridinyl, azetidinyl, pyrrolidinyl, piperidinyl, homopiperidinyl or azocanyl,
  a R20C(=O)O— group wherein R20 is the same as defined hereinabove,
  a 3 to 6-membered ring group containing 1 to 2 oxygen atoms,
  a R23-L2- group wherein R23 represents a C1-C6 alkyl group or a C1-C6 haloalkyl group, and L2 represents S, SO or SO$_2$,
  a R21R22N— group wherein R21 and R22 are the same as defined hereinabove, or
  a R24C(=O)N(R25)— group wherein R24 represents a hydrogen atom, a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or a R21R22N— group wherein R21 and R22 are the same as defined hereinabove, and R25 represents a hydrogen atom, a C1-C6 alkyl group optionally substituted with substituent B1, a C1-C6 haloalkyl group or a C3-C8 cycloalkyl group;
R3 represents a hydrogen atom,
  a halogen atom,
  a nitro group,
  a C1-C6 alkyl group optionally substituted with substituent C,
  a C1-C6 haloalkyl group,
  a C3-C8 cycloalkyl group optionally substituted with substituent C,
  a C1-C6 alkoxy group optionally substituted with substituent C,
  a C1-C6 haloalkoxy group,
  a C2-C6 alkenyl group optionally substituted with substituent C,
  a C2-C6 haloalkenyl group,
  a C2-C6 alkynyl group optionally substituted with substituent C,
  a C2-C6 haloalkynyl group,
  a R30-L3- group wherein R30 has the same definition as R23, and L3 has the same definition as L2,
  a R31R32N— group wherein R31 and R32 have the same definition as R21 and R22 or a R33C(=O)— group wherein R33 represents a C1-C6 alkyl group, a C1-C6 haloalkyl group or a C3-C8 cycloalkyl group;

n represents an integer of 0 to 5 with the proviso that when n is 2 or greater, the two or more R2 represent independent substituents;

X represents an oxygen atom or a sulfur atom;

Y represents phenyl, pyridyl, pyridazinyl, pyrimidinyl, pyrazinyl, triazinyl, tetrazinyl, thienyl, thiazolyl, isothiazolyl or thiadiazolyl,
  the phenyl is substituted with substituent D at an ortho position and is optionally further substituted with 0 to 4 independent substituents D1,
  the pyridyl, the pyrazinyl, the pyrimidinyl, the pyridazinyl, the triazinyl or the tetrazinyl is substituted with substituent D at an ortho position and is optionally further substituted with 0 to 3 independent substituents D1,
  the thienyl, the thiazolyl, the isothiazolyl or the thiadiazolyl is substituted with substituent D at an ortho position and is optionally further substituted with 0 to 2 independent substituents D1;

the bond with a broken line represents a double bond or a single bond, the substituent A is at least one selected from the group consisting of:
  a hydroxyl group, a cyano group, a C3-C8 cycloalkyl group, a C1-C6 alkoxy group, a C1-C6 haloalkoxy group, a C3-C8 cycloalkoxy group, a R12R13N— group wherein R12 and R13 each independently represents a hydrogen atom, a C1-C6 alkyl group, a C1-C6 haloalkyl group or a C3-C8 cycloalkyl group, or R12 and R13 together with the nitrogen atom to which they are bonded form aziridinyl, azetidinyl, pyrrolidinyl, piperidinyl, homopiperidinyl or azocanyl, and a R14-L1- group wherein R14 represents a C1-C6 alkyl group or a C1-C6 haloalkyl group, and L1 represents S, SO or $SO_2$;

the substituent B is at least one selected from the group consisting of:
a hydroxyl group, a cyano group, a C3-C8 cycloalkyl group, a C1-C6 alkoxy group, a C1-C6 haloalkoxy group, a C3-C8 cycloalkoxy group, a C2-C6 alkoxyalkoxy group, a R21R22N— group wherein R21 and R22 are the same as defined hereinabove, a R23-L2- group wherein R23 and L2 are the same as defined hereinabove, a R26R27R28Si— group wherein R26, R27 and R28 each independently represents a C1-C6 alkyl group, a R26R27R28Si—($CH_2$)s—O—group wherein s represents an integer of 1 to 3, and R26, R27 and R28 are the same as defined hereinabove, a R20C(=O)— group wherein R20 is the same as defined hereinabove and a 3 to 6-membered ring group containing 1 to 2 oxygen atoms;

the substituent B1 is at least one selected from the group consisting of:
  a cyano group, a C1-C6 alkoxy group, a C1-C6 haloalkoxy group and a C3-C8 cycloalkoxy group;

the substituent C is at least one selected from the group consisting of:
  a hydroxyl group, a cyano group, a C3-C8 cycloalkyl group, a C1-C6 alkoxy group, a C1-C6 haloalkoxy group, a C3-C8 cycloalkoxy group, a R31R32N— group wherein R31 and R32 have the same definition as R21 and R22 and a R30-L3- group wherein R30 has the same definition as R14, and L3 has the same definition as L1;

the substituent D is at least one selected from the group consisting of:
  a halogen atom, a C1-C6 alkyl group, a C1-C6 haloalkyl group, a C1-C6 alkoxy group and a C1-C6 haloalkoxy group; and the substituent D1 is at least one selected from the group consisting of:
  a hydroxyl group, a halogen atom, a C1-C6 alkyl group, a C1-C6 haloalkyl group, a C3-C8 cycloalkyl group, a C1-C6 alkoxy group, a C1-C6 haloalkoxy group and a C3-C8 cycloalkoxy group.

2. The method according to claim 1, wherein the parasitic pest is an insect pest of the order Acarina or nematodes.

3. The method according to claim 1, wherein the parasitic pest is animal parasitic nematodes.

4. The method according to claim 1, wherein the parasitic pest is nematodes of the order Spirurida.

5. The method according to claim 1, wherein the parasitic pest is a heartworm.

6. The method according to claim 1, wherein
R1 represents a cyano group,
  a C1-C6 alkyl group optionally substituted with substituent A,
  a C1-C6 haloalkyl group,
  a C3-C8 cycloalkyl group optionally substituted with substituent A,
  a C2-C6 alkenyl group optionally substituted with substituent A,
  a C2-C6 haloalkenyl group,
  a C2-C6 alkynyl group optionally substituted with substituent A, or
  a R10R11N— group wherein R10 and R11 each independently represents a hydrogen atom or a C1-C6 alkyl group;

R2 represents a halogen atom,
  a hydroxyl group,
  a cyano group,
  a C1-C6 alkyl group optionally substituted with substituent B,
  a C1-C6 haloalkyl group,
  a C1-C6 alkoxy group optionally substituted with substituent B,
  a C1-C6 haloalkoxy group,
  a C3-C8 cycloalkoxy group optionally substituted with substituent B,
  a C2-C6 alkenyloxy group optionally substituted with substituent B,
  a C3-C6 alkynyloxy group optionally substituted with substituent B,
  a R20C(=O)O— group wherein R20 represents a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or a R21R22N— group wherein R21 and R22 each independently represents a hydrogen atom, a C1-C6 alkyl group optionally substituted with substituent B1, a C1-C6 haloalkyl group or a C3-C8 cycloalkyl group, or R21 and R22 together with the nitrogen atom to which they are bonded form aziridinyl, azetidinyl, pyrrolidinyl, piperidinyl, homopiperidinyl or azocanyl, or
  a R23-L2- group wherein R23 represents a C1-C6 alkyl group or a C1-C6 haloalkyl group, and L2 represents S, SO or $SO_2$;

R3 represents a hydrogen atom,
  a halogen atom,
  a C1-C6 alkyl group optionally substituted with substituent C,
  a C3-C8 cycloalkyl group optionally substituted with substituent C,
  a C1-C6 alkoxy group optionally substituted with substituent C,
  a C2-C6 alkynyl group optionally substituted with substituent C, or
  a R30-L3- group wherein R30 has the same definition as R23, and L3 has the same definition as L2;
Y represents phenyl or pyridyl,
  the phenyl is substituted with substituent D at an ortho position and is optionally further substituted with 0 to 4 independent substituents D1, and
  the pyridyl is substituted with substituent D at an ortho position and is optionally further substituted with 0 to 3 independent substituents D1.

7. The method according to claim 1, wherein
R1 represents a C1-C6 alkyl group optionally substituted with substituent A, or a C1-C6 haloalkyl group;
R2 represents a halogen atom, a C1-C6 alkyl group optionally substituted with substituent B, or a C1-C6 alkoxy group optionally substituted with substituent B; and
R3 represents a hydrogen atom, a halogen atom, or a C1-C6 alkyl group optionally substituted with substituent C.

\* \* \* \* \*